US012501917B2

(12) United States Patent
Perea et al.

(10) Patent No.: US 12,501,917 B2
(45) Date of Patent: Dec. 23, 2025

(54) METHODS AND COMPOSITIONS FOR TREATING INTESTINAL DISORDER

(71) Applicants: MARS, INCORPORATED, McLean, VA (US); THE TRUSTEES OF THE UNIVERSITY OF PENNSYLVANIA, Philadelphia, PA (US)

(72) Inventors: Sally Christine Perea, Lewisburg, OH (US); Daniel P. Beiting, Philadelphia, PA (US)

(73) Assignees: Mars, Incorporated, McLean, VA (US); The Trustees of the University of Pennsylvania, Philadelphia, PA (US)

( * ) Notice: Subject to any disclaimer, the term of this patent is extended or adjusted under 35 U.S.C. 154(b) by 226 days.

(21) Appl. No.: 17/425,080

(22) PCT Filed: Jan. 23, 2020

(86) PCT No.: PCT/US2020/014823

§ 371 (c)(1),
(2) Date: Jul. 22, 2021

(87) PCT Pub. No.: WO2020/154523

PCT Pub. Date: Jul. 30, 2020

(65) Prior Publication Data

US 2022/0104517 A1 Apr. 7, 2022

Related U.S. Application Data

(60) Provisional application No. 62/796,021, filed on Jan. 23, 2019.

(51) Int. Cl.
*A61K 35/742* (2015.01)
*A23K 10/18* (2016.01)
(Continued)

(52) U.S. Cl.
CPC .............. *A23K 10/18* (2016.05); *A23K 50/40* (2016.05); *A23L 33/135* (2016.08);
(Continued)

(58) Field of Classification Search
CPC ....... A23K 10/18; A23K 50/40; A23L 33/135; A61K 31/575; A61K 35/742; A61P 1/00; C12Q 1/06
See application file for complete search history.

(56) References Cited

U.S. PATENT DOCUMENTS

2012/0201796 A1 8/2012 Beasley
2017/0087196 A1 3/2017 Pamer
2018/0064140 A1 3/2018 Li

FOREIGN PATENT DOCUMENTS

CN 102471370 A 5/2012
WO 2015/179437 A1 11/2015
(Continued)

OTHER PUBLICATIONS

AlShawaqfeh MK, Wajid B, Y. Minamoto, M. Markel, J.A. Lidbury, J.M. Steiner, E. Serpedin, and J.S. Suchodolski, A dysbiosis index to assess microbial changes in fecal samples of dogs with chronic inflammatory enteropathy. FEMS Microbiol Ecol (2017) 1; 93(11) (Year: 2017).*

(Continued)

*Primary Examiner* — Louise W Humphrey
*Assistant Examiner* — Mary A Crum
(74) *Attorney, Agent, or Firm* — Morrison & Foerster LLP

(57) ABSTRACT

Provided are methods for determining responsiveness of a companion animal having an intestinal disorder to a diet. These methods include measuring at least a first amount of a first intestinal microorganism, comparing the first amount of the first intestinal microorganism with a first reference
(Continued)

amount of the first intestinal microorganism, wherein the reference amount is determined based on the amounts of the intestinal microorganisms in a plurality of healthy companion animals; and determining that the companion animal is responsive to the diet, when the first amount of the intestinal microorganism is higher than the first reference amount of the first intestinal microorganism.

9 Claims, 20 Drawing Sheets

Specification includes a Sequence Listing.

(51) Int. Cl.
*A23K 50/40* (2016.01)
*A23L 33/135* (2016.01)
*A61K 31/575* (2006.01)
*A61P 1/00* (2006.01)
*C12Q 1/06* (2006.01)

(52) U.S. Cl.
CPC .......... *A61K 31/575* (2013.01); *A61K 35/742* (2013.01); *A61P 1/00* (2018.01); *C12Q 1/06* (2013.01); *G01N 2800/50* (2013.01); *G01N 2800/52* (2013.01)

(56) References Cited

FOREIGN PATENT DOCUMENTS

| | | | |
|---|---|---|---|
| WO | 2018/042304 | A1 | 3/2018 |
| WO | 2018/195467 | A1 | 10/2018 |
| WO | 2020/154523 | A2 | 7/2020 |

OTHER PUBLICATIONS

Malewska, K., et al. "Treatment of inflammatory bowel disease (IBD) in dogs and cats." Polish Journal of Veterinary Sciences (2011) (Year: 2011).*

Dandrieux, Julien Rodolphe Samuel, and Caroline Sarah Mansfield. "Chronic enteropathy in canines: prevalence, impact and management strategies." Veterinary Medicine: Research and Reports (2019): 203-214. (Year: 2019).*

Coelho, Luis Pedro, et al. "Similarity of the dog and human gut microbiomes in gene content and response to diet." Microbiome 6.1 (2018): 1-11. (Year: 2018).*

Appendix A—NCBI accesion NR_041343 Parabacteroides merdae 16S rRNA sequence and aligment NR_041343 vs KF842598.1. 1394 (Year: 2023).*

Appendix B NCBI accession KX577638 *Streptococcus infantarius* 16S rRNA sequence and alignement of KX577638 vs HK557089. 3.1395 (Year: 2023).*

Bresciani, Francesca, et al. "Effect of an extruded animal protein-free diet on fecal microbiota of dogs with food-responsive enteropathy." Journal of Veterinary Internal Medicine 32.6 (2018): 1903-1910 (Year: 2018).*

Guard, Blake Crosby. Microbial Characterization, Metabolomic Profiling, and Bile Acid Metabolism in Healthy Dogs and Dogs with Chronic Enteropathy. Diss. 2017 (Year: 2017).*

Doden et al. (May 2018). "Metabolism of Oxo-Bile Acids and Characterization of Recombinant 12α-Hydroxysteroid Dehydrogenases from Bile Acid 7α-Dehydroxylating Human Gut Bacteria", Applied and Environmental Microbiology 84(10):1-18.

Joseph D. et al. (2020). "Development of a targeted 7α-Dehydratase PCR Assat for Fecal Microbial Transplant Bile Acid Characterization" Grastroenterolgy 158(6):S479.

Reed et al. (Jun. 2020). "Strain-Dependent Inhibition of Clostridiodes difficile by Commensal Clostridia Carrying the Bile Acid-Inducible (bai) Operon" Journal of Bacteriology 202(11):1-15.

Ridlon et al. (2010). "Isolation and characterization of a bile acid inducible 7α-dehydroxylating operon in Clostridium Hylemonae TN271" Anaerobe 16(2010):137-146.

Ridlon et al. (May 2018). "Bile Acid 7α-Dehydroxylating Gut Clostridia: From Comparative Genomics to In Vivo Metatransciptiomics and Metabolomics to Gene Discovery" Gastroenterology 154(6):S639-S640.

Solbach et al. (2018). "BaiCD gene cluster abundance is negatively correlated with Clostridium difficile infection" PLOS One 13(5):1-20.

Wang et al. (2019). "Diet-induced remission in chronic enteropathy is associated with altered microbial community structure and synthesis of secondary bile acids" Microbiome (2019)7:126.

AlShawaqfeh et al. (2017). "A dysbiosis index to assess microbial changes in fecal samples of dogs with chronic inflammatory enteropathy" FEMS Microbiology Ecology 93(11): 1-8.

Bresciani et al. (May 2018). "Effect of an extruded animal protein-free diet on fecal microbiota of dogs with food-responsive enteropathy" Journal of Veterinary Internal Medicine 32:1903-1910.

Buffie et al. (Jan. 2015). "Precision microbiome reconstitution restores bile acid mediated resistance to Clostridium difficile," Nature 517: 16 pages.

Isaiah (Aug. 2018). "Clostridium Hiranonis, a Bile Acid 7α-Dehydroxylating Bacterium in Dogs" Doctoral Dissertation, Texas A&M University; 133 pages.

Li et al. (Jan./Feb. 2017). "Effects of the Dietary Protein and Carbohydrate Ratio on Gut Microbiomes in Dogs of Different Body Conditions." American Society of Microbiology 8(1):1-14.

* cited by examiner

METHODS AND COMPOSITIONS FOR TREATING INTESTINAL DISORDER

CROSS-REFERENCE TO RELATED APPLICATIONS

This application is a U.S. National Stage Patent Application under 35 U.S.C. § 371 of International Patent Application No. PCT/2020/014823, filed on Jan. 23, 2020, which claims the priority to U.S. Provisional Application No. 62/796,021, filed Jan. 23, 2019, the contents of each of which are incorporated herein by reference in their entireties, and to each of which priority is claimed.

SEQUENCE LISTINGS

The specification further incorporates by reference the Sequence Listing submitted herewith via EFS on Jul. 22, 2021. Pursuant to 37 C.F.R. § 1.52(e)(5), the Sequence Listing text file, identified as 0692690472SL.txt, is 203,756 bytes and was created on Jul. 22, 2021. The Sequence Listing, electronically filed herewith, does not extend beyond the scope of the specification and thus does not contain new matter.

FIELD

The presently disclosed subject matter relates to method, compositions and food products for improving intestinal health, treating intestinal dysbiosis and/or treating an intestinal disorder in a subject, e.g., a human or a companion animal.

BACKGROUND

Inflammatory bowel disease (IBD), including Crohn's disease and ulcerative colitis, is a multi-factorial and debilitating disease characterized by chronic immune-pathology, disruption of intestinal homeostasis and altered composition of the gut microbiome (dysbiosis). Several lines of evidence point to resident gut bacteria as important factors in the etiology of IBD. First, disease is often more severe in areas of the intestine with the highest microbial biomass, and antibiotics are frequently used as an adjunct therapy with immunosuppressants or monoclonal antibodies for managing IBD[1,2]. Second, genome-wide associations studies have identified numerous susceptibility loci in genes responsible for recognizing or responding to bacteria[3]. Finally, in some mouse models of colitis, disease can be transferred to naive hosts via fecal transplant[4-6], suggesting a causal role for gut microbes in disease. Collectively, these findings have led to a 'two-hit' model for IBD in which both host genetics and microbial factors influence disease presentation, highlighting an opportunity to develop novel treatments for IBD that target the microbiome. Thus, there is a need for novel methods and compositions for treating IBD and other intestinal disorders that target gut microbiome and metabolites thereof.

SUMMARY OF THE INVENTION

The presently disclosed subject matter provides a pharmaceutical composition, dietary supplement and functional food for medicament. In certain embodiments, the pharmaceutical composition, dietary supplement or functional food comprises an effective amount of a bacterium capable of producing a first bile acid for use as a medicament. In certain embodiments, the pharmaceutical composition, dietary supplement or functional food further comprises an effective amount of a second bile acid. In certain embodiments, the pharmaceutical composition, dietary supplement or functional food is for the treatment of an intestinal disorder in a subject in need thereof.

In certain embodiments, the bacterium comprises a bile acid-inducible operon (bai operon). In certain embodiments, the bile acid-inducible operon (bai operon) comprises a nucleotide sequence that is at least about 90% homologous or identical to SEQ ID NO: 1 or 3, or any functional fragment thereof. In certain embodiments, the bile acid-inducible operon (bai operon) comprises the nucleotide sequence set forth in SEQ ID NO: 1 or 3.

In certain embodiments, the bacterium comprises a 16s rRNA comprising a nucleotide sequence that is at least about 90% homologous or identical to SEQ ID NO: 2 or 4. In certain embodiments, the bacterium comprises a 16s rRNA comprising the nucleotide sequence set forth in SEQ ID NO: 2 or 4.

In certain embodiments, the bacterium is *C. hiranonis, C. scindens* or combination thereof. In certain embodiments, the bacterium is *C. hiranonis.*

In certain embodiments, the first bile acid and/or the second bile acid is selected from the group consisting of chenodeoxycholic acid, cholic acid, glycochenodeoxycholic acid, glycocholic acid, taurocholic acid, taurochenodeoxycholic acid, taurodeoxycholic acid, glycodeoxycholic acid, ursodeoxycholic acid, glycoursodeoxycholic acid, tauroursodeoxycholic acid, taurolithocholic acid, alpha-muricholic acid, deoxycholic acid, gamma-muricholic acid, glycolithocholic acid, taurolithocholic acid, lithocholic acid, omega-muricholic acid and any combination thereof.

In certain embodiments, the first bile acid and/or the second bile acid is a secondary bile acid. In certain embodiments, the secondary bile acid is selected from the group consisting of taurodeoxycholic acid, glycodeoxycholic acid, ursodeoxycholic acid, glycoursodeoxycholic acid, tauroursodeoxycholic acid, taurolithocholic acid, alpha-muricholic acid, deoxycholic acid, gamma-muricholic acid, glycolithocholic acid, taurolithocholic acid, lithocholic acid, omega-muricholic acid and any combination thereof. In certain embodiments, the secondary bile acid is deoxycholic acid and/or lithocholic acid.

In certain embodiments, the subject is a dog. In certain embodiments, the intestinal disorder is an acute enteropathy or a chronic enteropathy. In certain embodiments, the chronic enteropathy is selected from the group consisting of food responsive enteropathy, antibiotic responsive enteropathy, and idiopathic inflammatory bowel disease (IBD). In certain embodiments, the intestinal disorder is idiopathic inflammatory bowel disease (IBD).

In certain embodiments, the bacterium is transformed with a vector comprising a bile acid-inducible operon (bai operon). In certain embodiments, the bacterium is selected from the genus of *Clostridium.*

In certain embodiments, the amount of the bacterium is between about 10 thousand CFU and about 100 trillion CFU. In certain embodiments, the second bile acid is between about 10 mg/unit dose and about 500 mg/unit dose.

In certain embodiments, the first bile acid and the second bile acid are the same. In certain embodiments, the first bile acid and the second bile acid are different.

The presently disclosed subject matter provides *C. hiranonis* for use as a functional food or supplement to prevent onset of a GI condition or as a medicament. In certain embodiments, the *C. hiranonis* is for the treatment of an intestinal disorder in a subject in need thereof. The presently disclosed subject matter provides *C. scindens* functional food or supplement to prevent onset of a GI condition or for use as a medicament. In certain embodiments, the *C. scindens* is for the treatment of an intestinal disorder in a subject in need thereof.

The presently disclosed subject matter provides deoxycholic acid for the treatment of inflammatory bowel disease (IBD) in a subject in need thereof. The presently disclosed subject matter provides lithocholic acid for the treatment of inflammatory bowel disease (IBD) in a subject in need thereof.

The presently disclosed subject matter provides a dietary supplement or a food product comprising an effective amount of a bacterium capable of producing a first bile acid. In certain embodiments, the dietary supplement or a food product further comprises an effective amount of a second bile acid. In certain embodiments, the food product improves intestinal health in a subject. In certain embodiments, the amount of the bacterium is between about 10 thousand CFU and about 100 trillion CFU. In certain embodiments, the second bile acid is between about 100 mg/daily serving dose and about 1000 mg/daily serving dose.

In certain embodiments, the food product is a pet food product. In certain embodiments, the food product is a dog food product.

The presently disclosed subject matter provides a method of treating an intestinal disorder in a subject in need thereof, comprising administering to the subject an effective amount of a pharmaceutical composition, dietary supplement or functional food disclosed herein, an effective amount of a food product disclosed herein, or combination thereof. In certain embodiments, the method further comprises monitoring an intestinal microorganism in the subject. In certain embodiments, the intestinal microorganism is sampled from a fecal sample of the subject.

The presently disclosed subject matter provides a method for determining susceptibility of an intestinal disorder in a companion animal. In certain embodiments, the method comprises:

a) measuring a first amount of a first intestinal microorganism and/or a second amount of a second intestinal microorganism in the companion animal;

b) comparing the first amount of the first intestinal microorganism with a first reference amount of the first intestinal microorganism, and/or comparing the second amount of the second intestinal microorganism with a second reference amount of the second intestinal microorganism, wherein the reference amounts of the intestinal microorganisms are determined based on the amounts of the intestinal microorganisms in a plurality of healthy companion animals; and c) determining that the companion animal is susceptible of an intestinal disorder, when the first amount of the intestinal microorganism is higher than the first reference amount of the first intestinal microorganism, and/or when the second amount of the second intestinal microorganism is lower than the second reference amount of the second intestinal microorganism.

In certain embodiments, the first intestinal microorganism comprises one or more bacterium comprising a 16S rRNA comprising a nucleotide sequence that is at least about 90% homologous or identical to the 16S rRNA nucleotide sequence of HQ802983.1.1440, GQ449092.1.1375, GQ448744.1.1393, KF842598.1.1394, HG798451.1.1400, New.ReferenceOTU52, HK555938.1.1357, FJ957494.1.1454, FN667392.1.1495, New.ReferenceOTU54, HQ760911.1.1437, GQ006324.1.1342, FJ950694.1.1472, FM865905.1.1392, FJ506371.1.1371, FJ957528.1.1445, JF712675.1.1540, New.ReferenceOTU82, AB009242.1.1451, HQ751549.1.1448, AB506370.1.1516, DQ057365.1.1393, FN667422.1.1495, AJ270486.1.1241, FN668375.4306350.4307737, GQ867426.1.1494, GX182404.8.1529, JF224013.1.1362, GQ448246.1.1389, KC245406.1.1465, FN667084.1.1493, EU470512.1.1400, EU768569.1.1352, AY239462.1.1500, KC504009.1.1465, FM179752.1.1686, New.ReferenceOTU114, HK557089.3.1395, JQ208181.1.1352, HQ803964.1.1435, AM276759.1.1484, JN387556.1.1324, GQ448486.1.1387, HK694029.9.1487, HQ754680.1.1441, FN563300.1.1447, FP929060.3837.5503, GQ448506.1.1374, *Enterococcus durans, C. perfringens*, or *E. coli.*

In certain embodiments, the first intestinal microorganism is selected from the group consisting of HQ802983.1.1440, GQ449092.1.1375, GQ448744.1.1393, KF842598.1.1394, HG798451.1.1400, New.ReferenceOTU52, HK555938.1.1357, FJ957494.1.1454, FN667392.1.1495, New.ReferenceOTU54, HQ760911.1.1437, GQ006324.1.1342, FJ950694.1.1472, FM865905.1.1392, FJ506371.1.1371, FJ957528.1.1445, JF712675.1.1540, New.ReferenceOTU82, AB009242.1.1451, HQ751549.1.1448, AB506370.1.1516, DQ057365.1.1393, FN667422.1.1495, AJ270486.1.1241, FN668375.4306350.4307737, GQ867426.1.1494, GX182404.8.1529, JF224013.1.1362, GQ448246.1.1389, JF807116.1.1260, KC245406.1.1465, FN667084.1.1493, EU470512.1.1400, EU768569.1.1352, AY239462.1.1500, KC504009.1.1465, FM179752.1.1686, New.ReferenceOTU114, HK557089.3.1395, JQ208181.1.1352, HQ803964.1.1435, AM276759.1.1484, JN387556.1.1324, GQ448486.1.1387, HK694029.9.1487, HQ754680.1.1441, FN563300.1.1447, FP929060.3837.5503, GQ448506.1.1374, *Enterococcus durans, C. perfringens. E. coli* and any combination thereof. In certain embodiments, the first intestinal microorganism is *C. perfringens. E. coli* and any combination thereof.

In certain embodiments, the second intestinal microorganism comprises one or more bacterium comprising a 16S rRNA comprising a nucleotide sequence that is at least about 90% homologous or identical to the 16S rRNA nucleotide sequence of EU774020.1.1361, HQ793763.1.1451, HQ792787.1.1438, New.ReferenceOTU109, HQ792778.1.1436, or DQ113765.1.1450.

In certain embodiments, the second intestinal microorganism is selected from the group consisting of EU774020.1.1361, HQ793763.1.1451, HQ792787.1.1438, New.ReferenceOTU109, HQ792778.1.1436, DQ113765.1.1450, and any combination thereof.

In certain embodiments, the method further comprises providing a customized recommendation of a treatment regimen, and/or further monitoring the intestinal microorganism, when the first amount of the first intestinal microorganism is lower than the first reference amount of the first intestinal microorganism, and/or when the second amount of the second intestinal microorganism is higher than the second reference amount of the second intestinal microorganism.

The presently disclosed subject matter provides a method for determining responsiveness of a companion animal having an intestinal disorder to a diet. In certain embodiments, the method comprises:

a) measuring a first amount of a first intestinal microorganism and/or a second amount of a second intestinal microorganism in the companion animal;

b) comparing the first amount of the first intestinal microorganism with a first reference amount of the first intestinal microorganism, and/or comparing the second amount of the second intestinal microorganism with a second reference amount of the second intestinal microorganism, wherein the reference amounts of the intestinal microorganisms are determined based on the amounts of the intestinal microorganisms in a plurality of healthy companion animals; and c) determining that the companion animal is responsive to the diet, when the first amount of the intestinal microorganism is higher than the first reference amount of the first intestinal microorganism, and/or when the second amount of the second intestinal microorganism is lower than the second reference amount of the second intestinal microorganism, or determining that the companion animal is non-responsive to the diet, when the first amount of the intestinal microorganism is lower than the first reference amount of the first intestinal microorganism, and/or when the second amount of the second intestinal microorganism is higher than the second reference amount of the second intestinal microorganism.

In certain embodiments, the first intestinal microorganism comprises one or more bacterium comprising a 16S rRNA comprising a nucleotide sequence that is at least about 90% homologous or identical to the 16S rRNA nucleotide sequence of ReferenceOTU45, JRPJ01000002.1034290.1035971, KF842598.1.1394, JF920309.1.1340, FJ978526.1.1378, New.ReferenceOTU54, HQ793763.1.1451, DQ113765.1.1450, DQ797046.1.1403, ACBW01000012.3536.5054, JN387556.1.1324, New.ReferenceOTU52, or JQ208053.1.1336.

In certain embodiments, the first intestinal microorganism is selected from the group consisting of New.ReferenceOTU45, JRPJ01000002.1034290.1035971, KF842598.1.1394, JF920309.1.1340, FJ978526.1.1378, New.ReferenceOTU54, HQ793763.1.1451, DQ113765.1.1450, DQ797046.1.1403, ACBW01000012.3536.5054, JN387556.1.1324, New.ReferenceOTU52, JQ208053.1.1336, and any combination thereof.

In certain embodiments, the second intestinal microorganism comprises one or more bacterium comprising a 16S rRNA comprising a nucleotide sequence that is at least about 90% homologous or identical to the 16S rRNA nucleotide sequence of HK693629.1.1491, GQ493166.1.1359, GQ491426.1.1332, FJ957494.1.1454, GQ449092.1.1375, GQ448486.1.1387, AMCI01001631.34.1456, or HK555938.1.1357.

In certain embodiments, the second intestinal microorganism is selected from the group consisting of HK693629.1.1491, GQ493166.1.1359, GQ491426.1.1332, FJ957494.1.1454, GQ449092.1.1375, GQ448486.1.1387, AMCI01001631.34.1456, HK555938.1.1357, and any combination thereof.

In certain embodiments, the method further comprises administering the diet to the companion animal when companion animal is determined as responsive to the diet. In certain embodiments, the method further comprises administering the diet, a steroid and optionally an antibiotic to the companion animal when companion animal is determined as non-responsive to the diet.

In certain embodiments, the determination in step c) occurs before administering the diet or the diet, the steroid and optionally the antibiotic to the companion animal.

The presently disclosed subject matter provides a method for determining effectiveness of a diet for treating an intestinal disorder in a companion animal. In certain embodiments, the method comprises:

a) measuring a first amount of a first intestinal microorganism and/or a second amount of a second intestinal microorganism in the companion animal after administering a diet to a companion animal for treating an intestinal disorder;

b) comparing the first amount of the first intestinal microorganism with a first reference amount of the first intestinal microorganism, and/or comparing the second amount of the second intestinal microorganism with a second reference amount of the second intestinal microorganism, wherein the reference amounts of the intestinal microorganisms are determined based on the amounts of the intestinal microorganisms in a plurality of healthy companion animals; and c) determining that the diet is effective for treating an intestinal disorder, when the first amount of the intestinal microorganism is higher than the first reference amount of the first intestinal microorganism, and/or when the second amount of the second intestinal microorganism is lower than the second reference amount of the second intestinal microorganism, or determining that the diet is ineffective for treating an intestinal disorder, when the first amount of the intestinal microorganism is lower than the first reference amount of the first intestinal microorganism, and/or when the second amount of the second intestinal microorganism is higher than the second reference amount of the second intestinal microorganism.

In certain embodiments, the first intestinal microorganism comprises one or more bacterium comprising a 16S rRNA comprising a nucleotide sequence that is at least about 90% homologous or identical to the 16S rRNA nucleotide sequence of HK557089.3.1395, or GQ448336.1.1418.

In certain embodiments, the first intestinal microorganism is selected from the group consisting of HK557089.3.1395, GQ448336.1.1418, and combination thereof.

In certain embodiments, the second intestinal microorganism comprises one or more bacterium comprising a 16S rRNA comprising a nucleotide sequence that is at least about 90% homologous or identical to the 16S rRNA nucleotide sequence of KF842598.1.1394, GQ006324.1.1342, HQ802983.1.1440, JN387556.1.1324, FJ950694.1.1472, HG798451.1.1400, New.ReferenceOTU52, or GQ448468.1.1366.

In certain embodiments, the second intestinal microorganism is selected from the group consisting of KF842598.1.1394, GQ006324.1.1342, HQ802983.1.1440, JN387556.1.1324, FJ950694.1.1472, HG798451.1.1400, New.ReferenceOTU52, GQ448468.1.1366, and any combination thereof.

In certain embodiments, the method further comprises administering the diet to the companion animal when companion animal is determined as responsive to the diet. In certain embodiments, the method further comprises administering the diet, a steroid and optionally an antibiotic to the companion animal when companion animal is determined as non-responsive to the diet.

In certain embodiments, the determination in step c) occurs before administering the diet or the diet, the steroid and optionally the antibiotic to the companion animal.

In certain embodiments, the reference amount of an intestinal microorganism derived from a mean amount of the intestinal microorganism in a plurality of healthy companion animals. In certain embodiments, the amount of the intestinal bacterium is measured from a fecal sample of the subject.

The presently disclosed subject matter provides a diet for increase a population of a bacterium capable of producing a bile acid in a companion animal. In certain embodiments, the diet comprises protein, fat, crude fiber, total dietary fiber, carbohydrate, calcium, phosphorus, sodium, chloride, potassium, magnesium, iron, copper, manganese, zinc, iodine, selenium, vitamin A, vitamin D3, vitamin E, vitamin C, thiamine (vitamin B1), riboflavin (vitamin B2), pantothenic acid, niacin, pyridoxine (vitamin B6), folic acid, biotin, cobalannin (vitamin B12), choline, arginine, lysine, methionine, cystine, taurine, linoleic acid, arachidonic acid, Omega-6 fatty acids, Omega-3 fatty acids, EPA, and/or DHA.

In certain embodiments, the subject is a dog. In certain embodiments, the diet is a Royal Canin Veterinary Diet. In certain embodiments, the diet is selected from the group consisting of Ultamino, Hydrolyzed Protein Adult HP Dry, Hydrolyzed Protein Wet, Hydrolyzed Protein Adult PS Dry, Hydrolyzed Protein Moderate Calorie Dry, Hydrolyzed Protein Small Dog Dry, Hydrolyzed protein Treats, and any combination thereof.

In certain embodiments, the bacterium comprises a bile acid-inducible operon (bai operon). In certain embodiments, the bacterium is *C. hiranonis. C. scindens* or combination thereof. In certain embodiments, the bacterium is *C. hiranonis.*

The presently disclosed subject matter provides a Royal Canin Veterinary Diet for the treatment of an intestinal disorder in a dog, wherein the dog comprises a first amount of a first intestinal microorganism and/or a second amount of a second intestinal microorganism, and wherein the first amount of the first intestinal microorganism is higher than a first reference amount of the first intestinal microorganism, and/or the second amount of the second intestinal microorganism is lower than a second reference amount of the second intestinal microorganism.

In certain embodiments, the first intestinal microorganism comprises one or more bacterium comprising a 16S rRNA comprising a nucleotide sequence that is at least about 90% homologous or identical to the 16S rRNA nucleotide sequence of ReferenceOTU45, JRPJ01000002.1034290.1035971, KF842598.1.1394, JF920309.1.1340, FJ978526.1.1378, New.ReferenceOTU54, HQ793763.1.1451, DQ113765.1.1450, DQ797046.1.1403, ACBW01000012.3536.5054, JN387556.1.1324, New.ReferenceOTU52, or JQ208053.1.1336.

In certain embodiments, the first intestinal microorganism is selected from the group consisting of New.ReferenceOTU45, JRPJ01000002.1034290.1035971, KF842598.1.1394, JF920309.1.1340, FJ978526.1.1378, New.ReferenceOTU54, HQ793763.1.1451, DQ113765.1.1450, DQ797046.1.1403, ACBW01000012.3536.5054, JN387556.1.1324, New.ReferenceOTU52, JQ208053.1.1336, and any combination thereof.

In certain embodiments, the second intestinal microorganism comprises one or more bacterium comprising a 16S rRNA comprising a nucleotide sequence that is at least about 90% homologous or identical to the 16S rRNA nucleotide sequence of HK693629.1.1491, GQ493166.1.1359, GQ491426.1.1332, FJ957494.1.1454, GQ449092.1.1375, GQ448486.1.1387, AMCI01001631.34.1456, or HK555938.1.1357.

In certain embodiments, the second intestinal microorganism is selected from the group consisting of HK693629.1.1491, GQ493166.1.1359, GQ491426.1.1332, FJ957494.1.1454, GQ449092.1.1375, GQ448486.1.1387, AMCI01001631.34.1456, HK555938.1.1357, and any combination thereof.

In certain embodiments, the Royal Canin Veterinary Diet is selected from the group consisting of Ultamino, Hydrolyzed Protein Adult HP Dry, Hydrolyzed Protein Wet, Hydrolyzed Protein Adult PS Dry, Hydrolyzed Protein Moderate Calorie Dry, Hydrolyzed Protein Small Dog Dry, Hydrolyzed protein Treats, and any combination thereof.

The presently disclosed subject matter provides a bile acid for the treatment of an intestinal disorder in a dog. In certain embodiments, the bile acid is selected from the group consisting of chenodeoxycholic acid, cholic acid, glycochenodeoxycholic acid, glycocholic acid, taurocholic acid, taurochenodeoxycholic acid, taurodeoxycholic acid, glycodeoxycholic acid, ursodeoxycholic acid, glycoursodeoxycholic acid, tauroursodeoxycholic acid, taurolithocholic acid, alpha-muricholic acid, deoxycholic acid, gamma-muricholic acid, glycolithocholic acid, taurolithocholic acid, lithocholic acid, omega-muricholic acid and any combination thereof. In certain embodiments, the bile acid is a secondary bile acid. In certain embodiments, the secondary bile acid is selected from the group consisting of taurodeoxycholic acid, glycodeoxycholic acid, ursodeoxycholic acid, glycoursodeoxycholic acid, tauroursodeoxycholic acid, taurolithocholic acid, alpha-muricholic acid, deoxycholic acid, gamma-muricholic acid, glycolithocholic acid, taurolithocholic acid, lithocholic acid, omega-muricholic acid and any combination thereof. In certain embodiments, the secondary bile acid is deoxycholic acid and/or lithocholic acid.

The presently disclosed subject matter provides a kit comprising a presently disclosed pharmaceutical composition, dietary supplement, functional food, food product, diet or bile acid. In certain embodiments, the kit further comprises written instructions for treating and/or preventing an intestinal disorder.

BRIEF DESCRIPTION OF THE DRAWINGS

FIG. 1A is a schematic showing clinical study design for identifying diet responsive (DR) and non-diet responsive (NDR) dogs. Antibiotics (Abtx) and Prednisone (Pred) treatments are indicated. Abbreviated Canine Chronic Enteropathy Clinical Activity Index (CCECAI) scores were assessed at four different time points in DR (n=20) (FIG. 1B) and NDR (n=9) (FIG. 1C) animals. ns=not significant,  $p<0.01$, ** $p<0.0001$ using Wilcoxon rank sum test.

FIG. 2A is a ternary plot of phylum level OTUs from top 5 most abundant phyla among healthy (right), DR (left) and NDR (top) animals. Bubble size represents the log 2 OTU abundance. Relative abundance of *E. coli* (FIG. 2B) and *C. perfringens* (FIG. 2D) in animals with active disease (day 0) and healthy dogs. Spearman correlation between log 10 abundance of *E. coli* (FIG. 2C) or *Clostridium* sp. (FIG. 2E) and CCECAI disease score. FIG. 2F depicts differentially abundant OTUs between DR and DNR animals at day 0. Y-axis value represents the log 2 fold change for DR versus NDR Arrow marks the OTU corresponding to *C. perfringens*. * p<0.05, ** p<0.01 using Wilcoxon rank sum test (or Wilcoxon signed-rank test if available). Spearman correlations in panel C and E are significant (p<0.05) with correlation coefficients of 0.2109 and 0.2324, respectively.

FIG. 3A depicts Pielou's evenness index for DR animals at different time points in the study. FIG. 3B depicts the principal coordinate analysis (PCoA) based on unweighted Unifrac distance for DR. FIG. 3C depicts the phylogenetic distance (unweighted Unifrac) to healthy controls for DR animals. FIG. 3D depicts the stream plot showing phylum level dynamics of microbiota structure for DR animals throughout the study. FIG. 3E depicts the volcano plot showing differentially abundant OTUs enriched in either DR dogs with active disease (day 0, red points) or in remission after diet therapy (day 14, blue points). Selected taxa (e.g., *Escherichia-Shigella* spp., *Clostridium* spp.) are labeled. The relative abundance of *E. coli* (FIG. 3F) and *C. perfringens* (FIG. 3G) in DR animals throughout the study and compared to healthy controls. ns=not significant, *p<0.05, p<0.01, *p<0.0001 using Wilcoxon rank sum test (or Wilcoxon signed-rank test if paired data was available).

FIG. 4A depicts Pielou's evenness index in NDR animals, and their phylogenetic distance (unweighted Unifrac) to healthy dogs is shown in FIG. 4B. FIG. 4C depicts the stream plot showing phylum level dynamics of microbiota structure for NDR animals throughout the study. Diet therapy began at day 0, metronidazole administration at day 14, and prednisone at day 28 (see methods). FIG. 4D depicts the bubble plot showing differentially abundant genera (fold change>2 and P<0.05) between day 14 versus day 0 for DR (left) and NDR (right) animals. Bubble size indicates absolute log fold change between day 14 and day 0, and color reflects direction of change. FIGS. 4E and 4F depict the relative abundance of *E. coli* (FIG. 4E) and *C. perfringens* (FIG. 4F) in NDR animals throughout the study and compared to healthy controls. ns=not significant, *p<0.05, p<0.01, *p<0.0001 using Wilcoxon rank sum test (or Wilcoxon signed-rank test if paired data was available).

FIG. 5A depicts a PCA analysis of KEGG pathways based on the results of Tax4Fun analysis. FIG. 5B depicts the first principal component (Dim 1) from panel A, for all time points. FIG. 5C depicts a heatmap showing the shift of metabolic potentials from fat/lipid metabolism to carbohydrate/sugar metabolism as DR animals receive diet therapy. FIG. 5D depicts the relative abundance of the KEGG pathway for secondary bile acid biosynthesis, predicted based on 16S sequence data. FIGS. 5E-5H depict the levels of deoxycholic (FIG. 5E) and lithocholic acid (FIG. 5F) measured in the stool of DR animals and NDR animals (FIGS. 5G and 5H). ns=not significant, *p<0.05, p<0.01, *p<0.0001 using Wilcoxon rank sum test (or Wilcoxon signed-rank test if paired data was available).

FIG. 6A depicts the Spearman correlations between the abundance of bacteria genera and the levels of bile acids. Only genera that have significant (P<0.05) correlations with bile acids are shown. FIGS. 6B-6E depict the in vitro growth of canine clinical isolates of *E. coli* (FIGS. 6B and 6C) or *C. perfringens* (FIGS. 6D and 6E) in the presence of varying concentrations of lithocholic acid or deoxycholic acid (mean±s.d. shown). The in vitro inhibition tests were biologically repeated 2 times. Each point in the graphs represent one replicate well in the assay. FIG. 6F depicts the relative abundance of the OTU corresponding to *C. hiranonis* (FJ957494.1.1454) in 16S rRNA sequencing data for DR and NDR animals. FIG. 6G depicts the coverage of the bile acid operon (bai) from the *C. hiranonis* reference (ASM15605v1) with whole genome sequencing reads produced *C. hiranonis* (teal) and *C. perfringens* (red) canine clinical isolates. FIG. 6H is a schematic showing experimental design for mouse experiments. FIG. 6I depicts the length of colon at day 8. FIG. 6J depicts *E. coli* Nissle strain CFUs measured in colon contents at day 8 (mean±s.d. shown for n=5 mice). Experiments were repeated 3 times with similar results. Data shown are from a representative experiment. ns=not significant, *p<0.05, p<0.01, *p<0.0001 using Wilcoxon signed rank sum test for relative abundance comparisons or t test for the in vitro culture experiments.

FIGS. 7C and 7D depict Spearman correlations between log 10-transformed fecal calprotectin levels (FCP) and relative abundance of *C. scindens* (FIG. 7C) (R=−0.3515 for 'Responsive', P=0.0328; R=−0.0267 for 'Non.Responsive', P=0.8770) or bai operon (FIG. 7D) (R=−0.3944 for 'Responsive', P=0.0157; R=0.0490 for 'Non.Responsive', P=0.7766). FIG. 7E is a schematic showing proposed model for diet-induced remission. ns=not significant, *p<0.05, p<0.01, *p<0.0001 using Wilcoxon rank sum test for relative abundance comparisons.

FIG. 9C depicts the ratios of microbiota compositions at a phylum level. FIG. 9D depicts the Unifrac (unweighted) distances within the microbiomes of the dogs with CE or within those of the healthy dogs. ns=not significant, *p<0.05, p<0.01, *p<0.0001 using Wilcoxon rank sum test.

FIG. 10A depicts Faith's phylogenetic diversity. FIG. 10B depicts Shannon index diversity. FIG. 10C depicts principal coordinate Analysis (PCoA) based on Weighted Unifrac distance of the microbiomes. ns=not significant, *p<0.05, p<0.01, *p<0.0001 using Wilcoxon rank sum test.

DETAILED DESCRIPTION OF THE INVENTION

Figure 1A:
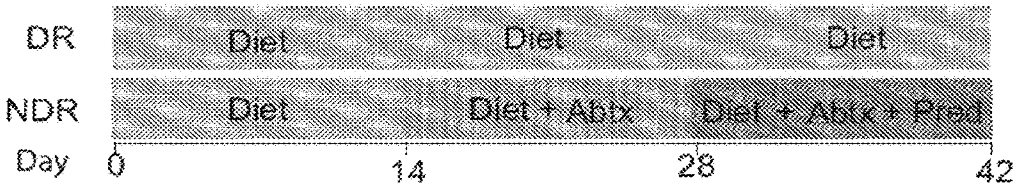
FIGS. 1A-1C depict that diet therapy induces rapid and durable remission in canine model of chronic enteritis.

To date, there remains a need for novel methods and compositions for treating IBD and other intestinal disorders that target gut microbiome and metabolites thereof. The present application relates to method, compositions and food products for improving intestinal health, treating intestinal dysbiosis and/or treating an intestinal disorder in a subject, e.g., a human or a companion animal, which is based, at least in part, on the discovery that intestinal microorganisms that produce bile acids can promote intestinal health and/or is associated with remission from an intestinal disorder after treatment, and that changes of intestinal microorganism population are associated to intestinal health status.

For clarity and not by way of limitation, the detailed description of the presently disclosed subject matter is divided into the following subsections:

1. Definitions;
2. Intestinal bacteria and health assessment tools relating to the same;
3. Pharmaceutical composition;
4. Food products;
5. Treatment methods; and
6 Kits.

1. Definitions

The terms used in this specification generally have their ordinary meanings in the art, within the context of the present disclosure and in the specific context where each term is used. Certain terms are discussed below, or elsewhere in the specification, to provide additional guidance to the practitioner in describing the methods and compositions of the present disclosure and how to make and use them.

As used herein, the use of the word "a" or "an" when used in conjunction with the term "comprising" in the claims and/or the specification can mean "one," but it is also consistent with the meaning of "one or more," "at least one," and "one or more than one." Still further, the terms "having," "including," "containing" and "comprising" are interchangeable and one of skill in the art is cognizant that these terms are open ended terms.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, or up to 10%, or up to 5%, or up to 1% of a given value. Alternatively, particularly with respect to biological systems or processes, the term can mean within an order of magnitude, e.g., within 5-fold or within 2-fold, of a value.

The term "effective treatment" or "effective amount" of a substance means the treatment or the amount of a substance that is sufficient to effect beneficial or desired results, including clinical results, and, as such, an "effective treatment" or an "effective amount" depends upon the context in which it is being applied. In the context of administering a composition to improving immunity, digestive function and/or decreasing inflammation, an effective amount of a composition described herein is an amount sufficient to improving immunity, digestive function and/or decreasing inflammation, as well as decrease the symptoms and/or reduce the likelihood of a digestive disorder and/or inflammation. An effective treatment described herein is a treatment sufficient to improving immunity, digestive function and/or decreasing inflammation, as well as decrease the symptoms and/or reduce the likelihood of a digestive disorder and/or inflammation. The decrease can be a 1%, 5%, 10%, 20%, 30%, 40%, 50%, 60%, 70%, 80%, 90%, 95%, 98% or 99% decrease in severity of symptoms of a digestive disorder or inflammation, or the likelihood of a digestive disorder or inflammation. An effective amount can be administered in one or more administrations. A likelihood of an effective treatment described herein is a probability of a treatment being effective, i.e., sufficient to treat or ameliorate a digestive disorder and/or inflammation, as well as decrease the symptoms.

As used herein, and as well-understood in the art, "treatment" is an approach for obtaining beneficial or desired results, including clinical results. For purposes of this subject matter, beneficial or desired clinical results include, but are not limited to, alleviation or amelioration of one or more symptoms, diminishment of extent of a disorder, stabilized (i.e., not worsening) state of a disorder, prevention of a disorder, delay or slowing of the progression of a disorder, and/or amelioration or palliation of a state of a disorder. The decrease can be a 1%, 5%, 10%, 20%, 30%, 40%, 50%, 60%, 70%, 80%, 90%, 95%, 98% or 99% decrease in severity of complications or symptoms. "Treatment" can also mean prolonging survival as compared to expected survival if not receiving treatment.

As used herein, and as well-understood in the art, a "probiotic" is a preparation or composition comprising microorganisms that can provide health benefits when consumed. The microorganisms include, but are not limited to bacteria, fungi, yeasts and archaea. In certain embodiments, the probiotic can modify the microbiome in the GI system to enhance the balance of the microbiome in GI system, e.g., by acting as an inoculum for an increased population of beneficial microbes, and/or by antagonizing growth of deleterious microbes. In certain embodiments, the probiotic is an animal probiotic, e.g., a feline probiotic or a canine probiotic.

As used herein, and as well-understood in the art, a "prebiotic" is a substance or a composition that can induce the growth or activity of one or more beneficial microorganism (e.g., one or more probiotics, e.g., bacteria, fungi, yeasts and archaea). In certain embodiments, the prebiotic can modify the microbiome in the GI system to enhance the balance of the microbiome in GI system. In certain embodiments, the prebiotic is indigestible to an animal. In certain embodiments, the prebiotic can induce the growth or activity of one or more animal probiotics, e.g., a feline probiotic or a canine probiotic.

The term "pet food" or "pet food composition" or "pet food product" or "final pet food product" means a product or composition that is intended for consumption by a companion animal, such as a cat, a dog, a guinea pig, a rabbit, a bird or a horse. For example, but not by way of limitation, the companion animal can be a "domestic" dog, e.g., *Canis*

*lupus familiaris*. In certain embodiments, the companion animal can be a "domestic" cat such as *Felis domesticus*. A "pet food" or "pet food composition" or "pet food product" or "final pet food product" includes any food, feed, snack, food supplement, liquid, beverage, treat, toy (chewable and/or consumable toys), meal substitute or meal replacement.

An "individual" or "subject" herein is a vertebrate, such as a human or non-human animal, for example, a mammal. Mammals include, but are not limited to, humans, non-human primates, farm animals, sport animals, rodents and pets. Non-limiting examples of non-human animal subjects include rodents such as mice, rats, hamsters, and guinea pigs; rabbits; dogs; cats; sheep; pigs; goats; cattle; horses; and non-human primates such as apes and monkeys.

As used herein, the term "in vitro" refers to an artificial environment and to processes or reactions that occur within an artificial environment. In vitro environments exemplified, but are not limited to, test tubes and cell cultures.

As used herein, the term "in vivo" refers to the natural environment (e.g., an animal or a cell) and to processes or reactions that occur within a natural environment, such as embryonic development, cell differentiation, neural tube formation, etc.

"Pharmaceutical composition" and "pharmaceutical formulation," as used herein, refer to a composition which is in such form as to permit the biological activity of an active ingredient contained therein to be effective, and which contains no additional components which are unacceptably toxic to a patient to which the formulation would be administered.

"Pharmaceutically acceptable," as used herein, e.g., with respect to a "pharmaceutically acceptable excipient," refers to the property of being nontoxic to a subject. A pharmaceutically acceptable ingredient in a pharmaceutical formulation can be an ingredient other than an active ingredient which is nontoxic. A pharmaceutically acceptable excipient can include a buffer, carrier, stabilizer, and/or preservative.

As used herein, the term "pharmaceutically acceptable salt" refers to any salt of a compound provided herein which retains its biological properties and which is not toxic or otherwise undesirable for pharmaceutical use. Such salts can be derived from a variety of organic and inorganic counterions well known in the art. Pharmaceutically acceptable salts further include, by way of example only and without limitation, sodium, potassium, calcium, magnesium, ammonium, tetraalkylammonium and the like, and when the compound contains a basic functionality, salts of non-toxic organic or inorganic acids.

2. Intestinal Microorganisms and Health Assessment Tools Relating to the Same The presently disclosed subject matter provides intestinal microorganisms and combinations thereof, which is based, at least in part, on the discovery that intestinal microorganisms that produce bile acids can promote intestinal health and/or is associated with remission from an intestinal disorder after treatment, and that changes of intestinal microorganism population are associated to intestinal health status.

Intestinal Microorganism Capable of Producing a Bile Acid

In certain embodiments, the intestinal microorganism is for use as a medicament. In certain embodiments, the intestinal microorganism is for the treatment of an intestinal disorder in a subject in need thereof.

In certain embodiments, the intestinal microorganism is a bacterium capable of producing a bile acid. In certain embodiments, the bile acid is chenodeoxycholic acid, cholic acid, glycochenodeoxycholic acid, glycocholic acid, taurocholic acid, taurochenodeoxycholic acid, taurodeoxycholic acid, glycodeoxycholic acid, ursodeoxycholic acid, glycoursodeoxycholic acid, tauroursodeoxycholic acid, taurolithocholic acid, alpha-muricholic acid, deoxycholic acid, gamma-muricholic acid, glycolithocholic acid, taurolithocholic acid, lithocholic acid, omega-muricholic acid or any combination thereof.

In certain embodiments, the bile acid is a primary bile acid. In certain embodiments, the primary bile acid is chenodeoxycholic acid, cholic acid, glycochenodeoxycholic acid, glycocholic acid, taurocholic acid, taurochenodeoxycholic acid or any combination thereof.

In certain embodiments, the bile acid is a secondary bile acid. In certain embodiments, the secondary bile acid is taurodeoxycholic acid, glycodeoxycholic acid, ursodeoxycholic acid, glycoursodeoxycholic acid, tauroursodeoxycholic acid, taurolithocholic acid, alpha-muricholic acid, deoxycholic acid, gamma-muricholic acid, glycolithocholic acid, taurolithocholic acid, lithocholic acid, omega-muricholic acid or any combination thereof. In certain embodiments, the secondary bile acid is deoxycholic acid and/or lithocholic acid.

In certain embodiments, the bacterium comprises a bile acid-inducible operon (bai operon). In certain embodiments, the bacterium comprises an enzyme having 7-dehydroxylation activity. In certain embodiments, the bai operon comprises a nucleotide sequence that is at least about 80% (e.g., at least about 85%, at least about 90%, or at least about 95%) homologous or identical to SEQ ID NO: 1 or 3, or any functional fragment thereof. In certain embodiments, the bai operon comprises the nucleotide sequence set forth in SEQ ID NO: 1 or 3. SEQ ID NO: 1 represents an exemplary sequence of *C. hiranonis* bile acid-inducible operon. SEQ ID NO: 3 represents an exemplary sequence of *C. scindens* bile acid-inducible operon.

```
                                                     [SEQ ID NO: 1]
  1gcaaattgat tttgattggt atttctttca ttcaaaatat ctcctttcct ttatttagct

 61gtattaaaat ttataaaaaa ttttcattgt taataaaaaa atattctttg ttagtattat

121agcataattt ataaaaataa tgataatgtt ttaatattga aataataaat atgtaaaaag

181gttggaaatt tatttaaaaa tgaccagaga taaaaagctc aggtcatttt ttttattatt

241acaagtaatt tgaaaaaaat atatgaaatg aatggagaaa atataactga gatacatttg

301ataatgaaaa aaacatttat cgaaattgta aatagactca ttgttataat taataaatat

361ttattatggc atagttgtta aaattatacc ctaaagaaac gtttcctcaa aaagtgggtt
```

-continued

421ataaaataaa tgttttttga cgaaagatgt gattttattt gtaccccttt tgtataaaga

481ttaaacagta tttttgtata aatatattgt atacagtata gagaatgtcg atgtaaaaaa

541gtatataaaa gtaaataata atcaaaaaaa ctagttttaa ttattaaaaa tgataaaaaa

601tattaataaa ataaagagtc aaaaatactt gttagttaaa tcacagattt tgtctaagta

661tagattaggt tttgtatttg aaaaggtcat ctatagtgtt gtaagaaagc gagttattag

721cacatattgt atctcaaaaa aatgttaaga taatatcaag atagggcgat aaagaaaaaa

781gcaaattgaa aaagaaaaaa gtaactataa gtttttacaa taaatcaaaa gagaattgat

841tttaaaagag ggaggcaaaa taccgatatg aatgatgtga aatgtaaata ttttaataaa

901tttaatacag gaatgtcaga ttttgttact ccaggaaaac agttagaata tgtagcaaaa

961tgcaagccag atgaaaaagc tatcatatat atagataaag aagacaatgt gagagatatc

1021acttggaagg aacttcacat agcttcaaat aaactagctt ggcatttaat gaaaaaggga

1081tttggaaaag gtcaggtagc aatggtatct ttcccaaatg gtatagaaca tatattagca

1141acattagctg tttggaaaac aggaggttgc tacatgccag tttcttgtaa gataacagat

1201acagagcttg gtgatatatg cagaataata aaaccaacag tttcttttac agataaagaa

1261atgccttgta gaacagaaag tataaaaata ggatcagtat tcgatgtttg taaagacgaa

1321tcagaagaaa tgccagaaga tatagctgca aatccaaata tgatttctcc atctggagga

1381acaacaggag agcctaagtt cataaaacag aatgtggcaa gtggcttatc tgatgaaatt

1441ataaaaagct ggtttgaaat gtcaggtatg gaatttgaac aaagacaatt attagtagga

1501ccacttttcc atggtgctcc tcatacagca gcatttaatg gattatttgt aggaaataca

1561ttgataatac ctagaaattt aagacctgaa agtatagtta gatatataaa agaatacaaa

1621atagaattta tacagatgat cccaacatta atgaatagaa taataaaatt agctgatgtt

1681gataaagaag attttaaatc aataaaagca ctacaccata ctggtggata ttgttctcca

1741tatttaaaag aaaagtggat cgatataata ggagctgaaa aagttcacga aatgtactct

1801atgacagagg caatcggtat cacttgtata agaggagatg aatggcttaa acactatgga

1861agcgtaggac ttccactagg aggaagcaga atatcaataa gagatgaaga aggaaatgaa

1921ttaggaccac atgaggttgg agaaattcat atgacttcac caagtgcttg ttgcatgaca

1981gaatacataa accataaacc acttgaaact aaagatggtg gatttagaag tgttggtgat

2041ttcggttatg tagatgaaga tggatacctt tacttctcag atagaagaag cgacatgctt

2101gttataggtg gagaaaacgt atttgcgact gaagttgaac cagtactacc agcttatgaa

2161aaagtagttg atgctgtggt agttggaata cctgatgaag agtggggaag aagattacac

2221gcaatagtac agaagaaaga agaagtttca gcagaagaat taatcgagta cttaggaaaa

2281cacttattac catataaagt tccaaagagc tttacatttg ttccttgcat accaagaggt

2341gacaatggaa aggtaaacag agataagatg ctaaaaggct taatagaaaa aaatctagtt

2401aataaagttt gctaggatat aaattcagtt aactatctgc accaagtgca gtggaaaata

2461aatcaaaatt aataaaataa attaataagg taaatttagg aggtctaaaa tgagttacga

2521cgcacttttt tcaccattta aaatcagagg attagaactt aaaaacagaa tagttctacc

2581aggtatgaat acaaaaatgg caaaaaataa acatgattta agcgatgata tgatagctta

2641ccatgttgca agagcaaaag caggttgtgc attaaatata tttgaatgtg ttgcgctatg

2701tccagcacct catgcatata tgtacatggg attatacaat gacaatcatg tagctcagtt

2761aaaaaaatta acagatgctg ttcacgaagt tggcggtaaa atggctgttc agttatggca

-continued

```
2821tggtggtttc agcccacaga tgttctttga taaaacaaat acattagaaa caccagatac
2881tataacagtt gaacgtattc atgaaatagt taaagagttt ggagaaggtg caagaagagc
2941tgttgaagct ggattcgatg cagttgaatt ccatgcagca cacagttact tacctcacga
3001attcctaagt ccaggaatga acaaaagaac tgacgaatat ggtggaaact tcgaaaatcg
3061ttgcagattc tgcttcgaag tagttgaagc tatacgtgca aatataccag aagatatgcc
3121attcttcatg agagttgact gcatagatga gttaatggat gaagtaatga cagaagaaga
3181aatagtagaa ttcataaata gatgtgctga tctaggagta gacgtagctg acttatcaag
3241aggtaatgct cagtcattcg caacagttta cgaagttcct cctttcaact tacagcacgg
3301tttcaatata gaaaacatat acaacatcaa aaaacagata aaaataccag taatgggtgt
3361tggacgtata aacacaggag aaatggctaa ccaggtaata gcagatggaa aatttgactt
3421agttggtata ggtcgtgctc agttagcaga tcaggattgg gttgctaaag ttagagaagg
3481taaagaagat ttaatacgtc attgtatagg atgtgaccag ggatgctacg atgcagttat
3541aaaccctcag atgactcata taacttgtac aagaaaccct cacttatgct tagaatacaa
3601aggtatgcca aaaactgatg aacctaaaaa agttatgata atcggtggtg gtatggctgg
3661tatattagca gctgaagtac ttaaaaaacg tggacatgaa ccagttatat tcgaagcttc
3721tgatcactta gcaggacagt tcgtattagc aggtaaagct ccaatgaaag aagactgggc
3781agctgcagct aaatgggaag ctgaagaagt agctcgttta ggaatagaag ttagatacaa
3841tacaaaagtt actccagaat taatagaaga attcgctcca gaccacgttg ttatagctat
3901aggatctgat tacgtagctc cagctatacc aggtatagat agtgacaaag tttacactca
3961gtatcaggta ttaaaaggtg aagtagaacc aaaaggacat gtagcagtag ttggttgtgg
4021attagttggt acagaagttg ctcagtactt agcagctaga ggagctcagg taacagctat
4081agaaagaaaa ggtgttggta caggtctaag catgcttaga agaatgttca tgaacccaga
4141attcaaatac tacaaaataa acaaaatgtc tggaactaac atagttggta tagaaccagg
4201aaaacttcac tacataatga ctaacaagaa aactcaggaa gttactgaag gtgtgttaga
4261atgtgatgca gcagtaatct gtacaggtat aactgctaga ccaagtgaag atttacagga
4321aaaatgtaaa gaattaggtg ttccattcaa cgtaataggt gacgcagctg gtgctagaga
4381tgctagaata gctactcagg aaggttacga agtaggtatg agtatataat ttaaaaatta
4441tataattata taaattaaaa gttattaaat tacaagaaag aggcgaataa aatgacttta
4501gaagcaagaa tagaagcatt agaaaaagaa atacagagat taaacgatat agaagctata
4561aaacagttaa aagctaaata tttccgttgc ctagatggaa aattatggga tgaattagaa
4621actactcttt ctcctaacat agaaacttct tactctgatg gaaaattagt attccacagc
4681ccaaaagaag taactgaata tttagcagca gcaatgccta aagaagaaat aagtatgcac
4741atgggacata ctccagaaat aactatagac agcgaaaata ctgctacagg aagatggtac
4801ttagaagata acctaatatt cacagacgga aaatacaaaa acgttggaat aaacggtgga
4861gcattctaca cagataaata tgaaaaaata gacggacagt ggtacataaa agaaactgga
4921tatgttcgta tatttgaaga acatttcatg agagatccaa aatacatat aactagcaac
4981atgcataaag aaaaataata actgattgct aataaacaag atataaacag ggggctggta
5041aacagccagc cctctgaaaa ataaactaaa aaactataat cttttaaaat cttaattaaa
5101gtagaaggag ataagacaat gaacttagta caggacaaaa tagttataat aacaggtgga
5161acaagtggta taggtctttg cgcagcaaaa atattcatgg ataacggtgc aacagtttct
5221atattcggaa aaactcagga agaagtagat gctgctaaag cagaattaaa agaaactcac
```

-continued

5281ccagataaag aagtattagg atttgctcca gatttaacta atagagatga agttatggct
5341gcagttggtg cagtagctga aaaatacgga agattagacg ttatgataaa caatgctggt
5401gttactagct caaacgtatt ctcaagagtt agcccagaag aattcacata tttaatggat
5461ataaacgtta caggtgtatt ccatggtgct tgggctgctt accactgcct gaaaggtgaa
5521aagaagatta taataaatac tgcttcagta acaggaatac acggatcatt atcaggagtt
5581ggatacccaa caagtaaatc agctgttgta ggattcactc aggctcttgg tagagaaata
5641atacgtaaaa acataagagt tgttggtgtt gcaccaggtg ttgttaacac tccaatggtt
5701ggtaatatac cagatgaaat attagatgga tacctaagct cattcccaat gaagagaatg
5761ttagaaccag aagaaatagc taacacttac ttattcttag cttctgactt agctagtggt
5821ataacagcta caactgtaag cgttgacggt gcttatagac catcataaga tttactttaa
5881tttaaaactg taattagata gataatacga cgattaatat aaaaaatgtt ctttaaaaga
5941aaaggagaaa taaaatggct ggattaaaag attttcctaa atttggtgca ctttctggat
6001taaaaatatt agatagtgga tctaacatag ctggacctct aggtggtgga cttttagcag
6061aatgtggtgc tacagttata cacttcgaag gacctaaaaa acctgacaac cagagaggtt
6121ggtatggata ccctcagaac cacagaaacc agttatcaat ggttgctgat ataaaatctg
6181aagaaggtag aaaaatattc ttagacttaa taaaatgggc tgacatatgg gttgaatcat
6241caaaaggtgg acagtacgac agactaagtc tttctgatga agttatatgg tcagtaaacc
6301ctaaaatagc tatagttcac gtttctggat acggacaggt tggagatcca tcatacgtaa
6361caaaagcttc ttatgatgct gttggacagg cattcagtgg atacatgtca ttaaatggtg
6421ttaatgaagc attaaaaata aatccttacc taagtgactt cgtatgtgtt cttactactt
6481gctgggcaat gttagcatgc tacgtaagta ctcagttaac tggaaaagga gaatctgtag
6541acgttgctca gtacgaagca ttagctcgta taatggacgg acgtatgata cagtacgcta
6601ctgatggtgt aagtgttcca aaaactggta acaaagatgc tcaggcagct ctattcagct
6661tctatacttg taaagatgga agaactatat tcataggtat gactggtgct gaagtatgta
6721agagaggatt ccctgtaata gggcttccag ttcctggtac aggtgaccct gacttcccag
6781aaggattcac aggatggatg ataaatactc cagttggaca gagaatggaa aaagctatgg
6841aagcattcgt tgctgaaaga actatgccag aagttgaaaa agctatgata gatgctcaga
6901taccatgcca gagagtttat gatcttgaag actgcttaaa cgaccctcac tggaatgctc
6961gtggaactat aatggaatgg gatgacccaa tgatgggaca cataaaaggt cttggattaa
7021taaacaaatt caaaaacaac ccttctgaaa tatggagagg tgctccatta ttcggtatgg
7081acaacagaga cataattaga gaccttggat attctgagga ggaagttaac gatttatacg
7141ctaaaggtat tgtaaacgaa ttcgaccttg aaacaactat aaaacgttac aaacttgatc
7201aggttatacc tcacatggct aaaaaagata aataagaaac gtattaaata ataaaatata
7261aatgtcgagc ctgccagaat gagaattttg acaggcttga tattataacg aaatgttata
7321aaaaaaacaa aataaaaatt gcttaaattt tatacaagga gaattgaaat gacagcaaca
7381aacgcaaact ataaaaaagg ctttatccca tttgctatag cagcgttact agtaggtctt
7441ataggtggtt tcacagccgt tctagcacct gcattcgtag cagatatggg tcttaacgat
7501aacaatacta catggatagc actagcgctt gcaatgtcta cagctgcatg tgctccaata
7561cttggtaaat taggtgacgt acttggacgt cgtaaaactt tattattagg aatcatagta
7621ttcacaatag gtaacgtatt aacagcaata gcatcttcat taatattcat gctaggtgca -continued

```
7681agatttatag ttggggttgg tacagcggct atagctccag ttataatggc ttacatagtt

7741acagaatatc caccagaaga aactggtaag ggattcgctc tttatatgtt aatatcaagt

7801gctgcagttg ttgttggtcc aacttgtggt ggattaataa tgcaggcatt tggatggaga

7861atgatgatgt gggtttgtgt tgccctttgt gtagtaacat tcttcatatg ttcagtaatg

7921attaagaaaa cagactttga aaagaaaagt cttgataact tcgataaaaa aggtgcagta

7981tgcgtactaa tattcttcag tttagtatta tgtataccat catttggaca gaatataggt

8041tggacatcag cgccattcct aggtgttaca gcagtagctt tagtaacatt attcttatta

8101ataaaagctg aaagcagtgc agaaaaccca atattaagtg gtaaatttat gaaacgtaaa

8161gaattcatat taccagtatt aatattattc cttactcagg gattaatgca ggctaacatg

8221actaacgtaa tattattcgt tagagctact cagccagaaa atacaataat atcaagtttc

8281gcaatatcaa tcctttacat aggtatgtct ttaggttcag tattcatagg acctatggca

8341gataaaaaag aaccaaaaac tgtacttaca ggatcacttc tattcactgg tataggttgt

8401gcaatgatgt acttcttcac agaaactgca ccattcgcaa tgttagctgg atctctagga

8461atgttaggta taggacttgg aggaaatgct acaatactaa tgaaagtttc attatctgga

8521ttatctcagg cagaagctgg atcaggaaca ggaacatacg gattattcag agatatatca

8581gctccatttg gtgttgcggt attcgtacca ctatttgcaa acacagttac aacaagaatg

8641gctggagtaa tggctaacgg aactgcagaa gctgctgcta aatcattagc atctgtttct

8701tctatacata cattagcatt agttgaagta tgctgtgtaa tattagcaat agttgcagtt

8761agaatgctac caaaaataca caataaataa tttaaaaata ataacagagt tgaaaaaaca

8821ctcaattaaa agaggggcct tgagcccctt ttttagtgta aaaatgacaa aatactatca

8881atttatataa atgataatta aactcgtcaa ccaaagaaat attcacaaag tagataataa

8941tagatattca aaaagtgata tattattagg caaaaagtgc aagaaattag cgagtattcg

9001acaacttttt gtccaatggt agaaaagaat atttgttatc ataaatatag acaaagggct

9061ttgaccaaaa ctaaggaaaa agtttgcata atataaaaaa taaaataaaa taaaaaaata

9121aaaataaaat aaaagcgaaa ggaaaaaaca acatcatgga tatgaaaaat tctaaactat

9181tctcaccttt aacaatagga tcattaacat taaacaacag agttggtatg gcaccaatga

9241gtatggacta cgaagctgct gacggaacag ttccaaaaag attagcagat atatttgttc

9301gtagagctga aggtggaaca ggatatgtaa caatagacgc ggtaacaata gatagtaaat

9361ataaatatat gggtaataca actgctttag attctgatga tttagttact cagttcaaag

9421aatttgcaac aagagttaga gaagcaggaa gcacattaat acctcaggtt atacatccag

9481gaccagaatc aatatgtgga tacagacaca tagcaccact tggaccatca gttaatacaa

9541atgctaactg ccacgtgagc cgtgctataa gtgtagatga aatacatgaa ataataaaac

9601agtttggaca ggctgctaga agagttgaag aagcaggatg cggtggtata ggattacact

9661gtgcacatgc ttacatgcta ccaggttcat tcttatctcc attaagaaac aaaagaatgg

9721atgaatacgg cggatgtcta gataacagag caagattcgt aatagaaatg atagaagaag

9781ttcgtagaaa tgtaagtcct gatttcccaa taatgcttag aatatctggg gatgaaagaa

9841tgataggagg aaactcttta gaagatatgt tatacttagc tccaaaattt gttgaagctg

9901gtgtaaatat gtttgaagtt tctggaggta ctcagtacga aggattagaa cacataatac

9961caagtcagaa caaaagcata ggtgtaaacg tacacgaagc atctgaaatc aaaaaagttg

10021tagatgttcc agtttacgct gttggtaaaa taaatgacat aagatacgct gctgaaatag

10081ttgaaagagg actagttgat ggggtatcaa taggtagacc attattagca gatccagact
```

-continued

```
10141tatgtaataa agcaaaagaa aacttatttg atgaaataac tccatgtgca agctgtggag
10201gaagctgtat aagccgtact gcagatagac ctcagtgtcg ttgccatata aacccaagag
10261ttggattcga atatgattat ccagaagttc cagctgaaaa atctaaaaaa gttctagttg
10321taggtgctgg acctggtggt atgatggcag cagttacagc agctgaaaga ggacatgatg
10381taacactttg ggaagctgac actcagatag gtggacagat aaacttagca gtagtagctc
10441caggtaaaca ggaaatgact aaatggttat ctcacttaaa ctacagagct aaaaaagctg
10501gagttaaaat ggtattagga aaagaagcta cagtagaaaa cataaaagaa tttgctccag
10561aagcagttat agttgcaaca ggtgctagac cattagttcc accaataaaa ggaactcagg
10621actacccagt tcttacagct catgacttct taagaggaaa attcgttata ccaaaaggaa
10681aagtttgtgt actaggtgga ggagctgttg cttgtgaaac tgcagaaaca gtattagaaa
10741acgctagacc aaacgcattc actagaggat ttgatgctag tatcggtgat gtagatgtta
10801cattagtaga aatgttacca cagttattaa caggagtatg tgctccaaat agaactccat
10861taataagaaa acttaaaaac aaaggtgttc atataaatgt aaatactaaa atattagaag
10921taactgacca cgacgttaaa gttcagagag ctgacggtgc agaagaatgg ttaaaaggat
10981tcgactacat actattcgga cttggttcta gaaactacga tccaatatct gaacagataa
11041aagaattcgt tccagaagta cacgttgttg gggatgctaa gagagctaga caggcaagct
11101ttgcaatgtg ggaagctttc gaagcagcat acagcttata a
```

[SEQ ID NO: 3]

```
   1aaaagatatt aagcattaag aaaatgcaca aaaaatcagc gtgtgagagg gagggcaagg
  61agttgaagcg tgactttttt aacaagttta atttggggac atcgaacttt gtcacgccgg
 121gaaaacagtt ggaatacgtt tcggaatgca agccagattc tactgcggtc atttgcttag
 181ataaagaaca gaactgttcc gttattactt ggcatcagct gcacgtctat tccagccagc
 241tggcatggta ccttatagaa aatgagattg gcccggggtc gatcgtactt acaatgtttc
 301cgaacagcat cgagcacatt attgcggtat ttgcaatctg gaaggcgggc gcctgctata
 361tgcccatgtc ctataaggcg gcggaatccg agatcaggga ggcctgcgat accatccacc
 421cgaatgcggc ttttgcggaa tgcaagattc caggattaaa attctgcctt agcgcagacg
 481agatatatga ggcgatggaa ggaagatcca aggagatgcc ttcggaccgt ctggccaatc
 541cgaacatgat atccttatca ggcggaacca gcggaaagat gaagttcatc cgtcagaacc
 601ttccatgcgg gctggacgat gagacgatca gaagctggtc tttgatgtct ggaatgggat
 661ttgagcagcg ccagctgctg gtaggcccgc tgtttcatgg cgcgcctcac tccgcggcgt
 721ttaatggact gttcatgggc aacaccctgg tactgaccag gaacctttgc ccgggaaata
 781tcctgaacat gattaagaaa tataagattg aatttataca gatggtgccg accctgatga
 841accggcttgc caaactggag ggagtcggaa aagaagactt tgcatccctg aaggcgctgt
 901gccatacagg gggcgtctgt tctccctggc ttaagcagat ctggatcgac ctgctggggc
 961ctgaaaagat ctatgagatg tattccatga cggaatgcat cggccttacc tgcatccggg
1021gagacgagtg ggtgaagcat ccgggaagca tcggacggcc agtgggcgat agcaaggtgt
1081ctatccggga tgagaatggc aaggaagttg cgccttttga gattggcgag atctatatga
1141cagcgccggc ctcctatctg gttaccgagt acatcaattg ggaaccgctg gaagtgaaag
1201agggaggctt ccgaagcgta ggggatatcg gctacgtgga tgagcagggc tatctgtact
1261tttctgaccg gcgcagcgac atgctggtat caggcggaga aaacgtgttc gccaccgaag
1321tcgagacggc gcttttgaga tataaggata tcctggacgc tgtagtggta gggataccgg
```

-continued

1381atgaagatct ggggcgaagg ctccatgcgg tcattgagac agggaaagag ataccggcag

1441aggaactgaa aacattcctg agaaagtatc tgactccata taagatacca aagacgttcg

1501agttcgtaag gagcatacga aggggagaca atggaaaggc cgacaggaag cggatcctgg

1561aagattgtat tgcccgcggg ggatgattct ataaatgcaa agaaaacaaa ttatataaag

1621gaggagtaac aaaatgagtt acgaagcact tttttcacca ttcaaggtca gaggactgga

1681acttaaaaac cgtatcgtcc tgcctggaat gaacaccaag atggcaaaga acaagcacga

1741cataggcgag gatatgatag cctaccatgt tgccagggca aaagcgggat gcgcgttaaa

1801tatatttgaa tgcgtagcat tatgtccggc gcctcacgct tatatgtata tggggcttta

1861tacggaccat catgtagaac agcttaagaa attgacggat gcagtccatg aagcaggcgg

1921caagatgggc atccagctgt ggcatggagg attcagcccg cagatgttct ttgacgagac

1981caacaccctg gaaactccgg acactcttac ggtagagagg attcatgaga tcgtagaaga

2041attcggacgc ggcgcaagga tggctgttca ggctggattt gacgcagtag aattccatgc

2101ggctcacagt tatctgcctc acgagttctt aagccctgga atgaacaaac gtacggatga

2161gtacggcgga agttttgaga accgctgcag attctgttat gaagtcgttc aggcaatccg

2221ttccaatatc ccggatgaca tgccattctt tatgcgtgca gactgcatcg acgaattaat

2281ggaacagacc atgacagagg aagagatcgt tacatttatc aataagtgcg cagaacttgg

2341cgtggatgtg gcagaccttt cccgtggaaa cgcgacttca ttcgcaaccg tatatgaagt

2401tccgccattc aacctggctc atggcttcaa catagagaat atttacaaca tcaaaaagca

2461gatcaatatc ccggttatgg gagttggccg tatcaataca ggagagatgg caaacaaggt

2521cattgaagaa ggcaagtttg acctggtagg catcggacgc gcccagcttg cagatccaaa

2581ctggatcacc aaagtaagag aaggcaaaga agacctgatc cgccactgta tcggatgtga

2641ccagggatgc tatgacgcag tcatcaatcc aaagatgaag catatcacct gcacccacaa

2701tccaggattg tgcttagagt atcagggaat gccaaagaca gacgctccta agaaagtcat

2761gatcgtagga ggcggaatgg caggcatgat cgctgcggaa gtattaaaga ccagaggcca

2821taacccggta atcttcgagg catccgacaa gcttgcagga cagttcaggc tggcaggcgt

2881agcgccgatg aagcaggatt gggcagatgt tgcagaatgg gaagcaaaag aagtagagcg

2941ccttggaatc gaagtacgtc tgaataccga agtgactgca gagaccatca aggaattcaa

3001tccggataat gtcatcatcg cagtaggctc tacctatgcg ctgcctgaga ttccgggaat

3061cgacagccca agcgtatact cccagtatca ggtactgaaa ggggaagtaa atccgacagg

3121ccgtgtagcc gttatcggat gcggactggt tggtacggaa gtcgcagaac ttctggcatc

3181cagaggcgca caggtaatcg cgatcgagag gaagggcgta ggtaccggcc ttagcatgct

3241tcgcagaatg ttcatgaacc cggaattcaa atattacaag atcgccaaga tgtccggaac

3301aaatgtcacc gctttagagc agggcaaggt tcactacatc atgacagaca agaagaccaa

3361agaagtgacg cagggagtcc tggaatgcga cgctaccgtt atctgtacag gaattaccgc

3421acgtccaagc gatgggctta aggcaagatg cgaagaactt ggaatcccgg ttgaggtgat

3481cggagacgct gctggcgcaa gagactgcac gatcgcgaca cgcgaaggct atgacgcagg

3541aatggcaatc tagaaaatca gaacttatca atcttacata tagaaaggat gatacatatg

3601acattagaag agagagttga agcattagaa aaagaattgc aggagatgaa ggatattgag

3661gcaatcaagg aactgaaagg aaagtatttc cgctgcctgg acggaaagat gtgggatgag

3721ctggagacca ccctgtcacc aaatatcgta acctcttatt ccaacgggaa actggtattc

-continued

3781catagcccga aggaagttac cgattactta aagagctcga tgccaaaaga agagatcagc
3841atgcatatgg gccacacgcc ggagatcacc attgacagcg agactacggc tacgggcaga
3901tggtatctgg aagatagact gatctttacg gacggtaagt acaaagacgt aggaatcaat
3961ggcggcgcgt tctatacaga caaatatgag aagatagacg gccagtggta catccttgaa
4021accggctatg tacgaatcta tgaagaacat ttcatgcgtg atccaaagat ccatatcacg
4081atgaacatgc acaaataaga atattgtaaa agaaaggcag gagtaagagt atgaatctcg
4141tacaagacaa agttacgatc atcacaggcg gcacaagagg tattggattc gccgctgcca
4201aaatatttat cgacaatggc gcaaaagtat ccatcttcgg agagacgcag gaagaagtag
4261atacagcgct tgcacagtta aaagaacttt atccggaaga agaggttctg ggattcgcgc
4321cggatcttac atccagagac gcagttatgg cagcggtagg ccaggtagca cagaaatatg
4381gcagactgga tgtcatgatc aacaatgcag gaattaccag caacaacgta ttctccagag
4441tgtctgaaga agagttcaag catattatgg acatcaacgt aacaggcgta ttcaacggcg
4501catggtgcgc ataccagtgc atgaaggatg ccaaaaaggg cgttatcatc aacacggcat
4561ccgttacagg catcttcgga tcactctcag gcgtaggata tccggccagc aaggcaagcg
4621tgatcggact cacccatgga cttggaagag agatcatccg caagaatatc cgtgtagtag
4681gagtggctcc tggagttgtg aacacggata tgaccaatgg caatcctccg gagatcatgg
4741aaggatatct gaaggcgctt ccgatgaaga gaatgcttga gccggaagag atcgctaatg
4801tatacctgtt cctggcatct gacttggcaa gcggcattac ggctactacg gtcagcgtag
4861acggggctta cagaccataa ttttaatttt tactaagtag aatatgtgat atagaaaagg
4921agatataaaa acatggctgg aataaaagat tttccaaaat tcggagctct tgcagggctt
4981aagatacttg acagcggatc taacatcgcc ggacctttag gcggaggcct tctggcagaa
5041tgcggagcaa cggtcatcca ttttgaagga ccaaagaaac ctgataacca gagaggatgg
5101tacggctatc cacagaatca ccgtaatcag ctgtctatgg tagcagacat caaatctgaa
5161gaaggaagaa agatcttcct tgatctgatc aaatgggcag atatctgggt agagtcatcc
5221aaaggcggac agtatgacag gctgggactt tccgatgaag tcatctggga agtaaatcct
5281aagattgcca tcgtgcacgt atccggatat ggacagacag gagacccgtc ttacgttaca
5341cgtgcatcct atgacgcagt aggccaggca ttcagcggct atatgtcact gaacggaaca
5401acggaagcgc tgaagatcaa tccttatctg agcgatttcg tatgcggact taccacatgc
5461tgggctatgc ttgcctgcta tgtaagcacc attcttaccg gaaaaggcga atctgttgac
5521gttgcacagt acgaagcgct ggcacgtatc atggacggac gtatgatcca gtacgctaca
5581gacggcgtga agatgccaag aaccggcaat aaggatgcgc aggctgccct gttcagcttc
5641tacacctgta aagacggacg tacgatcttt atcggaatga ctggcgcgga agtatgtaag
5701agaggcttcc cgatcatcgg acttccggta cctggaaccg gagacccgga cttcccggaa
5761ggcttcacag gctggatgat ctatactcct gtaggacaga gaatggaaaa ggctatggag
5821aagtatgtat ctgagcatac gatggaagaa gtagaggctg agatgcaggc acaccagatt
5881ccatgccaga gagtatacga gctggaagac tgcctgaacg atcctcactg gaaagcacgt
5941ggaactatta cggagtggga tgacccgatg atgggacata tcacaggcct tggactgatc
6001aacaagttca agagaaatcc ttccgaaatc tggagaggcg ctccgctgtt cggtatggat
6061aaccgcgata tcctgaaaga cctgggatat gacgatgcaa agatcgatga actctatgag
6121cagggcatcg tcaatgaatt cgaccttgac actactatca aacgctatag actggatgaa
6181gtaattccac atatgagaaa gaaagaggag taagagtatg agcaccgtag ccaatccaaa -continued 6241ttataagaaa ggttttgtcc cctttgcaat tgcagcactc ctggtgagcc tgatcggcgg 6301ttttaccgcc gttctcggcc cggccttcgt ggcggaccag gggattgact ataataatac 6361cacatggatt tccctggcgc tggcgatgtc ttccgccgca tgcgctccaa tccttggaaa 6421actgggagac gtgctaggac gcaggacgac gctgcttctg ggtattgtga tctttgcggc 6481cggcaatgtg ctgacagccg tagccacgtc cctgatattc atgctggcag cccgttttat 6541cgtaggtatc ggaacagcag cgatctcacc gatcgttatg gcctatatcg taaccgagta 6601tccgcaggag gagacaggaa aggcctttgg cctgtatatg ctgatctcca gcggcgccgt 6661cgtggtagga cctacctgtg gcggcctgat catgaatgcg gctggctgga gagtcatgat 6721gtgggtatgc gtcgctctgt gcgtcgttgt attcctgatc tgcacattct ccatcaagaa 6781gactgcattt gagaagaaga gcatggcagg atttgacaag ccgggcgcag ccctggtagt 6841cgtattcttc agtttgttcc tgtgcatccc atccttcgga cagaatatcg gatggtcttc 6901cacagcattt atcgcagcag cggcagtagc gctggtagca cttttcatcc tggtaatggt 6961agaaaagaaa gcgaagagtc cgatcatgaa cggcaagttt atggcacgca aggaattcgt 7021gcttccagta ttgatcctgt tccttacaca gggacttatg atggcaaata tgaccaatgt 7081catcgtgttc gtgcgctata cgcagccgga caatgtcatt atatcaagtt ttgcgatctc 7141catcatgtac ataggaatgt ccttaggctc cgttatcatt ggacctgttg cagataagaa 7201agagccaaag acggttctga cattctctct ggtactgaca gccatcggct gtgcgctgat 7261gtatctgttc aaggcagatt cctccgtcgc tatctttgcg gcatccttgg gaatccttgg 7321atttggcctt ggaggaaatg caaccatctt catgaaggta gcgctttccg gcctgtccag 7381cgaagtagct ggctctggta ctggaaccta tggcctgttc agagatatct cggcaccatt 7441cggcgtggca gtgttcgtgc ctatgtttgc caacggcgta acagcgaata ttgcgaaata 7501cgcgtcaggc ggcatggaag aaggcgccgc tacggtaaaa gcagccatct catccatcca 7561gacgctgaca ctggttgaac ttggatgtat cgttgtggga atcatccttg tgagaatgct 7621gccaagaatc tatcagaaga aagaggcata aataagttaa gaaaagaggt aattataaat 7681ggatatgaaa cattccagat tattttcgcc gcttcagatc ggatccctga cactgtctaa 7741ccgtgtcggc atggctccca tgagcatgga ctatgaagca gcagacggaa ctgtgcccaa 7801gaggctggcg gacgtatttg tccgccgcgc cgagggaggc acaggctacg tcatgatcga 7861cgcggtgacg atagacagca agtatcctta tatgggaaat acaacggccc ttgaccgtga 7921tgaactggtt ccccagttta aggaatttgc tgacagagta aaagaagcag gcagcacgct 7981ggtgccgcag atcattcatc cgggtccgga atccgtatgc ggctaccggc atatcgctcc 8041gcttggacct tctgccaaca ccaatgcaaa ctgccacgtg agcagatcga tcagcataga 8101tgagatccat gacatcatta agcagttcgg ccaggcggca cgccgcgccg aagaagcagg 8161atgcggggca atctccctgc actgcgcgca tgcgtatatg ctgccaggat ccttcctgtc 8221accgcttcgc aacaagcgca tggatgaata tggcggaagc cttgacaacc gtgcccgttt 8281cgtgatcgag atgattgagg aggcccgcag gaatgtgagt cctgatttcc cgatcttcct 8341tcgtatctcc ggagacgaga gaatggtagg aggcaacagc cttgaagata tgctctacct 8401ggcaccgaag ttcgaggctg ccggcgtaag catgctggaa gtatccggcg gaacccagta 8461tgaaggcctg gaacatatca ttccttgcca gaataagagc aggggcgtca atgtatatga 8521agcttctgag atcaagaaag tagtgggcat cccggtatac gcagtaggaa agatcaacga 8581tatacgctat gcggcagaga tcgtagaacg cggcctggta gacggcgtgg ctatgggacg -continued

```
8641tccgcttctg gcagatccgg acctttgcaa gaaggcagtg gaaggccagt ttgacgagat

8701cactccatgc gcaagctgcg gcggaagctg catcagccgt tctgaggcag cgcctgagtg

8761ccattgccat attaatccaa ggcttggccg ggagtatgaa ttcccggatg tgcctgccga

8821gaagtccaag aaggtactgg ttatcggcgc aggccctgga ggaatgatgg ctgccgtgac

8881agctgcggaa cgcggccatg atgttacggt atgggaggct gacgacaaga tcggcggcca

8941gctgaacctg gcagtagtgg ctcctggcaa gcaggagatg acccagtgga tggtacatct

9001gaactatcgc gcgaagaaag caggcgtgaa gtttgaattc aataaagaag cgacggcaga

9061agatgtcaag gcgctggcgc cggaagcagt gatcgttgct acaggcgcga agccgctggt

9121tcctccgatt aaaggaacac aggattatcc ggtgcttact gcccatgatt tccttcgcgg

9181caagttcgtg attccgaagg gacgcgtctg cgtgctggga ggaggcgcgg ttgcctgcga

9241gactgccgag acagccctgg agaatgcacg tccgaattct tataccagag gatacgatgc

9301aagcatcgga gatatcgatg tcacgcttgt ggagatgctt ccgcagctcc ttaccggcgt

9361atgcgcgccg aaccgcgagc ctttgatccg caagttaaag agcaagggcg tacacatcaa

9421cgtcaatacc aagatcatgg aagtaacaga ccatgaagta aaggttcaga gacaggatgg

9481aacgcaggaa tggctggaag gatttgacta tgtcctcttt ggccttggtt ccagaaatta

9541cgatccgctt tcagagaccc tcaaggaatt cgttccggaa gtacatgtca tcggcgatgc

9601cgtaagggcg cgccaggcaa gctacgcaat gtgggaagga tttgagaagg catacagcct

9661gtaaaagcgg tttgagtaaa aggaggctta agaaatggca gtgaaggcaa tctcaggctg

9721cgacaaggat caggaactga tca
```

In certain embodiments, the bacterium is transformed with a vector comprising a bile acid-inducible operon (bai operon). In certain embodiments, the bacterium stably expresses an enzyme having 7-dehydroxylation activity. In certain embodiments, the enzyme is a bile-acid 7-dehydroxylase. In certain embodiments, the enzyme is selected from the group consisting of a bile-acid 7-dehydroxylase, bile-acid 7-alpha-dehydroxylase, 7-alpha-dehydratase, bile acid CoA ligase, 3 alpha-HSDH, CoA transferase, 3-dehydro-4-7-alpha-oxidoreductase, 3-dehydro-4-7-beta-oxidoreductase, CA/CDCA transporter, 7-beta-dehydratase and AraC/XyIS. In certain embodiments, the enzyme comprises an amino acid sequence that is at least about 80% (e.g., at least about 85%, at least about 90%, or at least about 95%) homologous or identical to the amino acid of a bile-acid 7-dehydroxylase, bile-acid 7-alpha-dehydroxylase, 7-alpha-dehydratase, bile acid CoA ligase, 3 alpha-HSDH, CoA transferase, 3-dehydro-4-7-alpha-oxidoreductase, 3-dehydro-4-7-beta-oxidoreductase, CA/CDCA transporter, 7-beta-dehydratase__ or AraC/XyIS.

In certain embodiments, the bacterium is selected from the group consisting of Ruminococcus, Alloprevotella, Allisonella, Anaerostipes, Anaerobiospirillum, *Bacteroides*, Blautia, *Clostridium* sensu stricto 1, Collinsella, *Coprococcus* 1, *Corynebacterium* 1, *Campylobacter, Enterococcus*, Erysipelatoclostridium, *Escherichia-Shigella*, Faecalitalea, *Fusobacterium, Clostridium, Helicobacter*, Intestinibacter, Lachnoclostridium, *Lactobacillus*, Megasphaera, Methanobrevibacter, Parabacteroides, *Porphyromonas*, Phascolarctobacterium, Peptoclostridium, Prevotellaceae UCG-001, Pseudocitrobacter, Ruminiclostridium 9, Sarcina, *Streptococcus*, Succinivibrio, *Treponema* 2, Turicibacter, Tyzzerella, Tyzzerella 4 and any combination thereof. In certain embodiments, the bacterium is selected from the genus of *Clostridium.*

In certain embodiments, the intestinal microorganism comprises a 16s rRNA comprising a nucleotide sequence that is at least about 80% (e.g., at least about 85%, at least about 90%, or at least about 95%) homologous or identical to SEQ ID NO: 2. In certain embodiments, the intestinal microorganism comprises a 16s rRNA comprising the nucleotide sequence set forth in SEQ ID NO: 2 or 4. SEQ ID NO: 2 represents an exemplary sequence of 16S rRNA gene in *C. hiranonis*. SEQ ID NO: 4 represents an exemplary sequence of 16S rRNA gene in *C. scindens*.

[SEQ ID NO: 2]

```
  1 acatgcaagt cgagcgattc tcttcggaga agagcggcgg acgggtgagt aacgcgtggg

 61 taacctgccc tgtacacacg gataacatac cgaaaggtat gctaatacgg gataatatat

121 aagagtcgca tgacttttat atcaaagatt tttcggtaca ggatggaccc gcgtctgatt

181 agcttgttgg cggggtaacg gcccaccaag gcgacgatca gtagccgacc tgagagggtg

241 atcggccaca ttggaactga gacacggtcc aaactcctac gggaggcagc agtggggaat

301 attgcacaat gggcgcaagc ctgatgcagc aacgccgcgt gagcgatgaa ggccttcggg
```

-continued

```
 361 tcgtaaagct ctgtcctcaa ggaagataat gacggtactt gaggaggaag ccccggctaa
 421 ctacgtgcca gcagccgcgg taatacgtag ggggctagcg ttatccggat ttactgggcg
 481 taaagggtgc gtaggcggtc tttcaagtca ggagttaaag gctacggctc aaccgtagta
 541 agctcctgat actgtctgac ttgagtgcag gagaggaaag cggaattccc agtgtagcgg
 601 tgaaatgcgt agatattggg aggaacacca gtagcgaagg cggctttctg gactgtaact
 661 gacgctgagg cacgaaagcg tggggagcaa acaggattag ataccctggt agtccacgct
 721 gtaaacgatg agtactagtt gtcggaggtt accccttcgg tgccgcagct aacgcattaa
 781 gtactccgcc tggggagtac gcacgcaagt gtgaaactca aaggaattga cggggacccg
 841 cacaagtagc ggagcatgtg gtttaattcg aagcaacgcg aagaacctta cctaggcttg
 901 acatccttct gaccgaggac taatctcctc tttccctccg gggacagaag tgacaggtgg
 961 tgcatggttg tcgtcagctc gtgtcgtgag atgttgggtt aagtcccgca acgagcgcaa
1021 cccttgtctt tagttgccat cattaagttg ggcactctag agagactgcc agggataacc
1081 tggaggaagg tggggatgac gtcaaatcat catgcccctt atgcctaggg ctacacacgt
1141 gctacaatgg gtggtacaga gggcagccaa gccgtgaggt ggagcaaatc ccttaaagcc
1201 attctcagtt cggattgtag gctgaaactc gcctacatga agctggagtt actagtaatc
1261 gcagatcaga atgctgcggt gaatgcgttc ccgggtcttg tacacaccgc ccgtcacacc
1321 atgggagttg gagacacccg aagccgacta tctaaccttt tgggagaagt cgtcccccctc
1381 gaatcaatac ccc
```

[SEQ ID NO: 4]

```
   1 gagagtttga tcctggctca ggatgaacgc tggcggcgtg cctaacacat gcaagtcgaa
  61 cgaagcgctt ccgctagatt ttcttcggag atgaaggcgg ctgcgactga gtggcggacg
 121 ggtgagtaac gcgtgggcaa cctgccttgc actgggggat aacagccaga aatggctgct
 181 aataccgcat aagaccgaag cgccgcatgg cgcagcggcc aaagccccgg cggtgcaaga
 241 tgggcccgcg tctgattagg tagttggcgg ggtaacggcc caccaagccg acgatcagta
 301 gccgacctga gagggtgacc ggccacattg ggactgagac acggcccaga ctcctacggg
 361 aggcagcagt ggggaatatt gcacaatggg ggaaaccctg atgcagcgac gccgcgtgaa
 421 ggatgaagta tttcggtatg taaacttcta tcagcaggga agaagatgac ggtacctgac
 481 taagaagccc cggctaacta cgtgccagca gccgcggtaa tacgtagggg gcaagcgtta
 541 tccggattta ctgggtgtaa agggagcgta gacggcgatg caagccagat gtgaaagccc
 601 ggggctcaac cccgggactg catttggaac tgcgtggctg gagtgtcgga gaggcaggcg
 661 gaattcctag tgtagcggtg aaatgcgtag atattaggag gaacaccagt ggcgaaggcg
 721 gcctgctgga cgatgactga cgttgaggct cgaaagcgtg gggagcaaac aggattagat
 781 accctggtag tccacgccgt aaacgatgac tactaggtgt cgggtggcaa ggccattcgg
 841 tgccgcagca aacgcaataa gtagtccacc tggggagtac gttcgcaaga atgaaactca
 901 aaggaattga cggggacccg cacaagcggt ggagcatgtg gtttaattcg aagcaacgcg
 961 aagaacctta cctgatcttg acatcccgat gccaaagcgc gtaacgcgct ctttcttcgg
1021 aacatcggtg acaggtggtg catggttgtc gtcagctcgt gtcgtgaggt gttgggttaa
1081 gtcccgcaac gagcgcaacc cctatcttca gtagccagca tttcggatgg gcactctgga
1141 gagactgcca gggacaacct ggaggaaggt ggggatgacg tcaaatcatc atgcccctta
1201 tgaccagggc tacacacgtg ctacaatggc gtaaacaaag ggaggcgaac ccgcgagggt
1261 gggcaaatcc caaaaataac gtctcagttc ggattgtagt ctgcaactcg actacatgaa
```

-continued

```
1321 gctggaatcg ctagtaatcg cgaatcagaa tgtcgcggtg aatacgttcc cgggtcttgt

1381 acacaccgcc cgtcacacca tgggagtcag taacgcccga agccggtgac ccaacccgca

1441 agggagggag ccgtcgaagg tgggaccgat aactggggtg aagtcgtaac aaggtagccg

1501 tatcggaagg tgcggctgga tcacctcctt c
```

In certain embodiments, the intestinal microorganism comprises *C. hiranonis. C. scindens* or combination thereof. In certain embodiments, the intestinal microorganism comprises *C. hiranonis*. In certain embodiments, the intestinal microorganism comprises *C. scindens.*

By "percentage of identity" between two nucleic acid or amino acid sequences in the sense of the present disclosure, it is intended to indicate a percentage of nucleotides or of identical amino acid residues between the two sequences to be compared, obtained after the best alignment (optimum alignment), this percentage being purely statistical and the differences between the two sequences being distributed randomly and over their entire length. The comparisons of sequences between two nucleic acid or amino acid sequences are traditionally carried out by comparing these sequences after having aligned them in an optimum manner, said comparison being able to be carried out by segment or by "comparison window". The optimum alignment of the sequences for the comparison can be carried out, in addition to manually, by means of the local homology algorithm of Smith and Waterman (1981) [Ad. App. Math. 2:482], by means of the local homology algorithm of Neddleman and Wunsch (1970) [J. Mol. Biol. 48: 443], by means of the similarity search method of Pearson and Lipman (1988) [Proc. Natl. Acad. Sci. USA 85:2444), by means of computer software using these algorithms (GAP, BESTFIT, FASTA and TFASTA in the Wisconsin Genetics Software Package, Genetics Computer Group, 575 Science Dr., Madison, WI, or else by BLAST N or BLAST P comparison software).

The percentage of identity between two nucleic acid or amino acid sequences is determined by comparing these two sequences aligned in an optimum manner and in which the nucleic acid or amino acid sequence to be compared can comprise additions or deletions with respect to the reference sequence for an optimum alignment between these two sequences. The percentage of identity is calculated by determining the number of identical positions for which the nucleotide or the amino acid residue is identical between the two sequences, by dividing this number of identical positions by the total number of positions in the comparison window and by multiplying the result obtained by 100 in order to obtain the percentage of identity between these two sequences.

For example, it is possible to use the BLAST program, "BLAST 2 sequences" (Tatusova et al., "Blast 2 sequences—a new tool for comparing protein and nucleotide sequences", FEMS Microbiol Lett. 174:247-250) available on the site www.ncbi.nlm.nih.gov, the parameters used being those given by default (in particular for the parameters "open gap penalty": 5, and "extension gap penalty": 2; the matrix chosen being, for example, the matrix "BLOSUM 62" proposed by the program), the percentage of identity between the two sequences to be compared being calculated directly by the program. It is also possible to use other programs such as "ALIGN" or "Megalign" (DNASTAR) software.

By amino acid sequence having at least about 80%, e.g., at least about 85%, at least about 90%, at least about 95% and at least about 98% identity with a reference amino acid sequence, those having, with respect to the reference sequence, certain modifications, in particular a deletion, addition or substitution of at least one amino acid, a truncation or an elongation are preferred. In the case of a substitution of one or more consecutive or nonconsecutive amino acid(s), the substitutions are preferred in which the substituted amino acids are replaced by "equivalent" amino acids. The expression "equivalent amino acids" is aimed here at indicating any amino acid capable of being substituted with one of the amino acids of the base structure without, however, essentially modifying the biological activities of the corresponding antibodies and such as will be defined later, especially in the examples. These equivalent amino acids can be determined either by relying on their structural homology with the amino acids which they replace, or on results of comparative trials of biological activity between the different antibodies capable of being carried out.

By way of non-limiting example, Table 1 represents the possibilities of substitution capable of being carried out without resulting in a profound modification of the biological activity of the corresponding modified antibody, the reverse substitutions being naturally envisageable under the same conditions.

TABLE 1

| Original residue | Substitution(s) |
|---|---|
| Ala (A) | Val, Gly, Pro |
| Arg (R) | Lys, His |
| Asn (N) | Gln |
| Asp (D) | Glu |
| Cys (C) | Ser |
| Gln (Q) | Asn |
| Glu (G) | Asp |
| Gly (G) | Ala |
| His (H) | Arg |
| Ile (I) | Leu |
| Leu (L) | Ile, Val, Met |
| Lys (K) | Arg |
| Met (M) | Leu |
| Phe (F) | Tyr |
| Pro (P) | Ala |
| Ser (S) | Thr, Cys |
| Thr (T) | Ser |
| Trp (W) | Tyr |
| Tyr (Y) | Phe, Trp |
| Val (V) | Leu, Ala |

Intestinal Microorganism Indicating Intestinal Health

In certain embodiments, the intestinal microorganism can be used to indicate intestinal health in a subject. In certain embodiments, the intestinal microorganism is associated with an intestinal disorder. In certain embodiments, the intestinal microorganism is associated with a heathy intestinal status. In certain embodiments, the intestinal microorganism more abundant in a healthy subject compared to a subject having an intestinal disorder. In certain embodiments, the intestinal microorganism less abundant in a healthy subject compared to a subject having an intestinal disorder.

In certain embodiments, the intestinal microorganism comprises one or more bacteria and/or archaea of one or more phylum selected from the group consisting of Actinobacteria, Bacteroidetes, Euryarchaeota, Firmicutes, Fusobacteria, Proteobacteria and Spirochaetae.

In certain embodiments, the intestinal microorganism comprises one or more bacteria and/or archaea of one or more class selected from the group consisting of Actinobacteria. Bacilli. Bacteroidia, Clostridia, Coriobacteria, Erysipelotrichia, Fusobacteria, Gammaproteobacteria, Methanobacteria, and Spirochaetes.

In certain embodiments, the intestinal microorganism comprises one or more bacteria and/or archaea of one or more order selected from the group consisting of Bacteriodales, Clostridiales, Coriobacteriales, Corynebacteriales, Enterobacteriales, Erysipelotrichales, Fusobacteriales, Lactobacillaes, Methanobacteriales and Spirochaetales.

In certain embodiments, the intestinal microorganism comprises one or more bacteria and/or archaea of one or more family selected from the group consisting of Bacteroidaceae, Clostridiaceae 1, Coriobacteriaceae, Corynebacteriaceae, Enterobacteriaceae, Erysipelotrichaceae, Fusobacteriaceae, Lachnospiraceae, Methanobacteriaceae, Peptostreptococcaceae, Porphyromonadaceae, Prevotellaceae, Ruminococcaceae, Spirochaetaceae, and Streptococcaceae.

In certain embodiments, the intestinal microorganism comprises one or more bacteria and/or archaea of one or more genus selected from the group consisting of Ruminococcus, Alloprevotella, Allisonella, Anaerostipes, Anaerobiospirillum, *Bacteroides, Blautia, Clostridium* sensu stricto 1, Collinsella, *Coprococcus* 1, *Corynebacterium* 1, *Campylobacter, Enterococcus*, Erysipelatoclostridium, *Escherichia-Shigella*, Faecalitalea, *Fusobacterium, Helicobacter*, Intestinibacter, Lachnoclostridium, *Lactobacillus*, Megasphaera, Methanobrevibacter, Parabacteroides, *Porphyromonas*, Phascolarctobacterium, Peptoclostridium, Prevotellaceae UCG-001, Pseudocitrobacter, Ruminiclostridium 9, Sarcina, *Streptococcus*, Succinivibrio, *Treponema* 2, Turicibacter, Tyzzerella, and Tyzzerella 4.

In certain embodiments, the intestinal microorganism comprises one or more bacteria and/or archaea of one or more species selected from the group consisting of *Enterococcus durans. E. coli* and *C. perfringens*. In certain embodiments, the intestinal microorganism comprises *E. coli* and *C. perfringens.*

In certain embodiments, the intestinal microorganism is selected from the group consisting of *C, hiranonis, C, scindens*, Veillonellaceae, Streptococcaceae, *Bacteroides, Fusobacterium*, Collinsella, Sarcina, *Clostridium* sensu stricto 1, Faecalitalea, *Streptococcus*, Erysipelatoclostridium, Megasphaera, Blautia, Alloprevotella, Peptoclostridium, and any combination thereof. In certain embodiments, the intestinal microorganism is *C. hiranonis. C. scindens* or combination thereof.

In certain embodiments, the intestinal microorganism comprises one or more bacterium comprising a 16S rRNA comprising a nucleotide sequence that is at least about 80% (e.g., at least about 85%, at least about 90%, or at least about 95%, at least about 96%, at least about 97%, at least about 98%, at least about 99%, at least about 99.5%, or at least about 99.9%) homologous or identical to any sequence in Table 11.

In certain embodiments, the intestinal microorganism comprises one or more bacterium comprising a 16S rRNA comprising a nucleotide sequence that is at least about 80% (e.g., at least about 85%, at least about 90%, or at least about 95%, at least about 96%, at least about 97%, at least about 98%, at least about 99%, at least about 99.5%, or at least about 99.9%) homologous or identical to the 16S rRNA nucleotide sequence of HQ802983.1.1440, FJ950694.1.1472, HG798451.1.1400, New.ReferenceOTU52, New.ReferenceOTU82, GQ449092.1.1375, FJ506371.1.1371, GQ448744.1.1393, FJ957494.1.1454, HQ760911.1.1437, GQ006324.1.1342, GQ448246.1.1389, KC245406.1.1465, New.ReferenceOTU54, HQ751549.1.1448, JF712675.1.1540, JQ208181.1.1352, GX182404.8.1529, FP929060.3837.5503, FN667392.1.1495, FN667422.1.1495, HK557089.3.1395, HQ803964.1.1435, AM276759.1.1484, HK555938.1.1357, KF842598.1.1394, HQ792778.1.1436, FM865905.1.1392, FN563300.1.1447, HQ754680.1.1441, GQ867426.1.1494, EU470512.1.1400, AY239462.1.1500, New.ReferenceOTU114, FN668375.4306350.4307737, AB009242.1.1451, HQ792787.1.1438, AB506370.1.1516, DQ057365.1.1393, FN667084.1.1493, DQ113765.1.1450, HK694029.9.1487, AJ270486.1.1241, EU768569.1.1352, FM179752.1.1686, FJ957528.1.1445, KC504009.1.1465, GQ448506.1.1374, JF224013.1.1362, EU774020.1.1361, GQ448486.1.1387, HQ793763.1.1451, JN387556.1.1324, or New.ReferenceOTU109 in Table 11.

In certain embodiments, the intestinal microorganism comprises one or more bacteria and/or archaea of one or more Operational Taxonomic Units (OTUs) selected from the group consisting of HQ802983.1.1440, FJ950694.1.1472, HG798451.1.1400, New.ReferenceOTU52, New.ReferenceOTU82, GQ449092.1.1375, FJ506371.1.1371, GQ448744.1.1393, FJ957494.1.1454, HQ760911.1.1437, GQ006324.1.1342, GQ448246.1.1389, KC245406.1.1465, New.ReferenceOTU54, HQ751549.1.1448, JF712675.1.1540, JQ208181.1.1352, GX182404.8.1529, FP929060.3837.5503, FN667392.1.1495, FN667422.1.1495, HK557089.3.1395, HQ803964.1.1435, AM276759.1.1484, HK555938.1.1357, KF842598.1.1394, HQ792778.1.1436, FM865905.1.1392, FN563300.1.1447, HQ754680.1.1441, GQ867426.1.1494, EU470512.1.1400, AY239462.1.1500, New.ReferenceOTU114, FN668375.4306350.4307737, AB009242.1.1451, HQ792787.1.1438, AB506370.1.1516, DQ057365.1.1393, FN667084.1.1493, DQ113765.1.1450, HK694029.9.1487, AJ270486.1.1241, EU768569.1.1352, FM179752.1.1686, JF807116.1.1260, FJ957528.1.1445, KC504009.1.1465, GQ448506.1.1374, JF224013.1.1362, EU774020.1.1361, GQ448486.1.1387, HQ793763.1.1451, JN387556.1.1324, and New.ReferenceOTU109.

In certain embodiments, the intestinal microorganism comprises one or more bacterium comprising a 16S rRNA comprising a nucleotide sequence that is at least about 80% (e.g., at least about 85%, at least about 90%, or at least about 95%, at least about 96%, at least about 97%, at least about 98%, at least about 99%, at least about 99.5%, or at least about 99.9%) homologous or identical to the 16S rRNA nucleotide sequence of JRPJ01000002.1034290.1035971, JF920309.1.1340, FJ978526.1.1378, New.ReferenceOTU45, HK555938.1.1357, FJ957494.1.1454, New.ReferenceOTU52, DQ797046.1.1403, GQ449092.1.1375, AMCI01001631.34.1456, KF842598.1.1394, HQ793763.1.1451, DQ113765.1.1450, ACBW01000012.3536.5054, HK693629.1.1491, JQ208053.1.1336, GQ493166.1.1359, GQ448486.1.1387, GQ491426.1.1332, New.ReferenceOTU54, or JN387556.1.1324 in Table 11.

In certain embodiments, the intestinal microorganism comprises one or more bacteria and/or archaea of one or more Operational Taxonomic Units (OTUs) selected from the group consisting of JRPJ01000002.1034290.1035971, JF920309.1.1340, FJ978526.1.1378, New.ReferenceOTU45, HK555938.1.1357, FJ957494.1.1454, New.ReferenceOTU52, DQ797046.1.1403, GQ449092.1.1375, AMCI01001631.34.1456, KF842598.1.1394, HQ793763.1.1451, DQ113765.1.1450, ACBW01000012.3536.5054, HK693629.1.1491, JQ208053.1.1336, GQ493166.1.1359, GQ448486.1.1387, GQ491426.1.1332, New.ReferenceOTU54, and JN387556.1.1324.

In certain embodiments, the intestinal microorganism comprises one or more bacterium comprising a 16S rRNA comprising a nucleotide sequence that is at least about 80% (e.g., at least about 85%, at least about 90%, or at least about 95%, at least about 96%, at least about 97%, at least about 98%, at least about 99%, at least about 99.5%, or at least about 99.9%) homologous or identical to the 16S rRNA nucleotide sequence of GQ006324.1.1342, New.ReferenceOTU52, HG798451.1.1400, HK557089.3.1395, GQ448336.1.1418, KF842598.1.1394, FJ950694.1.1472, HQ802983.1.1440, GQ448468.1.1366, or JN387556.1.1324 in Table 11.

In certain embodiments, the intestinal microorganism comprises one or more bacteria and/or archaea of one or more Operational Taxonomic Units (OTUs) selected from the group consisting of GQ006324.1.1342, New.ReferenceOTU52, HG798451.1.1400, HK557089.3.1395, GQ448336.1.1418, KF842598.1.1394, FJ950694.1.1472, HQ802983.1.1440, GQ448468.1.1366, and JN387556.1.1324.

In certain embodiments, the intestinal microorganism comprises one or more bacterium comprising a 16S rRNA comprising a nucleotide sequence that is at least about 80% (e.g., at least about 85%, at least about 90%, or at least about 95%, at least about 96%, at least about 97%, at least about 98%, at least about 99%, at least about 99.5%, or at least about 99.9%) homologous or identical to the 16S rRNA nucleotide sequence of JRPJ01000002.1034290.1035971, New.ReferenceOTU45, GQ006324.1.1342, HK555938.1.1357, FJ957551.1.1489, FJ957494.1.1454, New.ReferenceOTU52, FM865905.1.1392, GQ016239.1.1362, HG798451.1.1400, EU461791.1.1414, GU303759.1.1517, New.ReferenceOTU114, AB506154.1.1541, EU774370.1.1398, HK557089.3.1395, HQ807346.1.1456, HQ748204.1.1442, GU179917.1.1382, GQ448336.1.1418, DQ804865.1.1390, GQ491757.1.1361, New.ReferenceOTU56, KF842598.1.1394, HQ802052.1.1445, GX182404.8.1529, FJ950694.1.1472, GQ448506.1.1374, HQ802983.1.1440, DQ793824.1.1370, GQ448468.1.1366, EU774020.1.1361, GQ491183.1.1360, GQ491426.1.1332, GQ493039.1.1311, JN387556.1.1324, and EU775983.1.1288 in Table 11.

In certain embodiments, the intestinal microorganism comprises one or more bacteria and/or archaea of one or more Operational Taxonomic Units (OTUs) selected from the group consisting of JRPJ01000002.1034290.1035971, New.ReferenceOTU45, GQ006324.1.1342, HK555938.1.1357, FJ957551.1.1489, FJ957494.1.1454, New.ReferenceOTU52, FM865905.1.1392, GQ016239.1.1362, HG798451.1.1400, EU461791.1.1414, GU303759.1.1517, New.ReferenceOTU114, AB506154.1.1541, EU774370.1.1398, HK557089.3.1395, HQ807346.1.1456, HQ748204.1.1442, GU179917.1.1382, GQ448336.1.1418, DQ804865.1.1390, GQ491757.1.1361, New.ReferenceOTU56, KF842598.1.1394, HQ802052.1.1445, GX182404.8.1529, FJ950694.1.1472, GQ448506.1.1374, HQ802983.1.1440, DQ793824.1.1370, GQ448468.1.1366, EU774020.1.1361, GQ491183.1.1360, GQ491426.1.1332, GQ493039.1.1311, JN387556.1.1324, and EU775983.1.1288.

In certain embodiments, the intestinal microorganism comprises one or more bacterium comprising a 16S rRNA comprising a nucleotide sequence that is at least about 80% (e.g., at least about 85%, at least about 90%, or at least about 95%, at least about 96%, at least about 97%, at least about 98%, at least about 99%, at least about 99.5%, or at least about 99.9%) homologous or identical to the 16S rRNA nucleotide sequence of GQ449137.1.1391, HK555938.1.1357, GQ358246.1.1466, New.ReferenceOTU82, New.ReferenceOTU52, GQ138615.1.1402, JN681884.1.1409, GU303759.1.1517, New.ReferenceOTU114, EU774881.1.1422, AB469559.1.1551, HK557089.3.1395, EU358719.1.1513, HQ748204.1.1442, GQ338727.1.1397, HQ803964.1.1435, FJ951866.1.1493, EU772870.1.1289, GQ448468.1.1366, EU774020.1.1361, HQ782658.1.1415, DQ794633.1.1395, FN668375.4306350.4307737, or GQ867445.1.1457 in Table 11.

In certain embodiments, the intestinal microorganism comprises one or more bacteria and/or archaea of one or more Operational Taxonomic Units (OTUs) selected from the group consisting of GQ449137.1.1391, HK555938.1.1357, GQ358246.1.1466, New.ReferenceOTU82, New.ReferenceOTU52, GQ138615.1.1402, JN681884.1.1409, GU303759.1.1517, New.ReferenceOTU114, EU774881.1.1422, AB469559.1.1551, HK557089.3.1395, EU358719.1.1513, HQ748204.1.1442, GQ338727.1.1397, HQ803964.1.1435, FJ951866.1.1493, EU772870.1.1289, GQ448468.1.1366, EU774020.1.1361, HQ782658.1.1415, DQ794633.1.1395, FN668375.4306350.4307737, and GQ867445.1.1457.

Health Assessment Tools

The presently disclosed subject matter further provides a health assessment tool relating to the microorganisms disclosed herein. In certain embodiments, the health assessment tool is for monitoring intestinal health status or dysbiosis. In certain embodiments, the health assessment tool comprises one or more probe for detecting an amount of one or more microorganisms disclosed herein. In certain embodiments, the health assessment tool comprises a microarray of one or more probe for detecting an amount of one or more microorganism disclosed herein. In certain embodiments, the probe comprises a nucleic acid probe for detecting a signature gene of a microorganism disclosed herein. In certain embodiments, the probe detects a 16S rRNA sequence of a microorganism disclosed herein. In certain embodiments, the probe comprises an antibody. In certain embodiments, the antibody binds to a surface protein/antigen of a microorganism disclosed herein.

In certain embodiments, the amount of the microorganism is measured from a fecal sample of the subject. In certain embodiments, the health assessment tool monitoring intestinal health status or dysbiosis by comparing the amount of the one or more microorganism with a reference amount of the one or more microorganism.

In certain embodiments, the health assessment tool comprises probes for detecting at least about 1, at least about 2, at least about 3, at least about 4, at least about 5, at least about 6, at least about 7, at least about 8, at least about 9, at least about 10, at least about 12, at least about 14, at least about 26 or more microorganisms disclosed herein. In certain embodiments, the health assessment tool comprises probes for detecting about 1, about 2, about 3, about 4, about 5, about 6, about 7, about 8, about 9, about 10, about 12, about 14, or about 26 microorganisms disclosed herein. In certain embodiments, the health assessment tool comprises probes for detecting between about 1 to about 500, between about 1 to about 100, between about 1 to about 26, between about 5 to about 100, between about 5 to about 26, between about 10 to about 26, between about 15 to about 50, or between about 50 to about 100 microorganisms disclosed herein.

In certain embodiments, the one or more microorganism comprises a bacterium comprising a 16S rRNA comprising a nucleotide sequence that is at least about 80% (e.g., at least about 85%, at least about 90%, or at least about 95%, at least about 96%, at least about 97%, at least about 98%, at least about 99%, at least about 99.5%, or at least about 99.9%) homologous or identical to any sequence in Table 11.

3. Pharmaceutical Composition

The presently disclosed subject matter provides a pharmaceutical composition for use as a medicament. In certain embodiments, the pharmaceutical composition comprises an effective amount of a bacterium capable of producing a first bile acid. In certain embodiments, the pharmaceutical composition further comprises an effective amount of a second bile acid. In certain embodiments, the bacterium is any bacterium disclosed in the above section. In certain embodiments, the first bile acid and/or the second bile acid is any bile acid disclosed in the above section or a pharmaceutically acceptable salt thereof. In certain embodiments, the first bile acid and the second bile acid are the same. In certain embodiments, the first bile acid and the second bile acid are different.

In certain embodiments, the bacterium comprised in the pharmaceutical composition is between about 1 thousand CFU and about 100 trillion CFU. In certain embodiments, the bacterium is between about 1 thousand CFU and about 1 trillion CFU, between about 1 million CFU and about 1 trillion CFU, between about 100 million CFU and about 100 billion CFU, between about 1 billion CFU and about 1 trillion CFU, between about 1 billion CFU and about 100 billion CFU, between about 100 million CFU and about 100 billion CFU, between about 1 billion CFU and about 50 billion CFU, between about 100 million CFU and about 50 billion CFU, or between about 1 billion CFU and about 10 billion CFU. In certain embodiments, the bacterium comprised in the pharmaceutical composition is at least about 1 thousand CFU, at least about 1 million CFU, at least about 10 million CFU, at least about 100 million CFU, at least about 1 billion CFU, at least about 10 billion CFU, at least about 100 billion CFU or more.

In certain embodiments, the second bile acid comprised in the pharmaceutical composition is between about 1 μg/unit dose and about 1 g/unit dose. In certain embodiments, the second bile acid comprised in the pharmaceutical composition is between about 10 μg/unit dose and about 1 g/unit dose, between about 10 μg/unit dose and about 500 mg/unit dose, between about 100 μg/unit dose and about 500 mg/unit dose, between about 1 mg/unit dose and about 500 mg/unit dose, between about 10 mg/unit dose and about 500 mg/unit dose, between about 100 mg/unit dose and about 500 mg/unit dose, between about 10 mg/unit dose and about 100 mg/unit dose, between about 50 mg/unit dose and about 300 mg/unit dose. In certain embodiments, the second bile acid comprised in the pharmaceutical composition is at least about 1 μg/unit dose, at least about 10 pg/unit dose, at least about 100 μg/unit dose, at least about 1 mg/unit dose, at least about 10 mg/unit dose, at least about 100 mg/unit dose, at least about 1 g/unit dose or more The presently disclosed subject matter provides a bile acid for the treatment of an intestinal disorder in a dog. In certain embodiments, the bile acid is selected from the group consisting of chenodeoxycholic acid, cholic acid, glycochenodeoxycholic acid, glycocholic acid, taurocholic acid, taurochenodeoxycholic acid, taurodeoxycholic acid, glycodeoxycholic acid, ursodeoxycholic acid, glycoursodeoxycholic acid, tauroursodeoxycholic acid, taurolithocholic acid, alpha-muricholic acid, deoxycholic acid, gamma-muricholic acid, glycolithocholic acid, taurolithocholic acid, lithocholic acid, omega-muricholic acid and any combination thereof. In certain embodiments, the bile acid is a secondary bile acid. In certain embodiments, the secondary bile acid is selected from the group consisting of taurodeoxycholic acid, glycodeoxycholic acid, ursodeoxycholic acid, glycoursodeoxycholic acid, tauroursodeoxycholic acid, taurolithocholic acid, alpha-muricholic acid, deoxycholic acid, gamma-muricholic acid, glycolithocholic acid, taurolithocholic acid, lithocholic acid, omega-muricholic acid and any combination thereof. In certain embodiments, the secondary bile acid is deoxycholic acid and/or lithocholic acid.

In certain embodiments, the pharmaceutical composition is for the treatment of an intestinal disorder in a subject in need thereof. In certain embodiments, the intestinal disorder is selected from the ground consisting of irritable bowel syndrome, constipation, gastritis, colitis, inflammatory bowel disease (IBD), gastrointestinal ulcers, haemorrhagic gastroenteritis, diarrhea, Crohn's disease, ulcerative colitis, enteritis, antibiotic associated diarrhea, acute or chronic enteropathy, necrotizing enterocoloitis, and any combination thereof.

In certain embodiments, the subject is a dog. In certain embodiments, the intestinal disorder is an acute enteropathy or a chronic enteropathy. In certain embodiments, the intestinal disorder is a chronic enteropathy selected from the group consisting of food responsive enteropathy, antibiotic responsive enterophaty, and idiophathic inflammatory bowel disease (IBD).

In certain non-limiting embodiments, the subject is a mammal. In certain embodiments, the subject is a human. In certain embodiments, the subject is a companion animal is a feline (e.g., a domestic cat) or a canine (e.g., a domestic dog).

The exact dose and frequency of administration depends on the particular condition being treated, the age, weight and general physical condition of the particular patient as well as other medication the individual can be taking, as is well known to those skilled in the art. Generally, the daily dose of a pharmaceutical composition disclosed herein can be in the range of between about 0.01 mg to about 1000 mg/day. In certain embodiments, the pharmaceutical composition can be about 0.05 mg to about 1000 mg/day, about 0.1 mg to about 1000 mg/day, about 1 mg to about 500 mg/day, about 0.01 mg to about 500 mg/day, about 0.05 mg to about 200 mg/day, about 1 mg to about 500 mg/day, about 1 mg to about 200 mg/day, about 5 mg to about 500 mg/day, about 50 mg to about 200 mg/day, about 100 mg to about 200 mg/day, about 100 mg to about 1000 mg/day, about 20 mg to about 50 mg/day, or about 20 mg to about 100 mg/day.

In certain embodiments, the pharmaceutical composition disclosed herein can be administered from about 10 times per day to about once per day, from about 5 times per day to about once per day, or from about thrice per day to about once per day. In certain embodiments, the pharmaceutical composition disclosed herein can be administered once per day. In certain embodiments, the pharmaceutical composition disclosed herein can be administered once per two days, once per three days, once per four days, once per five days, once per six days, once a week, once per two weeks, once per three weeks, or once per month.

The pharmaceutical composition disclosed herein can be administered in a variety of forms. In certain embodiments, the pharmaceutical composition disclosed herein can be administered orally, parenterally, rectally. In certain embodiments, orally administered pharmaceutical composition in solid dosage forms can be administered as capsules, dragees, granules, pills, powders, and tablets. In certain embodiments, the pharmaceutical composition can be administered in liquid form as elixirs, emulsions, microemulsions, solutions, suspensions, and syrups. In certain embodiments, parenterally administered pharmaceutical composition can be administered as aqueous or oleaginous solutions or aqueous or oleaginous suspensions, which suspensions comprise crystalline, amorphous, or otherwise insoluble forms of the pharmaceutical composition. In certain embodiments, rectally administered pharmaceutical composition can be administered as creams, gels, lotions, ointments, and pastes.

Depending upon the form of administration, the pharmaceutical composition disclosed herein can be formulated or administered with or without a pharmaceutically acceptable excipient. In certain embodiments, the excipients include encapsulating materials or formulation additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents, solution aid, and any combination thereof. In certain embodiments, the pharmaceutical composition disclosed herein is administered without a solubilization aid.

In certain embodiments, the pharmaceutical composition can separately be provided or packaged as kits.

4. Food Products

The presently disclosed subject matter provides a food product for improving intestinal health. In certain embodiments, the food product comprises an effective amount of a bacterium capable of producing a first bile acid. In certain embodiments, the food product further comprises an effective amount of a second bile acid. In certain embodiments, the bacterium is any bacterium disclosed in the above section. In certain embodiments, the first bile acid and/or the second bile acid is any bile acid disclosed in the above section or an edible salt thereof. In certain embodiments, the first bile acid and the second bile acid are the same. In certain embodiments, the first bile acid and the second bile acid are different.

In certain embodiments, the food product is a dietary supplement. In certain embodiments, the food product is a human food product. In certain embodiments, the food product is a pet food product, e.g., a cat food product or a dog food product. In certain embodiments, the food product is a dog food product. In certain embodiments, the food product is a pet dietary supplement.

In certain embodiments, the bacterium comprised in the pharmaceutical composition is between about 10 thousand CFU and about 100 trillion CFU. In certain embodiments, the bacterium is between about 1 thousand CFU and about 1 trillion CFU, between about 1 million CFU and about 1 trillion CFU, between about 100 million CFU and about 100 billion CFU, between about 1 billion CFU and about 1 trillion CFU, between about 1 billion CFU and about 100 billion CFU, between about 100 million CFU and about 100 billion CFU, between about 1 billion CFU and about 50 billion CFU, between about 100 million CFU and about 50 billion CFU, or between about 1 billion CFU and about 10 billion CFU. In certain embodiments, the bacterium comprised in the pharmaceutical composition is at least about 1 thousand CFU, at least about 1 million CFU, at least about 10 million CFU, at least about 100 million CFU, at least about 1 billion CFU, at least about 10 billion CFU, at least about 100 billion CFU or more.

In certain embodiments, the second bile acid comprised in the pharmaceutical composition is between about 1 μg/daily serving dose and about 1 g/daily serving dose. In certain embodiments, the second bile acid comprised in the pharmaceutical composition is between about 10 μg/daily serving dose and about 1 g/daily serving dose, between about 10 μg/daily serving dose and about 500 mg/daily serving dose, between about 100 μg/daily serving dose and about 500 mg/daily serving dose, between about 1 mg/daily serving dose and about 500 mg/daily serving dose, between about 10 mg/daily serving dose and about 500 mg/daily serving dose, between about 100 mg/daily serving dose and about 500 mg/daily serving dose, between about 10 mg/daily serving dose and about 100 mg/daily serving dose, between about 50 mg/daily serving dose and about 300 mg/daily serving dose. In certain embodiments, the second bile acid comprised in the pharmaceutical composition is at least about 1 μg/daily serving dose, at least about 10 μg/daily serving dose, at least about 100 μg/daily serving dose, at least about 1 mg/daily serving dose, at least about 10 mg/daily serving dose, at least about 100 mg/daily serving dose, at least about 1 g/daily serving dose or more.

In certain embodiments, a formulation of the presently disclosed subject matter can further comprise an additional active agent. Non-limiting examples of additional active agents that can be present within a formulation of the presently disclosed subject matter include a nutritional agent (e.g., amino acids, peptides, proteins, fatty acids, carbohydrates, sugars, nucleic acids, nucleotides, vitamins, minerals, etc.), a prebiotic, a probiotic, an antioxidant, and/or an agent that improves animal health.

In certain embodiments, the food product comprises one or more probiotic. In certain embodiments, the probiotic is a human probiotic. In certain embodiments, the probiotic is an animal probiotic. In certain embodiments, the animal probiotic is a feline probiotic. In certain embodiments, the animal probiotic is a canine probiotic. In certain embodiments, the probiotic is *bifidobacterium*, lactic acid bacterium and/or *enterococcus*. In certain embodiments, the probiotic is selected from the group consisting of any organism from lactic acid bacteria and more specifically from the following bacterial genera; *Lactococcus* spp., *Pediococcus* spp., *Bifidobacterium* spp. (e.g., *B. longum B. bifidum. B. pseudolongum. B. animalis*). *Lactobacillus* spp. (e.g. *L.bulgaricus. L. acidophilus. L. brevis. L. casei. L. rhamnosus. L. plantarum. L. reuteri. L. fermentum. Enterococcus* spp. (e.g. *E. faecium*). *Prevotella* spp.. Fusobacteria spp. Alloprevotella spp, and any combination thereof. In certain embodiments, the probiotic is administered to a companion animal in an amount of from about 1 colony forming unit (CFU) to about 100 billion CFUs per day for the maintenance of GI microflora. In certain embodiments, the probiotic is administered to a companion animal in an amount of from about 1 colony forming unit (CFU) to about 20 billion CFUs per day for the maintenance of GI microflora. In certain embodiments, the probiotic is administered to a companion animal in an amount of from about 1 billion CFUs to about 20 billion CFUs per day for the maintenance of GI microflora. In certain embodiments, the probiotic is administered to a companion animal in amounts of from about 0.01 billion to about 100 billion live bacteria per day. In certain embodiments, the probiotic is administered to a companion animal in amounts of from about 0.1 billion to about 10 billion live bacteria per day.

In certain embodiments, an additional prebiotic can be included, such as fructooligosaccharides (FOS), xylooligosaccharides (XOS), galactooligosaccharides (GOS), glucans, galactans, arabinogalactan, inulin and/or mannooligosaccharides. In certain embodiments, the additional prebiotic is administered in amounts sufficient to positively stimulate the GI microflora and/or cause one or more probiotics to proliferate.

In certain embodiments, the companion animal food product can further contain additives known in the art. In certain embodiments, such additives are present in amounts that do not impair the purpose and effect provided by the presently disclosed subject matter. Examples of contemplated additives include, but are not limited to, substances that are functionally beneficial to improving health, substances with a stabilizing effect, organoleptic substances, processing aids, substances that enhance palatability, coloring substances, and substances that provide nutritional benefits. In certain embodiments, the stabilizing substances include, but are not limited to, substances that tend to increase the shelf life of the product. In certain embodiments, such substances include, but are not limited to, preservatives, synergists and sequestrants, packaging gases, stabilizers, emulsifiers, thickeners, gelling agents, and humectants. In certain embodiments, the emulsifiers and/or thickening agents include, for example, gelatin, cellulose ethers, starch, starch esters, starch ethers, and modified starches.

In certain embodiments, the additives for coloring, palatability, and nutritional purposes include, for example, colorants; iron oxide, sodium chloride, potassium citrate, potassium chloride, and other edible salts; vitamins; minerals; and flavoring. The amount of such additives in a product typically is up to about 5% (dry basis of the product).

In certain embodiments, the companion animal food product is a dietary supplement. In certain embodiments, the dietary supplements include, for example, a feed used with another feed to improve the nutritive balance or performance of the total. In certain embodiments, the supplements include compositions that are fed undiluted as a supplement to other feeds, offered free choice with other parts of an animal's ration that are separately available, or diluted and mixed with an animal's regular feed to produce a complete feed. The AAFCO, for example, provides a discussion relating to supplements in the American Feed Control Officials, Incorp. Official Publication, p. 220 (2003). Supplements can be in various forms including, for example, powders, liquids, syrups, pills, tablets, encapsulated compositions, etc.

In certain embodiments, the companion animal food product is a treat. In certain embodiments, treats include, for example, compositions that are given to an animal to entice the animal to eat during a non-meal time. In certain embodiments, the companion animal food product is a treat for canines include, for example, dog bones. Treats can be nutritional, wherein the product comprises one or more nutrients, and can, for example, have a composition as described above for food. Non-nutritional treats encompass any other treats that are non-toxic.

In certain embodiments, a bacterium and/or a bile acid of the presently disclosed subject matter can be incorporated into the composition during the processing of the formulation, such as during and/or after mixing of other components of the product. Distribution of these components into the product can be accomplished by conventional means.

In certain embodiments, companion animal food products of the presently disclosed subject matter can be prepared in a canned or wet form using conventional companion animal food processes. In certain embodiments, ground animal (e.g., mammal, poultry, and/or fish) proteinaceous tissues are mixed with the other ingredients, such as milk fish oils, cereal grains, other nutritionally balancing ingredients, special purpose additives (e.g.. vitamin and mineral mixtures, inorganic salts, cellulose and beet pulp, bulking agents, and the like); and water that sufficient for processing is also added. These ingredients are mixed in a vessel suitable for heating while blending the components. Heating of the mixture can be effected using any suitable manner, such as, for example, by direct steam injection or by using a vessel fitted with a heat exchanger. Following the addition of the last ingredient, the mixture is heated to a temperature range of from about 50° F. to about 212° F. Temperatures outside this range are acceptable but can be commercially impractical without use of other processing aids. When heated to the appropriate temperature, the material will typically be in the form of a thick liquid. The thick liquid is filled into cans. A lid is applied, and the container is hermetically sealed. The sealed can is then placed into conventional equipment designed to sterilize the contents. This is usually accomplished by heating to temperatures of greater than about 230° F. for an appropriate time, which is dependent on, for example, the temperature used and the composition.

In certain embodiments, companion animal food products of the presently disclosed subject matter can be prepared in a dry form using conventional processes. In certain embodiments, dry ingredients, including, for example, animal protein sources, plant protein sources, grains, etc., are ground and mixed together. In certain embodiments, moist or liquid ingredients, including fats, oils, animal protein sources, water, etc., are then added to and mixed with the dry mix. In certain embodiments, the mixture is then processed into kibbles or similar dry pieces. In certain embodiments, the companion animal food product is kibble. In certain embodiments, kibble is formed using an extrusion process in which the mixture of dry and wet ingredients is subjected to mechanical work at a high pressure and temperature and forced through small openings and cut off into kibble by a rotating knife. In certain embodiments, the wet kibble is then dried and optionally coated with one or more topical coatings which can include, for example, flavors, fats, oils, powders, and the like. In certain embodiments, kibble can also be made from the dough using a baking process, rather than extrusion, wherein the dough is placed into a mold before dry-heat processing.

In certain embodiments, treats of the presently disclosed subject matter can be prepared by, for example, an extrusion or baking process similar to those described above for dry food.

The presently disclosed subject matter provides a diet for increase a population of a bacterium capable of producing a bile acid in a companion animal. In certain embodiments, the diet comprises protein, fat, crude fiber, total dietary fiber, carbohydrate, calcium, phosphorus, sodium, chloride, potassium, magnesium, iron, copper, manganese, zinc, iodine, selenium, vitamin A, vitamin D3, vitamin E, vitamin C, thiamine (vitamin B1), riboflavin (vitamin B2), pantothenic acid, niacin, pyridoxine (vitamin B6), folic acid, biotin, cobalannin (vitamin B12), choline, arginine, lysine, methionine, cystine, taurine, linoleic acid, arachidonic acid, Omega-6 fatty acids, Omega-3 fatty acids, EPA, and/or DHA.

In certain embodiments, the subject is a dog. In certain embodiments, the diet is a Royal Canin Veterinary Diet. In certain embodiments, the diet is selected from the group consisting of Ultamino, Hydrolyzed Protein Adult HP Dry, Hydrolyzed Protein Wet, Hydrolyzed Protein Adult PS Dry, Hydrolyzed Protein Moderate Calorie Dry, Hydrolyzed Protein Small Dog Dry, Hydrolyzed protein Treats, and any combination thereof.

In certain embodiments, the bacterium comprises a bile acid-inducible operon (bai operon). In certain embodiments, the bacterium is *C. hiranonis. C. scindens* or combination thereof. In certain embodiments, the bacterium is *C. hiranonis.*

The presently disclosed subject matter provides a Royal Canin Veterinary Diet for the treatment of an intestinal disorder in a dog, wherein the dog comprises a first amount of a first intestinal microorganism and/or a second amount of a second intestinal microorganism, and wherein the first amount of the first intestinal microorganism is higher than a first reference amount of the first intestinal microorganism, and/or the second amount of the second intestinal microorganism is lower than a second reference amount of the second intestinal microorganism.

In certain embodiments, the first intestinal microorganism is selected from the group consisting of New.ReferenceOTU45, JRPJ01000002.1034290.1035971, KF842598.1.1394, JF920309.1.1340, FJ978526.1.1378, New.ReferenceOTU54, HQ793763.1.1451, DQ113765.1.1450, DQ797046.1.1403, ACBW01000012.3536.5054, JN387556.1.1324, New.ReferenceOTU52, JQ208053.1.1336, and any combination thereof. In certain embodiments, the second intestinal microorganism is selected from the group consisting of HK693629.1.1491, GQ493166.1.1359, GQ491426.1.1332, FJ957494.1.1454, GQ449092.1.1375, GQ448486.1.1387, AMCI01001631.34.1456, HK555938.1.1357, and any combination thereof.

5. Treatment Methods

In certain non-limiting embodiments, the presently disclosed subject matter provides for a method for improving intestinal health and/or treating an intestinal disorder of a subject in need thereof. In certain embodiments, the method can improve immunity, digestive function and/or decrease inflammation of a companion animal.

In certain non-limiting embodiments, the presently disclosed subject matter provides for a method for determining susceptibility of an intestinal disorder in a companion animal. In certain embodiments, the method comprises:

a) measuring a first amount of a first intestinal microorganism and/or a second amount of a second intestinal microorganism in the companion animal;

b) comparing the first amount of the first intestinal microorganism with a first reference amount of the first intestinal microorganism, and/or comparing the second amount of the second intestinal microorganism with a second reference amount of the second intestinal microorganism, wherein the reference amounts of the intestinal microorganisms are determined based on the amounts of the intestinal microorganisms in a plurality of healthy companion animals; and c) determining that the companion animal is susceptible of an intestinal disorder, when the first amount of the intestinal microorganism is higher than the first reference amount of the first intestinal microorganism, and/or when the second amount of the second intestinal microorganism is lower than the second reference amount of the second intestinal microorganism.

In certain embodiments, the first intestinal microorganism comprises one or more bacterium comprising a 16S rRNA comprising a nucleotide sequence that is at least about 90% homologous or identical to the 16S rRNA nucleotide sequence of HQ802983.1.1440, GQ449092.1.1375, GQ448744.1.1393, KF842598.1.1394, HG798451.1.1400, New.ReferenceOTU52, HK555938.1.1357, FJ957494.1.1454, FN667392.1.1495, New.ReferenceOTU54, HQ760911.1.1437, GQ006324.1.1342, FJ950694.1.1472, FM865905.1.1392, FJ506371.1.1371, FJ957528.1.1445, JF712675.1.1540, New.ReferenceOTU82, AB009242.1.1451, HQ751549.1.1448, AB506370.1.1516, DQ057365.1.1393, FN667422.1.1495, AJ270486.1.1241, FN668375.4306350.4307737, GQ867426.1.1494, GX182404.8.1529, JF224013.1.1362, GQ448246.1.1389, JF807116.1.1260, KC245406.1.1465, FN667084.1.1493, EU470512.1.1400, EU768569.1.1352, AY239462.1.1500, KC504009.1.1465, FM179752.1.1686, New.ReferenceOTU114, HK557089.3.1395, JQ208181.1.1352, HQ803964.1.1435, AM276759.1.1484, JN387556.1.1324, GQ448486.1.1387, HK694029.9.1487, HQ754680.1.1441, FN563300.1.1447, FP929060.3837.5503, GQ448506.1.1374, *Enterococcus durans. C. perfringens.* or *E. coli.*

In certain embodiments, the first intestinal microorganism is selected from the group consisting of HQ802983.1.1440, GQ449092.1.1375, GQ448744.1.1393, KF842598.1.1394, HG798451.1.1400, New.ReferenceOTU52, HK555938.1.1357, FJ957494.1.1454, FN667392.1.1495, New.ReferenceOTU54, HQ760911.1.1437, GQ006324.1.1342, FJ950694.1.1472, FM865905.1.1392, FJ506371.1.1371, FJ957528.1.1445, JF712675.1.1540, New.ReferenceOTU82, AB009242.1.1451, HQ751549.1.1448, AB506370.1.1516, DQ057365.1.1393, FN667422.1.1495, AJ270486.1.1241, FN668375.4306350.4307737, GQ867426.1.1494, GX182404.8.1529, JF224013.1.1362, GQ448246.1.1389, JF807116.1.1260, KC245406.1.1465, FN667084.1.1493, EU470512.1.1400, EU768569.1.1352, AY239462.1.1500, KC504009.1.1465, FM179752.1.1686, New.ReferenceOTU114, HK557089.3.1395, JQ208181.1.1352, HQ803964.1.1435, AM276759.1.1484, JN387556.1.1324, GQ448486.1.1387, HK694029.9.1487, HQ754680.1.1441, FN563300.1.1447, FP929060.3837.5503, GQ448506.1.1374, *Enterococcus durans. C. perfringens. E. coli* and any combination thereof.

In certain embodiments, the first intestinal microorganism is *C. perfringens. E. coli* and any combination thereof.

In certain embodiments, the second intestinal microorganism comprises one or more bacterium comprising a 16S rRNA comprising a nucleotide sequence that is at least about 90% homologous or identical to the 16S rRNA nucleotide sequence of EU774020.1.1361, HQ793763.1.1451, HQ792787.1.1438, New.ReferenceOTU109, HQ792778.1.1436, or DQ 113765.1.1450.

In certain embodiments, the second intestinal microorganism is selected from the group consisting of EU774020.1.1361, HQ793763.1.1451, HQ792787.1.1438, New.ReferenceOTU109, HQ792778.1.1436, DQ113765.1.1450, and any combination thereof.

In certain embodiments, the method further comprises providing a customized recommendation of a treatment regimen, and/or further monitoring the intestinal microorganism, when the first amount of the first intestinal microorganism is lower than the first reference amount of the first intestinal microorganism, and/or when the second amount of the second intestinal microorganism is higher than the second reference amount of the second intestinal microorganism.

In certain non-limiting embodiments, the presently disclosed subject matter provides for a method for determining responsiveness of a companion animal having an intestinal disorder to a diet. In certain embodiments, the method comprises:

a) measuring a first amount of a first intestinal microorganism and/or a second amount of a second intestinal microorganism in the companion animal;
b) comparing the first amount of the first intestinal microorganism with a first reference amount of the first intestinal microorganism, and/or comparing the second amount of the second intestinal microorganism with a second reference amount of the second intestinal microorganism, wherein the reference amounts of the intestinal microorganisms are determined based on the amounts of the intestinal microorganisms in a plurality of healthy companion animals; and
c) determining that the companion animal is responsive to the diet, when the first amount of the intestinal microorganism is higher than the first reference amount of the first intestinal microorganism, and/or when the second amount of the second intestinal microorganism is lower than the second reference amount of the second intestinal microorganism, or determining that the companion animal is non-responsive to the diet, when the first amount of the intestinal microorganism is lower than the first reference amount of the first intestinal microorganism, and/or when the second amount of the second intestinal microorganism is higher than the second reference amount of the second intestinal microorganism.

In certain embodiments, the first intestinal microorganism comprises one or more bacterium comprising a 16S rRNA comprising a nucleotide sequence that is at least about 90% homologous or identical to the 16S rRNA nucleotide sequence of ReferenceOTU45, JRPJ01000002.1034290.1035971, KF842598.1.1394, JF920309.1.1340, FJ978526.1.1378, New.ReferenceOTU54, HQ793763.1.1451, DQ113765.1.1450, DQ797046.1.1403, ACBW01000012.3536.5054, JN387556.1.1324, New.ReferenceOTU52, JQ208053.1.1336, and any combination thereof. In certain embodiments, the second intestinal microorganism is selected from the group consisting of HK693629.1.1491, GQ493166.1.1359, GQ491426.1.1332, FJ957494.1.1454, GQ449092.1.1375, GQ448486.1.1387, AMCI01001631.34.1456, or HK555938.1.1357.

In certain embodiments, the first intestinal microorganism is selected from the group consisting of New.ReferenceOTU45, JRPJ01000002.1034290.1035971, KF842598.1.1394, JF920309.1.1340, FJ978526.1.1378, New.ReferenceOTU54, HQ793763.1.1451, DQ113765.1.1450, DQ797046.1.1403, ACBW01000012.3536.5054, JN387556.1.1324, New.ReferenceOTU52, JQ208053.1.1336, and any combination thereof.

In certain embodiments, the second intestinal microorganism comprises one or more bacterium comprising a 16S rRNA comprising a nucleotide sequence that is at least about 90% homologous or identical to the 16S rRNA nucleotide sequence of HK693629.1.1491, GQ493166.1.1359, GQ491426.1.1332, FJ957494.1.1454, GQ449092.1.1375, GQ448486.1.1387, AMCI01001631.34.1456, or HK555938.1.1357.

In certain embodiments, the second intestinal microorganism is selected from the group consisting of HK693629.1.1491, GQ493166.1.1359, GQ491426.1.1332, FJ957494.1.1454, GQ449092.1.1375, GQ448486.1.1387, AMCI01001631.34.1456, HK555938.1.1357, and any combination thereof.

In certain embodiments, the method further comprises administering the diet to the companion animal when companion animal is determined as responsive to the diet. In certain embodiments, the method further comprises administering the diet, a steroid and optionally an antibiotic to the companion animal when companion animal is determined as non-responsive to the diet.

In certain embodiments, the determination in step c) occurs before administering the diet or the diet, the steroid and optionally the antibiotic to the companion animal.

In certain non-limiting embodiments, the presently disclosed subject matter provides for a method for determining effectiveness of a diet for treating an intestinal disorder in a companion animal. In certain embodiments, the method comprises:

a) measuring a first amount of a first intestinal microorganism and/or a second amount of a second intestinal microorganism in the companion animal before or after administering a diet to a companion animal for treating an intestinal disorder;
b) comparing the first amount of the first intestinal microorganism with a first reference amount of the first intestinal microorganism, and/or comparing the second amount of the second intestinal microorganism with a second reference amount of the second intestinal microorganism, wherein the reference amounts of the intestinal microorganisms are determined based on the amounts of the intestinal microorganisms in a plurality of healthy companion animals; and
c) determining that the diet is effective for treating an intestinal disorder, when the first amount of the intestinal microorganism is higher than the first reference amount of the first intestinal microorganism, and/or when the second amount of the second intestinal microorganism is lower than the second reference amount of the second intestinal microorganism, or determining that the diet is ineffective for treating an intestinal disorder, when the first amount of the intestinal microorganism is lower than the first reference amount of the first intestinal microorganism, and/or when the second amount of the second intestinal microorganism is higher than the second reference amount of the second intestinal microorganism.

In certain embodiments, the first intestinal microorganism comprises one or more bacterium comprising a 16S rRNA comprising a nucleotide sequence that is at least about 90% homologous or identical to the 16S rRNA nucleotide sequence of HK557089.3.1395, or GQ448336.1.1418. In certain embodiments, the first intestinal microorganism is selected from the group consisting of HK557089.3.1395, GQ448336.1.1418, and combination thereof.

In certain embodiments, the second intestinal microorganism comprises one or more bacterium comprising a 16S rRNA comprising a nucleotide sequence that is at least about 90% homologous or identical to the 16S rRNA nucleotide sequence of KF842598.1.1394, GQ006324.1.1342, HQ802983.1.1440, JN387556.1.1324, FJ950694.1.1472, HG798451.1.1400, New.ReferenceOTU52, or GQ448468.1.1366.

In certain embodiments, the second intestinal microorganism is selected from the group consisting of KF842598.1.1394, GQ006324.1.1342, HQ802983.1.1440, JN387556.1.1324, FJ950694.1.1472, HG798451.1.1400, New.ReferenceOTU52, GQ448468.1.1366, and any combination thereof.

In certain embodiments, the method further comprises administering the diet to the companion animal when companion animal is determined as responsive to the diet. In certain embodiments, the method further comprises administering the diet, a steroid and optionally an antibiotic to the companion animal when companion animal is determined as non-responsive to the diet.

In certain embodiments, the determination in step c) occurs before administering the diet or the diet, the steroid and optionally the antibiotic to the companion animal.

In certain embodiments, the reference amount of an intestinal microorganism derived from a mean amount of the intestinal microorganism in a plurality of healthy companion animals. In certain embodiments, the amount of the intestinal bacterium is measured from a fecal sample of the subject.

In certain embodiments, the method comprises administering to the subject an effective amount of a presently disclosed pharmaceutical composition, an effective amount of a presently disclosed food product, or any combination thereof. In certain embodiments, the method further comprises monitoring an intestinal microorganism in the subject. In certain embodiments, the intestinal microorganism is sampled from a fecal sample of the subject.

In certain embodiments, the intestinal microorganism is selected from the group consisting of Ruminococcus, Alloprevotella, Allisonella, Anaerostipes, Anaerobiospirillum, *Bacteroides*, Blautia, *Clostridium* sensu stricto 1, Collinsella, *Coprococcus* 1, *Corynebacterium* 1, *Campylobacter, Enterococcus*, Erysipelatoclostridium, *Escherichia-Shigella*, Faecalitalea, *Fusobacterium, Helicobacter*, Intestinibacter, Lachnoclostridium, *Lactobacillus*, Megasphaera, Methanobrevibacter, Parabacteroides, *Porphyromonas*, Phascolarctobacterium, Peptoclostridium, Prevotellaceae UCG-001, Pseudocitrobacter, Ruminiclostridium 9, Sarcina, *Streptococcus*, Succinivibrio, *Treponema* 2, Turicibacter, Tyzzerella, Tyzzerella 4 and any combination thereof.

In certain embodiments, the intestinal microorganism is selected from the group consisting of *Escherichia-Shigella. Clostridium* sensu stricto 1. *Enterococcus. Fusobacterium* and any combination thereof. In certain embodiments, the intestinal microorganism is *E. coli. C. perfringens* or combination thereof.

In certain embodiments, an amount of the intestinal bacterium is decreased after administration of the pharmaceutical composition. In certain embodiments, an amount of the intestinal bacterium is decreased within about 14 days after administration of the pharmaceutical composition. In certain embodiments, an amount of the intestinal bacterium is decreased within about 21 days, within about 14 days, within about 12 days, within about 10 days, within about 7 days, within about 6 days, within about 5 days, within about 4 days, within about 3 days, within about 2 days, or within about 1 day after administration of the pharmaceutical composition. In certain embodiments, an amount of the intestinal bacterium is decreased within about 1 day to about 21 days, within about 1 days to about 14 days, within about 3 days to about 14 days, within about 5 days to about 14 days, within about 7 days to about 14 days, within about 10 days to about 14 days, or within about 7 days to about 21 days after administration of the pharmaceutical composition.

In certain embodiments, the intestinal microorganism is selected from the group consisting of *C. hiranonis, C. scindens*, Veillonellaceae, Streptococcaceae, *Bacteroides, Fusobacterium*, Collinsella, Sarcina, *Clostridium sensu stricto* 1, Faecalitalea, *Streptococcus*, Erysipelatoclostridium, Megasphaera, Blautia, Alloprevotella, Peptoclostridium, and any combination thereof. In certain embodiments, the intestinal microorganism is *C. hiranonis. C. scindens* or combination thereof.

In certain embodiments, an amount of the intestinal microorganism is increased after administration of the pharmaceutical composition and/or the food product. In certain embodiments, the amount of the intestinal microorganism is increased within about 14 days after administration of the pharmaceutical composition and/or the food product. In certain embodiments, an amount of the intestinal bacterium is increased within about 21 days, within about 14 days, within about 12 days, within about 10 days, within about 7 days, within about 6 days, within about 5 days, within about 4 days, within about 3 days, within about 2 days, or within about 1 day after administration of the pharmaceutical composition. In certain embodiments, an amount of the intestinal bacterium is increased within about 1 day to about 21 days, within about 1 days to about 14 days, within about 3 days to about 14 days, within about 5 days to about 14 days, within about 7 days to about 14 days, within about 10 days to about 14 days, or within about 7 days to about 21 days after administration of the pharmaceutical composition.

In certain embodiments, the method comprises:

a) measuring a first amount of one or more intestinal microorganism in the subject;

b) administering a treatment regimen to the subject for treating the intestinal disorder;

c) measuring a second amount of the intestinal microorganism in the subject after step b); and d) continuing administering the treatment regimen, when the second amount of the intestinal microorganism is reduced compared to the first amount of the intestinal microorganism.

In certain embodiments, the second amount of the intestinal microorganism is measured between about 7 days and about 14 days after step b). In certain embodiments, an amount of the intestinal microorganism is decreased within about 21 days, within about 14 days, within about 12 days, within about 10 days, within about 7 days, within about 6 days, within about 5 days, within about 4 days, within about 3 days, within about 2 days, or within about 1 day after step b). In certain embodiments, an amount of the intestinal bacterium is decreased within about 1 day to about 21 days, within about 1 days to about 14 days, within about 3 days to about 14 days, within about 5 days to about 14 days, within about 7 days to about 14 days, within about 10 days to about 14 days, or within about 7 days to about 21 days after step b).

In certain embodiments, the intestinal microorganism is measured from a fecal sample of the subject.

In certain embodiments, the method comprises:

a) measuring the first amount of one or more intestinal microorganism in the subject;

b) comparing the first amount of the intestinal microorganism with a reference amount of the intestinal microorganism, wherein the reference amount of the intestinal microorganism is determined based on the amount of the intestinal microorganism in a plurality of healthy subjects;

c) providing a customized recommendation of a treatment regimen, and/or further monitoring the intestinal microorganism, when the first amount of the intestinal microorganism is above the reference amount of the intestinal microorganism.

In certain embodiments, the method further comprises measuring a second amount of the intestinal microorganism in the subject after step c), and continuing the treatment regimen when the second amount of the intestinal microorganism is decreased compared to the first amount of the intestinal microorganism and is above the reference amount of the intestinal microorganism.

In certain embodiments, the second amount of the intestinal bacterium is measured between about 7 days and about 14 days after step c). In certain embodiments, an amount of the intestinal microorganism is decreased within about 21 days, within about 14 days, within about 12 days, within about 10 days, within about 7 days, within about 6 days, within about 5 days, within about 4 days, within about 3 days, within about 2 days, or within about 1 day after step b). In certain embodiments, an amount of the intestinal microorganism is decreased within about 1 day to about 21 days, within about 1 days to about 14 days, within about 3 days to about 14 days, within about 5 days to about 14 days, within about 7 days to about 14 days, within about 10 days to about 14 days, or within about 7 days to about 21 days after step c).

In certain embodiments, the intestinal microorganism is measured from a fecal sample of the subject.

In certain embodiments, the intestinal microorganism is selected from the group consisting of Ruminococcus, Alloprevotella, Allisonella, Anaerostipes, Anaerobiospirillum, *Bacteroides*, Blautia, *Clostridium* sensu stricto 1, Collinsella, *Coprococcus* 1, *Corynebacterium* 1, *Campylobacter, Enterococcus*, Erysipelatoclostridium, *Escherichia-Shigella*, Faecalitalea, *Fusobacterium, Helicobacter*, Intestinibacter, Lachnoclostridium, *Lactobacillus*, Megasphaera, Methanobrevibacter, Parabacteroides, *Porphyromonas*, Phascolarctobacterium, Peptoclostridium, Prevotellaceae UCG-001, Pseudocitrobacter, Ruminiclostridium 9, Sarcina, *Streptococcus*, Succinivibrio, *Treponema* 2, Turicibacter, Tyzzerella, Tyzzerella 4 and any combination thereof. In certain embodiments, the intestinal microorganism is selected from the group consisting of *Escherichia-Shigella, Clostridium sensu stricto* 1, *Enterococcus, Fusobacterium* and any combination thereof. In certain embodiments, the intestinal microorganism is *E. coli, C. perfringens* or combination thereof.

In certain embodiments, the treatment regimen comprises administering an effective amount of a presently disclosed pharmaceutical composition, an effective amount of a presently disclosed food product, or any combination thereof.

In certain non-limiting embodiments, the subject is a mammal. In certain embodiments, the subject is a human. In certain embodiments, the subject is a companion animal is a feline (e.g., a domestic cat) or a canine (e.g., a domestic dog). In certain non-limiting embodiments, the companion animal is at risk of an intestinal disorder and/or inflammation. In certain non-limiting embodiments, the companion animal is not known to be at risk of an intestinal disorder and/or inflammation. In certain non-limiting embodiments, the companion animal has an intestinal disorder and/or inflammation. In certain non-limiting embodiments, the companion animal is not known to have an intestinal disorder and/or inflammation. In certain non-limiting embodiments, the companion animal is under a treatment for a digestive disorder and/or inflammation. In certain non-limiting embodiments, the treatment is a dietary therapy. In certain embodiments, the companion animal is a dog. In certain embodiments, the intestinal disorder is an acute enteropathy or a chronic enteropathy. In certain embodiments, the intestinal disorder is a chronic enteropathy selected from the group consisting of food responsive enteropathy, antibiotic responsive enterophaty, and idiophathic inflammatory bowel disease (IBD).

In certain embodiments, the pharmaceutical composition and/or the food product can be administered to a subject from 20 times per day to once per day, from 10 times per day to once per day, or from 5 times per day to once per day. In certain embodiments, the pharmaceutical composition and/or the food product can be administered to a subject once per day, twice per day, thrice per day, 4 times per day, 5 times per day, 6 times per day, 7 times per day, 8 times per day, 9 times per day, 10 or more times per day. In certain embodiments, the pharmaceutical composition and/or the food product can be administered to a subject once per two days, once per three days, once per four days, once per five days, once per six days, once a week, once per two weeks, once per three weeks, or once per month. In certain embodiments, the food product can be administered to an animal in a constant manner, e.g., where the animal grazes on a constantly available supply of the subject food product.

In certain embodiments, the dosage of the pharmaceutical composition is between about 1 mg/kg body weight per day and about 5000 mg/kg body weight per day. In certain embodiments, the dosage of the pharmaceutical composition is between about 5 mg/kg body weight per day and about 1000 mg/kg body weight per day, between about 10 mg/kg body weight per day and about 500 mg/kg body weight per day, between about 10 mg/kg body weight per day and about 250 mg/kg body weight per day, between about 10 mg/kg body weight per day and about 200 mg/kg body weight per day, between about 20 mg/kg body weight per day and about 100 mg/kg body weight per day, between about 20 mg/kg body weight per day and about 50 mg/kg body weight per day or any intermediate range thereof. In certain embodiments, the dosage of the pharmaceutical composition is at least about 1 mg/kg body weight per day, at least about 5 mg/kg body weight per day, at least about 10 mg/kg body weight per day, at least about 20 mg/kg body weight per day, at least about 50 mg/kg body weight per day, at least about 100 mg/kg body weight per day, at least about 200 mg/kg body weight per day or more. In certain embodiments, the dosage of the pharmaceutical composition is no more than about 5 mg/kg body weight per day, no more than about 10 mg/kg body weight per day, no more than about 20 mg/kg body weight per day, no more than about 50 mg/kg body weight per day, no more than about 100 mg/kg body weight per day, no more than about 200 mg/kg body weight per day, no more than about 500 mg/kg body weight per day or more.

In certain embodiments, the amount of the pharmaceutical composition and/or the food product decreases over the course of feeding a companion animal. In certain embodiments, the concentration of the pharmaceutical composition and/or the food product increases over the course of feeding a companion animal. In certain embodiments, the concentration of the pharmaceutical composition and/or the food product is modified based on the age of the companion animal.

6. Kits

The presently disclosed subject matter provides kits for treating and/or preventing an intestinal disorder in a subject. In certain embodiments, the kit comprises an effective amount of the presently disclosed pharmaceutical composition, dietary supplement, functional food, food product, diet or any combination thereof. In certain embodiments, the kit comprises a sterile container; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

If desired, the pharmaceutical composition, dietary supplement, functional food, food product, and/or diet are provided together with instructions for administering the same to a subject having or at risk of developing an intestinal disorder. The instructions generally include information about the use of the pharmaceutical composition, dietary supplement, functional food, food product, diet for the treatment and/or prevention of an intestinal disorder. In certain embodiments, the instructions include at least one of the following: description of the therapeutic agent; dosage schedule and administration for treatment or prevention of an intestinal disorder or symptoms thereof; precautions; warnings; indications; counter-indications; over-dosage information; adverse reactions; animal pharmacology; clinical studies; and/or references. The instructions can be printed directly on the container (when present), or as a label applied to the container, or as a separate sheet, pamphlet, card, or folder supplied in or with the container.

Advantageously, the kit can be packaged in per use groupings such that, for example, a daily prescription of each component can be identified in order to enhance patient compliance. Sets of the pharmaceutical composition can be identified in a variety of ways. For example, in certain embodiments, a set of the pharmaceutical composition, dietary supplement, functional food, food product, diet can be identified on the package containing the same. In certain embodiments, external instructions can be provided with a set or sets of the pharmaceutical composition, dietary supplement, functional food, food product, diet that, for example, identify a grouping and instruct a patient/animal owner appropriate times to take the pharmaceutical composition, dietary supplement, functional food, food product, diet of the kit.

EXAMPLES

The presently disclosed subject matter will be better understood by reference to the following Example, which is provided as exemplary of the present disclosure, and not by way of limitation.

Example 1

Introduction

Although a wide range of environmental factors have been shown to influence the microbiome, diet is regarded as one of the most potent modulators of the composition and function of the gut-resident microbial community in healthy humans and other mammals[7,8] and can act as both a risk factor and a treatment modality for IBD[9,10]. Epidemiologic data and studies in mice have shown that diets high in fat and/or low in fiber, as well as dietary additives such as emulsifiers, are either risk factors for IBD, or in some cases can directly compromise intestinal barrier function leading to disease[11-13]. Diet can be also leveraged to treat IBD, with perhaps the clearest example of this being the use of exclusive enteral nutrition (EEN) as first-line therapy for pediatric Crohn's disease[14]. High remission rates (≥60%) are observed following EEN and, compared to corticosteroids, EEN achieves better patient growth along with a reduction in biomarkers of disease, such as fecal calprotectin and C-reactive protein[15-18]. Interestingly, EEN has a marked effect on the microbiome, but the precise nature of this effect has been complicated to discern, with some studies reporting reduced microbiome diversity following EEN therapy[19-21], while others point to relatively unchanged[22,23] or increased diversity[24].

The mechanisms by which diet impacts the gut microbiome to ameliorate IBD symptoms are unclear and are complicated to dissect from human subject research were diet is challenging to control, necessitating either retrospective studies in conjunction with extensive food intake surveys[25], controlled feeding studies[26], or focusing on populations with different subsistence practices[27-29]. In contrast, mouse models of colitis have yielded important insights into the pathophysiology of intestinal inflammation, but these often involve chemical or genetic perturbation, rather than spontaneous disease development. Moreover, the ubiquitous use of autoclaved food and acidified water for mouse husbandry, together with the tendency for cage effects to dominate in mouse microbiome studies, raises concerns about clinical relevance of diet-microbiome studies in these models of colitis. As companion animals, dogs share the same environment as humans, and spontaneously develop a chronic enteritis that clinically resembles human IBD, including similar gastrointestinal pathology, responsiveness to similar treatments[30,31], involvement of some of the same susceptibility loci[30-32], and shared disease-associated microbial taxa[33-35]. Intriguingly, after treatment with dietary therapy, over 50% of dogs with chronic enteritis enter a long-lasting state of remission[36], making the use of prescription diets the first-line treatment for IBD in companion animal medicine. A recent metagenomic study produced a catalog of over one million taxonomically and functionally annotated microbial genes from the canine gut and showed that—compared to other mammals, such as the mouse and pig—the microbial environment in dogs most closely resembles that of humans[37]. Furthermore, the canine microbiome was markedly altered by diet change in a manner that resembles what has been reported in humans[37]. Together, these data argue that dogs are an ideal animal model in which to study diet-microbiome interactions in the context of intestinal disease.

Despite the fact that the gut microbiome has been implicated in IBD pathogenesis, and that diet profoundly alters the microbiome and can be used to manage symptoms of IBD, there is limited insight into the mechanisms by which this occurs. In this study, treatment-naive dogs were examined with chronic enteritis and changes in their fecal microbial community structure and metabolites in response to treatment were monitored. By comparing changes over time in diet-responsive dogs, versus animals that failed diet therapy and required subsequent combination therapy, it was shown that diet induces rapid remission by shaping the community structure and re-programming the metabolic function of the microbiome. Notably, it was demonstrated that secondary bile acids, likely produced by clostridia, are involved in the diet induced alterations of microbiota community by inhibiting the growth of potential pathogens. These findings provide a general mechanism by which diet can modulate microbial communities to reduce GI disease.

Methods

Diagnosis and Treatment of Canine Chronic Enteritis (CCE)

Client-owned animals presenting with clinical signs of CCE were screened at the Ryan Veterinary Hospital of the University of Pennsylvania. All animal work was carried out in accordance within the guidelines of the University of Pennsylvania IACUC (Protocol 805283), and signed owner consent was obtained before enrollment. Dogs were screened if they had any one of the following clinical signs for ≥3 weeks' duration: vomiting, diarrhea or weight loss despite adequate caloric intake. Dogs were excluded from screening if they had been treated with a hydrolyzed protein diet, antibiotics, corticosteroids or probiotics within the previous two weeks. At the time of screening, the following were performed on each animal: complete physical examination, routine fecal screening (including zinc sulfate flotation for parasite identification, gram stain and culture for *Salmonella* spp. and *Campylobacter* spp.), complete blood count, serum biochemical profile, serum measurement of canine trypsin-like immunoreactivity, cobalamin and folate, urinalysis, abdominal ultrasound examination, and disease severity scoring using the Canine Chronic Enteropathy Clinical Activity Index (CCECAI)[36]. If these initial screening tests failed to identify a cause for the clinical signs, upper and/or lower gastrointestinal endoscopy with mucosal biopsies was performed. Biopsies were fixed in formalin, embedded in paraffin, and sections were stained with hematoxylin and eosin, and slides were examined by a board-certified veterinary pathologist. Dogs were enrolled if histopathology revealed intestinal inflammation with no identifiable underlying cause (such as infectious agents). Dogs were excluded if another histopathologic diagnosis was identified.

Three 14-day treatment tiers were included in the trial (FIG. 1A), and dogs were evaluated for a therapeutic response at the conclusion of each tier using CCECAI. Remission was determined using an abbreviated CCECAI that included scores to the first five indices (attitude/activity, appetite, vomiting, stool consistency, and stool frequency), and was defined as an abbreviated CCECAI score: S 2, with no score >1 for any of the five indices. Animals were first administered a therapeutic hydrolyzed protein diet (Royal Canin HP). Dogs that entered remission following this treatment were designated as diet-response (DR) and were maintained on therapeutic diet for the reminder of the trial. Animals that did not respond to therapeutic diet (NDR) subsequently began a two-week course of metronidazole (10 mg/kg PO q 12 hours) while being maintained on the therapeutic diet. Dogs that entered remission following antibiotic treatment were maintained on the combination of antibiotics and therapeutic diet for the reminder of the trial. Animals that still failed to show a favorable response remained on diet and metronidazole but received prednisone (1 mg/kg PO q 12 hours) (Tier 3) for the final 14 days of the trial. Dogs that presented with hypoalbuminemia (protein-losing enteropathy) at the initial screening were presumed to have more severe disease and poorer prognoses and thus were immediately administered all three interventions and were not included in the analyses. All dogs in which serum cobalamin was low at screening were supplemented with cyanocobalamin (50 mcg/kg SQ q 7 days) for the duration of the study. At the conclusion of the study, all animals returned to the clinic for the primary endpoint, which included a full re-evaluation of dogs including complete physical examination, complete blood count, serum chemistry, serum measurement of cobalamin and folate (if low at screening visit), urinalysis, CCECAI scoring and final fecal collections.

16S rRNA Gene Sequencing and Data Analysis

Genomic DNA was extracted from stool using the PowerSoil DNA Isolation Kit (MO BIO Laboratories, Carlsbad, CA) following the manufacturer's recommendations. A mock community pool containing purified genomic DNA from 12 known bacterial isolates was amplified and sequenced as a quality control. Additional controls included extraction of blank-processed samples (in which the DNA extraction process was followed without addition of input material), and water only, to determine background microbial signal. A dual-index amplicon sequencing method was employed for PCR amplification of the V4 region of the 16S rRNA gene[61]. Pico-green based Amplicons were sequenced on a MiSeq platform (Illumina, San Diego, CA) using 250 base pair paired-end chemistry. Reads were filtered to remove sequences with average Phred quality score ≤20 using Quantitative Insights into Microbial Ecology (QIIME) [62] with filtering options (-q 20-p 0.75 -r 3). Homopolymers >10 bp in length and sequences <248 bp and >255 bp were removed using Mothur[63]. Chimeric sequences were identified and removed by usearch61,64 against the representative 16S sequences of SILVA128 (97_otus_16S.fasta)[65,66]. Quality-controlled sequences were then clustered against the SILVA128 database (SILVA_128_QIIME_release) using the open-reference OTU picking as implemented in QIIME with default parameters. The OTU table was rarefied to 10600 sequences per sample. In order to get a taxonomic assignment at species level for the OTUs from *Clostridium sensu stricto* 1, the corresponding representative sequences in SILVA database were used to search against NCBI 'nr' database. Species were temporarily assigned by the best hits (P<1e-5) and further confirmation were done by comparing the relative abundances of these species determined by metagenomic shotgun sequencing method and by 16S sequencing method. The OTU 'New.ReferenceOTU52' represents *C. perfringens*, which is the most dominant OTU in some dogs, and the OTU 'FJ957494.1.1454' is corresponding to *C. hiranonis*.

Analysis of OTU tables was carried out using the R statistical environment[67], the bioconductor suite of software[68], and the Phyloseq2 package[69]. Singletons and OTUs with ambiguous annotations were removed from the OTU table. Alpha diversity (Shannon diversity index and Faith's Phylogenetic Diversity) and Beta diversity (weighted and unweighted UniFrac) were calculated using Phyloseq2. Pielou's evenness index was calculated according to the literature[70]. Functional potential of microbial communities (KEGG pathways and KEGG Orthologs) was predicted by Tax4Fun[71] with default parameters against SILVA123 database. Wilcoxon sum rank test was used for comparisons of KEGG pathways at different timepoints (FDR<0.05). Principal component analysis for KEGG pathways and orthologs was performed by the R package factoextra. For differential abundance analysis and association analysis, filtering was carried out to remove taxa with a max abundance <0.1% across all samples and present in <10% of all samples. The resulting 381 species accounted for an average 96.23% of the total microbial composition. DESeq2[72] implemented in Phyloseq2 (test="Wald", fitType="parametric") was used for differential abundance analysis on different taxonomy levels (Fold change >2 and P value <0.05) using un-rarefied reads. The Spearman correlation was computed between the abundance of each microbial composition (Log-transformed) and the values of different factors (i.e., CCECAI for each dog, time points, concentration of each metabolite). To avoid taking log of the zero value, 1 read was added to the abundance for each composition before calculating the Spearman correlation. All p values in the above analysis were adjusted by the FDR (Benjamini-Hochberg) method for multiple comparisons except where noted.

Metagenomic Sequencing and Data Analysis

Sequencing libraries were prepared using Illumina Nextera XT with Ing of canine stool collected at days 0, 14 and 42 from 19 out of the 20 diet-responsive dogs in the study. Sizing and quantification of libraries was carried out using a Tapestation 4200 (Agilent) and Qubit 3 (Thermo Fisher), respectively. Equimolar amounts of each library were pooled and sequenced on an Illumina NextSeq 500 instrument to produce 150 bp, paired-end sequences. Sequencing adapters and low quality reads were trimmed and filtered by Trimmomatic (v0.36) (leading:3 trailing:3 slidingwindow: 4:15 minlen:36). High quality reads were mapped to the canine reference genome (CanFam3.1), using Bowtie2 v2.3.4.1 (-very-sensitive), and aligned reads were removed using SamTools[73]. After host filtering, each sample was sequenced to a depth of >10 million paired-end reads (median depth=35.8 million). Taxonomic annotation for each sample was generated using Metaphlan2[46]. The identified *Clostridium* spp. and *Eubacterium* spp. were further searched for the existence of genes involved in secondary bile acid production (bai operon) using tBlastn against the reference genomes of these species in GeneBank with the protein sequence of genes in 7α-dehydroxylation pathway (baiG, baiB, baiA, baiF, baiCD and baiE) (p-value≤1e-5).

Metagenomic data from pediatric Crohn's disease patients before and after exclusive enteral nutrition (EEN) have been described previously[23] and were downloaded from European Nucleotide Archive (ENA) (SRP057027). The same filtering steps and settings for the metagenomic data analysis above in this study were used for these datasets. After filtering out human reads, taxonomic annotation for each sample using Metaphlan2 showed the presence of *Clostridium*. Among them, *Clostridium scindens* has been well known for the secondary BA producing ability. Paired reads with PCR duplicates removed by samtools[73] were aligned to the *C. scindens* reference genome (ASM15450v1, strain ATCC 35704) as well as strain VE202-05 (ASM47184v1) using bwa-mem (v0.7.17-r1188)[74] with default settings to estimate the abundances of bacteria among different samples (proportion of mapped reads in total reads). Wilcoxon sum rank test was used to test for significant differences in read mapping, and Spearman correlation was used to compare number of reads mapped with log-transformed fecal calprotectin (FCP) levels[23].

Anaerobic Culture and Identification of Bacterial Isolates by Whole Genome Sequencing Rectal swabs freshly collected from dogs with active disease (day 0) and/or in remission at the end of the study (day 42) were transferred to an anaerobic chamber (97.5% nitrogen, 2.5% hydrogen; Coy Labs, Grass Lake, MI) within one hour of collection. The tip of the swabs was homogenized in 1 mL of pre-reduced PBS with 1% cysteine (PBSc). Serial dilutions made in PBSc (down to $10^{-5}$) were plated on brain-heart infusion (BHI), yeast casitone fatty acid with carbohydrate (YCFAC)[75], gut microbiota medium (GMM)[76], and De Man, Rogosa and Sharpe (MRS)[77] agars (Anaerobe Systems, Morgan Hill, CA). After incubation at 37° C. for 1-3 days, single colonies were picked from plates and grown overnight in BHI, YCFAC, GMM, or MRS broth (Anaerobe Systems, Morgan Hill, CA). Overnight cultures were saved as glycerol stocks (25% glycerol) and frozen neat for DNA extraction. DNA was purified from bacterial isolates using the High Pure PCR template kit (Roche) and used for PCR with primers specific for the bacterial 16S rRNA gene, including 27F (5'-AGAGTT-GATCMTGGCTCAG-3' (SEQ ID NO: 5)), 515F (5'-GTGCCAGCMGCCGCGGTAA-3' (SEQ ID NO: 6)), and 1492R (5'-CGGTTACCTTGTTACGACTT-3' (SEQ ID NO: 7)). PCR products were purified using QiaQuick PCR Purification kit (Qiagen), Sanger sequenced, and sequences were assembled using Geneious software v11.1.5 (Biomatters Inc.). The longest high quality stretch of assembled sequence (at least 800 bp) was used for BLAST to find closest the match in Genbank. In addition, for selected *C. hiranonis, C. perfringens* and *E. coli* isolates, 1 ng of DNA was used to construct sequencing libraries using Illumina Nextera XT. Libraries were sized and quantified as described above for metagenomic sequencing. For each sample, at least ~10 million, 150 bp single-end reads were generated using an Illumina NextSeq 500 instrument. Quality control steps were the same as the metagenomic analysis above. High quality reads were mapped to the genome of *C. hiranonis* (ASM15605v1) using Stampy[78] (--substitution-rate=0.1), which allows mapping of reads that are highly divergent from the reference genome. PCR duplicates were removed by Samtools. Coverage of genomic regions representing the bai operon were calculated for each isolate to show the existence of genes in 7a-dehydroxylation pathway.

Metabolomics and In Vitro Bacterial Growth Inhibition Assays

Bile acids were quantified in stool using a Waters Acquity uPLC System with a QDa single quadrupole mass detector and an autosampler (192 sample capacity) as described previously[79]. Briefly, fecal samples were suspended in methanol (5 μL/mg stool), vortexed for 1 minute, and centrifuged at 13,000 g for 5 minutes. The supernatant was transferred to a new vial and analyzed on an Acquity uPLC with a Cortecs UPLC C-18+ 1.6 mm 2.1×50 mm column. All chemicals and reagents were mass spectrometry grade. Canine isolates of *C. perfringens* (n=3) and *E. coli* were revived from glycerol stocks in Modified Reinforced Clostridial Broth (MRCB, Fisher Scientific) or Luria broth (LB, Fisher Scientific), respectively and grown overnight in the anaerobic chamber at 37° C. Lithocholic and deoxycholic acids (Sigma) were dissolved in 100% ethanol (30 mg/mL). Growth inhibition by deoxycholic acid was determined by microbroth dilution and assessed by $OD_{630}$ after overnight growth. Due to low solubility (<1 mg/L), inhibition by lithocholic acid was assessed by counting colonies on agar plates with LCA (0, 0.1, 0.25, 0.5, 0.75, or 1 mg/mL and LB plates for *E. coli*, and 0, 0.01, 0.025, 0.05, 0.075, or 0.01 mg/mL and Columbia blood agar supplemented with 5% defibrinated sheep's blood for *C. perfringens* that were incubated anaerobically, at 37° C. for 24 (*E. coli*) or 48 (*C. perfringens*) hours.

Mouse Experiments

Female C57BL/6 (7 weeks old) (Jackson Laboratory) were orally pre-colonized with a kanamycin-resistant *E. coli* strain (Nissle 1917) ($1\times10^9$ CFU/mouse) 4 days prior to the to the start of dextran sulfate sodium (DSS) treatment. Animals were randomly assigned to groups (cages) at baseline and drinking water was replaced with either filter-sterilized water (mock-treatment), or a filter-sterilized solution of 2.5% (w/v) DSS (relative molecular mass ~40,000; Sigma-Aldrich) in water. The mice treated with mock or DSS were orally gavaged *C. hiranonis* ($1\times10^8$ CFU/mouse, in anaerobic PBS) or PBS (control) from days 0 to 4. *C. hiranonis* was grown overnight in MRCB, anaerobically, at 37° C. Culture density was assessed via optical density (630 nm) and the required volume of culture was spun at 10,000 g for 15 min. Bacterial pellets were resuspended in PBS to obtain a dose of $1\times10^8$ CFU/mouse. All procedures were performed in accordance with the guidelines of the University of Pennsylvania Institutional Animal Care and Use Committee. The mice were then euthanized at day eight and colon contents and tissues were collected. Colon contents were weighted and cultured on LB agar plates with kanamycin (100 μg/mL) for 16 hours. Stool samples from baseline and colon contents from day eight were collected and stored at −80° C. for the detection of bile acid levels. Colons were fixed in formalin and sections stained with haematoxylin and eosin (H&E). Pathology was blindly evaluated by an board-certified veterinary pathologist (C.B.) according to standard criteria for DSS colitis.

Data Availability

Raw 16S rRNA gene sequences for canine stool samples have been deposited in the Sequence Read Archive ($SRA_{80}$; accession number pending). Processed OTU tables and metadata can be accessed through MicrobiomeDB[56]. Metagenomic and whole genome sequence data are also available on SRA (accession numbers pending).

Results

Dietary Therapy Induces Rapid and Durable Remission

Figure 1B:
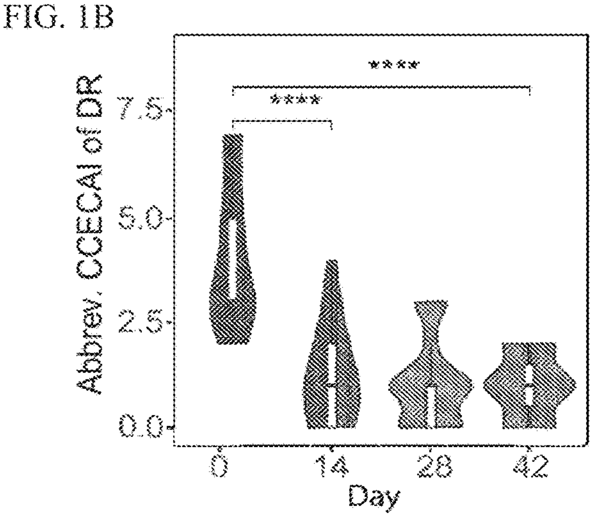
Figure 1C:
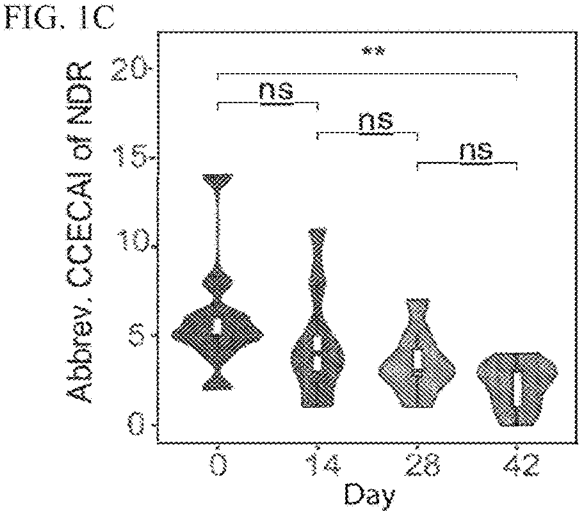
Figure 8:
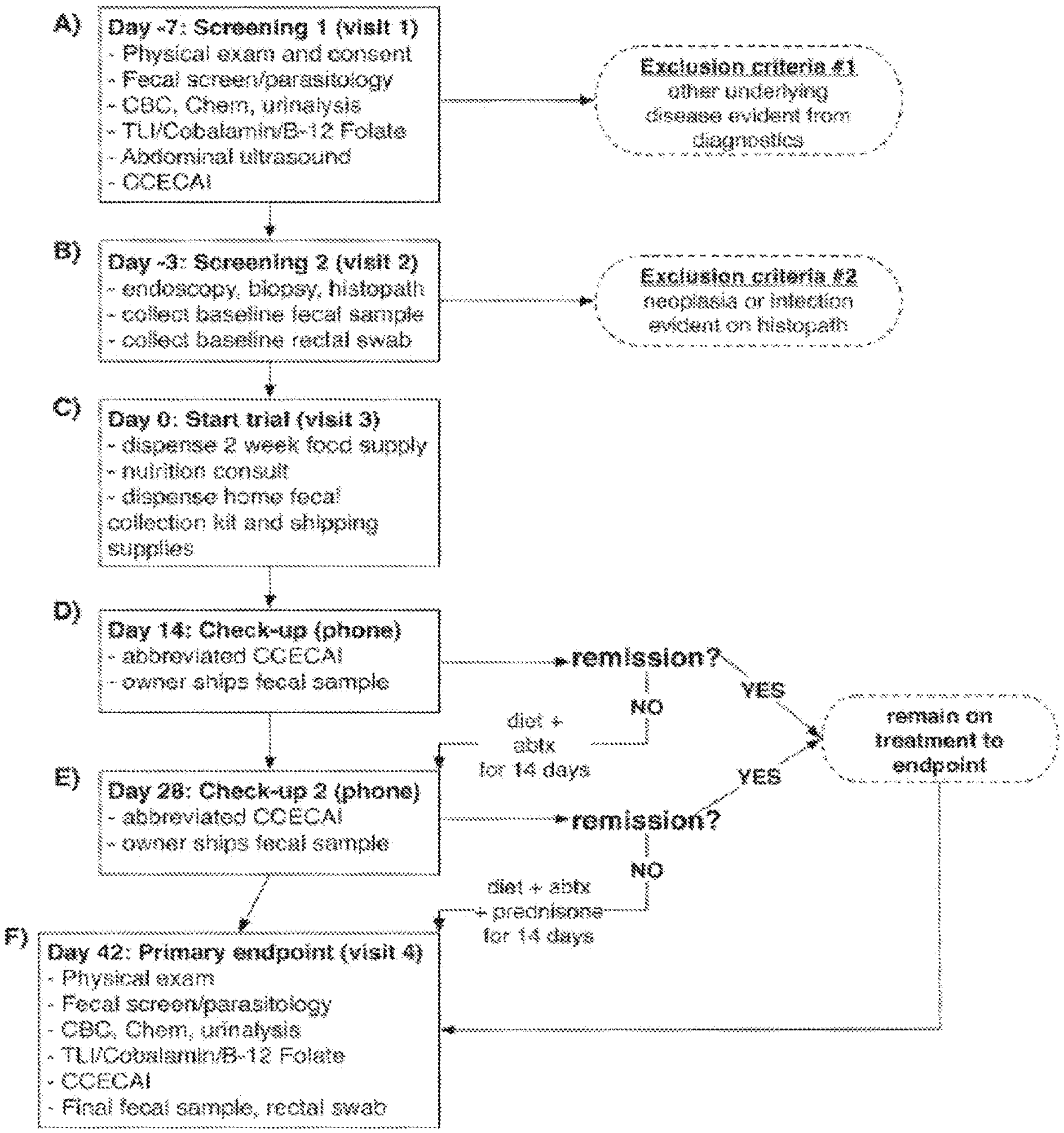
FIG. 8 depicts detailed clinical design for canine chronic enteritis study.

To investigate the impact of a therapeutic diet on disease and the microbiome, treatment-naive dogs (n=29) with chronic enteritis (CE) were enrolled in a study to evaluate the impact of diet on disease and the microbiome. Dogs with active disease were switched from their current diet to a commercially-available therapeutic hydrolyzed protein diet (FIG. 1A). Impact of treatment on disease was monitored using the Canine Chronic Enteropathy Clinical Activity Index (CCECAI; hereafter referred to as 'disease score'), which is positively correlated with poor clinical outcome[36]. After two weeks on therapeutic diet, 69% (20/29) of animals entered remission, marked by a reduction in the mean disease score from 4.1 (95% CI=4.8-3.3) to 1.3 (95% CI=1.8-0.7). These diet-responsive (DR) animals were maintained on diet for the remainder of the study with no additional interventions (FIG. 1B). At the conclusion of the study (day 42), DR animals had an mean disease score of 0.9 (95% CI=1.3-0.6), constituting an >4-fold reduction in disease severity compared to day 0 (FIG. 1B). In contrast, 31% (9/29) of animals failed to show a significant reduction in disease score after two weeks on therapeutic diet (FIG. 1C). These non-diet-responsive (NDR) animals presented with more severe disease scores (mean score=6.1; 95% CI=7.4-4.7) than DR animals (P<0.05 at day 0) and did not show a significant reduction after 2 week diet therapy (FIG. 1C). NDR animals were maintained on diet therapy for the reminder of the study, but also received combination therapy that included antibiotics (at day 14) and prednisone (at day 28) (FIG. 1A and FIG. 8, see methods), but showed only incremental improvement in disease scores (FIG. 1C). These data highlight a rapid clinical response to hydrolyzed diet in the majority of dogs with chronic enteritis.

Figure 2A:
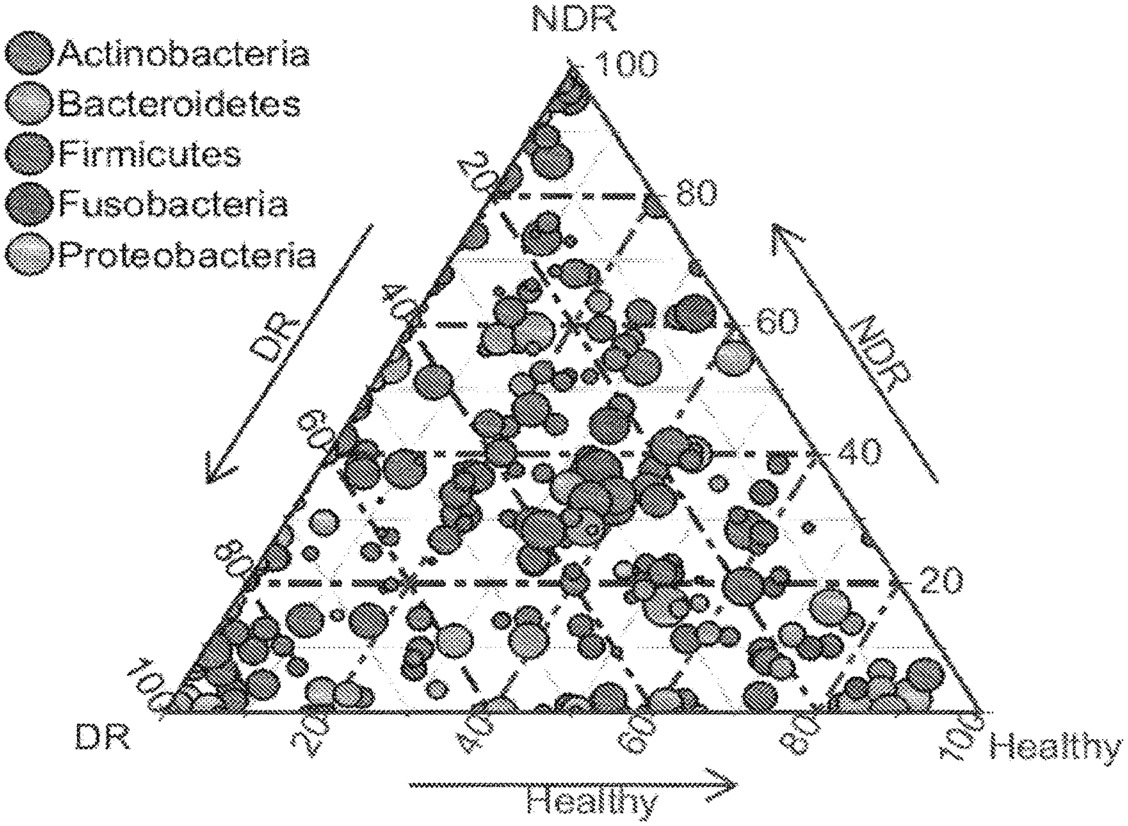
FIG. 2A-2F depict identification of microbial community profiles associated with treatment outcome.
Figure 9A:
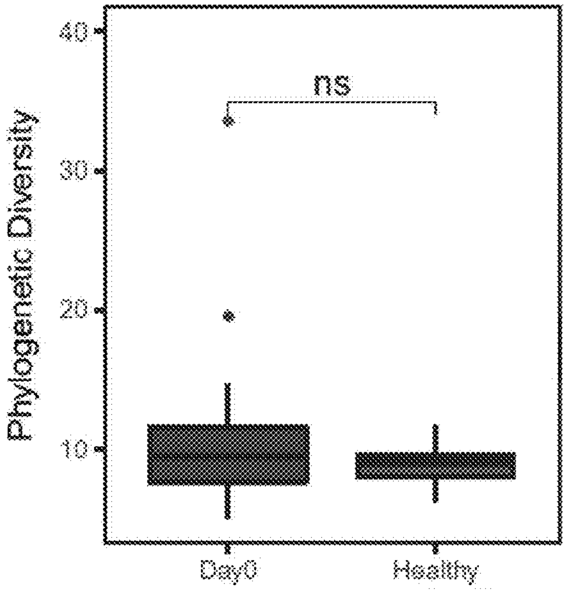
FIGS. 9A-9D depict community structures of microbiomes in the dogs with CE and in the healthy dogs. Faith's phylogenetic diversity (FIG. 9A) and Shannon index (FIG. 9B) were compared between the samples from the dogs with CE (day 0) and the samples from healthy dogs.
Figure 9B:
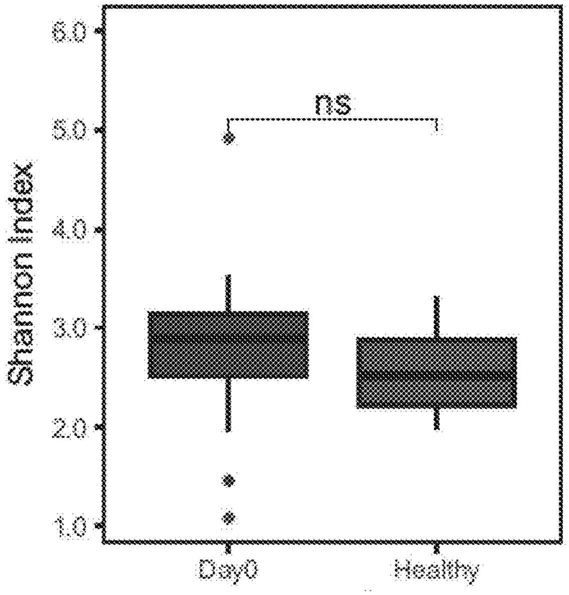
Figure 9C:
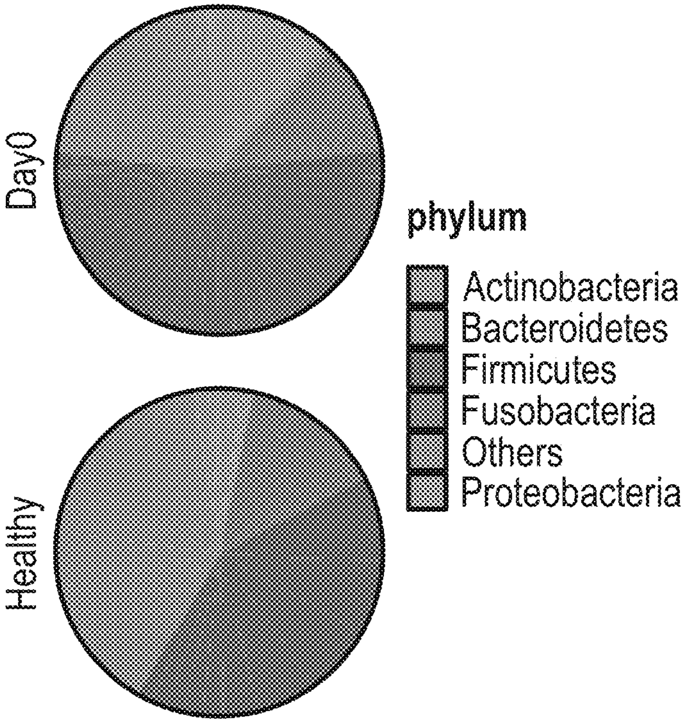
Figure 9D:
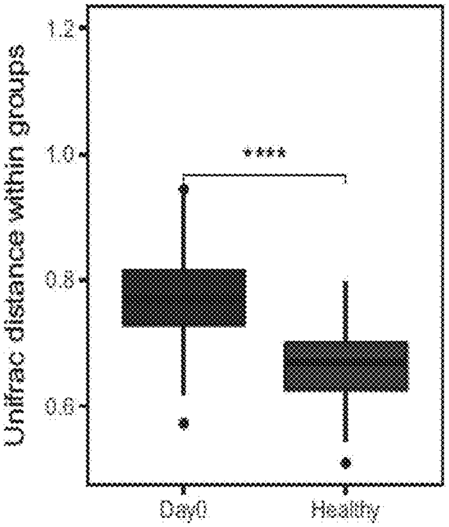

Identification of Microbial Community Profiles Associated with Treatment Outcome To determine whether treatment with hydrolyzed diet alone is sufficient to alter the microbial community in the gut, 16S rRNA gene profiling was carried out on fecal samples collected from DR, NDR and healthy control animals (n=11). Consistent with previous reports 3[8], it was found that the diversity of the canine fecal microbiome was not significantly altered in dogs with CE, compared to healthy controls (FIG. 9A-B), and that the communities in both groups were predominantly comprised of Firmicutes, Bacteroidetes, Proteobacteria, Actinobacteria, and Fusobacteria (FIG. 9C). However, compared to healthy dogs, animals with CE showed greater between-individual distance in microbial community structure by unweighted Unifrac (FIG. 9D). Using a ternary plot visualization, an enrichment of Operational Taxonomic Units (OTUs) was observed from Firmicutes and Proteobacteria in animals with active disease, while Bacteroidetes were enriched in healthy animals (FIG. 2A). Interestingly, a subset of proteobacterial OTUs was highly enriched in DR animals compared to both NDR and healthy controls (FIG. 2A), tan points in lower left corner).

Figures 2B, 2C, 2D, 2E, 2F:
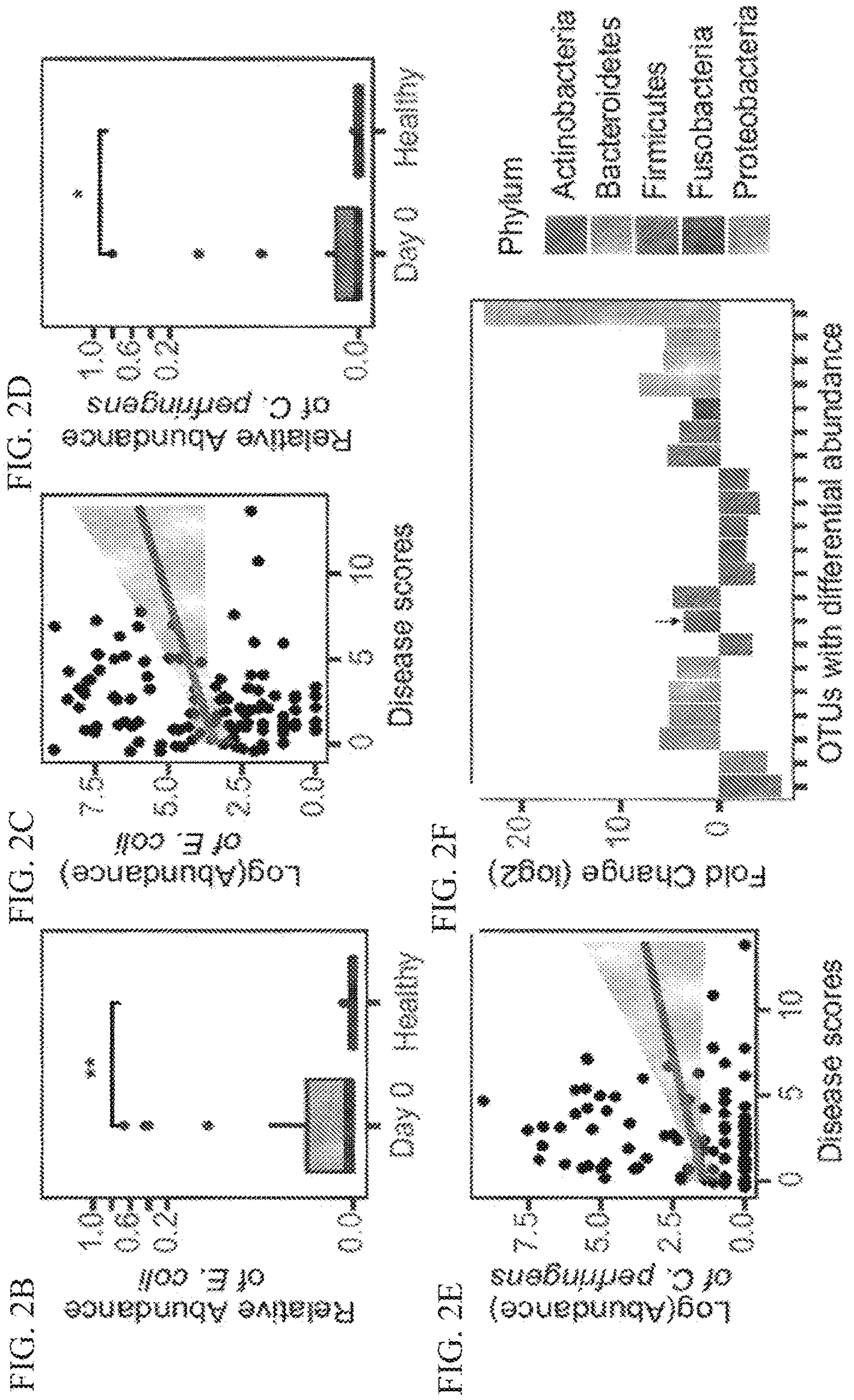

These differences prompted us to carry out a formal differential abundance analysis, identifying 55 OTUs that distinguish healthy animals from those with disease (Table 2). For example, *Escherichia coli*, which is commonly associated with intestinal diseases, was over-represented in animals with CE (FIG. 2B), showing a significant, albeit weak, positive correlation with disease score (R=0.2109, P=0.02626) (FIG. 2C). OTUs from *Clostridium* sensu stricto 1 were also enriched in CE, including *Clostridium perfringens* (FIG. 2D), which was also positively correlated with disease scores (FIG. 2E) (R=0.2324, P=0.01412). These bacteria have been implicated in large bowel diarrhea/colitis in dogs[39]. Taken together with previously published work[40], these data demonstrate that dysbiosis during CE is marked by the presence of pathobionts. Next, whether the microbiome in DR and NDR animals differed prior to the start of treatment (day 0) was investigated. Although no differences were observed between the two groups in community diversity, evenness or distance from healthy controls (unweighted or weighted Unifrac), 21 OTUs were identified that were differentially abundant between DR and NDR animals, 13 of which were enriched in animals that ended up responding to diet treatment (FIG. 2F and Table 3). Interestingly, Proteobacteria and *C. perfringens* were found to be more abundant in DR animals (FIG. 2F). Collectively, these results highlight distinct microbial signatures during disease that are associated with different clinical outcomes following diet therapy.

Therapeutic Diet Ameliorates Dysbiosis Associated with Chronic Enteritis

Figure 3A:
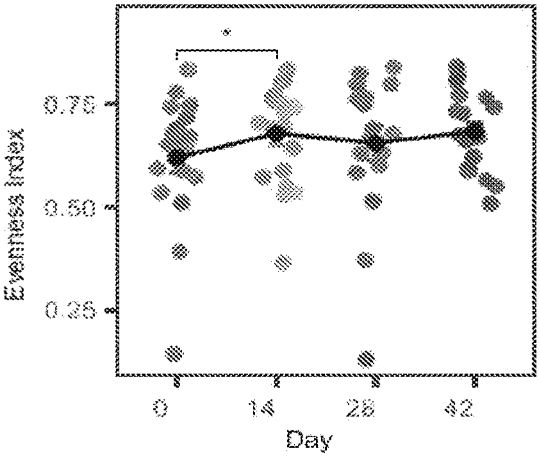
FIGS. 3A-3F depict that therapeutic diet ameliorates dysbiosis associated with chronic enteritis.
Figure 3B:
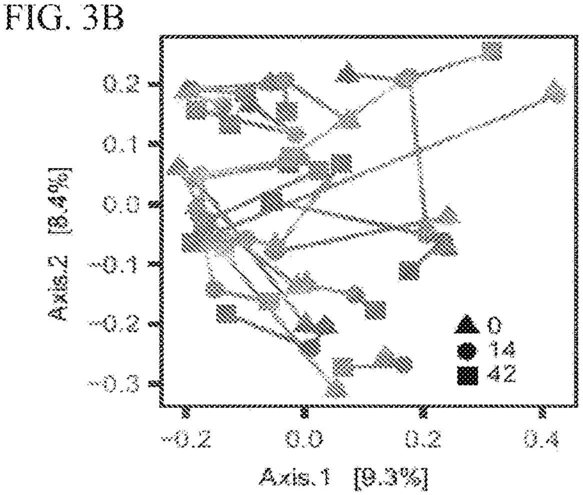
Figure 3C:
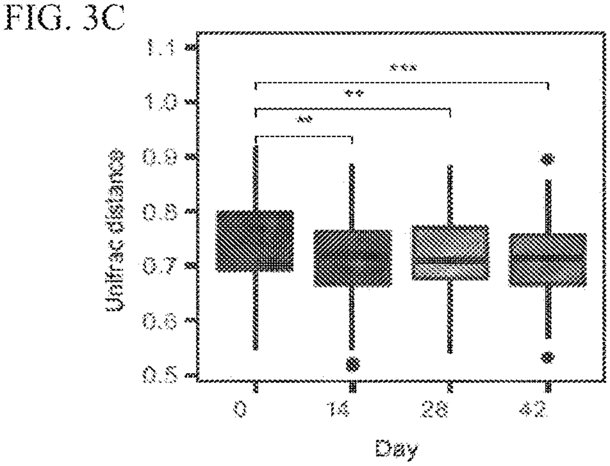
Figure 10A:
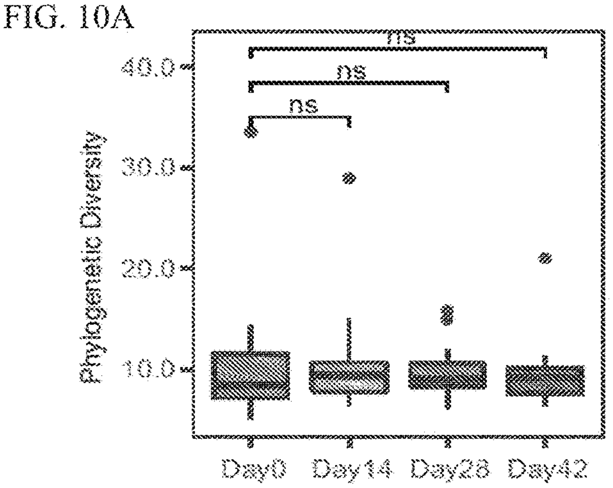
FIGS. 10A-10C depict that microbiota community structure changes induced by diet therapy in diet responsive dogs.
Figure 10B:
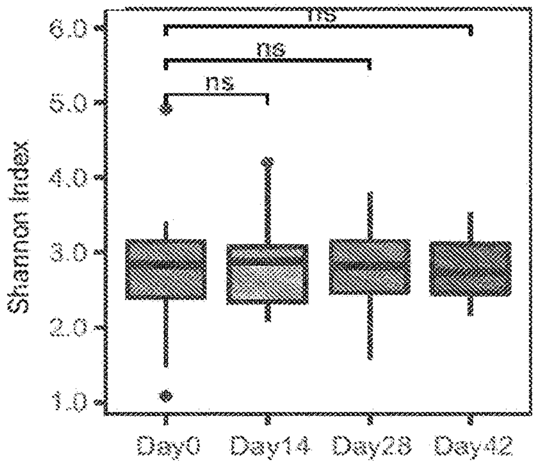
Figure 10C:
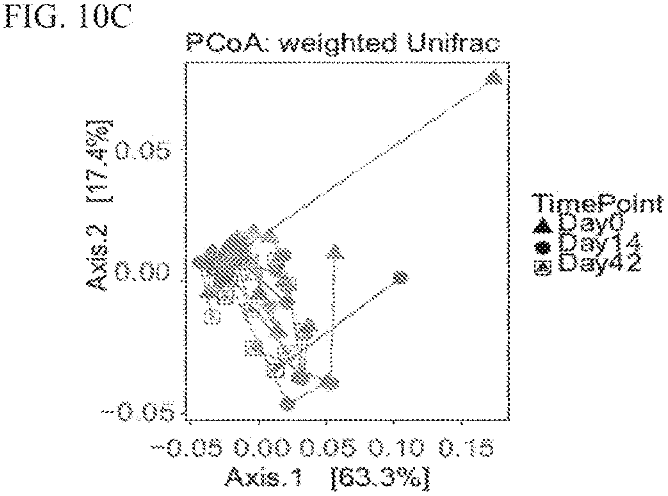

To assess whether diet-induced remission is accompanied by alterations in dysbiosis, the microbial community structures were compared before and after administration of therapeutic diet in DR animals. No significant change was observed in phylogenetic distance or shannon diversity (FIG. 10A-B) but did see a marked increase in community evenness following diet administration (FIG. 3A) when focusing on the top 40 most abundant OTUs among the samples, which account for 83% of the total reads. Principal coordinate analysis based on unweighted (FIG. 3B) or weighted (FIG. 10C) UniFrac showed a clear separation between dogs, even at day 0, before diet therapy was administered, highlighting heterogeneity in dysbiosis associated with clinical disease. Despite this baseline difference between animals, community structure underwent a marked shift away from disease-state by 14 and 42 days after diet therapy (FIG. 3B). Comparing unweighted Unifrac distances between DR and healthy animals at each time point, it was observed that diet-induced remission was marked by decreased phylogenetic distance relative to healthy controls, a trend that continued through day 42, when the phylogenetic similarity to day 0 was lowest and similarity to healthy dogs was highest (FIG. 3C).

Figure 3D:
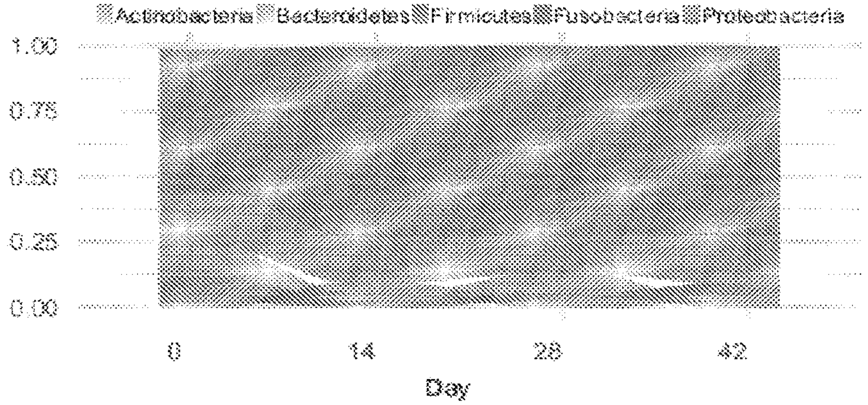
Figure 3E:
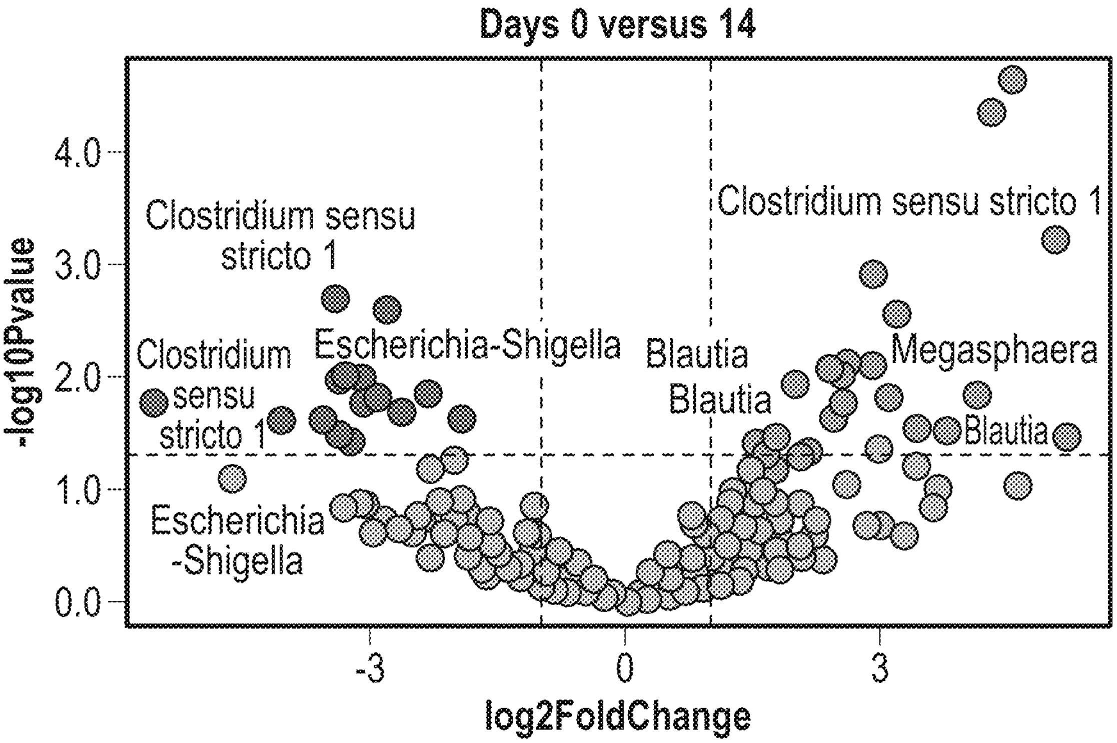
Figure 3F:
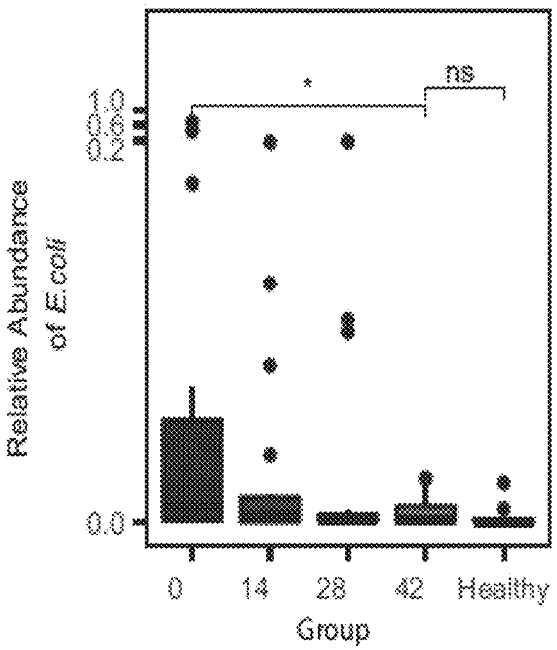
Figure 3G:
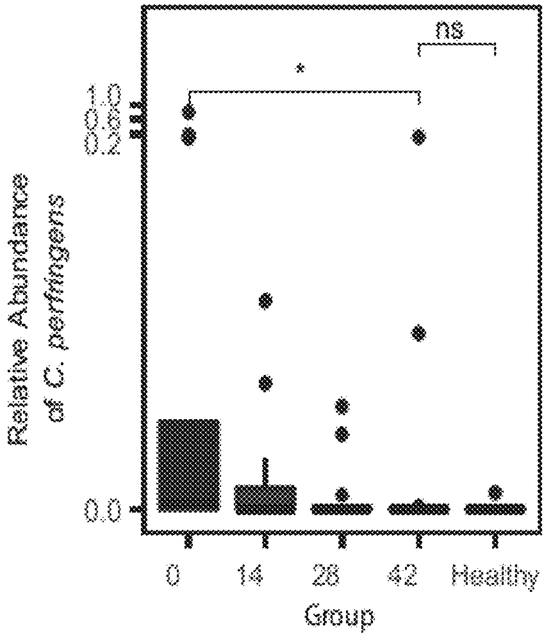

Given that therapeutic diet shifted the community structure of the microbiome in DR animals, it was reasoned that composition of the fecal microbiome would be rapidly altered by dietary intervention. Administration of therapeutic diet was broadly characterized by an increase of Firmicutes and a decrease of Proteobacteria (FIG. 3D). Fourteen days after beginning diet therapy, ten genera were differentially abundant compared to pre-treatment (day 0) in DR animals (Table 4). Potential pathogenic genera associated with IBD were found under-represented after diet treatment. For example, *Escherichia-Shigella, Clostridium* sensu stricto 1, *Enterococcus* and *Fusobacterium* had a higher relative abundance at Day 0 and were significantly reduced after 14 days on therapeutic diet. When evaluated at species level, 36 OTUs were significantly differential abundant between samples collected at day 0 compared to day 14 (FIG. 3E) (Table 5). *E. coli* was typically enriched in the animals at day 0 in this study (FIG. 3E), and its relative abundance declined dramatically after two-weeks on therapeutic diet, eventually reaching levels nearly undetectable by day 42 that were also indistinguishable from levels observed in healthy dogs (FIG. 3F). *C. perfringens* also showed significant lower prevalence in the samples at day 14 and in healthy dogs, compared to day 0 samples (FIG. 3G). In turn, several increased OTUs were from the genera that have been suggested as beneficial commensals in human studies, such as Blautia[41] (Table 5). Taken together, these results point to ameliorated dysbiosis with a reduction of pathobionts and increase of beneficial commensal taxa as a hallmark of diet therapy.

Remission-Specific Changes in the Microbiome Following Diet Therapy

Figure 4A:
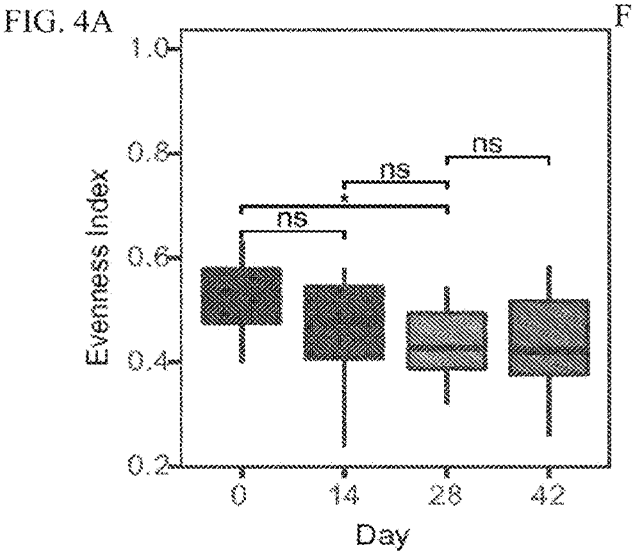
FIGS. 4A-4F depict diet-induced changes in the microbiome associated with remission.
Figure 4B:
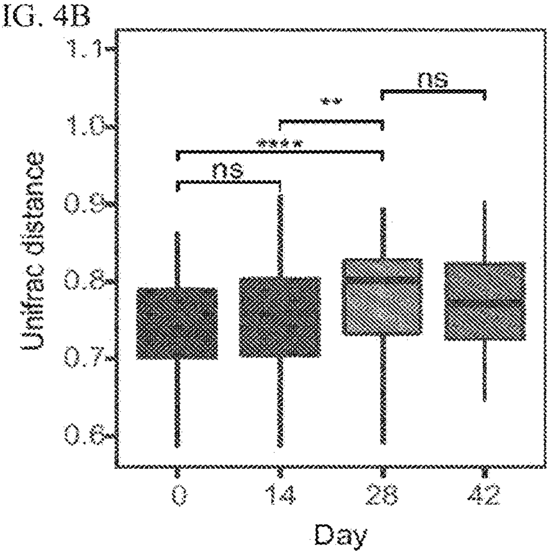
Figure 4C:
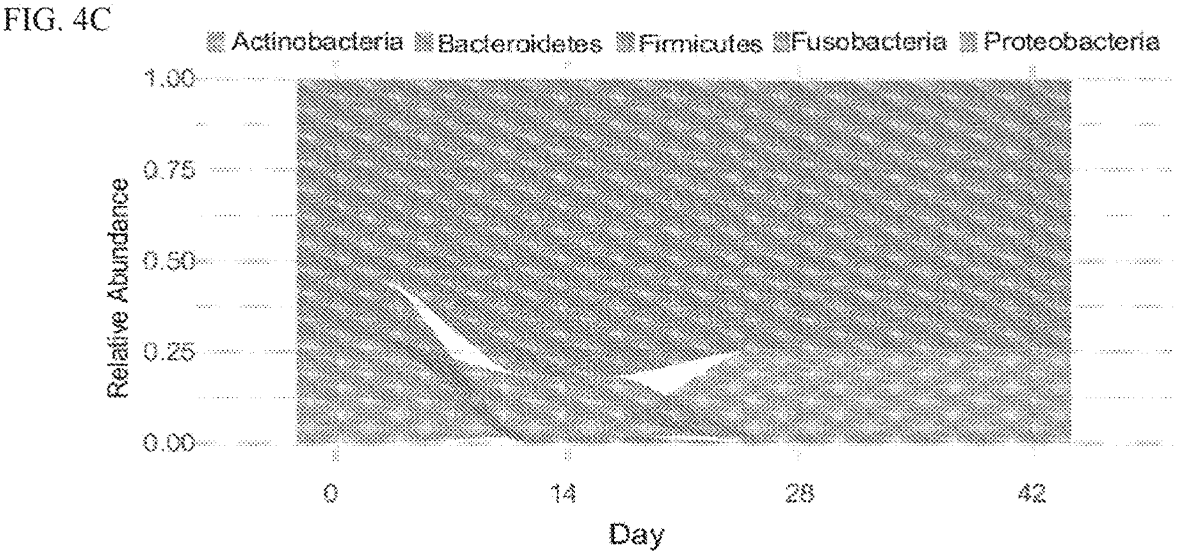
Figure 4D:
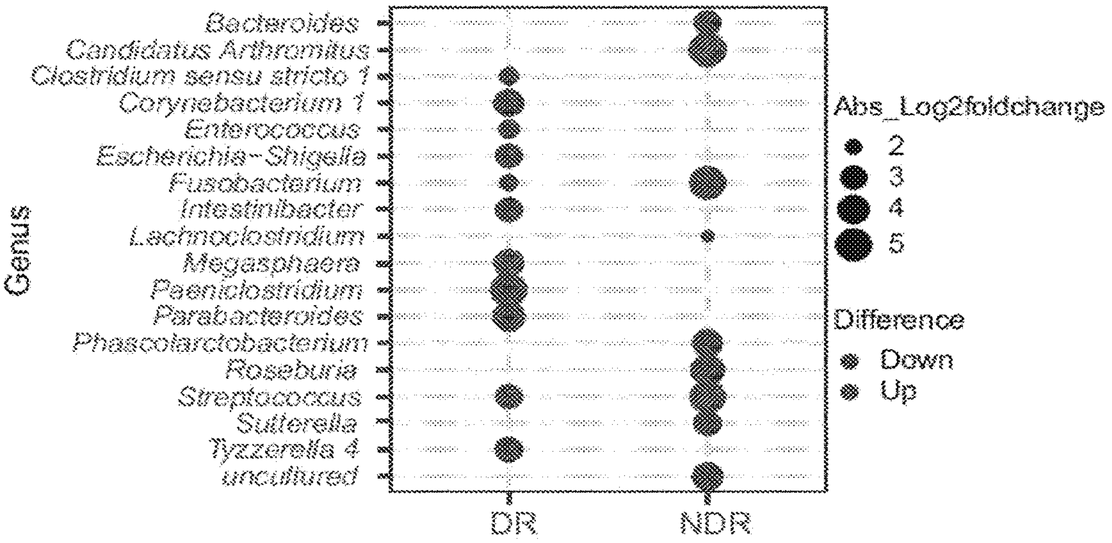
Figure 4E:
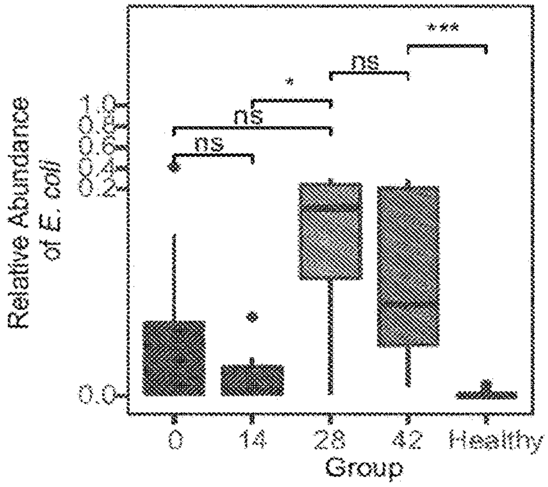
Figure 4F:
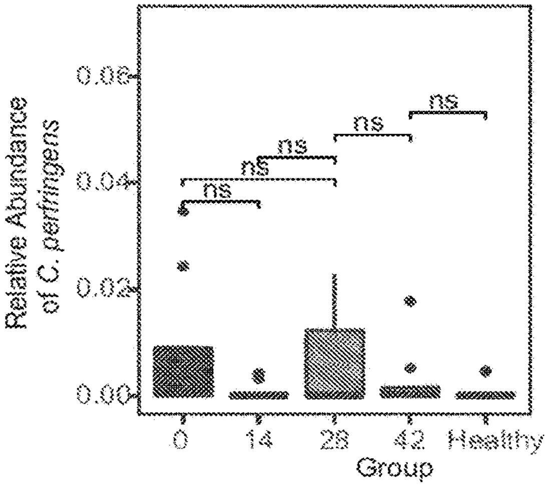
Figure 11:
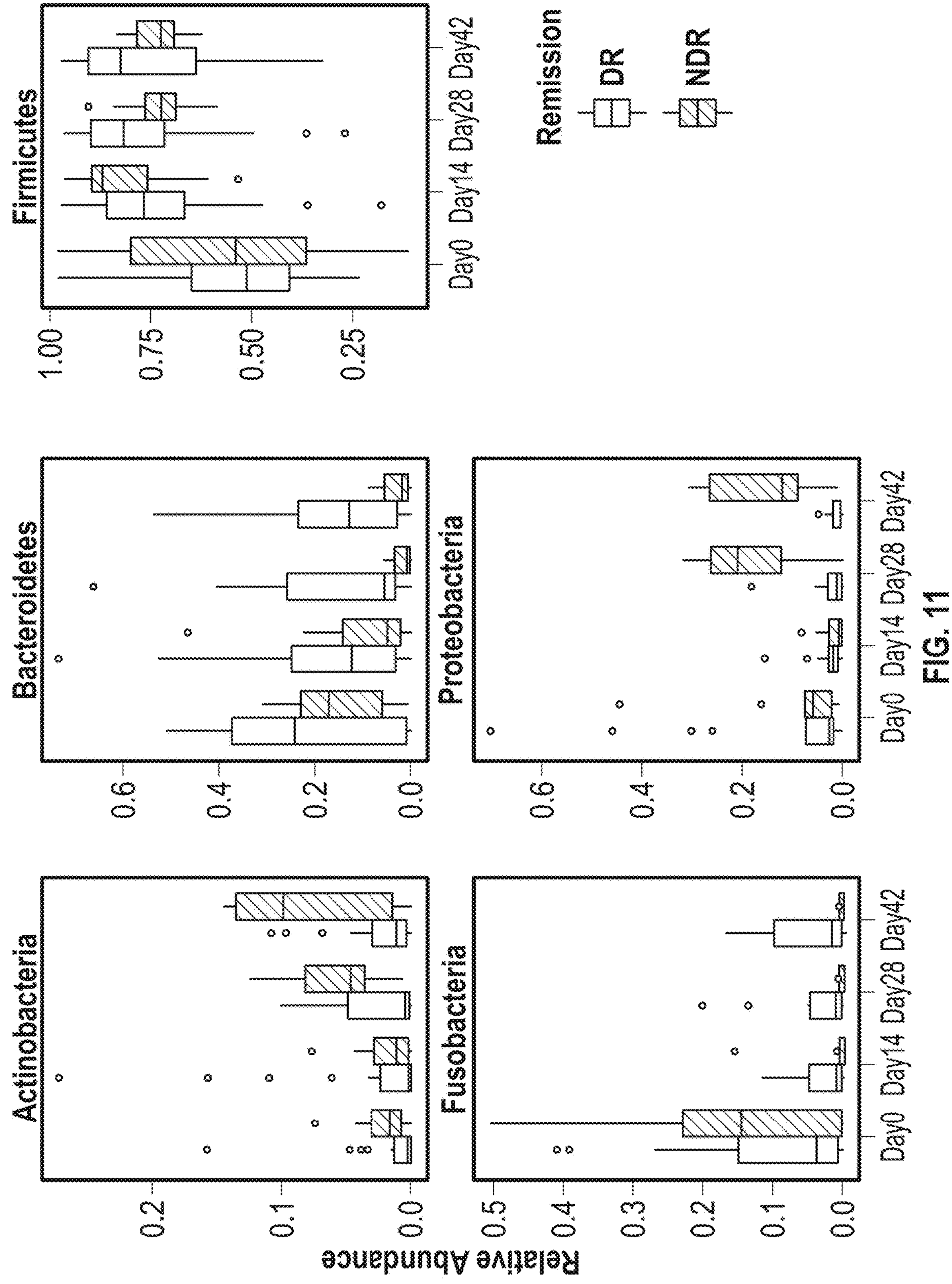
FIG. 11 depicts that dynamics of microbiome changes at a phylum level for diet responsive dogs (DRs) and non-diet responsive dogs (NDRs).

It was hypothesized that the changes observed following diet therapy in DR animals are associated with remission, rather than merely a response to diet that is independent of clinical outcome. To test this hypothesis, the impact of therapeutic diet on dogs that entered remission following diet therapy alone (DR), was compared with changes observed in non-diet-responsive (NDR) animals that failed to enter remission after diet therapy, and which require additional therapies after day 14. Whereas diet therapy in DR animals was associated with increased community evenness (FIG. 3A) and a decreased phylogenetic distance from health dogs (FIG. 3C), the same treatment in NDR dogs did not significantly affect the microbial community evenness or Unifrac distance to healthy dogs (FIGS. 4A and 4B). Just as it was observed in DR animals (FIG. 3D), diet also altered the gut microbiota compositions in NDR animals (FIG. 4C). Differential abundance analysis comparing NDR animals at day 0 versus day 14, when they received only therapeutic diet, identified 24 OTUs (Table 6). However, this shift was distinct from that observed in DR animals (FIG. 4D and FIG. 11). For example, diet therapy was associated with a decrease in the relative abundance of *Fusobacterium* and Phascolarctobacterium in NDR animals at day 14, compared to day 0, while these taxa were either unchanged or more modestly altered by diet therapy in DR animals. Conversely, *Escherichia-Shigella, Enterococcus* and some of *Clostridium* sensu stricto 1 are only reduced in animals that enter remission after diet treatment (FIG. 4D). The disease associated bacteria *E. coli* and *C. perfringens* were not significantly changed in NDR animals after diet therapy (FIGS. 4E and 4F). After 14 days on therapeutic diet, NDR dogs were maintained on diet, but were also administered metronidazole, an antibiotic that largely targets anaerobes. Interestingly, antibiotic treatment exacerbated dysbiosis, resulting in a precipitous decline in community evenness (FIG. 4A), increased distance from healthy controls (FIG. 43), and increased relative abundance of potential pathogens (FIGS. 4E and 4F).

Diet-Induced Remission is Associated with Metabolic Reprogramming and Increased Levels of Secondary Bile Acids.

Figure 5A:
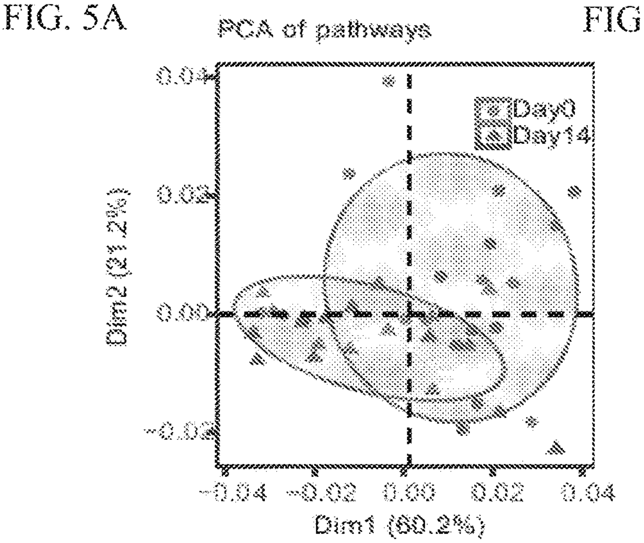
FIGS. 5A-5H depict that diet-induced remission is associated with metabolic reprogramming and increased levels of secondary bile acids.
Figure 5B:
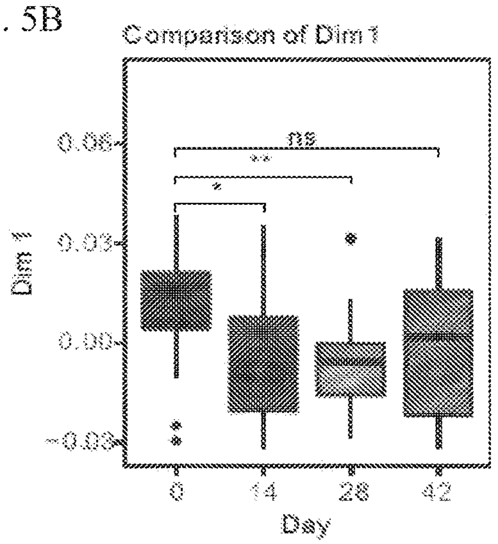
Figure 5C:
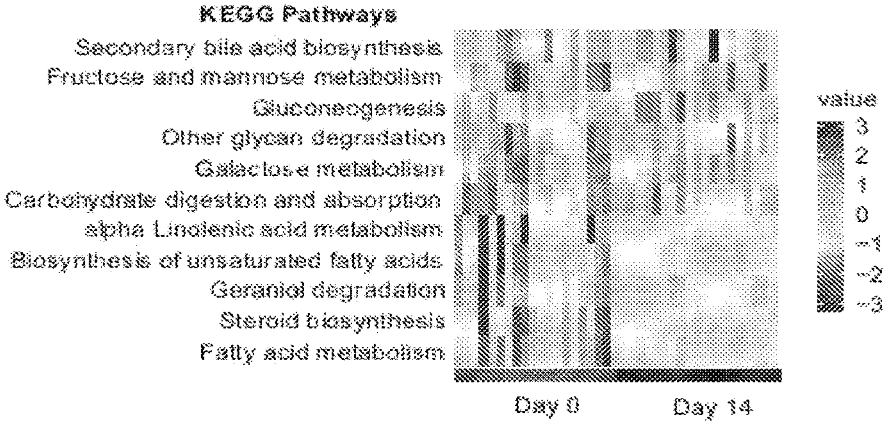
Figure 5D:
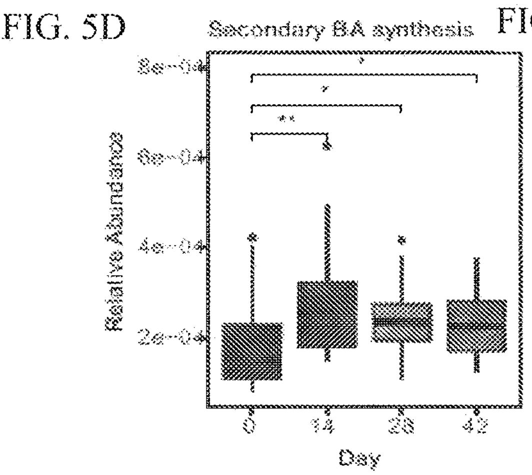
Figure 5E:
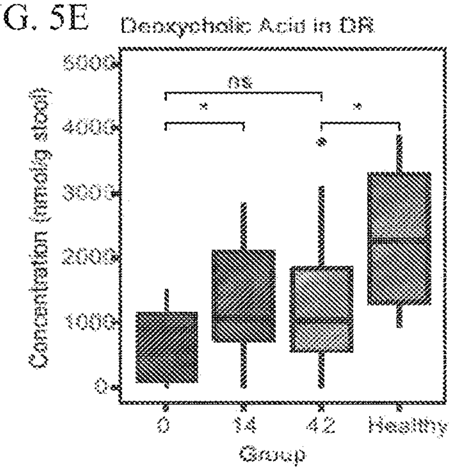
Figure 5F:
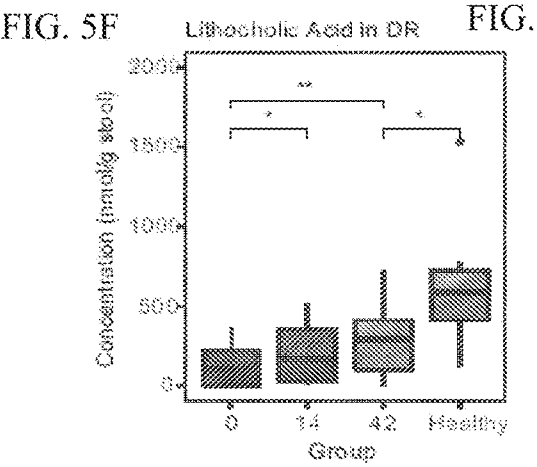
Figure 5G:
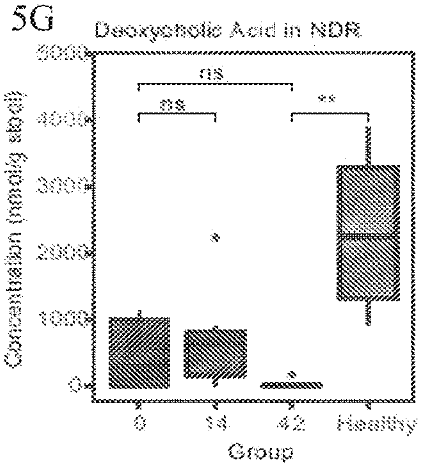
Figure 5H:
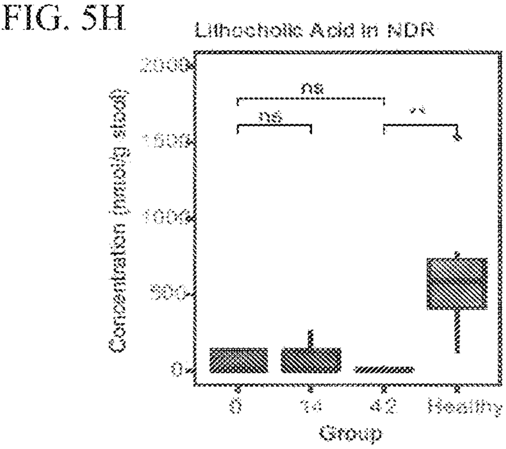
Figure 12:
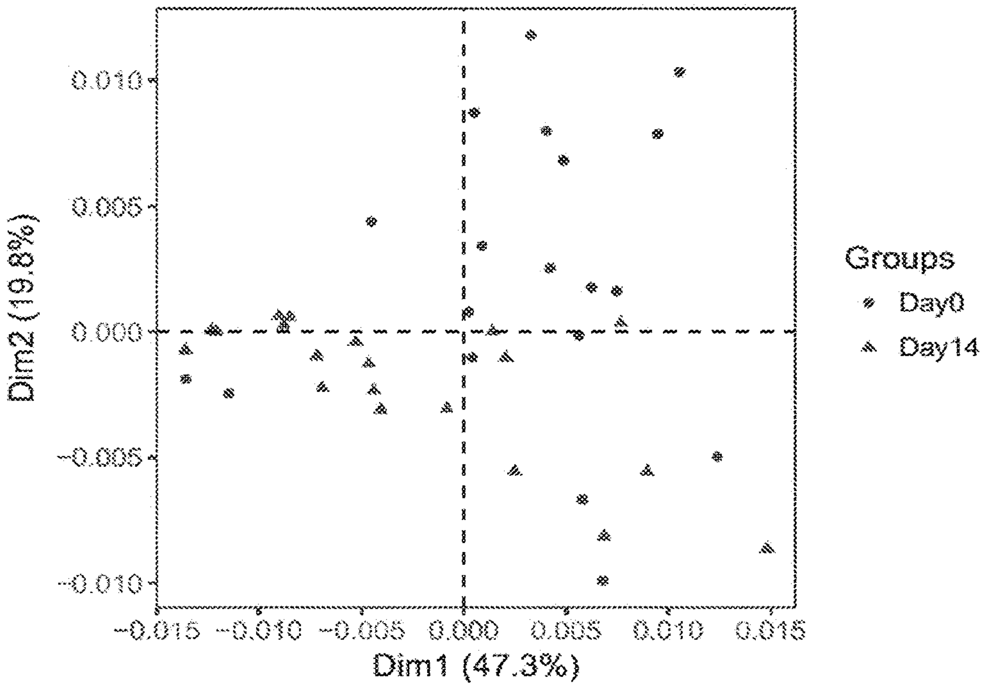
FIG. 12 depicts principal component analysis based on the abundances of KO (KEGG Orthology) for the samples of day 0 and day 14.
Figure 13:
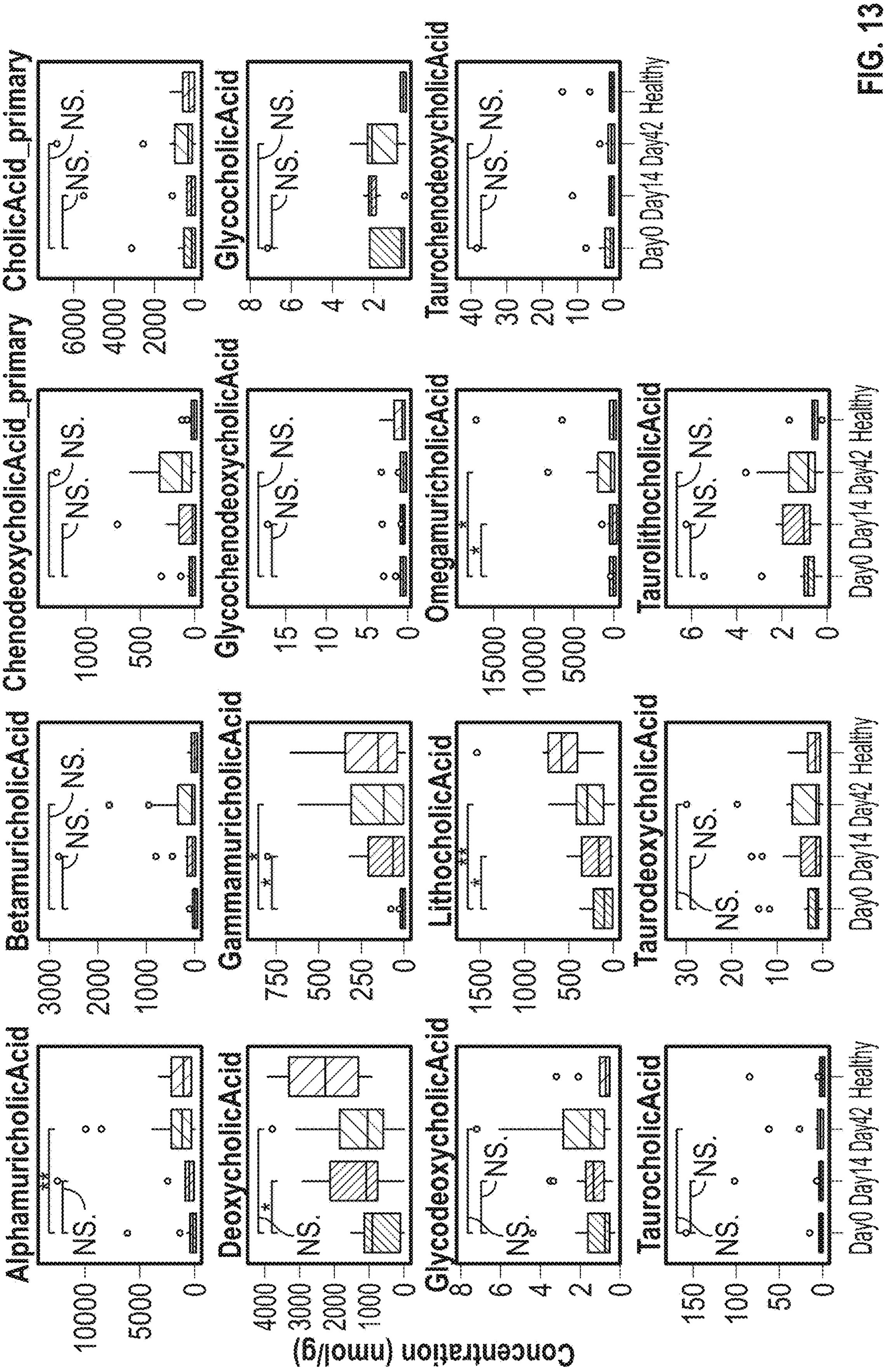
FIG. 13 depicts concentrations of bile acids detected in the fecal samples of diet responsive dogs. NS=not significant, *p<0.05, p<0.01, *p<0.0001 using Wilcoxon signed-rank test.

To determine if diet induced changes in microbial community structure would translate to altered microbial metabolism the 16S rRNA gene sequencing data were used to assess the relative abundance of predicted KEGG pathways. Principal component analysis of metabolic pathway abundance data showed a separation between samples from animals with active disease (day 0) and those in remission (day 14) (FIG. 12, FIGS. 5A and 5B). Differential abundance analysis identified 36 pathways were increased in relative abundance as a result of diet treatment in DR animals (Table 7), including several involved in carbohydrate metabolism and secondary bile acid synthesis (FIGS. 5C and 5D). In contrast, 50 pathways were reduced, including fatty acid and steroid biosynthesis (FIG. 5C). *Ibis* shift in metabolic potential away from lipid biosynthesis toward carbohydrate and bile acid synthesis as animals entered remission prompted us to quantify bile acids in stool. Using targeted metabolomics, levels of 15 bile acids in stool of healthy dogs were measured, compared with stool collected at days 0, 14 and 42 in the study (FIG. 13, Table 10). Consistent with the 16S data, the secondary bile acids deoxycholic acid (FIG. 5E) and lithocholic acid (FIG. 5F) were high in healthy controls but low in animals with active disease (day 0) and were significantly increased after the diet treatment in DR animals at day 14 and 42 (FIGS. 5E and 5F, and Table 8). Notably, levels of these secondary bile acids were not elevated by diet treatment in NDR animals (FIGS. 5G and 5H), suggesting that this metabolic shift is linked to diet-induced remission.

Lithocholic and Deoxycholic Acid Inhibit the Growth of *E. coli* and *C. perfringens*. In Vitro.

Figure 6A:
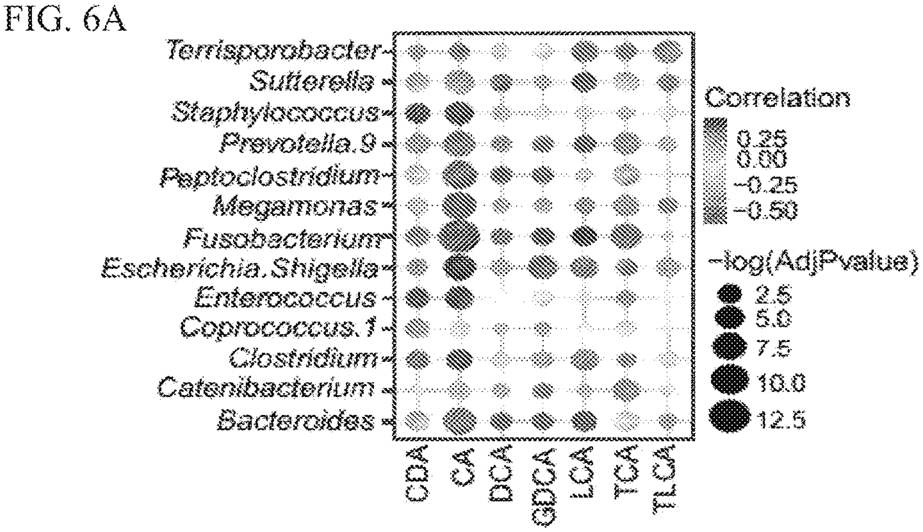
FIGS. 6A-6J depict that *C. hiranonis* is a diet-responsive species with the ability to produce secondary bile acids that inhibit the expansion of potential pathogens in vitro and in vivo.
Figure 6B:
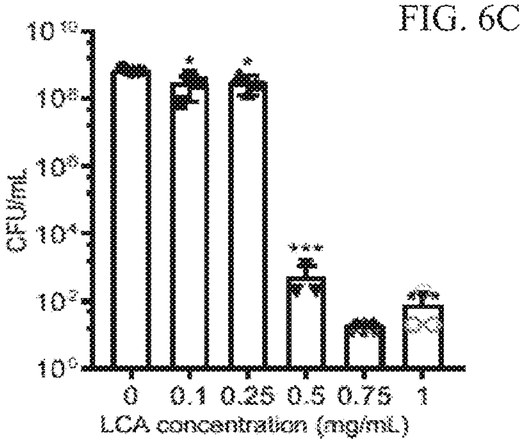
Figure 6C:
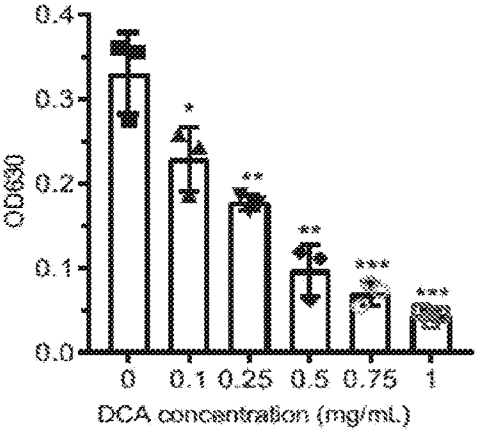
Figure 6D:
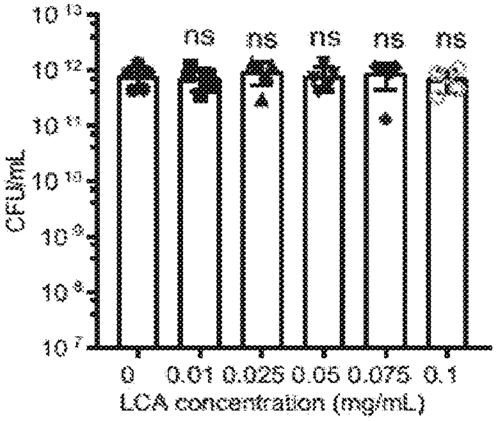
Figure 6E:
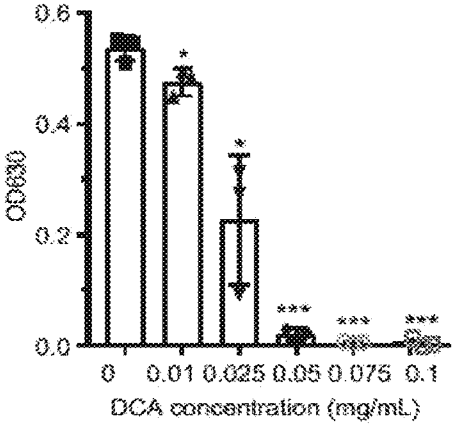

Diet-induced remodeling of the microbiome could be due, at least in part, to the inhibitory role of secondary bile acids on harmful bacteria. Correlation analysis of the metabolomics and microbiome data identified thirteen genera significantly associated with at least one bile acid (Spearman, R>0.04 or <−0.04) (FIG. 6A). The primary bile acid, cholic acid, was negatively correlated with 11 OTUs, consistent with the reported ability of this bile acid to negatively regulate bacterial growth[42]. It was also observed that the increase in secondary bile acids following diet treatment correlated with a reduction in relative abundance of certain bacteria (e.g., OTUs from *Escherichia-Shigella, Clostridium* and *Fusobacterium*) (Table 9). To directly test this hypothesis, lithocholic or deoxycholic acid were assessed for their ability to inhibit the in vitro growth of *E. coli* (n=1) or *C. perfringens* (n=3) isolates derived from the dogs with active disease, since these species or their genera were associated with disease in the animal model. Deoxycholic acid blocked the growth of both species at a concentration comparable to what was detected in the fecal samples (FIGS. 6C and 6E), while lithocholic acid blocked the growth of *E. coli* but not *C. perfringens* (FIGS. 6B and 6D, respectively). Collectively, these results show that the inhibitory activity of these bile acids varies for different bacteria and suggest that elevated secondary bile acids observed following diet therapy can contribute to the decrease of potentially harmful bacteria.

*C. hiranonis* is a Diet-Responsive Species with the Ability to Produce Secondary Bile Acids.

Figure 6F:
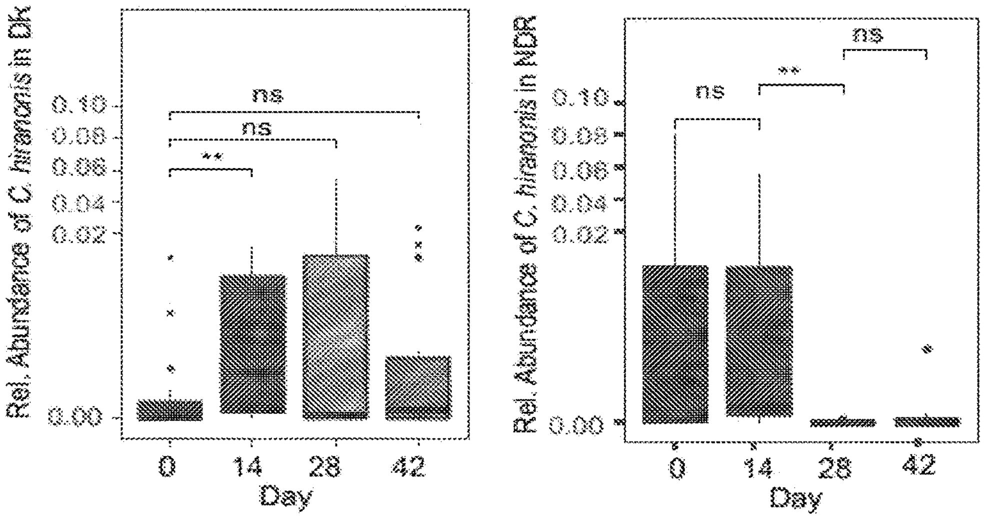
Figure 6G:
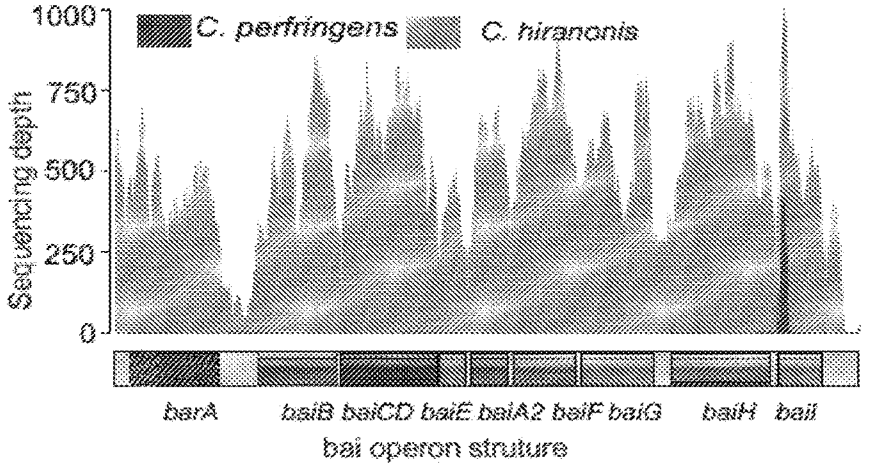
Figure 14:
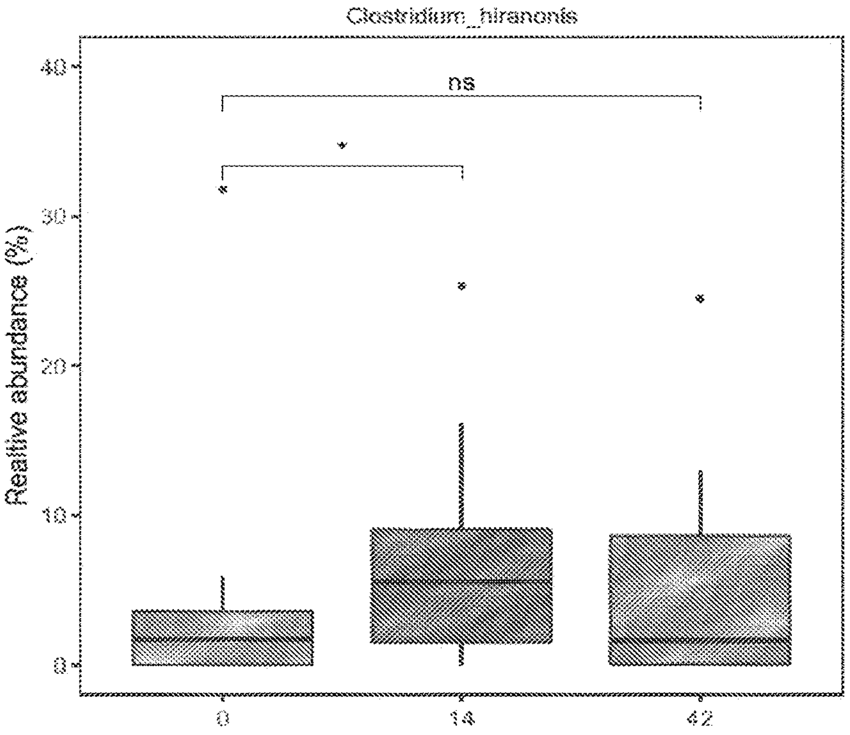
FIG. 14 depicts relative abundance of *C. hiranonis* in diet responsive dogs calculated from metagenomic data.

Next, the source of lithocholic and deoxycholic acids after diet treatment was identified. Production of these from primary bile acids requires the 7-dehydroxylation activity conferred by the bile acid-inducible (bai) operon—an activity unique to a limited number of anaerobes representing a small fraction of the microbiome, including some Clostridial and Eubacterial species 4. Given the finding that certain clostridial OTUs, as well as levels of lithocholic and deoxycholic acids, increase after diet-induced remission (FIG. 3G and FIG. 5E-F, respectively), potential bile acid producers in DR animals were identified. Stool samples collected day 0, 14 and 42 after starting diet therapy were subjected to metagenomic sequencing. Taxonomic assignment of reads identified six *Clostridium* species (*C. perfringens, C. hiranonis, C. nexile, C. colicanis. C. glycolicum* and *C. ramosum*) and 2 *Eubacterium* species (*Eubacterium biforme* and *E. dolichum*) present in these samples at a relative abundance >0.01% in at least 10% samples. Of these species only *C. hiranonis* has been reported to have the bai operon[44], and this was confirmed by BLAST against the reference genomes of these species in GenBank. Moreover, the metagenomic data (FIG. 14) and 16S sequencing data showed that the relative abundance of *C. hiranonis* was significantly increased after diet treatment in DR animals (FIG. 6F, left) but not in NDR animals that failed diet therapy (FIG. 6F, right). Since the *Clostridium* genus exhibits a high level of genetic divergence, even at the species level, that canine *C. hiranonis* possesses the bai operon was confirmed. Anaerobic culture of rectal swabs collected during the study, followed by isolate picking and Sanger sequencing of full-length 16S rRNA gene, was used to assemble a canine culture collection from 7 dogs with chronic enteritis before and/or after treatment. In total, 49 *Clostridium* isolates belonging to 5 species were identified (*C. baratii, C. perfringens, C. sartagoforme, C. hiranonis*, and *C. lactatifermentans*). 82% (31/39) of the clostridial isolates from animals with active disease were *C. perfringens*, consistent with the reported involvement of this organism in canine[39] and human[45] gastrointestinal disease. Two *C. hiranonis* isolates were obtained from independent diet-responsive animals in remission at day 42. These *C. hiranonis* isolates and three *C. perfringens* isolates were selected for whole genome sequencing. Reads were aligned to the reference *C. hiranoni*, revealing an intact bai operon in canine *C. hiranonis*, but not *C. perfringens* (FIG. 6G). Taken together, these data point to *C. hiranonis*, a species originally isolated from human stool[44], as a likely bile acid producer associated with diet-induced remission in dogs.

Figure 6H:
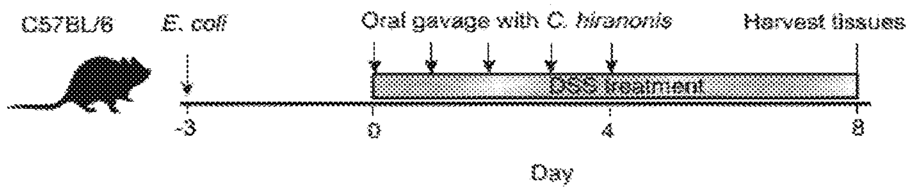
Figure 6I:
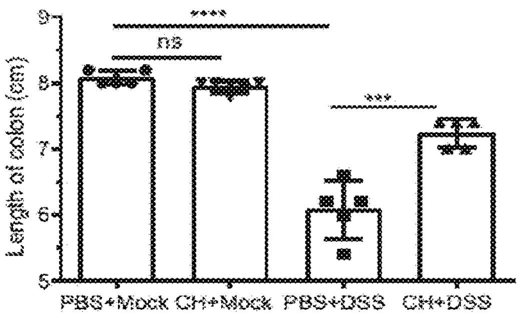
Figure 6J:
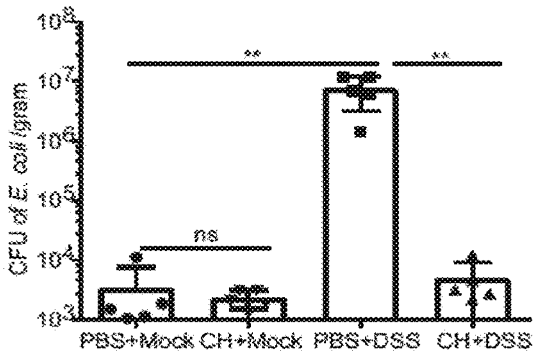

*C. hiranonis* Inhibits Inflammation-Induced Expansion of *E. coli* in a Mouse Model of DSS Colitis The ability of *C. hiranonis* to produce secondary bile acids, combined with the observation that lithocholic and deoxycholic acids were potent inhibitors of *E. coli* and *C. perfringens* growth, in vitro, prompted us to test whether *C. hiranonis* could restrict expansion of potential pathogens in vivo during inflammation. Mice were first colonized with drug-selectable *E. coli* (Nissle 1917 strain), inflammation was triggered by administration of dextran sodium sulfate (DSS) in the drinking water, and animals were either orally administered PBS daily (mock) or *C. hiranonis* (FIG. 6H). DSS treatment resulted in reduced colon length (FIG. 6I), and a dramatic bloom of the *E. coli* Nissle strain (FIG. 6J). In contrast, DSS-treated mice that received *C. hiranonis* daily showed a marked reduction of colonic shortening, and a near complete abrogation of *E. coli* expansion. Taken together with the finding that lithocholic and deoxycholic acids can inhibit growth of pathobionts, these data suggest that *C. hiranonis* or secondary bile acids produced by this species, mediate colonization resistance during enteritis.

Figure 7A:
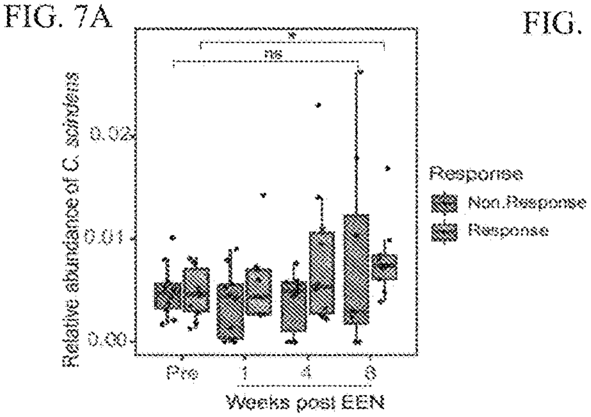
FIGS. 7A-7E depict that the bile acid producer, *C. scindens*. is associated with diet-induced remission in human pediatric Crohn's disease. Analysis of public data[23] from human pediatric Crohn's disease patients treated with exclusive enteral nutrition (EEN). Relative abundance of reads (mapping ratio) aligning to *C. scindens* reference (FIG. 7A) or bai operon (FIG. 7B) from 20 patients at pretreatment and 1, 4 and 8 weeks following administration of EEN. Patients that responded to treatment and entered remission (n=10, red) and those that failed therapy (n=10, green) are shown.
Figure 7B:
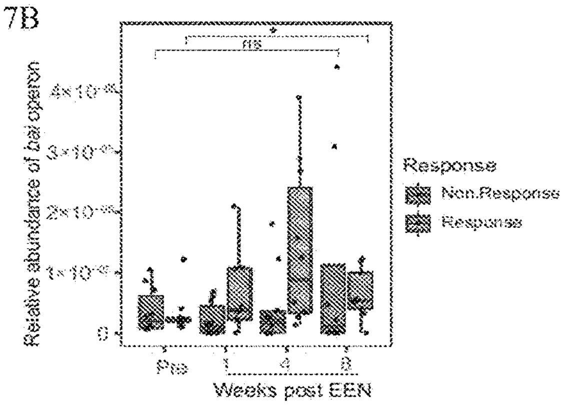
Figure 7C:
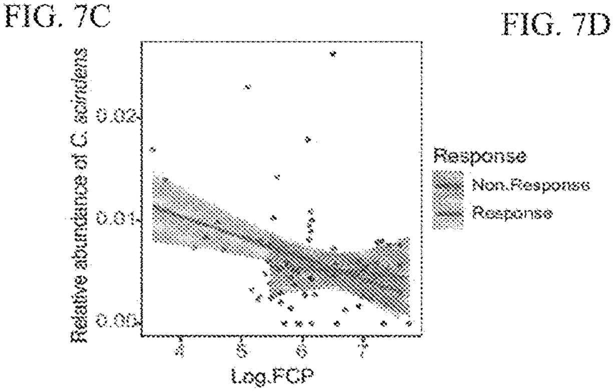
Figure 7D:
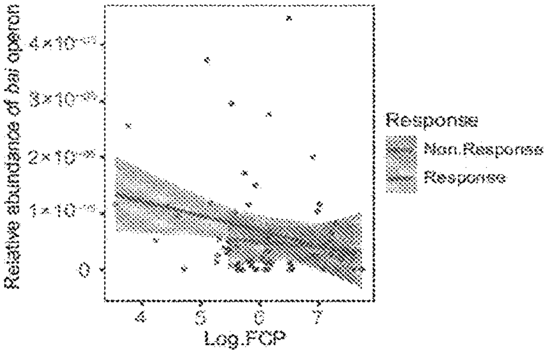
Figure 7E:
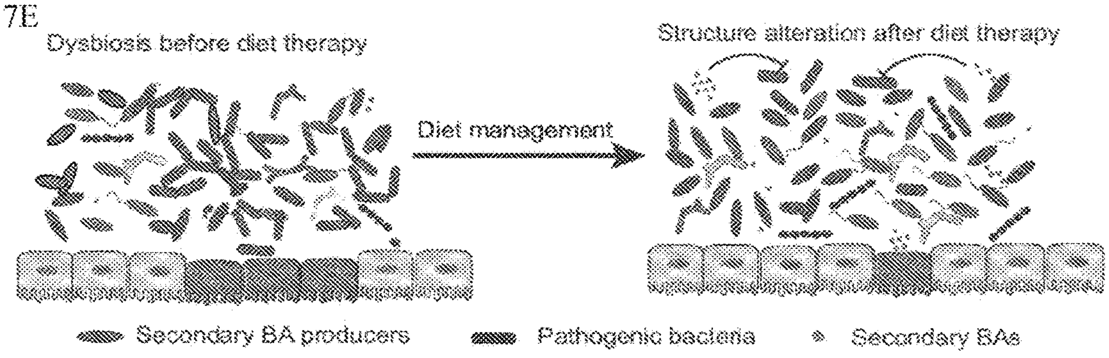

*C. scindens* is Associated with Diet-Induced Remission in Pediatric Crohn's Disease Given that high remission rates are observed in both dogs and humans following dietary therapy, it was hypothesized that a similar induction of bai operon-containing clostridia can occur in pediatric Crohn's disease patients being treated with exclusive enteral nutrition (EEN). To test this, publicly available data from a recent study that examined approximately 20 patients before and after treatment with EEN were analyzed[23], in which half responded to treatment while other half failed EEN therapy. Classifications of bacterial taxa present in each sample using standard metagenomic analysis methods[46] revealed the presence of *C. scindens*, which is recognized for having high 7-dehydroxylation activity[44,47]. The relative abundance was further estimated using the proportion of total reads that map the reference genome of *C. scindens*. As shown in FIG. 7A, this bacterium increased significantly from pretreatment to 8 weeks post-EEN, as did the number of reads mapping to the bai operon (FIG. 7B). Remarkably, this increase was only observed in patients that entered remission following EEN (Responsive, n=10) but not those that failed therapy (Non.Responsive, n=10) (FIGS. 7A and 7B). In addition, the correlation analysis between the relative abundance of *C. scindens* and fecal calprotectin (FCP), a biomarker of disease activity for IBD[23], indicated a significantly negative correlation (FIG. 7C) in EEN 'Responsive' patients (R=−0.3515, P=0.03287), but not in EEN 'Non.Responsive' patients (R=−0.0267, P=0.877). Similarly, a significant negative correlation between bai operon and FCP was observed in diet-responsive (R=−0.3944, P=0.0157), but not non-responsive patients (R=0.0490, P=0.7766)(FIG. 7D). These results collectively point to bile acid producing clostridia as key features of diet-induced remission and potent inhibitors of pathobiont colonization in both animals and humans (FIG. 7E).

Discussion

Using a diet-responsive animal model to study the role of the microbiome in chronic enteritis, remission-specific changes in microbiome composition and function were identified. All animals enrolled in the study had active disease, yet their baseline microbiome composition differed greatly (FIG. 3), perhaps reflecting variation in their environment, genetic background (breed), age and weight. This variation in composition supports the idea that enteric disease is driven not by a single dysbiotic state, but rather dysbiosis reflects a loss of community stability[48]. Rather than dramatic changes in microbial community structure following diet therapy, a shift from lipid metabolism to carbohydrate and bile acid synthesis was observed. Although the metabolomics analysis was focused on bile acids, a broader picture of the metabolites produced before and after diet therapy, as well as the macro- and micronutrients present in the diets themselves, can improve the understanding of the mechanisms by which diet achieves remission.

One important open question is precisely how therapeutic diets such as EEN or prescription pet foods alter the microbiome and whether there are general principles that could be used to guide the development of better dietary therapies. Studies in pediatric Crohn's disease have reported higher remission rates with EEN compared to partial enteral nutrition (PEN), which includes some table food. These observations have led some to postulate that a highly monotonous diet that is reduced in complexity can constitute an essential part of nutritional therapies for IBD. Consistent with this notion, mice fed a monotonous diet exhibited lower microbial diversity and were more susceptible to DSS colitis than mice fed an alternating diet[49]. However, the prevalence and treatment of chronic enteritis in veterinary medicine highlights that disease routinely develops even when diets are monotonous and that rapid and robust remission can be achieved with solid food. Hydrolyzed protein diets, such as the one used in the study, have been shown to be effective in the management of canine chronic enteropathies[50,51], and have previously been shown to be more effective for long term management when compared to a highly digestible diet formulated with non-hydrolyzed protein sources[50,51]. While it is uncertain what characteristic of these hydrolyzed formulas are driving the response, the low molecular weight of hydrolyzed proteins can reduce their ability to be recognized by the immune system while providing improved digestibility. In summary, the results suggest that the dog would be a useful model to dissect the beneficial and harmful roles of different diets, particularly since formulated diets have long been a standard of care for treating numerous diseases in companion animals.

Secondary bile acids and bile acid-producing clostridial species were identified as key features of diet-induced remission in humans and dogs. These findings complement recent studies examining the mechanisms by which fecal microbiota transplant (FMT) cure *Clostridium difficile* infection[52]. Buffy et al. identified *Clostridium scindens* as associated with resistance to *C. difficile* infection in both humans and mice, and they showed that transfer of *C. scindens*, or a consortium containing this organism, protected mice from *C. difficile* challenge. Moreover, inhibition of *C. difficile* growth in vitro by *C. scindens* was associated with secondary bile acid production. These data are consistent with microbiological studies showing that primary bile acids induce germination of *C. difficile*, while certain secondary bile acids can block vegetative growth[53]. Although *C. dfficile* was not observed in the animals, *C. perfringens* and *E. coli* were identified as major disease-associated taxa, and it was shown that physiologic levels of secondary bile acids potently block in vitro growth of these organisms. It is not known whether bile acids can restrict these organisms in vivo in the canine model but elucidating these mechanisms could have important health implications beyond veterinary medicine. Although *C. difficile* is the leading cause of nosocomial diarrhea in humans, *C. perfringens* and *E. coli* are both common human commensals and have been implicated in both diarrheal disease and colitis in humans and dogs. Moreover, the ability of *C. perfringens* to produce numerous toxins make it a leading cause of foodborne illness and soft tissue infections. Interestingly, when data from a cohort of pediatric Crohn's disease patients before and after diet therapy were examined, it was found that *C. scindens* was associated with diet-induced remission (FIG. 7), and a related study showed that sustained remission following EEN was characterized by low levels of proteobacteria, while patients that relapsed showed a marked increase in proteobacteria[54]. The data, together with previous studies in dogs[35,35], highlight the importance of leveraging animal models and advocate for the use of newly developed analytical methods[55] and database approaches[56,57] for comparing across multiple microbiome studies to take a 'One Health' approach that could identify conserved themes in host-microbiome interactions.

*C. difficile* infections frequently arise after antibiotic treatment, a phenomenon attributed to the effect of antibiotics on secondary bile acid levels[58]. Interestingly, it was also observed that antibiotics antagonized the diet-induced shifts in microbiome composition and function, promoting a more dysbiotic state coincident with dramatically reduced levels of lithocholic and deoxycholic acid (FIG. 4 and FIG. 5). Taken together, these data support a more general model for microbe-microbe interactions in the gut in which bile acid producing clostridia restrict the growth of a range of bile acid-sensitive pathobionts to limit disease and highlight that these processes are exquisitely sensitive to antimicrobials. The parallels between the findings and those reported for FMT and *C. scindens* would suggest that FMT might also be beneficial for treating enteritis. Clinical trials testing this hypothesis in IBD patients have shown moderate success, in marked contrast to *C. dfficile* infections where FMT is curative for the vast majority of patients[59]. This discrepancy can be related to different pathobionts contributing to IBD pathogenesis. Interestingly, colitis is a common side-effect observed in cancer patients undergoing immune checkpoint blockade, and a recent study demonstrated complete resolution of this colitis following FMT[60], raising the possibility that bile acid producers can be important in treating certain types of colitis.

TABLE 2

OTUs with differential abundances between samples of healthy dogs and dogs with CCE at day 0 (Fold change > 2 and P-value < 0.05).

| OTU | Base Mean | log2 Fold Change | P value | Kingdom | Phylum | Class | Order | Family | Genus | Species |
|---|---|---|---|---|---|---|---|---|---|---|
| HQ802983.1.1440 | 134.78 | −9.14 | 3.28E−10 | Bacteria | Firmicutes | Clostridia | Clostridiales | Lachnospiraceae | *Tyzzerella* 4 | NA |
| FJ950694.1.1472 | 2052.29 | −5.56 | 6.45E−09 | Bacteria | Proteobacteria | Gammaproteobacteria | Enterobacteriales | Enterobacteriaceae | *Escherichia-Shigella* | *Escherichia coli* |
| HG798451.1.1400 | 30.74 | −6.70 | 1.14E−07 | Bacteria | Firmicutes | Bacilli | Lactobacillies | Enterococcaceae | *Enterococcus* | *Enterococcus durans* |
| New.ReferenceOTU52 | 676.55 | −6.51 | 8.89E−07 | Bacteria | Firmicutes | Clostridia | Clostridiales | Clostridiaceae 1 | *Clostridium sensu stricto* 1 | perfringes |
| New.ReferenceOTU82 | 35.49 | −4.87 | 6.27E−05 | Bacteria | Firmicutes | Clostridia | Clostridiales | Clostridiaceae 1 | *Clostridium sensu stricto* 1 | NA |
| GQ449092.1.1375 | 69.30 | −7.04 | 7.97E−05 | Bacteria | Firmicutes | Clostridia | Clostridiales | Lachnospiraceae | *Tyzzerella* | NA |
| FJ506371.1.1371 | 34.88 | −5.40 | 0.00012 | Bacteria | Firmicutes | Erysipelotrichia | Erysipelotrichales | Erysipelotrichaceae | *Erysipelatoclostridium* | NA |
| GQ448744.1.1393 | 81.06 | −6.86 | 0.00011 | Bacteria | Bacteroidetes | Bacteroidia | Bacteroidales | Bacteroidaceae | *Bacteroides* | *Ambiguous_taxa* |
| FJ957494.1.1454 | 19.18 | −6.33 | 0.00037 | Bacteria | Firmicutes | Clostridia | Clostridiales | Clostridiaceae 1 | *Clostridium sensu stricto* 1 | *Ambiguous_taxa* |
| HQ760911.1.1437 | 11.66 | −5.91 | 0.00045 | Bacteria | Firmicutes | Clostridia | Clostridiales | Lachnospiraceae | *Anaerostipes* | NA |
| GQ006324.1.1342 | 10.73 | −5.77 | 0.00084 | Bacteria | Actinobacteria | Actinobacteria | Corynebacteriales | Corynebacteriaceae | *Corynebacterium* 1 | uncultured bacterium |
| GQ448246.1.1389 | 313.30 | −3.87 | 0.00079 | Bacteria | Bacteroidetes | Bacteroidia | Bacteroidales | Bacteroidaceae | *Bacteroides* | *Ambiguous_taxa* |
| KC245406.1.1465 | 3.79 | −3.70 | 0.0007 | Bacteria | Firmicutes | Clostridia | Clostridiales | Lachnospiraceae | *Lachnoclostridium* | uncultured bacterium |
| New.ReferenceOTU54 | 39.95 | −5.91 | 0.0009 | Bacteria | Firmicutes | Clostridia | Clostridiales | Lachnospiraceae | *Blautia* | uncultured bacterium |
| HQ751549.1.1448 | 10.41 | −4.70 | 0.0012 | Bacteria | Firmicutes | Clostridia | Clostridiales | Lachnospiraceae | uncultured | NA |
| JF712675.1.1540 | 6.38 | −5.03 | 0.0012 | Bacteria | Proteobacteria | Gammaproteobacteria | Enterobacteriales | Enterobacteriaceae | *Escherichia-Shigella* | uncultured bacterium |
| JQ208181.1.1352 | 148.49 | −2.99 | 0.0012 | Bacteria | Firmicutes | Clostridia | Clostridiales | Lachnospiraceae | [*Ruminococcus*] *gauvreauii* group | *Ambiguous_taxa* |
| GX182404.8.1529 | 3.29 | −4.08 | 0.0020 | Bacteria | Proteobacteria | Gammaproteobacteria | Enterobacteriales | Enterobacteriaceae | *Escherichia-Shigella* | NA |
| FP929060.3837.5503 | 375.58 | −1.82 | 0.0020 | Bacteria | Firmicutes | Clostridia | Clostridiales | Lachnospiraceae | NA | NA |
| FN667392.1.1495 | 12.19 | −5.97 | 0.0025 | Bacteria | Firmicutes | Bacilli | Lactobacillus | Lactobacilluse | *Lactobacillus* | uncultured bacterium |
| FN667422.1.1495 | 5.84 | −4.33 | 0.0034 | Bacteria | Firmicutes | Bacilli | Lactobacillies | Lactobacilliae | *Lactobacillus* | *Ambiguous_taxa* |
| HK557089.3.1395 | 1340.69 | −3.02 | 0.0046 | Bacteria | Firmicutes | Bacilli | Lactobacillies | Streptococcaceae | *Streptococcus* | uncultured bacterium |
| HQ803964.1.1435 | 335.70 | −2.90 | 0.0046 | Bacteria | Firmicutes | Clostridia | Clostridiales | Lachnospiraceae | *Lachnoclostridium* | uncultured bacterium |
| AM276759.1.1484 | 6.84 | −2.87 | 0.0045 | Bacteria | Firmicutes | Clostridia | Clostridiales | Lachnospiraceae | *Blautia* | uncultured bacterium |
| HK555938.1.1357 | 21.72 | −6.40 | 0.0054 | Bacteria | Actinobacteria | Coriobacteriia | Coriobacteriales | Coriobacteriaceae | *Collinsella* | uncultured bacterium |
| KF842598.1.1394 | 22.60 | −6.80 | 0.0054 | Bacteria | Bacteroidetes | Bacteroidia | Bacteroidales | Porphyromonadaceae | *Parabacteroides* | NA |
| HQ792778.1.1436 | 5.38 | 3.62 | 0.0058 | Bacteria | Bacteroidetes | Bacteroidia | Bacteroidales | Bacteroidaceae | *Bacteroides* | uncultured |
| FM865905.1.1392 | 8.52 | −5.45 | 0.0066 | Bacteria | Firmicutes | Clostridia | Clostridiales | Clostridiaceae 1 | *Clostridium sensu stricto* 1 | NA |
| FN563300.1.1447 | 1147.14 | −1.92 | 0.0064 | Bacteria | Firmicutes | Clostridia | Clostridiales | Lachnospiraceae | *Blautia* | uncultured bacterium |
| HQ754680.1.1441 | 10.15 | −2.20 | 0.0065 | Bacteria | Firmicutes | Clostridia | Clostridiales | Lachnospiraceae | NA | NA |
| GQ867426.1.1494 | 3.36 | −4.08 | 0.0072 | Bacteria | Proteobacteria | Gammaproteobacteria | Enterobacteriales | Enterobacteriaceae | *Escherichia-Shigella* | uncultured bacterium |
| EU470512.1.1400 | 2.07 | −3.40 | 0.0079 | Bacteria | Proteobacteria | Gammaproteobacteria | Enterobacteriales | Enterobacteriaceae | *Escherichia-Shigella* | uncultured bacterium |
| AY239462.1.1500 | 2.71 | −3.20 | 0.0080 | Bacteria | Firmicutes | Clostridia | Clostridiales | Lachnospiraceae | [*Ruminococcus*] *gauvreauii* group | *Ambiguous_taxa* |
| New.ReferenceOTU114 | 8.57 | −3.10 | 0.0091 | Bacteria | Firmicutes | Bacilli | Lactobacillies | Streptococcaceae | *Streptococcus* | uncultured bacterium |
| FN668375.4306350.4307737 | 9.14 | −4.09 | 0.0093 | Bacteria | Firmicutes | Clostridia | Clostridiales | Peptostreptococcaceae | NA | NA |
| AB009242.1.1451 | 8.33 | −4.81 | 0.0097 | Bacteria | Spirochaetae | Spirochactes | Spirochactales | Spirochaetaceae | *Treponema* 2 | NA |
| HQ792787.1.1438 | 1.61 | 3.45 | 0.0128 | Bacteria | Bacteroidetes | Bacteroidia | Bacteroidales | Bacteroidaceae | *Bacteroides* | uncultured bacterium |
| AB506370.1.1516 | 5.92 | −4.63 | 0.0194 | Bacteria | Bacteroidetes | Bacteroidia | Bacteroidales | Prevotellaceae | *Prevotellaceae* UCG-001 | *Ambiguous_taxa* |
| DQ057365.1.1393 | 5.11 | −4.42 | 0.0202 | Bacteria | Firmicutes | Clostridia | Clostridiales | Lachnospiraceae | Lachnoclostridium | *Ambiguous_taxa* |
| FN667084.1.1493 | 8.26 | −3.53 | 0.0216 | Bacteria | Firmicutes | Bacilli | Lactobacillus | Lactobacilloeae | *Lactobacillus* | uncultured bacterium |

TABLE 2-continued

OTUs with differential abundances between samples of healthy dogs and dogs with CCE at day 0 (Fold change > 2 and P-value < 0.05).

| OTU | Base Mean | log2 Fold Change | P value | Kingdom | Phylum | Class | Order | Family | Genus | Species |
|---|---|---|---|---|---|---|---|---|---|---|
| DQ113765.1.1450 | 1500.29 | 3.82 | 0.0230 | Bacteria | Bacteroidetes | Bacteroidia | Bacteroidales | Bacteroidaceae | *Bacteroides* | NA |
| HK694029.9.1487 | 6.57 | −2.66 | 0.0244 | Bacteria | Firmicutes | Erysipelotrichia | Erysipelotrichales | Erysipelotrichaceae | *Faecalitalea* | NA |
| AJ270486.1.1241 | 10.92 | −4.24 | 0.0290 | Bacteria | Firmicutes | Clostridia | Clostridiales | Lachnospiraceae | *Coprococcus* 1 | *Ambiguous_taxa* |
| EU768569.1.1352 | 5.69 | −3.37 | 0.0314 | Bacteria | Firmicutes | Clostridia | Clostridiales | Ruminococcaceae | *Ruminiclostridium* 9 | uncultured bacterium |
| FM179752.1.1686 | 1.66 | −3.11 | 0.0324 | Bacteria | Proteobacteria | Gammaproteobacteria | Enterobacteriales | Enterobacteriaceae | *Pseudocitrobacter* | NA |
| JF807116.1.1260 | 2.54 | −3.70 | 0.0351 | Bacteria | Euryarchaeota | Methanobacteria | Methanobacteriales | Methanobacteriaceae | *Methanobrevibacter* | uncultured archaeon |
| FJ957528.1.1445 | 14.75 | −5.09 | 0.0356 | Bacteria | Firmicutes | Clostridia | Clostridiales | Clostridiaceae 1 | *Sarcina* | uncultured bacterium |
| KC504009.1.1465 | 3.67 | −3.15 | 0.0350 | Bacteria | Proteobacteria | Gammaproteobacteria | Enterobacteriales | Enterobacteriaceae | *Escherichia-Shigella* | NA |
| GQ448506.1.1374 | 304.58 | −1.58 | 0.0335 | Bacteria | Firmicutes | Clostridia | Clostridiales | Lachnospiraceae | *Blautia* | uncultured bacterium |
| JF224013.1.1362 | 2.89 | −3.89 | 0.0390 | Bacteria | Bacteroidetes | Bacteroidia | Bacteroidales | Porphyromonadaceae | *Porphyromonas* | uncultured bacterium |
| EU774020.1.1361 | 12.85 | 2.51 | 0.0391 | Bacteria | Fusobacteria | Fusobacteriia | Fusobacteriales | Fusobacteriaceae | *Fusobacterium* | uncultured bacterium |
| GQ448486.1.1387 | 48.95 | −2.72 | 0.0384 | Bacteria | Firmicutes | Clostridia | Clostridiales | Lachnospiraceae | *Blautia* | uncultured bacterium |
| HQ793763.1.1451 | 13.41 | 3.32 | 0.0434 | Bacteria | Bacteroidetes | Bacteroidia | Bacteroidales | Bacteroidaceae | *Bacteroides* | NA |
| JN387556.1.1324 | 164.12 | −2.78 | 0.0459 | Bacteria | Firmicutes | Clostridia | Clostridiales | Peptostreptococcaceae | *Intestinibacter* | NA |
| New.ReferenceOTU109 | 34.47 | 3.54 | 0.0488 | Bacteria | Bacteroidetes | Bacteroidia | Bacteroidales | Bacteroidaceae | *Bacteroides* | NA |

TABLE 3

OTUs with differential abundances between day 0-samples of diet responsive dogs and diet non-responsive dogs.

| OTU | Base Mean | log2 Fold Change | P value | Kingdom | Phylum |
|---|---|---|---|---|---|
| JRPJ01000002.1034290.1035971 | 111.72 | 8.05 | 0.000330185 | Bacteria | Proteobacteria |
| JF920309.1.1340 | 22.79 | 5.56 | 0.00409 | Bacteria | Proteobacteria |
| FJ978526.1.1378 | 8.93 | 5.36 | 0.04034 | Bacteria | Proteobacteria |
| New.ReferenceOTU45 | 47.39 | 23.74 | 3.66E−14 | Bacteria | Proteobacteria |
| HK555938.1.1357 | 19.48 | −6.16 | 0.04481 | Bacteria | Actinobacteria |
| FJ957494.1.1454 | 20.74 | −3.37 | 0.01429 | Bacteria | Firmicutes |
| New.ReferenceOTU52 | 1115.31 | 3.54 | 0.01242 | Bacteria | Firmicutes |
| DQ797046.1.1403 | 14.74 | 4.64 | 0.02361 | Bacteria | Firmicutes |
| GQ449092.1.1375 | 15.00 | −3.58 | 0.04561 | Bacteria | Firmicutes |
| AMCI01001631.34.1456 | 77.88 | −4.66 | 0.00349 | Bacteria | Bacteroidetes |
| KF842598.1.1394 | 6.52 | 5.98 | 0.02931 | Bacteria | Bacteroidetes |
| HQ793763.1.1451 | 5.57 | 5.09 | 0.01396 | Bacteria | Bacteroidetes |
| DQ113765.1.1450 | 201.87 | 5.02 | 0.00453 | Bacteria | Bacteroidetes |
| ACBW01000012.3536.5054 | 4.37 | 4.18 | 0.02909 | Bacteria | Bacteroidetes |
| HK693629.1.1491 | 23.00 | −2.59 | 0.01037 | Bacteria | Firmicutes |
| JQ208053.1.1336 | 14.50 | 2.58 | 0.04454 | Bacteria | Fusobacteria |
| GQ493166.1.1359 | 231.28 | −2.75 | 0.00391 | Bacteria | Firmicutes |
| GQ448486.1.1387 | 39.63 | −4.02 | 0.00023 | Bacteria | Firmicutes |
| GQ491426.1.1332 | 461.01 | −2.89 | 0.03894 | Bacteria | Firmicutes |
| New.ReferenceOTU54 | 18.10 | 5.21 | 0.00152 | Bacteria | Firmicutes |
| JN387556.1.1324 | 167.47 | 3.99 | 0.00791 | Bacteria | Firmicutes |

| OTU | Class | Order | Family | Genus | Species |
|---|---|---|---|---|---|
| JRPJ01000002.1034290.1035971 | Epsilon-proteobacteria | Campylo-bacterales | Helicobacteraceae | *Helicobacter* | Ambiguou_taxa |
| JF920309.1.1340 | Epsilon-proteobacteria | Campylo-bacterales | Campylobacteraceae | *Campylo-bacter* | NA |
| FJ978526.1.1378 | Gamma-proteobacteria | Aero-monadales | Succinivibrionaceae | *Succini-vibrio* | uncultured bacterium |
| New.ReferenceOTU45 | Gamma-proteobacteria | Aero-monadales | Succinivibrionaceae | *Anaerobio-spirillum* | Ambiguou_taxa |
| HK555938.1.1357 | Coriobacteriia | Corio-bacteriales | Coriobacteriaceae | *Collinsella* | uncultured bacterium |
| FJ957494.1.1454 | Clostridia | Clostridiales | Clostridiaceae 1 | *Clostridium sensu stricto* 1 | Ambiguou_taxa |
| New.ReferenceOTU52 | Clostridia | Clostridiales | Clostridiaceae 1 | *Clostridium sensu stricto* 1 | NA |
| DQ797046.1.1403 | Negativicutes | Seleno-monadales | Veillonellaceae | *Allisonella* | uncultured bacterium |
| GQ449092.1.1375 | Clostridia | Clostridiales | Lachnospiraceae | *Tyzzerella* | NA |
| AMCI01001631.34.1456 | Bacteroidia | Bacteroidales | Bacteroidaceae | *Bacteroides* | uncultured bacterium |
| KF842598.1.1394 | Bacteroidia | Bacteroidales | Porphyromonadaceae | *Para-bacteroides* | NA |
| HQ793763.1.1451 | Bacteroidia | Bacteroidales | Bacteroidaceae | *Bacteroides* | NA |
| DQ113765.1.1450 | Bacteroidia | Bacteroidales | Bacteroidaceae | *Bacteroides* | NA |
| ACBW01000012.3536.5054 | Bacteroidia | Bacteroidales | Bacteroidaceae | *Bacteroides* | uncultured bacterium |
| HK693629.1.1491 | Clostridia | Clostridiales | Lachnospiraceae | *Blautia* | NA |
| JQ208053.1.1336 | Fusobacteriia | Fusobacteriales | Fusobacteriaceae | *Fusobacterium* | NA |
| GQ493166.1.1359 | Clostridia | Clostridiales | Lachnospiraceae | NA | NA |
| GQ448486.1.1387 | Clostridia | Clostridiales | Lachnospiraceae | *Blautia* | uncultured bacterium |
| GQ491426.1.1332 | Clostridia | Clostridiales | Lachnospiraceae | *Blautia* | uncultured bacterium |
| New.ReferenceOTU54 | Clostridia | Clostridiales | Lachnospiraceae | *Blautia* | uncultured bacterium |
| JN387556.1.1324 | Clostridia | Clostridiales | Peptostreptococcaceae | *Intestinibacter* | NA |

TABLE 4

Genera with differential abundances between samples of dogs at day 14 and day 0 (day 14 versus day 0) for diet responsive dogs.

| OUT IDs | Base Mean | log2Fold-Change | P value | Kingdom | Phylum | Class | Order | Family | Genus |
|---|---|---|---|---|---|---|---|---|---|
| GQ006324.1.1342 | 15.64 | −3.74 | 0.00137 | Bacteria | Actino-bacteria | Actino-bacteria | Coryne-bacteriales | Corynebacteriaceae | *Corynebacterium* 1 |
| New.Ref-erenceOTU52 | 1991.15 | −2.20 | 0.01222 | Bacteria | Firmicutes | Clostridia | Clostridiales | Clostridiaceae 1 | *Clostridium sensu stricto* 1 |
| HG798451.1.1400 | 25.03 | −2.31 | 0.00911 | Bacteria | Firmicutes | Bacilli | Lacto-bacillales | Enterococcaceae | *Enterococcus* |
| HK557089.3.1395 | 6043.88 | 3.13 | 0.00124 | Bacteria | Firmicutes | Bacilli | Lacto-bacillales | Streptococcaceae | *Streptococcus* |
| GQ448336.1.1418 | 34.22 | 3.62 | 0.02080 | Bacteria | Firmicutes | Negativicutes | Seleno-monadales | Veillonellaceae | *Megasphaera* |
| KF842598.1.1394 | 4.25 | −4.15 | 0.02349 | Bacteria | Bacteroidetes | Bacteroidia | Bacteroidales | Porphyromonadaceae | *Parabacteroides* |
| FJ950694.1.1472 | 1259.08 | −3.07 | 0.00109 | Bacteria | Proteo-bacteria | Gamma-proteobacteria | Entero-bacteriales | Enterobacteriaceae | *Escherichia-Shigella* |
| HQ802983.1.1440 | 40.41 | −3.23 | 0.002803 | Bacteria | Firmicutes | Clostridia | Clostridiales | Lachnospiraceae | *Tyzzerella* 4 |
| GQ448468.1.1366 | 2058.39 | −2.10 | 0.01036 | Bacteria | Fusobacteria | Fusobacteriia | Fuso-bacteriales | Fusobacteriaceae | *Fusobacterium* |
| JN387556.1.1324 | 161.95 | −3.09 | 0.01172 | Bacteria | Firmicutes | Clostridia | Clostridiales | Peptostrepto-coccaceae | *Intestinibacter* |

TABLE 5

OTUs with differential abundances between samples day 14 and day 0 in diet responsive dogs (day 14 versus day 0).

| OTU + A2:K39 | Base Mean | log2 Fold Change | P value | Kingdom | Phylum |
|---|---|---|---|---|---|
| JRPJ01000002.1034290.1035971 | 38.04 | −3.39 | 0.034 | Bacteria | Proteo-bacteria |
| New.ReferenceOTU45 | 32.86 | −5.37 | 0.017 | Bacteria | Proteo-bacteria |
| GQ006324.1.1342 | 10.99 | −3.41 | 0.002 | Bacteria | Actino-bacteria |
| HK555938.11357 | 13.49 | 5.19 | 0.034 | Bacteria | Actino-bacteria |
| FJ957551.1.1489 | 5.64 | 2.44 | 0.023 | Bacteria | Firmicutes |
| FJ957494.1.1454 | 22.52 | 2.91 | 0.001 | Bacteria | Firmicutes |
| New.ReferenceOTU52 | 899.64 | −2.89 | 0.015 | Bacteria | Firmicutes |
| FM865905.1.1392 | 21.51 | −3.54 | 0.024 | Bacteria | Firmicutes |
| GQ016239.1.1362 | 12.55 | 3.10 | 0.015 | Bacteria | Firmicutes |
| HG798451.11400 | 21.63 | −1.92 | 0.023 | Bacteria | Firmicutes |
| EU461791.1.1414 | 5.48 | 2.9 | 0.043 | Bacteria | Firmicutes |
| GU303759.1.1517 | 22.26 | 2.50 | 0.010 | Bacteria | Firmicutes |
| New.ReferenceOTU114 | 33.26 | 3.17 | 0.002 | Bacteria | Firmicutes |
| AB506154.11541 | 7.45 | 2.91 | 0.008 | Bacteria | Firmicutes |
| EU774370.1.1398 | 2.18 | 3.43 | 0.029 | Bacteria | Firmicutes |
| HK557089.3.1395 | 4123.56 | 2.62 | 0.007 | Bacteria | Firmicutes |
| HQ807346.1.1456 | 11.88 | 4.56 | 2.35E−05 | Bacteria | Firmicutes |
| HQ748204.1.1442 | 15.13 | 4.30 | 4.58E−05 | Bacteria | Firmicutes |
| GU179917.1.1382 | 29.72 | 2.15 | 0.044 | Bacteria | Firmicutes |
| GQ448336.1.1418 | 49.68 | 4.13 | 0.014 | Bacteria | Firmicutes |
| DQ804865.11390 | 32.02 | 3.80 | 0.030 | Bacteria | Firmicutes |
| GQ491757.1.1361 | 6.02 | 1.79 | 0.034 | Bacteria | Firmicutes |
| New.ReferenceOTU56 | 33.71 | 5.05 | 0.000604 | Bacteria | Bacteroidetes |
| KF842598.1.1394 | 4.29 | −4.06 | 0.024 | Bacteria | Bacteroidetes |
| HQ802052.1.1445 | 3.40 | −3.37 | 0.010 | Bacteria | Bacteroidetes |
| GX182404.81529 | 2.29 | −3.22 | 0.035 | Bacteria | Proteobacteria |
| FJ950694.1.1472 | 1165.27 | −2.81 | 0.002 | Bacteria | Proteobacteria |
| GQ448506.11374 | 489.25 | 2.00 | 0.011 | Bacteria | Firmicutes |
| HQ802983.1.1440 | 25.95 | −2.62 | 0.020 | Bacteria | Firmicutes |
| DQ793824.11370 | 11.84 | −3.29 | 0.009 | Bacteria | Firmicutes |
| GQ448468.1.1366 | 2756.51 | −2.30 | 0.013 | Bacteria | Fusobacteria |
| EU774020.1.1361 | 2.57 | −3.07 | 0.011 | Bacteria | Fusobacteria |
| GQ491183.11360 | 618.96 | 1.51 | 0.040 | Bacteria | Firmicutes |
| GQ491426.11332 | 506.28 | 2.55 | 0.017 | Bacteria | Firmicutes |
| GQ493039.11311 | 82.93 | −3.08 | 0.016 | Bacteria | Firmicutes |
| JN387556.1.1324 | 135.02 | −3.10 | 0.010 | Bacteria | Firmicutes |
| EU775983.1.1288 | 2.84 | 2.40 | 0.008 | Bacteria | Firmicutes |

TABLE 5-continued

OTUs with differential abundances between samples day 14 and day 0 in diet responsive dogs (day 14 versus day 0).

| OTU + A2:K39 | Class | Order | Family | Genus | Species |
|---|---|---|---|---|---|
| JRPJ01000002.1034290.1035971 | Epsilon-proteobacteria | Campylo-bacterales | Helico-bacteraceae | *Helicobacter* | *Ambiguous_taxa* |
| New.ReferenceOTU45 | Gamma-proteobacteria | Aeromonadales | Succini-vibrionaceae | *Anaero-biospirillum* | *Ambiguous_taxa* |
| GQ006324.1.1342 | Actinobacteria | Coryne-bacteriales | Coryne-bacteriaceae | *Coryne-bacterium* 1 | uncultured bacterium |
| HK555938.11357 | Coriobacteriia | Coryne-bacteriales | Corio-bacteriaceae | *Collinsella* | uncultured bacterium |
| FJ957551.1.1489 | Clostridia | Clostridiales | Clostridiaceae 1 | *Sarcina* | uncultured bacterium |
| FJ957494.1.1454 | Clostridia | Clostridiales | Clostridiaceae 1 | *Clostridium sensu stricto* 1 | *Ambiguous_taxa* |
| New.ReferenceOTU52 | Clostridia | Clostridiales | Clostridiaceae 1 | *Clostridium sensu stricto* 1 | NA |
| FM865905.1.1392 | Clostridia | Clostridiales | Clostridiaceae 1 | *Clostridium sensu stricto* 1 | NA |
| GQ016239.1.1362 | Erysipelo-trichia | Erysipelo-trichales | Erysipelo-trichaceae | *Faecalitalea* | *Ambiguous_taxa* |
| HG798451.11400 | Bacilli | Lacto-bacillales | Enteroc-occaceae | *Enterococcus* | *Enterococcus durans* |
| EU461791.1.1414 | Bacilli | Lacto-bacillales cillales | Strepto-coccaceae | *Streptococcus* | uncultured bacterium |
| GU303759.1.1517 | Bacilli | Lacto-bacillales | Strepto-coccaceae | *Streptococcus* | uncultured bacterium |
| New.ReferenceOTU114 | Bacilli | Lacto-bacillales | Strepto-coccaceae | *Streptococcus* | uncultured bacterium |
| AB506154.11541 | Bacilli | Lacto-bacillales | Strepto-coccaceae | *Streptococcus* | uncultured bacterium |
| EU774370.1.1398 | Bacilli | Lacto-bacillales | Strepto-coccaceae | *Streptococcus* | uncultured bacterium |
| HK557089.3.1395 | Bacilli | Lacto-bacillales | Streptoc-occaceae | *Streptococcus* | uncultured bacterium |
| HQ807346.1.1456 | Bacilli | Lacto-bacillales | Streptoc-occaceae | *Streptococcus* | uncultured bacterium |
| HQ748204.1.1442 | Bacilli | Lacto-bacillales | Streptoc-occaceae | *Streptococcus* | uncultured bacterium |
| GU179917.1.1382 | Erysipelotrichia | Erysipelo-trichales | Erysipel-otrichaceae | *Erysipelato-clostridium* | *Ambiguous_taxa* |
| GQ448336.1.1418 | Negativicutes | Seleno-monadales | Veillonel-laceae | *Megasphaera* | uncultured bacterium |
| DQ804865.11390 | Clostridia | Clostridiales | Lachnos-piraceae | *NA* | NA |
| GQ491757.1.1361 | Clostridia | Clostridiales | Lachnos-piraceae | *Blautia* | uncultured bacterium |
| New.ReferenceOTU56 | Bacteroidia | Bacteroidales | Prevotel-laceae | *Alloprevotella* | *Ambiguous_taxa* |
| KF842598.1.1394 | Bacteroidia | Bacteroidales | Porphyro-monadaceae | *Parabacteroides* | NA |
| HQ802052.1.1445 | Bacteroidia | Bacteroidales | Bacteroidaceae | *Bacteroides* | *Ambiguous_taxa* |
| GX182404.81529 | Gamma proteobacteria | Entero-bacteriales | Entero-bacteriaceae | *Escherichia-Shigella* | NA |
| FJ950694.1.1472 | Gamma proteobacteria | Entero-bacteriales | Entero-bacteriaceae | *Escherichia-Shigella* | *Escherichia coli* |
| GQ448506.11374 | Clostridia | Clostridiales | Lachnos-piraceae | *Blautia* | uncultured bacterium |
| HQ802983.1.1440 | Clostridia | Clostridiales | Lachnos-piraceae | *Tyzzerella* 4 | NA |
| DQ793824.11370 | Clostridia | Clostridiales | Lachnos-piraceae | [*Ruminococcus*] *gauvreauii* group | uncultured bacterium |
| GQ448468.1.1366 | Fusobacteriia | Fusobacteriales | Fusobac-teriaceae | *Fusobacterium* | uncultured bacterium |
| EU774020.1.1361 | Fusobacteriia | Fusobacteriales | Fusobac-teriaceae | *Fusobacterium* | uncultured bacterium |
| GQ491183.11360 | Clostridia | Clostridiales | Lachnos-piraceae | NA | NA |
| GQ491426.11332 | Clostridia | Clostridiales | Lachnos-piraceae | *Blautia* | uncultured bacterium |
| GQ493039.11311 | Clostridia | Clostridiales | Peptostrepto-coccaceae | NA | NA |

TABLE 5-continued

OTUs with differential abundances between samples day 14 and day 0 in diet responsive dogs (day 14 versus day 0).

| | | | | | |
|---|---|---|---|---|---|
| JN387556.1.1324 | Clostridia | Clostridiales | Peptostrepto-coccaceae | *Intestinibacter* | NA |
| EU775983.1.1288 | Clostridia | Clostridiales | Peptostrepto-coccaceae | *Peptoclostridium* | uncultured bacterium |

TABLE 6

OTUs with differential abundances between samples of day 0 and day 14 (day 0 versus day 14) for die non-responsive dogs (Fold change > 2 and P-value < 0.05).

| OTU | Base Mean | log2 Fold Change | P value | Kingdom | Phylum | Class | Order | Family | Genus | Species |
|---|---|---|---|---|---|---|---|---|---|---|
| GQ449137.1.1391 | 461.15 | −3.51 | 0.0187 | Bacteria | Proteo-bacteria | Betaproteo-bacteria | Burk-holderiales | Alcalige naceae | *Sutterella* | NA |
| HK555938.1.1357 | 30.11 | −6.18 | 0.0121 | Bacteria | Actino-bacteria | Corio-bacteriia | Corio-bacteriales | Corio-bacteriaceae | *Collinsella* | uncultured bacterium |
| GQ358246.1.1466 | 302.41 | −3.70 | 0.0182 | Bacteria | Firmi-cutes | Nega-tivicutes | Seleno-monadales | Acidamin ococcaceae | *Phasco-larcto bacterium* | uncultured *Veillonel-laceae bacterium* |
| New.ReferenceOTU82 | 61.40 | 3.34 | 0.0262 | Bacteria | Firmi-cutes | Clostridia | Clos-tridiales | Clostridi-aceae 1 | *Clostridium sensu stricto* 1 | NA |
| New.ReferenceOTU52 | 222.71 | 4.55 | 0.0022 | Bacteria | Firmi-cutes | Clostridia | Clos-tridiales | Clostridi-aceae 1 | *Clostridium sensu stricto* 1 | NA |
| GQ138615.1.1402 | 321.54 | −3.56 | 0.0059 | Bacteria | Firmi-cutes | Erysipelo-trichia | Erysipelo-trichales | Erysipelo-trichaceae | *Turici-bacter* | uncultured bacterium |
| JN681884.1.1409 | 384.68 | 3.09 | 0.0084 | Bacteria | Firmi-cutes | Bacilli | Lacto-bacillales | Strepto-coccaceae | *Strepto-coccus* | NA |
| GU303759.1.1517 | 48.18 | 2.96 | 0.0180 | Bacteria | Firmi-cutes | Bacilli | Lacto-bacillales | Strepto-coccaceae | *Strepto-coccus* | uncultured bacterium |
| New.ReferenceOTU114 | 53.48 | 4.21 | 8.04E−05 | Bacteria | Firmi-cutes | Bacilli | Lacto-bacillales | Strepto-coccaceae | *Strepto-coccus* | uncultured bacterium |
| EU774881.1.1422 | 3.84 | 3.39 | 0.0224 | Bacteria | Firmi-cutes | Bacilli | Lacto-bacillales | Strepto-coccaceae | *Strepto-coccus* | uncultured bacterium |
| AB469559.1.1551 | 13.56 | 5.00 | 0.0016 | Bacteria | Firmi-cutes | Bacilli | Lacto-bacillales | Strepto-coccaceae | *Strepto-coccus* | uncultured bacterium |
| HK557089.3.1395 | 9232.07 | 4.47 | 2.88E−05 | Bacteria | Firmi-cutes | Bacilli | Lacto-bacillales | Strepto-coccaceae | *Strepto-coccus* | uncultured bacterium |
| EU358719.1.1513 | 12.02 | 2.71 | 0.0180 | Bacteria | Firmi-cutes | Bacilli | Lacto-bacillales | Strepto-coccaceae | *Strepto-coccus* | uncultured bacterium |
| HQ748204.1.1442 | 17.52 | 2.85 | 0.0045 | Bacteria | Firmi-cutes | Bacilli | Lacto-bacillales | Strepto-coccaceae | *Strepto-coccus* | uncultured bacterium |
| GQ338727.1.1397 | 9.95 | 6.38 | 0.0313 | Bacteria | Firmi-cutes | Clostridia | Clos-tridiales | Lachnos-piraceae | *Anaero-stipes* | uncultured bacterium |
| HQ803964.1.1435 | 247.41 | −2.80 | 0.0294 | Bacteria | Firmi-cutes | Clostridia | Clos-tridiales | Lachnos-piraceae | *Lachno-clostridium* | uncultured bacterium |
| FJ951866.1.1493 | 7.83 | −5.45 | 0.0177 | Bacteria | Firmi-cutes | Clostridia | Clos-tridiales | Lachnos-piraceae | *Roseburia* | NA |
| EU772870.1.1289 | 34.63 | −4.27 | 0.0079 | Bacteria | Fuso-bacteria | Fuso-bacteriia | Fuso-bacteriales | Fusobac-teriaceae | *Fuso-bacterium* | uncultured bacterium |
| GQ448468.1.1366 | 4335.90 | −4.03 | 0.0125 | Bacteria | Fuso-bacteria | Fuso-bacteriia | Fuso-bacteriales | Fusobac-teriaceae | *Fuso-bacterium* | uncultured bacterium |
| EU774020.1.1361 | 7.55 | −4.76 | 0.0112 | Bacteria | Fuso-bacteria | Fuso-bacteriia | Fuso-bacteriales | Fusobac-teriaceae | *Fuso-bacterium* | uncultured bacterium |
| HQ782658.1.1415 | 506.92 | −6.12 | 0.0001 | Bacteria | Fuso-bacteria | Fuso-bacteriia | Fuso-bacteriales | Fusobac-teriaceae | *Fuso-bacterium* | *Ambi-guous_taxa* |
| DQ794633.1.1395 | 23.54 | −3.68 | 0.0209 | Bacteria | Firmi-cutes | Clostridia | Clos-tridiales | Lachnos-piraceae | NA | NA |
| FN668375.4306350.4307737 | 12.13 | −5.24 | 0.0016 | Bacteria | Firmi-cutes | Clostridia | Clos-tridiales | Peptostrepto-coccaceae | NA | NA |
| GQ867445.1.1457 | 24.68 | −2.23 | 0.0150 | Bacteria | Firmi-cutes | Clostridia | Clos-tridiales | Lachnos-piraceae | NA | NA |

TABLE 7

Comparisons of KEGG pathways between different timepoints in the trial for diet responsive dogs.

| KEGG pathways | Days0vs14_lfc | Days0vs14_pvalue | Days0vs14_fdr |
|---|---|---|---|
| ko00100; Steroid biosynthesis | −2.04 | 0.000209808 | 0.005895615 |
| ko00312; beta-Lactam resistance | 0.44 | 7.25E−05 | 0.005895615 |
| ko00524; Butirosin and neomycin biosynthesis | 0.31 | 0.000164032 | 0.005895615 |
| ko00630; Glyoxylate and dicarboxylate metabolism | −0.39 | 0.000125885 | 0.005895615 |
| ko00910; Nitrogen metabolism | −0.39 | 0.000209808 | 0.005895615 |
| ko03070; Bacterial secretion system | −0.46 | 0.000125885 | 0.005895615 |
| ko04144; Endocytosis | −1.76 | 0.000209808 | 0.005895615 |
| ko04912; GnRH signaling pathway | −1.76 | 0.000209808 | 0.005895615 |
| ko05210; Colorectal cancer | −1.63 | 0.000209808 | 0.005895615 |
| ko05416; Viral myocarditis | −1.63 | 0.000209808 | 0.005895615 |
| ko00640; Propanoate metabolism | −0.25 | 0.000267029 | 0.006821372 |
| ko00010; Glycolysis/Gluconeogenesis | 0.19 | 0.000419617 | 0.006936017 |
| ko00311; Penicillin and cephalosporin biosynthesis | 0.32 | 0.000419617 | 0.006936017 |
| ko00920; Sulfur metabolism | −0.38 | 0.000419617 | 0.006936017 |
| ko04721; Synaptic vesicle cycle | −1.15 | 0.000419617 | 0.006936017 |
| ko04962; Vasopressin-regulated water reabsorption | −1.15 | 0.000419617 | 0.006936017 |
| ko05150; Staphylococcus aureus infection | 0.86 | 0.000335693 | 0.006936017 |
| ko00020; Citrate cycle (TCA cycle) | −0.31 | 0.000644684 | 0.006967545 |
| ko00052; Galactose metabolism | 0.40 | 0.000644684 | 0.006967545 |
| ko00240; Pyrimidine metabolism | 0.12 | 0.000522614 | 0.006967545 |
| ko00410; beta-Alanine metabolism | −0.41 | 0.000644684 | 0.006967545 |
| ko00473; D-Alanine metabolism | 0.29 | 0.000644684 | 0.006967545 |
| ko00592; alpha−Linolenic acid metabolism | −1.38 | 0.000644684 | 0.006967545 |
| ko00633; Nitrotoluene degradation | −0.67 | 0.000644684 | 0.006967545 |
| ko03410; Base excision repair | 0.10 | 0.000522614 | 0.006967545 |
| ko04115; p53 signaling pathway | −1.57 | 0.000522614 | 0.006967545 |
| ko00550; Peptidoglycan biosynthesis | 0.18 | 0.000965118 | 0.008748331 |
| ko00909; Sesquiterpenoid and triterpenoid biosynthesis | −1.52 | 0.000965118 | 0.008748331 |
| ko04621; NOD-like receptor signaling pathway | 0.43 | 0.000965118 | 0.008748331 |
| ko04930; Type II diabetes mellitus | 0.17 | 0.000965118 | 0.008748331 |
| ko05168; Herpes simplex infection | −1.28 | 0.000965118 | 0.008748331 |
| ko00281; Geraniol degradation | −0.58 | 0.001411438 | 0.01166512 |
| ko00540; Lipopolysaccharide biosynthesis | −0.53 | 0.001411438 | 0.01166512 |
| ko04622; RIG-I-like receptor signaling pathway | 0.57 | 0.001411438 | 0.01166512 |
| ko00071; Fatty acid metabolism | −0.55 | 0.001693726 | 0.012863159 |
| ko00120; Primary bile acid biosynthesis | 0.51 | 0.001693726 | 0.012863159 |
| ko00121; Secondary bile acid biosynthesis | 0.51 | 0.001693726 | 0.012863159 |
| ko00430; Taurine and hypotaurine metabolism | −0.32 | 0.00202179 | 0.013856655 |
| ko00590; Arachidonic acid metabolism | −0.39 | 0.00202179 | 0.013856655 |
| ko05012; Parkinsons disease | −0.60 | 0.00202179 | 0.013856655 |
| ko05111; Vibrio cholerae pathogenic cycle | −0.58 | 0.00202179 | 0.013856655 |
| ko00051; Fructose and mannose metabolism | 0.18 | 0.002399445 | 0.014046748 |
| ko00310; Lysine degradation | −0.27 | 0.002399445 | 0.014046748 |
| ko00351; DDT degradation | −0.89 | 0.002399445 | 0.014046748 |
| ko00520; Amino sugar and nucleotide sugar metabolism | 0.14 | 0.002399445 | 0.014046748 |
| ko00561; Glycerolipid metabolism | 0.27 | 0.002399445 | 0.014046748 |
| ko01040; Biosynthesis of unsaturated fatty acids | −0.32 | 0.002399445 | 0.014046748 |
| ko04011; MAPK signaling pathway - yeast | 0.27 | 0.002399445 | 0.014046748 |
| ko00130; Ubiquinone and other terpenoid-quinone biosynthesis | −0.38 | 0.002838135 | 0.014241355 |
| ko00380; Tryptophan metabolism | −0.58 | 0.002838135 | 0.014241355 |
| ko00680; Methane metabolism | −0.15 | 0.002838135 | 0.014241355 |
| ko02060; Phosphotransferase system (PTS) | 0.52 | 0.002838135 | 0.014241355 |
| ko04626; Plant-pathogen interaction | −0.09 | 0.002838135 | 0.014241355 |
| ko04940; Type I diabetes mellitus | 0.09 | 0.002838135 | 0.014241355 |
| ko05110; Vibrio cholerae infection | −1.3 | 0.002838135 | 0.014241355 |
| ko05145; Toxoplasmosis | −1.25 | 0.002838135 | 0.014241355 |
| ko00300; Lysine biosynthesis | 0.07 | 0.003341675 | 0.015915434 |
| ko02040; Flagellar assembly | −0.63 | 0.003341675 | 0.015915434 |
| ko04973; Carbohydrate digestion and absorption | 0.46 | 0.003341675 | 0.015915434 |
| ko05340; Primary immunodeficiency | 0.29 | 0.003917694 | 0.018347867 |
| ko00511; Other glycan degradation | 0.45 | 0.004577637 | 0.020098686 |
| ko00791; Atrazine degradation | −0.24 | 0.004577637 | 0.020098686 |
| ko00983; Drug metabolism - other enzymes | 0.14 | 0.004577637 | 0.020098686 |
| ko03430; Mismatch repair | 0.13 | 0.004577637 | 0.020098686 |
| ko00230; Purine metabolism | 0.08 | 0.005329132 | 0.022689184 |
| ko04260; Cardiac muscle contraction | −0.76 | 0.005329132 | 0.022689184 |
| ko00620; Pyruvate metabolism | −0.06 | 0.00617981 | 0.025918306 |
| ko00190; Oxidative phosphorylation | −0.11 | 0.007144928 | 0.028277814 |
| ko00330; Arginine and proline metabolism | −0.13 | 0.007144928 | 0.028277814 |
| ko00943; Isoflavonoid biosynthesis | 0.55 | 0.007144928 | 0.028277814 |
| ko04614; Renin-angiotensin system | 0.52 | 0.007144928 | 0.028277814 |

TABLE 7-continued

Comparisons of KEGG pathways between different timepoints in the trial for diet responsive dogs.

| KEGG pathways | Days0vs14_lfc | Days0vs14_pvalue | Days0vs14_fdr |
|---|---|---|---|
| ko00062; Fatty acid elongation | 0.43 | 0.008232117 | 0.030437168 |
| ko02020; Two-component system | −0.19 | 0.008232117 | 0.030437168 |
| ko03008; Ribosome biogenesis in eukaryotes | 0.22 | 0.008232117 | 0.030437168 |
| ko04122; Sulfur relay system | −0.23 | 0.008232117 | 0.030437168 |
| ko04910; Insulin signaling pathway | 0.22 | 0.008232117 | 0.030437168 |
| ko00471; D-Glutamine and D-glutamate metabolism | 0.15 | 0.00945282 | 0.033623321 |
| ko00500; Starch and sucrose metabolism | 0.20 | 0.00945282 | 0.033623321 |
| ko00860; Porphyrin and chlorophyll metabolism | −0.24 | 0.00945282 | 0.033623321 |
| ko05132; Salmonella infection | −0.33 | 0.010826111 | 0.038026714 |
| ko00603; Glycosphingolipid biosynthesis - globo series | 0.37 | 0.012359619 | 0.041844012 |
| ko03030; DNA replication | 0.08 | 0.012359619 | 0.041844012 |
| ko05142; Chagas disease (American trypanosomiasis) | −0.63 | 0.012359619 | 0.041844012 |
| ko00720; Carbon fixation pathways in prokaryotes | −0.12 | 0.014068604 | 0.045968344 |
| ko01057; Biosynthesis of type II polyketide products | −0.50 | 0.014068604 | 0.045968344 |
| ko04146; Peroxisome | −0.21 | 0.014068604 | 0.045968344 |

TABLE 8

Comparisons of bile acids between samples at different timepoints for diet responsive dogs.

| Bile acid | Days0vs14_fc | Days0vs14_pvalue | Days0vs42_fc | Days0vs42_pvalue |
|---|---|---|---|---|
| AlphamuricholicAcid | 1.74 | 0.192517572 | 2.91 | 0.006835938 |
| DeoxycholicAcid | 1.74 | 0.019058892 | 1.70 | 0.1015625 |
| GammamuricholicAcid | 16.18 | 0.024390241 | 18.33 | 0.014266187 |
| LithocholicAcid | 1.50 | 0.053710938 | 2.02 | 0.010826921 |
| OmegamuricholicAcid | 8.22 | 0.022494271 | 33.55 | 0.042315275 |

TABLE 9

Spearman correlations between abundance of OTUs and concentration of Bile acids in diet responsive dogs.

| Taxa | Bile acid | Spearman correlation | Pvalue | Adjusted Pvalue |
|---|---|---|---|---|
| Fusobacterium_uncultured.bacterium | Chenodeoxy-cholic.Acid_primary | −0.468045036 | 0.000533 | 0.022042405 |
| Bacteroides_NA | Chenodeoxy-cholic.Acid_primary | −0.474431034 | 0.000436 | 0.022042405 |
| Fusobacterium_uncultured.bacterium | Cholic.Acid_primary | −0.646842527 | 3.11E−08 | 3.86E−06 |
| Fusobacterium_Ambiguous_taxa | Cholic.Acid_primary | −0.60748964 | 3.36E−07 | 2.09E−05 |
| Bacteroides_NA | Cholic.Acid_primary | −0.592565032 | 7.64E−07 | 2.37E−05 |
| Peptoclostridium_uncultured.bacterium | Cholic.Acid_primary | −0.561738193 | 3.67E−06 | 9.11E−05 |
| Megamonas_uncultured.bacterium | Cholic.Acid_primary | −0.518655946 | 2.57E−05 | 0.000532 |
| Bacteroides_uncultured.bacterium | Cholic.Acid_primary | −0.499276241 | 5.69E−05 | 0.001007674 |
| Prevotella.9_uncultured.bacterium | Cholic.Acid_primary | −0.4938089 | 7.05E−05 | 0.001093381 |
| Escherichia.Shigella_Escherichia.coli | Cholic.Acid_primary | 0.487797189 | 8.90E−05 | 0.001226177 |
| Sutterella_NA | Cholic.Acid_primary | −0.456507609 | 0.000279 | 0.003458925 |
| Staphylococcus_Ambiguous_taxa | Cholic.Acid_primary | 0.418106228 | 0.000984 | 0.01108803 |
| Escherichia.Shigella_uncultured.bacterium | Cholic.Acid_primary | 0.407320492 | 0.001366 | 0.014111373 |
| Enterococcus Enterococcus.durans | Cholic.Acid_primary | 0.394491205 | 0.00199 | 0.018979727 |
| Fusobacterium_uncultured.organism | Cholic.Acid_primary | −0.391629335 | 0.00216 | 0.019129515 |
| Faecalibacterium uncultured.bacterium | Cholic.Acid_primary | −0.382982602 | 0.002755 | 0.022772609 |
| Clostridium.sensu.stricto.1_NA | Cholic.Acid_primary | 0.365158178 | 0.004459 | 0.030717827 |
| Phascolarctobacterium_uncultured.Veillonel-laceae.bacterium | Cholic.Acid_primary | −0.365156122 | 0.004459 | 0.030717827 |
| Erysipelatoclostridium_NA | Cholic.Acid_primary | 0.369363009 | 0.003989 | 0.030717827 |
| Lactobacillus_uncultured.bacterium | Cholic.Acid_primary | 0.362651494 | 0.004761 | 0.030741248 |
| Enterobacter_NA | Cholic.Acid_primary | 0.361092059 | 0.004958 | 0.030741248 |
| Fusobacterium_Ambiguous_taxa | Deoxycholic.Acid | 0.544270884 | 5.29E−05 | 0.00439602 |

TABLE 9-continued

Spearman correlations between abundance of OTUs and concentration of Bile acids in diet responsive dogs.

| Taxa | Bile acid | Spearman correlation | Pvalue | Adjusted Pvalue |
|---|---|---|---|---|
| uncultured.bacterium_uncultured.bacterium | Deoxycholic.Acid | −0.536454836 | 7.09E−05 | 0.00439602 |
| Enterococcus NA | Glycochenode-oxycholic.Acid | 0.551370353 | 0.000275 | 0.034071581 |
| Fusobacterium_uncultured.bacterium | Glycocholic.Acid | −0.4919575 | 0.000383 | 0.047524989 |
| Escherichia.Shigella Escherichia.coli | Glycochenode-oxycholic.Acid | −0.500010873 | 0.00016 | 0.006632914 |
| Escherichia.Shigella_uncultured.bacterium | Glycochenode-oxycholic.Acid | −0.503678278 | 0.000141 | 0.006632914 |
| Escherichia.Shigella_NA | Glycochenode-oxycholic.Acid | −0.513698449 | 9.83E−05 | 0.006632914 |
| Bacteroides_NA | Lithocholic.Acid | 0.602216745 | 1.21E−05 | 0.001495011 |
| Escherichia.Shigella_Escherichia.coli | Lithocholic.Acid | −0.505136952 | 0.000402 | 0.01214716 |
| Clostridium.sensu.stricto.1 uncultured.bacterium | Lithocholic.Acid | −0.498644383 | 0.00049 | 0.01214716 |
| Alloprevotella_NA | Lithocholic.Acid | 0.525651352 | 0.000209 | 0.01214716 |
| Fusobacterium_uncultured.bacterium | Lithocholic.Acid | 0.465544021 | 0.00127 | 0.022503866 |
| Terrisporobacter_uncultured.bacterium | Lithocholic.Acid | −0.468902352 | 0.001158 | 0.022503866 |
| Fusobacterium_Ambiguous_taxa | Taurocholic.Acid | −0.597078223 | 9.46E−07 | 0.000117322 |
| Bacteroides_uncultured.bacterium | Taurocholic.Acid | −0.478414977 | 0.000167 | 0.006908181 |
| Fusobacterium_uncultured.bacterium | Taurocholic.Acid | −0.467425093 | 0.000247 | 0.007641602 |
| Peptoclostridium_uncultured.bacterium | Taurocholic.Acid | −0.447367036 | 0.000485 | 0.012022892 |
| Prevotella.9 uncultured.bacterium | Taurocholic.Acid | −0.432173393 | 0.000788 | 0.015017592 |
| Catenibacterium_uncultured.bacterium | Taurocholic.Acid | −0.429812058 | 0.000848 | 0.015017592 |
| Bacteroides_NA | Taurocholic.Acid | −0.419308054 | 0.001168 | 0.018102789 |
| Megamonas_uncultured.bacterium | Taurocholic.Acid | −0.395318261 | 0.002339 | 0.032219997 |
| Sutterella NA | Taurocholic.Acid | −0.379322634 | 0.003614 | 0.044819403 |
| Parasutterella_uncultured.organism | Taurocholic.Acid | 0.372251442 | 0.004352 | 0.049062689 |
| Terrisporobacter_uncultured.bacterium | Taurolithocholic.Acid | −0.47287393 | 0.000104 | 0.012896126 |
| Escherichia.Shigella_NA | Taurolithocholic.Acid | −0.408085979 | 0.000993 | 0.046070117 |
| Prevotellaceae.UCG.003_uncultured.bacterium | Taurolithocholic.Acid | −0.404397284 | 0.001115 | 0.046070117 |

TABLE 10

Comparison of the amount of bile acids in the fecal samples of healthy dogs, diet responsive dogs with CCE and diet non-responsive dogs with CCE.

| Group | Timepoint | Bile Acid | Mean (nmol/g) | CI lower | CI upper | Std. Error | (mg/g) | # % |
|---|---|---|---|---|---|---|---|---|
| DR | 0 | Deoxycholic | 753.4492 | 385.5109 | 1121.3876 | 167.1698 | 0.295783059 | 0.029578 |
| DR | 14 | Deoxycholic | 1232.6501 | 787.5515 | 1677.7488 | 209.9616 | 0.483903915 | 0.04839 |
| DR | 42 | Deoxycholic | 1229.1665 | 663.6408 | 1794.6923 | 266.7693 | 0.482536351 | 0.048254 |
| NDR | 0 | Deoxycholic | 487.2588 | −186.5451 | 1161.0627 | 242.6858 | 0.191284162 | 0.019128 |
| NDR | 14 | Deoxycholic | 736.7662 | −124.4111 | 1597.9436 | 335.0126 | 0.289233781 | 0.028923 |
| NDR | 42 | Deoxycholic | 33.16975 | −57.53601 | 123.87551 | 32.66975 | 0.013021515 | 0.001302 |
| Healthy | | Deoxycholic | 2328.5853 | 1519.0883 | 3138.0823 | 357.8429 | 0.914137388 | 0.091414 |
| DR | 0 | Lithocholic | 132.0341 | 46.31136 | 217.75684 | 38.94744 | 0.049720424 | 0.004972 |
| DR | 14 | Lithocholic | 209.8332 | 120.17778 | 299.48862 | 42.29218 | 0.079017434 | 0.007902 |
| DR | 42 | Lithocholic | 266.74216 | 153.50886 | 379.97547 | 53.41432 | 0.100447789 | 0.010045 |
| NDR | 0 | Lithocholic | 56.86471 | −39.08019 | 152.80961 | 34.55674 | 0.021413692 | 0.002141 |
| NDR | 14 | Lithocholic | 74.4107 | −46.58682 | 195.40822 | 47.07009 | 0.028021031 | 0.002802 |
| NDR | 42 | Lithocholic | 1.718967 | −1.665428 | 5.103362 | 1.218967 | 0.000647316 | 6.47E−05 |
| Healthy | | Lithocholic | 601.7535 | 314.6058 | 888.9013 | 126.9354 | 0.22660388 | 0.02266 |

Note:
The values <1 nmol/g were under the limit of detection; so an appropriate value 0.5 was used for the calculation.

TABLE 11

16S rRNA Sequences of OTUs in Tables 2-5
OTUs in Table 2

JRPJ01000002.1034290.1035971
AGAGTTTGATCCTGGCTCAGAGTGAACGCTGGCGGCGTGCCTAATACATGCAAGTCGAACGATGAAACTTCTAGCT
TGCTAGAAGTGGATTAGTGGCGCACGGGTGAGTAATGCATAGGTAACATGCCCTTTAGTCTGGGATAGCCACTGGA
AACGGTGATTAATACTGGATACTCCCTACGGGGGAAAGGGGCTTTCAATAAAGAATTTCTCTTTTTAGTGTTTTGT
GTTGTTGGCACAAAATTCTAGTATTTGGAATGAGAAATTGGTGTTGTGAAGCAATTTGTGCGGAGATTAGACTTAG
TGTCTGTCGTGTCAGCAAATTGCGAACTCATCGATTTATCATCCAAAGACGAATTTTTATTGAAAGCCTTCGCTA
AAGGATTGGCCTATGTCCTATCAGCTTGTTGGTGAGGTAATGGCTCACCAAGGCTATGACGGGTATCCGGCCTGAG

TABLE 11-continued 16S rRNA Sequences of OTUs in Tables 2-5
OTUs in Table 2

AGGGTGATCGGACACACTGGAACTGAGACACGGTCCAGACTCCTACGGGAGGCAGCAGTAGGGAATATTGCTCAAT
GGGGGAAACCCTGAAGCAGCAACGCCGCGTGGAGGATGAAGGTTTTAGGATTGTAAACTCCTTTTGTAAGAGAAGA
TTATGACGGTATCTTACGAATAAGCACCGGCTAACTCCGTGCCAGCAGCCGCGGTAATACGGAGGGTGCAAGCGTT
ACTCGGAATCACTGGGCGTAAAGAGCGCGTAGGCGGGTGGTCAAGTCAGATGTGAAATCCTGTAGCTTAACTACAG
AACTGCATTTGAAACTGACCATCTAGAGTATGGGAGAGGTAGGTGGAATTCTTGGTGTAGGGGTAAAATCCGTAGA
GATCAAGAGGAATACTCATTGCGAAGGCGACCTGCTGGAACATTACTGACGCTGATGCGCGAAAGCGTGGGGAGCA
AACAGGATTAGATACCCTGGTAGTCCACGCCCTAAACGATGAATGCTAGTTGTTGTGAGGCTTGTCCTTGCAGTAA
TGCAGCTAACGCATTAAGCATTCCGCCTGGGGAGTACGGTCGCAAGATTAAAACTCAAAGGAATAGACGGGGACCC
GCACAAGCGGTGGAGCATGTGGTTTAATTCGATGATACGCGAAGAACCTTACCTAGGCTTGACATTGATAGAATCT
ACTAGAGATAGTGGAGTGCCCTTTTAGGGAGCTTGAAAACAGGTGCTGCACGGCTGTCGTCAGCTCGTGTCGTGAG
ATGTTGGGTTAAGTCCCGCAACGAGCGCAACCCTCGTCCTTAGTTGCTAGCAGTTTGGCTGAGCACTCTAAGGAGA
CTGCCTTCGTAAGGAGGAGGAAGGTGAGGACGACGTCAAGTCATCATGGCCCTTACGCCTAGGGCTACACACGTGC
TACAATGGGGTGCACAAAGAGATGCAATAGTGTGAGCTGGAGCCAATCTCTAAAACATCTCTCAGTTCGGATTGTA
GTCTGCAACTCGACTACATGAAGCTGGAATCGCTAGTAATCGCAAATCAGCAATGTTGCGGTGAATACGTTCCCGG
GTCTTGTACTCACCGCCCGTCACACCATGGGAGTTGTATTTGCCTTAAGTCGGAATGCTAAATTGGCTACCGCCCA
CGGCAGATGCAGCGACTGGGGTGAAGTCGTAACAAGGTAACCGTAGGTGAACCTGCGGTTG

JF920309.1.1340
AGTGAACGCTGGCGGCGTGCCTAATACATGCAAGTCGAACGATGAAGCTTCTAGCTTGCTAGAAGTGGATTAGTGG
CGCACGGGTGAGTAAGGTATAGTTAATCTGCCCTACACAAGAGGACAACACCTAGAAATGGGTGCTAATACTCTAT
ACTCCTGCTTAACACAAGTTGAGTAGGGAAAGTTTTTCGGTGTAGGATGAGACTATATAGTATCAGCTAGTTGGTA
AGGTAAAGGCTTACCAAGGCTATGACGCTTAAGAGGTCTGAGAGGATGATCTCTCACACTGGAACTGAGACACGGT
CCAGACTCCTACGGGAGGCAGCAGTAGGGAATATTGCGCAATGGGCGAAAGCCTGACGCAGCAACGCCGCGTGGAG
GATGACACTTTTAGGAGCGTAAACTCCTTTTCTTAGGGAAGAATTCTGACGGTACCTAAGGAATAAGCACCGGCTA
ACTCCGTGCCAGCAGCCGCGGTAATACGGAGGGTGCAAGCGTTACTCGGAATCACTGGGCGTAAAGGGCGCGTAGG
CGGATTATCAAGTCTCTTGTGAAATCTAATGGCTTAACCATTAAACTGCTTGGGAAACTGATAGTCTAGAGTGAGG
GAGAGGCAGATGGAATTGGTGGTGTAGGGGTAAAATCCGTAGATATCACCAAGAATACCCATTGCGAAGGCGATCT
GCTGGAACTCAACTGACGCTAAGGCGCGAAAGCGTGGGGAGCAAACAGGATTAGATACCCTGGTAGTCCACGCCCT
AAACGATGTATGCTAGTTGTTGGGCTGCTAGTCAGCTCAGTAATGCAGCTAACGCATTAAGCATACCGCCTGGGGA
GTACGGTCGCAAGATTAAAACTCAAAGGAATAGACGGGGACCCGCACAAGCGGTGGAGCATGTGGTTTAATTCGAA
GATACGCGAAGAACCTTACCTAGGCTTGATATCCAACAAAGCTTCTAGAGATAGAAGTGTGCTAGCTTGCTAGAAT
GTTGAGACAGGTGCTGCACGGCTGTCGTCAGCTCGTGTCGTGAGATGTTGGGTTAAGTCCCGCAACGAGCGCAACC
CACGTATTTAGTTGCTAACACTTCGGGTGAGCACTCTAAATAGACTGCCTTCGTAAGGAGGAGGAAGGTGTGGACG
ACGTCAAGTCATCATGGCCCTTATGCCTAGGGCGACACACGTGCTACAATGGCATATACAATGAGACGCAATACCG
CGAGGTGGAGCAAATCTATAAAATATGTCCCAGTTCGGATTGTTCTCTGCAACTCGAGAGCATGAAGCCGGAATCG
CTAGTAATCGCAAATCAGCCATGTTGCGGTGAATACGTTCCCGGGTCT

FJ978526.1.1378
CATGCAAGTCGAACGGTAACATAGAGGAAGCTTGCTTTCTCTGATGACGAGTGGCGGACGGGTGAGTAAGGTCTGG
GAAACTGCCTGACAGAGGGGGACAACAACTGGAAACGGTTGCTAATACCGCATACACCCTGAGGGGGAAAGTCGAA
AGACGCTGTCAGATGTGCCCAGATGGGATTAGCTAGTAGGTGAGGTAAAGGCTCACCTAGGCGACGATCTCTAGCT
GGTCTGAGAGGATGATCAGCCACATTGGGACTGAGACACGGCCCAGACTCCTACGGGAGGCAGCAGTAGGGAATAT
TGCACAATGGGGGGAACCCTGATGCAGCCATGCCGCGTGTGTGAAGAAGGCCTTCGGGTTGTAAAGCACTTTCAGA
GGGGAGGAAAATGACGTTACCCTCAGAAGAAGCACCGGCTAACTCCGTGCCAGCAGCCGCGGTAATACGGAGGGTG
CAAGCGTTAATCGGAATAACTGGGCGTAAAGGGCATGCAGGCGGTTCTGCAAGTAGGGTGTGAAAGCCCGGGGCTC
AACCTCGGAATTGCACTCTAAACTGTGGGACTAGAGTATTGCAGGGGGAGACGGAATTCCAGGTGTAGCGGTGGAA
TGCGTAGAGATCTGGAAGAACACCAAAGGCGAAGGCAGTCTCCTGGGCAAATACTGACGCTCATATGCGAAAGCGT
GGGTAGCAAACAGGATTAGATACCCTGGTAGTCCACGCCGTAAACGATGTTGATTAGAAGCTTGCTTGTAAGAGTG
GGTTTCGCAGCTAACGCGATAAATCAACCGCCTGGGGAGTACGGCCGCAAGGTTAAAACTCAAATGAATTGACGGG
GGCCCGCACAAGCGGTGGAGCATGTGGTTTAATTCGACGCAACGCGATGAACCTTACCTGATCTTGACATCGCGAG
AATTACTTGTAATGAGTAAGTGCCTTCGGGAACTCGCAGACAGGTGCTGCATGGCTGTCGTCAGCTCGTGTCGTGA
GATGTTGGGTTAAGTCCCGCAACGAGCGCAACCCTTGTCCTTTGTTGCCAGCGGGTAGAGCCGGGAACTCAAAGGA
GACTGCCAGTGATAAACTGGAGGAAGGTAGGGATGACGTCAAGTCATCATGGCCCTTACGGTCAGGGCTACACACG
TGCTACAATGGGGCGTACAGAGGGAAACGAAACTGCGAGGTGGAGTGGAACCCAGAAAGCGTCCCTAAGTTCGGAT
TGGAGTCTGCAACTCGACTCCATGAAGTCGGAATCGCTAGTAATCGCAAATCAGAATGTTGCGGTGAATACGTTCC
CGGGCCTTGTACACACCGCCCGTCACACCATGGGAGTGGATTGCACCAGAAGTGGCCAGCCTAACTGCAAAGAGGG
CGGTACCACG

New.ReferenceOTU45
TACGGAGGGTGCAAGCGTTAATCGGAATAACTGGGCGTAAAGGGCATGTAGGCGGAAAGGCAAGCAAGATGTGAAA
GACCTGGGCTCAACCTGGGTTGGTCATTTTGAACTACCTTTCTAGAGTATTGCAGAGGGAGATGGAATTTCAGGTG
TAGCGGTGGAATGCGTAGATATCTGAAAGAACACCAGAGGCGAAGGCGGTCTCCTGGGCAAATACTGACGCTGAGG
TGCGAAAGCGTGGGGAGCAAACAGG HK555938.1.1357
ACGGCACCCCTCTCCGGAGGGAAGCGAGTGGCGAACGGCTGAGTAACACGTGGAGAACCTGCCCCCTCCCCCGGGA
TAGCCGCCCGAAAGGACGGGTAATACCGGATACCCCCGGGCGCCGCATGGCGCCCGGGCTAAAGCCCCGACGGGAG
GGGATGGCTCCGCGGCCCATCAGGTAGACGGCGGGGTGACGGCCCACCGTGCCGACAACGGGTAGCCGGGTTGAGA
GACCGACCGGCCAGATTGGGACTGAGACACGGCCCAGACTCCTACGGGAGGCAGCAGTGGGGAATCTTGCGCAATG
GGGGGAACCCTGACGCAGCGACGCCGCGTGCGGGACGGAGGCCTTCGGGTCGTAAACCGCTTTCAGCAGGGAAGAG
TCAAGACTGTACCTGCAGAAGAAGCCCCGGCTAACTACGTGCCAGCAGCCGCGGTAATACGTAGGGGGCGAGCGTT
ATCCGGATTCATTGGGCGTAAAGCGCGCGTAGGCGGCCCGGCAGGCCGGGGGTCGAAGCGGGGGGCTCAACCCCCC
GAAGCCCCCGGAACCTCCGCGGCTTGGGTCCGGTAGGGGAGGGTGGAACACCCGGTGTAGCGGTGGAATGCGCAGA
TATCGGGTGGAACACCGGTGGCGAAGGCGGCCCTCTGGGCCGAGACCGACGCTGAGGCGCGAAAGCTGGGGGAGCG
AACAGGATTAGATACCCTGGTAGTCCCAGCCGTAAACGATGGACGCTGGGTGTGGGGGGACGATCCCCCCGTGCCG
CAGCCNACGCATTAAGCGTCCCGCCTGGGGAGTACGGCCGCAAGGCTAAAACTCAAAGGAATTGACGGGGGCCCGC
ACAAGCAGCGGAGCATGTGGCTTAATTCGAAGCAACGCGAAGAACCTTACGGCGCATCCCCCCGAGGCCCACGGGG TABLE 11-continued

| 16S rRNA Sequences of OTUs in Tables 2-5<br>OTUs in Table 2 |
| --- |
| GGTCCGCCGCGTGGGTCAGAGGAGCGCATACGGGAGGTGCATGGTTGTCGTCAGCTCGTGTCGTGAGATGTTGGGT<br>TAAGTCCCGCAACGAGCGCAACCCCCGCCGCGTGTTGCCATCGGGTGATGCCGGGAACCCACGCGGGACCGCCGCC<br>GTCAAGGCGGAGGAGGGCGGGGACGACGTCAAGTCATCATGCCCCTTATGCCCTGGGCTGCACACGTGCTACAATG<br>GCCGGTACAGAGGGATGCCACCCCGCGAGGGGGAGCGGATCCCGGAAAGCCGGCCCCAGTTCGGATTGGGGGCTGC<br>AACCCGCCCCCATGAAGTCGGAGTTGCTAGTAATCGCGGATCAGCATGCCGCGGTGAATGCGTTCCCGGGCCTTGT<br>ACACACCGCCCGTCACACCACCCGAGTCGTCTGCACCCGAAGTCGCCGGCCCAACCGCAAGGGGG |
| FJ957494.1.1454<br>TGAGTTTGATCATGGCTCAGGACGAACGCTGGCGGCGTGCCTAACACATGCAAGTCGAGCGATGAAATTTTCTTCG<br>GAAAATGGATTAGCGGCGGACGGGTGAGTAACACGTGGGTAACCTGCCCTATAGAGAGGGATAGCCTTCCGAAAGG<br>GAGATTAATACCTCATAATATCCTAGTATCGCATGATACATGGATTAAAGGAGCAATCCGCTATAGGATGGACCCG<br>CGGCGCATTAGCTAGTTGGTGAGGTAACGGCTCACCAAGGCGACGATGCGTAGCCGACCTGAGAGGGTGATCGGCC<br>ACATTGGGACTGAGACACGGCCCAGACTCCTACGGGAGGCAGCAGTGGGGAATATTGCACAATGGGGGAAACCCTG<br>ATGCAGCAACGCCGCGTGAGTGATGACGGTCTTCGGATTGTAAAGCTCTGTCTTTAGGGACGATAATGACGGTACC<br>TAAGGAGGAAGCCACGGCTAACTACGTGCCAGCAGCCGCGGTAATACGTAGGTGGCAAGCGTTGTCCGGATTTACT<br>GGGCGTAAAGGGAGCGTAGGCGGATCTTTAAGTGGGATGTGAAATACTCGGGCTCAACCTGGGGGCTGCATTCCAA<br>ACTGGGGATCTAGAGTACAGGAGGGGNGAGTGGAATTCCTAGTGTAGCGGTGAAATGCGTAGAGATTAGGAAGAAC<br>ACCAGTGGCGAAGGCGACTNTCTGGACTGTAACTGACGCTGAGGCTCGAAAGCGTGGGGAGCAAACAGGATTAGAT<br>ACCCTGGTAGTCCACGCCGTAAACGATGAATACTAGGTGTAGGGGGTGTCAACTCCCCCTGTGCCGCCGCTAACGC<br>ATTAAGTATTCCGCCTGGGGAGTACGGTCGCAAGATTAAAACTCAAAGGAATTGACGGGGGCCCGCACAAGTAGCG<br>GAGCATGTGGTTTAATTCGACGCAACGCGAAGAACCTTACCTAGACTTGACATCTTCTGCATTACCCTTAATCGGG<br>GAAGTTCCTTCGGGGACAGAATGACAGGTGGTGCATGGTTGTCGTCAGCTCGTGTCGTGAGATGTTGGGTTAAGTC<br>CCGCAACGAGCGCAACCCTTAAGCTTAGTTGCCATCATTAAGTTGGGCACTCTAAGTTGACTGCCGGTGACAAACC<br>GGAGGAAGGTGGGGATGACGTCAAATCATCATGCCCCTTATGTCTAGGGCTACACACGTGCTACAATGGCAAGTAC<br>AAAGAGAAGCAATACTGTGAAGTGGAGCAAAACTCAAAAACTTGTCTCAGTTCGGATTGTAGGCTGAAACTCGCCT<br>ACATGAAGCTGGAGTTGCTAGTAATCGCGAATCAGAATGTCGCGGTGAATACGTTCCCGGGTCTTGTACACACCGC<br>CCGTCACACCATGAGAGTTGGCAATACCCGAAGTCCGTAAGCTAACCGTAAGGAGGCAGCGGCCGAAGGTAGGGTC<br>AGCGATGGGG |
| New.ReferenceOTU52<br>TACGTAGGTGGCGAGCGTTATCCGGATTTACTGGGCGTAAAGGGAGCGTAGGCGGATGATTAAGTGGGATGTGAAA<br>TACCCGGGCTCAACTTGGGTGCTGCATTCCAAACTGGTTATCTAGAGTGCAGGAGAGGAGAGTGGAATTCCTAGTG<br>TAGCGGTGAAATGCGTAGAGATTAGGAAGAACACCAGTGGCGAAGGCGACTCTCTGGACTGTAACTGACGCTGAGG<br>CTCGAAAGCGTGGGGAGCAAACAGG |
| DQ797046.1.1403<br>AGAGTTTGATCCTGGCTCAGGACGAACGCTGGCGGCATGCTTAACACATGCAAGTCGAACGGACTGATTCCTTCGG<br>GATGAAAGTTAGTGGCGAACGGGTGAGTAATGTATGAGCAACCTGCCTCTGTCAACGGGATAACAGTTGGAAACGA<br>CTGCTAATACGGTATATGACCACGGCACCGCATGGTGCAGCGGTAAAAGATTTTATCGGACAGAGATGGGCTCATA<br>TCCCATTAGGTAGTTGGTGAGATAACAGCCCACCAAGCCGACGATCAGTAGCCGGTCTGAGAGGATGAACGGCCAC<br>ACTGGAACTGAGACACGGTCCAGACTCCTACGGGAGGCAGCAGTGGGGAATCTTCCGCAATGGACGAAAGTCTGAC<br>GGAGCAACGCCGCGTGAACGATGAAGGTCTTCGGATTGTAAAGTTCTGTGATCCGGGACGAAGGCATTGATTGAGA<br>ACATTGATTGATGTTGACGGTACCGGAAAAGCAAGCCACGGCTAACTACGTGCCAGCAGCCGCGGTAATACGTAGG<br>TGGCAAGCGTTGTCCGGAATTATTGGGCGTAAAGCGCGCGCAGGCGGCCGTGCAAGTCCATCTTAAAAGCGTGGGG<br>CTTAACCCCATGAGGGGATGGAAACTGCAGGGCTGGAGTGTCGGAGGGGAAAGTGGAATTCCTAGTGTAGCGGTGA<br>AATGCGTAGAGATTAGGAAGAACACCGGTGGCGAAGGCGACTTTCTAGACGACAACTGACGCTGAGGCGCGAAAGC<br>GTGGGGAGCAAACAGGATTAGATACCCTGGTAGTCCACGCCGTAAACGATGGATACTAGGTGTAGGAGGTATCGAC<br>CCCTTCTGTGCCGGAGTTAACGCAATAAGTATCCCGCCTGGGAAGTACGATCGCAAGATTAAAACTCAAAGGAATT<br>GACGGGGGCCCGCACAAGCGGTGGAGTATGTGGTTTAATTCGACGCAACGCGAAGAACCTTACCAAGCCTTGACAT<br>TGATCGCAATCCGCAGAAATGCGGAGTTCCTCTTCGGAGGACGAGAAAACAGGTGGTGCACGGCTGTCGTCAGCTC<br>GTGTCGTGAGATGTTGGGTTAAGTCCCGCAACGAGCGCAACCCCTATCTTCTGTTGCCAGCACGTAAAGGTGGGAA<br>CTCAGGAGAGACCGCCGCGGACAACGCGGAGGAAGGCGGGGATGACGTCAAGTCATCATGCCCCTTATGGCTTGGG<br>CTACACACGTACTACAATGGGTGCAAACAAAGAGAAGCGAAGTCGCGAGATGGAGCGGACCTCATAAACGCACTCC<br>CAGTTCAGATTGCAGGCTGCAACCCGCCTGCATGAAGTAGGAATCGCTAGTAATCGCGGTCAGCATACCGCGGTG<br>AATACGTTCCCGGGCCTTGTACACACCGCCCGTCA |
| GQ449092.1.1375<br>CTGGCTCAGGATGAACGCTGGCGGCGTGCTTAACACATGCAAGTCGAACGAAGAGGGTTAGAATGAGAGCTTCGGC<br>AGGATTTCTTTCCATCTTAGTGGCGGACGGGTGAGTAACGTGTGGGCAACCTGCCCTGTACTGGGGGATAATCATT<br>GGAAACGATGACTAATACCGCATGTGGTTCTCGGAAGGCATCTTCTGAGGAAGAAAGGATTTATTCGGTACAGGAT<br>GGGCCCGCATCTGATTAGCTAGTTGGTGAGATAACAGCCCACCAAGGCGACGATCAGTAGCCGACCTGAGAGGGTG<br>ATCGGCCACATTGGGACTGAGACACGGCCCAAACTCCTACGGGAGGCAGCAGTGGGGAATATTGCACAATGGGCGA<br>AAGCCTGATGCAGCAACGCCGCGTGAAGGATGAAGGGTTTCGGCTCGTAAACTTCTATCAATAGGGAAGAAACAAA<br>TGACGGTACCTAAATAAGAAGCCCCGGCTAACTACGTGCCAGCAGCCGCGGTAATACGTAGGGGGCAAGCGTTATC<br>CGGAATTACTGGGTGTAAAGGGAGCGTAGGCGGCATGGTAAGCCAGATGTGAAAGCCTTGGGCTTAACCCGAGGAT<br>TGCATTTGGAACTATCAAGCTAGAGTACAGGAGAGGAAAGCGGAATTCCTAGTGTAGCGGTGAAATGCGTAGATAT<br>TAGGAAGAACACCAGTGGCGAAGGCGGCTTTCTGGACTGAAACTGACGCTGAGGCTCGAAAGCGTGGGGAGCAAAC<br>AGGATTAGATACCCTGGTAGTCCACGCCGTAAACGATGAGTGCTAGGTGTCGGGGAGGAATCCTCGGTGCCGTAGC<br>TAACGCAATAAGCACTCCACCTGGGGAGTACGACCGCAAGGTTGAAACTCAAAGGAATTGACGGGGGCCCGCACAA<br>GCGGTGGAGCATGTGGTTTAATTCGAAGCAACGCGAAGAACCTTACCAAGGCTTGACATCCCGATGACCGTCCTAG<br>AGATAGGACTTCTCTTCGGAGCATCGGTGACAGGTGGTGCATGGTTGTCGTCAGCTCGTGTCGTGAGATGTTGGGT<br>TAAGTCCCGCAACGAGCGCAACCCTTGTCACTAGTTGCTACGAAAGGGCACTCTAGTGAGACTGCCGGTGACAAAC<br>CGGAGGAAGGTGGGGATGACGTCAAGTCCTCATGGCCCTTATGGGTAGGGCTTCACACGTCATACAATGGTCGGAA<br>CAGAGGGCAGCGAAGCCGTGAGGCGGAGCCAATCCCAGAAAACCGATCGTAGTCCGGATTGCAGTCTGCAACTCGA<br>CTGCATGAAGTCGGAATCGCTAGTAATCGCGGATCAGCATGCCGCGGTGAATACGTTCCCGGGTCTTGTACACACC<br>GCCCGTA |

TABLE 11-continued

| 16S rRNA Sequences of OTUs in Tables 2-5 OTUs in Table 2 |
|---|
| AMCI01001631.34.1456<br>GGCGCACGGGTGAGTAACACGTATCCAACCTGCCGATAACTCGGGGATAGCCTTTCGAAAGAAAGATTAATACCCG<br>ATGGCATGTAAAGACCTCCTGGTCTTTACATTAAAGAATTTCGGTTATCGATGGGGATGCGTTCCATTAGATAGTA<br>GGCGGGGTAACGGCCCACCTAGTCCACGATGGATAGGGGTTCTGAGAGGAAGGTCCCCCACATTGGAACTGAGACA<br>CGGTCCAAACTCCTACGGGAGGCAGCAGTGAGGAATATTGGTCAATGGACGCGAGTCTGAACCAGCCAAGTAGCGT<br>GAAGGAAGACTGCCCTATGGGTTGTAAACTTCTTTTATACGGGAATAAAGTATTCCACGTGTGGGATTTTGTATGT<br>ACCGTATGAATAAGGATCGGCTAACTCCGTGCCAGCAGCCGCGGTAATACGGAGGATCCGAGCGTTATCCGGATTT<br>ATTGGGTTTAAAGGGAGCGTAGGTGGAAGATTAAGTCAGCCTGTGAAAGTTTGCGGCTTAACCGTAAAATTGCAGT<br>TGATACTGGTTTTCTTGAGTGCAGTAGAGGTGGGCGGAATTCGTGGTGTAGCGGTGAAATGCTTAGATATCACGAA<br>GAACTCCGATTGCGAAGGCAGCTCACTGGACTGTAACTGACACTGATGCTCGAAAGTGTGGGTATCAAACAGGATT<br>AGATACCCTGGTAGTCCACACAGTAAACGATGAATACTCGCTGTTTGCGATATACAGTAAGCGGCCAAGCGAAAGC<br>GTTAAGTATTCCACCTGGGGAGTACGCCGGCAACGGTGAAACTCAAAGGAATTGACGGGGGCCCGCACAAGCGGAG<br>GAACATGTGGTTTAATTCGATGATACGCGAGGAACCTTACCCGGGCTTAAATTACACCTGAATAGATTGGAAACAT<br>TTTAGCCGCAAGGCAGGTGTGAAGGTGCTGCATGGTTGTCGTCAGCTCGTGCCGTGAGGTGTCGGCTTAAGTGCCA<br>TAACGAGCGCAACCCTTATCTTCAGTTACTAACAGTTATAGCTGAGGACTCTGAAGAGACTGCCGTCGTAAGATGT<br>GAGGAAGGTGGGGATGACGTCAAATCAGCACGGCCCTTACGTCCGGGGCTACACACGTGTTACAATGGGGGGTACA<br>GAAGGCTGCTACCTGGCGACAGGATGCCAATCCTTAAATCCTCTCTCAGTTCGGACTGGAGTCTGCAACCCGACTC<br>CACGAAGCTGGATTCGCTAGTAATCGCGCATCAGCCATGGCGCGGTGAATACGTTCCCGGGCCTTGTACACACCGC<br>CCGTCAAGCCATGAAAGCCGGGGGTACCTGAAGTGCGTAACCGCAAGGAGCGTCCTAGGGTAAAACTGGTAATTGG<br>GGCTAAGTCGTAACAAGGTAGCCGTACCGGAAGGTGCGGCTG |
| KF842598.1.1394<br>AGAGTTTGATCCTGGCTCAGGATGAACGCTAGCGACAGGCTTAACACATGCAAGTCGAGGGGCAGCATGATTTGTA<br>GCAATACAGATTGATGGCGACCGGCGCACGGGTGAGTAACGCGTATGCAACTTACCTATCAGAGGGGGATAGCCCG<br>GCGAAAGTCGGATTAATACCCCATAAAACAGGGGTCCCGCATGGGAATATTTGTTAAAGATTCATCGCTGATAGAT<br>AGGCATGCGTTCCATTAGGCAGTTGGCGGGGTAACGGCCCACCAAACCGACGATGGATAGGGGTTCTGAGAGGAAG<br>GTCCCCCACATTGGTACTGAGACACGGACCAAACTCCTACGGGAGGCAGCAGTGAGGAATATTGGTCAATGGCCGA<br>GAGGCTGAACCAGCCAAGTCGCGTGAAGGAAGAAGGATCTATGGTCTGTAAACTTCTTTTATAGGGGAATAAAGTG<br>GAGGACGTGTCCTTTTTTGTATGTACCCTATGAATAAGCATCGGCTAACTCCGTGCCAGCAGCCGCGGTAATACGG<br>AGGATGCGAGCGTTATCCGGATTTATTGGGTTTAAAGGGTGCGTAGGTGGTGATTTAAGTCAGCGGTGAAAGTTTG<br>TGGCTCAACCATAAAATTGCCGTTGAAACTGGGTTACTTGAGTGTGTTTGAGGTAGGCGGAATGCGTGGTGTAGCG<br>GTGAAATGCATAGATATCACGCAGAACTCCGATTGCGAAGGCAGCTTACTAAACCATAACTGACACTGAAGCACGA<br>AAGCGTGGGGATCAAACAGGATTAGATACCCTGGTAGTCCACGCAGTAAACGATGATTACTAGGAGTTTGCGATAC<br>AATGTAAGCTCTACAGCGAAAGCGTTAAGTAATCCACCTGGGGAGTACGCCGGCAACGGTGAAACTCAAAGGAATT<br>GACGGGGGCCCGCACAAGCGGAGGAACATGTGGTTTAATTCGATGATACGCGAGGAACCTTACCCGGGTTTGAACG<br>TAGTCTGACCGGAATGGAAACACTCCTTCTAGCAATAGCAGATTACAAGGTGCTGCATGGTTGCCTCAACTCCGGC<br>CCGGAAGGTCCGGCTTAATTGCCATAACAAGCGCACCCTTTTACCAAGGTTCAAACAGGTGAAGCTTGAAGACTCT<br>GTGGAACCTCCCCCCTAACCTGTGAGAAGAAGTGGGGATACACTCAATAAACCACGGCCCTTAATCCCGGGGGGAA<br>CACTGGTTACAATGGGTTGGGAAAGGGGGCTTCCTGGCGACAGGATGCTAATCTCCAAACCATGTCTCAGTTCGGA<br>TCGGAGTCTGCAACTCGACTCCGTGAAGCTGGATTCGCTAGTAATCGCGCATCAGCCATGGCGCGGTGAATACGTT<br>CCCGGGCCTTGTACACACCGCCCGTC |
| HQ793763.1.1451<br>GATGAACGCTAGCTACAGGCTTAACACATGCAAGTCGAGGGGCAGCATGGTCTTAGCTTGCTAAGGCTGATGGCGA<br>CCGGCGCACGGGTGAGTAACACGTATCCAACCTGCCGTCTACTCTTGGCCAGCCTTCTGAAAGGAAGATTAATCCA<br>GGATGGGATCATGAGTTCACATGTCCGCATGATTAAAGGTATTTTCCGGTAGACGATGGGGATGCGTTCCATTAGA<br>TAGTAGGCGGGGTAACGGCCCACCTAGTCAACGATGGATAGGGGTTCTGAGAGGAAGGTCCCCCACATTGGAACTG<br>AGACACGGTCCAAACTCCTACGGGAGGCAGCAGTGAGGAATATTGGTCAATGGGCGCGAGCCTGAACCAGCCAAGT<br>AGCGTGAAGGATGACTGCCCTATGGGTTGTAAACTTCTTTTGTCCGGGAATAAAACCGCCTACGTGTAGGCGCTTG<br>TATGTACCGGTACGAATAAGCATCGGCTAACTCCGTGCCAGCAGCCGCGGTAATACGGAGGATGCGAGCGTTATCC<br>GGATTTATTGGGTTTAAAGGGAGCGCAGACGGGTTTTTAAGTCAGCTGTGAAAGTTTGGGGCTCAACCTTAAAATT<br>GCAGTTGATACTGGAGACCTTGAGTGCAGTTGAGGCAGGCGGAATTCGTGGTGTAGCGGTGAAATGCTTAGATATC<br>ACGAAGAACTCCGATTGCGAAGGTAGCTTGCTAAAGTGTAACTGACGTTCATGCTCGAAAGTGTGGGTATCAAACA<br>GGATTAGATACCCTGGTAGTCCACACGGTAAACGATGGATACTCGCTGTTGGCGATATACGGTCAGCGGCTTAGCG<br>AAAGCGTTAAGTATCCCACCTGGGGAGTACGCCGGCAACGGTGAAACTCAAAGGAATTGACGGGGGCCCGCACAAG<br>CGGAGGAACATGTGGTTTAATTCGATGATACGCGAGGAACCTTACCCGGGCTTAAATTGCACTGGACTATTCTGGA<br>AACAGGATATTCTTCGGACCAGTGTGAAGGTGCTGCATGGTTGTCGTCAGCTCGTGCCGTGAGGTGTCGGCTTAAG<br>TGCCATAACGAGCGCAACCCTTGCTGCCAGTTACTAACAGGTAATGCTGAGGACTCTGGCGGGACTGCCATCGTAA<br>GATGCGAGGAAGGTGGGGATGACGTCAAATCAGCACGGCCCTTACGTCCGGAGCTACACACGTGTTACAATGGTAG<br>GTACAGAGGGTAGCTACCCAGCGATGGGATGCGAATCTCGAAAGCCTATCTCAGTTCGGATTGGAGGCTGAAACCC<br>GCCTCCATGAAGTTGGATTCGCTAGTAATCGCGCATCAGCCATGGCGCGGTGAATACGTTCCCGGGCCTTGTACAC<br>ACCGCCCGTCAAGCCATGGGAGCCGGGGGTACCTGAAGTACGTAACCGCAAGGATCGTCCTAGGGTAAAACTGGTG<br>ACTGGGG |
| DQ113765.1.1450<br>GATGAACGCTAGCTACAGGCTTAACACATGCAAGTCGAGGGGCAGCATGAAGTTTGCTTGCAAACTTTGATGGCGA<br>CCGGCGCACGGGTGAGTAACGCGTATCCAACCTCCCGCATACTCGGGGATAGCCTTCTGAAAGGAAGATTAATACC<br>CGATGGTATCTTAAGCGCACATGCAATTAAGATTAAAGAATTTCGGTATGCGATGGGGATGCGTTCCATTAGGTAG<br>TAGGCGGGGTAACGGCCCACCTAGCCATCGATGGATAGGGGTTCTGAGAGGAAGGTCCCCCACATTGGAACTGAGA<br>CACGGTCCAAACTCCTACGGGAGGCAGCAGTGAGGAATATTGGTCAATGGGCGCGAGCCTGAACCAGCCAAGTAGC<br>GTGAAGGATGACTGCCCTATGGGTTGTAAACTTCTTTTGTCCGGGAATAAAACCGCCTACGTGTAGGCGCTTGTAT<br>GTACCGGTACGAATAAGCATCGGCTAACTCCGTGCCAGCAGCCGCGGTAATACGGAGGATGCGAGCGTTATCCGGA<br>TTTATTGGGTTTAAAGGGAGCGCAGACGGGTTTTTAAGTCAGCTGTGAAAGTTTGGGGCTCAACCTTAAAATTGCA<br>GTTGATACTGGAGACCTTGAGTGCAGTTGAGGCAGGCGGAATTCGTGGTGTAGCGGTGAAATGCTTAGATATCACG<br>AAGAACTCCGATTGCGAAGGCAGCTTGCTAAAGTGTAACTGACGTTCATGCTCGAAAGTGTGGGTATCAAACAGGA<br>TTAGATACCCTGGTAGTCCACACGGTAAACGATGGATACTCGCTGTTGGCGATATACGGTCAGCGGCTTAGCGAAA<br>GCGTTAAGTATCCCACCTGGGGAGTACGCCGGCAACGGTGAAACTCAAAGGAATTGACGGGGGCCCGCACAAGCGG |

TABLE 11-continued 16S rRNA Sequences of OTUs in Tables 2-5
OTUs in Table 2

AGGAACATGTGGTTTAATTCGATGATACGCGAGGAACCTTACCCGGGCTTAAATTGCACTGGACTTTCCCGGAAAC
GGGATTTTCTTCGGACCAGTGTGAAGGTGCTGCATGGTTGTCGTCAGCTCGTGCCGTGAGGTGTCGGCTTAAGTGC
CATAACGAGCGCAACCCTTGCTGCCAGTTACTAACAGGTAATGCTGAGGACTCTGGCGGGACTGCCATCGTAAGAT
GCGAGGAAGGTGGGGATGACGTCAAATCAGCACGGCCCTTACGTCCGGGGCTACACACGTGTTACAATGGGGGGTA
CAGAAGGCCGCTACCCGGCAACGGGATGCCAATCTCCAAAACCCCTCTCAGTTCGGACTGGAGTCTGCAACCCGAC
TCCACGAAGCTGGATTCGCTAGTAATCGCGCATCAGCCACGGCGCGGTGAATACGTTCCCGGGCCTTGTACACACC
GCCCGTCAAGCCATGAAAGCCGGGGGTACCTGAAGTGCGTAACCGCAAGGAGCGCCCTAGGGTAAAACTGGTAATT
GGGGCT

ACBW01000012.3536.5054
AGAGTTTGATCCTGGCTCAGGATGAACGCTAGCTACAGGCTTAACACATGCAAGTCGAGGGGCAGCGGGATTGAAG
CTTGCTTCAATTGCCGGCGACCGGCGCACGGGTGAGTAACGCGTATCCAACCTTCCGCTTACTCGGGGATAGCCTT
TCGAAAGAAAGATTAATACCCGATGGTATCTTAAGCACGCATGAGATTAAGATTAAAGATTTATCGGTAAGCGATG
GGGATGCGTTCCATTAGGCAGTTGGCGGGGTAACGGCCCACCAAACCTACGATGGATAGGGGTTCTGAGAGGAAGG
TCCCCCACATTGGAACTGAGACACGGTCCAAACTCCTACGGGAGGCAGCAGTGAGGAATATTGGTCAATGGGCGAG
AGCCTGAACCAGCCAAGTAGCGTGAAGGATGACGGCCCTACGGGTTGTAAACTTCTTTTGTGCGGGAATAAAGGAA
CCTACGTGTAGGTTTTTGCATGTACCGTAACGAATAAGCATCGGCTAACTCCGTGCCAGCAGCCGCGGTAATACGG
AGGATGCGAGCGTTATCCGGATTTATTGGGTTTAAAGGGAGCGTAGACGGGTTTTTAAGTCAGCTGTGAAAGTTTG
GGGCTCAACCTTAAAATTGCAGTTGAAACTGGAGACCTTGAGTACGGTTGAGGCAGGCGGAATTCGTGGTGTAGCG
GTGAAATGCTTAGATATCACGAAGAACCCCGATTGCGAAGGCAGCCTGCTAAGCCGCCACTGACGTTGAGGCTCGA
AAGTGCGGGTATCAAACAGGATTAGATACCCTGGTAGTCCGCACGGTAAACGATGGATACTCGCTGTTGGCGATAG
ACAGTCAGCGGCCAAGCGAAAGCGTTAAGTATCCCACCTGGGGAGTACGCCGGCAACGGTGAAACTCAAAGGAATT
GACGGGGGCCCGCACAAGCGGAGGAACATGTGGTTTAATTCGATGATACGCGAGGAACCTTACCCGGGCTTGAACT
GCAGTGGAATTATCCGGAAACGGATAAGCGAGCAATCGCCGCTGTGGAGGTGCTGCATGGTTGTCGTCAGCTCGTG
CCGTGAGGTGTCGGCTTAAGTGCCATAACGAGCGCAACCCTTGCTGCCAGTTACTAACAGGTCATGCTGAGGACTC
TGGCAGGACTGCCATCGTAAGATGCGAGGAAGGTGGGGATGACGTCAAATCAGCACGGCCCTTACGTCCGGGGCTA
CACACGTGTTACAATGGGGAGTACAGAGGGCAGCTACCGGGCGACCGGATGCGAATCCCGAAAGCTCCTCTCAGTT
CGGACTGGAGTCTGCAACCCGACTCCACGAAGCTGGATTCGCTAGTAATCGCGCATCAGCCACGGCGCGGTGAATA
CGTTCCCGGGCCTTGTACACACCGCCCGTCAAGCCATGAAAGCCGGGGGTACCTGAAGTACGTAACCGCGAGGATC
GTCCTAGGGTAAAACCGGTAATTGGGGCTAAGTCGTAACAAGGTAGCCGTACCGGAAGGTGCGGCTG

HK693629.1.1491
AGAGTTTGATCCTGGCTCAGGATGAACGCTGGCGGCGTGCTTAACACATGCAAGTCGAACGAGAAACATTTTAATG
AAGCTTCGGCAGATTTAGTTTGTTTCTAGTGGCGGACGGGTGAGTAACGCGTGGGTAACCTGCCTCACACTGGGGG
ATAACAGTCAGAAATGACTGCTAATACCGCATAAGCGCACGGAACCGCATGGTTTTGTGTGAAAAACTCCGGTGGT
GTGAGATGGACCCGCGTTGGATTAGCCAGTTGGCAGGGTAACGGCCTACCAAAGCGACGATCCATAGCCGGCCTGA
GAGGGTGAACGGCCACATTGGGACTGAGACACGGCCCAGACTCCTACGGGAGGCAGCAGTGGGGAATATTGCACAA
TGGGGGAAACCCTGATGCAGCGACGCCGCGTGAAGGAAGAAGTATCTCGGTATGTAAACTTCTATCAGCAGGGAAG
ATAATGACGGTACCTGACTAAGAAGCCCCGGCTAACTACGTGCCAGCAGCCGCGGTAATACGTAGGGGGCAAGCGT
TATCCGGATTTACTGGGTGTAAAGGGAGCGTAGACGGAGCAGCAAGTCTGATGTGAAAGGCAGGGGCTCAACCCCT
GGACTGCATTGGAAACTGTTGATCTTGAGTACCGGAGGGGTAAGCGGAATTCCTAGTGTAGCGGTGAAATGCGTAG
ATATTAGGAGGAACACCAGTGGCGAAGGCGGCTTACTGGACGGTAACTGACGTTGAGGCTCGAAAGCGTGGGGAGC
AAACAGGATTAGATACCCTGGTAGTCCACGCCGTAAACGATGAATACTAGGTGTCGGGTGGCAGAGCCATTCGGTG
CCGCAGCAAACGCAGTAAGTATTCCACCTGGGGAGTACGTTCGCAAGAATGAAACTCAAAGGAATTGACGGGGACC
CGCACAAGCGGTGGAGCATGTGGTTTAATTCGAAGCAACGCGAAGAACCTTACCAAGTCTTGACATCCCTCTGACC
GGTCCTTAACCGGACCTTTCCTTCGGGACAGAGGAGACAGGTGGTGCATGGTTGTCGTCAGCTCGTGTCGTGAGAT
GTTGGGTTAAGTCCCGCAACGAGCGCAACCCCTATCCCCAGTAGCCAGCATTTAAGGTGGGCACTCTGAGGAGACT
GCCAGGGATAACCTGGAGGAAGGCGGGGATGACGTCAAATCATCATGCCCCTTATGATTTGGGCTACACACGTGCT
ACAATGGCGTAAACAAAGGGAAGCAGAGCGGTGACGCCGAGCAAATCCCAAAAATAACGTCCCAGTTCGGACTGCA
GTCTGCAACTCGACTGCACGAAGCTGGAATCGCTAGTAATCGCGGATCAGAATGCCGCGGTGAATACGTTCCCGGG
TCTTGTACACACCGCCCGTCACACCATGGGAGTCAGTAACGCCCGAAGTCAGTGACCTAACCGAAAGGGAGGAGCT
GCCGAAGGCGGGACGGATGACTGGGGTGAAGTCGTAACAAGGTAACC

JQ208053.1.1336
GATGAACGCTGACAGAATGCTTAACACATGCAAGTCTACTTGAATTCACTTCGGTGATAGTAAGGTGGCGGACGGG
TGAGTAACACGTAAAGAACTTGCCTTACAGTCTGGGACAACTATTGGAAACGATAGCTAATACCGGATATTATGCG
AGAGTCGCATGACTCTTGTATGAAAGCTATATGCGCTGTAAGAGAGCTTTGCGTCCCATTAGCTAGTTGGTGAGGT
AACGGCTCACCAAGGCCACGATGGGTAGCCGGCCTGAGAGGGTGAACGGCCACAAGGGGACTGAGACACGGCCCTT
ACTCCTACGGGAGGCAGCAGTGGGGAATATTGGACAATGGACCAAAAGTCTGATCCAGCAATTCTGTGTGCACGAT
GACGGTCTTAGGATTGTAAAGTGCTTTCAATTGGGAAGAAAAAAATGACGGTACCAATAGAAGAAGCGACGGCTAA
ATACGTGCCAGCAGCCGCGGTAATACGTATGTCGCAAGCGTTATCCGGATTTATTGGGCGTAAAGCGCGTCTAGGT
GGTTTGGTAAGTCTGATGTGAAAATGCGGGGCTCAACTCCGTATTGCGTTGGAAACTGCCTAACTAGAGTATCGGA
GAGGTGGGCGGAACTACAAGTGTAGAGGTGAAATTCGTAGATATTTGTAGGAATGCCGATAGAGAAGTCAGCTCAC
TGGACGAATACTGACACTGAAGCGCGAAAGCATGGGGAGCAAACAGGATTAGATACCCTGGTAGTCCATGCTGTAA
ACGATGATTACTAAGCGTCGGGGGTCGAACCTCGGCACTCAAGCTAACGCGATAAGTAATCCGCCTGGGGAGTACG
TACGCAAGTATGAAACTCAAAGGAATTGACGGGGACCCGCACAAGTGGTGGAGCATGTGGTTTAATTCGACGCAAC
GCGAGGAACCTTACCAGCGTTTGACATCCTAGGAATGAGAAAGAGATTTCTTAGTGCTCCTTCGGGAGAACCTAGA
GACAGGTGGTGCATGGCTGTCGTCAGCTCGTGTCGTGAGATGTTGGGTTAAGTCCCGCAACGAGCGCAACCCCTAT
TGTATGTTGCCATCATTAAGTTGGGCACTCATGCGATACTGCCTGCGATGAGCAGGAGGAAGGTGGGGATGACGTC
AAGTCATCATGCCCCTTATACGCTGGGCTACACACGTGCTACAATGGGCAGTACAGAGAGAAGCAAATCTGCGAGG
AGGAGCAAATCTCACAAAGCTGTTCGTAGTTCGGATTGTACTCTGCAACTCGAGTACATGAAGTTGGAATCACTAG
TAATCGCAAATCAGCTATGTTGCGGTGAATACGTTCTCGGGTCT

GQ493166.1.1359
GATGAACGCTGGCGGCGTGCTTAACACATGCAAGTCGAACGGGAAACATTTTAATGAAGCTTCGGCAGATTTAGCT
TGTTTCTAGTGGCGGACGGGTGAGTAACGCGTGGGTAACCTGCCTCACACTGGGGGATAACAGTCAGAAATGACTG
CTAATACCGCATAAGCGCACGGAACCGCATGGTTTTGTGTGAAAAACTCCGGTGGTGTGAGATGGACCCGCGTTGG

TABLE 11-continued 16S rRNA Sequences of OTUs in Tables 2-5
OTUs in Table 2

ATTAGCCAGTTGGCAGGGTAACGGCCTACCAAAGCGACGATCCATAGCCGGCCTGAGAGGGTGAACGGCCACATTG
GGACTGAGACACGGCCCAGACTCCTACGGGAGGCAGCAGTGGGGAATATTGCACAATGGGGGAAACCCTGATGCAG
CGACGCCGCGTGAAGGAAGAAGTATCTCGGTATGTAAACTTCTATCAGCAGGGAAGAAAATGACGGTACCTGACTA
AGAAGCCCCGGCTAACTACGTGCCAGCAGCCGCGGTAATACGTAGGGGGCAAGCGTTATCCGGATTTACTGGGTGT
AAAGGGAGCGTAGACGGAATGGCAAGTCTGATGTGAAAGGCAGGGGCTCAACCCCTGGACTGCATTGGAAACTGTC
AGTCTTGAGTACCGGAGGGGTAAGCGGAATTCCTAGTGTAGCGGTGAAATGCGTAGATATTAGGAGGAACACCAGT
GGCGAAGGCGGCTTACTGGACGGTAACTGACGTTGAGGCTCGAAAGCGTGGGGAGCAAACAGGATTAGATACCCTG
GTAGTCCACGCCGTAAACGATGAATACGAGGTGTCGGGTGGGCAAAGCCATTCGGTGCCGCAGCAAACGCAAAAAG
TAATCCCACCTGGGGGAGTACGTTCCCAAGAATGAAACTCAAAGGAAATAGCGGGGACCCGCACAAGCGGTGGAGC
ATGTGGTGTATTTGAAGCAACGCGAAGAACCTTACCAAGTCTTGACATCCCTCTGACCGGTCCTTAACCGGACCTC
TCCTTCGGGACAGGGGAGACAGGTGGTGCATGGTTGTCGTCAGCTCGTGTCGTGAGATGTTGGGTTAAGTCCCGCA
ACGAGCGCAACCCCTATCCTTAGTAGCCAGCATCTGAGGTGGGCACTCTGAGGAGACTGCCAGGGATAACCTGGAG
GAAGGCGGGGAGGACGTCAAATCATCATGCCCCCTATGATTTGGGCTACACACGTGCTACAATGGCGTAAACAAAG
GGAAGCAGAGCGGTGACGCCGAGCAAATCCCAAAAATAACGTCCCAGTTCGGACTGCAGTCTGCAACTCGACTGCA
CGAAGCTGGAATCGCTAGTAATCGCGGATCAGAATGCCGCGGTGAATAAAAGCCCGGGTCTTGCACT

GQ448486.1.1387
AGAGTTTGATCATGGCTCAGGATGAACGCTGGCGGCGTGCTTAACACATGCAAGTCGAACGGGAATTACTTTATTG
AAGCTTTGGTCGATTTAATTTAATTATAGTGGCGGACGGGTGAGTAACGCGTGGGTAACCTGCCTTATACAGGGGG
ATAACAGTCAGAAATGGCTGCTAATACCGCATAAGCGCACAGAGCTGCATGGCTCAGTGTGAAAAACTCCGGTGGT
ATAAGATGGACCCGCGTTGGATTAGTTGGTTGGTGGGGTAACGGCCCACCAAGGCGACGATCCATAGCCGGCCTGA
GAGGGTGAACGGCCACATTGGGACTGAGACACGGCCCAGACTCATACGGGAGGCAGCAGTGGGGAATATTGCACAA
TGGGGGAAACCCTGATGCAGCGACGCCGCGTGAAGGAAGAAGTATCTCGGTATGTAAACTTCTATCAGCAGGGAAG
ATAGTGACGGTACCTGACTAAGAAGCCCCGGCTAACTACGTGCCAGCAGCCGCGGTAATACGTAGGGGGCAAGCGT
TATCCGGATTTACTGGGTGTAAAGGGAGCGTAGACGGTGTGGCAAGTCTGATGTGAAAGGCATGGGCTCAACCTGT
GGACTGCATTGGAAACTGTCATACTTGAGTGCCGGAGGGGTAAGCGGAATTCCTAGTGTAGCGGTGAAATGCGTAG
ATATTAGGAGGAACACCAGTGGCGAAGGCGGCTTACTGGACGGTAACTGACGTTGAGGCTCGAAAGCGTGGGGAGC
AAACAGGATTAGATACCCTGGTAGTCCACGCCGTAAACGATGAATACTAGGTGTCGGGTGGCAAAGCCATTCGGTG
CCGTCGCAAACGCAGTAAGTATTCCACCTGGGGAGTACGTTCGCAAGAATGAAACTCAAAGGAATTGACGGGGACC
CGCACAAGCGGTGGAGCATGTGGTTTAATTCGAAGCAACGCGAAGAACCTTACCAAGTCTTGACATCCGCCTGACC
GATCCTTAACCGGATCTTTCCTTCGGGACAGGCGAGACAGGTGGTGCATGGTTGTCGTCAGCTCGTGTCGTGAGAT
GTTGGGTTAAGTCCCGCAACGAGCGCAACCCCTATCCTCAGTAGCCAGCATTAAGTTGGGCACTCATGCGATACTG
CCTGCGATGAGCAGGAGGAAGGTGGGGATGACGTCAAGTCATCATGCCCCTTATACGCTGGGCTACACACGTGCTA
CAATGGGTAGTACAGAGAGTCGCAAACCTGCGAGGGGGAGCTAATCTCAGAAAACTATTCTCAGTTCGGATTGTAC
TCTGCAACTCGAGTACATGAAGTTGGAATCGCTAGTAATCGCAAATCAGCTATGTTGCGGTGAATACGTTCTCGGG
TCTTGCACTCACCGCCCGT

GQ491426.1.1332
GCTCAGGATGAACGCTGGCGGCGTGCTTAACACATGCAAGTCGAGCGAAGCACTTGCCATTGACTCTTCGGAAGAT
TTGGCATTTGACTGAGCGGCGGACGGGTGAGTAACGCGTGGGTAACCTGCCTCATACGGGGGAATAACAGTTAGAA
ATGGCTGCTAATGCCGCATAACCGCACAGGACCGCATGGACTGGTGTGAAAAACTGAGGTGGTATGAGATGGGCCC
GCGTCTGATTAGGTTAGTTGGCGGGGTAACGGCCCACCAAGCCGACGATCAGTAGCCGACCTGAGAGGGACCGGCC
ACATTGGGACTGAGACATGGCCCAGACTCCTACGGGAGGCAGCAGTGGGGAATATTGCACAATGGAGGAAACTCTG
ATGCAGCGACGCCGCATGAAGGAAGAAGTATCTCGGTATGTAAACTTCTATCAGCAGGGAAGAAAATGACGGTACC
TGACTAAGAAGCCCCGGCTAACTACGTGCCAGCAGCCGCGGTAATACGTAGGGGGCAAGCGTTATCCGGATTTACT
GGGTGTAAAGGGAGCGTAGACGGACGGGCAAGTCTGATGTGAAAGCCCGGGGCTTAACCCCGGGACTGCATTGGAA
ACTGTCCATCTTGAGTGCCGGAGAGGTAAGCGGAATTCCTAGTGTAGCGGTGAAATGCGTAGATATTAGGAGGAAC
ACCAGTGGCGAAGGCGGCTTACTGGACGGTAACTGACGTTGAGGCTCGAAAGCGTGGGGAGCAAACAGGATTAGAT
ACCCTGGTAGTCCACGCCGTAAACGATCAATAATGGGTGTCGGGTTGCAAAGCAATCCGGTGCCGCAGCAAACGCA
GTAAGTATTCCCCCTCGGGAGTACGTTCGCAAGAATGAAACTCAAAGGAAGGGACGGGGATCCGCACAAGCGGCGG
AGCATGTGGTTTAATTAGAAGCAACGCGAAGAACCTTACCAAGTCTTGACATCTGCCTGACCGTTCCTTAACCGGA
ACTATCTTTCGGGACAGGCAAGACAGGTGGTGCATGGTTGTCGTCAGCTCGTGTCGTGAGATGTTGGGTTAAGTCC
CGCAACGAGCGCAACCCCTGTCCTTAGTAGCCAGCAGTCCGGCTGGGCACTCTAGGGAGACTGCCGGGGGTAACCC
GGAGGAAGGCGGGGAGGAGGTCAAATCATCATGCCCCCCCTGATTTGGGCTACACACGTGGTACAATGGCGTAAAC
AAAGGGAAGCGGAGTGGTGACGCTGAGCAAATCTCAAAAATAACGTCCCACTTCGGACTGCAGTCTGCAACTCGAC
TGCACGAAGCTGGAATCGCTAGTAATCGCGAATCAGAATG

New.ReferenceOTU54
TACGTAGGGGGCAAGCGTTATCCGGATTTACTGGGTGTAAAGGGAGCGTAGACGGCATGGCAAGTCTGATGTGAAA
GGCAGGGGCTCAACTCCTGGACTGCATTGGAAACTGCCAGGCTTGAGTGCCGGAGGGGTAAGCGGAATTCCTAGTG
TAGCGGTGAAATGCGTAGATATTAGGAGGAACACCAGTGGCGAAGGCGGCTTACTGGACGGTAACTGACGTTGAGG
CTCGAAAGCGTGGGGAGCAAACAGG JN387556.1.1324
CGTAAGTAACCTGCCCTGTACACACGGATAACATACCGAAAGGTATGCTAATACGGGATAATATATTTTGATCGCA
TGGTCGAGATATCAAAGCTCCGGCGGTACACCAGGGACCCCCGACAGAGGAGCTAGTTGGTAGTAATGTCACCAAG
GCGACGATCAGAAGCCGAACTGAGAGGGGGATCCGCACATGACTGAGACACGGTCAAACTCCTACGGGAGGCAGCA
GTGGGGAATATGCCAATGGGCGAAAGCTGATGCAGCACGCGCGTGAGCGATGAGGCTCGGGTCGTAAAGCTCGTCT
CAAGGAAGATAATGACGGTACTTGAGGAGGAAGCCCCGGCTAACTACGTGCCAGCAGCCGCGGTAATACGTAGGGG
GCTAGCGTTATCCGGAATTACTGGGCGTAAAGGGTGCGTAGGCGGTCTTTCAAGTCAGGAGTGAAAGGCTACGGCT
CAACCGTAGTAAGCTCTTGAAACTGTAAGACTTGAGTGCAGGAGAGGAGAGTGGAATTCCTAGTGTAGCGGTGAAA
TGCGTAGATATTAGGAGGAACACCAGTTGCGAAGGCGGCTCTCTGGACTGTAACTGACGCTGAGGCACGAAAGCGT
GGGGAGCAAACAGGATTAGATACCCTGGTAGTCCACGCCGTAAACGATGAGTACTAGCTGTCGGAGGTTACCCCCT
TCGGTGGCGCAGCTAACGCATTAAGTACTCCGCCTGGGAAGTACGCTCGCAAGAGTGAAACTCAAAGGAATTGACG
GGGACCCGCACAAGTAGCGGAGCATGTGGTTTAATTCGAAGCAACGCGAAGAACCTTACCTAAGCTTGACATCCCA
CTGACCCTTCCCTAATCGGAAGCTTCCCTTCGGGACAGTGGTGACAGGTGGTGCATGGTTGTCGTCAGCTCGTGTC
GTGAGATGTTGGGTTAAGTCCCGCAACGAGCGCAACCCTTGCCTTTAGTTGCCAGCATTAAGTTGGGCACTCTAGA TABLE 11-continued 16S rRNA Sequences of OTUs in Tables 2-5
OTUs in Table 2

GGGACTGCCAGGGATAACCCGGAGGAGTGGGGATGACGTCAAATCATCATGCCCTTATGCTAGGCTACACACGTGC
TACAATGGGTGGTCAGAGGCCAGCCAGTCGTGAGGCCGAGCTATCCCATAAGCCATTCTCGTCCGGATTGTAGGCT
GAACTCGCCTACATGAGCTGGAATTACAAGTATGCGATCGATGCTGCGTGATGCGTCCGGGTCTTGTACACACCGC
CCGTCACACCATGGGAGTTGGGGGCGCCCGAAGCCGGATTGCTAACCTTTTGGAAGCGTCCGTCGAAGGTGAAACC
AATAACTGGGGTGAAGTCGTAACAAGGTAACC

OTUs in Table 3

GQ006324.1.1342
GACGAACGCTGGCGGCGTGCTTAACACATGCAAGTCGAACGGAAAGGCCCCAGCTCGCTGGGGTACTCGAGTGGCG
AACGGGTGAGTAACACGTGGGTGATCTGCCTTGCACTCTGGGATAAGCTTGGGAAACTGGGTCTAATACCGGATAT
GAACTGCCTTTAGTGTGGTGGTTGGAAAGTTTTTTCGGTGCAAGATGAGCTCGCGGCCTATCAGCTTGTTGGTGGG
GTAATGGCCTACCAAGGCGTCGACGGGTAGCCGGCCTGAGAGGGTGTACGGCCACATTGGGACTGAGATACGGCCC
AGACTCCTACGGGAGGCAGCAGTGGGGAATATTGCACAATGGGCGGAAGCCTGATGCAGCGACGCCGCGTGGGGGA
TGACGGCCTTCGGGTTGTAAACTCCTTTCGACAGGGACGAAGCTTTTTGTGACGGTACCTGTATAAGAAGCACCGG
CTAACTACGTGCCAGCAGCCGCGGTAATACGTAGGGTGCGAGCGTTGTCCGGAATTACTGGGCGTAAAGAGCTCGT
AGGTGGTTTGTCGCGTCGTCTGTGAAATTCCGGGGCTTAACTCCGGGCGTGCAGGCGATACGGGCATAACTTGAGT
ACTGTAGGGGAGACTGGAATTCCTGGTGTAGCGGTGAAATGCGCAGATATCAGGAGGAACACCGGTGGCGAAGGCG
GGTCTCTGGGCAGTAACTGACGCTGAGGAGCGAAAGCATGGGGAGCGAACAGGATTAGATACCCTGGTAGTCCATG
CCGTAAACGGTGGGCGCTAGGTGTGGGTTTCCTTCCACGGGATCCGTGCCGTAGCTAACGCATTAAGCGCCCCGCC
TGGGGAGTACGGCCGCAAGGCTAAAACTCAAAGGAATTGACGGGGGCCCGCACAAGCGGCGGAGCATGTGGATTAA
TTCGATGCAACGCGAAGAACCTTACCTGGGCTTGACATACACTGGATCGGGCTAGAGATAGTCTTTCCCTTTGTGG
CTGGTGTACAGGTGGTGCATGGTTGTCGTCAGCTCGTGTCGTGAGATGTTGGGTTAAGTCCCGCAACGAGCGCAAC
CCTTGTCTTATGTTGCCAGCATTTGGTTGGGGACTCATGAGAGACTGCCGGGGTCAACTCGGAGGAAGGTGGGGAT
GACGTCAAATCATCATGCCCCTTATGTCCAGGGCTTCACACATGCTACAATGGTCGGTACAACGCGCAGCGACACT
GTGAGGTGGAGCGAATCGCTGAAAGCCGGCCTTAGTTCGGATTGGGGTCTGCAACTCGACCCCATGAAGTCGGAGT
CGCTAGTAATCGCAGATCAGCAATGCTGCGGTGAATACGTTCCCGGGCCT

New.ReferenceOTU52
TACGTAGGTGGCGAGCGTTATCCGGATTTACTGGGCGTAAAGGGAGCGTAGGCGGATGATTAAGTGGGATGTGAAA
TACCCGGGCTCAACTTGGGTGCTGCATTCCAAACTGGTTATCTAGAGTGCAGGAGAGGAGAGTGGAATTCCTAGTG
TAGCGGTGAAATGCGTAGAGATTAGGAAGAACACCAGTGGCGAAGGCGACTCTCTGGACTGTAACTGACGCTGAGG
CTCGAAAGCGTGGGGAGCAAACAGG HG798451.1.1400
CTTGTGTCACCAACCATAGGGAGGGGGAAAACATGGAAACGGGGTTCATACCGCATAACTTTTTTAGCCCAATGCA
TAAGAAGAAAGGCCTTTCGGGTTTCGGTAAAGGAGGCCCCCGCGGCTCTTATAGTGTGTGTGGAAGTAACCGCTTC
CACAAGGCCCAGGTTTCATACCCGACTGGAGAGTGTGTTCGCCACACTGGGGAAAGGACCCCCGGCCCAGTCTCTC
TAGGGGAGGCAGCAGTAGGAATTTTCGGCAAAGGAAAAAATTTCTGACCGAACAACGCCGGTTGAATGAAGAAGTT
TTTCGGATCGAAAAACTCTGTTGTTAGAGAAGAACAAGGACGTTAGTAACTGAACGTCCCCTGACGGTATCTAACC
AGAAAGCCACGGCTAATTACGTGCCAGCAGCCGCGGTAATACGTAGGTGGCAAGCGTTGTCCGGATTTATTGGGCG
TAAAGCGAGCGCAGGCGGTTTCTTAAGTCTGATGTGAAAGCCCCCGGCTCAACCGGGGAGGGTCATTGGAAACTGG
GAGACTTGAGTGCAGAAGAGGAGAGTGGAATTCCATGTGTAGCGGTGAAATGCGTAGATATATGGAGGAACACCAG
TGGCGAAGGCGGCTCTCTGGTCTGTAACTGACGCTGAGGCTCGAAAGCGTGGGGAGCAAACAGGATTAGATACCCT
GGTAGTCCACGCCGTAAACGATGAGTGCTAAGTGTTGGAGGGTTTCCGCCCTTCAGTGCTGCAGCAAACGCATTAA
GCACTCCGCCTGGGGAGTACGACCGCAAGGTTGAAACTCAAAGGAATTGACGGGGGCCCGCACAAGCGGTGGAGCA
TGTGGTTTAATTCGAAGCAACGCGAAGAACCTTACCAGGTCTTGACATCCTTTGACCACTCTAGAGATAGAGCTTT
CCCTTCGGGGACAAAGTGACAGGTGGTGCATGGTTGTCGTCAGCTCGTGTCGTGAGATGTTGGGTTAAGTCCCGCA
ACGAGCGCAACCCTTATTGTTAGTTGCCATCATTTAGTTGGGCACTCTAGCGAGACTGCCGGTGACAAACCGGAGG
AAGGTGGGGATGACGTCAAATCATCATGCCCCTTATGACCTGGGCTACACACGTGCTACAATGGGAAGTACAACGA
GTCGCTAGACCGCGAGGTCATGCAAATCTCTTAAAGCTTCTCTCAGTTCGGATTGCAGGCTGCAACTCGCCTGCAT
GAAGCCGGAATCGCTAGTAATCGCGGATCAGCACGCCGCGGTGAATACGTTCCCGGGCCTTGTACACACCGCCCGT
CACACCACGAGAGTTTGTAACACCCGAAGTCGGTGAGGTAACCTTTTTGGAGCCAGCCGCCTAAGGTGGGATAGAT
GATTGGGGTGAAGTCGTAACCAACGTATGCC HK557089.3.1395
AGACTTTAGCTTGCTAAAGTTGGAAGAGTTGCGAACGGGTGAGTAACGCGTAGGTAACCTGCCTACTAGCGGGGGA
TAACTATTGGAAACGATAGCTAATACCGCATAACAGCATTTAACCCATGTTAGATGCTTGAAAGGAGCAATTGCTT
CACTAGTAGATGGACCTGCGTTGTATTAGCTAGTTGGTGAGGTAACGGCTCACCAAGGCGACGATACATAGCCGAC
CTGAGAGGGTGATCGGCCACACTGGGACTGAGACACGGCCCAGACTCCTACGGGAGGCAGCAGTAGGGAATCTTCG
GCAATGGGGGCAACCCTGACCGAGCAACGCCGCGTGAGTGAAGAAGGTTTTCGGATCGTAAAGCTCTGTTGTAAGA
GAAGAACGTGTGTGAGAGTGGAAAGTTCACACAGTGACGGTAACTTACCAGAAAGGGACGGCTAACTACGTGCCAG
CAGCCGCGGTAATACGTAGGTCCCGAGCGTTGTCCGGATTTATTGGGCGTAAAGCGAGCGCAGGCGGTTTAATAAG
TCTGAAGTTAAAGGCAGTGGCTTAACCATTGTTCGCTTTGGAAACTGTTAGACTTGAGTGCAGAAGGGGAGAGTGG
AATTCCATGTGTAGCGGTGAAATGCGTAGATATATGGAGGAACACCGGTGGCGAAAGCGGCTCTCTGGTCTGTAAC
TGACGCTGAGGCTCGAAAGCGTGGGGAGCAAACAGGATTAGATACCCTGGTAGTCCACGCCGTAAACGATGAGTGC
TAGGTGTTAGGCCCTTTCCGGGGCTTAGTGCCGCAGCTAACGCATTAAGCACTCCGCCTGGGGAGTACGACCGCAA
GGTTGAAACTCAAAGGAATTGACGGGGGCCCGCACAAGCGGTGGAGCATGTGGTTTAATTCGAAGCAACGCGAAGA
ACCTTACCAGGTCTTGACATCCCGATGCTATTCCTAGAGATAGGAAGTTTCTTCGGAACTGTGAGACTTGAGGGCA
GAAGGGTAGAGTGCACTTGTATGGGGAGCTGTGGAATGCGTTCCCGCAACGAGCGCAACCCCTATTGTTAGTTGCC
ATCATTAAGTTGGGCACTCTAGCGAGACTGCCGGTAATAAACCGGAGGAAGGTGGGGATGACGTCAAATCATCATG
CCCCTTATGACCTGGGCTACACACGTGCTACAATGGTTGGTACAACGAGTCGCGAGTCGGTGACGGCAAGCAAATC
TCTTAAAGCCAATCTCAGTTCGGATTGTAGGCTGCAACTCGCCTACATGAAGTCGGAATCGCTAGTAATCGCGGAT
CAGCACGCCGCGGTGAATACGTTCCCGGGCCTTGTACACACCGCCCGTCACACCACGAGAGTTTGTAACACCCGAA
GTCGGTGAGGTANCCTTTTAGGAGC TABLE 11-continued 16S rRNA Sequences of OTUs in Tables 2-5
OTUs in Table 2

GQ448336.1.1418
AGAGTTTGATCATGGCTCAGGACGAACGCTGGCGGCGTGCTTAACACATGCAAGTCGAACGAGAAGAGATGAGAAG
CTTGCTTCTTATCTCTTCGAGTGGCAAACGGGTGAGTAACGCGTAAGCAACCTGCCCTTCAGATGGGGACAACAGC
TGGAAACGGCTGCTAATACCGAATACGTTCTTTTTGTCGCATGGCAGAGGGAAGAAAGGGAGGCTCTTCGGAGCTT
TCGCTGAAGGAGGGGCTTGCGTCTGATTAGCTAGTTGGAGGGGTAACGGCCCACCAAGGCGACGATCAGTAGCCGG
TCTGAGAGGATGAACGGCCACATTGGGACTGAGACACGGCCCAGACTCCTACGGGAGGCAGCAGTGGGGAATCTTC
CGCAATGGACGAAAGTCTGACGGAGCAACGCCGCGTGAACGATGACGGCCTTCGGGTTGTAAAGTTCTGTTATACG
GGACGAATGGCGTAGCGGTCAATACCCGTTACGAGTGACGGTACCGTAAGAGAAAGCCACGGCTAACTACGTGCCA
GCAGCCGCGGTAATACGTAGGTGGCAAGCGTTGTCCGGAATTATTGGGCGTAAAGGGCGCGCAGGCGGCGTCGTAA
GTCGGTCTTAAAAGTGCGGGGCTTAACCCCGTGAGGGGACCGAAACTGCGATGCTAGAGTATCGGAGAGGAAAGCG
GAATTCCTAGTGTAGCGGTGAAATGCGTAGATATTAGGAGGAACACCAGTGGCGAAAGCGGCTTTCTGGACGACAA
CTGACGCTGAGGCGCGAAAGCCAGGGGAGCAAACGGGATTAGATACCCCGGTAGTCCTGGCCGTAAACGATGGATA
CTAGGTGTAGGAGGTATCGACCCCTTCTGTGCCGGAGTTAACGCAATAAGTATCCCGCCTGGGGAGTACGGCCGCA
AGGCTGAAACTCAAAGGAATTGACGGGGGCCCGCACAAGCGGTGGAACATGTGGTTTAATTCGATGATACGCGAGG
AACCTTACCCGGGCTTAAATTGCAGTGGAATGATGTGGAAACATGTCAGTGAGCAATCACCGCTGTGAAGGTGCTG
CATGGTTGTCGTCAGCTCGTGCCGTGAGGTGTCGGCTTAAGTGCCATAACGAGCGCAACCCTTATCTTCAGTTACT
AACAGGTCATGCTGAGGACTCTGGAGAGACTGCCGTCGTAAGATGTGAGGAAGGTGGGGATGACGTCAAATCAGCA
CGGCCCTTACGTCCGGGGCTACACACGTGTTACAATGGGGGGTACAGAGGGCCGCTACCACGCGAGTGGATGCCAA
TCCCAAAAACCTCTCTCAGTTCGGACTGGAGTCTGCAACCCGACTCCACGAAGCTGGATTCGCTAGTAATCGCGCA
TCAGCCACGGCGCGGTGAATACGTTCCCGGGCCTTGCACTCACCGCCCGT

KF842598.1.1394
AGAGTTTGATCCTGGCTCAGGATGAACGCTAGCGACAGGCTTAACACATGCAAGTCGAGGGGCAGCATGATTTGTA
GCAATACAGATTGATGGCGACCGGCGCACGGGTGAGTAACGCGTATGCAACTTACCTATCAGAGGGGGATAGCCCG
GCGAAAGTCGGATTAATACCCCATAAAACAGGGGTCCCGCATGGGAATATTTGTTAAAGATTCATCGCTGATAGAT
AGGCATGCGTTCCATTAGGCAGTTGGCGGGGTAACGGCCCACCAAACCGACGATGGATAGGGGTTCTGAGAGGAAG
GTCCCCCACATTGGTACTGAGACACGGACCAAACTCCTACGGGAGGCAGCAGTGAGGAATATTGGTCAATGGCCGA
GAGGCTGAACCAGCCAAGTCGCGTGAAGGAAGAAGGATCTATGGTCTGTAAACTTCTTTTATAGGGGAATAAAGTG
GAGGACGTGTCCTTTTTTGTATGTACCCTATGAATAAGCATCGGCTAACTCCGTGCCAGCAGCCGCGGTAATACGG
AGGATGCGAGCGTTATCCGGATTTATTGGGTTTAAAGGGTGCGTAGGTGGTGATTTAAGTCAGCGGTGAAAGTTTG
TGGCTCAACCATAAAATTGCCGTTGAAACTGGGTTACTTGAGTGTGTTTGAGGTAGGCGGAATGCGTGGTGTAGCG
GTGAAATGCATAGATATCACGCAGAACTCCGATTGCGAAGGCAGCTTACTAAACCATAACTGACACTGAAGCACGA
AAGCGTGGGGATCAAACAGGATTAGATACCCTGGTAGTCCACGCAGTAAACGATGATTACTAGGAGTTTGCGATAC
AATGTAAGCTCTACAGCGAAAGCGTTAAGTAATCCACCTGGGGAGTACGCCGGCAACGGTGAAACTCAAAGGAATT
GACGGGGGCCCGCACAAGCGGAGGAACATGTGGTTTAATTCGATGATACGCGAGGAACCTTACCCGGGTTTGAACG
TAGTCTGACCGGAATGGAAACACTCCTTCTAGCAATAGCAGATTACAAGGTGCTGCATGGTTGCCTCAACTCCGGC
CCGGAAGGTCCGGCTTAATTGCCATAACAAGCGCACCCTTTTACCAAGGTTCAAACAGGTGAAGCTTGAAGACTCT
GTGGAACCTCCCCCCTAACCTGTGAGAAGAAGTGGGGATACACTCAATAAACCACGGCCCTTAATCCCGGGGGGAA
CACTGGTTACAATGGGTTGGGAAAGGGGGCTTCCTGGCGACAGGATGCTAATCTCCAAACCATGTCTCAGTTCGGA
TCGGAGTCTGCAACTCGACTCCGTGAAGCTGGATTCGCTAGTAATCGCGCATCAGCCATGGCGCGGTGAATACGTT
CCCGGGCCTTGTACACACCGCCCGTC

FJ950694.1.1472
CGCCCTGATTGACGGCTATACACATGCAAGTCGAACGGTAACAGGAAACAGCTTGCTTCTTTGCTGACGAGTGGCG
GACGGGTGAGTAATGTCTGGGAAACTGCCTGATGGAGGGGGATAACTACTGGAAACGGTAGCTAATACCGCATAAC
GTCGCAAGACCAAAGAGGGGGACCTTCGGGCCTCTTGCCATCGGATGTGCCCAGATGGGATTAGCTAGTAGGTGGG
GTAACGGCTCCATCCCTAGGCGAGCCGAATCCTTAGCCTGGTCTGAGAGGAATGACCAGCCACACTGGGACTGAGA
ACACGGTCCAGACTCCTACGGGAGGCAGCAGTGGGGAATATTGCACAATGGGCGCAAGCCTGATGCAGCCATGCCG
CGTGTATGAAGAAGGCCTTCGGGTTGTAAAGTACTTTCAGCGGGGAGGAAGGGAGTAAAGTTAATACCCTTTGCTC
ATTGACGTTACCCGCAGAAGAAGCACCGGCTAACTCCGTGCCAGCAGCCGCGGTAATACGGAGGGTGCAAGCGTTA
ATCGGAATTACTGGGCGTAAAGCGCACGCAGGCGGTTTGTTAAGTCAGATGTGAAATCCCCGGGCTCAACCTGGGA
ACTGCATCTGATACTGGCAAGCTTGAGTCTCGTAGAGGGGGGTAGAATTCCAGGTGTAGCGGTGAAATGCGTAGAG
ATCTGGAGGAATACCGGTGGCGAAGGCGGCCCCCTGGACGAAGACTGACGCTCAGGTGCGAAAGCGTGGGGAGCAA
ACAGGATTAGATACCCTGGTAGTCCACGCCGTAAACGATGTCGACTTGGAGGTTGTGCCCTTGAGGCGTGGCTTCC
GGAGCTAACGCGTTAAGTCGACCGCCTGGGGAGTACGGCCGCAAGGTTAAAACTCAAATGAATTGACGGGGGCCCG
CACAAGCGGTGGAGCATGTGGTTTAATTCGATGCAACGCGAAGAACCTTACCTGGTCTTGACATCCACGGGAAGTT
TTCAGAGATGAGAATGTGCCTTCGGGAACCGTGAGACAGGTGCTGCATGGCTGTCGTCAGCTCGTGTTGTGAAATG
TTGGGTTAAGTCCCGCAACGAGCGCAACCCTTATCCTTTGTTGCCAGCGGTCCGGCCGGGAACTCAAAGGAGACTG
CCAGTGATAAACTGGAGGAAGGTGGGGATGACGTCCAGGTCATCATGGCCCTTACGAACCAGGGCTACACACGTGC
CTACAATGGACGCATCCAAAGAGAGAGCGAACCCTGCCCGCGAGAGCAAGCGGACCTCATAAAGTGCGTCGTAGTC
CGGATTGGAGTCTGCAACTCGACTCCATGAAGTCGGAATCGCTAGTAATCGTGGATCAGAATGCCACGGTGAATAC
GTTCCCGGGCCTTGTACACACCGCCCGTCACACCATGGGAGTGGGTTGCAAAAGAAGTAGGTAGCTTAACCTTCGG
GAGGGCGCTTACCACTTTGGATGCGAGG

HQ802983.1.1440
TAAGATGAACGCTGGCGGCGTGCTTAACACATGCAAGTCCTATGAAGCGCTTAAACGGATTTCTTCGGATTGAAGT
TTTTGTGACTGAGTGGCGGACGGGTGAGTAACGCGTGGGTAACTTGCCTCATACAGGGGGATAACAGTTAGAAATG
ACTGCTAATACCGCATAAGCGCACAGTGCTGCATGGCACAGTGTGAAAAACTCCGGTGGTATGAGATGGACCCGCG
TCTGATTAGCTAGTTGGTGGGGTAACGGCCTACCAAGGCGACGATCAGTAGCCGGCCTGAGAGGGTGAACGGCCAC
ATTGGGACTGAGACACGGCCCAAACTCCTACGGGAGGCAGCAGTGGGGAATATTGCACAATGGGGGAAACCCTGAT
GCAGCGACGCCGCGTGAGCGAAGAAGTATTTCGGTATGTAAAGCTCTATCAGCAGGGAAGAAAATGACGGTACCTG
ACTAAGAAGCACCGGCTAAATACGTGCCAGCAGCCGCGGTAATACGTATGGTGCAAGCGTTATCCGGATTTACTGG
GTGTAAAGGGAGCGTAGACGGTTGTGTAAGTCTGATGTGAAAGCCCGGGGCTCAACCCCGGGACTGCATTGGAAAC
TATGTAACTAGAGTGTCGGAGAGGTAAGCGGAATTCCTAGTGTAGCGGTGAAATGCGTAGATATTAGGAGGAACAC
CAGTGGCGAAGGCGGCTTACTGGACGATCACTGACGTTGAGGCTCGAAAGCGTGGGGAGCAAACAGGATTAGATAC
CCTGGTAGTCCACGCCGTAAACGATGACTACTAGGTGTCGGGGCCCATAAGGGCTTCGGTGCCGCAGCAAACGCAA

TABLE 11-continued 16S rRNA Sequences of OTUs in Tables 2-5
OTUs in Table 2

TAAGTATTCCACCTGGGGAGTACGTTCGCAAGAATGAAACTCAAAGGAATTGACGGGGACCCGCACAAGCGGTGGA
GCATGTGGTTTAATTCGAAGCAACGCGAAGAACCTTACCTGGTCTTGACATCCCACTGACCGGACAGTAATGTGTC
CTTTCCTCCGGGACAGTGGAGACAGGTGGTGCATGGTTGTCGTCAGCTCGTGTCGTGAGATGTTGGGTTAAGTCCC
GCAACGAGCGCAACCCCTATCCTTAGTAGCCAGCAGTAAGATGGGCACTCTAGGGAGACTGCCAGGGATAACCTGG
AGGAAGGTGGGGATGACGTCAAATCATCATGCCCCTTATGACTTGGGCTACACACGTGCTACAATGGCGTAAACAA
AGTGAAGCGAAGTCGTGAGGCCAAGCAAATCACAAAAATAACGTCTCAGTTCGGATTGTAGTCTGCAACTCGACTA
CAAGAAGCTGGAATCGCTAGTAATCGCAGATCAGAATGCTGCGGTGAATACGTTCCCGGGTCTTGTACACACCGCC
CGTCACACCATGGGAGTCGAAAATGCCCGAAGTCGGTGACCTAACGAAAGAAGGAGCCGCCGAAGGCAGGTT

GQ448468.1.1366
AGAGTTTGATCCTGGCTCAGGATGAACGCTGACAGAATGCTTAACACATGCAAGTATACTTGATCCTTCGGGTGAT
GGTGGCGGACGGGTGAGTAACGCGTAAAGAACTTGCCCTGCAGTCTGGGACAACATTTGGAAACGAATGCTAATCC
CGCATAAGCCCACAGCTCGGCATCGAGCAGAGGGAAAAGGAGTGATCTGCTTTGAGATGGCCTCGCGTCCGATTAG
CTGGTTGGTGAGGTGACGGCCCATCAAGGCAACGATCGGTAGCCGGACTGAGAGGTTGAACGGCCACATTGGGATT
GAGACACGGCCCTTACTCCTACGGGAGGCAGCAGTGGGGAATATTGGACAATGGACCAAAAGTCTGATCCAGCAAT
TCTGTGTGCACGATGAAGTTTTTCGGAATGTAAAGTGCTTTCAGTTGGGACGAAGTAAGTGACGGTACCAACAGAA
GAAGCGACGGCTAAATACGTGCCAGCAGCCGCGGTAATACGTATGTCGCAAGCGTTATCCGGATTTATTGGGCGTA
AAGCGCGTCTAGGCGGTTTGGTAAGTCTGATGTGAAAATGCGGGGCTCAACTCCGTATTGCGTTGGAAACTGCCAA
ACTAGAGTACTGGAGAGGTGGGCGGAACTACAAGTGTAGAGGTGAAATTCGTAGATATTTGTAGGAATGCCGATGG
GGAAGCCAGCCCACTGGACAGATACTGACGCTAAAGCGCGAAAGCGTGGGTAGCAAACAGGATTAGATACCCTGGT
AGTCCACGCCGTAAACGATGATTACTAGGTGTTGGGGGTCGAACCTCAGCGCCCAAGCTAACGCGATAAGTAATCC
GCCTGGGGAGTACGTACGCAAGTATGAAACTCAAAGGAATTGACGGGGACCCGCACAAGCGGTGGAGCATGTGGTT
TAATTCGACGCAACGCGAGGAACCTTACCAGCGTTTGACATCCTAAGAAATTAGCAGAGATGCTTTTGTGCCCCTT
CGGGGGAACTTAGTGACAGGTGGTGCATGGCTGTCGTCAGCTCGTGTCGTGAGATGTTGGGTTAAGTCCCGCAACG
AGCGCAACCCCTTTCGTATGTTGCCATCATTAAGTTGGGCACTCATGCGATACTGCCTGCGATGAGCAGGAGGAAG
GTGGGGATGACGTCAAGTCATCATGCCCCTTATACGCTGGGCTACACACGTGCTACAATGGGTAGTACAGAGAGTC
GCAAACCTGCGAGGGGGAGCTAATCTCAGAAAACTATTCTCAGTTCGGATTGTACTCTGCAACTCGAGTACATGAA
GTTGGAATCGCTAGTAATCGCAAATCAGCTATGTTGCGGTGAATACGTTCTCGGGTCTTGTACACACCGCCCGT

JN387556.1.1324
CGTAAGTAACCTGCCCTGTACACACGGATAACATACCGAAAGGTATGCTAATACGGGATAATATATTTTGATCGCA
TGGTCGAGATATCAAAGCTCCGGCGGTACACCAGGGACCCCCGACAGAGGAGCTAGTTGGTAGTAATGTCACCAAG
GCGACGATCAGAAGCCGAACTGAGAGGGGGATCCGCACATGACTGAGACACGGTCAAACTCCTACGGGAGGCAGCA
GTGGGGAATATGCCAATGGGCGAAAGCTGATGCAGCACGCGCGTGAGCGATGAGGCTCGGGTCGTAAAGCTCGTCT
CAAGGAAGATAATGACGGTACTTGAGGAGGAAGCCCCGGCTAACTACGTGCCAGCAGCCGCGGTAATACGTAGGGG
GCTAGCGTTATCCGGAATTACTGGGCGTAAAGGGTGCGTAGGCGGTCTTTCAAGTCAGGAGTGAAAGGCTACGGCT
CAACCGTAGTAAGCTCTTGAAACTGTAAGACTTGAGTGCAGGAGAGGAGAGTGGAATTCCTAGTGTAGCGGTGAAA
TGCGTAGATATTAGGAGGAACACCAGTTGCGAAGGCGGCTCTCTGGACTGTAACTGACGCTGAGGCACGAAAGCGT
GGGGAGCAAACAGGATTAGATACCCTGGTAGTCCACGCCGTAAACGATGAGTACTAGCTGTCGGAGGTTACCCCCT
TCGGTGGCGCAGCTAACGCATTAAGTACTCCGCCTGGGAAGTACGCTCGCAAGAGTGAAACTCAAAGGAATTGACG
GGGACCCGCACAAGTAGCGGAGCATGTGGTTTAATTCGAAGCAACGCGAAGAACCTTACCTAAGCTTGACATCCCA
CTGACCCTTCCCTAATCGGAAGCTTCCCTTCGGGACAGTGGTGACAGGTGGTGCATGGTTGTCGTCAGCTCGTGTC
GTGAGATGTTGGGTTAAGTCCCGCAACGAGCGCAACCCTTGCCTTTAGTTGCCAGCATTAAGTTGGGCACTCTAGA
GGGACTGCCAGGGATAACCCGGAGGAGTGGGGATGACGTCAAATCATCATGCCCTTATGCTAGGCTACACACGTGC
TACAATGGGTGGTCAGAGGCCAGCCAGTCGTGAGGCCGAGCTATCCCATAAGCCATTCTCGTCCGGATTGTAGGCT
GAACTCGCCTACATGAGCTGGAATTACAAGTATGCGATCGATGCTGCGTGATGCGTCCGGGTCTTGTACACACCGC
CCGTCACACCATGGGAGTTGGGGGCGCCCGAAGCCGGATTGCTAACCTTTTGGAAGCGTCCGTCGAAGGTGAAACC
AATAACTGGGGTGAAGTCGTAACAAGGTAACC

OTUs in Table 4

JRPJ01000002.1034290.1035971
AGAGTTTGATCCTGGCTCAGAGTGAACGCTGGCGGCGTGCCTAATACATGCAAGTCGAACGATGAAACTTCTAGCT
TGCTAGAAGTGGATTAGTGGCGCACGGGTGAGTAATGCATAGGTAACATGCCCTTTAGTCTGGGATAGCCACTGGA
AACGGTGATTAATACTGGATACTCCCTACGGGGGAAAGGGGCTTTCAATAAAGAATTTCTCTTTTTAGTGTTTTGT
GTTGTTGGCACAAAATTCTAGTATTTGGAATGAGAAATTGGTGTTGTGAAGCAATTTGTGCGGAGATTAGACTTAG
TGTCTGTCGTGTCAGCAAATTGCGAACTCATCGATTTATCATCCAAAGACGAATTTTTTATTGAAAGCCTTCGCTA
AAGGATTGGCCTATGTCCTATCAGCTTGTTGGTGAGGTAATGGCTCACCAAGGCTATGACGGGTATCCGGCCTGAG
AGGGTGATCGGACACACTGGAACTGAGACACGGTCCAGACTCCTACGGGAGGCAGCAGTAGGGAATATTGCTCAAT
GGGGGAAACCCTGAAGCAGCAACGCCGCGTGGAGGATGAAGGTTTTAGGATTGTAAACTCCTTTTGTAAGAGAAGA
TTATGACGGTATCTTACGAATAAGCACCGGCTAACTCCGTGCCAGCAGCCGCGGTAATACGGAGGGTGCAAGCGTT
ACTCGGAATCACTGGGCGTAAAGAGCGCGTAGGCGGGTGGTCAAGTCAGATGTGAAATCCTGTAGCTTAACTACAG
AACTGCATTTGAAACTGACCATCTAGAGTATGGGAGAGGTAGGTGGAATTCTTGGTGTAGGGGTAAAATCCGTAGA
GATCAAGAGGAATACTCATTGCGAAGGCGACCTGCTGGAACATTACTGACGCTGATGCGCGAAAGCGTGGGGAGCA
AACAGGATTAGATACCCTGGTAGTCCACGCCCTAAACGATGAATGCTAGTTGTTGTGAGGCTTGTCCTTGCAGTAA
TGCAGCTAACGCATTAAGCATTCCGCCTGGGGAGTACGGTCGCAAGATTAAAACTCAAAGGAATAGACGGGGACCC
GCACAAGCGGTGGAGCATGTGGTTTAATTCGATGATACGCGAAGAACCTTACCTAGGCTTGACATTGATAGAATCT
ACTAGAGATAGTGGAGTGCCCTTTTAGGGAGCTTGAAAACAGGTGCTGCACGGCTGTCGTCAGCTCGTGTCGTGAG
ATGTTGGGTTAAGTCCCGCAACGAGCGCAACCCTCGTCCTTAGTTGCTAGCAGTTTGGCTGAGCACTCTAAGGAGA
CTGCCTTCGTAAGGAGGAGGAAGGTGAGGACGACGTCAAGTCATCATGGCCCTTACGCCTAGGGCTACACACGTGC
TACAATGGGGTGCACAAAGAGATGCAATAGTGTGAGCTGGAGCCAATCTCTAAAACATCTCTCAGTTCGGATTGTA
GTCTGCAACTCGACTACATGAAGCTGGAATCGCTAGTAATCGCAAATCAGCAATGTTGCGGTGAATACGTTCCCGG
GTCTTGTACTCACCGCCCGTCACACCATGGGAGTTGTATTTGCCTTAAGTCGGAATGCTAAATTGGCTACCGCCCA
CGGCAGATGCAGCGACTGGGGTGAAGTCGTAACAAGGTAACCGTAGGTGAACCTGCGGTTG

New.ReferenceOTU45
TACGGAGGGTGCAAGCGTTAATCGGAATAACTGGGCGTAAAGGGCATGTAGGCGGAAAGGCAAGCAAGATGTGAAA
GACCTGGGCTCAACCTGGGTTGGTCATTTTGAACTACCTTTCTAGAGTATTGCAGAGGGAGATGGAATTTCAGGTG TABLE 11-continued

| 16S rRNA Sequences of OTUs in Tables 2-5 OTUs in Table 2 |
|---|

TAGCGGTGGAATGCGTAGATATCTGAAAGAACACCAGAGGCGAAGGCGGTCTCCTGGGCAAATACTGACGCTGAGG
TGCGAAAGCGTGGGGAGCAAACAGG

GQ006324.1.1342
GACGAACGCTGGCGGCGTGCTTAACACATGCAAGTCGAACGGAAAGGCCCCAGCTCGCTGGGGTACTCGAGTGGCG
AACGGGTGAGTAACACGTGGGTGATCTGCCTTGCACTCTGGGATAAGCTTGGGAAACTGGGTCTAATACCGGATAT
GAACTGCCTTTAGTGTGGTGGTTGGAAAGTTTTTTCGGTGCAAGATGAGCTCGCGGCCTATCAGCTTGTTGGTGGG
GTAATGGCCTACCAAGGCGTCGACGGGTAGCCGGCCTGAGAGGGTGTACGGCCACATTGGGACTGAGATACGGCCC
AGACTCCTACGGGAGGCAGCAGTGGGGAATATTGCACAATGGGCGGAAGCCTGATGCAGCGACGCCGCGTGGGGGA
TGACGGCCTTCGGGTTGTAAACTCCTTTCGACAGGGACGAAGCTTTTTGTGACGGTACCTGTATAAGAAGCACCGG
CTAACTACGTGCCAGCAGCCGCGGTAATACGTAGGGTGCGAGCGTTGTCCGGAATTACTGGGCGTAAAGAGCTCGT
AGGTGGTTTGTCGCGTCGTCTGTGAAATTCCGGGGCTTAACTCCGGGCGTGCAGGCGATACGGGCATAACTTGAGT
ACTGTAGGGGAGACTGGAATTCCTGGTGTAGCGGTGAAATGCGCAGATATCAGGAGGAACACCGGTGGCGAAGGCG
GGTCTCTGGGCAGTAACTGACGCTGAGGAGCGAAAGCATGGGGAGCGAACAGGATTAGATACCCTGGTAGTCCATG
CCGTAAACGGTGGGCGCTAGGTGTGGGTTTCCTTCCACGGGATCCGTGCCGTAGCTAACGCATTAAGCGCCCCGCC
TGGGGAGTACGGCCGCAAGGCTAAAACTCAAAGGAATTGACGGGGGCCCGCACAAGCGGCGGAGCATGTGGATTAA
TTCGATGCAACGCGAAGAACCTTACCTGGGCTTGACATACACTGGATCGGGCTAGAGATAGTCTTTCCCTTTGTGG
CTGGTGTACAGGTGGTGCATGGTTGTCGTCAGCTCGTGTCGTGAGATGTTGGGTTAAGTCCCGCAACGAGCGCAAC
CCTTGTCTTATGTTGCCAGCATTTGGTTGGGGACTCATGAGAGACTGCCGGGGTCAACTCGGAGGAAGGTGGGGAT
GACGTCAAATCATCATGCCCCTTATGTCCAGGGCTTCACACATGCTACAATGGTCGGTACAACGCGCAGCGACACT
GTGAGGTGGAGCGAATCGCTGAAAGCCGGCCTTAGTTCGGATTGGGGTCTGCAACTCGACCCCATGAAGTCGGAGT
CGCTAGTAATCGCAGATCAGCAATGCTGCGGTGAATACGTTCCCGGGCCT

HK555938.1.1357
ACGGCACCCCTCTCCGGAGGGAAGCGAGTGGCGAACGGCTGAGTAACACGTGGAGAACCTGCCCCCTCCCCCGGGA
TAGCCGCCCGAAAGGACGGGTAATACCGGATACCCCCGGGCGCCGCATGGCGCCCGGGCTAAAGCCCCGACGGGAG
GGGATGGCTCCGCGGCCCATCAGGTAGACGGCGGGGTGACGGCCCACCGTGCCGACAACGGGTAGCCGGGTTGAGA
GACCGACCGGCCAGATTGGGACTGAGACACGGCCCAGACTCCTACGGGAGGCAGCAGTGGGGAATCTTGCGCAATG
GGGGGAACCCTGACGCAGCGACGCCGCGTGCGGGACGGAGGCCTTCGGGTCGTAAACCGCTTTCAGCAGGGAAGAG
TCAAGACTGTACCTGCAGAAGAAGCCCCGGCTAACTACGTGCCAGCAGCCGCGGTAATACGTAGGGGGCGAGCGTT
ATCCGGATTCATTGGGCGTAAAGCGCGCGTAGGCGGCCCGGCAGGCCGGGGGTCGAAGCGGGGGGCTCAACCCCCC
GAAGCCCCCGGAACCTCCGCGGCTTGGGTCCGGTAGGGGAGGGTGGAACACCCGGTGTAGCGGTGGAATGCGCAGA
TATCGGGTGGAACACCGGTGGCGAAGGCGGCCCTCTGGGCCGAGACCGACGCTGAGGCGCGAAAGCTGGGGGAGCG
AACAGGATTAGATACCCTGGTAGTCCCAGCCGTAAACGATGGACGCTGGGTGTGGGGGGACGATCCCCCCGTGCCG
CAGCCNACGCATTAAGCGTCCCGCCTGGGGAGTACGGCCGCAAGGCTAAAACTCAAAGGAATTGACGGGGGCCCGC
ACAAGCAGCGGAGCATGTGGCTTAATTCGAAGCAACGCGAAGAACCTTACGGCGCATCCCCCCGAGGCCCACGGGG
GGTCCGCCGCGTGGGTCAGAGGAGCGCATACGGGAGGTGCATGGTTGTCGTCAGCTCGTGTCGTGAGATGTTGGGT
TAAGTCCCGCAACGAGCGCAACCCCCGCCGCGTGTTGCCATCGGGTGATGCCGGGAACCCACGCGGGACCGCCGCC
GTCAAGGCGGAGGAGGGCGGGGACGACGTCAAGTCATCATGCCCCTTATGCCCTGGGCTGCACACGTGCTACAATG
GCCGGTACAGAGGGATGCCACCCCGCGAGGGGGAGCGGATCCCGGAAAGCCGGCCCCAGTTCGGATTGGGGGCTGC
AACCCGCCCCCATGAAGTCGGAGTTGCTAGTAATCGCGGATCAGCATGCCGCGGTGAATGCGTTCCCGGGCCTTGT
ACACACCGCCCGTCACACCACCCGAGTCGTCTGCACCCGAAGTCGCCGGCCCAACCGCAAGGGGG

FJ957551.1.1489
AGAGTTTGATCCTGGCTCAGGACGAACGCTGGCGGCGTGCCTAATACATGCAAGTCGAGCGGAGTTACTTTGAGAG
CTTGCTTTCAAAGTAACTTAGCGGCGGACGGGTGAGTAACACGTAGGCAACCTGCCCCTTAGACTGGGATAACTAC
CGGAAACGGTAGCTAATACCGGATAATTTCTTTTTTCTCCTGAAGGAAGAATGAAAGACGGAGCAATCTGTCACTG
AGGGATGGGCCTGCGGCGCATTAGCTAGTTGGTGGGGTAACGGCCCACCAAGGCGACGATGCGTAGCCGACCTGAG
AGGGTGATCGGCCACATTGGAACTGAGATACGGTCCAGACTCCTACGGGAGGCAGCAGTGGGGAATATTGCACAAT
GGGGGAAACCCTGATGCAGCAACGCCGCGTGAGTGATGAAGGTCTTCGGATTGTAAAGCTCTGTCTTTAGGGACGA
TAATGACGGTACCTAAGGAGGAAGCCACGGCTAACTACGTGCCAGCAGCCGCGGTAATACGTAGGTGGCAAGCGTT
ATCCGGATTTACTGGGCGTAAAGGGAGCGTAGGCGGATATTTAAGTGGGATGTGAAATACCCGAGCTTAACTTGGG
AGCTGCATTCCAAACTGGATATCTAGAGTGCAGGAGAGGAGAATGGAATTCCTAGTGTAGCGGTGAAATGCGTAGA
GATTAGGAAGAACACCAGTGGCGAAGGCGATTCTCTGGACTGTAACTGACGCTGAGGCTCGAAAGCGTGGGGAGCA
AACAGGATTAGATACCCTGGTAGTCCACGCCGTAAACGATGAATACCAGGTGTAGGGGCCCCAAGCCTCTGTGCCG
CCGCTAACGCATTAAGTATTCCGCCTGGGGAGTACGGTCGCAAGATTAAAACTCAAAGGAATTGACGGGGACCCGC
ACAAGCAGCGGAGCATGTGGTTTAATTCGAAGCAACGCGAAGAACCTTACCTAGACTTGACATGTCCTGAATTACC
AGTAATGTGGGAAGTTCCTTCGGGAACAGGAACACAGGTGGTGCATGGTTGTCGTCAGCTCGTGTCGTGAGATGTT
GGGTTAAGTCCCGCAACGAGCGCAACCCTTATTGTTAGTTGGTACCATTAAGTTGACCACTCTAGCGAGACTGCCC
GGGTTAACCGGGAGGAAGGTGGGGATGACGTCAAATCATCATGCCCCTTATGTCTAGGGCTACACACGTGCTACAA
TGGCAAGTACAAAGAGAAGCAATACTGTGAAGTGGAGCAAAACTCAAAAACTTGTCTCAGTTCGGATTGTAGGCTG
AAACTCGCCTACATGAAGCTGGAGTTGCTAGTAATCGCGAATCAGAATGTCGCGGTGAATACGTTCCCGGGTCTTG
TACACACCGCCCGTCACACCATGAGAGTTGGCAATACCCGAAGTCCGTAAGCTAACCGTAAGGAGGCAGCGGCCGA
AGGTAGGGTCAGCGATTGGGGTGAAGTCGTAACAAGGTAACCAA

FJ957494.1.1454
TGAGTTTGATCATGGCTCAGGACGAACGCTGGCGGCGTGCCTAACACATGCAAGTCGAGCGATGAAATTTTCTTCG
GAAAATGGATTAGCGGCGGACGGGTGAGTAACACGTGGGTAACCTGCCCTATAGAGAGGGATAGCCTTCCGAAAGG
GAGATTAATACCTCATAATATCCTAGTATCGCATGATACATGGATTAAAGGAGCAATCCGCTATAGGATGGACCCG
CGGCGCATTAGCTAGTTGGTGAGGTAACGGCTCACCAAGGCGACGATGCGTAGCCGACCTGAGAGGGTGATCGGCC
ACATTGGGACTGAGACACGGCCCAGACTCCTACGGGAGGCAGCAGTGGGGAATATTGCACAATGGGGGAAACCCTG
ATGCAGCAACGCCGCGTGAGTGATGACGGTCTTCGGATTGTAAAGCTCTGTCTTTAGGGACGATAATGACGGTACC
TAAGGAGGAAGCCACGGCTAACTACGTGCCAGCAGCCGCGGTAATACGTAGGTGGCAAGCGTTGTCCGGATTTACT
GGGCGTAAAGGGAGCGTAGGCGGATCTTTAAGTGGGATGTGAAATACTCGGGCTCAACCTGGGGGCTGCATTCCAA
ACTGGGGATCTAGAGTACAGGAGGGGNGAGTGGAATTCCTAGTGTAGCGGTGAAATGCGTAGAGATTAGGAAGAAC
ACCAGTGGCGAAGGCGACTNTCTGGACTGTAACTGACGCTGAGGCTCGAAAGCGTGGGGAGCAAACAGGATTAGAT
ACCCTGGTAGTCCACGCCGTAAACGATGAATACTAGGTGTAGGGGGTGTCAACTCCCCCTGTGCCGCCGCTAACGC

TABLE 11-continued 16S rRNA Sequences of OTUs in Tables 2-5
OTUs in Table 2

ATTAAGTATTCCGCCTGGGGAGTACGGTCGCAAGATTAAAACTCAAAGGAATTGACGGGGGCCCGCACAAGTAGCG
GAGCATGTGGTTTAATTCGACGCAACGCGAAGAACCTTACCTAGACTTGACATCTTCTGCATTACCCTTAATCGGG
GAAGTTCCTTCGGGGACAGAATGACAGGTGGTGCATGGTTGTCGTCAGCTCGTGTCGTGAGATGTTGGGTTAAGTC
CCGCAACGAGCGCAACCCTTAAGCTTAGTTGCCATCATTAAGTTGGGCACTCTAAGTTGACTGCCGGTGACAAACC
GGAGGAAGGTGGGGATGACGTCAAATCATCATGCCCCTTATGTCTAGGGCTACACACGTGCTACAATGGCAAGTAC
AAAGAGAAGCAATACTGTGAAGTGGAGCAAAACTCAAAAACTTGTCTCAGTTCGGATTGTAGGCTGAAACTCGCCT
ACATGAAGCTGGAGTTGCTAGTAATCGCGAATCAGAATGTCGCGGTGAATACGTTCCCGGGTCTTGTACACACCGC
CCGTCACACCATGAGAGTTGGCAATACCCGAAGTCCGTAAGCTAACCGTAAGGAGGCAGCGGCCGAAGGTAGGGTC
AGCGATGGGG

New.ReferenceOTU52
TACGTAGGTGGCGAGCGTTATCCGGATTTACTGGGCGTAAAGGGAGCGTAGGCGGATGATTAAGTGGGATGTGAAA
TACCCGGGCTCAACTTGGGTGCTGCATTCCAAACTGGTTATCTAGAGTGCAGGAGAGGAGAGTGGAATTCCTAGTG
TAGCGGTGAAATGCGTAGAGATTAGGAAGAACACCAGTGGCGAAGGCGACTCTCTGGACTGTAACTGACGCTGAGG
CTCGAAAGCGTGGGGAGCAAACAGG FM865905.1.1392
GGGAATCTCCAGGATCTGATTAGCGGCGGACGGGTGAGTACACGTGGGTAACCTGCCTCATAGAGTGGAATAGCCT
TCCGAAAGGAAGATTAATACCGCATAACGTTGAAAGATGGCATCATCATTCAACCAAAGGAGCAATCCGCTATGAG
ATGGACCCGCGGCGCATTAGCTAGTTGGTGGGGTAACGGCCTACCAAGGCGACGATGCGTAGCCGACCTGAGAGGG
TGATCGGCCACATTGGGACTGAGACACGGCCCAGACTCCTACGGGAGGCAGCAGTGGGGAATATTGCACAATGGGG
GAAACCCTGATGCAGCAACGCCGCGTGAGTGATGAAGGTTTTCGGATCGTAAAGCTCTGTCTTTGGGGAAGATAAT
GACGGTACCCAAGGAGGAAGCCACGGCTAACTACGTGCCAGCAGCCGCGGTAATACGTAGGTGGCGAGCGTTATCC
GGATTTACTGGGCGTAAAGGGAGCGTAGGCGGATGATTAAGTGGGATGTGAAATACCCGGGCTCAACTTGGGTGCT
GCATTCCAAACTGGTTATCTAGAGTGCAGGAGAGGAGAGTGGAATTCCTAGTGTAGCGGTGAAATGCGTAGAGATT
AGGAAGAACACCAGTGGCGAAGGCGACTCTCTGGACTGTAACTGACGCTGAGGCTCGAAAGCGTGGGGAGCAAACA
GGATTAGATACCCTGGTAGTCCACGCCGTAAACGATGAATACTAGGTGTGGGGGTTTCAACACCTCCGTGCCGCCG
CTAACGCATTAAGTATTCCGCCTGGGGAGTACGGTCGCAAGATTAAAACTNAAAGGAATTGACGGGGATCNNCACN
AGTAGCGGAGCATGTGGTTTAATTCGAAGCAACGCGAAGAACCTTACCTACACTTGACATCCCTTGCATTACTCTT
AATCGAGGAAATCTCTTCGGGGACAAGGTGACAGGTGGTGCATGGTTGTCGTCAGCTCGTGTCGTGAGATGTTGGG
TTAAGTCCCGNAACGAGGGGAACCNTTGTCGTTAGTTACTACCATTAAGTTGAGGACTNTAGNGAGACNGCTGGGT
TAACNAGGAGGAAGGTGGGGATGACTCAATCTCTGGNCNTTATGTGTAGGGNTACACACGTGCTACAATGGCTGGT
ACAGAGAGATGCATACCGGGAGGTGGANTCAATTTAAAAACAGTNTCNTTCGGATTGTAGGNTGAANTNNCCTACT
GAAGNTGGAGTTANTAGTAATCGCGAATCAGAATGTCGCGGTGAATACGTTCCCGGGTCTTGTACACNCCNCCCGT
CACNCCATGAGAGTTGGCAATACCCGAAGTCCGTGAGCTAACCGCAAGGAGGCAGCGGCCGAAGGTAGGGTCAGCG
ATTGGGGTGAAGTCGTAACAGGNA GQ016239.1.1362
GATGAACGCTGGCGGCATGCCTAATACATGCAAGTCGAACGGAGCGAATATGGAAGCTTGCTTCCGTAAGAGCTCA
GTGGCGAACGGGTGAGTAACACGTAGGTAACCTGCCCATGTGCCCGGGATAACTGCTGGAAACGGTAGCTAAAACC
GGATAGGTGAATAGGAGGCATCTCTTATTCATTAAAGGACCTGTAAGGGTGCGAACATGGATGGACCTGCGGCGCA
TTAGCTGGTTGGAGTGGTAACGGCACACCAAGGCGACGATGCGTAGCCGACCTGAGAGGGCGAACGGCCACATTGG
GACTGAGACACGGCCCAAACTCCTACGGGAGGCAGCAGTAGGGAATTTTCGTCAATGGGGGGAACCCTGAACGAGC
AATGCCGCGTGAGTGAAGAAGGTCTTCGGATCGTAAAGCTCTGTTGTAAGTGAAGAACGGTCAGTAGAGGAAATGA
TACTGAAGTGACGGTAGCTTACCAGAAAGCCACGGCTAACTACGTGCCAGCAGCCGCGGTAATACGTAGGTGGCGA
GCGTTATCCGGAATCATTGGGCGTAAAGGGTGCGCAGGTGGTACATTAAGTCCGAAGTAAAAGGCAGCAGCTCAAC
TGCTGTTGGCTTTGGAAACTGGTGAACTGGAGTGCAGGAGAGGGCGATGGAATTCCATGTGTAGCGGTAAAATGCG
TAGATATATGGAGGAACACCAGTGGCGAAGGCGGTCGCCTGGCCTGCAACTGACACTGAGGCACGAAAGCGTGGGG
AGCAAATAGGATTAGATACCCTAGTAGTCCACGCCGTAAACGATGAGAACTAAGTGTTGGGGAGACTCAGTGCTGC
AGTTAACGCAATAAGTTCTCCGCCTGGGGAGTATGCACGCAAGTGTGAAACTCAAAGGAATTGACGGGGGCCCGCA
CAAGCGGTGGAGTATGTGGTTTAATTCGAAGCAACGCGAAGAACCTTACCAGGCCTTGACATGGATGTAAATGTTC
TAGAGATAGAAAGATAGCTATACATCACACAGGTGGTGCATGGTTGTCGTCAGCTCGTGTCGTGAGATGTTGGGTT
AAGTCCCGCAACGAGCGCAACCCTTATCGCATGTTACCAGTATTGAGTTAGGGACTCATGCGAGACTGCCGGTGAC
AAACCGGAGGAAGGTGGGGATGACGTCAAATCATCATGCCCCTTATGGCCTGGGCTACACACGTACTACAATGGCG
GCTACAAAGAGAAGCGAACCTGCGAGGGGGAGCGGAACTCATAAAGGCCGTCTCAGTTCGGATTGGAGTCTGCAAC
TCGACTCCATGAAGTCGGAATCGCTAGTAATCGCAGATCAGCATGCTGCGGTGAATACGTTCTCGGGCCT HG798451.1.1400
CTTGTGTCACCAACCATAGGGAGGGGGAAAACATGGAAACGGGGTTCATACCGCATAACTTTTTTAGCCCAATGCA
TAAGAAGAAAGGCCTTTCGGGTTTCGGTAAAGGAGGCCCCCGCGGCTCTTATAGTGTGTGTGGAAGTAACCGCTTC
CACAAGGCCCAGGTTTCATACCCGACTGGAGAGTGTGTTCGCCACACTGGGGAAAGGACCCCCGGCCCAGTCTCTC
TAGGGGAGGCAGCAGTAGGAATTTTCGGCAAAGGAAAAAATTTCTGACCGAACAACGCCGGTTGAATGAAGAAGTT
TTTCGGATCGAAAAACTCTGTTGTTAGAGAAGAACAAGGACGTTAGTAACTGAACGTCCCCTGACGGTATCTAACC
AGAAAGCCACGGCTAATTACGTGCCAGCAGCCGCGGTAATACGTAGGTGGCAAGCGTTGTCCGGATTTATTGGGCG
TAAAGCGAGCGCAGGCGGTTTCTTAAGTCTGATGTGAAAGCCCCCGGCTCAACCGGGGAGGGTCATTGGAAACTGG
GAGACTTGAGTGCAGAAGAGGAGAGTGGAATTCCATGTGTAGCGGTGAAATGCGTAGATATATGGAGGAACACCAG
TGGCGAAGGCGGCTCTCTGGTCTGTAACTGACGCTGAGGCTCGAAAGCGTGGGGAGCAAACAGGATTAGATACCCT
GGTAGTCCACGCCGTAAACGATGAGTGCTAAGTGTTGGAGGGTTTCCGCCCTTCAGTGCTGCAGCAAACGCATTAA
GCACTCCGCCTGGGGAGTACGACCGCAAGGTTGAAACTCAAAGGAATTGACGGGGGCCCGCACAAGCGGTGGAGCA
TGTGGTTTAATTCGAAGCAACGCGAAGAACCTTACCAGGTCTTGACATCCTTTGACCACTCTAGAGATAGAGCTTT
CCCTTCGGGGACAAAGTGACAGGTGGTGCATGGTTGTCGTCAGCTCGTGTCGTGAGATGTTGGGTTAAGTCCCGCA
ACGAGCGCAACCCTTATTGTTAGTTGCCATCATTTAGTTGGGCACTCTAGCGAGACTGCCGGTGACAAACCGGAGG
AAGGTGGGGATGACGTCAAATCATCATGACCCTTATGACCTGGGCTACACACGTGCTACAATGGAAGTACAACGA
GTCGCTAGACCGCGAGGTCATGCAAATCTCTTAAAGCTTCTCTCAGTTCGGATTGCAGGCTGCAACTCGCCTGCAT
GAAGCCGGAATCGCTAGTAATCGCGGATCAGCACGCCGCGGTGAATACGTTCCCGGGCCTTGTACACACCGCCCGT
CACACCACGAGAGTTTGTAACACCCGAAGTCGGTGAGGTAACCTTTTTGGAGCCAGCCGCCTAAGGTGGGATAGAT
GATTGGGGTGAAGTCGTAACCAACGTATGCC TABLE 11-continued 16S rRNA Sequences of OTUs in Tables 2-5
OTUs in Table 2

EU461791.1.1414
AGAGTTTGATCCTGGCTCAGGACTAACGCTGGCGGCGTGCCTAATACATGCAAGTAGAACGCTGAAGACTTTAGCT
TGCTAAAGTTGGAAGAGTTGCGAACGGGTGAGTAACGCGTAGGTAACCTGCCTACTAGCGGGGGATAACTATTGGA
AACGATAGCTAATACCGCATAACAGCATTTAACCCATGTTAGATGCTTGAAAGGAGCAATTGCTTCACTAGTAGAT
GGACCTGCGTTGTATTAGCTAGTTGGTGAGGTAACGGCTCACCAAGGCGACGATACATAGCCGACCTGAGAGGGTG
ATCGGCCACACTGGGACTGAGACACGGCCCAGACTCCTACGGGAGGCAGCAGTAGGGAATCTTCGGCAATGGGGGC
AACCCTGACCGAGCAACGCCGCGTGAGTGAAGAAGGTTTTCGGATCGTAAAGCTCTGTTGTAAGAGAAGAACGTGT
GTGAGAGTGGAAAGTTCACACAGTGACGGTAACTTACCAGAAAGGGACGGCTAACTACGTGCCAGCAGCCGCGGTA
ATACGTAGGTCCCGAGCGTTGTCCGGATTTATTGGGCGTAAAGCGAGCGCAGGCGGTTTAATAAGTCTGAAGTTAA
AGGCAGTGGCTTAACCATTGTTCGCTTTGGAAACTGTTAGACTTGAGTGCAGAAGGGGAGAGTGGAATTCCATGTG
TAGCGGTGAAATGCGTAGATATATGAGGAACACCGGTGGCGAAAGCGGCTCTCTGGTCTGTAACTGACGCTGAGG
CTCGAAAGCGTGGGGAGCAAACAGGATTAGATACCCTGGTAGTCCACGCCGTAAACGATGAGTGAAAGGTGTTAGG
CCCTTTCCGGGGCTTAGTTGCTGCACGCTAACTGCATTATGACACTCCGCCAGGGGAGTACGACCGCTAGGTTGAA
ACTCAAAGGAGTTGACGGGGGCCAGCACAACCGGTGGAGCATGTGGTTGAATTGGAAGCAACGCGAAGAGCCTTAC
CAGGTCTTGACATCCCGACGCTATTCCTAGAGATAGGAAGTTTCTTCGGGACATTCGGTGGCAGGTGGTGCATGGT
AGTCGTCAGCTCGTGTCGTGAGATGTTGGGTTAAGTCCCGCAACGAGCGCAACCCCTATTGTTAGTTGCCATACAT
TAAGTTGGGCACTCTAGCGAGACTGCCGGTAATAAACCGGAGGAAGGTGGGGATGACGTCAAATCATCATGCCCCT
TATGACCTGGGCTACACACGACGCTACAATGGTTGGTACAACGAGTCGCGAGTCGGTGACGGCAAGCAAATCTCTT
AAAGCCAATCTCAGTTCGGATTGTAGGCTGCAACTCGCCTACATGAAGTCGGAATCGCTAGTAATCGCGGATCAGC
ACGCCGCGGTGAATACGTTCCCGGGCCTTGCACTCACCGCCCGTCA

GU303759.1.1517
AGAGTTTGATCATGGCTCAGGACGAACGCCGGCGGCGTGCCTAATACATGCAAGTAGAACGCTGAAGACTTTAGCT
TGCTAAAGTTGGAAGAGTTGCGAACGGGTGAGTAACGCGTAGGTAACCTGCCTACTAGCGGGGGATAACTATTGGA
AACGATAGCTAATACCGTATAACAGCATTTAACACATGTTAGATGCTTGAAAGGAGCAATTGCTTCACTAGTAGAT
GGACCTGCGTTGTATTAGCTAGTTGGTGAGGTAACGGCTCACCAAGGCGACGATACATAGCCGACCTGAGAGGGTG
ATCGGCCACACTGGGACTGAGACACGGCCCAGACTCCTACGGGAGGCAGCAGTAGGGAATCTTCGGCAATGGGGGC
AACCCTGACCGAGCAACGCCGCGTGAGTGAAGAAGGTTTTCGGATCGTAAAGCTCTGTTGTAAGAGAAGAACGTGT
GTGAGAGTGGAAAGTTCACACAGTGACGGTAACTTACCAGAAAGGGACGGCTAACTACGTGCCAGCAGCCGCGGTA
ATACGTAGGTCCCGAGCGTTGTCCGGATTTATTGGGCGTAAAGCGAGCGCAGGCGGTTTAATAAGTCTGAAGTTAA
AGGCAGTGGCTTAACCATTGTTCGCTTTGGAAACTGTTAGACTTGAGTGCAGAAGGGGAGAGTGGAATTCCATGTG
TAGCGGTGAAATGCGTAGATATATGGARGGAAACACCGGTGGCGAAAGCGGCTCTCTGGTCTGTAACTGACGCTGA
GGCTCGAGAAGCGTGGGGAGCAAACAGGATTAGATACCCTGGTAGTCCACGCCGTAAGCGATGAGTGCTAGGTGTT
AGGCCCTTTCCGGGGCTTAGTGCCGCAGCTAACGCATTAAGCACTCCGCCTGGGGAGTACGACCGCAAGGTTGAAA
CTCAAAGGAATTGACGGGGGCCCGCACAAGCGGTGGAGCATGTGGTTTAATTCGAAGCAACGCGAAGAACCTTACC
AGGTCTTGACATCCCGATGCTATTCCTAGAGATAGGAAGTTTCTTCGGAACATCGGTGACAGGTGGTGCATGGTTG
TCGTCAGCTCGTGTCGTGAGATGTTGGGTTAAGTCCCGCAACGAGCGCAACCCCTATTGTTAGTTGCCATCATTAA
GTTGGGCACTCTAGCGAGACTGCCGGTAATAAACCGGAGGAAGGTGGGGATGACGTCAAATCATCATGCCCCTTAT
GACCTGGGCTACACACGTGCTACAATGGCGGTCAACAGAGGGAAGCAATACTGTGAAGTGGAGCAAACCCCTAAAA
GCCGTCCCAGTTCGGATTGCAGGCTGCAACCCGCCTGTATGAAGTTGGAATCGCTAGTAATCGCGGATCAGCATGC
CGCGGTGAATACGTTCCCGGGCCTTGTACACACCGCCCGTCACACCATGAGAGTCGGGAACACCCGAAGTCCGTAG
CCTAACTTTCACGAGGGGGCGCGGCCGAAGGTGGGTTCGATAATTGGGGTGAAGTCGTAACAAGGTAACCGTA

New.ReferenceOTU114
TACGTAGGTCCCGAGCGTTGTCCGGATTTATTGGGCGTAAAGCGAGCGCAGGCGGTTTAATAAGTCTGAAGTTAAA
GGCAGTGGCTTAACCATTTTTCGCTTTGGAAACTGTTAGACTTGAGTGCAGAAGGGGAGAGTGGAATTCCATGTGT
AGCGGTGAAATGCGTAGATATATGGAGGAACACCGGTGGCGAAAGCGGCTCTCTGGTCTGTAACTGACGCTGAGGC
TCGAAAGCGTGGGGAGCAAACAGG AB506154.1.1541
AGAGTTTGATCCTGGCTCAGGACGAACGCTGGCGGCGTGCCTAATACATGCAAGTAGAACGCTGAAGAAAGGAGCT
TGCTTCTTTTGGATGAGTTGCGAACGGGTGAGTAACGCGTAGGTAACCTGCCTTGTAGCGGGGGATAACTATTGGA
AACGATAGCTAATACCGCATAACAGCTTTTGACACATGTTAGAAGCTTGAAAGATGCAATTGCATCACTACGAGAT
GGACCTGCGTTGTATTAGCTAGTAGGTAGGGTAACGGCCTACCTAGGCGACGATACATAGCCGACCTGAGAGGGTG
ATCGGCCACACTGGGACTGAGACACGGCCCAGACTCCTACGGGAGGCAGCAGTAGGGAATCTTCGGCAATGGGGGC
AACCCTGACCGAGCAACGCCGCGTGAGTGAAGAAGGTTTTCGGATCGTAAAGCTCTGTTGTAAGAGAAGAACGTGT
GTGAGAGTGGAAAGTTCACACAGTGACGGTAACTTACCAGAAAGGGACGGCTAACTACGTGCCAGCAGCCGCGGTG
ATACGTAGGTCCCGAGCGTTGTCCGGATTTATTGGGCGTAAAGCGAGCGCAGGCGGTTTAATAAGTCTGAAGTTAA
AGGCAGTGGCTTAACCATTGTTCGCTTTGGAAACTGTTAAACTTGAGTGCAGAAGGGGAGAGTGGAATTCCATGTG
TAGCGGTGAAATGCGTAGATATATGGAGGAACACCGGTGGCGAAAGCGGCTCTCTGGTCTGTAACTGACGCTGAGG
CTCGAAAGCGTGGGGAGCAAACAGGATTAGATACCCTGGTAGTCCACGCCGTAAACGATGAGTGCTAGGTGTTAGG
CCCTTTCCGGGGCTTAGTGCCGCAGCTAACGCATTAAGTATTCCGCCTGGGGAGTACGGTCGCAAGATTAAAACTC
AAAGGAATTGACGGGGGCCCGCACAAGCAGCGGAGCATGTGGTTTAATTCGAAGCAACGCGAAGAACCTTACCTAG
ACTTGACATCTCCTGCATTACTCTTAATCGAGGAAGTCCCTTCGGGGACAGGATGACAGGTGGTGCATGGTTGTCG
TCAGCTCGTGTCGTGAGATGTTGGGTTAAGTCCCGCAACGAGCGCAACCCTTATTGTTAGTTGCCATCATTAAGTT
GGGCACTCTAGCGAGACTGCCCGGGTTAACCGGGAGGAAGGTGGGGATGACGTCAAATCATCATGCCCCTTATGTC
TAGGGCTACACACGTGCTACAATGGTCGGTACAATAAGACGCAAGCCCGCGAGGGGGAGCAAAACTGGAAAACCGA
TCTCAGTTCGGATTGTAGGCTGAAACTCGCCTACATGAAGCTGGAGTTGCTAGTAATCGCGAATCAGCATGTCGCG
GTGAATACGTTCCCGGGCCTTGTACACACCGCCCGTCACACCATGAGAGTTGGCAATACCCAAAGTACGTGATCTA
ACCCGCAAGGGAGGAAGCGTCCTAAGGTAGGGTCAGCGATTGGGGTGAAGTCGTAACAAGGTAGCCGTAGGAGAAC
CTGCGGCTG EU774370.1.1398
AGAGTTTGCTCTTGGGTCAGGATGAACGCTGGCGGCGTGCTTAACACATGCAAGTCGAGCGAGAAAAGTTCTTCGG
AGCTTTTCTAGCGGCGGACGGGTGAGTAACACGTGGGCAACCTGCCTCATAGAGGGGAATAGCCTTCCGAAAGGAA
GATTAATACCGCATAACATTGTTGAAAGGCATCTTTTAACAATCAAAGGAGCAATCCGCTATGAGATGGGCCCGCG TABLE 11-continued 16S rRNA Sequences of OTUs in Tables 2-5
OTUs in Table 2

GCGCATTAGCTAGTTGGTGAGGTAACGGCTCACCAAGGCGACGATGCGTAGCCGACCTGAGAGGGTGATCGGCCAC
ATTGGAACTGAGACACGGTCCAGACTCCTACGGGAGGCAGCAGTGGGGAATATTGCACAATGGGGGAAACCCTGAT
GCAGCGACGCCGCGTGAGTGAAGAAGTATTTCGGTATGTAAAGCTCTGTTGTAAGAGAAGAACGTGTGTGAGAGTG
GAAAGTTCACACAGTGACGGTAACTTACCAGAGAGGGACGGCTAACTACGTGCCAGCAGCCGCGGTAATACGTAGG
TCCCGAGCGTTGTCCGGATTTATTGGGCGTAAAGCGAGCGCAGGCGGTTTAATAAGTCTGAAGTTAAAGGCAGTGG
CTTAACCATTGTTCGCTTTGGAAACTGTTAGACTTGAGTGCAGAAGGGGAGAGTGGAATTCCATGTGTAGCGGTGA
AATGCGTAGATATATGGAGGAACACCGGTGGCGAAAGCGGCTCTCTGGTCTGTAACTGACGCTGAGGCTCGAAAGC
GTGGGGAGCAAACAGGATTAGATACCCTGGTAGTCCACGCCGTAAACGATGAGTGCTAGGTGTTAGGCCCTTTCCG
GGGCTTAGTGCCGCAGCTAACGCATTAAGCACTCCGCCTGGGGAGTACGACCGCAAGGTTGAAACTCAAAGGAATT
GACGGGGGCCCGCACAAGCGGTGGAGCATGTGGTTTAATTCGAAGCAACGCGAAGAACCTTACCAGGTCTTGACAT
CCCGATGCTATTCCTAGAGATAGGAAGTTTCTTCGGAACATCGGTGACAGGTGGTGCATGGTTGTCGTCAGCTCGT
GTCGTGAGATGTTGGGTTAAGTCCCGCAACGAGCGCAACCCCTATTGTTAGTTGCCATCATTAAGTTGGGCACTCT
AGCGAGACTGCCGGTAATAAACCGGAGGAAGGTGGGGATGACGTCAAATCATCATGCCCCTTATGACCTGGGCTAC
ACACGTGCTACAATGGTTGGTACAACGAGTCGCGAGTCGGTGACGGCAAGCAAATCTCTTAAAGCCAATCTCAGTT
CGGATTGTAGGCTGCAACTCGCCTACATGAAGTCGGAATCGCTAGTAATCGCGGATCAGCACGCCGCGGTGAATAC
GTTCCCGGGCCTTGCACTCACCGCCCGTCA

HK557089.3.1395
AGACTTTAGCTTGCTAAAGTTGGAAGAGTTGCGAACGGGTGAGTAACGCGTAGGTAACCTGCCTACTAGCGGGGGA
TAACTATTGGAAACGATAGCTAATACCGCATAACAGCATTTAACCCATGTTAGATGCTTGAAAGGAGCAATTGCTT
CACTAGTAGATGGACCTGCGTTGTATTAGCTAGTTGGTGAGGTAACGGCTCACCAAGGCGACGATACATAGCCGAC
CTGAGAGGGTGATCGGCCACACTGGGACTGAGACACGGCCCAGACTCCTACGGGAGGCAGCAGTAGGGAATCTTCG
GCAATGGGGGCAACCCTGACCGAGCAACGCCGCGTGAGTGAAGAAGGTTTTCGGATCGTAAAGCTCTGTTGTAAGA
GAAGAACGTGTGTGAGAGTGGAAAGTTCACACAGTGACGGTAACTTACCAGAAAGGGACGGCTAACTACGTGCCAG
CAGCCGCGGTAATACGTAGGTCCCGAGCGTTGTCCGGATTTATTGGGCGTAAAGCGAGCGCAGGCGGTTTAATAAG
TCTGAAGTTAAAGGCAGTGGCTTAACCATTGTTCGCTTTGGAAACTGTTAGACTTGAGTGCAGAAGGGGAGAGTGG
AATTCCATGTGTAGCGGTGAAATGCGTAGATATATGGAGGAACACCGGTGGCGAAAGCGGCTCTCTGGTCTGTAAC
TGACGCTGAGGCTCGAAAGCGTGGGGAGCAAACAGGATTAGATACCCTGGTAGTCCACGCCGTAAACGATGAGTGC
TAGGTGTTAGGCCCTTTCCGGGGCTTAGTGCCGCAGCTAACGCATTAAGCACTCCGCCTGGGGAGTACGACCGCAA
GGTTGAAACTCAAAGGAATTGACGGGGGCCCGCACAAGCGGTGGAGCATGTGGTTTAATTCGAAGCAACGCGAAGA
ACCTTACCAGGTCTTGACATCCCGATGCTATTCCTAGAGATAGGAAGTTTCTTCGGAACTGTGAGACTTGAGGGCA
GAAGGGTAGAGTGCACTTGTATGGGGAGCTGTGGAATGCGTTCCCGCAACGAGCGCAACCCCTATTGTTAGTTGCC
ATCATTAAGTTGGGCACTCTAGCGAGACTGCCGGTAATAAACCGGAGGAAGGTGGGGATGACGTCAAATCATCATG
CCCCTTATGACCTGGGCTACACACGTGCTACAATGGTTGGTACAACGAGTCGCGAGTCGGTGACGGCAAGCAAATC
TCTTAAAGCCAATCTCAGTTCGGATTGTAGGCTGCAACTCGCCTACATGAAGTCGGAATCGCTAGTAATCGCGGAT
CAGCACGCCGCGGTGAATACGTTCCCGGGCCTTGTACACACCGCCCGTCACACCACGAGAGTTTGTAACACCCGAA
GTCGGTGAGGTANCCTTTTAGGAGC

HQ807346.1.1456
TTCAGGACGAACGCTGGCGGCGTGCCTAATACATGCAAGTAGAACGCTGAAGACTTTAGCTTGCTAAAGTTGGAAG
AGTTGCGAACGGGTGAGTAACGCGTAGGTAACCTGCCTACTAGCGGGGGATAACTATTGGAAACGATAGCTAATAC
CGCATAACAGCATTTAACCCATGTTAGATGCTTGAAAGGAGCAATTGCTTCACTAGTAGATGGACCTGCGTTGTAT
TAGCTAGTTGGTGAGGTAACGGCTCACCAAGGCGACGATACATAGCCGACCTGAGAGGGTGATCGGCCACACTGGG
ACTGAGACACGGCCCAGACTCCTACGGGAGGCAGCAGTAGGGAATCTTCGGCAATGGGGGCAACCCTGACCGAGCA
ACGCCGCGTGAGTGAAGAAGGTTTTCGGATCGTAAAGCTCTGTTGTAAGAGAAGAACGTGTGTGAGAGTGGAAAGT
TCACACAGTGACGGTAACTTACCAGAAAGGGACGGCTAACTACGTGCCAGCAGCCGCGGTAATACGTAGGTCCCGA
GCGTTGTCCGGATTTATTGGGCGTAAAGCGAGCGCAGGCGGTTTAATAAGTCTGAAGTTAAAGGCAGTGGCTTAAC
CATTGTTCGCTTTGGAAACTGTTAGACTTGAGTGCAGAAGGGGAGAGTGGAATTCCATGTGTAGCGGTGAAATGCG
TAGATATATGGAGGAACACCGGTGGCGAAAGCGGCTCTCTGGTCTGTAACTGACGCTGAGGCTCGAAAGCGTGGGG
AGCAAACAGGATTAGATACCCTGGTAGTCCACGCCGTAAACGATGAGTGCTAGGTGTTAGGCCCTTTCCGGGGCTT
AGTGCCGCAGCTAACGCATTAAGCACTCCGCCTGGGGAGTACGACCGCAAGGTTGAAACTCAAAGGAATTGACGGG
GGCCCGCACAAGCGGTGGAGCATGTGGTTTAATTCGAAGCAACGCGAAGAACCTTACCAGGTCTTGACATCCTTTG
ACCACTCTAGAGATAGAGCTTCCCCTTCGGGGGCAAAGTGACAGGTGGTGCATGGTTGTCGTCAGCTCGTGTCGTG
AGATGTTGGGTTAAGTCCCGCAACGAGCGCAACCCTTATTGTTAGTTGCCATCATTTAGTTGGGCACTCTAGCGAG
ACTGCCGGTGACAAACCGGAGGAAGGTGGGGATGACGTCAAATCATCATGCCCCTTATGACCTGGGCTACACACGT
GCTACAATGGGAAGTACAACGAGTTGCGAAGTCGCGAGGCTAAGCTAATCTCTTAAAGCTTCTCTCAGTTCGGATT
GTAGGCTGCAACTCGCCTACATGAAGCCGGAATCGCTAGTAATCGCGGATCAGCACGCCGCGGTGAATACGTTCCC
GGGCCTTGTACACACCGCCCGTCACACCACGAGAGTTTGTAACACCCGAAGTCGGTGAGGTAACCTTTTAGGAGCC
AGCCGCCTAAGG

HQ748204.1.1442
CTAATACATGCGAGGAGAACGCTGAAGACTTTCTTTTGCTATAGTTGGGAGAGTTGCTAACGGGTGAGTAACGCGT
AGGTGACCTGCCTACTAGCGGGGGATAACTATTGCAAACGATAGCTAATACCGCATAACAGCCTTTAACCCATGTT
AGATGCTTGAAAGGAGCAATTGCTTCACTAGTAGATGGACCTGCGTTGTATTAGCTAGTTGGTGAGGTAACGGCTC
ACCAAGGCGACGATACATAGCCGACCTGAGAGGGTGATCGGCCACACTGGGACTGAGACACGGCCCATACTCCTAC
GGGAGGCACCAGTAGGGAATCTTCGGGAATGGGGGCAACCCTGACCGAGCAACGCCGCGTGAGTGAAGAAGGTTTT
CGGATCGTAAAGCTCTGTTGTAAGAGAAGAACGTGTGTGAGAGTGGAAAGTTCACACTGTGACGGTAACTTACCAG
AAAGGGACGGCTAACTACGTGCCAGCAGCCGCGGTAATACGTAGGTCCCGAGCGTTGTCCGGATTTATTGGGCGTA
AAGCGAGCGCAGGCGGTTTAATAAGTCTGAAGTTAAAGGCAGTGGCTTAACCATTGTTCGCTTTGGAAACTGTTAG
ACTTGAGTGCATAAGGGGAGAGTGGAATTCCATGTGTAGCGGTGAAATGCGTAGATATATGGAGGAACACCGGTGG
CGAAAGCGGCTCTCTGGTCTGTAACTGACGTTGAGGCTCGAAAGCGTGGGGAGCAAACAGGATTAGATACCCTGGT
AGTCCACGCTGTAAACGATGAGTGGTAGGTGTTAGGCCCTTTCTGGGGTTTAGTGCCGCAGATTACGCATTAAGCC
ATTCGCCTGGGGAGTACGACCGCAAGGTTGAAACTTAAAGGAATTGACGGGGGCCCGCACAAGCGGTGGAGCATGT
GGTTTAATTAGAAGCAACGCGAAGAACCTTACCAGGTCTTGACATCCCGATGCTATTCTTAGAGATAGGAAGTTTC
TTCGGAACATCGGTGACAGGTGGTGCATGGTTGTCGTCAGCTCGTGTCGAGAGATGTTGGGTTAAGTCCCTCAACG
AGCGCAACCCCTATTTTTATTTGCCATCATTAAGTTGGGCAATCTAGCGAGACTGCCGGTAATAAACCGGAGGAAG
GTGGGGATGACGTCAAATCATCATGCTCCTTATGTCATGGGGTACACACGTGGTACAATGGTTGGTACAACGAGTC

TABLE 11-continued 16S rRNA Sequences of OTUs in Tables 2-5
OTUs in Table 2

GCGAGTTGGTGAAGGCAAGCAAATCTCTTAAAGCCAATATCAGTTCGGATTGTAGGCTGCAAATAGCCTACATGTA
GTCGGAATTGTTAGTAATCGGGGATCAGCACTCCGCGGTGAATACGTTTCCGGGCCTTGTACACCCCGCCCGTCTA
CACCACGAGAGTTTGTAACACCCGAAGTCGGTGAGGTAACTCTTTTAGGAGCCAGCCGCCTAAGGTGGGATAGA

GU179917.1.1382
AGAGTTTGATTATGGCTCAGGATGAACGCTGGCGGCGTGCCTAATACATGCAAGTCGAACGCGAGCAGCAATGCTC
GAGTGGCGAACGGGTGAGTAATACATAAGTAACCTGCCCTAGACAGGGGGATAACTGCTGGAAACGGCAGCTAAGA
CCGCATAGGTATGGACACTGCATGGTGACCATATTAAAAGTGCCAAGGCACTGGTAGAGGATGGACTTATGGCGCA
TTAGCTGGTTGGTGAGGTAACGGCTCACCAAGGCGACGATGCGTAGCCGACCTGAGAGGGTGACCGGCCACACTGG
GACTGAGACACGGCCCAGACTCCTACGGGAGGCAGCAGTAGGGAATTTTCGGCAATGGGGGGAACCCTGACCGAGC
AACGCCGCGTGAAGGAAGAAGGAATTCGTTCTGTAAACTTCTGTTATAAAGGAAGAACGGCGGATATAGGGAATGA
TATCCGAGTGACGGTACTTTATGAGAAAGCCACGGCTAACTACGTGCCAGCAGCCGCGGTAATACGTAGGTGGCGA
GCGTTATCCGGAATTATTGGGCGTAAAGAGGGAGCAGGCGGCGGCAGAGGTCTGTGGTGAAAGACTGAAGCTTAAC
TTCAGTAAGCCATAGAAACCGGGCTGCTAGAGTGCAGGAGAGGATCGTGGAATTCCATGTGTAGCGGTGAAATGCG
TAGATATATGGAGGAACACCAGTGGCGAAGGCGACGGTCTGGCCTGTAACTGACGCTCATTCCCGAAAGCGTGGGG
AGCAAATAGGATTAGATACCCTAGTAGTCCACGCCGTAAACGATGAGTACTAAGTGTTGGGAGTCAAATTTCAGTG
CTGCAGTTAACGCAATAAGTACTCCGCCTGAGTAGTACGTTCGCAAGAATGAAACTCAAAGGAATTGACGGGGGCC
CGCACAAGCGGTGGAGCATGTGGTTTAATTCGATGATACGCGAGGAACCTTACCAGGGCTTAAATGTGACTGACAG
GTCCGGAAACGGACTTTTCTTCGGACAGTTACAGGTGCTGCATGGTTGTCGTCAGCTCGTGCCGTGAGGTGTCAGG
TTAAGTCCTATAACGAGCGCAACCCCTGTCGCTAGTTGCCAGCGAGTAATGTCGGGAACTCTAGCGAGACTGCCAG
TGCAAACTGCGAGGAAGGTGGGGATGACGTCAAATCATCACGGCCCTTACGCCCTGGGCTACACACGTGCTACAAT
GGCCGGTACAGAGAGCAGCCACCCCGCGAGGGGGAGCGAATCTACAAAACCGGTCACAGTTCGGATCGGAGTCTGC
AACTCGACTCCGTGAAGCTGGAATCGCTAGTAATCGGATATCAGCCATGATCCGGTGAATACGTTCCCGGGCCTTG
TACACACCCCCGTC

GQ448336.1.1418
AGAGTTTGATCATGGCTCAGGACGAACGCTGGCGGCGTGCTTAACACATGCAAGTCGAACGAGAAGAGATGAGAAG
CTTGCTTCTTATCTCTTCGAGTGGCAAACGGGTGAGTAACGCGTAAGCAACCTGCCCTTCAGATGGGGACAACAGC
TGGAAACGGCTGCTAATACCGAATACGTTCTTTTTGTCGCATGGCAGAGGGAAGAAAGGGAGGCTCTTCGGAGCTT
TCGCTGAAGGAGGGGCTTGCGTCTGATTAGCTAGTTGGAGGGGTAACGGCCCACCAAGGCGACGATCAGTAGCCGG
TCTGAGAGGATGAACGGCCACATTGGGACTGAGACACGGCCCAGACTCCTACGGGAGGCAGCAGTGGGGAATCTTC
CGCAATGGACGAAAGTCTGACGGAGCAACGCCGCGTGAACGATGACGGCCTTCGGGTTGTAAAGTTCTGTTATACG
GGACGAATGGCGTAGCGGTCAATACCCGTTACGAGTGACGGTACCGTAAGAGAAAGCCACGGCTAACTACGTGCCA
GCAGCCGCGGTAATACGTAGGTGGCAAGCGTTGTCCGGAATTATTGGGCGTAAAGGGCGCGCAGGCGGCGTCGTAA
GTCGGTCTTAAAAGTGCGGGGCTTAACCCCGTGAGGGGACCGAAACTGCGATGCTAGAGTATCGGAGAGGAAAGCG
GAATTCCTAGTGTAGCGGTGAAATGCGTAGATATTAGGAGGAACACCAGTGGCGAAAGCGGCTTTCTGGACGACAA
CTGACGCTGAGGCGCGAAAGCCAGGGGAGCAAACGGGATTAGATACCCCGGTAGTCCTGGCCGTAAACGATGGATA
CTAGGTGTAGGAGGTATCGACCCCTTCTGTGCCGGAGTTAACGCAATAAGTATCCCGCCTGGGGAGTACGGCCGCA
AGGCTGAAACTCAAAGGAATTGACGGGGGCCCGCACAAGCGGTGGAACATGTGGTTTAATTCGATGATACGCGAGG
AACCTTACCCGGGCTTAAATTGCAGTGGAATGATGTGGAAACATGTCAGTGAGCAATCACCGCTGTGAAGGTGCTG
CATGGTTGTCGTCAGCTCGTGCCGTGAGGTGTCGGCTTAAGTGCCATAACGAGCGCAACCCTTATCTTCAGTTACT
AACAGGTCATGCTGAGGACTCTGGAGAGACTGCCGTCGTAAGATGTGAGGAAGGTGGGGATGACGTCAAATCAGCA
CGGCCCTTACGTCCGGGGCTACACACGTGTTACAATGGGGGGTACAGAGGGCCGCTACCACGCGAGTGGATGCCAA
TCCCAAAAACCTCTCTCAGTTCGGACTGGAGTCTGCAACCCGACTCCACGAAGCTGGATTCGCTAGTAATCGCGCA
TCAGCCACGGCGCGGTGAATACGTTCCCGGGCCTTGCACTCACCGCCCGT

DQ804865.1.1390
AGAGTTTGATCCTGGCTCAGGATGAACGCTGGCGGCGTGCTTAACACATGCAAGTCGAACGGGAAACTTTTCATTG
AAGCTTCGGCAGATTTGGTCTGTTTCTAGTGGCGGACGGGTGAGTAACGCGTGGGTAACCTGCCTTATACAGGGGG
ATAACAACCAGAAATGGTTGCTAATACCGCATAAGCGCACAGGACCGCATGGTCCGGTGTGAAAAACTCCGGTGGT
ATAAGATGGACCCGCGTTGGATTAGCTAGTTGGCAGGGTAACGGCCTACCAAGGCGACGATCCATAGCCGGCCTGA
GAGGGTGAACGGCCACATTGGGACTGAGACACGGCCCAGACTCCTACGGGAGGCAGCAGTGGGGAATATTGCACAA
TGGGGGAAACCCTGATGCAGCGACGCCGCGTGAAGGAAGAAGTATCTCGGTATGTAAACTTCTATCAGCAGGGAAG
ATAGTGACGGTACCTGACTAAGAAGCCCCGGCTAAATACGTGCCAGCAGCCGCGGTAATACGTATGGTTCAAGCGT
TATCCGGATTTACTGGGTGTAAAGGGTGAGTAGGCGGTTATGCAAGTCATATGTGAAATGTCGGGGCTCAACTCCG
GCCTGCATAAGAAACTGTATAACTAGAGTGCAGGAGAGGCAAGCGGAATTCCTAGTGTAGCGGTGAAATGCGTAGA
TATTAGGAAGAACACCGGTGGCGAAGGCGGCTTGCTGGACTGTTACTGACGCTGAGTCACGAAAGCGTGGGGAGCA
AACAGGATTAGATACCCTGGTAGTCCACGCCGTAAACGATGAATACTAGGTGTCGGGTGGCAAAGCCATTCGGTGC
CGCAGCAAACGCAATAAGTATTCCACCTGGGGAGTACGTTCGCAAGAATGAAACTCAAAGGAATTGACGGGGACCC
GCACAAGCGGTGGAGTATGTGGTTTAATTCGAAGCAACGCGAAGAACCTTACCAGGCCTTGACATGGATATAAATG
TTCTAGAGATAGAAAGATAGCTATATATCACACAGGTGGTGCATGGTTGTCGTCAGCTCGTGTCGTGAGATGTTGG
GTTAAGTCCCGCAACGAGCGCAACCCTTGTCTTCTGTTACCAGCATTGAGTTGGGGACTCAGGAGAGACTGCCGGT
GACAAACCGGAGGAAGGTGGGGATGACGTCAAATCATCATGCCCCTTATGGCCTGGGCTACACACGTACTACAATG
GCGCCTACAAAGAGCAGCGACACCGCGAGGTGAAGCGAATCTCATAAAGGGCGTCTCAGTTCGGATTGAAGTCTGC
AACTCGACTTCATGAAGTCGGAATCGCTAGTAATCGCAGATCAGCATGCTGCGGTGAATACGTTCCCGGGTCTTGT
ACTCACCGCCCGTCA

GQ491757.1.1361
GATGAACGCTGGCGGCGTGCTTAACACATGCAAGTCGAGCGAAGCACTTAAGTGGATCTCTTCGGATTGAAACTTA
TTTGACTGAGCGGCGGACGGGTGAGTAACGCGTGGGTAACCTGCCTCATACAGGGGGATAACAGTTAGAAATGGCT
GCTAATACCGCATAAGCGCACAGGACCGCATGGTCTGGTGTGAAAAACTCCGGTGGTATGAGATGGACCCGCGTCT
GATTAGCTAGTTGGAGGGGTAACGGCCCACCAAGGCGACGATCAGTAGCCGGCCTGAGAGGGTGAACGGCCACATT
GGGACTGAGACACGGCCCAGACTCCTACGGGAGGCAGCAGTGGGGAATATTGCACAATGGGGGAAACCCTGATGCA
GCGACGCCGCGTGAAGGAAGAAGTATCTCGGTATGTAAACTTCTATCAGCAGGGAAGAAAATGACGGTACCTGACT
AAGAAGCCCCGGCTAACTACGTGCCAGCAGCCGCGGTAATACGTAGGGGGCAAGCGTTATCCGGATTTACTGGGTG
TAAAGGGAGCGTAGACGGAAGAGCAAGTCTGATGTGAAAGGCTGGGGCTTAACCCCAGGACTGCATTGGAAACTGT
TTTTCTAGAGTGCCGGAGAGGTAAGCGGAATTCCTAGTGTAGCGGTGAAATGCGTAGATATTAGGAGGAACACCGG

TABLE 11-continued 16S rRNA Sequences of OTUs in Tables 2-5
OTUs in Table 2

TGGCGAAGGCGGCTTACTGGACGACCACTGACGCTGAGGCTCGAAAGCGTGGGGAGCAAACAGGATTAGATACCCT
GGTAGTCCACGCCGTAAACCGATGAATAATAGGTGTCGGGGAACAATAGTTCTTTGGTGCCGCAGCAAAACGCATT
AAGTATTCCACCTGGGGAGTACGTTCGCAAGAATGAAACTCAAAGGAATTGACGGGGACCCGCACAAGCGGTGGAG
CATGTGGTTTAATTCGATGCAACGCGAAGAACCTTACCTGCTCTTGACATCCCACTGACCGGACAGTAATGTGTCC
TTTTCTTCTGAACAGTGGAGACAGGTGGTGCATGGTTGTCGTCAGCTCGTGTCGTGAGATGTTGGGTTAAGTCCCG
CAACGAGCGCAACCCTCGTCTTTAGTAGCCAGCAGTCCGGCTGGGCACTCTAGAGAGACTGCCAGGGATAACCTGG
AGGAAGGCGGGGAGGACGTCAAATCATCATGCCCCTTACGAGCAGGGCTACACACGTGCTACAATGGCGTAAACAA
AGGGAAGCGACCCCGTGAAGGTGAGCAAATCTCAAAAATAACGTCTCAGTTCGGATTGTAGTCTGCAACTCGACTA
CATGAAGCTGGAATCGCTAGTAATCGCGAATCAGAATGTCGCGGTGAATAAAAGGCCGGGTCTTGCACA

New.ReferenceOTU56
TACGGAAGGTCCAGGCGTTATCCGGATTTATTGGGTTTAAAGGGAGCGCAGGCGGACTCTTAAGTCAGTTGTGAAA
TACGGCGGCTCAACCGTCGGACTGCAGTTGATACTGGGAGTCTTGAGTACACGCAGAGATACTGGAATTCATGGTG
TAGCGGTGAAATGCTCAGATATCATGAGGAACTCCGATCGCGAAGGCAGGTATCTGGAGTGTAACTGACGCTGAGG
CTCGAAAGTGCGGGTATCAAACAGG KF842598.1.1394
AGAGTTTGATCCTGGCTCAGGATGAACGCTAGCGACAGGCTTAACACATGCAAGTCGAGGGGCAGCATGATTTGTA
GCAATACAGATTGATGGCGACCGGCGCACGGGTGAGTAACGCGTATGCAACTTACCTATCAGAGGGGGATAGCCCG
GCGAAAGTCGGATTAATACCCCATAAAACAGGGGTCCCGCATGGGAATATTTGTTAAAGATTCATCGCTGATAGAT
AGGCATGCGTTCCATTAGGCAGTTGGCGGGGTAACGGCCCACCAAACCGACGATGGATAGGGGTTCTGAGAGGAAG
GTCCCCCACATTGGTACTGAGACACGGACCAAACTCCTACGGGAGGCAGCAGTGAGGAATATTGGTCAATGGCCGA
GAGGCTGAACCAGCCAAGTCGCGTGAAGGAAGAAGGATCTATGGTCTGTAAACTTCTTTTATAGGGGAATAAAGTG
GAGGACGTGTCCTTTTTTGTATGTACCCTATGAATAAGCATCGGCTAACTCCGTGCCAGCAGCCGCGGTAATACGG
AGGATGCGAGCGTTATCCGGATTTATTGGGTTTAAAGGGTGCGTAGGTGGTGATTTAAGTCAGCGGTGAAAGTTTG
TGGCTCAACCATAAAATTGCCGTTGAAACTGGGTTACTTGAGTGTGTTTGAGGTAGGCGGAATGCGTGGTGTAGCG
GTGAAATGCATAGATATCACGCAGAACTCCGATTGCGAAGGCAGCTTACTAAACCATAACTGACACTGAAGCACGA
AAGCGTGGGGATCAAACAGGATTAGATACCCTGGTAGTCCACGCAGTAAACGATGATTACTAGGAGTTTGCGATAC
AATGTAAGCTCTACAGCGAAAGCGTTAAGTAATCCACCTGGGGAGTACGCCGGCAACGGTGAAACTCAAAGGAATT
GACGGGGGCCCGCACAAGCGGAGGAACATGTGGTTTAATTCGATGATACGCGAGGAACCTTACCCGGGTTTGAACG
TAGTCTGACCGGAATGGAAACACTCCTTCTAGCAATAGCAGATTACAAGGTGCTGCATGGTTGCCTCAACTCCGGC
CCGGAAGGTCCGGCTTAATTGCCATAACAAGCGCACCCTTTTACCAAGGTTCAAACAGGTGAAGCTTGAAGACTCT
GTGGAACCTCCCCCCTAACCTGTGAGAAGAAGTGGGGATACACTCAATAAACCACGGCCCTTAATCCCGGGGGGAA
CACTGGTTACAATGGGTTGGGAAAGGGGGCTTCCTGGCGACAGGATGCTAATCTCCAAACCATGTCTCAGTTCGGA
TCGGAGTCTGCAACTCGACTCCGTGAAGCTGGATTCGCTAGTAATCGCGCATCAGCCATGGCGCGGTGAATACGTT
CCCGGGCCTTGTACACACCGCCCGTC HQ802052.1.1445
TACAGGCTTAACACATGCAAGTCGAGGGGCAGCATGATTGAAGCTTGCTTCAATTGATGGCGACCGGCGCACGGGT
GAGTAACACGTATCCAACCTTCCGTACACTCAGGGATAGCCTTTCGAAAGAAAGATTAATACCTGATGGTATCTTA
AGCACACATGTAATTAAGATTAAAGATTTATCGGTGTACGATGGGGATGCGTTCCATTAGGTAGTAGGCGGGGTAA
CGGCCCACCTAGCCTACGATGGATGGGGGTTCTGAGAGGAAGGTCCCCCACATTGGAACTGAGACACGGTCCAAAC
TCCTACGGGAGGCAGCAGTGAGGAATATTGGTCAATGGACGAGAGTCTGAACCAGCCAAGTAGCGTGAAGGATGAA
GGTCCTACGGATTGTAAACTTCTTTTATAAGGGAATAAAACCTCCCACGTGTGGGAGCTTGTATGTACCTTATGAA
TAAGCATCGGCTAACTCCGTGCCAGCAGCCGCGGTAATACGGAGGATGCGAGCGTTATCCGGATTTATTGGGTTTA
AAGGGAGCGCAGACGGGTCGTTAAGTCAGCTGTGAAAGTTTGGGGCTCAACCTTAAAATTGCAGTTGATACTGGCG
TCCTTGAGTGCGGTTGAGGTGTGCGGAATTCGTGGTGTAGCGGTGAAATGCTTAGATATCACGAAGAACTCCGATT
GCGAAGGCAGCACACTAAGCCGTAACTGACGTTCATGCTCGAAAGTGTGGGTATCAAACAGGATTAGATACCCTGG
TAGTCCACACAGTAAACGATGAATACTCGCTGTTTGCGATATACAGTAAGCGGCCAAGCGAAAGCATTAAGTATTC
CACCTGGGGAGTACGCCGGCAACGGTGAAACTCAAAGGAATTGACGGGGGCCCGCACAAGCGGAGGAACATGTGGT
TTAATTCGATGATACGCGAGGAACCTTACCCGGGCTTAAATTGCATTTGAATATATTGGAAACAGTATAGCCGTAA
GGCAAATGTGAAGGTGCTGCATGGTTGTCGTCAGCTCGTGCCGTGAGGTGTCGGCTTAAGTGCCATAACGAGCGCA
ACCCTTATCTTCAGTTACTAACAGGTCATGCTGAGGACTCTGGAGAGACTGCCGTCGTAAGATGTGAGGAAGGTGG
GGATGACGTCAAATCAGCACGGCCCTTACGTCCGGGGCTACACACGTGTTACAATGGGGGGTACAGAAGGCCGCTA
CCTGGTGACAGGATGCTAATCCCAAAAGCCTCTCTCAGTTCGGATCGAAGTCTGCAACCCGACTTCGTGAAGCTGG
ATTCGCTAGTAATCGCGCATCAGCCATGGCGCGGTGAATACGTTCCCGGGCCTTGTACACACCGCCCGTCAAGCCA
TGAAAGCCGGGGGTACCTGAAGTACGTAACCGCAAGGAGCGTCCTAGGGTAAAACTGGTAATTGGGGCTAAGTCAT
A GX182404.8.1529
AGAGTTTGATCATGGCTCAGATTGAACGCTGGCGGCAGGCCTAACACATGCAAGTCGAACGGTAACAGGAAGAAGC
TTGCTTCTTTGCTGACGAGTGGCGGACGGGTGAGTAATGTCTGGGAAACTGCCTGATGGAGGGGGATAACTACTGG
AAACGGTAGCTAATACCGCATAACGTCGCAAGACCAAAGAGGGGGACCTTCGGGCCTCTTGCCATCGGATGTGCCC
AGATGGGATTAGCTAGTAGGTGGGGTAACGGCTCACCTAGGCGACGATCCCTAGCTGGTCTGAGAGGATGACCAGC
CACACTGGAACTGAGACACGGTCCAGACTCCTACGGGAGGCAGCAGTGGGGAATATTGCACAATGGGCGCAAGCCT
GATGCAGCCATGCCGCGTGTATGAAGAAGGCCTTCGGGTTGTAAAGTACTTTCAGCGGGGAGGAAGGGAGTAAAGT
TAATACCTTTGCTCATTGACGTTACCCGCAGAAGAAGCACCGGCTAACTCCGTGCCAGCAGCCGCGGTAATACGGA
GGGTGCAAGCGTTAATCGGAATTACTGGGCGTAAAGCGCACGCAGGCGGTTTGTTAAGTCAGATGTGAAATCCCCG
GGCTCAACCTGGGAACTGCATCTGATACTGGCAAGCTTGAGTCTCGTAGAGGGGGGTAGAATTCCAGGTGTAGCGG
TGAAATGCGTAGAGATCTGGAGGAATACCGGTGGCGAAGGCGGCCCCCTGGACGAAGACTGACGCTCAGGTGCGAA
AGCGTGGGGAGCAAACAGGATTAGATACCCTGGTAGTCCACGCCGTAAACGATGTCGACTTGGAGGTTGTGCCCTT
GAGGCGTGGCTTCCGGAGCTAACGCGTTAAGTCGACCGCCTGGGGAGTACGGCCGCAAGGTTAAAACTCAAATGAA
TTGACGGGGGCCCGCACAAGCGGTGGAGCATGTGGTTTAATTCGATGCAACGCGAAGAACCTTACCTGGGTTTGAC
ATGCACAGGACGCGTCTAGAGATAGGCGTTCCCTTGTGGCCTGTGTGCAGGTGGTGCATGGCTGTCGTCAGCTCGT
GTCGTGAGATGTTGGGTTAAGTCCCGCAACGAGCGCAACCCTTGTCTCATGTTGCCAGCACGTAATGGTGGGGACT
CGTGAGAGACTGCCGGGGTCAACTCGGAGGAAGGTGGGGATGACGTCAAGTCATCATGCCCCTTATGTCCAGGGCT
TCACACATGCTACAATGGCCGGTACAAAGGGCTGCGATGCCGCGAGGTTAAGCGAATCCTTAAAAGCCGGTCTCAG TABLE 11-continued 16S rRNA Sequences of OTUs in Tables 2-5
OTUs in Table 2

TTCGGATCGGGGTCTGCAACTCGACCCCGTGAAGTCGGAGTCGCTAGTAATCGCAGATCAGCAACGCTGCGGTGAA
TACGTTCCCGGGCCTTGTACACACCGCCCGTCACGTCATGAAAGTCGGTAACACCCGAAGCCAGTGGCCTAACCCT
CGGGAGGGAGCTGTCGAAGGTGGGATCGGCGATTGGGACGAAGTCGTAACAAGGTAACCGTAGGGGAACCTGCGGT
TG

FJ950694.1.1472
CGCCCTGATTGACGGCTATACACATGCAAGTCGAACGGTAACAGGAAACAGCTTGCTTCTTTGCTGACGAGTGGCG
GACGGGTGAGTAATGTCTGGGAAACTGCCTGATGGAGGGGGATAACTACTGGAAACGGTAGCTAATACCGCATAAC
GTCGCAAGACCAAAGAGGGGGACCTTCGGGCCTCTTGCCATCGGATGTGCCCAGATGGGATTAGCTAGTAGGTGGG
GTAACGGCTCCATCCCTAGGCGAGCCGAATCCTTAGCCTGGTCTGAGAGGAATGACCAGCCACACTGGGACTGAGA
ACACGGTCCAGACTCCTACGGGAGGCAGCAGTGGGGAATATTGCACAATGGGCGCAAGCCTGATGCAGCCATGCCG
CGTGTATGAAGAAGGCCTTCGGGTTGTAAAGTACTTTCAGCGGGGAGGAAGGGAGTAAAGTTAATACCCTTTGCTC
ATTGACGTTACCCGCAGAAGAAGCACCGGCTAACTCCGTGCCAGCAGCCGCGGTAATACGGAGGGTGCAAGCGTTA
ATCGGAATTACTGGGCGTAAAGCGCACGCAGGCGGTTTGTTAAGTCAGATGTGAAATCCCCGGGCTCAACCTGGGA
ACTGCATCTGATACTGGCAAGCTTGAGTCTCGTAGAGGGGGGTAGAATTCCAGGTGTAGCGGTGAAATGCGTAGAG
ATCTGGAGGAATACCGGTGGCGAAGGCGGCCCCCTGGACGAAGACTGACGCTCAGGTGCGAAAGCGTGGGGAGCAA
ACAGGATTAGATACCCTGGTAGTCCACGCCGTAAACGATGTCGACTTGGAGGTTGTGCCCTTGAGGCGTGGCTTCC
GGAGCTAACGCGTTAAGTCGACCGCCTGGGGAGTACGGCCGCAAGGTTAAAACTCAAATGAATTGACGGGGGCCCG
CACAAGCGGTGGAGCATGTGGTTTAATTCGATGCAACGCGAAGAACCTTACCTGGTCTTGACATCCACGGGAAGTT
TTCAGAGATGAGAATGTGCCTTCGGGAACCGTGAGACAGGTGCTGCATGGCTGTCGTCAGCTCGTGTTGTGAAATG
TTGGGTTAAGTCCCGCAACGAGCGCAACCCTTATCCTTTGTTGCCAGCGGTCCGGCCGGGAACTCAAAGGAGACTG
CCAGTGATAAACTGGAGGAAGGTGGGGATGACGTCCAGGTCATCATGGCCCTTACGAACCAGGGCTACACACGTGC
CTACAATGGACGCATCCAAAGAGAGAGCGAACCCTGCCCGCGAGAGCAAGCGGACCTCATAAAGTGCGTCGTAGTC
CGGATTGGAGTCTGCAACTCGACTCCATGAAGTCGGAATCGCTAGTAATCGTGGATCAGAATGCCACGGTGAATAC
GTTCCCGGGCCTTGTACACACCGCCCGTCACACCATGGGAGTGGGTTGCAAAAGAAGTAGGTAGCTTAACCTTCGG
GAGGGCGCTTACCACTTTGGATGCGAGG

GQ448506.1.1374
AGAGTTTGATCATGGCTCAGGATGAACGCTAGCTACAGGCTTAACACATGCAAGTCGAGGGGCAGCATGGTCTTAG
CTTGCTAAGGCCGATGGCGACCGGCGCACGGGTGAGTAACACGTATCCAACCTGCCGTCTACTCTTGGACAGCCTT
CTGAAAGGAAGATTAATACAAGATGGCATCATGAGTCCGCATGTTCACATGATTAAAGGTATTCCGGTAGACGATG
GGGATGCGTTCCATTAGATAGTAGGCGGGGTAACGGCCCACCTAGTCTTCGATGGGTAGGGGTTCTGAGAGGAAGG
TCCCCCACATTGGAACTGAGACACGGCCCAAACTCATACGGGAGGCAGCAGTGGGGAATATTGCACAATGGGGGAA
ACCCTGATGCAGCGACGCCGCGTGAAGGATGAAGTATTTCGGTATGTAAACTTCTATCAGCAGGGAAGAAAATGAC
GGTACCTGACTAAGAAGCCCCGGCTAACTACGTGCCAGCAGCCGCGGTAATACGTAGGGGGCAAGCGTTATCCGGA
TTTACTGGGTGTAAAGGGAGCGTAGACGGCAGTGCAAGTCTGAAGTGAAAGCCCGGGGCTCAACCCCGGGACTGCT
TTGGAAACTGTGCAGCTAGAGTGTCGGAGAGGCAAGCGGAATTCCTAGTGTAGCGGTGAAATGCGTAGATATTAGG
AGGAACACCAGTGGCGAAGGCGGCTTGCTGGACGATGACTGACGTTGAGGCTCGAAAGCGTGGGGAGCAAACAGGA
TTAGATACCCTGGTAGTCCACGCCGTAAACGATGACTACTAGGTGTCGGGGAGCAAAGCTCTTCGGTGCCGCAGCC
AACGCAATAAGTAGTCCACCTGGGGAGTACGTTCGCAAGAATGAAACTCAAAGGAATTGACGGGGACCCGCACAAG
CGGTGGAGCATGTGGTTTAATTCGAAGCAACGCGAAGAACCTTACCTGCTCTTGACATCCCTCTGACCGCTCTTTA
ATCGGAGCTTTCCTTCGGGACAGAGGAGACAGGTGGTGCATGGTTGTCGTCAGCTCGTGTCGTGAGATGTTGGGTT
AAGTCCCGCAACGAGCGCAACCCTTATGGTCAGTTACTACGCAAGAGGACTCTGGCCAGACTGCCGTTGACAAAAC
GGAGGAAGGTGGGGATGACGTCAAATCATCATGCCCTTTATGACTTGGGCTACACACGTACTACAATGGCGTTAAA
CAAAGAGAAGCGAGACCGCGAGGTGGAGCAAAACTCGGAAACAACGTCCCAGTTCGGACTGCAGGCTGCAACTCGC
CTGCACGAAGTCGGAATTGCTAGTAATCGCAGATCAGCATGCTGCGGTGAATACGTTCCCGGGCCTTGCACTCACC
GCCCGT

HQ802983.1.1440
TAAGATGAACGCTGGCGGCGTGCTTAACACATGCAAGTCCTATGAAGCGCTTAAACGGATTTCTTCGGATTGAAGT
TTTTGTGACTGAGTGGCGGACGGGTGAGTAACGCGTGGGTAACTTGCCTCATACAGGGGGATAACAGTTAGAAATG
ACTGCTAATACCGCATAAGCGCACAGTGCTGCATGGCACAGTGTGAAAAACTCCGGTGGTATGAGATGGACCCGCG
TCTGATTAGCTAGTTGGTGGGGTAACGGCCTACCAAGGCGACGATCAGTAGCCGGCCTGAGAGGGTGAACGGCCAC
ATTGGGACTGAGACACGGCCCAAACTCCTACGGGAGGCAGCAGTGGGGAATATTGCACAATGGGGGAAACCCTGAT
GCAGCGACGCCGCGTGAGCGAAGAAGTATTTCGGTATGTAAAGCTCTATCAGCAGGGAAGAAAATGACGGTACCTG
ACTAAGAAGCACCGGCTAAATACGTGCCAGCAGCCGCGGTAATACGTATGGTGCAAGCGTTATCCGGATTTACTGG
GTGTAAAGGGAGCGTAGACGGTTGTGTAAGTCTGATGTGAAAGCCCGGGGCTCAACCCCGGGACTGCATTGGAAAC
TATGTAACTAGAGTGTCGGAGAGGTAAGCGGAATTCCTAGTGTAGCGGTGAAATGCGTAGATATTAGGAGGAACAC
CAGTGGCGAAGGCGGCTTACTGGACGATCACTGACGTTGAGGCTCGAAAGCGTGGGGAGCAAACAGGATTAGATAC
CCTGGTAGTCCACGCCGTAAACGATGACTACTAGGTGTCGGGGCCCATAAGGGCTTCGGTGCCGCAGCAAACGCAA
TAAGTATTCCACCTGGGGAGTACGTTCGCAAGAATGAAACTCAAAGGAATTGACGGGGACCCGCACAAGCGGTGGA
GCATGTGGTTTAATTCGAAGCAACGCGAAGAACCTTACCTGGTCTTGACATCCCACTGACCGGACAGTAATGTGTC
CTTTCCTCCGGGACAGTGGAGACAGGTGGTGCATGGTTGTCGTCAGCTCGTGTCGTGAGATGTTGGGTTAAGTCCC
GCAACGAGCGCAACCCCTATCCTTAGTAGCCAGCAGTAAGATGGGCACTCTAGGGAGACTGCCAGGGATAACCTGG
AGGAAGGTGGGGATGACGTCAAATCATCATGCCCCTTATGACTTGGGCTACACACGTGCTACAATGGCGTAAACAA
AGTGAAGCGAAGTCGTGAGGCCAAGCAAATCACAAAAATAACGTCTCAGTTCGGATTGTAGTCTGCAACTCGACTA
CAAGAAGCTGGAATCGCTAGTAATCGCAGATCAGAATGCTGCGGTGAATACGTTCCCGGGTCTTGTACACACCGCC
CGTCACACCATGGGAGTCGAAAATGCCCGAAGTCGGTGACCTAACGAAAGAAGGAGCCGCCGAAGGCAGGTT

DQ793824.1.1370
ATGAACGCTGGCGGCGTGCCTAACACATGCAAGTCGAACGAAGCGCTTGAACGGATATCTTCGGACTGAAGTTCTT
GCGACTGAGTGGCGGACGGGTGAGTAACGCGTGGGTAACCTGCCTCATACAGGGGGATAACAGTTAGAAATGACTG
CTAATACCGCATAAGCGCACAGCTTCGCATGGAGCAGTGTGAAAAACTCCGGTGGTATGAGATGGACCCGCGTCAG
ATTAGCTAGTTGGCAGGGTAACGGCCTACCAAGGCGACGATCTGTAGCCGACCTGAGAGGGTGACCGGCCACATTG
GGACTGAGACACGGCCCAAACTCCTACGGGAGGCAGCAGTGGGGAATATTGCACAATGGGGGAAACCCTGATGCAG
CGACGCCGCGTGAGCGAAGAAGTATTTCGGTATGTAAAGCTCTATCAGCAGGGAAGATAATGACGGTACCTGACTA
AGAAGCTCCGGCTAAATACGTGCCAGCAGCCGCGGTAATACGTATGGAGCAAGCGTTATCCGGATTTACTGGGTGT

TABLE 11-continued 16S rRNA Sequences of OTUs in Tables 2-5
OTUs in Table 2

AAAGGGAGCGTAGACGGTTTGACAAGTCTGATGTGAAATTCCAGGGCTTAACCCTGGACCTGCATTGGAAACTGTC
GGACTAGAGTGTCGGAGAGGTGAGTGGAATTCCTAGTGTAGCGGTGAAATGCGTAGATATTAGGAGGAACACCAGT
GGCGAAGGCGGCTCACTGGACGATAACTGACGTTGAGGCTCGAAAGCGTGGGGAGCAAACAGGATTAGATACCCTG
GTAGTCCACGCCGTAAACGATGTGTACTAGGTGTTGGGGAGCAAAGCTCTTCGGTGCCGTCGCAAACGCAGTAAGT
ACACCACCTGGGGAGTACGTTCGCAAGAATGAAACTCAAAGGAATTGACGGGGACCCGCACAAGCGGTGGAGCATG
TGGTTTAATTCGAAGCAACGCGAAGAACCTTACCAAATCTTGACATCGGAGTGACCGCTCTTTAATCGGAGCTTTC
CTTCGGGACACTCCAGACAGGTGGTGCATGGTTGTCGTCAGCTCGTGTCGTGAGATGTTGGGTTAAGTCCCGCAAC
GAGCGCAACCCTTATCCTTAGTAGCCAGCAAGTGAAGTTGGGCACTCTAGGGAGACTGCCAGGGATAACCTGGAGG
AAGGTGGGGATGACGTCAAATCATCATGCCCCTTATGATTTGGGCTACACACGTGCTACAATGGCGTAAACAAAGG
GAAGCGATCACGTGAGTGTGAGCAAATCTCAAAAATAACGTCCCAGTTCGGACTGTAGTCTGCAACCCGACTACAC
GAAGCTGGAATCGCTAGTAATCGCAGGTCAGCATACTGCGGTGAATACGTTCCCGGGTCTTGCACACACCGCCCGT
CA

GQ448468.1.1366
AGAGTTTGATCCTGGCTCAGGATGAACGCTGACAGAATGCTTAACACATGCAAGTATACTTGATCCTTCGGGTGAT
GGTGGCGGACGGGTGAGTAACGCGTAAAGAACTTGCCCTGCAGTCTGGGACAACATTTGGAAACGAATGCTAATCC
CGCATAAGCCCACAGCTCGGCATCGAGCAGAGGGAAAAGGAGTGATCTGCTTTGAGATGGCCTCGCGTCCGATTAG
CTGGTTGGTGAGGTGACGGCCCATCAAGGCAACGATCGGTAGCCGGACTGAGAGGTTGAACGGCCACATTGGGATT
GAGACACGGCCCTTACTCCTACGGGAGGCAGCAGTGGGGAATATTGGACAATGGACCAAAAGTCTGATCCAGCAAT
TCTGTGTGCACGATGAAGTTTTTCGGAATGTAAAGTGCTTTCAGTTGGGACGAAGTAAGTGACGGTACCAACAGAA
GAAGCGACGGCTAAATACGTGCCAGCAGCCGCGGTAATACGTATGTCGCAAGCGTTATCCGGATTTATTGGGCGTA
AAGCGCGTCTAGGCGGTTTGGTAAGTCTGATGTGAAAATGCGGGGCTCAACTCCGTATTGCGTTGGAAACTGCCAA
ACTAGAGTACTGGAGAGGTGGGCGGAACTACAAGTGTAGAGGTGAAATTCGTAGATATTTGTAGGAATGCCGATGG
GGAAGCCAGCCCACTGGACAGATACTGACGCTAAAGCGCGAAAGCGTGGGTAGCAAACAGGATTAGATACCCTGGT
AGTCCACGCCGTAAACGATGATTACTAGGTGTTGGGGGTCGAACCTCAGCGCCCAAGCTAACGCGATAAGTAATCC
GCCTGGGGAGTACGTACGCAAGTATGAAACTCAAAGGAATTGACGGGGACCCGCACAAGCGGTGGAGCATGTGGTT
TAATTCGACGCAACGCGAGGAACCTTACCAGCGTTTGACATCCTAAGAAATTAGCAGAGATGCTTTTGTGCCCCTT
CGGGGGAACTTAGTGACAGGTGGTGCATGGCTGTCGTCAGCTCGTGTCGTGAGATGTTGGGTTAAGTCCCGCAACG
AGCGCAACCCCTTTCGTATGTTGCCATCATTAAGTTGGGCACTCATGCGATACTGCCTGCGATGAGCAGGAGGAAG
GTGGGGATGACGTCAAGTCATCATGCCCCTTATACGCTGGGCTACACACGTGCTACAATGGGTAGTACAGAGAGTC
GCAAACCTGCGAGGGGGAGCTAATCTCAGAAAACTATTCTCAGTTCGGATTGTACTCTGCAACTCGAGTACATGAA
GTTGGAATCGCTAGTAATCGCAAATCAGCTATGTTGCGGTGAATACGTTCTCGGGTCTTGTACACACCGCCCGT

EU774020.1.1361
AGAGTTTGATCCTGGCTCAGGACGAACGCTGGCGGCGTGCCTAACACATGCAAGTCGAGCGATTCTCTTCGGAGAA
GAGCGGCGGACGGGTGAGTAACGCGTGGGTAACCTGCCCTGTACACACGGATAACATACCGAAAGGTATGCTAATA
CGGGATAATATATAAGAGTCGCATGACTTTTATATCAAAGATTTTTCGGTACAGGATGGACCCGCGTCTGATTAGC
TTGTTGGCGGGGTAACGGCCCACCAAGGCGACGATCAGTAGCCGACCTGAGAGGGTGATCGGCCACATTGGAACTG
AGACACGGTCCAAACTCCTACGGGAGGCAGCAGTGGGGAATATTGCACAATGGGCGCAAGCCTGATGCAGCAACGC
CGCGTGAGCGATGAAGGCCTTCGGGTCGTAAAGCTCTGTCCTCAAGGAAGATAATGACGGTACTTGAGGAGGAAGC
CCCGGCTAACTACATGCCAGCAGCCGCGGTAATACGTATGTCGCAAGCGTTATCCGGATTTATTGGGCGTAAAGCG
CGTCTAGGTGGTTTGGTAAGTCTGATGTGAAAATGCGGGGCTCAACTCCGTATTGCGTTGGAAACTGCCAAACTAG
AGTACTGGAGAGGTAGGCGGAACTACAAGTGTAGAGGTGAAATTCGTAGATATTTGTAGGAATGCCGATGGGGAAG
CCAGCCTACTGGACAGATACTGACGCTAAAGCGCGAAAGCGTGGGTAGCAAACAGGATTAGATACCCTGGTAGTCC
ACGCCGTAAACGATGATTACTAGGTGTTGGGGGTCGAACCTCAGCGCCCAAGCTAACGCGATAAGTAATCCGCCTG
GGGAGTACGTACGCAAGTATGAAACTCAAAGGAGTTGACGGGGACCCGCACAAGCGGTGGAGCATGTGGTTTAATT
CGACGCAACGCGAGGAACCTTACCAGCGTTTGACATCCTAGGAATGAGAAAGAGATTTCTTAGTGCTCCTTCGGGA
GAACCTAGAGACAGGTGGTGCATGGCTGTCGTCAGCTCGTGTCGTGAGATGTTGGGTTAAGTCCCGCAACGAGCGC
AACCCCTATTGTATGTTGCCATCATTAAGTTGGGCACTCATGCGATACTGCCTGCGATGAGCAGGAGGAAGGTGGG
GATGACGTCAAGTCATCATGCCCCTTATACGCTGGGCTACACACGTGCTACAATGGGCAGTACAGAGAGAAGCAAT
ACCGCGAGGTGGAGCCAAACTTAAAAACCAGTCTCAGTTCGGATTGTAGGCTGAAACTCGCCTACATGAAGCTGGA
GTTACTAGTAATCGCGAATCAGAATGTCGCGGTGAATACGTACCCGGGTCTTGTACACACCGCCCGTCA

GQ491183.1.1360
GATGAACCCTTGCGGCGTGCTTAACACATGCAAGTCGAACGGGAAACATTTTATTGAAGCTTCGGCAGATCTAGCT
TGTTTCTAGTGGCGGACGGGTGAGTAACGCGTGGGCAACCTGCCTCACACTGGGGGATAACAGTCAGAAATGGCTG
CTAATACCGCATAAGCGCACAGCATCGCATGATGCAGTGTGAAAAACTCCGGTGGTGTGAGATGGACCCGCGTTGG
ATTAGCTAGTTGGCAGGGCAGCGGCCTACCAAGGCGACGATCCATAGCCGGCCTGAGAGGGTGAACGGCCACATTG
GGACTGAGACACGGCCCAGACTCCCACGGGAGGCAGCAGTGGGGAATATTGCACAATGGGGGAAACCCTGATGCAG
CGACGCCGCGTGAAGGAAGAAGTATCTCGGTATGTAAACTTCTATCAGCAGGGAAGAAAATGACGGTACCTGACTA
AGAAGCCCCGGCTAACTACGTGCCAGCAGCCGCGGTAATACGTAGGGGGCAAGCGTTATCCGGATTTACTGGGTGT
AAAGGGAGCGTAGACGGTGTTGCAAGTCTGATGTGAAAGGCGGGGGCTCAACCCCTGGACTGCATTGGAAACTGTG
ATACTCGAGTGCCGGAGAGGTAAGCGGAATTCCTAGTGTAGCGGTGAAATGCGTAGATATTAGAAGGAATACCAGT
GGCGAAGGCGGCTTACTGGACGGTAACTGACGTTGAGGCTCGAAAGCGTGGGGAGCAAACAAGATTAAGAAACCTC
TGGGTAGTCCACGCCCGTAAACGAAGGAATAAAGGGGTCGGGAGCAGAGCTTTTCGGTGCCGCAGCAAACCCAATA
AGTATTCCACCTTGAGAGGACGTTCGCAAGAATGAAACTCAAAGGAATTGACGGGGGACCCGCACAAGCGGTGGAG
CATGTGGTTTAATTCGAAGCAACGCGAAGAACCTTACCAAGTCTTGACATCCCTCTGACCGCACCTTAACCGGTGC
TTTCCTTCGGGACAGAGGAGACAGGTGGTGCATGGTTGTCGTCAGCTCGTGTCGTGAGATGTTGGGTTAAGTCCCG
CAACGAGCGCAACCCTTATCCTTAGTAGCCAGCGGTCCGGCCGGGCACTCTGGGGAGACTGCCAGGGATAACCTGG
AGGAAGGTGGGGATGACGTCAAATCATCATGCCCCTTATGATTTGGGCTACACACGTGCTACAATGGCGTAAACAA
AGGGAAGCGATCACGTGAGTGCGAGCAAATCTCAAAAATAACGTCCCAGTTCGGACTGTAGTCTGCAACCCGACTA
CACGAAGCTGGAATCGCTAGTAATCGCAGGTCAGCATACTGCGGTGAATACGTTCCCGGGTCTTGTAC

GQ491426.1.1332
GCTCAGGATGAACGCTGGCGGCGTGCTTAACACATGCAAGTCGAGCGAAGCACTTGCCATTGACTCTTCGGAAGAT
TTGGCATTTGACTGAGCGGCGGACGGGTGAGTAACGCGTGGGTAACCTGCCTCATACGGGGGAATAACAGTTAGAA
ATGGCTGCTAATGCCGCATAACCGCACAGGACCGCATGGACTGGTGTGAAAAACTGAGGTGGTATGAGATGGGCCC

TABLE 11-continued

| 16S rRNA Sequences of OTUs in Tables 2-5<br>OTUs in Table 2 |
|---|
| GCGTCTGATTAGGTTAGTTGGCGGGGTAACGGCCCACCAAGCCGACGATCAGTAGCCGACCTGAGAGGGACCGGCC<br>ACATTGGGACTGAGACATGGCCCAGACTCCTACGGGAGGCAGCAGTGGGGAATATTGCACAATGGAGGAAACTCTG<br>ATGCAGCGACGCCGCATGAAGGAAGAAGTATCTCGGTATGTAAACTTCTATCAGCAGGGAAGAAAATGACGGTACC<br>TGACTAAGAAGCCCCGGCTAACTACGTGCCAGCAGCCGCGGTAATACGTAGGGGGCAAGCGTTATCCGGATTTACT<br>GGGTGTAAAGGGAGCGTAGACGGACGGGCAAGTCTGATGTGAAAGCCCGGGGCTTAACCCCGGGACTGCATTGGAA<br>ACTGTCCATCTTGAGTGCCGGAGAGGTAAGCGGAATTCCTAGTGTAGCGGTGAAATGCGTAGATATTAGGAGGAAC<br>ACCAGTGGCGAAGGCGGCTTACTGGACGGTAACTGACGTTGAGGCTCGAAAGCGTGGGGAGCAAACAGGATTAGAT<br>ACCCTGGTAGTCCACGCCGTAAACGATCAATAATGGGTGTCGGGTTGCAAAGCAATCCGGTGCCGCAGCAAACGCA<br>GTAAGTATTCCCCCTCGGGAGTACGTTCGCAAGAATGAAACTCAAAGGAAGGGACGGGGATCCGCACAAGCGGCGG<br>AGCATGTGGTTTAATTAGAAGCAACGCGAAGAACCTTACCAAGTCTTGACATCTGCCTGACCGTTCCTTAACCGGA<br>ACTATCTTTCGGGACAGGCAAGACAGGTGGTGCATGGTTGTCGTCAGCTCGTGTCGTGAGATGTTGGGTTAAGTCC<br>CGCAACGAGCGCAACCCCTGTCCTTAGTAGCCAGCAGTCCGGCTGGGCACTCTAGGGAGACTGCCGGGGGTAACCC<br>GGAGGAAGGCGGGGAGGAGGTCAAATCATCATGCCCCCCTGATTTGGGCTACACACGTGGTACAATGGCGTAAAC<br>AAAGGGAAGCGGAGTGGTGACGCTGAGCAAATCTCAAAAATAACGTCCCACTTCGGACTGCAGTCTGCAACTCGAC<br>TGCACGAAGCTGGAATCGCTAGTAATCGCGAATCAGAATG |
| GQ493039.1.1311<br>GATGAACGCTGGCGGCGTGCCTAACACATGCAAGTCGAGCGATTTACTTCGGTAAAGAGCGGCGGACGGGTGAGTA<br>ACGCGTGGGTAACCTGCCCTGTACACACGGATAACATACCGAAAGGTATGCTAATACGAGATAATATGCTTTTATC<br>GCATGGTAGAAGTATCAAAGCTTTTGCGGTACAGGATGGACCCGCGTCTGATTAGCTAGTTGGTAAGGTAACGGCT<br>TACCAAGGCAACGATCAGTAGCCGACCTGAGAGGGTGATCGGCCACATTGGAACTGAGACACGGTCCAAACTCCTA<br>CGGGAGGCAGCAGTGGGGAATATTGCACAATGGGCGAAAGCCTGATGCAGCAACGCCGCGTGAGCGATGAAGGCCT<br>TCGGGTCGTAAAGCTCTGTCCTCAAGGAAGATAATGACGGTACTTGAGGAGGAAGCCCCGGCTAACTACGTGCCAG<br>CAGCCGCGGTAATACGTAGGGGGCTAGCGTTATCCGGAATTACTGGGCGTAAAGGGTGCGTAGGTGGTTTCTTAAG<br>TCAGAGGTGAAAGGCTACGGCTCAACCGTAGTAAGCCTTTGAAACTGGGAAACTTGAGTGCAGGAGAGGAGAGTGG<br>AATTCCTAGTGTAGCGGTGAAATGCGTAGATATTAGGAGGAACACCAGTTGCGAAGGCGGCTCTCTGGACTGTAAC<br>TGACACTGAGGCACGAAAGCGTGGGGAGCAAACAAGATTAGNTNCCCTGGTAGTCCNCGCCGTNNCCGCCCATAAAG<br>AGCTGTCGGAGGTTACCCCCTTCGGTGGCGCAGGTAACGCAATAAAGAATTCCGCCTGGGAAGGAACGCTTCGCAA<br>GAGTGAAATTAAAAGGAATAGACGGGGACCCGCTCAAGTAGTGGAGCATGTGGTTTAATTCGAAGCAACGCGAAGA<br>ACTTTCTCTAAGCTTGACATCCTTTTGACCGATGCCTAATAGCATCAATCCCTTCTGGGACAGAAGTGACAGGTGG<br>TGCATGGTTGTTGTCAGCTCGTGTCGTGAGATGTTGGGTTAAGTCCCGCAACGAGCGCAACCCTTGCCTTTAGTTG<br>CCAGCATTAAGTTGGGCACTCTATAGGGACTGCCAGGGATAACCTGGAGGAAGGTGGGGATGACGTCAAATCATCA<br>TGCCCCTTATGCTTAGGGCTACACACGTGCTACAATGGGTGGTACAGAGGGCAGCCAAGTCGTGAGGCGGAGCTAA<br>TCCCTTAAAGCCATTCTCAGTTCGGATTGTAGGCTGAAACTCGCCTACATGAAGCTGGAGTTACTAGTAATCGCAG<br>ATCAGAATGATGCGGTGAA |
| JN387556.1.1324<br>CGTAAGTAACCTGCCCTGTACACACGGATAACATACCGAAAGGTATGCTAATACGGGATAATATATTTTGATCGCA<br>TGGTCGAGATATCAAAGCTCCGGCGGTACACCAGGGACCCCCGACAGAGGAGCTAGTTGGTAGTAATGTCACCAAG<br>GCGACGATCAGAAGCCGAACTGAGAGGGGGATCCGCACATGACTGAGACACGGTCAAACTCCTACGGGAGGCAGCA<br>GTGGGGAATATGCCAATGGGCGAAAGCTGATGCAGCACGCGCGTGAGCGATGAGGCTCGGGTCGTAAAGCTCGTCT<br>CAAGGAAGATAATGACGGTACTTGAGGAGGAAGCCCCGGCTAACTACGTGCCAGCAGCCGCGGTAATACGTAGGGG<br>GCTAGCGTTATCCGGAATTACTGGGCGTAAAGGGTGCGTAGGCGGTCTTTCAAGTCAGGAGTGAAAGGCTACGGCT<br>CAACCGTAGTAAGCTCTTGAAACTGTAAGACTTGAGTGCAGGAGAGGAGAGTGGAATTCCTAGTGTAGCGGTGAAA<br>TGCGTAGATATTAGGAGGAACACCAGTTGCGAAGGCGGCTCTCTGGACTGTAACTGACGCTGAGGCACGAAAGCGT<br>GGGGAGCAAACAGGATTAGATACCCTGGTAGTCCACGCCGTAAACGATGAGTACTAGCTGTCGGAGGTTACCCCCT<br>TCGGTGGCGCAGCTAACGCATTAAGTACTCCGCCTGGGAAGTACGCTCGCAAGAGTGAAACTCAAAGGAATTGACG<br>GGGACCCGCACAAGTAGCGGAGCATGTGGTTTAATTCGAAGCAACGCGAAGAACCTTACCTAAGCTTGACATCCCA<br>CTGACCCTTCCCTAATCGGAAGCTTCCCTTCGGGACAGTGGTGACAGGTGGTGCATGGTTGTCGTCAGCTCGTGTC<br>GTGAGATGTTGGGTTAAGTCCCGCAACGAGCGCAACCCTTGCCTTTAGTTGCCAGCATTAAGTTGGGCACTCTAGA<br>GGGACTGCCAGGGATAACCCGGAGGAGTGGGGATGACGTCAAATCATCATGCCCTTATGCTAGGCTACACACGTGC<br>TACAATGGGTGGTCAGAGGCCAGCCAGTCGTGAGGCCGAGCTATCCCATAAGCCATTCTCGTCCGGATTGTAGGCT<br>GAACTCGCCTACATGAGCTGGAATTACAAGTATGCGATCGATGCTGCGTGATGCGTCCGGGTCTTGTACACACCGC<br>CCGTCACACCATGGGAGTTGGGGGCGCCCGAAGCCGGATTGCTAACCTTTTGGAAGCGTCCGTCGAAGGTGAAACC<br>AATAACTGGGGTGAAGTCGTAACAAGGTAACC |
| EU775983.1.1288<br>GAAAGCGGCGGACGGGTGAGTAACGCGTAGGCAACCTGCCCCATACAGAGGGATAGCATCTGGAAACGGATATTAA<br>TACCTCATAATACTTAGAGATCACATGGTAACTAAGTCAAAGATTTATCGGTATGGGATGGGCCTGCGTCTGATTA<br>GCTAGTTGGTGGGGTAACGGCTCACCAAGGCGACGATCAGTAGCCGACCTGAGAGGGTGATCGGCCACATTGGAAC<br>TGAGACACGGTCCAAACTCCTACGGGAGGCAGCAGTGGGGAATATTGCACAATGGGCGCAAGCCTGATGCAGCAAC<br>GCCGCGTGAGCGATGAAGGCCTTCGGGTCGTAAAGCTCTGTCCTCAAGGAAGATAATGACGGTACTTGAGGAGGAA<br>GCCCCGGCTAACTACGTGCCAGCAGCCGCGGTAATACGTAGGGGGCTAGCGTTATCCGGATTTACTGGGCGTAAAG<br>GGTGCGTAGGCGGTCTTTCAAGTCAGGAGTTAAAGGCTACGGCTCAACCGTAGTAAGCTCCTGATACTGTCTGACT<br>TGAGTGCAGGAGAGGAAAGCGGAATTCCCAGTGTAGCGGTGAAATGCGTAGATATTGGGAGGAACACCAGTAGCGA<br>AGGCGGCTTTCTGGACTGTAACTGACGCTGAGGCACGAAAGCGTGGGGAGCAAACAGGATTAGATACCCTGGTAGT<br>CCACGCTGTAAACGATGAGTACTAGGTGTCGGAGGTTACCCCCTTCGGTGCCGCAGCTAACGCATTAAGTACTCCG<br>CCTGGGGAGTACGCACGCAAGTGTGAAACTCAAAGGAATTGACGGGGACCCGCACAAGTAGCGGAGCATGTGGTTT<br>AATTCGAAGCAACGCGAAGAACCTTACCTAGGCTTGACATCCTTCTGACCGAGGACTAATCTCCTCTTTCCCTCCG<br>GGGACAGAAGTGACAGGTGGTGCATGGTTGTCGTCAGCTCGTGTCGTGAGATGTTGGGTTAAGTCCCGCAACGAGC<br>GCAACCCTTGTCTTTAGTTGCCATCATTAAGTTGGGCACTCTAGAGAGACTGCCAGGGATAACCTGGAGGAAGGTG<br>GGGATGACGTCAAATCATCATGCCCCTTATGCCTAGGGCTACACACGTGCTACAATGGGTGGTACAGAGGGCAGCC<br>AAGCCGTGAGGTGGAGCAAATCCCTTAAAGCCATTCTCAGTTCGGATTGTAGGCTGAAACTCGCCTACATGAAGCT<br>GGAGTTACTAGTAATCGCAGATCAGAATGCTGCGGTGAATGCGTTCCCGGGTCTTGCACACACCGCCCGTCA |

TABLE 11-continued 16S rRNA Sequences of OTUs in Tables 2-5
OTUs in Table 2

OTUs in Table 5

GQ449137.1.1391
CTGGCTCAGGATGAACGCTAGCGACAGGCTTAACACATGCAAGTCGAGGGGCATCACGGGAGGTAGCAATACCTTC
TGGTGGCGACCGGCGCACGGGTGAGTAACACGTATGCAACCTGCCCTGTACAGAGGGACAAGCGGTGGAAACGCCG
TCTAATCCCGCATGCACTCTTCCGGGGGCATCCCCGGGAGAGTAAAGGAGAGATCCGGTACAGGATGGACATGCGG
CGCATTAGTTAGTTGGCGGGGTAACGGCCCACCAAGACGACGATGCGTAGGGGTTCTGAGAGGAAGGTCCCCCACA
TTGGAACTGAGACACGGTCCAAACTCCTACGGGAGGCAGCAGTGAGGAATATTGGTCAATGGGCGGAAGCCTGAAC
CAGCCAAGTCGCGTGAGGGAAGACGGCCCTACGGGTTGTAAACCTCTTTTGTCGGGGAGCAATGCCGCCTTTGCGA
AGGCGGAGGGAGAGTACCCGAAGAAAAAGCACCGGCTAACTACGTGCCAGCAGCCGCGGTAATACGTAGGGTGCAA
GCGTTAATCGGAATTACTGGGCGTAAAGCGTGCGCAGGCGGTTCTGTAAGACAGATGTGAAATCCCCGGGCTCAAC
CTGGGAATTGCATTTGTGACTGCAGGACTAGAGTTCATCAGAGGGGGGTGGAATTCCAAGTGTAGCAGTGAAATGC
GTAGATATTTGGAAGAACACCAATGGCGAAGGCAGCCCCCTGGGATGCGACTGACGCTCATGCACGAAAGCGTGGG
GAGCAAACAGGATTAGATACCCTGGTAGTCCACGCCCTAAACGATGTCTACTGGTTGTTGGGGATTAATATCCTTG
GTAACGAAGCTAACGCGTGAAGTAGACCGCCTGGGGAGTACGGTCGCAAGATTAAAACTCAAAGGAATTGACGGGG
ACCCGCACAAGCGGTGGATGATGTGGATTAATTCGATGATACGCGAGGAACCTTACCCGGGCTCAAACGGCACAGT
GATACTTTTGAAAGGAGGTAGCTCTACGGAGACTGTGCCGAGGTGCTGCATGGTTGTCGTCAGCTCGTGCCGTGAG
GTGTCGGCTTAAGTGCCATAACGAGCGCAACCCCTATTGTCAGTTGCCAGCAGGTAAAGCTGGGGACTCTGACGAG
ACTGCCGGCGCAAGCTGAGAGGAAGGCGGGGATGACGTCAAATCAGCACGGCCCTTACGTCCGGGGCGACACACGT
GTTACAATGGCAGGCACAGCGGGAAGCCACCCGGCGACGGGGAGCGGAACCCGAAAGCCTGTCTCAGTTCGGATCG
GAGTCTGCAACTCGACTCCGTGAAGCTGGATTCGCTAGTAATCGCGCATCAGCCATGGCGCGGTGAATACGTTCCC
GGGCCTTGTACACACCGCCCGTA

HK555938.1.1357
ACGGCACCCCTCTCCGGAGGGAAGCGAGTGGCGAACGGCTGAGTAACACGTGGAGAACCTGCCCCCTCCCCCGGGA
TAGCCGCCCGAAAGGACGGGTAATACCGGATACCCCCGGGCGCCGCATGGCGCCCGGGCTAAAGCCCCGACGGGAG
GGGATGGCTCCGCGGCCCATCAGGTAGACGGCGGGGTGACGGCCCACCGTGCCGACAACGGGTAGCCGGGTTGAGA
GACCGACCGGCCAGATTGGGACTGAGACACGGCCCAGACTCCTACGGGAGGCAGCAGTGGGGAATCTTGCGCAATG
GGGGGAACCCTGACGCAGCGACGCCGCGTGCGGGACGGAGGCCTTCGGGTCGTAAACCGCTTTCAGCAGGGAAGAG
TCAAGACTGTACCTGCAGAAGAAGCCCCGGCTAACTACGTGCCAGCAGCCGCGGTAATACGTAGGGGGCGAGCGTT
ATCCGGATTCATTGGGCGTAAAGCGCGCGTAGGCGGCCCGGCAGGCCGGGGGTCGAAGCGGGGGGCTCAACCCCCC
GAAGCCCCCGGAACCTCCGCGGCTTGGGTCCGGTAGGGGAGGGTGGAACACCCGGTGTAGCGGTGGAATGCGCAGA
TATCGGGTGGAACACCGGTGGCGAAGGCGGCCCTCTGGGCCGAGACCGACGCTGAGGCGCGAAAGCTGGGGGAGCG
AACAGGATTAGATACCCTGGTAGTCCCAGCCGTAAACGATGGACGCTGGGTGTGGGGGGACGATCCCCCCGTGCCG
CAGCCNACGCATTAAGCGTCCCGCCTGGGGAGTACGGCCGCAAGGCTAAAACTCAAAGGAATTGACGGGGGCCCGC
ACAAGCAGCGGAGCATGTGGCTTAATTCGAAGCAACGCGAAGAACCTTACGGCGCATCCCCCCGAGGCCCACGGGG
GGTCCGCCGCGTGGGTCAGAGGAGCGCATACGGGAGGTGCATGGTTGTCGTCAGCTCGTGTCGTGAGATGTTGGGT
TAAGTCCCGCAACGAGCGCAACCCCCGCCGCGTGTTGCCATCGGGTGATGCCGGGAACCCACGCGGGACCGCCGCC
GTCAAGGCGGAGGAGGGCGGGGACGACGTCAAGTCATCATGCCCCTTATGCCCTGGGCTGCACACGTGCTACAATG
GCCGGTACAGAGGGATGCCACCCCGCGAGGGGGAGCGGATCCCGGAAAGCCGGCCCCAGTTCGGATTGGGGGCTGC
AACCCGCCCCCATGAAGTCGGAGTTGCTAGTAATCGCGGATCAGCATGCCGCGGTGAATGCGTTCCCGGGCCTTGT
ACACACCGCCCGTCACACCACCCGAGTCGTCTGCACCCGAAGTCGCCGGCCCAACCGCAAGGGGG

GQ358246.1.1466
AGAGTTGATCTGGCTCAGATTGAACGCTGGCGGCAGGCTTAATACATGCAAGTCGAACGGTAACAGCAAAAAAGCT
TGCTTTTTTGGCTGACGAGTGGCGGACGGGTGAGTAATACCTAGGAAGCTGCCTAAACGAGGGGGATAACACCTGG
AAACGGGTGCTAATACCGCATGATACCGCAAGGTCAAAGGTTGGTTTACCAATCGCGTTTAGATGCGCCTAGGAGG
GATTAGCTAGTTGGTGGGGTAACGGCTCACCAAGGCGATGATCAGTAGCCGGTCTGAGAGGATGAACGGCCACATT
GGGACTGAGACACGGCCCAGACTCCTACGGGAGGCAGCAGTGGGGAATCTTCCGCAATGGGCGAAAGCCTGACGGA
GCAATGCCGCGTGAGTGATGAAGGGATTCGTCCCGTAAAGCTCTGTTGTATATGACGAATGTGCAGATTGTGAATA
ATGATTTGTAATGACGGTAGTATACGAGGAAGCCACGGCTAACTACGTGCCAGCAGCCGCGGTAATACGTAGGTGG
CGAGCGTTGTCCGGAATTATTGGGCGTAAAGAGCATGTAGGCGGTTTTTTAAGTCTGGAGTGAAAATGCGGGGCTC
AACCCCGTATGGCTCTGGATACTGGAAGACTTGAGTGCAGGAGAGGAAAGGGGAATTCCCAGTGTAGCGGTGAAAT
GCGTAGATATTGGGAGGAACACCAGTGGCGAAGGCGCCTTTCTGGACTGTGTCTGACGCTGAGATGCGAAAGCCAG
GGTAGCGAACGGGATTAGATACCCCGGTAGTCCTGGCCGTAAACGATGGGTACTAGGTGTGGGAGGTATCGACCCC
TTCCGTGCCGGAGTTAACGCAATAAGTACCCCGCCTGGGGAGTACGTCCGCAAGGATGAAACTCAAAGGAATTGAC
GGGGGCCCGCACAAGCGGTGGAGTATGTGGTTTAATTCGACGCAACGCGAAGAACCTTACCAAGGCTTGACATTGA
TTGAAAGACCTAGAGATAGGTCCCTCTCTTCGGAGACAAGAAAACAGGTGGTGCATGGCTGTCGTCAGCTCGTGTC
GTGAGATGTTGGGTTAAGTCCCGCAACGAGCGCAACCCCTATCCTATGTTACCAGCGGGTAATGCCGGGGACTCAT
AGGAGACTGCCAAGGACAACTTGGAGGAAGGCGGGGATGACGTCAAGTCATCATGCCCCTTATGTCTTGGGCTACA
CACGTACTACAATGGTCGGCAACAGAGGGAAGCAAAGCCGCGAGGCAGAGCAAACCCCAGAAACCCGATCTCAGTT
CGGATTGCAGGCTGCAACTCGCCTGCATGAAGTCGGAATCGCTAGTAATCGCAGGTCAGCATACTGCGGTGATTAC
TATCCCGGGCGTTGTACTCACCGCCCGTCAGGCGGAGTTCGTACTTCAAATGTGCCACACTGGG

New.ReferenceOTU82
TACGTAGGTGGCAAGCGTTGTCCGGATTTACTGGGCGTAAAGGGAGCGTAGGCGGATTTTTAAGTGGGATGTGAAA
TACCCGGGCTCAACCTGGGTGCTGCATTCCAAACTGGAAATCTAGAGTGCAGGAGGGGAAAGTGGAATTCCTAGTG
TAGCGGTGAAATGCGTAGAGATTAGGAAGAACACCAGTGGCGAAGGCGACTTTCTGGACTGTAACTGACGCTGAGG
CTCGAAAGCGTGGGGAGCAAACAGG New.ReferenceOTU52
TACGTAGGTGGCGAGCGTTATCCGGATTTACTGGGCGTAAAGGGAGCGTAGGCGGATGATTAAGTGGGATGTGAAA
TACCCGGGCTCAACTTGGGTGCTGCATTCCAAACTGGTTATCTAGAGTGCAGGAGAGGAGAGTGGAATTCCTAGTG
TAGCGGTGAAATGCGTAGAGATTAGGAAGAACACCAGTGGCGAAGGCGACTCTCTGGACTGTAACTGACGCTGAGG
CTCGAAAGCGTGGGGAGCAAACAGG TABLE 11-continued 16S rRNA Sequences of OTUs in Tables 2-5
OTUs in Table 2

GQ138615.1.1402
AGAGTTTGATCCTGGCTCAGGATGAACGCTAGCGATAGGCCTAACACATGCAAGTCGAGGGGCAGCACATGAGTAG
CAATACGATGGTGGCGACCGGCGCACGGGTGAGTAACACGTATGCAACCTACCTTTAACAGGGGAATAACCCGTTG
AAAAACGGACTAATACTCCATAACACAGGGGTCCCGCATGGGAATATTTGTTAAAGATTTATCGGTTGAAGATGGG
CATGCGTTCCATTAGCTAGTTGGTAGGGTAAAGGCCTACCAAGGCGACGATGCGTAGCCGACCTGAGAGGGTGAAC
GGCCACACTGGGACTGAGACACGGCCCACACTCCTACGGGAGGCAGCAGTAGGGAATCTTCGGCAATGGGCGAAAG
CCTGACCGAGCAACGCCGCGTGAATGATGAAGGCCTTCGGGTTGTAAAATTCTGTTATAAGGGAAGAACGACTTTA
GTAGGAAATGGCTAGAGTGTGACGGTACCTTATGAGAAAGCCACGGCTAACTACGTGCCAGCAGCCGCGGTAATAC
GTAGGTGGCGAGCGTTATCCGGAATTATTGGGCGTAAAGAGCGCGCAGGTGGTTGATTAAGTCTGATGTGAAAGCC
CACGGCTTAACCGTGGAGGGTCATTGGAAACTGGTCGACTTGAGTGCAGAAGAGGGAAGTGGAATTCCATGTGTAG
CGGTGAAATGCGTAGAGATATGGAGGAACACCAGTGGCGAAGGCGGCTTCCTGGTCTGTAACTGACACTGAGGCGC
GAAAGCGTGGGGAGCAAACAGGATTAGATACCCTGGTAGTCCACGCCGTAAACGATGAGTGCTAAGTGTTGGGGGT
CGAACCTCAGTGCTGAAGTTAACGCATTAAGCACTCCGCCTGGGGAGTACGGTCGCAAGACTGAAACTCAAAGGAA
TTGACGGGGACCCGCACAAGCGGTGGAGCATGTGGTTTAATTCGAAGCAACGCGAAGAACCTTACCAGGTCTTGAC
ATACCATTGACCGTTCTAGAGATAGGATTTTCCCTTCGGGGACAATGGATACAGGTGGTGCATGGTTGTCGTCAGC
TCGTGTCGTGAGATGTTGGGTTAGGTCCCGCAACGAGCGCAACCCCTGTCGTTAGTTGCCAGCATTCAGTTGGGGA
CTCTAACGAGACTGCCAGTGACAAACTGGAGGAAGGTGGGGATGACGTCAAATCATCATGCCCCTTATGACCTGGG
CTACACACGTGCTACAATGGTTGGTACAAAGAGAAGCGAAGCGGTGACGTGGAGCAAACCTCATAAAGCCAATCTC
AGTTCGGATTGTAGGCTGCAACTCGCCTACATGAAGTTGGAATCGCTAGTAATCGCGAATCAGAATGTCGCGGTGA
ATACGTTCCCGGGTCTTGTACACACCGCCCGTCA

JN681884.1.1409
TGCAAGTAGAACGCTGAAGACTGGTGCTTGCACCGGTTGGAAGAGTTGCGAACGGGTGAGTAACGCGTAGGTAACC
TGCCTGATAGCGGGGGATAACTATTGGAAACGATAGCTAATACCGCATAACAGGGAATAACACATGTTATTTTTTT
GAAAGGGGCAATTGCTCCACTATCAGATGGACCTGCGTTGTATTAGCTAGTAGGTGAGGTAACGGCTCACCTAGGC
GACGATACATAGCCGACCTGAGAGGGTGATCGGCCACACTGGGACTGAGACACGGCCCAGACTCCTACGGGAGGCA
GCAGTAGGGAATCTTCGGCAATGGGGGCAACCCTGACCGAGCAACGCCGCGTGAGTGAAGAAGGTTTTCGGATCGT
AAAGCTCTGTTGTAAGAGAAGAACGTTGAGTAGAGTGGAAAGTTACTCAAGTGACGGTATCTTACCAGAAAGGGAC
GGCTAACTACGTGCCAGCAGCCGCGGTAATACGTAGGTCCCGAGCGTTGTCCGGATTTATTGGGCGTAAAGCGAGC
GCAGGCGGTTTAATAAGTCTGAAGTTAAAGGCAGTGGCTCAACCATTGTTCGCTTTGGAAACTGTTAAACTTGAGT
GCAGAAGGGGAGAGTGGAATTCCATGTGTAGCGGTGAAATGCGTAGATATATGGAGGAACACCGGTGGCGAAAGCG
GCTCTCTGGTCTGTAACTGACGCTGAGGCTCGAAAGCGTGGGTAGCGAACAGGATTAGATACCCTGGTAGTCCACG
CCGTAAACGATGAGTGCTAGGTGTTGGGTCCTTTCCGGGACTCAGTGCCGACGCTAACGCATTAAGCACTCCGCCT
GGGGAGTACGACCGCAAGGTTGAAACTCAAAGGAATTGACGGGGGCCCGCACAAGCGGTGGAGCATGTGGTTTAAT
TCGAAGCAACGCGAAGAACCTTACCAGGTCTTGACATCCCGATGCTATCCCTAGAGATAGGGAGTTACTTCGGTAC
ATCGGTGACAGGTGGTGCATGGTTGTCGTCAGCTCGTGTCGTGAGATGTTGGGTTAAGTCCCGCAACGAGCGCAAC
CCCTATTGTTAGTTGCCATCATTCAGTTGGGCACTCTAGCGAGACTGCCGGTAATAAACCGGAGGAAGGTGGGGAT
GACGTCAAATCATCATGCCCCTTATGACCTGGGCTACACACGTGCTACAATGGTTGGTACAACGAGTTGCGAGTCG
GTGACGGCAAGCTAATCTCTTAAAGCCAATCTCAGTTCGGATTGTAGGCTGCAACTCGCCTACATGAAGTCGGAAT
CGCTAGTAATCGCGGATCAGCACGCCGCGGTGAATACGTTCCCGGGCCTTGTACACACCGCCCGTCACACCACGAG
AGTTTGTAACACCCAAAGTCGGTGAGGTAACCTTCGGAGCC

GU303759.1.1517
AGAGTTTGATCATGGCTCAGGACGAACGCCGGCGGCGTGCCTAATACATGCAAGTAGAACGCTGAAGACTTTAGCT
TGCTAAAGTTGGAAGAGTTGCGAACGGGTGAGTAACGCGTAGGTAACCTGCCTACTAGCGGGGGATAACTATTGGA
AACGATAGCTAATACCGTATAACAGCATTTAACACATGTTAGATGCTTGAAAGGAGCAATTGCTTCACTAGTAGAT
GGACCTGCGTTGTATTAGCTAGTTGGTGAGGTAACGGCTCACCAAGGCGACGATACATAGCCGACCTGAGAGGGTG
ATCGGCCACACTGGGACTGAGACACGGCCCAGACTCCTACGGGAGGCAGCAGTAGGGAATCTTCGGCAATGGGGGC
AACCCTGACCGAGCAACGCCGCGTGAGTGAAGAAGGTTTTCGGATCGTAAAGCTCTGTTGTAAGAGAAGAACGTGT
GTGAGAGTGGAAAGTTCACACAGTGACGGTAACTTACCAGAAAGGGACGGCTAACTACGTGCCAGCAGCCGCGGTA
ATACGTAGGTCCCGAGCGTTGTCCGGATTTATTGGGCGTAAAGCGAGCGCAGGCGGTTTAATAAGTCTGAAGTTAA
AGGCAGTGGCTTAACCATTGTTCGCTTTGGAAACTGTTAGACTTGAGTGCAGAAGGGGAGAGTGGAATTCCATGTG
TAGCGGTGAAATGCGTAGATATATGGARGGAAACACCGGTGGCGAAAGCGGCTCTCTGGTCTGTAACTGACGCTGA
GGCTCGAGAAGCGTGGGGAGCAAACAGGATTAGATACCCTGGTAGTCCACGCCGTAAGCGATGAGTGCTAGGTGTT
AGGCCCTTTCCGGGGCTTAGTGCCGCAGCTAACGCATTAAGCACTCCGCCTGGGGAGTACGACCGCAAGGTTGAAA
CTCAAAGGAATTGACGGGGGCCCGCACAAGCGGTGGAGCATGTGGTTTAATTCGAAGCAACGCGAAGAACCTTACC
AGGTCTTGACATCCCGATGCTATTCCTAGAGATAGGAAGTTTCTTCGGAACATCGGTGACAGGTGGTGCATGGTTG
TCGTCAGCTCGTGTCGTGAGATGTTGGGTTAAGTCCCGCAACGAGCGCAACCCCTATTGTTAGTTGCCATCATTAA
GTTGGGCACTCTAGCGAGACTGCCGGTAATAAACCGGAGGAAGGTGGGGATGACGTCAAATCATCATGCCCCTTAT
GACCTGGGCTACACACGTGCTACAATGGCGGTCAACAGAGGGAAGCAATACTGTGAAGTGGAGCAAACCCCTAAAA
GCCGTCCCAGTTCGGATTGCAGGCTGCAACCCGCCTGTATGAAGTTGGAATCGCTAGTAATCGCGGATCAGCATGC
CGCGGTGAATACGTTCCCGGGCCTTGTACACACCGCCCGTCACACCATGAGAGTCGGGAACACCCGAAGTCCGTAG
CCTAACTTTCACGAGGGGGCGCGGCCGAAGGTGGGTTCGATAATTGGGGTGAAGTCGTAACAAGGTAACCGTA

New.ReferenceOTU114
TACGTAGGTCCCGAGCGTTGTCCGGATTTATTGGGCGTAAAGCGAGCGCAGGCGGTTTAATAAGTCTGAAGTTAAA
GGCAGTGGCTTAACCATTTTTCGCTTTGGAAACTGTTAGACTTGAGTGCAGAAGGGGAGAGTGGAATTCCATGTGT
AGCGGTGAAATGCGTAGATATATGGAGGAACACCGGTGGCGAAAGCGGCTCTCTGGTCTGTAACTGACGCTGAGGC
TCGAAAGCGTGGGGAGCAAACAGG EU774881.1.1422
AGAGTTTGATCCTGGCTCAGGACGAACGCTGGCGGCGTGCCTAATACATGCAAGTCGAGCGAGCGGAACTAACAGA
TTTACTTCGGTAATGACGTTAGGAAAGCGAGCGGCGGATGGGTGAGTAACACGTGGGGAACCTGCCCCATAGTCTG
GGATACCACTTGGAAACAGGTGCTAATACCGGATAAGAAAGCAGATCGCATGATCAGCTTTTAAAAGGCGGCGTAA
GCTGTCGCTATGGGATGGCCCCGCGGTGCATTAGCTAGTTGGTAAGGTAAAGGCTTACCAAGGCAATGATGCATAG
CCGAGTTGAGAGACTGATCGGCCACATTGGGACTGAGACACGGCCCAAACTCCTACGGGAGGCAGCAGTAGGGAAT TABLE 11-continued 16S rRNA Sequences of OTUs in Tables 2-5
OTUs in Table 2

CTTCCACAATGGACGCAAGTCTGATGGAGCAACGCCGCGTGAGTGAAGAAGGTTTTCGGATCGTAAAGCTCTGTTG
TTGGTGAAGAAGGATAGAGGTAGTAACTGGCCTTTATTTGACGGTAATCAACCAGAAAGTCACGGCTAACTACGTG
CCAGCAGCCGCGGTAATACGTAGGTGGCAAGCGTTGTCCGGATTTATTGGGCGTAAAGCGAGCGCAGGCGGTTTAA
TAAGTCTGAAGTTAAAGGCAGTGGCTTAACCATTGTTCGCTTTGGAAACTGTTAGACTTGAGTGCAGAAGGGGAGA
GTGGAATTCCATGTGTAGCGGTGAAATGCGTAGATATATGGAGGAACACCGGTGGCGAAAGCGGCTCTCTGGTCTG
TAACTGACGCTGAGGCTCGAAAGCGTGGGGAGCAAACAGGATTAGATACCCTGGTAGTCCACGCCGTAAACGATGA
GTGCTAGGTGTTAGGCCCTTTCCGGGGCTTAGTGCCGCAGCTAACGCATTAAGCACTCCGCCTGGGGAGTACGACC
GCAAGGTTGAAACTCAAAGGAATTGACGGGGGCCCGCACAAGCGGTGGAGCATGTGGTTTAATTCGAAGCAACGCG
AAGAACCTTACCAGGTCTTGACATCCCGATGCTATTCCTAGAGATAGGAAGTTTCTTCGGAACATCGGTGACAGGT
GGTGCATGGTTGTCGTCAGCTCGTGTCGTGAGATGTTGGGTTAAGTCCCGCAACGAGCGCAACCCCTATTGTTAGT
TGCCATCATTAAGTTGGGCACTCTAGCGAGACTGCCGGTAATAAACCGGAGGAAGGTGGGGATGACGTCAAGTCAT
CATGCCCCTTATGACCTGGGCTACACACGTGCTACAATGGGCAGTACAACGAGAAGCGAGCCTGCGAAGGCAAGCG
AATCTCTGAAAGCTGTTCTCAGTTCGGACTGCAGTCTGCAACTCGACTGCACGAAGCTGGAATCGCTAGTAATCGC
GGATCAGCACGCCGCGGTGAATACGTTCCCGGGCCTTGCACACACCGCCCGTCA

AB469559.1.1551
AGAGTTTGATCCTGGCTCAGGACGAACGCTGGCGGCGTGCCTAATACATGCAAGTGGAACGCACAGTTAGTATGTA
GTTTACTACAACATTACTTGTGAGTCGCGAACGGGTGAGTAACGCGTAGGTAACCTGCCTTGTAGCGGGGGATAAC
TATTGGAAACGATAGCTAATACCGCATAACAGTTGATAACTCATGTTATTAGCTTGAAAGATGCAACAGCATCACT
ACGAGATGGACCTGCGTTGTATTAGCTAGTTGGTGAGGTAAAGGCTCACCAAGGCCACGATACATAGCCGACCTGA
GAGGGTGATCGGCCACATTGGGACTGAGACACGGCCCAAACTCCTACGGGAGGCAGCAGTAGGGAATCTTCGGCAA
TGGGGGCAACCCTGACCGAGCAACGCCGCGTGAGTGAAGAAGGTTTTCGGATCGTAAAGCTCTGTTGTAAGAGAAG
AACGTTGATGAGAGTGGAAAATTCATCAAGTGACGGTATCTTACCAGAAAGGGACGGCTAACTACGTGCCAGCAGC
CGCGGTAATACGTAGGTCCCGAGCGTTGTCCGGATTTATTGGGCGTAAAGCGAGCGCAGGCGGTTTCGTAAGTCTG
AAGTTAAAGGCAGTGGCTCAACCATTGTTCGCTTTGGAAACTGCGAGACTTGAGTGCAGAAGGGGAGAGTGGAATT
CCATGTGTAGCGGTGAAATGCGTAGATATATGGAGGAACACCGGTGGCGAAAGCGGCTCTCTGGTCTGTAACTGAC
GCTGAGGCTCGAAAGCGTGGGGAGCAAACAGGATTAGATACCCTGGTAGTCCACGCCGTAAACGATGAGTGCTAGG
TGTTAGGCCCTTTCCGGGGCTTAGTGCCGCAGCTAACGCATTAAGCACTCCGCCTGGGGAGTACGACCGCAAGGTT
GAAACTCAAAGGAATTGACGGGGGCCCGCACAAGCGGTGGAGCATGTGGTTTAATTCGAAGCAACGCGAAGAACCT
TACCAGGTCTTGACATCCCGATGCCCGCTCTAGAGATAGAGTTTTACTTTTGTACATCGGTGACAGGTGGTGCATG
GTTGTCGTCAGCTCGTGTCGTGAGATGTTGGGTTAAGTCCCGCAACGAGCGCAACCCCTATTGTTAGTTGCCATCA
TTGAGTTGGGCACTCTAGCGAGACTGCCGGTAATAAACCGGAGGAAGGTGGGGATGACGTCAAATCATCATGCCCC
TTATGACCTGGGCTACACACGTGCTACAATGGCTGGTACAACGAGTCGCAAGCCGGTGACGGCAAGCTAATCTCTT
AAAGCCAGTCTCAGTTCGGATTGTAGGCTGCAACTCGCCTACATGAAGTCGGAATCGCTAGTAATCGCGGATCAGC
ACGCCGCGGTGAATACGTTCCCGGGCCTTGTACACACCGCCCGTCACACCACGAGAGTTTGTAACACCCGAAGTCG
GTGAGGTAACCTTTTAGGAGCCAGCCGCCTAAGGTGGGATAGATGATTGGGGTGAAGTCGTAACAAGGTAGCCGTA
TCGGAAGGTGCGGCTG

HK557089.3.1395
AGACTTTAGCTTGCTAAAGTTGGAAGAGTTGCGAACGGGTGAGTAACGCGTAGGTAACCTGCCTACTAGCGGGGGA
TAACTATTGGAAACGATAGCTAATACCGCATAACAGCATTTAACCCATGTTAGATGCTTGAAAGGAGCAATTGCTT
CACTAGTAGATGGACCTGCGTTGTATTAGCTAGTTGGTGAGGTAACGGCTCACCAAGGCGACGATACATAGCCGAC
CTGAGAGGGTGATCGGCCACACTGGGACTGAGACACGGCCCAGACTCCTACGGGAGGCAGCAGTAGGGAATCTTCG
GCAATGGGGGCAACCCTGACCGAGCAACGCCGCGTGAGTGAAGAAGGTTTTCGGATCGTAAAGCTCTGTTGTAAGA
GAAGAACGTGTGTGAGAGTGGAAAGTTCACACAGTGACGGTAACTTACCAGAAAGGGACGGCTAACTACGTGCCAG
CAGCCGCGGTAATACGTAGGTCCCGAGCGTTGTCCGGATTTATTGGGCGTAAAGCGAGCGCAGGCGGTTTAATAAG
TCTGAAGTTAAAGGCAGTGGCTTAACCATTGTTCGCTTTGGAAACTGTTAGACTTGAGTGCAGAAGGGGAGAGTGG
AATTCCATGTGTAGCGGTGAAATGCGTAGATATATGGAGGAACACCGGTGGCGAAAGCGGCTCTCTGGTCTGTAAC
TGACGCTGAGGCTCGAAAGCGTGGGGAGCAAACAGGATTAGATACCCTGGTAGTCCACGCCGTAAACGATGAGTGC
TAGGTGTTAGGCCCTTTCCGGGGCTTAGTGCCGCAGCTAACGCATTAAGCACTCCGCCTGGGGAGTACGACCGCAA
GGTTGAAACTCAAAGGAATTGACGGGGGCCCGCACAAGCGGTGGAGCATGTGGTTTAATTCGAAGCAACGCGAAGA
ACCTTACCAGGTCTTGACATCCCGATGCTATTCCTAGAGATAGGAAGTTTCTTCGGAACTGTGAGACTTGAGGGCA
GAAGGGTAGAGTGCACTTGTATGGGGAGCTGTGGAATGCGTTCCCGCAACGAGCGCAACCCCTATTGTTAGTTGCC
ATCATTAAGTTGGGCACTCTAGCGAGACTGCCGGTAATAAACCGGAGGAAGGTGGGGATGACGTCAAATCATCATG
CCCCTTATGACCTGGGCTACACACGTGCTACAATGGTTGGTACAACGAGTCGCGAGTCGGTGACGGCAAGCAAATC
TCTTAAAGCCAATCTCAGTTCGGATTGTAGGCTGCAACTCGCCTACATGAAGTCGGAATCGCTAGTAATCGCGGAT
CAGCACGCCGCGGTGAATACGTTCCCGGGCCTTGTACACACCGCCCGTCACACCACGAGAGTTTGTAACACCCGAA
GTCGGTGAGGTANCCTTTTAGGAGC

EU358719.1.1513
AGAGTTTGATCCTGGCTCAGGACGAACGCTGGCGGCGTGCCTAATACATGCAAGTAGAACGCTGAAGAAAGGAGCT
TGCTTCTTTTGGATGAGTTGCGAACGGGTGAGTAACGCGTAGGTAACCTGCCTTGTAGCGGGGGATAACTATTGGA
AACGATAGCTAATACCGCATAACAGCTTTTGACACATGTTAGAAGCTTGAAAGATGCAATTGCATCACTACGAGAT
GGACCTGCGTTGTATTAGCTAGTAGGTAGGGTAACGGCCTACCTAGGCGACGATACATAGCCGACCTGAGAGGGTG
ATCGGCCACACTGGGACTGAGACACGGCCCAGACTCCTACGGGAGGCAGCAGTAGGGAATCTTCGGCAATGGGGGC
AACCCTGACCGAGCAACGCCGCGTGAGTGAAGAAGGTTTTCGGATCGTAAAGCTCTGTTGTAAGAGAAGAACGTGT
GTGAGAGTGGAAAGTTCACACAGTGACGGTAACTTACCAGAAAGGGACGGCTAACTACGTGCCAGCAGCCGCGGTA
ATACGTAGGTCCCGAGCGTTGTCCGGATTTATTGGGCGTAAAGCGAGCGCAGGCGGTTTAATAAGTCTGAAGTTAA
AGGCAGTGGCTTAACCATTGTTCGCTTTGGAAACTGTTAAACTTGAGTGCAGAAGGGGAGAGTGGAATTCCATGTG
TAGCGGTGAAATGCGTAGATATATGGAGGAACACCGGTGGCGAAAGCGGCTCTCTGGTCTGTAACTGACGCTGAGG
CTCGAAAGCGTGGGGAGCAAACAGGATTAGATACCCTGGTAGTCCACGCCGTAAACGATGAGTGCTAGGTGTTAGG
CCCTTTCCGGGGCTTAGTGCCGCAGCTAACGCATTAAGCACTCCGCCTGGGGAGTACGACCGCAAGGTTGAAACTC
AAAGGAATTGACGGGGGCCCGCACAAGCGGTGGAGCATGTGGTTTAATTCGAAGCAACGCGAAGAACCTTACCAGG
TCTTGACATCCCAGTGACCGCTCTAGAGATAGAGTTTTTCTTCGGAACACTGGTGACAGGTGGTGCATGGTTGTCG
TCAGCTCGTGTCGTGAGATGTTGGGTTAAGTCCCGCAACGAGCGCAACCCTTATTGTTAGTTGCCATCATTCAGTT
GGGCACTCTAGCGAGACTGCCGGTAATAAACCGGAGGAAGGTGGGGATGACGTCAAATCATCATGCCCCTTATGAC
CTGGGCTACACACGTGCTACAATGGTTGGTACAACGAGTCGCAAGTCGGTGACGGCAAGCAAATCTCTTAAAGCCA

TABLE 11-continued 16S rRNA Sequences of OTUs in Tables 2-5
OTUs in Table 2

ATCTCAGTTCGGATTGTAGGCTGCAACTCGCCTACATGAAGCAGGAATTGCTAGTAATGGCAGGTCAGCATACTGC
CGTGAATACGTTCCCGGGCCTTGTACACACCGCCCGTCACACCATGAGAGTCTGTAACACCCGAAGTCGGTAGTCT
AACTACGGAGGACGCCGCCGAAGGTGGGACAGATAATTGGGGTGAAGTCGTAACAAGGTAGCCGTA

HQ748204.1.1442
CTAATACATGCGAGGAGAACGCTGAAGACTTTCTTTTGCTATAGTTGGGAGAGTTGCTAACGGGTGAGTAACGCGT
AGGTGACCTGCCTACTAGCGGGGGATAACTATTGCAAACGATAGCTAATACCGCATAACAGCCTTTAACCCATGTT
AGATGCTTGAAAGGAGCAATTGCTTCACTAGTAGATGGACCTGCGTTGTATTAGCTAGTTGGTGAGGTAACGGCTC
ACCAAGGCGACGATACATAGCCGACCTGAGAGGGTGATCGGCCACACTGGGACTGAGACACGGCCCATACTCCTAC
GGGAGGCACCAGTAGGGAATCTTCGGGAATGGGGGCAACCCTGACCGAGCAACGCCGCGTGAGTGAAGAAGGTTTT
CGGATCGTAAAGCTCTGTTGTAAGAGAAGAACGTGTGTGAGAGTGGAAAGTTCACACTGTGACGGTAACTTACCAG
AAAGGGACGGCTAACTACGTGCCAGCAGCCGCGGTAATACGTAGGTCCCGAGCGTTGTCCGGATTTATTGGGCGTA
AAGCGAGCGCAGGCGGTTTAATAAGTCTGAAGTTAAAGGCAGTGGCTTAACCATTGTTCGCTTTGGAAACTGTTAG
ACTTGAGTGCATAAGGGGAGAGTGGAATTCCATGTGTAGCGGTGAAATGCGTAGATATATGGAGGAACACCGGTGG
CGAAAGCGGCTCTCTGGTCTGTAACTGACGTTGAGGCTCGAAAGCGTGGGGAGCAAACAGGATTAGATACCCTGGT
AGTCCACGCTGTAAACGATGAGTGGTAGGTGTTAGGCCCTTTCTGGGGTTTAGTGCCGCAGATTACGCATTAAGCC
ATTCGCCTGGGGAGTACGACCGCAAGGTTGAAACTTAAAGGAATTGACGGGGGCCCGCACAAGCGGTGGAGCATGT
GGTTTAATTAGAAGCAACGCGAAGAACCTTACCAGGTCTTGACATCCCGATGCTATTCTTAGAGATAGGAAGTTTC
TTCGGAACATCGGTGACAGGTGGTGCATGGTTGTCGTCAGCTCGTGTCGAGAGATGTTGGGTTAAGTCCCTCAACG
AGCGCAACCCCTATTTTTATTTGCCATCATTAAGTTGGGCAATCTAGCGAGACTGCCGGTAATAAACCGGAGGAAG
GTGGGGATGACGTCAAATCATCATGCTCCTTATGTCATGGGGTACACACGTGGTACAATGGTTGGTACAACGAGTC
GCGAGTTGGTGAAGGCAAGCAAATCTCTTAAAGCCAATATCAGTTCGGATTGTAGGCTGCAAATAGCCTACATGTA
GTCGGAATTGTTAGTAATCGGGGATCAGCACTCCGCGGTGAATACGTTTCCGGGCCTTGTACACCCCGCCCGTCTA
CACCACGAGAGTTTGTAACACCCGAAGTCGGTGAGGTAACTCTTTTAGGAGCCAGCCGCCTAAGGTGGGATAGA

GQ338727.1.1397
CTACCTGCAGTCGACGAACACCTTATTTGATTTTCTTCGGAACTGAAGATTTGGTGATTGAGTGGCGGACGGGTGA
GTAACGCGTGGGTAACCTGCCCTGTACAGGGGGATAACAGTCAGAAATGACTGCTAATACCGCATAAGACCACAGC
ACCGCATGGTGCAGGGGTAAAAACTCCGGTGGTACAGGATGGACCCGCGTCTGATTAGCTGGTTGGTGAGGTAACG
GCTCACCAAGGCGACGATCAGTAGCCGGCTTGAGAAAGTGAACGGCCACATTGGGACTGAGACACGGCCCAAACTC
CTACGGGAGGCAGCAGTGGGGAATATTGCACAATGGGGGAAACCCTGATGCAGCGACGCCGCGTGAGTGAAGAAGT
ATCTCGGTATGTAAAGCTCTATCAGCAGGGAAGAAAATGACGGTACCTGACTAAGAAGCCCCGGCTAACTACGTGC
CAGCAGCCGCGGTAATACGTAGGGGGCAAGCGTTATCCGGAATTACTGGGTGTAAAGGGTGCGTAGGTGGTATGGC
AAGTCAGAAGTGAAAACCCAGGGCTTAACTCTGGGACTGCTTTTGAAACTGTCAGACTGGAGTGCAGGAGAGGTAA
GCGGAATTCCTAGTGTAGCGGTGAAATGCGTAGATATTAGGAGGAACATCAGTGGCGAAGGCGGCTTACTGGACTG
AAACTGACACTGAGGCACGAAAGCGTGGGGAGCAAACAGGATTAGATACCCTGGTAGTCCACGCCGTAAACGATGA
ATACTAGGTGTCGGGGCCGTAGAGGCTTCGGTGCCGCAGCCAACGCAGTAAGTATTCCACCTGGGGAGTACGTTCG
CAAGAATGAAACTCAAAGGAATTGACGGGGACCCGCACAAGTAGCGGAGCATGTGGTTTAATTCGAAGCAACGCGA
AGAACCTTACCTAAGCTTGACATCCTTTTGACCGATGCCTAATCGCATCTTTCCCTTCGGGGACAGAAGTGACAGG
TGGTGCATGGTTGTCGTCAGCTCGTGTCGTGAGATGTTGGGTTAAGTCCCGCAACGAGCGCAACCCTTGCCTTTAG
TTGCCATCATTAAGTTGGGCACTCTAGAGGGACTGCCAGGGATAACCTGGAGGAAGGTGGGGATGACGTCAAATCA
TCATGCCCCTTATGCTTAGGGCTACACACGTGCTACAATGGGTGGTACAGAGGGCAGCGAAGTCGTGAGGCCAAGC
TAATCCCTTAAAGCCATTCTCAGTTCGGATTGTAGGCTGAAACCCGCCTACATGAAGCTGGAGTTACTAGTAATCG
CAGATCAGAATGCTGCGGTGAATGCGTTCCCGGGTCTTGTACACACCGCCCGTCACACCATGGGAGTTGGGGGCGC
CCGAAGCCGGCTAGCTACTTTGGAAGCGT

HQ803964.1.1435
GGGGGGCTTAACACATGCAAGTCGAACGAAGCGCTTTCGCTTTAATCTTCGGAGGAAAGAGGAAGTGACTGAGTGG
CGGACGGGTGAGTAACGCGTGGGTAACCTGCCTCATACAGGGGGATAACAGTTAGAAATGGCTGCTAATACCGCAT
AAGCATACAGCACCGCATGGTGCAGTGTGAAAAACTCCGGTGGTATAAGATGGACCCGCGTCTGATTAGGTAGTTG
GTGGGGTAACGGCCTACCAAGCCGACGATCAGTAGCCGACCTGAGAGGGTGACCGGCCACATTGGGACTGAGACAC
GGCCCAAACTCCTACGGGAGGCAGCAGTGGGGAATATTGCACAATGGGGGAAACCCTGATGCAGCGACGCCGCGTG
AAGGAAGAAGTATTTCGGTATGTAAACTTCTATCAGCAGGGAAGAAAATGACGGTACCTGACTAAGAAGCCCCGGC
TAACTACGTGCCAGCAGCCGCGGTAATACGTAGGGGGCAAGCGTTATCCGGATTTACTGGGTGTAAAGGGAGCGTA
GACGGAAGTGCAAGTCTGAAGTGAAAGCCCGGGGCTCAACCCCGTGACTGCTTTGGAAACTGTGCTTCTAGAGTGT
CGGAGAGGTAAGCGGAATTCCTAGTGTAGCGGTGAAATGCGTAGATATTAGGAGGAACATCAGTGGCGAAGGCGGC
TTACTGGGCGATAACTGACGTTGAGGCTCGAAAGCGTGGGGAGCAAACAGGATTAGATACCCTGGTAGTCCACGCC
GTAAACGATGAATACTAGGTGTCGGGAAGCACAGCTTTTCGGTGCCGCCGCAAACGCATTAAGTATTCCACCTGGG
GAGTACGTTCGCAAGAATGAAACTCAAAGGAATTGACGGGGACCCGCACAAGCGGTGGAGCATGTGGTTTAATTCG
AAGCAACGCGAAGAACCTTACCAAGTCTTGACATCCCGGTGACCGGACAGTAATGTGTCCTTTTCTTCGGAACACC
GGTGACAGGTGGTGCATGGTTGTCGTCAGCTCGTGTCGTGAGATGTTGGGTTAAGTCCCGCAACGAGCGCAACCCT
TATCCCCAGTAGCCAGCGGTTCGGCCGGGCACTCTGAGGAGACTGCCAGGGATAACCTGGAGGAAGGTGGGGATGA
CGTCAAATCATCATGCCCCTTATGACTTGGGCTACACACGTGCTACAATGGCGTAAACAAAGGGAAGCGAGACCGT
GAGGTGGAGCAAATCCCAAAAATAACGTCTCAGTTCGGACTGTAGTCTGCAACCCGACTACACGAAGCTGGAATCG
CTAGTAATCGCAGATCAGAATGCTGCGGTGAATACGTTCCCGGGTCTTGTACACACCGCCCGTCACACCATGGGAG
TTGGAAATGCCCGAAGTCAGTGACCCAACCGCAAGGAGGGAGCTGCCGAAGGCAGGTTCGATAACTG

FJ951866.1.1493
AGAGTTTGATCCTGGCTCAGGATGAACGCTGGCGGCGTGCTTAACACATGCAAGTCGAACGAAGCACTTTAACTTG
ATTTTTTCGGAATGATTGTTCTTGTGACTGAGTGGCGGACGGGTGAGTAACGCGTGGGTAACCTGCCTCATACAGG
GGGATAACAGTTAGAAATGACTGCTAATACCGCATAAGCGCACGGTATCGCATGATACAGTGTGAAAAACTCCGGT
GGTATGAGATGGACCCGCGTCTGATTAGCTAGTTGGCGGGGTAACGGCCCACCAAGGCGACGATCAGTAGCCGACC
TGAGAGGGTGACCGGCCACATTGGGACTGAGACACGGCCCAAACTCCTACGGGAGGCAGCAGTGGGGAATATTGCA
CAATGGGCGAAAGCCTGATGCAGCGACGCCGCGTGAACGAAAAAGTATTTCGGTATGTAAAGTTCTATCAGCAGGG
AAGATAATGACGGTACCTGACTAAGAAGCACCGGCTAAATACGTGCCAGCAGCCGCGGTAATACGTATGGTGCAAG
CGTTATCCGGATTTACTGGGTGTAAAGGGAGCGCAGGCGGTACGGCAAGTCTGATGTGAAAGCCCGGGGCTCAACC
CCGGTACTGCATTGGAAACTGTCGAACTAGAGTGTCGGAGGGGTAAGCGGAATTCCTAGTGTAGCGGTGAAATGCG

TABLE 11-continued 16S rRNA Sequences of OTUs in Tables 2-5
OTUs in Table 2

TAGATATTAGGAGGAACACCAGTGGCGAAGGCGGCTTACTGGACGACAACTGACGCTGAGGCGCGAAAGCGTGGGG
AGCAAACAGGATTAGATACCCTGGTAGTCCACGCTGTAAACGATGAATACTAGGTGTGGGAGGACTGACCCCTTCC
GTGCCGCAGTTAACACAATAAGTATTCCACCTGGGGAGTACGGCCGCAAGGCTGAAACTCAAAGGAATTGACGGGG
GCCCGCACAAGCAGTGGATTATGTGGTTTAATTCGACGCAACGCGAAGAACCTTACCAGGACTTGACATCCAACTA
ACGAAGTAGAGATACATTAGGTGCCCTTCGGGGAAAGTTGAGACAGGTGGTGCATGGTTGTCGTCAGCTCGTGTCG
TGAGATGTTGGGTTAAGTCCCGCAACGAGCGCAACCCCTATTGTTAGTTGCTACGCAAGAGCACTCTAGCGAGACT
GCCGTTGACAAAACGGAGGAAGGCGGGGACGACGTCAAATCATCATGCCCCTTATGTCCTGGGCTACACACGTAAT
ACAATGGCCGTCAACAAAGGGAAGCAAAGCCGCGAGGTGGAGCAAATCCCCAAAAACGGTCTCAGTTCGGATTGCA
GGCTGCAACTCGCCTGCATGAAGCTGGAATTGCTAGTAATCGTGGATCAGCATGCCACGGTGAATACGTTCCCGGG
CCTTGTACACACCGCCCGTCACACCATGAGAGTCGGGAACACCCGAAGTCCGTAGTCTAACCGCAAGGAGGGCGCG
GCCGAAGGTGGGTCCGGTAATTGGGGTGAAGTCGTAACAAGGTAACCGT

EU772870.1.1289
AGTGGCGAACGGGTGAGTAACGCGTGAGGAACCTGCCTTTCAGTGGGGGACAACAGTTGGAAACGACTGCTAATAC
CGCATGATACTTTTTGGAGGCATCTCTGAAAAGTCAAAGCTTTATGTGCTGAAAGATGGTCTCGCGTCTGATTAGC
TAGTTGGTGAGGTAACGGCTCACCAAGGCGACGATCAGTAGCCGGTCTGAGAGGATGAACGGCCACATTGGGACTG
AGATACGGCCCAGACTCCTACGGGAGGCAGCAGTGGGGAATATTGGGCAATGGGGGAAACCCTGACCCAGCAACGC
CGCGTGAAGGAAGAAGGCCTTCGGGTTGTAAACTTCTTTTACCAGGGACGAAGAACGTGACGGTACCTGGAGAAAA
AGCAACGGCTAACTACGTGCCAGCAGCCGCGGTAATACGTAGGTTGCAAGCGTTATCCGGATTTATTGGGCGTAAA
GCGCGTCTAGGCGGTTTGGTAAGTCTGATGTGAAAATGCGGGGCTCAACTCCGTATTGCGTTGGAAACTGCTAAAC
TAGAGTACTGGAGAGGTAGGCGGAACTACAAGTGTAGAGGTGAAATTCGTAGATATTTGTAGGAATGCCGATGGGG
AAGCCAGCCTACTGGACAGATACTGACGCTAAAGCGCGAAAGCGTGGGGAGCAAACAGGATTAGATACCCTGGTAG
TCCACGCTGTAAACGATGAGTACTAGGTGTCGGAGGTTACCCCCTTCGGTGCCGCAGCTAACGCATTAAGTACTCC
GCCTGGGGAGTACGCACGCAAGTGTGGAACTCAAAGGAATTGACGGGGACCCGCACAAGTAGCGGAGCATGTGGTT
TAATTCGAAGCAACGCGAAGAACCTTACCTAGGCTTGACATCCTTCTGACCGAGGACTAATCTCCTCTTTCCCTCC
GGGGACAGAAGTGACAGGTGGTGCATGGTTGTCGTCAGCTCGTGTCGTGAGATGTTGGGTTAAGTCCCGCAACGAG
CGCAACCCTTGTCTTTAGTTGCCATCATTTAGTTGGGCACTCTGGAGAGACTGCCAGGGATAACCTGGAGGAAGGT
GGGGATGACGTCAAATCATCATGCCCCTTATGCCTAGGGCTACACACGTGCTACAATGGGTGGTACAGAGGGCAGC
TAAGCCGTGAGGTGGAGCAAATCCCTTAAAGCCATTCTCAGTTCGGATTGTAGGCTGAAACTCGCCTACATGAAGC
TGGAGTTACTAGTAATCGCAGATCAGAATGCTGCGGTGAATGCGTTCCCGGGTCTTGTACACACCGCCCGTCA

GQ448468.1.1366
AGAGTTTGATCCTGGCTCAGGATGAACGCTGACAGAATGCTTAACACATGCAAGTATACTTGATCCTTCGGGTGAT
GGTGGCGGACGGGTGAGTAACGCGTAAAGAACTTGCCCTGCAGTCTGGGACAACATTTGGAAACGAATGCTAATCC
CGCATAAGCCCACAGCTCGGCATCGAGCAGAGGGAAAAGGAGTGATCTGCTTTGAGATGGCCTCGCGTCCGATTAG
CTGGTTGGTGAGGTGACGGCCCATCAAGGCAACGATCGGTAGCCGGACTGAGAGGTTGAACGGCCACATTGGGATT
GAGACACGGCCCTTACTCCTACGGGAGGCAGCAGTGGGGAATATTGGACAATGGACCAAAAGTCTGATCCAGCAAT
TCTGTGTGCACGATGAAGTTTTTCGGAATGTAAAGTGCTTTCAGTTGGGACGAAGTAAGTGACGGTACCAACAGAA
GAAGCGACGGCTAAATACGTGCCAGCAGCCGCGGTAATACGTATGTCGCAAGCGTTATCCGGATTTATTGGGCGTA
AAGCGCGTCTAGGCGGTTTGGTAAGTCTGATGTGAAAATGCGGGGCTCAACTCCGTATTGCGTTGGAAACTGCCAA
ACTAGAGTACTGGAGAGGTGGGCGGAACTACAAGTGTAGAGGTGAAATTCGTAGATATTTGTAGGAATGCCGATGG
GGAAGCCAGCCCACTGGACAGATACTGACGCTAAAGCGCGAAAGCGTGGGTAGCAAACAGGATTAGATACCCTGGT
AGTCCACGCCGTAAACGATGATTACTAGGTGTTGGGGGTCGAACCTCAGCGCCCAAGCTAACGCGATAAGTAATCC
GCCTGGGGAGTACGTACGCAAGTATGAAACTCAAAGGAATTGACGGGGACCCGCACAAGCGGTGGAGCATGTGGTT
TAATTCGACGCAACGCGAGGAACCTTACCAGCGTTTGACATCCTAAGAAATTAGCAGAGATGCTTTTGTGCCCCTT
CGGGGGAACTTAGTGACAGGTGGTGCATGGCTGTCGTCAGCTCGTGTCGTGAGATGTTGGGTTAAGTCCCGCAACG
AGCGCAACCCCTTTCGTATGTTGCCATCATTAAGTTGGGCACTCATGCGATACTGCCTGCGATGAGCAGGAGGAAG
GTGGGGATGACGTCAAGTCATCATGCCCCTTATACGCTGGGCTACACACGTGCTACAATGGGTAGTACAGAGAGTC
GCAAACCTGCGAGGGGGAGCTAATCTCAGAAAACTATTCTCAGTTCGGATTGTACTCTGCAACTCGAGTACATGAA
GTTGGAATCGCTAGTAATCGCAAATCAGCTATGTTGCGGTGAATACGTTCTCGGGTCTTGTACACACCGCCCGT

EU774020.1.1361
AGAGTTTGATCCTGGCTCAGGACGAACGCTGGCGGCGTGCCTAACACATGCAAGTCGAGCGATTCTCTTCGGAGAA
GAGCGGCGGACGGGTGAGTAACGCGTGGGTAACCTGCCCTGTACACACGGATAACATACCGAAAGGTATGCTAATA
CGGGATAATATATAAGAGTCGCATGACTTTTATATCAAAGATTTTTCGGTACAGGATGGACCCGCGTCTGATTAGC
TTGTTGGCGGGGTAACGGCCCACCAAGGCGACGATCAGTAGCCGACCTGAGAGGGTGATCGGCCACATTGGAACTG
AGACACGGTCCAAACTCCTACGGGAGGCAGCAGTGGGGAATATTGCACAATGGGCGCAAGCCTGATGCAGCAACGC
CGCGTGAGCGATGAAGGCCTTCGGGTCGTAAAGCTCTGTCCTCAAGGAAGATAATGACGGTACTTGAGGAGGAAGC
CCCGGCTAACTACATGCCAGCAGCCGCGGTAATACGTATGTCGCAAGCGTTATCCGGATTTATTGGGCGTAAAGCG
CGTCTAGGTGGTTTGGTAAGTCTGATGTGAAAATGCGGGGCTCAACTCCGTATTGCGTTGGAAACTGCCAAACTAG
AGTACTGGAGAGGTAGGCGGAACTACAAGTGTAGAGGTGAAATTCGTAGATATTTGTAGGAATGCCGATGGGGAAG
CCAGCCTACTGGACAGATACTGACGCTAAAGCGCGAAAGCGTGGGTAGCAAACAGGATTAGATACCCTGGTAGTCC
ACGCCGTAAACGATGATTACTAGGTGTTGGGGGTCGAACCTCAGCGCCCAAGCTAACGCGATAAGTAATCCGCCTG
GGGAGTACGTACGCAAGTATGAAACTCAAAGGAGTTGACGGGGACCCGCACAAGCGGTGGAGCATGTGGTTTAATT
CGACGCAACGCGAGGAACCTTACCAGCGTTTGACATCCTAGGAATGAGAAAGAGATTTCTTAGTGCTCCTTCGGGA
GAACCTAGAGACAGGTGGTGCATGGCTGTCGTCAGCTCGTGTCGTGAGATGTTGGGTTAAGTCCCGCAACGAGCGC
AACCCCTATTGTATGTTGCCATCATTAAGTTGGGCACTCATGCGATACTGCCTGCGATGAGCAGGAGGAAGGTGGG
GATGACGTCAAGTCATCATGCCCCTTATACGCTGGGCTACACACGTGCTACAATGGGCAGTACAGAGAGAAGCAAT
ACCGCGAGGTGGAGCCAAACTTAAAAACCAGTCTCAGTTCGGATTGTAGGCTGAAACTCGCCTACATGAAGCTGGA
GTTACTAGTAATCGCGAATCAGAATGTCGCGGTGAATACGTACCCGGGTCTTGTACACACCGCCCGTCA

HQ782658.1.1415
AATGCTTAACACATGCAAGTCTACTTGATCCTTCGGGTGATGGTGGCGGACGGGTGAGTAACGCGTAAAGAACTTG
CCTTGCAGTCTGGGACAACGTCTGGAAACGGACGCTAATACCGGATATTATGCGAGAGTCGCATGGCTCTTTCATG
AAAGCTATATGCGCTGCAGGAGAGCTTTGCGTCCCATTAGTTAGTTGGTGAGGTAACGGCTCACCAAGACCGCGAT
GGGTAGCCGGCCTGAGAGGGTGAACGGCCACAAGGGGACTGAGACACGGCCCTTACTCCTACGGGAGGCAGCAGTG
GGGAATATTGGACAATGGACCAAAAGTCTGATCCAGCAATTCTGTGTGCACGATGACGGTCTTAGGATTGTAAAGT

TABLE 11-continued 16S rRNA Sequences of OTUs in Tables 2-5
OTUs in Table 2

GCTTTCAATCGGGAAAAAGAAAGTGATGGTACCGATAGAAGAAGCGACGGCTAAATACGTGCCAGCAGCCGCGGTA
ATACGTATGTCGCAAGCGTTATCCGGATTTATTGGGCGTAAAGCGCGTCTAGGCGGTCTGGTAAGTCTGATGTGGA
AATGCGGGGCTCAACTCCGTATTGCGTTGGAAACTGCCAGACTAGAGTACTGGAGAGGTGGGCGGAACTACAAGTG
TAGAGGTGAAATTCGTAGATATTTGTAGGAATGCCGATAGAGAAGTCAGCTCACTGGACAGATACTGACGCTGAAG
CGCGAAAGCATGGGGAGCAAACAGGATTAGATACCCTGGTAGTCCATGCCGTAAACGATGATTACTAAGCGTCGGG
GGTCGAACCTCGGCACTCAAGCTAACGCGATAAGTAATCCGCCTGGGGAGTACGTACGCAAGTATGAAACTCAAAG
GAATTGACGGGGACCCGCACAAGTGGTGGAGCATGTGGTTTAATTGGACGCAACGCGAGGAACTTTACCAGCGTGT
GACATCCTAGGAATGAGAAAGAGATTTTTCAGTGCTCCTTCGGGAGAACCCAGAGACAGGTGGTGCATGGCTGTGG
TCAGCTCGTGTCGTGAGATGTTGGGTTAAGTCCCGCAACGAGCGCAACCCCTATTGTATGTTGCCATCATTAAGTT
GGGCAATCATGCGATGCTGCCTGCGACGAGCAGGAGGAAGGTGGGGATGAGGTCAAGTCATCATGCCCGTTATATG
CTGGGCTACACACGTGCTACAATGGGCAGTACAGAGAGAAGCAAATATGCGAGGAGGAGCAAATGTCAGAAAGCTG
TTCGTAGTTCGGATTGTACTCTGCAACTGGAGTACATGAAGTTGGAATCAGTAGTAATCGCAAATCAGCAATGTTG
CGGTGAATACGTTCTCGGGTCTGGTACACACCGCCCGTCACACCACGAGAGTTGATTGCACCTGAAGTAGCAGGCC
TAACCGTAAGGAAGGGTGGTCCGAGGGTGTGGTTAGCGATTGGGGTG

DQ794633.1.1395
AGAGTTTGATCCTGGCTCAGGATGAACGCTGGCGGCGTGCTTAACACATGCAAGTCGAGCGAAGCGCTTTTACGGA
TTTCTTCGGATTGAAGTGATTGTGACTGAGCGGCGGACGGGTGAGTAACGCGTGGGTAACCTGCCTCATACAGGGG
GATAACAGTTAGAAATGACTGCTAATACCGCATAAGCGCACAGTACCGCATGGGTACGGTGTGAAAAACTCCGGTG
GTATGAGATGGACCCGCGTCTGATTAGGTAGTTGGTGGGGTAACGGCCTACCAAGCCAACGATCAGTAGCCGACCT
GAGAGGGCGACCGGCCACATTGGGACTGAGACACGGCCCAAACTCCTACGGGAGGCAGCAGTGGGGAATATTGCAC
AATGGGGGAAACCCTGATGCAGCGACGCCGCGTGAAGGATGAAGTATTTCGGTATGTAAACTTCTATCAGCAGGGA
AGAAAATAACGGTACCTGAGTAAGAAGCCCCGGCTAACTACGTGCCAGCAGCCGCGGTAATACGTAGGGGGCAAGC
GTTATCCGGATTTACTGGGTGTAAAGGGAGCGTAGACGGAAGTGCAAGTCTGATGTGAAAACCCGAGGCTCAACCA
CGGGACTGCATTGGAAACTGTGCTTCTAGAGTGCCGGAGAGGTAAGCGGAATTCCTAGTGTAGCGGTGAAATGCGT
AGATATTAGGAGGAACACCAGTGGCGAAGGCGGCTTACTGGACGGTAACTGACGTTGAGGCTCGAAAGCGTGGGGA
GCAAACAGGATTAGATACCCTGGTAGTCCACGCCGTAAACGATGACTTACTAGGGTGTCGGGCAGCAAAGCTGTTC
GGTTGCCGCAGCCATCGCAATAAGTAGTCCACCTGGGGGAGTACGTTCGCAAGAATGAAACTCAAAGGAATTGACG
GGGACCCGCACAAGCGGTGGAGCATGTGGTTTAATTCGAAGCAACGCGAAGAACCTTACCTGCTCTTGACATCCCT
CTGACCGGCAAGTAATGTTGCCTTTCCTTCGGGACAGAGGAGACAGGTGGTGCATGGTTGTCGTCAGCTCGTGTCG
TGAGATGTTGGGTTAAGTCCCGCAACGAGCGCAACCCCTATCTTCAGTAGCCAGCATTTAAGGTGGGCACTCAGGA
GAGACTGCCAGGGATAACCTGGAGGAAGGTGGGGATGACGTCAAATCATCATGCCCCTTATGAGCAGGGCTACACA
CGTGCTACAATGGCGTAAACAAAGGGAAGCGAAAGGGTGACCTGGAGCAAATCTCAGAAATAACGTCTCAGTTCGG
ATTGTAGTCTGCAACTCGACTACATGAAGCTGGAATCGCTAGTAATCGCGAATCAGCATGTCGCGGTGAATACGTT
CCCGGGTCTTGTACTCACCGCCCGTCA

FN668375.4306350.4307737
AGAGTTTGATCCTGGCTCAGGATGAACGCTGGCGGCGTGCCTAACACATGCAAGTTGAGCGATTTACTTCGGTAAA
GAGCGGCGGACGGGTGAGTAACGCGTGGGTAACCTACCCTGTACACACGGATAACATACCGAAAGGTATGCTAATA
CGGGATAATATATTTGAGAGGCATCTCTTGAATATCAAAGGTGAGCCAGTACAGGATGGACCCGCGTCTGATTAGC
TAGTTGGTAAGGTAACGGCTTACCAAGGCGACGATCAGTAGCCGACCTGAGAGGGTGATCGGCCACATTGGAACTG
AGACACGGTCCAAACTCCTACGGGAGGCAGCAGTGGGGAATATTGCACAATGGGCGAAAGCCTGATGCAGCAACGC
CGCGTGAGTGATGAAGGCCTTCGGGTCGTAAAACTCTGTCCTCAAGGAAGATAATGACGGTACTTGAGGAGGAAGC
CCCGGCTAACTACGTGCCAGCAGCCGCGGTAATACGTAGGGGGCTAGCGTTATCCGGATTTACTGGGCGTAAAGGG
TGCGTAGGCGGTCTTTCAAGTCAGGAGTGAAAGGCTACGGCTCAACCGTAGTAAGCTCTTGAAACTGGGAGACTTG
AGTGCAGGAGAGGAGAGTGGAATTCCTAGTGTAGCGGTGAAATGCGTAGATATTAGGAGGAACACCAGTTGCGAAG
GCGGCTCTCTGGACTGTAACTGACGCTGAGGCACGAAAGCGTGGGGAGCAAACAGGATTAGATACCCTGGTAGTCC
ACGCTGTAAACGATGAGTACTAGGTGTCGGGGGTTACCCCCTTCGGTGCCGCAGCTAACGCATTAAGTACTCCGCC
TGGGAAGTACGCTCGCAAGAGTGAAACTCAAAGGAATTGACGGGGACCCGCACAAGTAGCGGAGCATGTGGTTTAA
TTCGAAGCAACGCGAAGAACCTTACCTAAGCTTGACATCCCAATGACATCTCCTTAATCGGAGAGTTCCCTTCGGG
GACATTGGTGACAGGTGGTGCATGGTTGTCGTCAGCTCGTGTCGTGAGATGTTGGGTTAAGTCCCGCAACGAGCGC
AACCCTTGTCTTTAGTTGCCATCATTAAGTTGGGCACTCTAGAGAGACTGCCAGGGATAACCTGGAGGAAGGTGGG
GATGACGTCAAATCATCATGCCCCTTATGCTTAGGGCTACACACGTGCTGATTATGCTAAGGAAATAGGATTTACT
GGACAATTCTTAATAGAGCCTAAGCCAAAAGAGCCTACTAAACATCAATATGATTTTGATACTGCTACTGTTTTAG
GATTTTTAAGAAAGTATAATCTGGATAAATACTTCAAAGTGAATATAGAAGCAAACCATGCAACACTTGCAGGACA
TACTTTCCAACATGAATTAA

GQ867445.1.1457
CGCTGGCGGCGTGCTTAACACATGCAAGTCGAACGAAGCGATTTGGAGGAAGTTTTCGGATGAAATCTGAATTGAC
TGAGTGGCGGACGGGTGAGTAACGCGTGGGTAACCTGCCTCACACAGGGGGACAACAGTTAGAAATGGCTGCTAAT
ACCGCATAAGCGCACAGCTTCGCATGAAGCAGTGTGAAAAACTCCGGTGGTGTGAGATGGACCCGCGTCTGATTAG
GTAGTTGGTGGGGTAACGGCCTACCAAGCCGACGATCAGTAGCCGACCTGAGAGGGTGACCGGCCACATTGGGACT
GAGACACGGCCCAAACTCCTACGGGAGGCAGCAGTGGGGAATATTGCACAATGGGGGAAACCCTGATGCAGCGACG
CCGCGTGAGTGAAGAAGTATTTCGGTATGTAAAGCTCTATCAGCAGGGAAGAAAATGACGGTACCTGACTAAGAAG
CCCCGGCTAACTACGTGCCAGCAGCCGCGGTAATACGTAGGGGGCAAGCGTTATCCGGATTTACTGGGTGTAAAGG
GAGCGTAGACGGCTTGGCAAGTCTGAAGTGAAAGCCCGGGGCTCAACCCCGGGACTGCTTTGGAAACTGTCAGGCT
AGAGTGCTGGAGAGGTAAGTGGAATTCCTAGTGTAGCGGTGAAATGCATAGATATTAGGAGGAACACCAGTGGCGA
AGGCGGCTTACTGGACAGTAACTGACGTTGAGGCTCGAAAGCGTGGGGAGCAAACAGGATTAGATACCCTGGTAGT
CCACGCCGTAAACGATGAATACTAGGTGTTGGGGAGCAAAGCTCTTCGGTGCCGTCGCAAACGCAATAAGTATTCC
ACCTGGGAAGTACGTTCGCAAGAATGAAACTCAAAGGAATTGACGGGGACCCGCACAAGCGGTGGAGCATGTGGTT
TAATTCGAAGCAACGCGAAGAACCTTACCAAGTCTTGACATCCCATTGAAAAGCCCGTAACGGGGTTCCCTCTTCG
GAGCAATGGAGACAGGTGGTGCATGGTTGTCGTCAGCTCGTGTCGTGAGATGTTGGGTTAAGTCCCGCAACGAGCG
CAACCCTTATCCTAAGTAGCCAGCAGGTAGAGCTGGGCACTCTTGGGAGACTGCCAGGGACAACCTGGAGGAAGGT
GGGGATGACGTCAAATCATCATGCCCCTTATGATTTGGGCTACACACGTGCTACAATGGCGTAAACAAAGGGAAGC
GAAGCTGTGAAGCTAAGCAAATCTCAAAAATAACGTCTCAGTTCGGATTGTAGTCTGCAACTCGACTACATGAAGC

TABLE 11-continued

| 16S rRNA Sequences of OTUs in Tables 2-5<br>OTUs in Table 2 |
|---|
| TGGAATCGCTAGTAATCGCGGATCAGAATGCCGCGGTGAACACGTTCCCGGGTCTTGTACACACCGCCCGTCACAC<br>CATGGGAGTCAGTAACGCCCGAAGCCAGTGACCTAACCGCAAGGAAGGAGCTGTCGAAGGCGGGACCGATAACTGG<br>GGTGAAGTCGTAA |

REFERENCES

1. Nitzan, O., Elias, M., Peretz, A. & Saliba, W. Role of antibiotics for treatment of inflammatory bowel disease. *World J. Gastroenterol.* 22, 1078-1087 (2016).
2. Khan, K. J. et al. Antibiotic therapy in inflammatory bowel disease: a systematic review and meta-analysis. *Am. J. Gastroenterol.* 106, 661-673 (2011).
3. Knights, D., Lassen, K. G. & Xavier, R. J. Advances in inflammatory bowel disease pathogenesis: linking host genetics and the microbiome. *Gut* 62, 1505-1510 (2013).
4. Garrett, W. S. et al. Communicable ulcerative colitis induced by T-bet deficiency in the innate immune system. *Cell* 131, 33-45 (2007).
5. Couturier-Maillard, A. et al. NOD2-mediated dysbiosis predisposes mice to transmissible colitis and colorectal cancer. *J. Clin. Invest.* 123, 700-711 (2013).
6. Moon, C. et al. Vertically transmitted faecal IgA levels determine extra-chromosomal phenotypic variation. *Nature* 521, 90-93 (2015).
7. David, L. A. et al. Diet rapidly and reproducibly alters the human gut microbiome. *Nature* 505, 559-563 (2014).
8. Muegge, B. D. et al. Diet drives convergence in gut microbiome functions across mammalian phylogeny and within humans. *Science* 332, 970-974 (2011).
9. Lee, D. et al. Diet in the pathogenesis and treatment of inflammatory bowel diseases. *Gastroenterology* 148, 1087-1106 (2015).
10. Levine, A., Sigall Boneh, R. & Wine, E. Evolving role of diet in the pathogenesis and treatment of inflammatory bowel diseases. *Gut* 67, 1726-1738 (2018).
11. Chassaing, B. et al. Dietary emulsifiers impact the mouse gut microbiota promoting colitis and metabolic syndrome. *Nature* 519, 92-96 (2015).
12. Desai, M. S. et al. A Dietary Fiber-Deprived Gut Microbiota Degrades the Colonic Mucus Barrier and Enhances Pathogen Susceptibility. *Cell* 167, 1339-1353.e21 (2016).
13. Hou, J. K., Abraham, B. & El-Serag, H. Dietary intake and risk of developing inflammatory bowel disease: a systematic review of the literature. *Am. J. Gastroenterol.* 106, 563-573 (2011).
14. Ruemmele, F. M. et al. Consensus guidelines of ECCO/ESPGHAN on the medical management of pediatric Crohn's disease. *J Crohns Colitis* 8, 1179-1207 (2014).
15. Cohen-Dolev, N. et al. Differences in outcomes over time with exclusive enteral nutrition compared with steroids in children with mild to moderate crohn's disease: results from the GROWTH CD study. *J Crohns Colitis* 12, 306-312 (2018).
16. Sigall-Boneh, R. et al. Partial enteral nutrition with a Crohn's disease exclusion diet is effective for induction of remission in children and young adults with Crohn's disease. *Inflamm. Bowel Dis.* 20, 1353-1360 (2014).
17. Lee, D. et al. Comparative Effectiveness of Nutritional and Biological Therapy in North American Children with Active Crohn's Disease. *Inflamm. Bowel Dis.* 21, 1786-1793 (2015).
18. Borrelli, O. et al. Polymeric diet alone versus corticosteroids in the treatment of active pediatric Crohn's disease: a randomized controlled open-label trial. *Clin. Gastroenterol. Hepatol.* 4, 744-753 (2006).
19. Kaakoush, N. O. et al. Effect of exclusive enteral nutrition on the microbiota of children with newly diagnosed Crohn's disease. Clin. Transl. Gastroenterol. 6, e71 (2015).
20. Quince, C. et al. Extensive modulation of the fecal metagenome in children with crohn's disease during exclusive enteral nutrition. *Am. J. Gastroenterol.* 110, 1718-29; quiz 1730 (2015).
21. Gerasimidis, K. et al. Decline in presumptively protective gut bacterial species and metabolites are paradoxically associated with disease improvement in pediatric Crohn's disease during enteral nutrition. *Inflamm. Bowel Dis.* 20, 861-871 (2014).
22. Schwerd, T. et al. Exclusive enteral nutrition in active pediatric Crohn disease: Effects on intestinal microbiota and immune regulation. *J. Allergy Clin. Immunol.* 138, 592-596 (2016).
23. Lewis, J. D. et al. Inflammation, antibiotics, and diet as environmental stressors of the gut microbiome in pediatric crohn's disease. *Cell Host Microbe* 18, 489-500 (2015).
24. D'Argenio, V. et al. An altered gut microbiome profile in a child affected by crohn's disease normalized after nutritional therapy. *Am. J. Gastroenterol.* 108, 851-852 (2013).
25. Wu, G. D. et al. Linking long-term dietary patterns with gut microbial enterotypes. *Science* 334, 105-108 (2011).
26. Gurry, T. et al. Predictability and persistence of prebiotic dietary supplementation in a healthy human cohort. *Sci. Rep.* 8, 12699 (2018).
27. Wu, G. D. et al. Comparative metabolomics in vegans and omnivores reveal constraints on diet-dependent gut microbiota metabolite production. *Gut* 65, 63-72 (2016).
28. Obregon-Tito, A. J. et al. Subsistence strategies in traditional societies distinguish gut microbiomes. *Nat. Commun.* 6, 6505 (2015).
29. Smits, S. A. et al. Seasonal cycling in the gut microbiome of the Hadza hunter-gatherers of Tanzania. *Science* 357, 802-806 (2017).
30. Cerquetella, M. et al. Inflammatory bowel disease in the dog: differences and similarities with humans. *World J. Gastroenterol.* 16, 1050-1056 (2010).
31. Jergens, A. E. & Simpson, K. W. Inflammatory bowel disease in veterinary medicine. *Front Biosci* (*Elite Ed*) 4, 1404-1419 (2012).
32. Peiravan, A. et al. Genome-wide association studies of inflammatory bowel disease in German shepherd dogs. *PLoS ONE* 13, e0200685 (2018).
33. Vizquez-Baeza, Y., Hyde, E. R., Suchodolski, J. S. & Knight, R. Dog and human inflammatory bowel disease rely on overlapping yet distinct dysbiosis networks. *Nat. Microbiol.* 1, 16177 (2016).
34. Suchodolski, J. S., Dowd, S. E., Wilke, V., Steiner, J. M. & Jergens, A. E. 16S rRNA gene pyrosequencing reveals bacterial dysbiosis in the duodenum of dogs with idiopathic inflammatory bowel disease. *PLoS ONE* 7, e39333 (2012).
35. Simpson, K. W. et al. Adherent and invasive *Escherichia coli* is associated with granulomatous colitis in boxer dogs. *Infect. Immun.* 74,4778-4792 (2006).
36. Allenspach, K., Wieland, B., Grone, A. & Gaschen, F. Chronic enteropathies in dogs: evaluation of risk factors for negative outcome. *J Vet Intern Med* 21, 700-8 (2007).
37. Coelho, L. P. et al. Similarity of the dog and human gut microbiomes in gene content and response to diet. *Microbiome* 6, 72 (2018).
38. Kalenyak, K., Isaiah, A., Heilmann, R. M., Suchodolski, J. S. & Burgener, I. A. Comparison of the intestinal mucosal microbiota in dogs diagnosed with idiopathic inflammatory bowel disease and dogs with food-responsive diarrhea before and after treatment. *FEMS Microbiol. Ecol.* 94, (2018).
39. Minamoto, Y., Dhanani, N., Markel, M. E., Steiner, J. M. & Suchodolski, J. S. Prevalence of *Clostridium perfringens, Clostridium perfringens* enterotoxin and dysbiosis in fecal samples of dogs with diarrhea. *Vet. Microbiol.* 174, 463-473 (2014).
40. Ziese, A.-L. et al. Effect of probiotic treatment on the clinical course, intestinal microbiome, and toxigenic *Clostridium perfringens* in dogs with acute hemorrhagic diarrhea. *PLoS ONE* 13, e0204691 (2018).
41. Gevers, D. et al. The treatment-naive microbiome in new-onset Crohn's disease. *Cell Host Microbe* 15,382-392 (2014).
42. Islam, K. B. M. S. et al. Bile acid is a host factor that regulates the composition of the cecal microbiota in rats. *Gastroenterology* 141, 1773-1781 (2011).
43. Wells, J. E. & Hylemon, P. B. Identification and characterization of a bile acid 7alpha-dehydroxylation operon in *Clostridium* sp. strain TO-931, a highly active 7alpha-dehydroxylating strain isolated from human feces. *Appl. Environ. Microbiol.* 66, 1107-1113 (2000).
44. Kitahara, M., Takamine, F., Imamura, T. & Benno, Y. *Clostridium hiranonis* sp. nov., a human intestinal bacterium with bile acid 7alpha-dehydroxylating activity. *Int. J. Syst. Evol. Microbiol.* 51, 39-44 (2001).
45. Banaszkiewicz, A. et al. Enterotoxigenic *Clostridium perfringens* infection and pediatric patients with inflammatory bowel disease. *J Crohns Colitis* 8, 276-281 (2014).
46. Segata, N. et al. Metagenomic microbial community profiling using unique clade-specific marker genes. *Nat. Methods* 9, 811-814 (2012).
47. Kitahara, M., Takamine, F., Imamura, T. & Benno, Y. Assignment of *Eubacterium* sp. VPI 12708 and related strains with high bile acid 7alpha-dehydroxylating activity to *Clostridium scindens* and proposal of *Clostridium hylemonae* sp. nov., isolated from human faeces. *Int. J. Syst. Evol. Microbiol.* 50 Pr 3, 971-978 (2000).
48. Zaneveld, J. R, McMinds, R & Vega Thurber, R Stress and stability: applying the Anna Karenina principle to animal microbiomes. *Nat. Microbiol.* 2, 17121 (2017).
49. Nagy-Szakal, D. et al. Monotonous diets protect against acute colitis in mice: epidemiologic and therapeutic implications. *J. Pediatr. Gastroenterol. Nutr.* 56, 544-550 (2013).
50. Mandigers, P. J. J., Biourge, V., van den Ingh, T. S. G. A. M., Ankringa, N. & German, A. J. A randomized, open-label, positively-controlled field trial of a hydrolyzed protein diet in dogs with chronic small bowel enteropathy. *J. Vet. Intern. Med.* 24, 1350-1357 (2010).
51. Marks, S. L., Laflamme, D. P. & McAloose, D. Dietary trial using a commercial hypoallergenic diet containing hydrolyzed protein for dogs with inflammatory bowel disease. *Vet. Ther.* 3, 109-118 (2002).
52. Buffie, C. G. et al. Precision microbiome reconstitution restores bile acid mediated resistance to *Clostridium difficile. Nature* 517, 205-208 (2015).
53. Sorg, J. A. & Sonenshein, A. L. Bile salts and glycine as cogerminants for *Clostridium difficile* spores. *J. Bacteriol.* 190, 2505-2512 (2008).
54. Dunn, K. A. et al. Early Changes in Microbial Community Structure Are Associated with Sustained Remission After Nutritional Treatment of Pediatric Crohn's Disease. *Inflamm. Bowel Dis.* 22, 2853-2862 (2016).
55. Duvallet, C., Gibbons, S. M., Gurry, T., Irizarry, R A. & Alm, E. J. Meta-analysis of gut microbiome studies identifies disease-specific and shared responses. *Nat. Commun.* 8, 1784 (2017).
56. Oliveira, F. S. et al. MicrobiomeDB: a systems biology platform for integrating, mining and analyzing microbiome experiments. *Nucleic Acids Res.* 46, D684-D691 (2018).
57. Gonzalez, A. et al. Qiita: rapid, web-enabled microbiome meta-analysis. *Nat. Methods* 15, 796-798(2018).
58. Theriot, C. M., Bowman, A. A. & Young, V. B. Antibiotic-Induced Alterations of the Gut Microbiota Alter Secondary Bile Acid Production and Allow for *Clostridium difficile* Spore Germination and Outgrowth in the Large Intestine. mSphere 1, (2016).
59. van Nood, E. et al. Duodenal infusion of donor feces for recurrent *Clostridium difficile. N. Engl. J. Med.* 368, 407-415 (2013).
60. Wang, Y. et al. Fecal microbiota transplantation for refractory immune checkpoint inhibitor-associated colitis. *Nat. Med.* (2018). doi:10.1038/s41591-018-0238-9
61. Kozich, J. J., Westcott, S. L., Baxter, N. T., Highlander, S. K. & Schloss, P. D. Development of a dual-index sequencing strategy and curation pipeline for analyzing amplicon sequence data on the MiSeq Illumina sequencing platform. *Appl. Environ. Microbiol.* 79, 5112-5120 (2013).
62. Caporaso, J. G. et al. QIIME allows analysis of high-throughput community sequencing data. *Nat. Methods* 7, 335-336 (2010).
63. Schloss, P. D. et al. Introducing mothur: open-source, platform-independent, community-supported software for describing and comparing microbial communities. *Appl. Environ. Microbiol.* 75, 7537-7541 (2009).
64. Edgar, R. C. Search and clustering orders of magnitude faster than BLAST. *Bioinformatics* 26, 2460-2461 (2010).
65. Quast, C. et al. The SILVA ribosomal RNA gene database project: improved data processing and web-based tools. *Nucleic Acids Res.* 41, D590-6 (2013).
66. Pruesse, E. et al. SILVA: a comprehensive online resource for quality checked and aligned ribosomal RNA sequence data compatible with ARB. *Nucleic Acids Res.* 35, 7188-7196 (2007).
67. Core Team, R. R: A Language and Environment for Statistical Computing. (2017).
68. Huber, W. et al. Orchestrating high-throughput genomic analysis with Bioconductor. *Nat. Methods* 12, 115-121 (2015).
69. McMurdie, P. J. & Holmes, S. phyloseq: an R package for reproducible interactive analysis and graphics of microbiome census data. *PLoS ONE* 8, e61217 (2013).

70. Pielou, E. C. The measurement of diversity in different types of biological collections. *J. Theor. Biol.* 13, 131-144 (1966).
71. ABhauer, K. P., Wemheuer, B., Daniel, R & Meinicke, P. Tax4Fun: predicting functional profiles from metagenomic 16S rRNA data. *Bioinformatics* 31, 2882-2884 (2015).
72. Love, M. I., Huber, W. & Anders, S. Moderated estimation of fold change and dispersion for RNA-seq data with DESeq2. *Genome Biol.* 15, 550-550 (2014).
73. Li, H. et al. The Sequence Alignment/Map format and SAMtools. *Bioinformatics* 25, 2078-2079 (2009).
74. Li, H. & Durbin, R. Fast and accurate long-read alignment with Burrows-Wheeler transform. *Bioinformatics* 26, 589-595 (2010).
75. Browne, H. P. et al. Culturing of "unculturable" human microbiota reveals novel taxa and extensive sporulation. *Nature* 533, 543-546 (2016).
76. Goodman, A. L. et al. Extensive personal human gut microbiota culture collections characterized and manipulated in gnotobiotic mice. *Proc Natl Acad Sci USA* 108, 6252-6257 (2011).
77. De MAN, J. C., Rogosa, M. & Sharpe, M. E. A MEDIUM FOR THE CULTIVATION OF LACTOBACILLI. *Journal of Applied Bacteriology* 23, 130-135 (1960).
78. Lunter, G. & Goodson, M. Stampy: a statistical algorithm for sensitive and fast mapping of Illumina sequence reads. *Genome Res.* 21, 936-939 (2011).
79. Friedman, E. S. et al. FXR-Dependent Modulation of the Human Small Intestinal Microbiome by the Bile Acid Derivative Obeticholic Acid. *Gastroenterology* (2018). doi:10.1053/j.gastro.2018.08.022
80. Leinonen, R., Sugawara, H., Shumway, M. & International Nucleotide Sequence Database Collaboration. The sequence read archive. *Nucleic Acids Res.* 39, D19-21 (2011).

Although the presently disclosed subject matter and its advantages have been described in detail, it should be understood that various changes, substitutions and alterations can be made herein without departing from the spirit and scope of the present disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the presently disclosed subject matter, processes, machines, manufacture, compositions of matter, means, methods, or steps, presently existing or later to be developed that perform substantially the same function or achieve substantially the same result as the corresponding embodiments described herein can be utilized according to the presently disclosed subject matter. Accordingly, the appended claims are intended to include within their scope such processes, machines, manufacture, compositions of matter, means, methods, or steps.

Patents, patent applications, publications, product descriptions and protocols are cited throughout this application the disclosures of which are incorporated herein by reference in their entireties for all purposes.

What is claimed is:

1. A method for determining responsiveness of a companion animal having canine chronic enteritis to a diet, comprising:

a) administering the diet to the companion animal, wherein the diet comprises a food product comprising *Clostridium hiranonis;* b) measuring a first amount of a first intestinal microorganism, a second amount of a second intestinal microorganism, and a third amount of one or more secondary bile acids in the companion animal;

c) comparing the first amount of the first intestinal microorganism with a first reference amount of the first intestinal microorganism, comparing the second amount of the second intestinal microorganism with a second reference amount of the second intestinal microorganism, and comparing the third amount of one or more secondary bile acids with a third reference amount of the one or more secondary bile acids, wherein the reference amounts of the intestinal microorganisms and one or more secondary bile acids are determined based on the amounts of the intestinal microorganisms and the one or more secondary bile acids in a plurality of healthy companion animals;

d) determining that the companion animal is responsive to the diet, when the first amount of the intestinal microorganism is higher than the first reference amount of the first intestinal microorganism, when the second amount of the second intestinal microorganism is lower than the second reference amount of the second intestinal microorganism, and when the third amount of the one or more secondary bile acids is higher than the third reference amount of the one or more secondary bile acids, or determining that the companion animal is non-responsive to the diet, when the first amount of the intestinal microorganism is lower than the first reference amount of the first intestinal microorganism, when the second amount of the second intestinal microorganism is higher than the second reference amount of the second intestinal microorganism, and when the third amount of the one or more secondary bile acids is lower than the third reference amount of the one or more secondary bile acids.

2. The method of claim 1, wherein the first intestinal microorganism comprises one or more bacterium comprising a 16S rRNA comprising a nucleotide sequence that is at least about 90% homologous or identical to the 16S rRNA nucleotide sequence of SEQ ID NO:11, SEQ ID NO:8, SEQ ID NO:18, SEQ ID NO:9, SEQ ID NO:10, SEQ ID NO:27, SEQ ID NO:19, SEQ ID NO: 20, SEQ ID NO:15, SEQ ID NO:21, SEQ ID NO:28, SEQ ID NO:14, or SEQ ID NO:23.

3. The method of claim 1, wherein the second intestinal microorganism comprises one or more bacterium comprising a 16S rRNA comprising a nucleotide sequence that is at least about 90% homologous or identical to the 16S rRNA nucleotide sequence of SEQ ID NO:22, SEQ ID NO:24, SEQ ID NO:26, SEQ ID NO:13, SEQ ID NO:16, SEQ ID NO:25, SEQ ID NO:17, or SEQ ID NO:12.

4. The method of claim 1, further comprising administering the diet, a steroid and optionally an antibiotic to the companion animal when the companion animal is determined as non-responsive to the diet.

5. The method of claim 1, wherein the first intestinal microorganism comprises one or more bacterium comprising a 16S rRNA comprising a nucleotide sequence that is at least about 90% homologous or identical to a 16S rRNA nucleotide sequence selected from the group consisting of SEQ ID NO: 32 and SEQ ID NO: 33.

6. The method of claim 1, wherein the second intestinal microorganism comprises one or more bacterium comprising a 16S rRNA comprising a nucleotide sequence that is at least about 90% homologous or identical to a 16S rRNA nucleotide sequence selected from the group consisting of SEQ ID NOs: 29, 36, 38, 35, 48, 30, and 37.

7. The method of claim 1, wherein the method further comprises:

measuring a metabolic potential in the companion animal; and determining that the companion animal is responsive to the diet, when the metabolic potential has shifted from lipid metabolism to carbohydrate metabolism, or determining that the companion animal is not responsive to the diet, when the metabolic potential has not shifted from lipid metabolism to carbohydrate metabolism.

8. The method of claim 1, wherein the second intestinal microorganism is *Escherichia coli* or *Clostridium perfringens*.

9. The method of claim 1, wherein the one or more secondary bile acids comprise at least one of deoxycholic acid and lithocholic acid.

* * * * *

SEQUENCE LISTING

```
<160> NUMBER OF SEQ ID NOS: 99

<210> SEQ ID NO 1
<211> LENGTH: 11141
<212> TYPE: DNA
<213> ORGANISM: Clostridium hiranonis

<400> SEQUENCE: 1

gcaaattgat tttgattggt atttctttca ttcaaaatat ctcctttcct ttatttagct      60

gtattaaaat ttataaaaaa ttttcattgt taataaaaaa atattctttg ttagtattat     120

agcataattt ataaaaataa tgataatgtt ttaatattga aataataaat atgtaaaaag     180

gttggaaatt tatttaaaaa tgaccagaga taaaaagctc aggtcatttt ttttattatt     240

acaagtaatt tgaaaaaaat atatgaaatg aatggagaaa atataactga gatacatttg     300

ataatgaaaa aaacatttat cgaaattgta aatagactca ttgttataat taataaatat     360

ttattatggc atagttgtta aaattatacc ctaaagaaac gtttcctcaa aaagtgggtt     420

ataaaataaa tgttttttga cgaaagatgt gattttattt gtaccccttt tgtataaaga     480

ttaaacagta tttttgtata aatatattgt atacagtata gagaatgtcg atgtaaaaaa     540

gtatataaaa gtaaataata atcaaaaaaa ctagttttaa ttattaaaaa tgataaaaaa     600

tattaataaa ataaagagtc aaaaatactt gttagttaaa tcacagattt tgtctaagta     660

tagattaggt tttgtatttg aaaaggtcat ctatagtgtt gtaagaaagc gagttattag     720

cacatattgt atctcaaaaa aatgttaaga taatatcaag atagggcgat aaagaaaaaa     780

gcaaattgaa aaagaaaaaa gtaactataa gtttttacaa taaatcaaaa gagaattgat     840

tttaaaagag ggaggcaaaa taccgatatg aatgatgtga aatgtaaata ttttaataaa     900
```

```
tttaatacag gaatgtcaga ttttgttact ccaggaaaac agttagaata tgtagcaaaa    960
tgcaagccag atgaaaaagc tatcatatat atagataaag aagacaatgt gagagatatc   1020
acttggaagg aacttcacat agcttcaaat aaactagctt ggcatttaat gaaaaaggga   1080
tttggaaaag gtcaggtagc aatggtatct ttcccaaatg gtatagaaca tatattagca   1140
acattagctg tttggaaaac aggaggttgc tacatgccag tttcttgtaa gataacagat   1200
acagagcttg gtgatatatg cagaataata aaaccaacag tttcttttac agataaagaa   1260
atgccttgta gaacagaaag tataaaaata ggatcagtat tcgatgtttg taaagacgaa   1320
tcagaagaaa tgccagaaga tatagctgca aatccaaata tgatttctcc atctggagga   1380
acaacaggag agcctaagtt cataaaacag aatgtggcaa gtggcttatc tgatgaaatt   1440
ataaaaagct ggtttgaaat gtcaggtatg gaatttgaac aaagacaatt attagtagga   1500
ccacttttcc atggtgctcc tcatacagca gcatttaatg gattatttgt aggaaataca   1560
ttgataatac ctagaaattt aagacctgaa agtatagtta gatatataaa agaatacaaa   1620
atagaattta tacagatgat cccaacatta atgaatagaa taataaaatt agctgatgtt   1680
gataaagaag attttaaatc aataaaagca ctacaccata ctggtggata ttgttctcca   1740
tatttaaaag aaaagtggat cgatataata ggagctgaaa aagttcacga aatgtactct   1800
atgacagagg caatcggtat cacttgtata agaggagatg aatggcttaa acactatgga   1860
agcgtaggac ttccactagg aggaagcaga atatcaataa gagatgaaga aggaaatgaa   1920
ttaggaccac atgaggttgg agaaattcat atgacttcac caagtgcttg ttgcatgaca   1980
gaatacataa accataaacc acttgaaact aaagatggtg gatttagaag tgttggtgat   2040
ttcggttatg tagatgaaga tggatacctt tacttctcag atagaagaag cgacatgctt   2100
gttataggtg gagaaaacgt atttgcgact gaagttgaac cagtactacc agcttatgaa   2160
aaagtagttg atgctgtggt agttggaata cctgatgaag agtggggaag aagattacac   2220
gcaatagtac agaagaaaga agaagtttca gcagaagaat taatcgagta cttaggaaaa   2280
cacttattac catataaagt tccaaagagc tttacatttg ttccttgcat accaagaggt   2340
gacaatggaa aggtaaacag agataagatg ctaaaaggct taatagaaaa aaatctagtt   2400
aataaagttt gctaggatat aaattcagtt aactatctgc accaagtgca gtggaaaata   2460
aatcaaaatt aataaaataa attaataagg taaatttagg aggtctaaaa tgagttacga   2520
cgcacttttt tcaccattta aaatcagagg attagaactt aaaaacagaa tagttctacc   2580
aggtatgaat acaaaaatgg caaaaaataa acatgattta agcgatgata tgatagctta   2640
ccatgttgca agagcaaaag caggttgtgc attaaatata tttgaatgtg ttgcgctatg   2700
tccagcacct catgcatata tgtacatggg attatacaat gacaatcatg tagctcagtt   2760
aaaaaaatta acagatgctg ttcacgaagt tggcggtaaa atggctgttc agttatggca   2820
tggtggtttc agcccacaga tgttctttga taaaacaaat acattagaaa caccagatac   2880
tataacagtt gaacgtattc atgaaatagt taaagagttt ggagaaggtg caagaagagc   2940
tgttgaagct ggattcgatg cagttgaatt ccatgcagca cacagttact tacctcacga   3000
attcctaagt ccaggaatga acaaaagaac tgacgaatat ggtggaaact tcgaaaatcg   3060
ttgcagattc tgcttcgaag tagttgaagc tatacgtgca aatataccag aagatatgcc   3120
attcttcatg agagttgact gcatagatga gttaatggat gaagtaatga cagaagaaga   3180
aatagtagaa ttcataaata gatgtgctga tctaggagta gacgtagctg acttatcaag   3240
aggtaatgct cagtcattcg caacagttta cgaagttcct cctttcaact tacagcacgg   3300
```

```
tttcaatata gaaaacatat acaacatcaa aaaacagata aaaataccag taatgggtgt   3360
tggacgtata aacacaggag aaatggctaa ccaggtaata gcagatggaa aatttgactt   3420
agttggtata ggtcgtgctc agttagcaga tcaggattgg gttgctaaag ttagagaagg   3480
taaagaagat ttaatacgtc attgtatagg atgtgaccag ggatgctacg atgcagttat   3540
aaaccctcag atgactcata taacttgtac aagaaaccct cacttatgct tagaatacaa   3600
aggtatgcca aaaactgatg aacctaaaaa agttatgata atcggtggtg gtatggctgg   3660
tatattagca gctgaagtac ttaaaaaacg tggacatgaa ccagttatat tcgaagcttc   3720
tgatcactta gcaggacagt tcgtattagc aggtaaagct ccaatgaaag aagactgggc   3780
agctgcagct aaatgggaag ctgaagaagt agctcgttta ggaatagaag ttagatacaa   3840
tacaaaagtt actccagaat taatagaaga attcgctcca gaccacgttg ttatagctat   3900
aggatctgat tacgtagctc cagctatacc aggtatagat agtgacaaag tttacactca   3960
gtatcaggta tttaaaaggtg aagtagaacc aaaaggacat gtagcagtag ttggttgtgg   4020
attagttggt acagaagttg ctcagtactt agcagctaga ggagctcagg taacagctat   4080
agaaagaaaa ggtgttggta caggtctaag catgcttaga agaatgttca tgaacccaga   4140
attcaaatac tacaaaataa acaaaatgtc tggaactaac atagttggta tagaaccagg   4200
aaaacttcac tacataatga ctaacaagaa aactcaggaa gttactgaag gtgtgttaga   4260
atgtgatgca gcagtaatct gtacaggtat aactgctaga ccaagtgaag atttacagga   4320
aaaatgtaaa gaattaggtg ttccattcaa cgtaataggt gacgcagctg gtgctagaga   4380
tgctagaata gctactcagg aaggttacga agtaggtatg agtatataat ttaaaaatta   4440
tataattata taaattaaaa gttattaaat tacaagaaag aggcgaataa aatgacttta   4500
gaagcaagaa tagaagcatt agaaaaagaa atacagagat taaacgatat agaagctata   4560
aaacagttaa aagctaaata tttccgttgc ctagatggaa aattatggga tgaattagaa   4620
actactcttt ctcctaacat agaaacttct tactctgatg gaaaattagt attccacagc   4680
ccaaaagaag taactgaata tttagcagca gcaatgccta aagaagaaat aagtatgcac   4740
atgggacata ctccagaaat aactatagac agcgaaaata ctgctacagg aagatggtac   4800
ttagaagata acctaatatt cacagacgga aaatacaaaa acgttggaat aaacggtgga   4860
gcattctaca cagataaata tgaaaaaata gacggacagt ggtacataaa agaaactgga   4920
tatgttcgta tatttgaaga acatttcatg agagatccaa aatacatat aactagcaac    4980
atgcataaag aaaaataata actgattgct aataaacaag atataaacag ggggctggta   5040
aacagccagc cctctgaaaa ataaactaaa aaactataat cttttaaaat cttaattaaa   5100
gtagaaggag ataagacaat gaacttagta caggacaaaa tagttataat aacaggtgga   5160
acaagtggta taggtctttg cgcagcaaaa atattcatgg ataacggtgc aacagtttct   5220
atattcggaa aaactcagga agaagtagat gctgctaaag cagaattaaa agaaactcac   5280
ccagataaag aagtattagg atttgctcca gatttaacta atagagatga agttatggct   5340
gcagttggtg cagtagctga aaaatacgga agattagacg ttatgataaa caatgctggt   5400
gttactagct caaacgtatt ctcaagagtt agcccagaag aattcacata tttaatggat   5460
ataaacgtta caggtgtatt ccatggtgct tgggctgctt accactgcct gaaaggtgaa   5520
aagaagatta taataaatac tgcttcagta acaggaatac acggatcatt atcaggagtt   5580
ggatacccaa caagtaaatc agctgttgta ggattcactc aggctcttgg tagagaaata   5640
```

-continued

```
atacgtaaaa acataagagt tgttggtgtt gcaccaggtg ttgttaacac tccaatggtt   5700
ggtaatatac cagatgaaat attagatgga tacctaagct cattcccaat gaagagaatg   5760
ttagaaccag aagaaatagc taacacttac ttattcttag cttctgactt agctagtggt   5820
ataacagcta caactgtaag cgttgacggt gcttatagac catcataaga tttactttaa   5880
tttaaaactg taattagata gataatacga cgattaatat aaaaaatgtt ctttaaaaga   5940
aaaggagaaa taaaatggct ggattaaaag attttcctaa atttggtgca ctttctggat   6000
taaaaatatt agatagtgga tctaacatag ctggacctct aggtggtgga cttttagcag   6060
aatgtggtgc tacagttata cacttcgaag gacctaaaaa acctgacaac cagagaggtt   6120
ggtatggata ccctcagaac cacagaaacc agttatcaat ggttgctgat ataaaatctg   6180
aagaaggtag aaaaatattc ttagacttaa taaaatgggc tgacatatgg gttgaatcat   6240
caaaaggtgg acagtacgac agactaagtc tttctgatga agttatatgg tcagtaaacc   6300
ctaaaatagc tatagttcac gtttctggat acggacaggt tggagatcca tcatacgtaa   6360
caaaagcttc ttatgatgct gttggacagg cattcagtgg atacatgtca ttaaatggtg   6420
ttaatgaagc attaaaaata aatccttacc taagtgactt cgtatgtgtt cttactactt   6480
gctgggcaat gttagcatgc tacgtaagta ctcagttaac tggaaaagga gaatctgtag   6540
acgttgctca gtacgaagca ttagctcgta taatggacgg acgtatgata cagtacgcta   6600
ctgatggtgt aagtgttcca aaaactggta acaaagatgc tcaggcagct ctattcagct   6660
tctatacttg taaagatgga agaactatat tcataggtat gactggtgct gaagtatgta   6720
agagaggatt ccctgtaata gggcttccag ttcctggtac aggtgaccct gacttcccag   6780
aaggattcac aggatggatg ataaatactc cagttggaca gagaatggaa aaagctatgg   6840
aagcattcgt tgctgaaaga actatgccag aagttgaaaa agctatgata gatgctcaga   6900
taccatgcca gagagtttat gatcttgaag actgcttaaa cgaccctcac tggaatgctc   6960
gtggaactat aatggaatgg gatgacccaa tgatgggaca cataaaaggt cttggattaa   7020
taaacaaatt caaaaacaac ccttctgaaa tatggagagg tgctccatta ttcggtatgg   7080
acaacagaga cataattaga gaccttggat attctgagga ggaagttaac gatttatacg   7140
ctaaaggtat tgtaaacgaa ttcgaccttg aaacaactat aaaacgttac aaacttgatc   7200
aggttatacc tcacatggct aaaaaagata aataagaaac gtattaaata ataaaatata   7260
aatgtcgagc ctgccagaat gagaattttg acaggcttga tattataacg aaatgttata   7320
aaaaaaacaa aataaaaatt gcttaaattt tatacaagga gaattgaaat gacagcaaca   7380
aacgcaaact ataaaaaagg ctttatccca tttgctatag cagcgttact agtaggtctt   7440
ataggtggtt tcacagccgt tctagcacct gcattcgtag cagatatggg tcttaacgat   7500
aacaatacta catggatagc actagcgctt gcaatgtcta cagctgcatg tgctccaata   7560
cttggtaaat taggtgacgt acttggacgt cgtaaaactt tattattagg aatcatagta   7620
ttcacaatag gtaacgtatt aacagcaata gcatcttcat taatattcat gctaggtgca   7680
agatttatag ttggggttgg tacagcggct atagctccag ttataatggc ttacatagtt   7740
acagaatatc caccagaaga aactggtaag ggattcgctc tttatatgtt aatatcaagt   7800
gctgcagttg ttgttggtcc aacttgtggt ggattaataa tgcaggcatt tggatggaga   7860
atgatgatgt gggtttgtgt tgccctttgt gtagtaacat tcttcatatg ttcagtaatg   7920
attaagaaaa cagactttga aaagaaaagt cttgataact tcgataaaaa aggtgcagta   7980
tgcgtactaa tattcttcag tttagtatta tgtataccat catttggaca gaatataggt   8040
```

tggacatcag cgccattcct aggtgttaca gcagtagctt tagtaacatt attcttatta 8100
ataaaagctg aaagcagtgc agaaaaccca atattaagtg gtaaatttat gaaacgtaaa 8160
gaattcatat taccagtatt aatattattc cttactcagg gattaatgca ggctaacatg 8220
actaacgtaa tattattcgt tagagctact cagccagaaa atacaataat atcaagtttc 8280
gcaatatcaa tcctttacat aggtatgtct ttaggttcag tattcatagg acctatggca 8340
gataaaaaag aaccaaaaac tgtacttaca ggatcacttc tattcactgg tataggttgt 8400
gcaatgatgt acttcttcac agaaactgca ccattcgcaa tgttagctgg atctctagga 8460
atgttaggta taggacttgg aggaaatgct acaatactaa tgaaagtttc attatctgga 8520
ttatctcagg cagaagctgg atcaggaaca ggaacatacg gattattcag agatatatca 8580
gctccatttg gtgttgcggt attcgtacca ctatttgcaa acacagttac aacaagaatg 8640
gctggagtaa tggctaacgg aactgcagaa gctgctgcta aatcattagc atctgtttct 8700
tctatacata cattagcatt agttgaagta tgctgtgtaa tattagcaat agttgcagtt 8760
agaatgctac caaaaataca caataaataa tttaaaaata ataacagagt tgaaaaaaca 8820
ctcaattaaa agaggggcct tgagcccctt ttttagtgta aaaatgacaa aatactatca 8880
atttatataa atgataatta aactcgtcaa ccaaagaaat attcacaaag tagataataa 8940
tagatattca aaaagtgata tattattagg caaaaagtgc aagaaattag cgagtattcg 9000
acaacttttt gtccaatggt agaaaagaat atttgttatc ataaatatag acaaagggct 9060
ttgaccaaaa ctaaggaaaa agtttgcata atataaaaaa taaaataaaa taaaaaaata 9120
aaaataaaat aaaagcgaaa ggaaaaaaca acatcatgga tatgaaaaat tctaaactat 9180
tctcaccttt aacaatagga tcattaacat taaacaacag agttggtatg gcaccaatga 9240
gtatggacta cgaagctgct gacggaacag ttccaaaaag attagcagat atatttgttc 9300
gtagagctga aggtggaaca ggatatgtaa caatagacgc ggtaacaata gatagtaaat 9360
ataaatatat gggtaataca actgctttag attctgatga tttagttact cagttcaaag 9420
aatttgcaac aagagttaga gaagcaggaa gcacattaat acctcaggtt atacatccag 9480
gaccagaatc aatatgtgga tacagacaca tagcaccact tggaccatca gttaatacaa 9540
atgctaactg ccacgtgagc cgtgctataa gtgtagatga aatacatgaa ataataaaac 9600
agtttggaca ggctgctaga agagttgaag aagcaggatg cggtggtata ggattacact 9660
gtgcacatgc ttacatgcta ccaggttcat tcttatctcc attaagaaac aaaagaatgg 9720
atgaatacgg cggatgtcta gataacagag caagattcgt aatagaaatg atagaagaag 9780
ttcgtagaaa tgtaagtcct gatttcccaa taatgcttag aatatctggg gatgaaagaa 9840
tgataggagg aaactcttta gaagatatgt tatacttagc tccaaaattt gttgaagctg 9900
gtgtaaatat gtttgaagtt tctggaggta ctcagtacga aggattagaa cacataatac 9960
caagtcagaa caaaagcata ggtgtaaacg tacacgaagc atctgaaatc aaaaaagttg 10020
tagatgttcc agtttacgct gttggtaaaa taaatgacat aagatacgct gctgaaatag 10080
ttgaaagagg actagttgat ggggtatcaa taggtagacc attattagca gatccagact 10140
tatgtaataa agcaaaagaa aacttatttg atgaaataac tccatgtgca agctgtggag 10200
gaagctgtat aagccgtact gcagatagac ctcagtgtcg ttgccatata aacccaagag 10260
ttggattcga atatgattat ccagaagttc cagctgaaaa atctaaaaaa gttctagttg 10320
taggtgctgg acctggtggt atgatggcag cagttacagc agctgaaaga ggacatgatg 10380

-continued

```
taacactttg ggaagctgac actcagatag gtggacagat aaacttagca gtagtagctc  10440

caggtaaaca ggaaatgact aaatggttat ctcacttaaa ctacagagct aaaaaagctg  10500

gagttaaaat ggtattagga aaagaagcta cagtagaaaa cataaaagaa tttgctccag  10560

aagcagttat agttgcaaca ggtgctagac cattagttcc accaataaaa ggaactcagg  10620

actacccagt tcttacagct catgacttct taagaggaaa attcgttata ccaaaaggaa  10680

aagtttgtgt actaggtgga ggagctgttg cttgtgaaac tgcagaaaca gtattagaaa  10740

acgctagacc aaacgcattc actagaggat ttgatgctag tatcggtgat gtagatgtta  10800

cattagtaga aatgttacca cagttattaa caggagtatg tgctccaaat agaactccat  10860

taataagaaa acttaaaaac aaaggtgttc atataaatgt aaatactaaa atattagaag  10920

taactgacca cgacgttaaa gttcagagag ctgacggtgc agaagaatgg ttaaaaggat  10980

tcgactacat actattcgga cttggttcta gaaactacga tccaatatct gaacagataa  11040

aagaattcgt tccagaagta cacgttgttg ggatgctaa gagagctaga caggcaagct  11100

ttgcaatgtg ggaagctttc gaagcagcat acagcttata a                      11141
```

<210> SEQ ID NO 2
<211> LENGTH: 1393
<212> TYPE: DNA
<213> ORGANISM: Clostridium hiranonis

<400> SEQUENCE: 2

```
acatgcaagt cgagcgattc tcttcggaga agagcggcgg acgggtgagt aacgcgtggg     60

taacctgccc tgtacacacg gataacatac cgaaaggtat gctaatacgg gataatatat    120

aagagtcgca tgacttttat atcaaagatt tttcggtaca ggatggaccc gcgtctgatt    180

agcttgttgg cggggtaacg gcccaccaag gcgacgatca gtagccgacc tgagagggtg    240

atcggccaca ttggaactga gacacggtcc aaactcctac gggaggcagc agtggggaat    300

attgcacaat gggcgcaagc ctgatgcagc aacgccgcgt gagcgatgaa ggccttcggg    360

tcgtaaagct ctgtcctcaa ggaagataat gacggtactt gaggaggaag ccccggctaa    420

ctacgtgcca gcagccgcgg taatacgtag ggggctagcg ttatccggat ttactgggcg    480

taaagggtgc gtaggcggtc tttcaagtca ggagttaaag gctacggctc aaccgtagta    540

agctcctgat actgtctgac ttgagtgcag gagaggaaag cggaattccc agtgtagcgg    600

tgaaatgcgt agatattggg aggaacacca gtagcgaagg cggctttctg gactgtaact    660

gacgctgagg cacgaaagcg tggggagcaa acaggattag ataccctggt agtccacgct    720

gtaaacgatg agtactagtt gtcggaggtt acccccttcgg tgccgcagct aacgcattaa   780

gtactccgcc tggggagtac gcacgcaagt gtgaaactca aaggaattga cggggacccg    840

cacaagtagc ggagcatgtg gtttaattcg aagcaacgcg aagaacctta cctaggcttg    900

acatccttct gaccgaggac taatctcctc tttccctccg ggacagaagg tgacaggtgg    960

tgcatggttg tcgtcagctc gtgtcgtgag atgttgggtt aagtcccgca acgagcgcaa   1020

cccttgtctt tagttgccat cattaagttg ggcactctag agagactgcc agggataacc   1080

tggaggaagg tggggatgac gtcaaatcat catgcccctt atgcctaggg ctacacacgt   1140

gctacaatgg gtggtacaga gggcagccaa gccgtgaggt ggagcaaatc ccttaaagcc   1200

attctcagtt cggattgtag gctgaaactc gcctacatga agctggagtt actagtaatc   1260

gcagatcaga atgctgcggt gaatgcgttc ccgggtcttg tacacaccgc ccgtcacacc   1320

atgggagttg gagacacccg aagccgacta tctaaccttt tgggagaagt cgtcccctc    1380
```

gaatcaatac ccc 1393

<210> SEQ ID NO 3
<211> LENGTH: 9743
<212> TYPE: DNA
<213> ORGANISM: Clostridium scindens

<400> SEQUENCE: 3
aaaagatatt aagcattaag aaaatgcaca aaaaatcagc gtgtgagagg gagggcaagg 60
agttgaagcg tgactttttt aacaagttta atttggggac atcgaacttt gtcacgccgg 120
gaaaacagtt ggaatacgtt tcggaatgca agccagattc tactgcggtc atttgcttag 180
ataaagaaca gaactgttcc gttattactt ggcatcagct gcacgtctat tccagccagc 240
tggcatggta ccttatagaa aatgagattg gcccggggtc gatcgtactt acaatgtttc 300
cgaacagcat cgagcacatt attgcggtat ttgcaatctg gaaggcgggc gcctgctata 360
tgcccatgtc ctataaggcg gcggaatccg agatcaggga ggcctgcgat accatccacc 420
cgaatgcggc ttttgcggaa tgcaagattc caggattaaa attctgcctt agcgcagacg 480
agatatatga ggcgatggaa ggaagatcca aggagatgcc ttcggaccgt ctggccaatc 540
cgaacatgat atccttatca ggcggaacca gcggaaagat gaagttcatc cgtcagaacc 600
ttccatgcgg gctggacgat gagacgatca gaagctggtc tttgatgtct ggaatgggat 660
ttgagcagcg ccagctgctg gtaggcccgc tgtttcatgg cgcgcctcac tccgcggcgt 720
ttaatggact gttcatgggc aacaccctgg tactgaccag gaacctttgc ccgggaaata 780
tcctgaacat gattaagaaa tataagattg aatttataca gatggtgccg accctgatga 840
accggcttgc caaactggag ggagtcggaa aagaagactt tgcatccctg aaggcgctgt 900
gccatacagg gggcgtctgt tctccctggc ttaagcagat ctggatcgac ctgctggggc 960
ctgaaaagat ctatgagatg tattccatga cggaatgcat cggccttacc tgcatccggg 1020
gagacgagtg ggtgaagcat ccgggaagca tcggacggcc agtgggcgat agcaaggtgt 1080
ctatccggga tgagaatggc aaggaagttg cgccttttga gattggcgag atctatatga 1140
cagcgccggc ctcctatctg gttaccgagt acatcaattg ggaaccgctg gaagtgaaag 1200
agggaggctt ccgaagcgta ggggatatcg gctacgtgga tgagcagggc tatctgtact 1260
tttctgaccg gcgcagcgac atgctggtat caggcggaga aaacgtgttc gccaccgaag 1320
tcgagacggc gcttttgaga tataaggata tcctggacgc tgtagtggta gggataccgg 1380
atgaagatct ggggcgaagg ctccatgcgg tcattgagac agggaaagag ataccggcag 1440
aggaactgaa aacattcctg agaaagtatc tgactccata taagatacca aagacgttcg 1500
agttcgtaag gagcatacga aggggagaca atggaaaggc cgacaggaag cggatcctgg 1560
aagattgtat tgcccgcggg ggatgattct ataaatgcaa agaaaacaaa ttatataaag 1620
gaggagtaac aaaatgagtt acgaagcact tttttcacca ttcaaggtca gaggactgga 1680
acttaaaaac cgtatcgtcc tgcctggaat gaacaccaag atggcaaaga acaagcacga 1740
cataggcgag gatatgatag cctaccatgt tgccagggca aaagcgggat gcgcgttaaa 1800
tatatttgaa tgcgtagcat tatgtccggc gcctcacgct tatatgtata tggggcttta 1860
tacggaccat catgtagaac agcttaagaa attgacggat gcagtccatg aagcaggcgg 1920
caagatgggc atccagctgt ggcatggagg attcagcccg cagatgttct ttgacgagac 1980
caacaccctg gaaactccgg acactcttac ggtagagagg attcatgaga tcgtagaaga 2040
attcggacgc ggcgcaagga tggctgttca ggctggattt gacgcagtag aattccatgc 2100
ggctcacagt tatctgcctc acgagttctt aagccctgga atgaacaaac gtacggatga 2160
gtacggcgga agttttgaga accgctgcag attctgttat gaagtcgttc aggcaatccg 2220
ttccaatatc ccggatgaca tgccattctt tatgcgtgca gactgcatcg acgaattaat 2280
ggaacagacc atgacagagg aagagatcgt tacatttatc aataagtgcg cagaacttgg 2340
cgtggatgtg gcagaccttt cccgtggaaa cgcgacttca ttcgcaaccg tatatgaagt 2400
tccgccattc aacctggctc atggcttcaa catagagaat atttacaaca tcaaaaagca 2460
gatcaatatc ccggttatgg gagttggccg tatcaataca ggagagatgg caaacaaggt 2520
cattgaagaa ggcaagtttg acctggtagg catcggacgc gcccagcttg cagatccaaa 2580
ctggatcacc aaagtaagag aaggcaaaga agacctgatc cgccactgta tcggatgtga 2640
ccagggatgc tatgacgcag tcatcaatcc aaagatgaag catatcacct gcacccacaa 2700
tccaggattg tgcttagagt atcagggaat gccaaagaca gacgctccta agaaagtcat 2760
gatcgtagga ggcggaatgg caggcatgat cgctgcggaa gtattaaaga ccagaggcca 2820
taacccggta atcttcgagg catccgacaa gcttgcagga cagttcaggc tggcaggcgt 2880
agcgccgatg aagcaggatt gggcagatgt tgcagaatgg gaagcaaaag aagtagagcg 2940
ccttggaatc gaagtacgtc tgaataccga agtgactgca gagaccatca aggaattcaa 3000
tccggataat gtcatcatcg cagtaggctc tacctatgcg ctgcctgaga ttccgggaat 3060
cgacagccca agcgtatact cccagtatca ggtactgaaa ggggaagtaa atccgacagg 3120
ccgtgtagcc gttatcggat gcggactggt tggtacggaa gtcgcagaac ttctggcatc 3180
cagaggcgca caggtaatcg cgatcgagag gaagggcgta ggtaccggcc ttagcatgct 3240
tcgcagaatg ttcatgaacc cggaattcaa atattacaag atcgccaaga tgtccggaac 3300
aaatgtcacc gctttagagc agggcaaggt tcactacatc atgacagaca agaagaccaa 3360
agaagtgacg cagggagtcc tggaatgcga cgctaccgtt atctgtacag gaattaccgc 3420
acgtccaagc gatgggctta aggcaagatg cgaagaactt ggaatcccgg ttgaggtgat 3480
cggagacgct gctggcgcaa gagactgcac gatcgcgaca cgcgaaggct atgacgcagg 3540
aatggcaatc tagaaaatca gaacttatca atcttacata tagaaaggat gatacatatg 3600
acattagaag agagagttga agcattagaa aaagaattgc aggagatgaa ggatattgag 3660
gcaatcaagg aactgaaagg aaagtatttc cgctgcctgg acggaaagat gtgggatgag 3720
ctggagacca ccctgtcacc aaatatcgta acctcttatt ccaacgggaa actggtattc 3780
catagcccga aggaagttac cgattactta aagagctcga tgccaaaaga agagatcagc 3840
atgcatatgg gccacacgcc ggagatcacc attgacagcg agactacggc tacgggcaga 3900
tggtatctgg aagatagact gatctttacg gacggtaagt acaaagacgt aggaatcaat 3960
ggcggcgcgt tctatacaga caaatatgag aagatagacg gccagtggta catccttgaa 4020
accggctatg tacgaatcta tgaagaacat ttcatgcgtg atccaaagat ccatatcacg 4080
atgaacatgc acaaataaga atattgtaaa agaaaggcag gagtaagagt atgaatctcg 4140
tacaagacaa agttacgatc atcacaggcg gcacaagagg tattggattc gccgctgcca 4200
aaatatttat cgacaatggc gcaaaagtat ccatcttcgg agagacgcag gaagaagtag 4260
atacagcgct tgcacagtta aaagaacttt atccggaaga agaggttctg ggattcgcgc 4320
cggatcttac atccagagac gcagttatgg cagcggtagg ccaggtagca cagaaatatg 4380
gcagactgga tgtcatgatc aacaatgcag gaattaccag caacaacgta ttctccagag 4440

```
tgtctgaaga agagttcaag catattatgg acatcaacgt aacaggcgta ttcaacggcg   4500
catggtgcgc ataccagtgc atgaaggatg ccaaaaaggg cgttatcatc aacacggcat   4560
ccgttacagg catcttcgga tcactctcag gcgtaggata tccggccagc aaggcaagcg   4620
tgatcggact cacccatgga cttggaagag agatcatccg caagaatatc cgtgtagtag   4680
gagtggctcc tggagttgtg aacacggata tgaccaatgg caatcctccg gagatcatgg   4740
aaggatatct gaaggcgctt ccgatgaaga gaatgcttga gccggaagag atcgctaatg   4800
tatacctgtt cctggcatct gacttggcaa gcggcattac ggctactacg gtcagcgtag   4860
acggggctta cagaccataa ttttaatttt tactaagtag aatatgtgat atagaaaagg   4920
agatataaaa acatggctgg aataaaagat tttccaaaat tcggagctct tgcagggctt   4980
aagatacttg acagcggatc taacatcgcc ggacctttag gcggaggcct tctggcagaa   5040
tgcggagcaa cggtcatcca ttttgaagga ccaaagaaac ctgataacca gagaggatgg   5100
tacggctatc cacagaatca ccgtaatcag ctgtctatgg tagcagacat caaatctgaa   5160
gaaggaagaa agatcttcct tgatctgatc aaatgggcag atatctgggt agagtcatcc   5220
aaaggcggac agtatgacag gctgggactt tccgatgaag tcatctggga agtaaatcct   5280
aagattgcca tcgtgcacgt atccggatat ggacagacag gagacccgtc ttacgttaca   5340
cgtgcatcct atgacgcagt aggccaggca ttcagcggct atatgtcact gaacggaaca   5400
acggaagcgc tgaagatcaa tccttatctg agcgatttcg tatgcggact taccacatgc   5460
tgggctatgc ttgcctgcta tgtaagcacc attcttaccg gaaaaggcga atctgttgac   5520
gttgcacagt acgaagcgct ggcacgtatc atggacggac gtatgatcca gtacgctaca   5580
gacggcgtga agatgccaag aaccggcaat aaggatgcgc aggctgccct gttcagcttc   5640
tacacctgta aagacggacg tacgatcttt atcggaatga ctggcgcgga agtatgtaag   5700
agaggcttcc cgatcatcgg acttccggta cctggaaccg gagacccgga cttcccggaa   5760
ggcttcacag gctggatgat ctatactcct gtaggacaga gaatggaaaa ggctatggag   5820
aagtatgtat ctgagcatac gatggaagaa gtagaggctg agatgcaggc acaccagatt   5880
ccatgccaga gagtatacga gctggaagac tgcctgaacg atcctcactg gaaagcacgt   5940
ggaactatta cggagtggga tgacccgatg atgggacata tcacaggcct tggactgatc   6000
aacaagttca agagaaatcc ttccgaaatc tggagaggcg ctccgctgtt cggtatggat   6060
aaccgcgata tcctgaaaga cctgggatat gacgatgcaa agatcgatga actctatgag   6120
cagggcatcg tcaatgaatt cgaccttgac actactatca aacgctatag actggatgaa   6180
gtaattccac atatgagaaa gaaagaggag taagagtatg agcaccgtag ccaatccaaa   6240
ttataagaaa ggttttgtcc cctttgcaat tgcagcactc ctggtgagcc tgatcggcgg   6300
ttttaccgcc gttctcggcc cggccttcgt ggcggaccag ggattgact ataataatac   6360
cacatggatt tccctggcgc tggcgatgtc ttccgccgca tgcgctccaa tccttggaaa   6420
actgggagac gtgctaggac gcaggacgac gctgcttctg ggtattgtga tctttgcggc   6480
cggcaatgtg ctgacagccg tagccacgtc cctgatattc atgctggcag cccgttttat   6540
cgtaggtatc ggaacagcag cgatctcacc gatcgttatg gcctatatcg taaccgagta   6600
tccgcaggag gagacaggaa aggcctttgg cctgtatatg ctgatctcca gcggcgccgt   6660
cgtggtagga cctacctgtg gcggcctgat catgaatgcg gctggctgga gagtcatgat   6720
gtgggtatgc gtcgctctgt gcgtcgttgt attcctgatc tgcacattct ccatcaagaa   6780
```

```
gactgcattt gagaagaaga gcatggcagg atttgacaag ccgggcgcag ccctggtagt   6840
cgtattcttc agtttgttcc tgtgcatccc atccttcgga cagaatatcg gatggtcttc   6900
cacagcattt atcgcagcag cggcagtagc gctggtagca cttttcatcc tggtaatggt   6960
agaaaagaaa gcgaagagtc cgatcatgaa cggcaagttt atggcacgca aggaattcgt   7020
gcttccagta ttgatcctgt tccttacaca gggacttatg atggcaaata tgaccaatgt   7080
catcgtgttc gtgcgctata cgcagccgga caatgtcatt atatcaagtt ttgcgatctc   7140
catcatgtac ataggaatgt ccttaggctc cgttatcatt ggacctgttg cagataagaa   7200
agagccaaag acggttctga cattctctct ggtactgaca gccatcggct gtgcgctgat   7260
gtatctgttc aaggcagatt cctccgtcgc tatctttgcg gcatccttgg gaatccttgg   7320
atttggcctt ggaggaaatg caaccatctt catgaaggta gcgctttccg gcctgtccag   7380
cgaagtagct ggctctggta ctggaaccta tggcctgttc agagatatct cggcaccatt   7440
cggcgtggca gtgttcgtgc ctatgtttgc caacggcgta acagcgaata ttgcgaaata   7500
cgcgtcaggc ggcatggaag aaggcgccgc tacggtaaaa gcagccatct catccatcca   7560
gacgctgaca ctggttgaac ttggatgtat cgttgtggga atcatccttg tgagaatgct   7620
gccaagaatc tatcagaaga aagaggcata aataagttaa gaaaagaggt aattataaat   7680
ggatatgaaa cattccagat tattttcgcc gcttcagatc ggatccctga cactgtctaa   7740
ccgtgtcggc atggctccca tgagcatgga ctatgaagca gcagacggaa ctgtgcccaa   7800
gaggctggcg gacgtatttg tccgccgcgc cgagggaggc acaggctacg tcatgatcga   7860
cgcggtgacg atagacagca agtatcctta tatgggaaat acaacggccc ttgaccgtga   7920
tgaactggtt ccccagttta aggaatttgc tgacagagta aaagaagcag gcagcacgct   7980
ggtgccgcag atcattcatc cgggtccgga atccgtatgc ggctaccggc atatcgctcc   8040
gcttggacct tctgccaaca ccaatgcaaa ctgccacgtg agcagatcga tcagcataga   8100
tgagatccat gacatcatta agcagttcgg ccaggcggca cgccgcgccg aagaagcagg   8160
atgcggggca atctccctgc actgcgcgca tgcgtatatg ctgccaggat ccttcctgtc   8220
accgcttcgc aacaagcgca tggatgaata tggcggaagc cttgacaacc gtgcccgttt   8280
cgtgatcgag atgattgagg aggcccgcag gaatgtgagt cctgatttcc cgatcttcct   8340
tcgtatctcc ggagacgaga gaatggtagg aggcaacagc cttgaagata tgctctacct   8400
ggcaccgaag ttcgaggctg ccggcgtaag catgctggaa gtatccggcg gaacccagta   8460
tgaaggcctg gaacatatca ttccttgcca gaataagagc aggggcgtca atgtatatga   8520
agcttctgag atcaagaaag tagtgggcat cccggtatac gcagtaggaa agatcaacga   8580
tatacgctat gcggcagaga tcgtagaacg cggcctggta gacggcgtgg ctatgggacg   8640
tccgcttctg gcagatccgg acctttgcaa gaaggcagtg gaaggccagt ttgacgagat   8700
cactccatgc gcaagctgcg gcggaagctg catcagccgt tctgaggcag cgcctgagtg   8760
ccattgccat attaatccaa ggcttggccg ggagtatgaa ttcccggatg tgcctgccga   8820
gaagtccaag aaggtactgg ttatcggcgc aggccctgga ggaatgatgg ctgccgtgac   8880
agctgcggaa cgcggccatg atgttacggt atgggaggct gacgacaaga tcggcggcca   8940
gctgaacctg gcagtagtgg ctcctggcaa gcaggagatg acccagtgga tggtacatct   9000
gaactatcgc gcgaagaaag caggcgtgaa gtttgaattc aataaagaag cgacggcaga   9060
agatgtcaag gcgctggcgc cggaagcagt gatcgttgct acaggcgcga agccgctggt   9120
tcctccgatt aaaggaacac aggattatcc ggtgcttact gcccatgatt tccttcgcgg   9180
```

```
caagttcgtg attccgaagg gacgcgtctg cgtgctggga ggaggcgcgg ttgcctgcga   9240

gactgccgag acagccctgg agaatgcacg tccgaattct tataccagag gatacgatgc   9300

aagcatcgga gatatcgatg tcacgcttgt ggagatgctt ccgcagctcc ttaccggcgt   9360

atgcgcgccg aaccgcgagc ctttgatccg caagttaaag agcaagggcg tacacatcaa   9420

cgtcaatacc aagatcatgg aagtaacaga ccatgaagta aaggttcaga gacaggatgg   9480

aacgcaggaa tggctggaag gatttgacta tgtcctcttt ggccttggtt ccagaaatta   9540

cgatccgctt tcagagaccc tcaaggaatt cgttccggaa gtacatgtca tcggcgatgc   9600

cgtaagggcg cgccaggcaa gctacgcaat gtgggaagga tttgagaagg catacagcct   9660

gtaaaagcgg tttgagtaaa aggaggctta agaaatggca gtgaaggcaa tctcaggctg   9720

cgacaaggat caggaactga tca                                           9743
```

```
<210> SEQ ID NO 4
<211> LENGTH: 1531
<212> TYPE: DNA
<213> ORGANISM: Clostridium scindens

<400> SEQUENCE: 4

gagagtttga tcctggctca ggatgaacgc tggcggcgtg cctaacacat gcaagtcgaa     60

cgaagcgctt ccgctagatt ttcttcggag atgaaggcgg ctgcgactga gtggcggacg    120

ggtgagtaac gcgtgggcaa cctgccttgc actgggggat aacagccaga aatggctgct    180

aataccgcat aagaccgaag cgccgcatgg cgcagcggcc aaagccccgg cggtgcaaga    240

tgggcccgcg tctgattagg tagttggcgg ggtaacggcc caccaagccg acgatcagta    300

gccgacctga gagggtgacc ggccacattg ggactgagac acggcccaga ctcctacggg    360

aggcagcagt ggggaatatt gcacaatggg ggaaaccctg atgcagcgac gccgcgtgaa    420

ggatgaagta tttcggtatg taaacttcta tcagcaggga agaagatgac ggtacctgac    480

taagaagccc cggctaacta cgtgccagca gccgcggtaa tacgtagggg gcaagcgtta    540

tccggattta ctgggtgtaa agggagcgta gacggcgatg caagccagat gtgaaagccc    600

ggggctcaac cccgggactg catttggaac tgcgtggctg gagtgtcgga gaggcaggcg    660

gaattcctag tgtagcggtg aaatgcgtag atattaggag gaacaccagt ggcgaaggcg    720

gcctgctgga cgatgactga cgttgaggct cgaaagcgtg gggagcaaac aggattagat    780

accctggtag tccacgccgt aaacgatgac tactaggtgt cgggtggcaa ggccattcgg    840

tgccgcagca aacgcaataa gtagtccacc tggggagtac gttcgcaaga atgaaactca    900

aaggaattga cggggacccg cacaagcggt ggagcatgtg gtttaattcg aagcaacgcg    960

aagaacctta cctgatcttg acatcccgat gccaaagcgc gtaacgcgct ctttcttcgg   1020

aacatcggtg acaggtggtg catggttgtc gtcagctcgt gtcgtgaggt gttgggttaa   1080

gtcccgcaac gagcgcaacc cctatcttca gtagccagca tttcggatgg gcactctgga   1140

gagactgcca gggacaacct ggaggaaggt ggggatgacg tcaaatcatc atgcccctta   1200

tgaccagggc tacacacgtg ctacaatggc gtaaacaaag ggaggcgaac ccgcgagggt   1260

gggcaaatcc caaaaataac gtctcagttc ggattgtagt ctgcaactcg actacatgaa   1320

gctggaatcg ctagtaatcg cgaatcagaa tgtcgcggtg aatacgttcc cgggtcttgt   1380

acacaccgcc cgtcacacca tgggagtcag taacgcccga agccggtgac ccaacccgca   1440

agggagggag ccgtcgaagg tgggaccgat aactggggtg aagtcgtaac aaggtagccg   1500
```

tatcggaagg tgcggctgga tcacctcctt c 1531

<210> SEQ ID NO 5
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: source
<222> LOCATION: (1)..(20)
<223> OTHER INFORMATION: /note="Description of Artificial Sequence: Synthetic primer"

<400> SEQUENCE: 5
agagtttgat cmtggctcag 20

<210> SEQ ID NO 6
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: source
<222> LOCATION: (1)..(19)
<223> OTHER INFORMATION: /note="Description of Artificial Sequence: Synthetic primer"

<400> SEQUENCE: 6
gtgccagcmg ccgcggtaa 19

<210> SEQ ID NO 7
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: source
<222> LOCATION: (1)..(20)
<223> OTHER INFORMATION: /note="Description of Artificial Sequence: Synthetic primer"

<400> SEQUENCE: 7
cggttacctt gttacgactt 20

<210> SEQ ID NO 8
<211> LENGTH: 1657
<212> TYPE: DNA
<213> ORGANISM: Helicobacter sp.

<400> SEQUENCE: 8
agagtttgat cctggctcag agtgaacgct ggcggcgtgc ctaatacatg caagtcgaac 60
gatgaaactt ctagcttgct agaagtggat tagtggcgca cgggtgagta atgcataggt 120
aacatgccct ttagtctggg atagccactg gaaacggtga ttaatactgg atactcccta 180
cgggggaaag ggctttcaa taaagaattt ctctttttag tgttttgtgt tgttggcaca 240
aaattctagt atttggaatg agaaattggt gttgtgaagc aatttgtgcg gagattagac 300
ttagtgtctg tcgtgtcagc aaattgcgaa ctcatcgatt tatcatccaa agacgaattt 360
tttattgaaa gccttcgcta aaggattggc ctatgtccta tcagcttgtt ggtgaggtaa 420
tggctcacca aggctatgac gggtatccgg cctgagaggg tgatcggaca cactggaact 480
gagacacggt ccagactcct acgggaggca gcagtaggga atattgctca atgggggaaa 540

```
ccctgaagca gcaacgccgc gtggaggatg aaggttttag gattgtaaac tccttttgta    600
agagaagatt atgacggtat cttacgaata agcaccggct aactccgtgc cagcagccgc    660
ggtaatacgg agggtgcaag cgttactcgg aatcactggg cgtaaagagc gcgtaggcgg    720
gtggtcaagt cagatgtgaa atcctgtagc ttaactacag aactgcattt gaaactgacc    780
atctagagta tgggagaggt aggtggaatt cttggtgtag ggtaaaatc cgtagagatc    840
aagaggaata ctcattgcga aggcgacctg ctggaacatt actgacgctg atgcgcgaaa    900
gcgtggggag caaacaggat tagataccct ggtagtccac gccctaaacg atgaatgcta    960
gttgttgtga ggcttgtcct tgcagtaatg cagctaacgc attaagcatt ccgcctgggg   1020
agtacggtcg caagattaaa actcaaagga atagacgggg acccgcacaa gcggtggagc   1080
atgtggttta attcgatgat acgcgaagaa ccttacctag gcttgacatt gatagaatct   1140
actagagata gtggagtgcc cttttaggga gcttgaaaac aggtgctgca cggctgtcgt   1200
cagctcgtgt cgtgagatgt tgggttaagt cccgcaacga gcgcaaccct cgtccttagt   1260
tgctagcagt ttggctgagc actctaagga gactgccttc gtaaggagga ggaaggtgag   1320
gacgacgtca agtcatcatg gcccttacgc ctagggctac acacgtgcta caatggggtg   1380
cacaaagaga tgcaatagtg tgagctggag ccaatctcta aaacatctct cagttcggat   1440
tgtagtctgc aactcgacta catgaagctg gaatcgctag taatcgcaaa tcagcaatgt   1500
tgcggtgaat acgttcccgg gtcttgtact caccgcccgt cacaccatgg gagttgtatt   1560
tgccttaagt cggaatgcta aattggctac cgcccacggc agatgcagcg actggggtga   1620
agtcgtaaca aggtaaccgt aggtgaacct gcggttg                             1657
```

<210> SEQ ID NO 9
<211> LENGTH: 1340
<212> TYPE: DNA
<213> ORGANISM: Campylobacter sp.

<400> SEQUENCE: 9

```
agtgaacgct ggcggcgtgc ctaatacatg caagtcgaac gatgaagctt ctagcttgct     60
agaagtggat tagtggcgca cgggtgagta aggtatagtt aatctgccct acacaagagg    120
acaacaccta gaaatgggtg ctaatactct atactcctgc ttaacacaag ttgagtaggg    180
aaagtttttc ggtgtaggat gagactatat agtatcagct agttggtaag gtaaaggctt    240
accaaggcta tgacgcttaa gaggtctgag aggatgatct ctcacactgg aactgagaca    300
cggtccagac tcctacggga ggcagcagta gggaatattg cgcaatgggc gaaagcctga    360
cgcagcaacg ccgcgtggag gatgacactt ttaggagcgt aaactccttt tcttagggaa    420
gaattctgac ggtacctaag gaataagcac cggctaactc cgtgccagca gccgcggtaa    480
tacggagggt gcaagcgtta ctcggaatca ctgggcgtaa agggcgcgta ggcggattat    540
caagtctctt gtgaaatcta atggcttaac cattaaactg cttgggaaac tgatagtcta    600
gagtgaggga gaggcagatg gaattggtgg tgtaggggta aaatccgtag atatcaccaa    660
gaatacccat tgcgaaggcg atctgctgga actcaactga cgctaaggcg cgaaagcgtg    720
gggagcaaac aggattagat accctggtag tccacgccct aaacgatgta tgctagttgt    780
tgggctgcta gtcagctcag taatgcagct aacgcattaa gcataccgcc tggggagtac    840
ggtcgcaaga ttaaaactca aaggaataga cggggacccg cacaagcggt ggagcatgtg    900
gtttaattcg aagatacgcg aagaacctta cctaggcttg atatccaaca aagcttctag    960
agatagaagt gtgctagctt gctagaatgt tgagacaggt gctgcacggc tgtcgtcagc   1020
```

```
tcgtgtcgtg agatgttggg ttaagtcccg caacgagcgc aacccacgta tttagttgct   1080

aacacttcgg gtgagcactc taaatagact gccttcgtaa ggaggaggaa ggtgtggacg   1140

acgtcaagtc atcatggccc ttatgcctag ggcgacacac gtgctacaat ggcatataca   1200

atgagacgca ataccgcgag gtggagcaaa tctataaaat atgtcccagt tcggattgtt   1260

ctctgcaact cgagagcatg aagccggaat cgctagtaat cgcaaatcag ccatgttgcg   1320

gtgaatacgt tcccgggtct                                               1340
```

<210> SEQ ID NO 10
<211> LENGTH: 1378
<212> TYPE: DNA
<213> ORGANISM: Succinivibrio sp.

<400> SEQUENCE: 10

```
catgcaagtc gaacggtaac atagaggaag cttgctttct ctgatgacga gtggcggacg     60

ggtgagtaag gtctgggaaa ctgcctgaca gagggggaca acaactggaa acggttgcta    120

ataccgcata caccctgagg gggaaagtcg aaagacgctg tcagatgtgc ccagatggga    180

ttagctagta ggtgaggtaa aggctcacct aggcgacgat ctctagctgg tctgagagga    240

tgatcagcca cattgggact gagacacggc ccagactcct acgggaggca gcagtaggga    300

atattgcaca atgggggaa ccctgatgca gccatgccgc gtgtgtgaag aaggccttcg    360

ggttgtaaag cactttcaga ggggaggaaa atgacgttac cctcagaaga agcaccggct    420

aactccgtgc cagcagccgc ggtaatacgg agggtgcaag cgttaatcgg aataactggg    480

cgtaaagggc atgcaggcgg ttctgcaagt agggtgtgaa agcccggggc tcaacctcgg    540

aattgcactc taaactgtgg gactagagta ttgcaggggg agacggaatt ccaggtgtag    600

cggtggaatg cgtagagatc tggaagaaca ccaaaggcga aggcagtctc ctgggcaaat    660

actgacgctc atatgcgaaa gcgtgggtag caaacaggat tagataccct ggtagtccac    720

gccgtaaacg atgttgatta gaagcttgct tgtaagagtg ggtttcgcag ctaacgcgat    780

aaatcaaccg cctggggagt acggccgcaa ggttaaaact caaatgaatt gacgggggcc    840

cgcacaagcg gtggagcatg tggtttaatt cgacgcaacg cgatgaacct tacctgatct    900

tgacatcgcg agaattactt gtaatgagta agtgccttcg ggaactcgca gacaggtgct    960

gcatggctgt cgtcagctcg tgtcgtgaga tgttgggtta agtcccgcaa cgagcgcaac   1020

ccttgtcctt tgttgccagc gggtagagcc gggaactcaa aggagactgc cagtgataaa   1080

ctggaggaag gtagggatga cgtcaagtca tcatggccct tacggtcagg gctacacacg   1140

tgctacaatg ggcgtacag agggaaacga aactgcgagg tggagtggaa cccagaaagc   1200

gtccctaagt tcggattgga gtctgcaact cgactccatg aagtcggaat cgctagtaat   1260

cgcaaatcag aatgttgcgg tgaatacgtt cccgggcctt gtacacaccg cccgtcacac   1320

catgggagtg gattgcacca gaagtggcca gcctaactgc aaagagggcg gtaccacg     1378
```

<210> SEQ ID NO 11
<211> LENGTH: 253
<212> TYPE: DNA
<213> ORGANISM: Anaerobiospirillum sp.

<400> SEQUENCE: 11

```
tacggagggt gcaagcgtta atcggaataa ctgggcgtaa agggcatgta ggcggaaagg     60

caagcaagat gtgaaagacc tggctcaac ctgggttggt cattttgaac tacctttcta    120
```

gagtattgca gagggagatg gaatttcagg tgtagcggtg gaatgcgtag atatctgaaa 180
gaacaccaga ggcgaaggcg gtctcctggg caaatactga cgctgaggtg cgaaagcgtg 240
gggagcaaac agg 253

<210> SEQ ID NO 12
<211> LENGTH: 1357
<212> TYPE: DNA
<213> ORGANISM: Collinsella sp.
<220> FEATURE:
<221> NAME/KEY: modified_base
<222> LOCATION: (766)..(766)
<223> OTHER INFORMATION: a, c, t, g, unknown or other
<220> FEATURE:
<221> NAME/KEY: misc_feature
<222> LOCATION: (766)..(766)
<223> OTHER INFORMATION: n is a, c, g, or t

<400> SEQUENCE: 12
acggcacccc tctccggagg gaagcgagtg gcgaacggct gagtaacacg tggagaacct 60
gccccctccc ccgggatagc cgcccgaaag gacgggtaat accggatacc cccgggcgcc 120
gcatggcgcc cgggctaaag ccccgacggg aggggatggc tccgcggccc atcaggtaga 180
cggcggggtg acggcccacc gtgccgacaa cgggtagccg ggttgagaga ccgaccggcc 240
agattgggac tgagacacgg cccagactcc tacgggaggc agcagtgggg aatcttgcgc 300
aatgggggga accctgacgc agcgacgccg cgtgcgggac ggaggccttc gggtcgtaaa 360
ccgctttcag cagggaagag tcaagactgt acctgcagaa gaagccccgg ctaactacgt 420
gccagcagcc gcggtaatac gtagggggcg agcgttatcc ggattcattg ggcgtaaagc 480
gcgcgtaggc ggcccggcag gccgggggtc gaagcggggg gctcaacccc ccgaagcccc 540
cggaacctcc gcggcttggg tccggtaggg gagggtggaa cacccggtgt agcggtggaa 600
tgcgcagata tcgggtggaa caccggtggc gaaggcggcc ctctgggccg agaccgacgc 660
tgaggcgcga aagctggggg agcgaacagg attagatacc ctggtagtcc cagccgtaaa 720
cgatggacgc tgggtgtggg gggacgatcc ccccgtgccg cagccnacgc attaagcgtc 780
ccgcctgggg agtacggccg caaggctaaa actcaaagga attgacgggg gcccgcacaa 840
gcagcggagc atgtggctta attcgaagca acgcgaagaa ccttacggcg catccccccg 900
aggcccacgg ggggtccgcc gcgtgggtca gaggagcgca tacgggaggt gcatggttgt 960
cgtcagctcg tgtcgtgaga tgttgggtta agtcccgcaa cgagcgcaac cccccgccgcg 1020 tgttgccatc gggtgatgcc gggaacccac gcgggaccgc cgccgtcaag gcggaggagg 1080
gcggggacga cgtcaagtca tcatgcccct tatgccctgg gctgcacacg tgctacaatg 1140
gccggtacag agggatgcca ccccgcgagg gggagcggat cccggaaagc cggccccagt 1200
tcggattggg ggctgcaacc cgcccccatg aagtcggagt tgctagtaat cgcggatcag 1260
catgccgcgg tgaatgcgtt cccgggcctt gtacacaccg cccgtcacac cacccgagtc 1320
gtctgcaccc gaagtcgccg gcccaaccgc aaggggg 1357

<210> SEQ ID NO 13
<211> LENGTH: 1454
<212> TYPE: DNA
<213> ORGANISM: Clostridium sp.
<220> FEATURE:
<221> NAME/KEY: modified_base
<222> LOCATION: (635)..(635)
<223> OTHER INFORMATION: a, c, t, g, unknown or other
<220> FEATURE:
<221> NAME/KEY: misc_feature
<222> LOCATION: (635)..(635)
<223> OTHER INFORMATION: n is a, c, g, or t
<220> FEATURE:
<221> NAME/KEY: modified_base
<222> LOCATION: (704)..(704)
<223> OTHER INFORMATION: a, c, t, g, unknown or other
<220> FEATURE:
<221> NAME/KEY: misc_feature
<222> LOCATION: (704)..(704)
<223> OTHER INFORMATION: n is a, c, g, or t

<400> SEQUENCE: 13
tgagtttgat catggctcag gacgaacgct ggcggcgtgc ctaacacatg caagtcgagc 60
gatgaaattt tcttcggaaa atggattagc ggcggacggg tgagtaacac gtgggtaacc 120
tgccctatag agagggatag ccttccgaaa gggagattaa tacctcataa tatcctagta 180
tcgcatgata catggattaa aggagcaatc cgctatagga tggacccgcg gcgcattagc 240
tagttggtga ggtaacggct caccaaggcg acgatgcgta gccgacctga gagggtgatc 300
ggccacattg ggactgagac acggcccaga ctcctacggg aggcagcagt ggggaatatt 360
gcacaatggg ggaaaccctg atgcagcaac gccgcgtgag tgatgacggt cttcggattg 420
taaagctctg tctttaggga cgataatgac ggtacctaag gaggaagcca cggctaacta 480
cgtgccagca gccgcggtaa tacgtaggtg gcaagcgttg tccggattta ctgggcgtaa 540
agggagcgta ggcggatctt taagtgggat gtgaaatact cgggctcaac ctgggggctg 600
cattccaaac tggggatcta gagtacagga ggggngagtg gaattcctag tgtagcggtg 660
aaatgcgtag agattaggaa gaacaccagt ggcgaaggcg actntctgga ctgtaactga 720
cgctgaggct cgaaagcgtg gggagcaaac aggattagat accctggtag tccacgccgt 780
aaacgatgaa tactaggtgt agggggtgtc aactcccct gtgccgccgc taacgcatta 840
agtattccgc ctggggagta cggtcgcaag attaaaactc aaaggaattg acgggggccc 900
gcacaagtag cggagcatgt ggtttaattc gacgcaacgc gaagaacctt acctagactt 960
gacatcttct gcattaccct taatcgggga agttccttcg ggacagaat gacaggtggt 1020 gcatggttgt cgtcagctcg tgtcgtgaga tgttgggtta agtcccgcaa cgagcgcaac 1080
ccttaagctt agttgccatc attaagttgg gcactctaag ttgactgccg gtgacaaacc 1140
ggaggaaggt ggggatgacg tcaaatcatc atgcccctta tgtctagggc tacacacgtg 1200
ctacaatggc aagtacaaag agaagcaata ctgtgaagtg gagcaaaact caaaaacttg 1260
tctcagttcg gattgtaggc tgaaactcgc ctacatgaag ctggagttgc tagtaatcgc 1320
gaatcagaat gtcgcggtga atacgttccc gggtcttgta cacaccgccc gtcacaccat 1380
gagagttggc aatacccgaa gtccgtaagc taaccgtaag gaggcagcgg ccgaaggtag 1440
ggtcagcgat gggg 1454

<210> SEQ ID NO 14
<211> LENGTH: 253
<212> TYPE: DNA
<213> ORGANISM: Clostridium sp.

<400> SEQUENCE: 14
tacgtaggtg gcgagcgtta tccggattta ctgggcgtaa agggagcgta ggcggatgat 60
taagtgggat gtgaaatacc cgggctcaac ttgggtgctg cattccaaac tggttatcta 120
gagtgcagga gaggagagtg gaattcctag tgtagcggtg aaatgcgtag agattaggaa 180
gaacaccagt ggcgaaggcg actctctgga ctgtaactga cgctgaggct cgaaagcgtg 240
gggagcaaac agg 253

<210> SEQ ID NO 15
<211> LENGTH: 1403
<212> TYPE: DNA
<213> ORGANISM: Allisonella sp.

<400> SEQUENCE: 15
agagtttgat cctggctcag gacgaacgct ggcggcatgc ttaacacatg caagtcgaac 60
ggactgattc cttcgggatg aaagttagtg gcgaacgggt gagtaatgta tgagcaacct 120
gcctctgtca acgggataac agttggaaac gactgctaat acggtatatg accacggcac 180
cgcatggtgc agcggtaaaa gattttatcg gacagagatg ggctcatatc ccattaggta 240
gttggtgaga taacagccca ccaagccgac gatcagtagc cggtctgaga ggatgaacgg 300
ccacactgga actgagacac ggtccagact cctacgggag gcagcagtgg ggaatcttcc 360
gcaatggacg aaagtctgac ggagcaacgc cgcgtgaacg atgaaggtct tcggattgta 420
aagttctgtg atccgggacg aaggcattga ttgagaacat tgattgatgt tgacggtacc 480
ggaaaagcaa gccacggcta actacgtgcc agcagccgcg gtaatacgta ggtggcaagc 540
gttgtccgga attattgggc gtaaagcgcg cgcaggcggc cgtgcaagtc catcttaaaa 600
gcgtggggct taaccccatg aggggatgga aactgcaggg ctggagtgtc ggaggggaaa 660
gtggaattcc tagtgtagcg gtgaaatgcg tagagattag gaagaacacc ggtggcgaag 720
gcgactttct agacgacaac tgacgctgag gcgcgaaagc gtggggagca aacaggatta 780
gataccctgg tagtccacgc cgtaaacgat ggatactagg tgtaggaggt atcgacccct 840
tctgtgccgg agttaacgca ataagtatcc cgcctgggaa gtacgatcgc aagattaaaa 900
ctcaaaggaa ttgacggggg cccgcacaag cggtggagta tgtggtttaa ttcgacgcaa 960
cgcgaagaac cttaccaagc cttgacattg atcgcaatcc gcagaaatgc ggagttcctc 1020
ttcggaggac gagaaaacag gtggtgcacg gctgtcgtca gctcgtgtcg tgagatgttg 1080
ggttaagtcc cgcaacgagc gcaaccccta tcttctgttg ccagcacgta aaggtgggaa 1140
ctcaggagag accgccgcgg acaacgcgga ggaaggcggg gatgacgtca agtcatcatg 1200
ccccttatgg cttgggctac acacgtacta caatgggtgc aaacaaagag aagcgaagtc 1260
gcgagatgga gcggacctca taaacgcact cccagttcag attgcaggct gcaacccgcc 1320
tgcatgaagt aggaatcgct agtaatcgcg ggtcagcata ccgcggtgaa tacgttcccg 1380
ggccttgtac acaccgcccg tca 1403

<210> SEQ ID NO 16
<211> LENGTH: 1375
<212> TYPE: DNA
<213> ORGANISM: Tyzzerella sp.

<400> SEQUENCE: 16
ctggctcagg atgaacgctg gcggcgtgct taacacatgc aagtcgaacg aagagggtta 60
gaatgagagc ttcggcagga tttctttcca tcttagtggc ggacgggtga gtaacgtgtg 120
ggcaacctgc cctgtactgg gggataatca ttggaaacga tgactaatac cgcatgtggt 180
tctcggaagg catcttctga ggaagaaagg atttattcgg tacaggatgg gcccgcatct 240
gattagctag ttggtgagat aacagcccac caaggcgacg atcagtagcc gacctgagag 300
ggtgatcggc cacattggga ctgagacacg gcccaaactc ctacgggagg cagcagtggg 360
gaatattgca caatgggcga aagcctgatg cagcaacgcc gcgtgaagga tgaagggttt 420
cggctcgtaa acttctatca atagggaaga aacaaatgac ggtacctaaa taagaagccc 480
cggctaacta cgtgccagca gccgcggtaa tacgtagggg gcaagcgtta tccggaatta 540
ctgggtgtaa agggagcgta ggcggcatgg taagccagat gtgaaagcct tgggcttaac 600
ccgaggattg catttggaac tatcaagcta gagtacagga gaggaaagcg gaattcctag 660
tgtagcggtg aaatgcgtag atattaggaa gaacaccagt ggcgaaggcg gctttctgga 720
ctgaaactga cgctgaggct cgaaagcgtg gggagcaaac aggattagat accctggtag 780
tccacgccgt aaacgatgag tgctaggtgt cggggaggaa tcctcggtgc cgtagctaac 840
gcaataagca ctccacctgg ggagtacgac cgcaaggttg aaactcaaag gaattgacgg 900
gggcccgcac aagcggtgga gcatgtggtt taattcgaag caacgcgaag aaccttacca 960
aggcttgaca tcccgatgac cgtcctagag ataggacttc tcttcggagc atcggtgaca 1020
ggtggtgcat ggttgtcgtc agctcgtgtc gtgagatgtt gggttaagtc ccgcaacgag 1080
cgcaaccctt gtcactagtt gctacgaaag ggcactctag tgagactgcc ggtgacaaac 1140
cggaggaagg tggggatgac gtcaagtcct catggccctt atgggtaggg cttcacacgt 1200
catacaatgg tcggaacaga gggcagcgaa gccgtgaggc ggagccaatc ccagaaaacc 1260
gatcgtagtc cggattgcag tctgcaactc gactgcatga agtcggaatc gctagtaatc 1320
gcggatcagc atgccgcggt gaatacgttc ccgggtcttg tacacaccgc ccgta 1375

<210> SEQ ID NO 17
<211> LENGTH: 1410
<212> TYPE: DNA
<213> ORGANISM: Bacteroides sp.

<400> SEQUENCE: 17
ggcgcacggg tgagtaacac gtatccaacc tgccgataac tcggggatag cctttcgaaa 60
gaaagattaa tacccgatgg catgtaaaga cctcctggtc tttacattaa agaatttcgg 120
ttatcgatgg ggatgcgttc cattagatag taggcggggt aacggcccac ctagtccacg 180
atggataggg gttctgagag gaaggtcccc cacattggaa ctgagacacg gtccaaactc 240
ctacgggagg cagcagtgag gaatattggt caatggacgc gagtctgaac cagccaagta 300
gcgtgaagga agactgccct atgggttgta aacttctttt atacgggaat aaagtattcc 360
acgtgtggga ttttgtatgt accgtatgaa taaggatcgg ctaactccgt gccagcagcc 420
gcggtaatac ggaggatccg agcgttatcc ggatttattg ggtttaaagg gagcgtaggt 480
ggaagattaa gtcagcctgt gaaagtttgc ggcttaaccg taaaattgca gttgatactg 540
gttttcttga gtgcagtaga ggtgggcgga attcgtggtg tagcggtgaa atgcttagat 600
atcacgaaga actccgattg cgaaggcagc tcactggact gtaactgaca ctgatgctcg 660
aaagtgtggg tatcaaacag gattagatac cctggtagtc cacacagtaa acgatgaata 720
ctcgctgttt gcgatataca gtaagcggcc aagcgaaagc gttaagtatt ccacctgggg 780
agtacgccgg caacggtgaa actcaaagga attgacgggg gcccgcacaa gcggaggaac 840
atgtggttta attcgatgat acgcgaggaa ccttacccgg gcttaaatta cacctgaata 900
gattggaaac attttagccg caaggcaggt gtgaaggtgc tgcatggttg tcgtcagctc 960
gtgccgtgag gtgtcggctt aagtgccata acgagcgcaa cccttatctt cagttactaa 1020
cagttatagc tgaggactct gaagagactg ccgtcgtaag atgtgaggaa ggtggggatg 1080
acgtcaaatc agcacggccc ttacgtccgg ggctacacac gtgttacaat ggggggtaca 1140
gaaggctgct acctggcgac aggatgccaa tccttaaatc ctctctcagt tcggactgga 1200
gtctgcaacc cgactccacg aagctggatt cgctagtaat cgcgcatcag ccatggcgcg 1260
gtgaatacgt tcccgggcct tgtacacacc gcccgtcaag ccatgaaagc cgggggtacc 1320
tgaagtgcgt aaccgcaagg agcgtcctag ggtaaaactg gtaattgggg ctaagtcgta 1380
acaaggtagc cgtaccggaa ggtgcggctg 1410

<210> SEQ ID NO 18
<211> LENGTH: 1394
<212> TYPE: DNA
<213> ORGANISM: Parabacteroides sp.

<400> SEQUENCE: 18
agagtttgat cctggctcag gatgaacgct agcgacaggc ttaacacatg caagtcgagg 60
ggcagcatga tttgtagcaa tacagattga tggcgaccgg cgcacgggtg agtaacgcgt 120
atgcaactta cctatcagag gggatagcc cggcgaaagt cggattaata ccccataaaa 180
caggggtccc gcatgggaat atttgttaaa gattcatcgc tgatagatag gcatgcgttc 240
cattaggcag ttggcggggt aacggcccac caaaccgacg atggataggg gttctgagag 300
gaaggtcccc cacattggta ctgagacacg gaccaaactc ctacgggagg cagcagtgag 360
gaatattggt caatggccga gaggctgaac cagccaagtc gcgtgaagga agaaggatct 420
atggtctgta aacttctttt ataggggaat aaagtggagg acgtgtcctt ttttgtatgt 480
accctatgaa taagcatcgg ctaactccgt gccagcagcc gcggtaatac ggaggatgcg 540
agcgttatcc ggatttattg ggtttaaagg gtgcgtaggt ggtgatttaa gtcagcggtg 600
aaagtttgtg gctcaaccat aaaattgccg ttgaaactgg gttacttgag tgtgtttgag 660
gtaggcggaa tgcgtggtgt agcggtgaaa tgcatagata tcacgcagaa ctccgattgc 720
gaaggcagct tactaaacca taactgacac tgaagcacga aagcgtgggg atcaaacagg 780
attagatacc ctggtagtcc acgcagtaaa cgatgattac taggagtttg cgatacaatg 840
taagctctac agcgaaagcg ttaagtaatc cacctgggga gtacgccggc aacggtgaaa 900
ctcaaaggaa ttgacggggg cccgcacaag cggaggaaca tgtggtttaa ttcgatgata 960
cgcgaggaac cttacccggg tttgaacgta gtctgaccgg aatggaaaca ctccttctag 1020
caatagcaga ttacaaggtg ctgcatggtt gcctcaactc cggcccggaa ggtccggctt 1080
aattgccata acaagcgcac ccttttacca aggttcaaac aggtgaagct tgaagactct 1140
gtggaacctc ccccctaacc tgtgagaaga agtggggata cactcaataa accacggccc 1200
ttaatcccgg ggggaacact ggttacaatg ggttgggaaa gggggcttcc tggcgacagg 1260
atgctaatct ccaaaccatg tctcagttcg gatcggagtc tgcaactcga ctccgtgaag 1320
ctggattcgc tagtaatcgc gcatcagcca tggcgcggtg aatacgttcc cgggccttgt 1380
acacaccgcc cgtc 1394

<210> SEQ ID NO 19
<211> LENGTH: 1451
<212> TYPE: DNA
<213> ORGANISM: Bacteroides sp.

<400> SEQUENCE: 19
gatgaacgct agctacaggc ttaacacatg caagtcgagg ggcagcatgg tcttagcttg 60
ctaaggctga tggcgaccgg cgcacgggtg agtaacacgt atccaacctg ccgtctactc 120
ttggccagcc ttctgaaagg aagattaatc caggatggga tcatgagttc acatgtccgc 180
atgattaaag gtattttccg gtagacgatg ggatgcgtt ccattagata gtaggcgggg 240
taacggccca cctagtcaac gatggatagg ggttctgaga ggaaggtccc ccacattgga 300
actgagacac ggtccaaact cctacgggag gcagcagtga ggaatattgg tcaatgggcg 360
cgagcctgaa ccagccaagt agcgtgaagg atgactgccc tatgggttgt aaacttcttt 420
tgtccgggaa taaaaccgcc tacgtgtagg cgcttgtatg taccggtacg aataagcatc 480
ggctaactcc gtgccagcag ccgcggtaat acggaggatg cgagcgttat ccggatttat 540
tgggtttaaa gggagcgcag acgggttttt aagtcagctg tgaaagtttg gggctcaacc 600
ttaaaattgc agttgatact ggagaccttg agtgcagttg aggcaggcgg aattcgtggt 660
gtagcggtga aatgcttaga tatcacgaag aactccgatt gcgaaggtag cttgctaaag 720
tgtaactgac gttcatgctc gaaagtgtgg gtatcaaaca ggattagata ccctggtagt 780
ccacacggta aacgatggat actcgctgtt ggcgatatac ggtcagcggc ttagcgaaag 840
cgttaagtat cccacctggg gagtacgccg gcaacggtga aactcaaagg aattgacggg 900
ggcccgcaca agcggaggaa catgtggttt aattcgatga tacgcgagga accttacccg 960
ggcttaaatt gcactggact attctggaaa caggatattc ttcggaccag tgtgaaggtg 1020
ctgcatggtt gtcgtcagct cgtgccgtga ggtgtcggct taagtgccat aacgagcgca 1080
acccttgctg ccagttacta acaggtaatg ctgaggactc tggcgggact gccatcgtaa 1140
gatgcgagga aggtggggat gacgtcaaat cagcacggcc cttacgtccg gagctacaca 1200
cgtgttacaa tggtaggtac agagggtagc tacccagcga tgggatgcga atctcgaaag 1260
cctatctcag ttcggattgg aggctgaaac ccgcctccat gaagttggat tcgctagtaa 1320
tcgcgcatca gccatggcgc ggtgaatacg ttcccgggcc ttgtacacac cgcccgtcaa 1380
gccatgggag ccgggggtac ctgaagtacg taaccgcaag gatcgtccta gggtaaaact 1440
ggtgactggg g 1451

<210> SEQ ID NO 20
<211> LENGTH: 1450
<212> TYPE: DNA
<213> ORGANISM: Bacteroides sp.

<400> SEQUENCE: 20
gatgaacgct agctacaggc ttaacacatg caagtcgagg ggcagcatga agtttgcttg 60
caaactttga tggcgaccgg cgcacgggtg agtaacgcgt atccaacctc ccgcatactc 120
ggggatagcc ttctgaaagg aagattaata cccgatggta tcttaagcgc acatgcaatt 180
aagattaaag aatttcggta tgcgatgggg atgcgttcca ttaggtagta ggcggggtaa 240
cggcccacct agccatcgat ggataggggt tctgagagga aggtccccca cattggaact 300
gagacacggt ccaaactcct acgggaggca gcagtgagga atattggtca atgggcgcga 360
gcctgaacca gccaagtagc gtgaaggatg actgccctat gggttgtaaa cttcttttgt 420
ccgggaataa aaccgcctac gtgtaggcgc ttgtatgtac cggtacgaat aagcatcggc 480
taactccgtg ccagcagccg cggtaatacg gaggatgcga gcgttatccg gatttattgg 540
gtttaaaggg agcgcagacg ggtttttaag tcagctgtga aagtttgggg ctcaacctta 600
aaattgcagt tgatactgga gaccttgagt gcagttgagg caggcggaat tcgtggtgta 660
gcggtgaaat gcttagatat cacgaagaac tccgattgcg aaggcagctt gctaaagtgt 720
aactgacgtt catgctcgaa agtgtgggta tcaaacagga ttagataccc tggtagtcca 780

```
cacggtaaac gatggatact cgctgttggc gatatacggt cagcggctta gcgaaagcgt    840
taagtatccc acctggggag tacgccggca acggtgaaac tcaaaggaat tgacgggggc    900
ccgcacaagc ggaggaacat gtggtttaat tcgatgatac gcgaggaacc ttacccgggc    960
ttaaattgca ctggactttc ccggaaacgg gattttcttc ggaccagtgt gaaggtgctg   1020
catggttgtc gtcagctcgt gccgtgaggt gtcggcttaa gtgccataac gagcgcaacc   1080
cttgctgcca gttactaaca ggtaatgctg aggactctgg cgggactgcc atcgtaagat   1140
gcgaggaagg tggggatgac gtcaaatcag cacggccctt acgtccgggg ctacacacgt   1200
gttacaatgg ggggtacaga aggccgctac ccggcaacgg gatgccaatc tccaaaaccc   1260
ctctcagttc ggactggagt ctgcaacccg actccacgaa gctggattcg ctagtaatcg   1320
cgcatcagcc acggcgcggt gaatacgttc ccgggccttg tacacaccgc ccgtcaagcc   1380
atgaaagccg gggtacctg aagtgcgtaa ccgcaaggag cgccctaggg taaaactggt    1440
aattggggct                                                          1450
```

```
<210> SEQ ID NO 21
<211> LENGTH: 1511
<212> TYPE: DNA
<213> ORGANISM: Bacteroides sp.

<400> SEQUENCE: 21

agagtttgat cctggctcag gatgaacgct agctacaggc ttaacacatg caagtcgagg     60
ggcagcggga ttgaagcttg cttcaattgc cggcgaccgg cgcacgggtg agtaacgcgt    120
atccaacctt ccgcttactc ggggatagcc tttcgaaaga aagattaata cccgatggta    180
tcttaagcac gcatgagatt aagattaaag atttatcggt aagcgatggg gatgcgttcc    240
attaggcagt tggcggggta acggcccacc aaacctacga tggatagggg ttctgagagg    300
aaggtccccc acattggaac tgagacacgg tccaaactcc tacgggaggc agcagtgagg    360
aatattggtc aatgggcgag agcctgaacc agccaagtag cgtgaaggat gacggcccta    420
cgggttgtaa acttcttttg tgcgggaata aaggaaccta cgtgtaggtt tttgcatgta    480
ccgtaacgaa taagcatcgg ctaactccgt gccagcagcc gcggtaatac ggaggatgcg    540
agcgttatcc ggatttattg ggtttaaagg gagcgtagac gggtttttaa gtcagctgtg    600
aaagtttggg gctcaacctt aaaattgcag ttgaaactgg agaccttgag tacggttgag    660
gcaggcggaa ttcgtggtgt agcggtgaaa tgcttagata tcacgaagaa ccccgattgc    720
gaaggcagcc tgctaagccg ccactgacgt tgaggctcga aagtgcgggt atcaaacagg    780
attagatacc ctggtagtcc gcacggtaaa cgatggatac tcgctgttgg cgatagacag    840
tcagcggcca agcgaaagcg ttaagtatcc cacctgggga gtacgccggc aacggtgaaa    900
ctcaaaggaa ttgacggggg cccgcacaag cggaggaaca tgtggtttaa ttcgatgata    960
cgcgaggaac cttacccggg cttgaactgc agtggaatta tccggaaacg gataagcgag   1020
caatcgccgc tgtggaggtg ctgcatggtt gtcgtcagct cgtgccgtga ggtgtcggct   1080
taagtgccat aacgagcgca acccttgctg ccagttacta acaggtcatg ctgaggactc   1140
tggcaggact gccatcgtaa gatgcgagga aggtggggat gacgtcaaat cagcacggcc   1200
cttacgtccg ggctacaca cgtgttacaa tggggagtac agagggcagc taccgggcga   1260
ccggatgcga atcccgaaag ctcctctcag ttcggactgg agtctgcaac ccgactccac   1320
gaagctggat tcgctagtaa tcgcgcatca gccacggcgc ggtgaatacg ttcccgggcc   1380
ttgtacacac cgcccgtcaa gccatgaaag ccgggggtac ctgaagtacg taaccgcgag   1440
```

```
gatcgtccta gggtaaaacc ggtaattggg gctaagtcgt aacaaggtag ccgtaccgga   1500

aggtgcggct g                                                        1511


<210> SEQ ID NO 22
<211> LENGTH: 1491
<212> TYPE: DNA
<213> ORGANISM: Blautia sp.

<400> SEQUENCE: 22

agagtttgat cctggctcag gatgaacgct ggcggcgtgc ttaacacatg caagtcgaac     60

gagaaacatt ttaatgaagc ttcggcagat ttagtttgtt tctagtggcg gacgggtgag    120

taacgcgtgg gtaacctgcc tcacactggg ggataacagt cagaaatgac tgctaatacc    180

gcataagcgc acggaaccgc atggttttgt gtgaaaaact ccggtggtgt gagatggacc    240

cgcgttggat tagccagttg gcagggtaac ggcctaccaa agcgacgatc catagccggc    300

ctgagagggt gaacggccac attgggactg agacacggcc cagactccta cgggaggcag    360

cagtggggaa tattgcacaa tgggggaaac cctgatgcag cgacgccgcg tgaaggaaga    420

agtatctcgg tatgtaaact tctatcagca gggaagataa tgacggtacc tgactaagaa    480

gccccggcta actacgtgcc agcagccgcg gtaatacgta gggggcaagc gttatccgga    540

tttactgggt gtaaagggag cgtagacgga gcagcaagtc tgatgtgaaa ggcaggggct    600

caacccctgg actgcattgg aaactgttga tcttgagtac cggaggggta agcggaattc    660

ctagtgtagc ggtgaaatgc gtagatatta ggaggaacac cagtggcgaa ggcggcttac    720

tggacggtaa ctgacgttga ggctcgaaag cgtggggagc aaacaggatt agataccctg    780

gtagtccacg ccgtaaacga tgaatactag gtgtcgggtg gcagagccat tcggtgccgc    840

agcaaacgca gtaagtattc cacctgggga gtacgttcgc aagaatgaaa ctcaaaggaa    900

ttgacgggga cccgcacaag cggtggagca tgtggtttaa ttcgaagcaa cgcgaagaac    960

cttaccaagt cttgacatcc ctctgaccgg tccttaaccg gacctttcct tcgggacaga   1020

ggagacaggt ggtgcatggt tgtcgtcagc tcgtgtcgtg agatgttggg ttaagtcccg   1080

caacgagcgc aacccctatc cccagtagcc agcatttaag gtgggcactc tgaggagact   1140

gccagggata acctggagga aggcggggat gacgtcaaat catcatgccc cttatgattt   1200

gggctacaca cgtgctacaa tggcgtaaac aaagggaagc agagcggtga cgccgagcaa   1260

atcccaaaaa taacgtccca gttcggactg cagtctgcaa ctcgactgca cgaagctgga   1320

atcgctagta atcgcggatc agaatgccgc ggtgaatacg ttcccgggtc ttgtacacac   1380

cgcccgtcac accatgggag tcagtaacgc ccgaagtcag tgacctaacc gaaagggagg   1440

agctgccgaa ggcgggacgg atgactgggg tgaagtcgta acaaggtaac c            1491


<210> SEQ ID NO 23
<211> LENGTH: 1336
<212> TYPE: DNA
<213> ORGANISM: Fusobacterium sp.

<400> SEQUENCE: 23

gatgaacgct gacagaatgc ttaacacatg caagtctact tgaattcact tcggtgatag     60

taaggtggcg gacgggtgag taacacgtaa agaacttgcc ttacagtctg ggacaactat    120

tggaaacgat agctaatacc ggatattatg cgagagtcgc atgactcttg tatgaaagct    180

atatgcgctg taagagagct ttgcgtccca ttagctagtt ggtgaggtaa cggctcacca    240
```

aggccacgat gggtagccgg cctgagaggg tgaacggcca caaggggact gagacacggc 300
ccttactcct acgggaggca gcagtgggga atattggaca atggaccaaa agtctgatcc 360
agcaattctg tgtgcacgat gacggtctta ggattgtaaa gtgctttcaa ttgggaagaa 420
aaaaatgacg gtaccaatag aagaagcgac ggctaaatac gtgccagcag ccgcggtaat 480
acgtatgtcg caagcgttat ccggatttat tgggcgtaaa gcgcgtctag gtggtttggt 540
aagtctgatg tgaaaatgcg gggctcaact ccgtattgcg ttggaaactg cctaactaga 600
gtatcggaga ggtgggcgga actacaagtg tagaggtgaa attcgtagat atttgtagga 660
atgccgatag agaagtcagc tcactggacg aatactgaca ctgaagcgcg aaagcatggg 720
gagcaaacag gattagatac cctggtagtc catgctgtaa acgatgatta ctaagcgtcg 780
ggggtcgaac ctcggcactc aagctaacgc gataagtaat ccgcctgggg agtacgtacg 840
caagtatgaa actcaaagga attgacgggg acccgcacaa gtggtggagc atgtggttta 900
attcgacgca acgcgaggaa ccttaccagc gtttgacatc ctaggaatga gaaagagatt 960
tcttagtgct ccttcgggag aacctagaga caggtggtgc atggctgtcg tcagctcgtg 1020
tcgtgagatg ttgggttaag tcccgcaacg agcgcaaccc ctattgtatg ttgccatcat 1080
taagttgggc actcatgcga tactgcctgc gatgagcagg aggaaggtgg ggatgacgtc 1140
aagtcatcat gccccttata cgctgggcta cacacgtgct acaatgggca gtacagagag 1200
aagcaaatct gcgaggagga gcaaatctca caaagctgtt cgtagttcgg attgtactct 1260
gcaactcgag tacatgaagt tggaatcact agtaatcgca aatcagctat gttgcggtga 1320
atacgttctc gggtct 1336

<210> SEQ ID NO 24
<211> LENGTH: 1359
<212> TYPE: DNA
<213> ORGANISM: Unknown
<220> FEATURE:
<223> OTHER INFORMATION: Bacteria
<220> FEATURE:
<221> NAME/KEY: source
<222> LOCATION: (1)..(1359)
<223> OTHER INFORMATION: /note="Description of Unknown: Lachnospiraceae sequence"

<400> SEQUENCE: 24
gatgaacgct ggcggcgtgc ttaacacatg caagtcgaac gggaaacatt ttaatgaagc 60
ttcggcagat ttagcttgtt tctagtggcg gacgggtgag taacgcgtgg gtaacctgcc 120
tcacactggg ggataacagt cagaaatgac tgctaatacc gcataagcgc acggaaccgc 180
atggttttgt gtgaaaaact ccggtggtgt gagatggacc cgcgttggat tagccagttg 240
gcagggtaac ggcctaccaa agcgacgatc catagccggc ctgagagggt gaacggccac 300
attgggactg agacacggcc cagactccta cgggaggcag cagtggggaa tattgcacaa 360
tgggggaaac cctgatgcag cgacgccgcg tgaaggaaga agtatctcgg tatgtaaact 420
tctatcagca gggaagaaaa tgacggtacc tgactaagaa gccccggcta actacgtgcc 480
agcagccgcg gtaatacgta gggggcaagc gttatccgga tttactgggt gtaaagggag 540
cgtagacgga atggcaagtc tgatgtgaaa ggcaggggct caacccctgg actgcattgg 600
aaactgtcag tcttgagtac cggaggggta agcggaattc ctagtgtagc ggtgaaatgc 660
gtagatatta ggaggaacac cagtggcgaa ggcggcttac tggacggtaa ctgacgttga 720
ggctcgaaag cgtggggagc aaacaggatt agataccctg gtagtccacg ccgtaaacga 780

```
tgaatacgag gtgtcgggtg ggcaaagcca ttcggtgccg cagcaaacgc aaaaagtaat    840
cccacctggg ggagtacgtt cccaagaatg aaactcaaag gaaatagcgg ggacccgcac    900
aagcggtgga gcatgtggtg tatttgaagc aacgcgaaga accttaccaa gtcttgacat    960
ccctctgacc ggtccttaac cggacctctc cttcgggaca ggggagacag gtggtgcatg   1020
gttgtcgtca gctcgtgtcg tgagatgttg ggttaagtcc cgcaacgagc gcaaccccta   1080
tccttagtag ccagcatctg aggtgggcac tctgaggaga ctgccaggga taacctggag   1140
gaaggcgggg aggacgtcaa atcatcatgc cccttatgat ttgggctaca cacgtgctac   1200
aatggcgtaa acaaagggaa gcagagcggt gacgccgagc aaatcccaaa aataacgtcc   1260
cagttcggac tgcagtctgc aactcgactg cacgaagctg gaatcgctag taatcgcgga   1320
tcagaatgcc gcggtgaata aaagcccggg tcttgcact                          1359
```

<210> SEQ ID NO 25
<211> LENGTH: 1387
<212> TYPE: DNA
<213> ORGANISM: Blautia sp.

<400> SEQUENCE: 25

```
agagtttgat catggctcag gatgaacgct ggcggcgtgc ttaacacatg caagtcgaac     60
gggaattact ttattgaagc tttggtcgat ttaatttaat tatagtggcg gacgggtgag    120
taacgcgtgg gtaacctgcc ttatacaggg ggataacagt cagaaatggc tgctaatacc    180
gcataagcgc acagagctgc atggctcagt gtgaaaaact ccggtggtat aagatggacc    240
cgcgttggat tagttggttg gtggggtaac ggcccaccaa ggcgacgatc catagccggc    300
ctgagagggt gaacggccac attgggactg agacacggcc cagactcata cgggaggcag    360
cagtggggaa tattgcacaa tgggggaaac cctgatgcag cgacgccgcg tgaaggaaga    420
agtatctcgg tatgtaaact tctatcagca gggaagatag tgacggtacc tgactaagaa    480
gccccggcta actacgtgcc agcagccgcg gtaatacgta gggggcaagc gttatccgga    540
tttactgggt gtaaagggag cgtagacggt gtggcaagtc tgatgtgaaa ggcatgggct    600
caacctgtgg actgcattgg aaactgtcat acttgagtgc cggaggggta agcggaattc    660
ctagtgtagc ggtgaaatgc gtagatatta ggaggaacac cagtggcgaa ggcggcttac    720
tggacggtaa ctgacgttga ggctcgaaag cgtggggagc aaacaggatt agataccctg    780
gtagtccacg ccgtaaacga tgaatactag gtgtcgggtg gcaaagccat tcggtgccgt    840
cgcaaacgca gtaagtattc cacctgggga gtacgttcgc aagaatgaaa ctcaaaggaa    900
ttgacgggga cccgcacaag cggtggagca tgtggtttaa ttcgaagcaa cgcgaagaac    960
cttaccaagt cttgacatcc gcctgaccga tccttaaccg gatctttcct tcgggacagg   1020
cgagacaggt ggtgcatggt tgtcgtcagc tcgtgtcgtg agatgttggg ttaagtcccg   1080
caacgagcgc aacccctatc ctcagtagcc agcattaagt tgggcactca tgcgatactg   1140
cctgcgatga gcaggaggaa ggtggggatg acgtcaagtc atcatgcccc ttatacgctg   1200
ggctacacac gtgctacaat gggtagtaca gagagtcgca aacctgcgag gggggagctaa  1260
tctcagaaaa ctattctcag ttcggattgt actctgcaac tcgagtacat gaagttggaa   1320
tcgctagtaa tcgcaaatca gctatgttgc ggtgaatacg ttctcgggtc ttgcactcac   1380
cgcccgt                                                             1387
```

<210> SEQ ID NO 26
<211> LENGTH: 1332

<212> TYPE: DNA
<213> ORGANISM: Blautia sp.

<400> SEQUENCE: 26
gctcaggatg aacgctggcg gcgtgcttaa cacatgcaag tcgagcgaag cacttgccat 60
tgactcttcg gaagatttgg catttgactg agcggcggac gggtgagtaa cgcgtgggta 120
acctgcctca tacgggggaa taacagttag aaatggctgc taatgccgca taaccgcaca 180
ggaccgcatg gactggtgtg aaaaactgag gtggtatgag atgggcccgc gtctgattag 240
gttagttggc ggggtaacgg cccaccaagc cgacgatcag tagccgacct gagagggacc 300
ggccacattg ggactgagac atggcccaga ctcctacggg aggcagcagt ggggaatatt 360
gcacaatgga ggaaactctg atgcagcgac gccgcatgaa ggaagaagta tctcggtatg 420
taaacttcta tcagcaggga agaaaatgac ggtacctgac taagaagccc cggctaacta 480
cgtgccagca gccgcggtaa tacgtagggg gcaagcgtta tccggattta ctgggtgtaa 540
agggagcgta gacggacggg caagtctgat gtgaaagccc ggggcttaac cccgggactg 600
cattggaaac tgtccatctt gagtgccgga gaggtaagcg gaattcctag tgtagcggtg 660
aaatgcgtag atattaggag gaacaccagt ggcgaaggcg gcttactgga cggtaactga 720
cgttgaggct cgaaagcgtg gggagcaaac aggattagat accctggtag tccacgccgt 780
aaacgatcaa taatgggtgt cgggttgcaa agcaatccgg tgccgcagca aacgcagtaa 840
gtattccccc tcgggagtac gttcgcaaga atgaaactca aaggaaggga cggggatccg 900
cacaagcggc ggagcatgtg gtttaattag aagcaacgcg aagaacctta ccaagtcttg 960
acatctgcct gaccgttcct taaccggaac tatctttcgg gacaggcaag acaggtggtg 1020
catggttgtc gtcagctcgt gtcgtgagat gttgggttaa gtcccgcaac gagcgcaacc 1080
cctgtcctta gtagccagca gtccggctgg gcactctagg gagactgccg gggtaaccc 1140 ggaggaaggc ggggaggagg tcaaatcatc atgcccccc tgatttgggc tacacacgtg 1200
gtacaatggc gtaaacaaag ggaagcggag tggtgacgct gagcaaatct caaaaataac 1260
gtcccacttc ggactgcagt ctgcaactcg actgcacgaa gctggaatcg ctagtaatcg 1320
cgaatcagaa tg 1332

<210> SEQ ID NO 27
<211> LENGTH: 253
<212> TYPE: DNA
<213> ORGANISM: Blautia sp.

<400> SEQUENCE: 27
tacgtagggg gcaagcgtta tccggattta ctgggtgtaa agggagcgta gacggcatgg 60
caagtctgat gtgaaaggca ggggctcaac tcctggactg cattggaaac tgccaggctt 120
gagtgccgga ggggtaagcg gaattcctag tgtagcggtg aaatgcgtag atattaggag 180
gaacaccagt ggcgaaggcg gcttactgga cggtaactga cgttgaggct cgaaagcgtg 240
gggagcaaac agg 253

<210> SEQ ID NO 28
<211> LENGTH: 1324
<212> TYPE: DNA
<213> ORGANISM: Intestinibacter sp.

<400> SEQUENCE: 28
cgtaagtaac ctgccctgta cacacggata acataccgaa aggtatgcta atacgggata 60 atatatttg atcgcatggt cgagatatca aagctccggc ggtacaccag ggaccccga 120 cagaggagct agttggtagt aatgtcacca aggcgacgat cagaagccga actgagaggg 180
ggatccgcac atgactgaga cacggtcaaa ctcctacggg aggcagcagt ggggaatatg 240
ccaatgggcg aaagctgatg cagcacgcgc gtgagcgatg aggctcgggt cgtaaagctc 300
gtctcaagga agataatgac ggtacttgag gaggaagccc cggctaacta cgtgccagca 360
gccgcggtaa tacgtagggg gctagcgtta tccggaatta ctgggcgtaa agggtgcgta 420
ggcggtcttt caagtcagga gtgaaaggct acggctcaac cgtagtaagc tcttgaaact 480
gtaagacttg agtgcaggag aggagagtgg aattcctagt gtagcggtga aatgcgtaga 540
tattaggagg aacaccagtt gcgaaggcgg ctctctggac tgtaactgac gctgaggcac 600
gaaagcgtgg ggagcaaaca ggattagata ccctggtagt ccacgccgta aacgatgagt 660
actagctgtc ggaggttacc cccttcggtg gcgcagctaa cgcattaagt actccgcctg 720
ggaagtacgc tcgcaagagt gaaactcaaa ggaattgacg gggacccgca caagtagcgg 780
agcatgtggt ttaattcgaa gcaacgcgaa gaaccttacc taagcttgac atcccactga 840
cccttcccta atcggaagct tcccttcggg acagtggtga caggtggtgc atggttgtcg 900
tcagctcgtg tcgtgagatg ttgggttaag tcccgcaacg agcgcaaccc ttgcctttag 960
ttgccagcat taagttgggc actctagagg gactgccagg gataacccgg aggagtgggg 1020
atgacgtcaa atcatcatgc cccttatgcta ggctacacac gtgctacaat gggtggtcag 1080
aggccagcca gtcgtgaggc cgagctatcc cataagccat tctcgtccgg attgtaggct 1140
gaactcgcct acatgagctg gaattacaag tatgcgatcg atgctgcgtg atgcgtccgg 1200
gtcttgtaca caccgcccgt cacaccatgg gagttggggg cgcccgaagc cggattgcta 1260
accttttgga agcgtccgtc gaaggtgaaa ccaataactg gggtgaagtc gtaacaaggt 1320
aacc 1324

<210> SEQ ID NO 29
<211> LENGTH: 1342
<212> TYPE: DNA
<213> ORGANISM: Corynebacterium sp.

<400> SEQUENCE: 29
gacgaacgct ggcggcgtgc ttaacacatg caagtcgaac ggaaaggccc cagctcgctg 60
gggtactcga gtggcgaacg ggtgagtaac acgtgggtga tctgccttgc actctgggat 120
aagcttggga aactgggtct aataccggat atgaactgcc tttagtgtgg tggttggaaa 180
gttttttcgg tgcaagatga gctcgcggcc tatcagcttg ttggtggggt aatggcctac 240
caaggcgtcg acgggtagcc ggcctgagag ggtgtacggc cacattggga ctgagatacg 300
gcccagactc ctacgggagg cagcagtggg gaatattgca caatgggcgg aagcctgatg 360
cagcgacgcc gcgtggggga tgacggcctt cgggttgtaa actcctttcg acagggacga 420
agctttttgt gacggtacct gtataagaag caccggctaa ctacgtgcca gcagccgcgg 480
taatacgtag ggtgcgagcg ttgtccggaa ttactgggcg taaagagctc gtaggtggtt 540
tgtcgcgtcg tctgtgaaat tccggggctt aactccgggc gtgcaggcga tacgggcata 600
acttgagtac tgtaggggag actggaattc ctggtgtagc ggtgaaatgc gcagatatca 660
ggaggaacac cggtggcgaa ggcgggtctc tgggcagtaa ctgacgctga ggagcgaaag 720
catggggagc gaacaggatt agataccctg gtagtccatg ccgtaaacgg tgggcgctag 780
gtgtgggttt ccttccacgg gatccgtgcc gtagctaacg cattaagcgc cccgcctggg 840
gagtacggcc gcaaggctaa aactcaaagg aattgacggg ggcccgcaca agcggcggag 900
catgtggatt aattcgatgc aacgcgaaga accttacctg ggcttgacat acactggatc 960
gggctagaga tagtctttcc ctttgtggct ggtgtacagg tggtgcatgg ttgtcgtcag 1020
ctcgtgtcgt gagatgttgg gttaagtccc gcaacgagcg caacccttgt cttatgttgc 1080
cagcatttgg ttggggactc atgagagact gccggggtca actcggagga aggtggggat 1140
gacgtcaaat catcatgccc cttatgtcca gggcttcaca catgctacaa tggtcggtac 1200
aacgcgcagc gacactgtga ggtggagcga atcgctgaaa gccggcctta gttcggattg 1260
gggtctgcaa ctcgacccca tgaagtcgga gtcgctagta atcgcagatc agcaatgctg 1320
cggtgaatac gttcccgggc ct 1342

<210> SEQ ID NO 30
<211> LENGTH: 253
<212> TYPE: DNA
<213> ORGANISM: Clostridium sp.

<400> SEQUENCE: 30
tacgtaggtg gcgagcgtta tccggattta ctgggcgtaa agggagcgta ggcggatgat 60
taagtgggat gtgaaatacc cgggctcaac ttgggtgctg cattccaaac tggttatcta 120
gagtgcagga gaggagagtg gaattcctag tgtagcggtg aaatgcgtag agattaggaa 180
gaacaccagt ggcgaaggcg actctctgga ctgtaactga cgctgaggct cgaaagcgtg 240
gggagcaaac agg 253

<210> SEQ ID NO 31
<211> LENGTH: 1399
<212> TYPE: DNA
<213> ORGANISM: Enterococcus sp.

<400> SEQUENCE: 31
cttgtgtcac caaccatagg gagggggaaa acatggaaac ggggttcata ccgcataact 60
tttttagccc aatgcataag aagaaaggcc tttcgggttt cggtaaagga ggcccccgcg 120
gctcttatag tgtgtgtgga agtaaccgct tccacaaggc ccaggtttca tacccgactg 180
gagagtgtgt tcgccacact ggggaaagga cccccggccc agtctctcta ggggaggcag 240
cagtaggaat tttcggcaaa ggaaaaaatt tctgaccgaa caacgccggt tgaatgaaga 300
agtttttcgg atcgaaaaac tctgttgtta gagaagaaca aggacgttag taactgaacg 360
tcccctgacg gtatctaacc agaaagccac ggctaattac gtgccagcag ccgcggtaat 420
acgtaggtgg caagcgttgt ccggatttat tgggcgtaaa gcgagcgcag gcggtttctt 480
aagtctgatg tgaaagcccc cggctcaacc ggggagggtc attggaaact gggagacttg 540
agtgcagaag aggagagtgg aattccatgt gtagcggtga aatgcgtaga tatatggagg 600
aacaccagtg gcgaaggcgg ctctctggtc tgtaactgac gctgaggctc gaaagcgtgg 660
ggagcaaaca ggattagata ccctggtagt ccacgccgta aacgatgagt gctaagtgtt 720
ggagggtttc cgcccttcag tgctgcagca aacgcattaa gcactccgcc tggggagtac 780
gaccgcaagg ttgaaactca aaggaattga cgggggcccg cacaagcggt ggagcatgtg 840
gtttaattcg aagcaacgcg aagaacctta ccaggtcttg acatcctttg accactctag 900
agatagagct ttcccttcgg ggacaaagtg acaggtggtg catggttgtc gtcagctcgt 960
gtcgtgagat gttgggttaa gtcccgcaac gagcgcaacc cttattgtta gttgccatca 1020

```
tttagttggg cactctagcg agactgccgg tgacaaaccg gaggaaggtg gggatgacgt   1080

caaatcatca tgccccttat gacctgggct acacacgtgc tacaatggga agtacaacga   1140

gtcgctagac cgcgaggtca tgcaaatctc ttaaagcttc tctcagttcg gattgcaggc   1200

tgcaactcgc ctgcatgaag ccggaatcgc tagtaatcgc ggatcagcac gccgcggtga   1260

atacgttccc gggccttgta cacaccgccc gtcacaccac gagagtttgt aacacccgaa   1320

gtcggtgagg taaccttttt ggagccagcc gcctaaggtg ggatagatga ttggggtgaa   1380

gtcgtaacca acgtatgcc                                                1399


<210> SEQ ID NO 32
<211> LENGTH: 1393
<212> TYPE: DNA
<213> ORGANISM: Streptococcus sp.
<220> FEATURE:
<221> NAME/KEY: modified_base
<222> LOCATION: (1381)..(1381)
<223> OTHER INFORMATION: a, c, t, g, unknown or other
<220> FEATURE:
<221> NAME/KEY: misc_feature
<222> LOCATION: (1381)..(1381)
<223> OTHER INFORMATION: n is a, c, g, or t

<400> SEQUENCE: 32

agactttagc ttgctaaagt tggaagagtt gcgaacgggt gagtaacgcg taggtaacct     60

gcctactagc gggggataac tattggaaac gatagctaat accgcataac agcatttaac    120

ccatgttaga tgcttgaaag gagcaattgc ttcactagta gatggacctg cgttgtatta    180

gctagttggt gaggtaacgg ctcaccaagg cgacgataca tagccgacct gagagggtga    240

tcggccacac tgggactgag acacggccca gactcctacg ggaggcagca gtagggaatc    300

ttcggcaatg gggggcaaccc tgaccgagca acgccgcgtg agtgaagaag gttttcggat    360

cgtaaagctc tgttgtaaga gaagaacgtg tgtgagagtg gaaagttcac acagtgacgg    420

taacttacca gaaagggacg gctaactacg tgccagcagc cgcggtaata cgtaggtccc    480

gagcgttgtc cggatttatt gggcgtaaag cgagcgcagg cggtttaata agtctgaagt    540

taaaggcagt ggcttaacca ttgttcgctt tggaaactgt tagacttgag tgcagaaggg    600

gagagtggaa ttccatgtgt agcggtgaaa tgcgtagata tatggaggaa caccggtggc    660

gaaagcggct ctctggtctg taactgacgc tgaggctcga aagcgtgggg agcaaacagg    720

attagatacc ctggtagtcc acgccgtaaa cgatgagtgc taggtgttag gccctttccg    780

gggcttagtg ccgcagctaa cgcattaagc actccgcctg gggagtacga ccgcaaggtt    840

gaaactcaaa ggaattgacg gggcccgca caagcggtgg agcatgtggt ttaattcgaa    900

gcaacgcgaa gaaccttacc aggtcttgac atcccgatgc tattcctaga gataggaagt    960

ttcttcggaa ctgtgagact tgagggcaga agggtagagt gcacttgtat ggggagctgt   1020

ggaatgcgtt cccgcaacga gcgcaacccc tattgttagt tgccatcatt aagttgggca   1080

ctctagcgag actgccggta ataaaccgga ggaaggtggg gatgacgtca aatcatcatg   1140

ccccttatga cctgggctac acacgtgcta caatggttgg tacaacgagt cgcgagtcgg   1200

tgacggcaag caaatctctt aaagccaatc tcagttcgga ttgtaggctg caactcgcct   1260

acatgaagtc ggaatcgcta gtaatcgcgg atcagcacgc cgcggtgaat acgttcccgg   1320

gccttgtaca caccgcccgt cacaccacga gagtttgtaa cacccgaagt cggtgaggta   1380

ncctttagg agc                                                       1393
```

<210> SEQ ID NO 33
<211> LENGTH: 1418
<212> TYPE: DNA
<213> ORGANISM: Megasphaera sp.

<400> SEQUENCE: 33
agagtttgat catggctcag gacgaacgct ggcggcgtgc ttaacacatg caagtcgaac 60
gagaagagat gagaagcttg cttcttatct cttcgagtgg caaacgggtg agtaacgcgt 120
aagcaacctg cccttcagat ggggacaaca gctggaaacg gctgctaata ccgaatacgt 180
tctttttgtc gcatggcaga gggaagaaag ggaggctctt cggagctttc gctgaaggag 240
gggcttgcgt ctgattagct agttggaggg gtaacggccc accaaggcga cgatcagtag 300
ccggtctgag aggatgaacg gccacattgg gactgagaca cggcccagac tcctacggga 360
ggcagcagtg gggaatcttc cgcaatggac gaaagtctga cggagcaacg ccgcgtgaac 420
gatgacggcc ttcgggttgt aaagttctgt tatacgggac gaatggcgta gcggtcaata 480
cccgttacga gtgacggtac cgtaagagaa agccacggct aactacgtgc cagcagccgc 540
ggtaatacgt aggtggcaag cgttgtccgg aattattggg cgtaaagggc gcgcaggcgg 600
cgtcgtaagt cggtcttaaa agtgcggggc ttaaccccgt gaggggaccg aaactgcgat 660
gctagagtat cggagaggaa agcggaattc ctagtgtagc ggtgaaatgc gtagatatta 720
ggaggaacac cagtggcgaa agcggctttc tggacgacaa ctgacgctga ggcgcgaaag 780
ccaggggagc aaacgggatt agataccccg gtagtcctgg ccgtaaacga tggatactag 840
gtgtaggagg tatcgacccc ttctgtgccg gagttaacgc aataagtatc ccgcctgggg 900
agtacggccg caaggctgaa actcaaagga attgacgggg gcccgcacaa gcggtggaac 960
atgtggttta attcgatgat acgcgaggaa ccttacccgg gcttaaattg cagtggaatg 1020
atgtggaaac atgtcagtga gcaatcaccg ctgtgaaggt gctgcatggt tgtcgtcagc 1080
tcgtgccgtg aggtgtcggc ttaagtgcca taacgagcgc aacccttatc ttcagttact 1140
aacaggtcat gctgaggact ctggagagac tgccgtcgta agatgtgagg aaggtgggga 1200
tgacgtcaaa tcagcacggc ccttacgtcc ggggctacac acgtgttaca atggggggta 1260
cagagggccg ctaccacgcg agtggatgcc aatcccaaaa acctctctca gttcggactg 1320
gagtctgcaa cccgactcca cgaagctgga ttcgctagta atcgcgcatc agccacggcg 1380
cggtgaatac gttcccgggc cttgcactca ccgcccgt 1418

<210> SEQ ID NO 34
<211> LENGTH: 1394
<212> TYPE: DNA
<213> ORGANISM: Parabacteroides sp.

<400> SEQUENCE: 34
agagtttgat cctggctcag gatgaacgct agcgacaggc ttaacacatg caagtcgagg 60
ggcagcatga tttgtagcaa tacagattga tggcgaccgg cgcacgggtg agtaacgcgt 120
atgcaactta cctatcagag ggggatagcc cggcgaaagt cggattaata ccccataaaa 180
caggggtccc gcatgggaat atttgttaaa gattcatcgc tgatagatag gcatgcgttc 240
cattaggcag ttggcggggt aacggcccac caaaccgacg atggataggg gttctgagag 300
gaaggtcccc cacattggta ctgagacacg gaccaaactc ctacgggagg cagcagtgag 360
gaatattggt caatggccga gaggctgaac cagccaagtc gcgtgaagga agaaggatct 420
atggtctgta aacttctttt ataggggaat aaagtggagg acgtgtcctt ttttgtatgt 480

```
accctatgaa taagcatcgg ctaactccgt gccagcagcc gcggtaatac ggaggatgcg    540

agcgttatcc ggatttattg ggtttaaagg gtgcgtaggt ggtgatttaa gtcagcggtg    600

aaagtttgtg gctcaaccat aaaattgccg ttgaaactgg gttacttgag tgtgtttgag    660

gtaggcggaa tgcgtggtgt agcggtgaaa tgcatagata tcacgcagaa ctccgattgc    720

gaaggcagct tactaaacca taactgacac tgaagcacga aagcgtgggg atcaaacagg    780

attagatacc ctggtagtcc acgcagtaaa cgatgattac taggagtttg cgatacaatg    840

taagctctac agcgaaagcg ttaagtaatc cacctgggga gtacgccggc aacggtgaaa    900

ctcaaaggaa ttgacggggg cccgcacaag cggaggaaca tgtggtttaa ttcgatgata    960

cgcgaggaac cttacccggg tttgaacgta gtctgaccgg aatggaaaca ctccttctag   1020

caatagcaga ttacaaggtg ctgcatggtt gcctcaactc cggcccggaa ggtccggctt   1080

aattgccata acaagcgcac ccttttacca aggttcaaac aggtgaagct tgaagactct   1140

gtggaacctc ccccctaacc tgtgagaaga agtggggata cactcaataa accacggccc   1200

ttaatcccgg ggggaacact ggttacaatg ggttgggaaa gggggcttcc tggcgacagg   1260

atgctaatct ccaaaccatg tctcagttcg gatcggagtc tgcaactcga ctccgtgaag   1320

ctggattcgc tagtaatcgc gcatcagcca tggcgcggtg aatacgttcc cgggccttgt   1380

acacaccgcc cgtc                                                     1394
```

<210> SEQ ID NO 35
<211> LENGTH: 1472
<212> TYPE: DNA
<213> ORGANISM: Unknown
<220> FEATURE:
<223> OTHER INFORMATION: Bacteria
<220> FEATURE:
<221> NAME/KEY: source
<222> LOCATION: (1)..(1472)
<223> OTHER INFORMATION: /note="Description of Unknown: Escherichia-
Shigella sequence"

<400> SEQUENCE: 35

```
cgccctgatt gacggctata cacatgcaag tcgaacggta acaggaaaca gcttgcttct     60

ttgctgacga gtggcggacg ggtgagtaat gtctgggaaa ctgcctgatg gagggggata    120

actactggaa acggtagcta ataccgcata acgtcgcaag accaaagagg gggaccttcg    180

ggcctcttgc catcggatgt gcccagatgg gattagctag taggtggggt aacggctcca    240

tccctaggcg agccgaatcc ttagcctggt ctgagaggaa tgaccagcca cactgggact    300

gagaacacgg tccagactcc tacgggaggc agcagtgggg aatattgcac aatgggcgca    360

agcctgatgc agccatgccg cgtgtatgaa gaaggccttc gggttgtaaa gtactttcag    420

cggggaggaa gggagtaaag ttaataccct ttgctcattg acgttacccg cagaagaagc    480

accggctaac tccgtgccag cagccgcggt aatacggagg gtgcaagcgt taatcggaat    540

tactgggcgt aaagcgcacg caggcggttt gttaagtcag atgtgaaatc cccgggctca    600

acctgggaac tgcatctgat actggcaagc ttgagtctcg tagagggggg tagaattcca    660

ggtgtagcgg tgaaatgcgt agagatctgg aggaataccg gtggcgaagg cggccccctg    720

gacgaagact gacgctcagg tgcgaaagcg tggggagcaa acaggattag ataccctggt    780

agtccacgcc gtaaacgatg tcgacttgga ggttgtgccc ttgaggcgtg gcttccggag    840

ctaacgcgtt aagtcgaccg cctggggagt acggccgcaa ggttaaaact caaatgaatt    900

gacgggggcc cgcacaagcg gtggagcatg tggtttaatt cgatgcaacg cgaagaacct    960
```

tacctggtct tgacatccac gggaagtttt cagagatgag aatgtgcctt cgggaaccgt 1020
gagacaggtg ctgcatggct gtcgtcagct cgtgttgtga aatgttgggt taagtcccgc 1080
aacgagcgca acccttatcc tttgttgcca gcggtccggc cgggaactca aaggagactg 1140
ccagtgataa actggaggaa ggtggggatg acgtccaggt catcatggcc cttacgaacc 1200
agggctacac acgtgcctac aatggacgca tccaaagaga gagcgaaccc tgcccgcgag 1260
agcaagcgga cctcataaag tgcgtcgtag tccggattgg agtctgcaac tcgactccat 1320
gaagtcggaa tcgctagtaa tcgtggatca gaatgccacg gtgaatacgt tcccgggcct 1380
tgtacacacc gcccgtcaca ccatgggagt gggttgcaaa agaagtaggt agcttaacct 1440
tcgggagggc gcttaccact ttggatgcga gg 1472

<210> SEQ ID NO 36
<211> LENGTH: 1440
<212> TYPE: DNA
<213> ORGANISM: Tyzzerella sp.

<400> SEQUENCE: 36
taagatgaac gctggcggcg tgcttaacac atgcaagtcc tatgaagcgc ttaaacggat 60
ttcttcggat tgaagttttt gtgactgagt ggcggacggg tgagtaacgc gtgggtaact 120
tgcctcatac agggggataa cagttagaaa tgactgctaa taccgcataa gcgcacagtg 180
ctgcatggca cagtgtgaaa aactccggtg gtatgagatg gacccgcgtc tgattagcta 240
gttggtgggg taacggccta ccaaggcgac gatcagtagc cggcctgaga gggtgaacgg 300
ccacattggg actgagacac ggcccaaact cctacgggag gcagcagtgg ggaatattgc 360
acaatggggg aaaccctgat gcagcgacgc cgcgtgagcg aagaagtatt tcggtatgta 420
aagctctatc agcagggaag aaaatgacgg tacctgacta agaagcaccg gctaaatacg 480
tgccagcagc cgcggtaata cgtatggtgc aagcgttatc cggatttact gggtgtaaag 540
ggagcgtaga cggttgtgta agtctgatgt gaaagcccgg ggctcaaccc cgggactgca 600
ttggaaacta tgtaactaga gtgtcggaga ggtaagcgga attcctagtg tagcggtgaa 660
atgcgtagat attaggagga acaccagtgg cgaaggcggc ttactggacg atcactgacg 720
ttgaggctcg aaagcgtggg gagcaaacag gattagatac cctggtagtc cacgccgtaa 780
acgatgacta ctaggtgtcg gggcccataa gggcttcggt gccgcagcaa acgcaataag 840
tattccacct ggggagtacg ttcgcaagaa tgaaactcaa aggaattgac ggggacccgc 900
acaagcggtg gagcatgtgg tttaattcga agcaacgcga agaaccttac ctggtcttga 960
catcccactg accggacagt aatgtgtcct ttcctccggg acagtggaga caggtggtgc 1020
atggttgtcg tcagctcgtg tcgtgagatg ttgggttaag tcccgcaacg agcgcaaccc 1080
ctatccttag tagccagcag taagatgggc actctaggga gactgccagg gataacctgg 1140
aggaaggtgg ggatgacgtc aaatcatcat gccccttatg acttgggcta cacacgtgct 1200
acaatggcgt aaacaaagtg aagcgaagtc gtgaggccaa gcaaatcaca aaaataacgt 1260
ctcagttcgg attgtagtct gcaactcgac tacaagaagc tggaatcgct agtaatcgca 1320
gatcagaatg ctgcggtgaa tacgttcccg ggtcttgtac acaccgcccg tcacaccatg 1380
ggagtcgaaa atgcccgaag tcggtgacct aacgaaagaa ggagccgccg aaggcaggtt 1440

<210> SEQ ID NO 37
<211> LENGTH: 1366
<212> TYPE: DNA
<213> ORGANISM: Fusobacterium sp.

<400> SEQUENCE: 37
agagtttgat cctggctcag gatgaacgct gacagaatgc ttaacacatg caagtatact 60
tgatccttcg ggtgatggtg gcggacgggt gagtaacgcg taaagaactt gccctgcagt 120
ctgggacaac atttggaaac gaatgctaat cccgcataag cccacagctc ggcatcgagc 180
agagggaaaa ggagtgatct gctttgagat ggcctcgcgt ccgattagct ggttggtgag 240
gtgacggccc atcaaggcaa cgatcggtag ccggactgag aggttgaacg gccacattgg 300
gattgagaca cggcccttac tcctacggga ggcagcagtg gggaatattg gacaatggac 360
caaaagtctg atccagcaat tctgtgtgca cgatgaagtt tttcggaatg taaagtgctt 420
tcagttggga cgaagtaagt gacggtacca acagaagaag cgacggctaa atacgtgcca 480
gcagccgcgg taatacgtat gtcgcaagcg ttatccggat ttattgggcg taaagcgcgt 540
ctaggcggtt tggtaagtct gatgtgaaaa tgcggggctc aactccgtat tgcgttggaa 600
actgccaaac tagagtactg gagaggtggg cggaactaca agtgtagagg tgaaattcgt 660
agatatttgt aggaatgccg atggggaagc cagcccactg gacagatact gacgctaaag 720
cgcgaaagcg tgggtagcaa acaggattag ataccctggt agtccacgcc gtaaacgatg 780
attactaggt gttgggggtc gaacctcagc gcccaagcta acgcgataag taatccgcct 840
ggggagtacg tacgcaagta tgaaactcaa aggaattgac ggggacccgc acaagcggtg 900
gagcatgtgg tttaattcga cgcaacgcga ggaaccttac cagcgtttga catcctaaga 960
aattagcaga gatgcttttg tgccccttcg gggaactta gtgacaggtg gtgcatggct 1020
gtcgtcagct cgtgtcgtga gatgttgggt taagtcccgc aacgagcgca acccctttcg 1080
tatgttgcca tcattaagtt gggcactcat gcgatactgc ctgcgatgag caggaggaag 1140
gtggggatga cgtcaagtca tcatgcccct tatacgctgg gctacacacg tgctacaatg 1200
ggtagtacag agagtcgcaa acctgcgagg gggagctaat ctcagaaaac tattctcagt 1260
tcggattgta ctctgcaact cgagtacatg aagttggaat cgctagtaat cgcaaatcag 1320
ctatgttgcg gtgaatacgt tctcgggtct tgtacacacc gcccgt 1366

<210> SEQ ID NO 38
<211> LENGTH: 1324
<212> TYPE: DNA
<213> ORGANISM: Intestinibacter sp.

<400> SEQUENCE: 38
cgtaagtaac ctgccctgta cacacggata acataccgaa aggtatgcta atacgggata 60
atatattttg atcgcatggt cgagatatca aagctccggc ggtacaccag ggacccccga 120
cagaggagct agttggtagt aatgtcacca aggcgacgat cagaagccga actgagaggg 180
ggatccgcac atgactgaga cacggtcaaa ctcctacggg aggcagcagt ggggaatatg 240
ccaatgggcg aaagctgatg cagcacgcgc gtgagcgatg aggctcgggt cgtaaagctc 300
gtctcaagga agataatgac ggtacttgag gaggaagccc cggctaacta cgtgccagca 360
gccgcggtaa tacgtagggg gctagcgtta tccggaatta ctgggcgtaa agggtgcgta 420
ggcggtcttt caagtcagga gtgaaaggct acggctcaac cgtagtaagc tcttgaaact 480
gtaagacttg agtgcaggag aggagagtgg aattcctagt gtagcggtga aatgcgtaga 540
tattaggagg aacaccagtt gcgaaggcgg ctctctggac tgtaactgac gctgaggcac 600
gaaagcgtgg ggagcaaaca ggattagata ccctggtagt ccacgccgta aacgatgagt 660
actagctgtc ggaggttacc cccttcggtg gcgcagctaa cgcattaagt actccgcctg 720
ggaagtacgc tcgcaagagt gaaactcaaa ggaattgacg gggacccgca caagtagcgg 780
agcatgtggt ttaattcgaa gcaacgcgaa gaaccttacc taagcttgac atcccactga 840
cccttcccta atcggaagct tcccttcggg acagtggtga caggtggtgc atggttgtcg 900
tcagctcgtg tcgtgagatg ttgggttaag tcccgcaacg agcgcaaccc ttgcctttag 960
ttgccagcat taagttgggc actctagagg gactgccagg gataacccgg aggagtgggg 1020
atgacgtcaa atcatcatgc ccttatgcta ggctacacac gtgctacaat gggtggtcag 1080
aggccagcca gtcgtgaggc cgagctatcc cataagccat tctcgtccgg attgtaggct 1140
gaactcgcct acatgagctg gaattacaag tatgcgatcg atgctgcgtg atgcgtccgg 1200
gtcttgtaca caccgcccgt cacaccatgg gagttggggg cgcccgaagc cggattgcta 1260
accttttgga agcgtccgtc gaaggtgaaa ccaataactg gggtgaagtc gtaacaaggt 1320
aacc 1324

<210> SEQ ID NO 39
<211> LENGTH: 1657
<212> TYPE: DNA
<213> ORGANISM: Helicobacter sp.

<400> SEQUENCE: 39
agagtttgat cctggctcag agtgaacgct ggcggcgtgc ctaatacatg caagtcgaac 60
gatgaaactt ctagcttgct agaagtggat tagtggcgca cgggtgagta atgcataggt 120
aacatgccct ttagtctggg atagccactg gaaacggtga ttaatactgg atactcccta 180
cgggggaaag gggctttcaa taaagaattt ctctttttag tgttttgtgt tgttggcaca 240
aaattctagt atttggaatg agaaattggt gttgtgaagc aatttgtgcg gagattagac 300
ttagtgtctg tcgtgtcagc aaattgcgaa ctcatcgatt tatcatccaa agacgaattt 360
tttattgaaa gccttcgcta aaggattggc ctatgtccta tcagcttgtt ggtgaggtaa 420
tggctcacca aggctatgac gggtatccgg cctgagaggg tgatcggaca cactggaact 480
gagacacggt ccagactcct acgggaggca gcagtaggga atattgctca atgggggaaa 540
ccctgaagca gcaacgccgc gtggaggatg aaggttttag gattgtaaac tccttttgta 600
agagaagatt atgacggtat cttacgaata agcaccggct aactccgtgc cagcagccgc 660
ggtaatacgg agggtgcaag cgttactcgg aatcactggg cgtaaagagc gcgtaggcgg 720
gtggtcaagt cagatgtgaa atcctgtagc ttaactacag aactgcattt gaaactgacc 780
atctagagta tgggagaggt aggtggaatt cttggtgtag gggtaaaatc cgtagagatc 840
aagaggaata ctcattgcga aggcgacctg ctggaacatt actgacgctg atgcgcgaaa 900
gcgtggggag caaacaggat tagataccct ggtagtccac gccctaaacg atgaatgcta 960
gttgttgtga ggcttgtcct tgcagtaatg cagctaacgc attaagcatt ccgcctgggg 1020
agtacggtcg caagattaaa actcaaagga atagacgggg acccgcacaa gcggtggagc 1080
atgtggttta attcgatgat acgcgaagaa ccttacctag gcttgacatt gatagaatct 1140
actagagata gtggagtgcc cttttaggga gcttgaaaac aggtgctgca cggctgtcgt 1200
cagctcgtgt cgtgagatgt tgggttaagt cccgcaacga gcgcaaccct cgtccttagt 1260
tgctagcagt ttggctgagc actctaagga gactgccttc gtaaggagga ggaaggtgag 1320
gacgacgtca agtcatcatg gcccttacgc ctagggctac acacgtgcta caatggggtg 1380
cacaaagaga tgcaatagtg tgagctggag ccaatctcta aaacatctct cagttcggat 1440
tgtagtctgc aactcgacta catgaagctg gaatcgctag taatcgcaaa tcagcaatgt 1500
tgcggtgaat acgttcccgg gtcttgtact caccgcccgt cacaccatgg gagttgtatt 1560
tgccttaagt cggaatgcta aattggctac cgcccacggc agatgcagcg actggggtga 1620
agtcgtaaca aggtaaccgt aggtgaacct gcggttg 1657

<210> SEQ ID NO 40
<211> LENGTH: 253
<212> TYPE: DNA
<213> ORGANISM: Anaerobiospirillum sp.

<400> SEQUENCE: 40
tacggagggt gcaagcgtta atcggaataa ctgggcgtaa agggcatgta ggcggaaagg 60
caagcaagat gtgaaagacc tgggctcaac ctgggttggt cattttgaac tacctttcta 120
gagtattgca gagggagatg gaatttcagg tgtagcggtg gaatgcgtag atatctgaaa 180
gaacaccaga ggcgaaggcg gtctcctggg caaatactga cgctgaggtg cgaaagcgtg 240
gggagcaaac agg 253

<210> SEQ ID NO 41
<211> LENGTH: 1342
<212> TYPE: DNA
<213> ORGANISM: Corynebacterium sp.

<400> SEQUENCE: 41
gacgaacgct ggcggcgtgc ttaacacatg caagtcgaac ggaaaggccc cagctcgctg 60
gggtactcga gtggcgaacg ggtgagtaac acgtgggtga tctgccttgc actctgggat 120
aagcttggga aactgggtct aataccggat atgaactgcc tttagtgtgg tggttggaaa 180 gtttttttcgg tgcaagatga gctcgcggcc tatcagcttg ttggtggggt aatggcctac 240
caaggcgtcg acgggtagcc ggcctgagag ggtgtacggc cacattggga ctgagatacg 300
gcccagactc ctacgggagg cagcagtggg gaatattgca caatgggcgg aagcctgatg 360
cagcgacgcc gcgtggggga tgacggcctt cgggttgtaa actcctttcg acagggacga 420
agctttttgt gacggtacct gtataagaag caccggctaa ctacgtgcca gcagccgcgg 480
taatacgtag ggtgcgagcg ttgtccggaa ttactgggcg taaagagctc gtaggtggtt 540
tgtcgcgtcg tctgtgaaat tccggggctt aactccgggc gtgcaggcga tacgggcata 600
acttgagtac tgtaggggag actggaattc ctggtgtagc ggtgaaatgc gcagatatca 660
ggaggaacac cggtggcgaa ggcgggtctc tgggcagtaa ctgacgctga ggagcgaaag 720
catggggagc gaacaggatt agataccctg gtagtccatg ccgtaaacgg tgggcgctag 780
gtgtgggttt ccttccacgg gatccgtgcc gtagctaacg cattaagcgc cccgcctggg 840
gagtacggcc gcaaggctaa aactcaaagg aattgacggg ggcccgcaca agcggcggag 900
catgtggatt aattcgatgc aacgcgaaga accttacctg ggcttgacat acactggatc 960
gggctagaga tagtctttcc ctttgtggct ggtgtacagg tggtgcatgg ttgtcgtcag 1020
ctcgtgtcgt gagatgttgg gttaagtccc gcaacgagcg caacccttgt cttatgttgc 1080
cagcatttgg ttggggactc atgagagact gccggggtca actcggagga aggtggggat 1140
gacgtcaaat catcatgccc cttatgtcca gggcttcaca catgctacaa tggtcggtac 1200
aacgcgcagc gacactgtga ggtggagcga atcgctgaaa gccggcctta gttcggattg 1260
gggtctgcaa ctcgacccca tgaagtcgga gtcgctagta atcgcagatc agcaatgctg 1320
cggtgaatac gttcccgggc ct 1342

<210> SEQ ID NO 42
<211> LENGTH: 1357
<212> TYPE: DNA
<213> ORGANISM: Collinsella sp.
<220> FEATURE:
<221> NAME/KEY: modified_base
<222> LOCATION: (766)..(766)
<223> OTHER INFORMATION: a, c, t, g, unknown or other
<220> FEATURE:
<221> NAME/KEY: misc_feature
<222> LOCATION: (766)..(766)
<223> OTHER INFORMATION: n is a, c, g, or t

<400> SEQUENCE: 42
acggcacccc tctccggagg gaagcgagtg gcgaacggct gagtaacacg tggagaacct 60
gccccctccc ccgggatagc cgcccgaaag gacgggtaat accggatacc cccgggcgcc 120
gcatggcgcc cgggctaaag ccccgacggg aggggatggc tccgcggccc atcaggtaga 180
cggcggggtg acggcccacc gtgccgacaa cgggtagccg ggttgagaga ccgaccggcc 240
agattgggac tgagacacgg cccagactcc tacgggaggc agcagtgggg aatcttgcgc 300
aatgggggga accctgacgc agcgacgccg cgtgcgggac ggaggccttc gggtcgtaaa 360
ccgctttcag cagggaagag tcaagactgt acctgcagaa gaagccccgg ctaactacgt 420
gccagcagcc gcggtaatac gtagggggcg agcgttatcc ggattcattg ggcgtaaagc 480
gcgcgtaggc ggcccggcag gccgggggtc gaagcggggg gctcaacccc ccgaagcccc 540
cggaacctcc gcggcttggg tccggtaggg gagggtggaa cacccggtgt agcggtggaa 600
tgcgcagata tcgggtggaa caccggtggc gaaggcggcc ctctgggccg agaccgacgc 660
tgaggcgcga aagctggggg agcgaacagg attagatacc ctggtagtcc cagccgtaaa 720
cgatggacgc tgggtgtggg gggacgatcc ccccgtgccg cagccnacgc attaagcgtc 780
ccgcctgggg agtacggccg caaggctaaa actcaaagga attgacgggg gcccgcacaa 840
gcagcggagc atgtggctta attcgaagca acgcgaagaa ccttacggcg catccccccg 900
aggcccacgg ggggtccgcc gcgtgggtca gaggagcgca tacgggaggt gcatggttgt 960
cgtcagctcg tgtcgtgaga tgttgggtta agtcccgcaa cgagcgcaac cccgccgcg 1020 tgttgccatc gggtgatgcc gggaacccac gcgggaccgc cgccgtcaag gcggaggagg 1080
gcggggacga cgtcaagtca tcatgcccct tatgccctgg gctgcacacg tgctacaatg 1140
gccggtacag agggatgcca ccccgcgagg gggagcggat cccggaaagc cggccccagt 1200
tcggattggg ggctgcaacc cgcccccatg aagtcggagt tgctagtaat cgcggatcag 1260
catgccgcgg tgaatgcgtt cccgggcctt gtacacaccg cccgtcacac cacccgagtc 1320
gtctgcaccc gaagtcgccg gcccaaccgc aaggggg 1357

<210> SEQ ID NO 43
<211> LENGTH: 1488
<212> TYPE: DNA
<213> ORGANISM: Sarcina sp.

<400> SEQUENCE: 43
agagtttgat cctggctcag gacgaacgct ggcggcgtgc ctaatacatg caagtcgagc 60
ggagttactt tgagagcttg ctttcaaagt aacttagcgg cggacgggtg agtaacacgt 120
aggcaacctg ccccttagac tgggataact accggaaacg gtagctaata ccggataatt 180 tctttttct cctgaaggaa gaatgaaaga cggagcaatc tgtcactgag ggatgggcct 240

```
gcggcgcatt agctagttgg tggggtaacg gcccaccaag gcgacgatgc gtagccgacc    300

tgagagggtg atcggccaca ttggaactga gatacggtcc agactcctac gggaggcagc    360

agtggggaat attgcacaat gggggaaacc ctgatgcagc aacgccgcgt gagtgatgaa    420

ggtcttcgga ttgtaaagct ctgtctttag ggacgataat gacggtacct aaggaggaag    480

ccacggctaa ctacgtgcca gcagccgcgg taatacgtag gtggcaagcg ttatccggat    540

ttactgggcg taaagggagc gtaggcggat atttaagtgg gatgtgaaat acccgagctt    600

aacttgggag ctgcattcca aactggatat ctagagtgca ggagaggaga atggaattcc    660

tagtgtagcg gtgaaatgcg tagagattag gaagaacacc agtggcgaag gcgattctct    720

ggactgtaac tgacgctgag gctcgaaagc gtggggagca aacaggatta gataccctgg    780

tagtccacgc cgtaaacgat gaataccagg tgtaggggcc ccaagcctct gtgccgccgc    840

taacgcatta agtattccgc ctggggagta cggtcgcaag attaaaactc aaaggaattg    900

acggggaccc gcacaagcag cggagcatgt ggtttaattc gaagcaacgc gaagaacctt    960

acctagactt gacatgtcct gaattaccag taatgtggga agttccttcg ggaacaggaa   1020

cacaggtggt gcatggttgt cgtcagctcg tgtcgtgaga tgttgggtta agtcccgcaa   1080

cgagcgcaac ccttattgtt agttggtacc attaagttga ccactctagc gagactgccc   1140

gggttaaccg ggaggaaggt ggggatgacg tcaaatcatc atgcccctta tgtctagggc   1200

tacacacgtg ctacaatggc aagtacaaag agaagcaata ctgtgaagtg gagcaaaact   1260

caaaaacttg tctcagttcg gattgtaggc tgaaactcgc ctacatgaag ctggagttgc   1320

tagtaatcgc gaatcagaat gtcgcggtga atacgttccc gggtcttgta cacaccgccc   1380

gtcacaccat gagagttggc aatacccgaa gtccgtaagc taaccgtaag gaggcagcgg   1440

ccgaaggtag ggtcagcgat tggggtgaag tcgtaacaag gtaaccaa                1488
```

```
<210> SEQ ID NO 44
<211> LENGTH: 1454
<212> TYPE: DNA
<213> ORGANISM: Clostridium sp.
<220> FEATURE:
<221> NAME/KEY: modified_base
<222> LOCATION: (635)..(635)
<223> OTHER INFORMATION: a, c, t, g, unknown or other
<220> FEATURE:
<221> NAME/KEY: misc_feature
<222> LOCATION: (635)..(635)
<223> OTHER INFORMATION: n is a, c, g, or t
<220> FEATURE:
<221> NAME/KEY: modified_base
<222> LOCATION: (704)..(704)
<223> OTHER INFORMATION: a, c, t, g, unknown or other
<220> FEATURE:
<221> NAME/KEY: misc_feature
<222> LOCATION: (704)..(704)
<223> OTHER INFORMATION: n is a, c, g, or t

<400> SEQUENCE: 44

tgagtttgat catggctcag gacgaacgct ggcggcgtgc ctaacacatg caagtcgagc     60

gatgaaattt tcttcggaaa atggattagc ggcggacggg tgagtaacac gtgggtaacc    120

tgccctatag agagggatag ccttccgaaa gggagattaa tacctcataa tatcctagta    180

tcgcatgata catggattaa aggagcaatc cgctatagga tggacccgcg gcgcattagc    240

tagttggtga ggtaacggct caccaaggcg acgatgcgta gccgacctga gagggtgatc    300

ggccacattg ggactgagac acggcccaga ctcctacggg aggcagcagt ggggaatatt    360
```

gcacaatggg ggaaaccctg atgcagcaac gccgcgtgag tgatgacggt cttcggattg 420
taaagctctg tctttaggga cgataatgac ggtacctaag gaggaagcca cggctaacta 480
cgtgccagca gccgcggtaa tacgtaggtg gcaagcgttg tccggattta ctgggcgtaa 540
agggagcgta ggcggatctt taagtgggat gtgaaatact cgggctcaac ctgggggctg 600
cattccaaac tggggatcta gagtacagga ggggngagtg gaattcctag tgtagcggtg 660
aaatgcgtag agattaggaa gaacaccagt ggcgaaggcg actntctgga ctgtaactga 720
cgctgaggct cgaaagcgtg ggagcaaac aggattagat accctggtag tccacgccgt 780
aaacgatgaa tactaggtgt agggggtgtc aactccccct gtgccgccgc taacgcatta 840
agtattccgc ctggggagta cggtcgcaag attaaaactc aaaggaattg acgggggccc 900
gcacaagtag cggagcatgt ggtttaattc gacgcaacgc gaagaacctt acctagactt 960
gacatcttct gcattaccct taatcgggga agttccttcg ggacagaat gacaggtggt 1020 gcatggttgt cgtcagctcg tgtcgtgaga tgttgggtta agtcccgcaa cgagcgcaac 1080
ccttaagctt agttgccatc attaagttgg gcactctaag ttgactgccg gtgacaaacc 1140
ggaggaaggt ggggatgacg tcaaatcatc atgcccctta tgtctagggc tacacacgtg 1200
ctacaatggc aagtacaaag agaagcaata ctgtgaagtg gagcaaaact caaaaacttg 1260
tctcagttcg gattgtaggc tgaaactcgc ctacatgaag ctggagttgc tagtaatcgc 1320
gaatcagaat gtcgcggtga atacgttccc gggtcttgta cacaccgccc gtcacaccat 1380
gagagttggc aatacccgaa gtccgtaagc taaccgtaag gaggcagcgg ccgaaggtag 1440
ggtcagcgat gggg 1454

<210> SEQ ID NO 45
<211> LENGTH: 253
<212> TYPE: DNA
<213> ORGANISM: Clostridium sp.

<400> SEQUENCE: 45
tacgtaggtg gcgagcgtta tccggattta ctgggcgtaa agggagcgta ggcggatgat 60
taagtgggat gtgaaatacc cgggctcaac ttgggtgctg cattccaaac tggttatcta 120
gagtgcagga gaggagagtg gaattcctag tgtagcggtg aaatgcgtag agattaggaa 180
gaacaccagt ggcgaaggcg actctctgga ctgtaactga cgctgaggct cgaaagcgtg 240
gggagcaaac agg 253

<210> SEQ ID NO 46
<211> LENGTH: 1392
<212> TYPE: DNA
<213> ORGANISM: Clostridium sp.
<220> FEATURE:
<221> NAME/KEY: modified_base
<222> LOCATION: (811)..(811)
<223> OTHER INFORMATION: a, c, t, g, unknown or other
<220> FEATURE:
<221> NAME/KEY: misc_feature
<222> LOCATION: (811)..(811)
<223> OTHER INFORMATION: n is a, c, g, or t
<220> FEATURE:
<221> NAME/KEY: modified_base
<222> LOCATION: (831)..(832)
<223> OTHER INFORMATION: a, c, t, g, unknown or other
<220> FEATURE:
<221> NAME/KEY: misc_feature
<222> LOCATION: (831)..(832)
<223> OTHER INFORMATION: n is a, c, g, or t
<220> FEATURE:
<221> NAME/KEY: modified_base
<222> LOCATION: (836)..(836)
<223> OTHER INFORMATION: a, c, t, g, unknown or other
<220> FEATURE:
<221> NAME/KEY: misc_feature
<222> LOCATION: (836)..(836)
<223> OTHER INFORMATION: n is a, c, g, or t
<220> FEATURE:
<221> NAME/KEY: modified_base
<222> LOCATION: (999)..(999)
<223> OTHER INFORMATION: a, c, t, g, unknown or other
<220> FEATURE:
<221> NAME/KEY: misc_feature
<222> LOCATION: (999)..(999)
<223> OTHER INFORMATION: n is a, c, g, or t
<220> FEATURE:
<221> NAME/KEY: modified_base
<222> LOCATION: (1013)..(1013)
<223> OTHER INFORMATION: a, c, t, g, unknown or other
<220> FEATURE:
<221> NAME/KEY: misc_feature
<222> LOCATION: (1013)..(1013)
<223> OTHER INFORMATION: n is a, c, g, or t
<220> FEATURE:
<221> NAME/KEY: modified_base
<222> LOCATION: (1047)..(1047)
<223> OTHER INFORMATION: a, c, t, g, unknown or other
<220> FEATURE:
<221> NAME/KEY: misc_feature
<222> LOCATION: (1047)..(1047)
<223> OTHER INFORMATION: n is a, c, g, or t
<220> FEATURE:
<221> NAME/KEY: modified_base
<222> LOCATION: (1051)..(1051)
<223> OTHER INFORMATION: a, c, t, g, unknown or other
<220> FEATURE:
<221> NAME/KEY: misc_feature
<222> LOCATION: (1051)..(1051)
<223> OTHER INFORMATION: n is a, c, g, or t
<220> FEATURE:
<221> NAME/KEY: modified_base
<222> LOCATION: (1057)..(1057)
<223> OTHER INFORMATION: a, c, t, g, unknown or other
<220> FEATURE:
<221> NAME/KEY: misc_feature
<222> LOCATION: (1057)..(1057)
<223> OTHER INFORMATION: n is a, c, g, or t
<220> FEATURE:
<221> NAME/KEY: modified_base
<222> LOCATION: (1069)..(1069)
<223> OTHER INFORMATION: a, c, t, g, unknown or other
<220> FEATURE:
<221> NAME/KEY: misc_feature
<222> LOCATION: (1069)..(1069)
<223> OTHER INFORMATION: n is a, c, g, or t
<220> FEATURE:
<221> NAME/KEY: modified_base
<222> LOCATION: (1101)..(1101)
<223> OTHER INFORMATION: a, c, t, g, unknown or other
<220> FEATURE:
<221> NAME/KEY: misc_feature
<222> LOCATION: (1101)..(1101)
<223> OTHER INFORMATION: n is a, c, g, or t
<220> FEATURE:
<221> NAME/KEY: modified_base
<222> LOCATION: (1103)..(1103)
<223> OTHER INFORMATION: a, c, t, g, unknown or other
<220> FEATURE:
<221> NAME/KEY: misc_feature
<222> LOCATION: (1103)..(1103)
<223> OTHER INFORMATION: n is a, c, g, or t
<220> FEATURE:
<221> NAME/KEY: modified_base
<222> LOCATION: (1116)..(1116)
<223> OTHER INFORMATION: a, c, t, g, unknown or other
<220> FEATURE:
<221> NAME/KEY: misc_feature
<222> LOCATION: (1116)..(1116)
<223> OTHER INFORMATION: n is a, c, g, or t
<220> FEATURE:

<221> NAME/KEY: modified_base
<222> LOCATION: (1168)..(1168)
<223> OTHER INFORMATION: a, c, t, g, unknown or other
<220> FEATURE:
<221> NAME/KEY: misc_feature
<222> LOCATION: (1168)..(1168)
<223> OTHER INFORMATION: n is a, c, g, or t
<220> FEATURE:
<221> NAME/KEY: modified_base
<222> LOCATION: (1185)..(1185)
<223> OTHER INFORMATION: a, c, t, g, unknown or other
<220> FEATURE:
<221> NAME/KEY: misc_feature
<222> LOCATION: (1185)..(1185)
<223> OTHER INFORMATION: n is a, c, g, or t
<220> FEATURE:
<221> NAME/KEY: modified_base
<222> LOCATION: (1188)..(1188)
<223> OTHER INFORMATION: a, c, t, g, unknown or other
<220> FEATURE:
<221> NAME/KEY: misc_feature
<222> LOCATION: (1188)..(1188)
<223> OTHER INFORMATION: n is a, c, g, or t
<220> FEATURE:
<221> NAME/KEY: modified_base
<222> LOCATION: (1202)..(1202)
<223> OTHER INFORMATION: a, c, t, g, unknown or other
<220> FEATURE:
<221> NAME/KEY: misc_feature
<222> LOCATION: (1202)..(1202)
<223> OTHER INFORMATION: n is a, c, g, or t
<220> FEATURE:
<221> NAME/KEY: modified_base
<222> LOCATION: (1207)..(1207)
<223> OTHER INFORMATION: a, c, t, g, unknown or other
<220> FEATURE:
<221> NAME/KEY: misc_feature
<222> LOCATION: (1207)..(1207)
<223> OTHER INFORMATION: n is a, c, g, or t
<220> FEATURE:
<221> NAME/KEY: modified_base
<222> LOCATION: (1209)..(1210)
<223> OTHER INFORMATION: a, c, t, g, unknown or other
<220> FEATURE:
<221> NAME/KEY: misc_feature
<222> LOCATION: (1209)..(1210)
<223> OTHER INFORMATION: n is a, c, g, or t
<220> FEATURE:
<221> NAME/KEY: modified_base
<222> LOCATION: (1221)..(1221)
<223> OTHER INFORMATION: a, c, t, g, unknown or other
<220> FEATURE:
<221> NAME/KEY: misc_feature
<222> LOCATION: (1221)..(1221)
<223> OTHER INFORMATION: n is a, c, g, or t
<220> FEATURE:
<221> NAME/KEY: modified_base
<222> LOCATION: (1230)..(1230)
<223> OTHER INFORMATION: a, c, t, g, unknown or other
<220> FEATURE:
<221> NAME/KEY: misc_feature
<222> LOCATION: (1230)..(1230)
<223> OTHER INFORMATION: n is a, c, g, or t
<220> FEATURE:
<221> NAME/KEY: modified_base
<222> LOCATION: (1284)..(1284)
<223> OTHER INFORMATION: a, c, t, g, unknown or other
<220> FEATURE:
<221> NAME/KEY: misc_feature
<222> LOCATION: (1284)..(1284)
<223> OTHER INFORMATION: n is a, c, g, or t
<220> FEATURE:
<221> NAME/KEY: modified_base
<222> LOCATION: (1287)..(1287)
<223> OTHER INFORMATION: a, c, t, g, unknown or other
<220> FEATURE:
<221> NAME/KEY: misc_feature
<222> LOCATION: (1287)..(1287)
<223> OTHER INFORMATION: n is a, c, g, or t
<220> FEATURE:
<221> NAME/KEY: modified_base
<222> LOCATION: (1296)..(1296)
<223> OTHER INFORMATION: a, c, t, g, unknown or other
<220> FEATURE:
<221> NAME/KEY: misc_feature
<222> LOCATION: (1296)..(1296)
<223> OTHER INFORMATION: n is a, c, g, or t
<220> FEATURE:
<221> NAME/KEY: modified_base
<222> LOCATION: (1391)..(1391)
<223> OTHER INFORMATION: a, c, t, g, unknown or other
<220> FEATURE:
<221> NAME/KEY: misc_feature
<222> LOCATION: (1391)..(1391)
<223> OTHER INFORMATION: n is a, c, g, or t

<400> SEQUENCE: 46
gggaatctcc aggatctgat tagcggcgga cgggtgagta cacgtgggta acctgcctca 60
tagagtggaa tagccttccg aaaggaagat taataccgca taacgttgaa agatggcatc 120
atcattcaac caaaggagca atccgctatg agatggaccc gcggcgcatt agctagttgg 180
tggggtaacg gcctaccaag gcgacgatgc gtagccgacc tgagagggtg atcggccaca 240
ttgggactga gacacggccc agactcctac gggaggcagc agtggggaat attgcacaat 300
gggggaaacc ctgatgcagc aacgccgcgt gagtgatgaa ggttttcgga tcgtaaagct 360
ctgtctttgg ggaagataat gacggtaccc aaggaggaag ccacggctaa ctacgtgcca 420
gcagccgcgg taatacgtag gtggcgagcg ttatccggat ttactgggcg taaagggagc 480
gtaggcggat gattaagtgg gatgtgaaat acccgggctc aacttgggtg ctgcattcca 540
aactggttat ctagagtgca ggagaggaga gtggaattcc tagtgtagcg gtgaaatgcg 600
tagagattag gaagaacacc agtggcgaag gcgactctct ggactgtaac tgacgctgag 660
gctcgaaagc gtggggagca aacaggatta gataccctgg tagtccacgc cgtaaacgat 720
gaatactagg tgtgggggtt tcaacacctc cgtgccgccg ctaacgcatt aagtattccg 780
cctggggagt acggtcgcaa gattaaaact naaaggaatt gacggggatc nncacnagta 840
gcggagcatg tggtttaatt cgaagcaacg cgaagaacct tacctacact tgacatccct 900
tgcattactc ttaatcgagg aaatctcttc ggggacaagg tgacaggtgg tgcatggttg 960
tcgtcagctc gtgtcgtgag atgttgggtt aagtcccgna acgaggggaa ccnttgtcgt 1020
tagttactac cattaagttg aggactntag ngagacngct gggttaacna ggaggaaggt 1080
ggggatgact caatctctgg ncnttatgtg tagggntaca cacgtgctac aatggctggt 1140
acagagagat gcataccggg aggtggantc aatttaaaaa cagtntcntt cggattgtag 1200
gntgaantnn cctactgaag ntggagttan tagtaatcgc gaatcagaat gtcgcggtga 1260
atacgttccc gggtcttgta cacnccnccc gtcacnccat gagagttggc aatacccgaa 1320
gtccgtgagc taaccgcaag gaggcagcgg ccgaaggtag ggtcagcgat tggggtgaag 1380
tcgtaacagg na 1392

<210> SEQ ID NO 47
<211> LENGTH: 1362
<212> TYPE: DNA
<213> ORGANISM: Faecalitalea sp.

<400> SEQUENCE: 47
gatgaacgct ggcggcatgc ctaatacatg caagtcgaac ggagcgaata tggaagcttg 60
cttccgtaag agctcagtgg cgaacgggtg agtaacacgt aggtaacctg cccatgtgcc 120
cgggataact gctggaaacg gtagctaaaa ccggataggt gaataggagg catctcttat 180
tcattaaagg acctgtaagg gtgcgaacat ggatggacct gcggcgcatt agctggttgg 240
agtggtaacg gcacaccaag gcgacgatgc gtagccgacc tgagagggcg aacggccaca 300
ttgggactga gacacggccc aaactcctac gggaggcagc agtagggaat tttcgtcaat 360
ggggggaacc ctgaacgagc aatgccgcgt gagtgaagaa ggtcttcgga tcgtaaagct 420
ctgttgtaag tgaagaacgg tcagtagagg aaatgatact gaagtgacgg tagcttacca 480
gaaagccacg gctaactacg tgccagcagc cgcggtaata cgtaggtggc gagcgttatc 540
cggaatcatt gggcgtaaag ggtgcgcagg tggtacatta agtccgaagt aaaaggcagc 600
agctcaactg ctgttggctt tggaaactgg tgaactggag tgcaggagag ggcgatggaa 660
ttccatgtgt agcggtaaaa tgcgtagata tatggaggaa caccagtggc gaaggcggtc 720
gcctggcctg caactgacac tgaggcacga aagcgtgggg agcaaatagg attagatacc 780
ctagtagtcc acgccgtaaa cgatgagaac taagtgttgg ggagactcag tgctgcagtt 840
aacgcaataa gttctccgcc tggggagtat gcacgcaagt gtgaaactca aaggaattga 900
cgggggcccg cacaagcggt ggagtatgtg gtttaattcg aagcaacgcg aagaacctta 960
ccaggccttg acatggatgt aaatgttcta gagatagaaa gatagctata catcacacag 1020
gtggtgcatg gttgtcgtca gctcgtgtcg tgagatgttg ggttaagtcc cgcaacgagc 1080
gcaaccctta tcgcatgtta ccagtattga gttagggact catgcgagac tgccggtgac 1140
aaaccggagg aaggtgggga tgacgtcaaa tcatcatgcc ccttatggcc tgggctacac 1200
acgtactaca atggcggcta caaagagaag cgaacctgcg agggggagcg gaactcataa 1260
aggccgtctc agttcggatt ggagtctgca actcgactcc atgaagtcgg aatcgctagt 1320
aatcgcagat cagcatgctg cggtgaatac gttctcgggc ct 1362

<210> SEQ ID NO 48
<211> LENGTH: 1399
<212> TYPE: DNA
<213> ORGANISM: Enterococcus durans

<400> SEQUENCE: 48
cttgtgtcac caaccatagg gagggggaaa acatggaaac ggggttcata ccgcataact 60
tttttagccc aatgcataag aagaaaggcc tttcgggttt cggtaaagga ggcccccgcg 120
gctcttatag tgtgtgtgga agtaaccgct tccacaaggc ccaggtttca tacccgactg 180
gagagtgtgt tcgccacact ggggaaagga cccccggccc agtctctcta ggggaggcag 240
cagtaggaat tttcggcaaa ggaaaaaatt tctgaccgaa caacgccggt tgaatgaaga 300
agtttttcgg atcgaaaaac tctgttgtta gagaagaaca aggacgttag taactgaacg 360
tcccctgacg gtatctaacc agaaagccac ggctaattac gtgccagcag ccgcggtaat 420
acgtaggtgg caagcgttgt ccggatttat tgggcgtaaa gcgagcgcag gcggtttctt 480
aagtctgatg tgaaagcccc cggctcaacc ggggagggtc attggaaact gggagacttg 540
agtgcagaag aggagagtgg aattccatgt gtagcggtga aatgcgtaga tatatggagg 600
aacaccagtg gcgaaggcgg ctctctggtc tgtaactgac gctgaggctc gaaagcgtgg 660
ggagcaaaca ggattagata ccctggtagt ccacgccgta aacgatgagt gctaagtgtt 720
ggagggtttc cgcccttcag tgctgcagca aacgcattaa gcactccgcc tggggagtac 780
gaccgcaagg ttgaaactca aaggaattga cgggggcccg cacaagcggt ggagcatgtg 840
gtttaattcg aagcaacgcg aagaacctta ccaggtcttg acatcctttg accactctag 900
agatagagct ttcccttcgg ggacaaagtg acaggtggtg catggttgtc gtcagctcgt 960
gtcgtgagat gttgggttaa gtcccgcaac gagcgcaacc cttattgtta gttgccatca 1020
tttagttggg cactctagcg agactgccgg tgacaaaccg gaggaaggtg gggatgacgt 1080
caaatcatca tgccccttat gacctgggct acacacgtgc tacaatggga agtacaacga 1140
gtcgctagac cgcgaggtca tgcaaatctc ttaaagcttc tctcagttcg gattgcaggc 1200
tgcaactcgc ctgcatgaag ccggaatcgc tagtaatcgc ggatcagcac gccgcggtga 1260
atacgttccc gggccttgta cacaccgccc gtcacaccac gagagtttgt aacacccgaa 1320
gtcggtgagg taaccttttt ggagccagcc gcctaaggtg ggatagatga ttggggtgaa 1380
gtcgtaacca acgtatgcc 1399

<210> SEQ ID NO 49
<211> LENGTH: 1414
<212> TYPE: DNA
<213> ORGANISM: Streptococcus sp.

<400> SEQUENCE: 49
agagtttgat cctggctcag gactaacgct ggcggcgtgc ctaatacatg caagtagaac 60
gctgaagact ttagcttgct aaagttggaa gagttgcgaa cgggtgagta acgcgtaggt 120
aacctgccta ctagcggggg ataactattg gaaacgatag ctaataccgc ataacagcat 180
ttaacccatg ttagatgctt gaaaggagca attgcttcac tagtagatgg acctgcgttg 240
tattagctag ttggtgaggt aacggctcac caaggcgacg atacatagcc gacctgagag 300
ggtgatcggc cacactggga ctgagacacg gcccagactc ctacgggagg cagcagtagg 360
gaatcttcgg caatgggggc aaccctgacc gagcaacgcc gcgtgagtga agaaggtttt 420
cggatcgtaa agctctgttg taagagaaga acgtgtgtga gagtggaaag ttcacacagt 480
gacggtaact taccagaaag ggacggctaa ctacgtgcca gcagccgcgg taatacgtag 540
gtcccgagcg ttgtccggat ttattgggcg taaagcgagc gcaggcggtt taataagtct 600
gaagttaaag gcagtggctt aaccattgtt cgctttggaa actgttagac ttgagtgcag 660
aaggggagag tggaattcca tgtgtagcgg tgaaatgcgt agatatatgg aggaacaccg 720
gtggcgaaag cggctctctg gtctgtaact gacgctgagg ctcgaaagcg tggggagcaa 780
acaggattag ataccctggt agtccacgcc gtaaacgatg agtgaaaggt gttaggccct 840
ttccggggct tagttgctgc acgctaactg cattatgaca ctccgccagg ggagtacgac 900
cgctaggttg aaactcaaag gagttgacgg gggccagcac aaccggtgga gcatgtggtt 960
gaattggaag caacgcgaag agccttacca ggtcttgaca tcccgacgct attcctagag 1020
ataggaagtt tcttcgggac attcggtggc aggtggtgca tggtagtcgt cagctcgtgt 1080
cgtgagatgt tgggttaagt cccgcaacga gcgcaacccc tattgttagt tgccatacat 1140
taagttgggc actctagcga gactgccggt aataaaccgg aggaaggtgg ggatgacgtc 1200
aaatcatcat gccccttatg acctgggcta cacacgacgc tacaatggtt ggtacaacga 1260
gtcgcgagtc ggtgacggca agcaaatctc ttaaagccaa tctcagttcg gattgtaggc 1320
tgcaactcgc ctacatgaag tcggaatcgc tagtaatcgc ggatcagcac gccgcggtga 1380
atacgttccc gggccttgca ctcaccgccc gtca 1414

<210> SEQ ID NO 50
<211> LENGTH: 1517
<212> TYPE: DNA

<213> ORGANISM: Streptococcus sp.

<400> SEQUENCE: 50
agagtttgat catggctcag gacgaacgcc ggcggcgtgc ctaatacatg caagtagaac 60
gctgaagact ttagcttgct aaagttggaa gagttgcgaa cgggtgagta acgcgtaggt 120
aacctgccta ctagcggggg ataactattg gaaacgatag ctaataccgt ataacagcat 180
ttaacacatg ttagatgctt gaaaggagca attgcttcac tagtagatgg acctgcgttg 240
tattagctag ttggtgaggt aacggctcac caaggcgacg atacatagcc gacctgagag 300
ggtgatcggc cacactggga ctgagacacg gcccagactc ctacgggagg cagcagtagg 360
gaatcttcgg caatgggggc aaccctgacc gagcaacgcc gcgtgagtga agaaggtttt 420
cggatcgtaa agctctgttg taagagaaga acgtgtgtga gagtggaaag ttcacacagt 480
gacggtaact taccagaaag ggacggctaa ctacgtgcca gcagccgcgg taatacgtag 540
gtcccgagcg ttgtccggat ttattgggcg taaagcgagc gcaggcggtt taataagtct 600
gaagttaaag gcagtggctt aaccattgtt cgctttggaa actgttagac ttgagtgcag 660
aaggggagag tggaattcca tgtgtagcgg tgaaatgcgt agatatatgg arggaaacac 720
cggtggcgaa agcggctctc tggtctgtaa ctgacgctga ggctcgagaa gcgtggggag 780
caaacaggat tagataccct ggtagtccac gccgtaagcg atgagtgcta ggtgttaggc 840
cctttccggg gcttagtgcc gcagctaacg cattaagcac tccgcctggg gagtacgacc 900
gcaaggttga aactcaaagg aattgacggg ggcccgcaca agcggtggag catgtggttt 960
aattcgaagc aacgcgaaga accttaccag gtcttgacat cccgatgcta ttcctagaga 1020
taggaagttt cttcggaaca tcggtgacag gtggtgcatg gttgtcgtca gctcgtgtcg 1080
tgagatgttg ggttaagtcc cgcaacgagc gcaaccccta ttgttagttg ccatcattaa 1140
gttgggcact ctagcgagac tgccggtaat aaaccggagg aaggtgggga tgacgtcaaa 1200
tcatcatgcc ccttatgacc tgggctacac acgtgctaca atggcggtca acagagggaa 1260
gcaatactgt gaagtggagc aaacccctaa aagccgtccc agttcggatt gcaggctgca 1320
acccgcctgt atgaagttgg aatcgctagt aatcgcggat cagcatgccg cggtgaatac 1380
gttcccgggc cttgtacaca ccgcccgtca caccatgaga gtcgggaaca cccgaagtcc 1440
gtagcctaac tttcacgagg gggcgcggcc gaaggtgggt tcgataattg gggtgaagtc 1500
gtaacaaggt aaccgta 1517

<210> SEQ ID NO 51
<211> LENGTH: 252
<212> TYPE: DNA
<213> ORGANISM: Streptococcus sp.

<400> SEQUENCE: 51
tacgtaggtc ccgagcgttg tccggattta ttgggcgtaa agcgagcgca ggcggtttaa 60
taagtctgaa gttaaaggca gtggcttaac catttttcgc tttggaaact gttagacttg 120
agtgcagaag gggagagtgg aattccatgt gtagcggtga aatgcgtaga tatatggagg 180
aacaccggtg gcgaaagcgg ctctctggtc tgtaactgac gctgaggctc gaaagcgtgg 240
ggagcaaaca gg 252

<210> SEQ ID NO 52
<211> LENGTH: 1529
<212> TYPE: DNA
<213> ORGANISM: Streptococcus sp.

<400> SEQUENCE: 52
agagtttgat cctggctcag gacgaacgct ggcggcgtgc ctaatacatg caagtagaac 60
gctgaagaaa ggagcttgct tcttttggat gagttgcgaa cgggtgagta acgcgtaggt 120
aacctgcctt gtagcggggg ataactattg gaaacgatag ctaataccgc ataacagctt 180
ttgacacatg ttagaagctt gaaagatgca attgcatcac tacgagatgg acctgcgttg 240
tattagctag taggtagggt aacggcctac ctaggcgacg atacatagcc gacctgagag 300
ggtgatcggc cacactggga ctgagacacg gcccagactc ctacgggagg cagcagtagg 360
gaatcttcgg caatgggggc aaccctgacc gagcaacgcc gcgtgagtga agaaggtttt 420
cggatcgtaa agctctgttg taagagaaga acgtgtgtga gagtggaaag ttcacacagt 480
gacggtaact taccagaaag ggacggctaa ctacgtgcca gcagccgcgg tgatacgtag 540
gtcccgagcg ttgtccggat ttattgggcg taaagcgagc gcaggcggtt taataagtct 600
gaagttaaag gcagtggctt aaccattgtt cgctttggaa actgttaaac ttgagtgcag 660
aaggggagag tggaattcca tgtgtagcgg tgaaatgcgt agatatatgg aggaacaccg 720
gtggcgaaag cggctctctg gtctgtaact gacgctgagg ctcgaaagcg tggggagcaa 780
acaggattag ataccctggt agtccacgcc gtaaacgatg agtgctaggt gttaggccct 840
ttccggggct tagtgccgca gctaacgcat taagtattcc gcctggggag tacggtcgca 900
agattaaaac tcaaaggaat tgacgggggc ccgcacaagc agcggagcat gtggtttaat 960
tcgaagcaac gcgaagaacc ttacctagac ttgacatctc ctgcattact cttaatcgag 1020
gaagtccctt cggggacagg atgacaggtg gtgcatggtt gtcgtcagct cgtgtcgtga 1080
gatgttgggt taagtcccgc aacgagcgca acccttattg ttagttgcca tcattaagtt 1140
gggcactcta gcgagactgc ccgggttaac cgggaggaag gtggggatga cgtcaaatca 1200
tcatgcccct tatgtctagg gctacacacg tgctacaatg gtcggtacaa taagacgcaa 1260
gcccgcgagg gggagcaaaa ctggaaaacc gatctcagtt cggattgtag gctgaaactc 1320
gcctacatga agctggagtt gctagtaatc gcgaatcagc atgtcgcggt gaatacgttc 1380
ccgggccttg tacacaccgc ccgtcacacc atgagagttg gcaataccca aagtacgtga 1440
tctaacccgc aagggaggaa gcgtcctaag gtagggtcag cgattggggt gaagtcgtaa 1500
caaggtagcc gtaggagaac ctgcggctg 1529

<210> SEQ ID NO 53
<211> LENGTH: 1398
<212> TYPE: DNA
<213> ORGANISM: Streptococcus sp.

<400> SEQUENCE: 53
agagtttgct cttgggtcag gatgaacgct ggcggcgtgc ttaacacatg caagtcgagc 60
gagaaaagtt cttcggagct tttctagcgg cggacgggtg agtaacacgt gggcaacctg 120
cctcatagag gggaatagcc ttccgaaagg aagattaata ccgcataaca ttgttgaaag 180
gcatctttta acaatcaaag gagcaatccg ctatgagatg ggcccgcggc gcattagcta 240
gttggtgagg taacggctca ccaaggcgac gatgcgtagc cgacctgaga gggtgatcgg 300
ccacattgga actgagacac ggtccagact cctacgggag gcagcagtgg ggaatattgc 360
acaatggggg aaaccctgat gcagcgacgc cgcgtgagtg aagaagtatt tcggtatgta 420
aagctctgtt gtaagagaag aacgtgtgtg agagtggaaa gttcacacag tgacggtaac 480
ttaccagaga gggacggcta actacgtgcc agcagccgcg gtaatacgta ggtcccgagc 540
gttgtccgga tttattgggc gtaaagcgag cgcaggcggt ttaataagtc tgaagttaaa 600
ggcagtggct taaccattgt tcgctttgga aactgttaga cttgagtgca gaaggggaga 660
gtggaattcc atgtgtagcg gtgaaatgcg tagatatatg gaggaacacc ggtggcgaaa 720
gcggctctct ggtctgtaac tgacgctgag gctcgaaagc gtggggagca aacaggatta 780
gataccctgg tagtccacgc cgtaaacgat gagtgctagg tgttaggccc tttccggggc 840
ttagtgccgc agctaacgca ttaagcactc cgcctgggga gtacgaccgc aaggttgaaa 900
ctcaaaggaa ttgacggggg cccgcacaag cggtggagca tgtggtttaa ttcgaagcaa 960
cgcgaagaac cttaccaggt cttgacatcc cgatgctatt cctagagata ggaagtttct 1020
tcggaacatc ggtgacaggt ggtgcatggt tgtcgtcagc tcgtgtcgtg agatgttggg 1080
ttaagtcccg caacgagcgc aacccctatt gttagttgcc atcattaagt tgggcactct 1140
agcgagactg ccggtaataa accggaggaa ggtggggatg acgtcaaatc atcatgcccc 1200
ttatgacctg ggctacacac gtgctacaat ggttggtaca acgagtcgcg agtcggtgac 1260
ggcaagcaaa tctcttaaag ccaatctcag ttcggattgt aggctgcaac tcgcctacat 1320
gaagtcggaa tcgctagtaa tcgcggatca gcacgccgcg gtgaatacgt tcccgggcct 1380
tgcactcacc gcccgtca 1398

<210> SEQ ID NO 54
<211> LENGTH: 1393
<212> TYPE: DNA
<213> ORGANISM: Streptococcus sp.
<220> FEATURE:
<221> NAME/KEY: modified_base
<222> LOCATION: (1381)..(1381)
<223> OTHER INFORMATION: a, c, t, g, unknown or other
<220> FEATURE:
<221> NAME/KEY: misc_feature
<222> LOCATION: (1381)..(1381)
<223> OTHER INFORMATION: n is a, c, g, or t

<400> SEQUENCE: 54
agactttagc ttgctaaagt tggaagagtt gcgaacgggt gagtaacgcg taggtaacct 60
gcctactagc gggggataac tattggaaac gatagctaat accgcataac agcatttaac 120
ccatgttaga tgcttgaaag gagcaattgc ttcactagta gatggacctg cgttgtatta 180
gctagttggt gaggtaacgg ctcaccaagg cgacgataca tagccgacct gagagggtga 240
tcggccacac tgggactgag acacggccca gactcctacg ggaggcagca gtagggaatc 300
ttcggcaatg gggcaaccc tgaccgagca acgccgcgtg agtgaagaag gttttcggat 360
cgtaaagctc tgttgtaaga gaagaacgtg tgtgagagtg gaaagttcac acagtgacgg 420
taacttacca gaaagggacg gctaactacg tgccagcagc cgcggtaata cgtaggtccc 480
gagcgttgtc cggatttatt gggcgtaaag cgagcgcagg cggtttaata agtctgaagt 540
taaaggcagt ggcttaacca ttgttcgctt tggaaactgt tagacttgag tgcagaaggg 600
gagagtggaa ttccatgtgt agcggtgaaa tgcgtagata tatggaggaa caccggtggc 660
gaaagcggct ctctggtctg taactgacgc tgaggctcga aagcgtgggg agcaaacagg 720
attagatacc ctggtagtcc acgccgtaaa cgatgagtgc taggtgttag gccctttccg 780
gggcttagtg ccgcagctaa cgcattaagc actccgcctg gggagtacga ccgcaaggtt 840
gaaactcaaa ggaattgacg gggcccgca caagcggtgg agcatgtggt ttaattcgaa 900
gcaacgcgaa gaaccttacc aggtcttgac atcccgatgc tattcctaga gataggaagt 960
ttcttcggaa ctgtgagact tgagggcaga agggtagagt gcacttgtat ggggagctgt 1020
ggaatgcgtt cccgcaacga gcgcaacccc tattgttagt tgccatcatt aagttgggca 1080
ctctagcgag actgccggta ataaaccgga ggaaggtggg gatgacgtca aatcatcatg 1140
ccccttatga cctgggctac acacgtgcta caatggttgg tacaacgagt cgcgagtcgg 1200
tgacggcaag caaatctctt aaagccaatc tcagttcgga ttgtaggctg caactcgcct 1260
acatgaagtc ggaatcgcta gtaatcgcgg atcagcacgc cgcggtgaat acgttcccgg 1320
gccttgtaca caccgcccgt cacaccacga gagtttgtaa cacccgaagt cggtgaggta 1380
nccttttagg agc 1393

<210> SEQ ID NO 55
<211> LENGTH: 1456
<212> TYPE: DNA
<213> ORGANISM: Streptococcus sp.

<400> SEQUENCE: 55
ttcaggacga acgctggcgg cgtgcctaat acatgcaagt agaacgctga agactttagc 60
ttgctaaagt tggaagagtt gcgaacgggt gagtaacgcg taggtaacct gcctactagc 120
gggggataac tattggaaac gatagctaat accgcataac agcatttaac ccatgttaga 180
tgcttgaaag gagcaattgc ttcactagta gatggacctg cgttgtatta gctagttggt 240
gaggtaacgg ctcaccaagg cgacgataca tagccgacct gagagggtga tcggccacac 300
tgggactgag acacggccca gactcctacg ggaggcagca gtagggaatc ttcggcaatg 360 gggcaaccc tgaccgagca acgccgcgtg agtgaagaag gttttcggat cgtaaagctc 420
tgttgtaaga gaagaacgtg tgtgagagtg gaaagttcac acagtgacgg taacttacca 480
gaaagggacg gctaactacg tgccagcagc cgcggtaata cgtaggtccc gagcgttgtc 540
cggatttatt gggcgtaaag cgagcgcagg cggtttaata agtctgaagt taaaggcagt 600
ggcttaacca ttgttcgctt tggaaactgt tagacttgag tgcagaaggg gagagtggaa 660
ttccatgtgt agcggtgaaa tgcgtagata tatggaggaa caccggtggc gaaagcggct 720
ctctggtctg taactgacgc tgaggctcga aagcgtgggg agcaaacagg attagatacc 780
ctggtagtcc acgccgtaaa cgatgagtgc taggtgttag gccctttccg gggcttagtg 840
ccgcagctaa cgcattaagc actccgcctg gggagtacga ccgcaaggtt gaaactcaaa 900
ggaattgacg gggcccgca caagcggtgg agcatgtggt ttaattcgaa gcaacgcgaa 960
gaaccttacc aggtcttgac atcctttgac cactctagag atagagcttc cccttcgggg 1020
gcaaagtgac aggtggtgca tggttgtcgt cagctcgtgt cgtgagatgt tgggttaagt 1080
cccgcaacga gcgcaaccct tattgttagt tgccatcatt tagttgggca ctctagcgag 1140
actgccggtg acaaaccgga ggaaggtggg gatgacgtca aatcatcatg ccccttatga 1200
cctgggctac acacgtgcta caatgggaag tacaacgagt tgcgaagtcg cgaggctaag 1260
ctaatctctt aaagcttctc tcagttcgga ttgtaggctg caactcgcct acatgaagcc 1320
ggaatcgcta gtaatcgcgg atcagcacgc cgcggtgaat acgttcccgg gccttgtaca 1380
caccgcccgt cacaccacga gagtttgtaa cacccgaagt cggtgaggta accttttagg 1440
agccagccgc ctaagg 1456

<210> SEQ ID NO 56
<211> LENGTH: 1442
<212> TYPE: DNA

<213> ORGANISM: Streptococcus sp.

<400> SEQUENCE: 56

```
ctaatacatg cgaggagaac gctgaagact ttcttttgct atagttggga gagttgctaa      60
cgggtgagta acgcgtaggt gacctgccta ctagcggggg ataactattg caaacgatag     120
ctaataccgc ataacagcct ttaacccatg ttagatgctt gaaaggagca attgcttcac     180
tagtagatgg acctgcgttg tattagctag ttggtgaggt aacggctcac caaggcgacg     240
atacatagcc gacctgagag ggtgatcggc cacactggga ctgagacacg gcccatactc     300
ctacgggagg caccagtagg gaatcttcgg gaatgggggc aaccctgacc gagcaacgcc     360
gcgtgagtga agaaggtttt cggatcgtaa agctctgttg taagagaaga acgtgtgtga     420
gagtggaaag ttcacactgt gacggtaact taccagaaag ggacggctaa ctacgtgcca     480
gcagccgcgg taatacgtag gtcccgagcg ttgtccggat ttattgggcg taaagcgagc     540
gcaggcggtt taataagtct gaagttaaag gcagtggctt aaccattgtt cgctttggaa     600
actgttagac ttgagtgcat aaggggagag tggaattcca tgtgtagcgg tgaaatgcgt     660
agatatatgg aggaacaccg gtggcgaaag cggctctctg gtctgtaact gacgttgagg     720
ctcgaaagcg tggggagcaa acaggattag ataccctggt agtccacgct gtaaacgatg     780
agtggtaggt gttaggccct ttctggggtt tagtgccgca gattacgcat taagccattc     840
gcctggggag tacgaccgca aggttgaaac ttaaaggaat tgacgggggc ccgcacaagc     900
ggtggagcat gtggtttaat tagaagcaac gcgaagaacc ttaccaggtc ttgacatccc     960
gatgctattc ttagagatag gaagtttctt cggaacatcg gtgacaggtg gtgcatggtt    1020
gtcgtcagct cgtgtcgaga gatgttgggt taagtccctc aacgagcgca acccctattt    1080
ttatttgcca tcattaagtt gggcaatcta gcgagactgc cggtaataaa ccggaggaag    1140
gtggggatga cgtcaaatca tcatgctcct tatgtcatgg ggtacacacg tggtacaatg    1200
gttggtacaa cgagtcgcga gttggtgaag gcaagcaaat ctcttaaagc caatatcagt    1260
tcggattgta ggctgcaaat agcctacatg tagtcggaat tgttagtaat cggggatcag    1320
cactccgcgg tgaatacgtt tccgggcctt gtacaccccg cccgtctaca ccacgagagt    1380
ttgtaacacc cgaagtcggt gaggtaactc ttttaggagc cagccgccta aggtgggata    1440
ga                                                                   1442
```

<210> SEQ ID NO 57
<211> LENGTH: 1382
<212> TYPE: DNA
<213> ORGANISM: Erysipelatoclostridium sp.

<400> SEQUENCE: 57

```
agagtttgat tatggctcag gatgaacgct ggcggcgtgc ctaatacatg caagtcgaac      60
gcgagcagca atgctcgagt ggcgaacggg tgagtaatac ataagtaacc tgccctagac     120
agggggataa ctgctggaaa cggcagctaa gaccgcatag gtatggacac tgcatggtga     180
ccatattaaa agtgccaagg cactggtaga ggatggactt atggcgcatt agctggttgg     240
tgaggtaacg gctcaccaag gcgacgatgc gtagccgacc tgagagggtg accggccaca     300
ctgggactga gacacggccc agactcctac gggaggcagc agtagggaat tttcggcaat     360
ggggggaacc ctgaccgagc aacgccgcgt gaaggaagaa ggaattcgtt ctgtaaactt     420
ctgttataaa ggaagaacgg cggatatagg gaatgatatc cgagtgacgg tactttatga     480
gaaagccacg gctaactacg tgccagcagc cgcggtaata cgtaggtggc gagcgttatc     540
```

cggaattatt gggcgtaaag agggagcagg cggcggcaga ggtctgtggt gaaagactga 600
agcttaactt cagtaagcca tagaaaccgg gctgctagag tgcaggagag gatcgtggaa 660
ttccatgtgt agcggtgaaa tgcgtagata tatggaggaa caccagtggc gaaggcgacg 720
gtctggcctg taactgacgc tcattcccga aagcgtgggg agcaaatagg attagatacc 780
ctagtagtcc acgccgtaaa cgatgagtac taagtgttgg gagtcaaatt tcagtgctgc 840
agttaacgca ataagtactc cgcctgagta gtacgttcgc aagaatgaaa ctcaaaggaa 900
ttgacggggg cccgcacaag cggtggagca tgtggtttaa ttcgatgata cgcgaggaac 960
cttaccaggg cttaaatgtg actgacaggt ccggaaacgg acttttcttc ggacagttac 1020
aggtgctgca tggttgtcgt cagctcgtgc cgtgaggtgt caggttaagt cctataacga 1080
gcgcaacccc tgtcgctagt tgccagcgag taatgtcggg aactctagcg agactgccag 1140
tgcaaactgc gaggaaggtg gggatgacgt caaatcatca cggcccttac gccctgggct 1200
acacacgtgc tacaatggcc ggtacagaga gcagccaccc cgcgaggggg agcgaatcta 1260
caaaaccggt cacagttcgg atcggagtct gcaactcgac tccgtgaagc tggaatcgct 1320
agtaatcgga tatcagccat gatccggtga atacgttccc gggccttgta cacacccccg 1380
tc 1382

<210> SEQ ID NO 58
<211> LENGTH: 1418
<212> TYPE: DNA
<213> ORGANISM: Megasphaera sp.

<400> SEQUENCE: 58
agagtttgat catggctcag gacgaacgct ggcggcgtgc ttaacacatg caagtcgaac 60
gagaagagat gagaagcttg cttcttatct cttcgagtgg caaacgggtg agtaacgcgt 120
aagcaacctg cccttcagat ggggacaaca gctggaaacg gctgctaata ccgaatacgt 180
tctttttgtc gcatggcaga gggaagaaag ggaggctctt cggagctttc gctgaaggag 240
gggcttgcgt ctgattagct agttggaggg gtaacggccc accaaggcga cgatcagtag 300
ccggtctgag aggatgaacg gccacattgg gactgagaca cggcccagac tcctacggga 360
ggcagcagtg gggaatcttc cgcaatggac gaaagtctga cggagcaacg ccgcgtgaac 420
gatgacggcc ttcgggttgt aaagttctgt tatacgggac gaatggcgta gcggtcaata 480
cccgttacga gtgacggtac cgtaagagaa agccacggct aactacgtgc cagcagccgc 540
ggtaatacgt aggtggcaag cgttgtccgg aattattggg cgtaaagggc gcgcaggcgg 600
cgtcgtaagt cggtcttaaa agtgcggggc ttaaccccgt gaggggaccg aaactgcgat 660
gctagagtat cggagaggaa agcggaattc ctagtgtagc ggtgaaatgc gtagatatta 720
ggaggaacac cagtggcgaa agcggctttc tggacgacaa ctgacgctga ggcgcgaaag 780
ccaggggagc aaacgggatt agataccccg gtagtcctgg ccgtaaacga tggatactag 840
gtgtaggagg tatcgacccc ttctgtgccg gagttaacgc aataagtatc ccgcctgggg 900
agtacggccg caaggctgaa actcaaagga attgacgggg gcccgcacaa gcggtggaac 960
atgtggttta attcgatgat acgcgaggaa ccttacccgg gcttaaattg cagtggaatg 1020
atgtggaaac atgtcagtga gcaatcaccg ctgtgaaggt gctgcatggt tgtcgtcagc 1080
tcgtgccgtg aggtgtcggc ttaagtgcca taacgagcgc aacccttatc ttcagttact 1140
aacaggtcat gctgaggact ctggagagac tgccgtcgta agatgtgagg aaggtgggga 1200

```
tgacgtcaaa tcagcacggc ccttacgtcc ggggctacac acgtgttaca atggggggta   1260

cagagggccg ctaccacgcg agtggatgcc aatcccaaaa acctctctca gttcggactg   1320

gagtctgcaa cccgactcca cgaagctgga ttcgctagta atcgcgcatc agccacggcg   1380

cggtgaatac gttcccgggc cttgcactca ccgcccgt                           1418
```

<210> SEQ ID NO 59
<211> LENGTH: 1383
<212> TYPE: DNA
<213> ORGANISM: Unknown
<220> FEATURE:
<223> OTHER INFORMATION: Bacteria
<220> FEATURE:
<221> NAME/KEY: source
<222> LOCATION: (1)..(1383)
<223> OTHER INFORMATION: /note="Description of Unknown: Lachnospiraceae sequence"

<400> SEQUENCE: 59

```
agagtttgat cctggctcag gatgaacgct ggcggcgtgc ttaacacatg caagtcgaac     60

gggaaacttt tcattgaagc ttcggcagat ttggtctgtt tctagtggcg gacgggtgag    120

taacgcgtgg gtaacctgcc ttatacaggg ggataacaac cagaaatggt tgctaatacc    180

gcataagcgc acaggaccgc atggtccggt gtgaaaaact ccggtggtat aagatggacc    240

cgcgttggat tagctagttg gcagggtaac ggcctaccaa ggcgacgatc catagccggc    300

ctgagagggt gaacggccac attgggactg agacacggcc cagactccta cgggaggcag    360

cagtggggaa tattgcacaa tgggggaaac cctgatgcag cgacgccgcg tgaaggaaga    420

agtatctcgg tatgtaaact tctatcagca gggaagatag tgacggtacc tgactaagaa    480

gccccggcta aatacgtgcc agcagccgcg gtaatacgta tggttcaagc gttatccgga    540

tttactgggt gtaaagggtg agtaggcggt tatgcaagtc atatgtgaaa tgtcggggct    600

caactccggc ctgcataaga aactgtataa ctagagtgca ggagaggcaa gcggaattcc    660

tagtgtagcg gtgaaatgcg tagatattag gaagaacacc ggtggcgaag gcggcttgct    720

ggactgttac tgacgctgag tcacgaaagc gtggggagca aacaggatta gataccctgg    780

tagtccacgc cgtaaacgat gaatactagg tgtcgggtgg caaagccatt cggtgccgca    840

gcaaacgcaa taagtattcc acctggggag tacgttcgca agaatgaaac tcaaaggaat    900

tgacggggac ccgcacaagc ggtggagtat gtggtttaat tcgaagcaac gcgaagaacc    960

ttaccaggcc ttgacatgga tataaatgtt ctagagatag aaagatagct atatatcaca   1020

caggtggtgc atggttgtcg tcagctcgtg tcgtgagatg ttgggttaag tcccgcaacg   1080

agcgcaaccc ttgtcttctg ttaccagcat tgagttgggg actcaggaga gactgccggt   1140

gacaaaccgg aggaaggtgg ggatgacgtc aaatcatcat gccccttatg gcctgggcta   1200

cacacgtact acaatggcgc ctacaaagag cagcgacacc gcgaggtgaa gcgaatctca   1260

taaagggcgt ctcagttcgg attgaagtct gcaactcgac ttcatgaagt cggaatcgct   1320

agtaatcgca gatcagcatg ctgcggtgaa tacgttcccg ggtcttgtac tcaccgcccg   1380

tca                                                                 1383
```

<210> SEQ ID NO 60
<211> LENGTH: 1361
<212> TYPE: DNA
<213> ORGANISM: Blautia sp.

<400> SEQUENCE: 60

```
gatgaacgct ggcggcgtgc ttaacacatg caagtcgagc gaagcactta agtggatctc     60

ttcggattga aacttatttg actgagcggc ggacgggtga gtaacgcgtg ggtaacctgc    120

ctcatacagg gggataacag ttagaaatgg ctgctaatac cgcataagcg cacaggaccg    180

catggtctgg tgtgaaaaac tccggtggta tgagatggac ccgcgtctga ttagctagtt    240

ggaggggtaa cggcccacca aggcgacgat cagtagccgg cctgagaggg tgaacggcca    300

cattgggact gagacacggc ccagactcct acgggaggca gcagtgggga atattgcaca    360

atgggggaaa ccctgatgca gcgacgccgc gtgaaggaag aagtatctcg gtatgtaaac    420

ttctatcagc agggaagaaa atgacggtac ctgactaaga agccccggct aactacgtgc    480

cagcagccgc ggtaatacgt agggggcaag cgttatccgg atttactggg tgtaaaggga    540

gcgtagacgg aagagcaagt ctgatgtgaa aggctggggc ttaaccccag gactgcattg    600

gaaactgttt ttctagagtg ccggagaggt aagcggaatt cctagtgtag cggtgaaatg    660

cgtagatatt aggaggaaca ccggtggcga aggcggctta ctggacgacc actgacgctg    720

aggctcgaaa gcgtggggag caaacaggat tagataccct ggtagtccac gccgtaaacc    780

gatgaataat aggtgtcggg gaacaatagt tctttggtgc cgcagcaaaa cgcattaagt    840

attccacctg gggagtacgt tcgcaagaat gaaactcaaa ggaattgacg gggacccgca    900

caagcggtgg agcatgtggt ttaattcgat gcaacgcgaa gaaccttacc tgctcttgac    960

atcccactga ccggacagta atgtgtcctt ttcttctgaa cagtggagac aggtggtgca   1020

tggttgtcgt cagctcgtgt cgtgagatgt tgggttaagt cccgcaacga gcgcaaccct   1080

cgtctttagt agccagcagt ccggctgggc actctagaga gactgccagg gataacctgg   1140

aggaaggcgg ggaggacgtc aaatcatcat gccccttacg agcagggcta cacacgtgct   1200

acaatggcgt aaacaaaggg aagcgacccc gtgaaggtga gcaaatctca aaaataacgt   1260

ctcagttcgg attgtagtct gcaactcgac tacatgaagc tggaatcgct agtaatcgcg   1320

aatcagaatg tcgcggtgaa taaaaggccg ggtcttgcac a                       1361
```

<210> SEQ ID NO 61
<211> LENGTH: 253
<212> TYPE: DNA
<213> ORGANISM: Alloprevotella sp.

<400> SEQUENCE: 61

```
tacggaaggt ccaggcgtta tccggattta ttgggtttaa agggagcgca ggcggactct     60

taagtcagtt gtgaaatacg gcggctcaac cgtcggactg cagttgatac tgggagtctt    120

gagtacacgc agagatactg gaattcatgg tgtagcggtg aaatgctcag atatcatgag    180

gaactccgat cgcgaaggca ggtatctgga gtgtaactga cgctgaggct cgaaagtgcg    240

ggtatcaaac agg                                                       253
```

<210> SEQ ID NO 62
<211> LENGTH: 1394
<212> TYPE: DNA
<213> ORGANISM: Parabacteroides sp.

<400> SEQUENCE: 62

```
agagtttgat cctggctcag gatgaacgct agcgacaggc ttaacacatg caagtcgagg     60

ggcagcatga tttgtagcaa tacagattga tggcgaccgg cgcacgggtg agtaacgcgt    120

atgcaactta cctatcagag gggatagcc cggcgaaagt cggattaata ccccataaaa    180

caggggtccc gcatgggaat atttgttaaa gattcatcgc tgatagatag gcatgcgttc    240
```

```
cattaggcag ttggcggggt aacggcccac caaaccgacg atggataggg gttctgagag    300
gaaggtcccc cacattggta ctgagacacg gaccaaactc ctacgggagg cagcagtgag    360
gaatattggt caatggccga gaggctgaac cagccaagtc gcgtgaagga agaaggatct    420
atggtctgta aacttctttt ataggggaat aaagtggagg acgtgtcctt ttttgtatgt    480
accctatgaa taagcatcgg ctaactccgt gccagcagcc gcggtaatac ggaggatgcg    540
agcgttatcc ggatttattg ggtttaaagg gtgcgtaggt ggtgatttaa gtcagcggtg    600
aaagtttgtg gctcaaccat aaaattgccg ttgaaactgg gttacttgag tgtgtttgag    660
gtaggcggaa tgcgtggtgt agcggtgaaa tgcatagata tcacgcagaa ctccgattgc    720
gaaggcagct tactaaacca taactgacac tgaagcacga aagcgtgggg atcaaacagg    780
attagatacc ctggtagtcc acgcagtaaa cgatgattac taggagtttg cgatacaatg    840
taagctctac agcgaaagcg ttaagtaatc cacctgggga gtacgccggc aacggtgaaa    900
ctcaaaggaa ttgacggggg cccgcacaag cggaggaaca tgtggtttaa ttcgatgata    960
cgcgaggaac cttacccggg tttgaacgta gtctgaccgg aatggaaaca ctccttctag   1020
caatagcaga ttacaaggtg ctgcatggtt gcctcaactc cggcccggaa ggtccggctt   1080
aattgccata acaagcgcac ccttttacca aggttcaaac aggtgaagct tgaagactct   1140
gtggaacctc ccccctaacc tgtgagaaga agtggggata cactcaataa accacggccc   1200
ttaatcccgg ggggaacact ggttacaatg ggttgggaaa gggggcttcc tggcgacagg   1260
atgctaatct ccaaaccatg tctcagttcg gatcggagtc tgcaactcga ctccgtgaag   1320
ctggattcgc tagtaatcgc gcatcagcca tggcgcggtg aatacgttcc cgggccttgt   1380
acacaccgcc cgtc                                                     1394
```

<210> SEQ ID NO 63
<211> LENGTH: 1445
<212> TYPE: DNA
<213> ORGANISM: Bacteroides sp.

<400> SEQUENCE: 63

```
tacaggctta acacatgcaa gtcgaggggc agcatgattg aagcttgctt caattgatgg     60
cgaccggcgc acgggtgagt aacacgtatc caaccttccg tacactcagg gatagccttt    120
cgaaagaaag attaatacct gatggtatct taagcacaca tgtaattaag attaaagatt    180
tatcggtgta cgatggggat gcgttccatt aggtagtagg cggggtaacg gcccacctag    240
cctacgatgg atggggggttc tgagaggaag gtcccccaca ttggaactga gacacggtcc    300
aaactcctac gggaggcagc agtgaggaat attggtcaat ggacgagagt ctgaaccagc    360
caagtagcgt gaaggatgaa ggtcctacgg attgtaaact tcttttataa gggaataaaa    420
cctcccacgt gtgggagctt gtatgtacct tatgaataag catcggctaa ctccgtgcca    480
gcagccgcgg taatacggag gatgcgagcg ttatccggat ttattgggtt taaagggagc    540
gcagacgggt cgttaagtca gctgtgaaag tttggggctc aaccttaaaa ttgcagttga    600
tactggcgtc cttgagtgcg gttgaggtgt gcggaattcg tggtgtagcg gtgaaatgct    660
tagatatcac gaagaactcc gattgcgaag gcagcacact aagccgtaac tgacgttcat    720
gctcgaaagt gtgggtatca aacaggatta gataccctgg tagtccacac agtaaacgat    780
gaatactcgc tgtttgcgat atacagtaag cggccaagcg aaagcattaa gtattccacc    840
tggggagtac gccggcaacg gtgaaactca aaggaattga cgggggcccg cacaagcgga    900
```

```
ggaacatgtg gtttaattcg atgatacgcg aggaacctta cccgggctta aattgcattt    960

gaatatattg gaaacagtat agccgtaagg caaatgtgaa ggtgctgcat ggttgtcgtc   1020

agctcgtgcc gtgaggtgtc ggcttaagtg ccataacgag cgcaaccctt atcttcagtt   1080

actaacaggt catgctgagg actctggaga gactgccgtc gtaagatgtg aggaaggtgg   1140

ggatgacgtc aaatcagcac ggcccttacg tccggggcta cacacgtgtt acaatggggg   1200

gtacagaagg ccgctacctg gtgacaggat gctaatccca aaagcctctc tcagttcgga   1260

tcgaagtctg caacccgact tcgtgaagct ggattcgcta gtaatcgcgc atcagccatg   1320

gcgcggtgaa tacgttcccg ggccttgtac acaccgcccg tcaagccatg aaagccgggg   1380

gtacctgaag tacgtaaccg caaggagcgt cctagggtaa aactggtaat tggggctaag   1440

tcata                                                               1445
```

<210> SEQ ID NO 64
<211> LENGTH: 1522
<212> TYPE: DNA
<213> ORGANISM: Unknown
<220> FEATURE:
<223> OTHER INFORMATION: Bacteria
<220> FEATURE:
<221> NAME/KEY: source
<222> LOCATION: (1)..(1522)
<223> OTHER INFORMATION: /note="Description of Unknown: Escherichia-
Shigella sequence"

<400> SEQUENCE: 64

```
agagtttgat catggctcag attgaacgct ggcggcaggc ctaacacatg caagtcgaac     60

ggtaacagga agaagcttgc ttctttgctg acgagtggcg gacgggtgag taatgtctgg    120

gaaactgcct gatggagggg gataactact ggaaacggta gctaataccg cataacgtcg    180

caagaccaaa gagggggacc ttcgggcctc ttgccatcgg atgtgcccag atgggattag    240

ctagtaggtg gggtaacggc tcacctaggc gacgatccct agctggtctg agaggatgac    300

cagccacact ggaactgaga cacggtccag actcctacgg gaggcagcag tggggaatat    360

tgcacaatgg gcgcaagcct gatgcagcca tgccgcgtgt atgaagaagg ccttcgggtt    420

gtaaagtact ttcagcgggg aggaagggag taaagttaat acctttgctc attgacgtta    480

cccgcagaag aagcaccggc taactccgtg ccagcagccg cggtaatacg gagggtgcaa    540

gcgttaatcg gaattactgg gcgtaaagcg cacgcaggcg gtttgttaag tcagatgtga    600

aatccccggg ctcaacctgg gaactgcatc tgatactggc aagcttgagt ctcgtagagg    660

ggggtagaat tccaggtgta gcggtgaaat gcgtagagat ctggaggaat accggtggcg    720

aaggcggccc cctggacgaa gactgacgct caggtgcgaa agcgtgggga gcaaacagga    780

ttagataccc tggtagtcca cgccgtaaac gatgtcgact tggaggttgt gcccttgagg    840

cgtggcttcc ggagctaacg cgttaagtcg accgcctggg gagtacggcc gcaaggttaa    900

aactcaaatg aattgacggg ggcccgcaca agcggcggag catgtggatt aattcgatgc    960

aacgcgaaga accttacctg ggtttgacat gcacaggacg cgtctagaga taggcgttcc   1020

cttgtggcct gtgtgcaggt ggtgcatggc tgtcgtcagc tcgtgtcgtg agatgttggg   1080

ttaagtcccg caacgagcgc aacccttgtc tcatgttgcc agcacgtaat ggtggggact   1140

cgtgagagac tgccggggtc aactcggagg aaggtgggga tgacgtcaag tcatcatgcc   1200

ccttatgtcc agggcttcac acatgctaca atggccggta caaagggctg cgatgccgcg   1260

aggttaagcg aatccttaaa agccggtctc agttcggatc ggggtctgca actcgacccc   1320
```

gtgaagtcgg agtcgctagt aatcgcagat cagcaacgct gcggtgaata cgttcccggg 1380
ccttgtacac accgcccgtc acgtcatgaa agtcggtaac acccgaagcc agtggcctaa 1440
ccctcgggag ggagctgtcg aaggtgggat cggcgattgg gacgaagtcg taacaaggta 1500
accgtagggg aacctgcggt tg 1522

<210> SEQ ID NO 65
<211> LENGTH: 1472
<212> TYPE: DNA
<213> ORGANISM: Unknown
<220> FEATURE:
<223> OTHER INFORMATION: Bacteria
<220> FEATURE:
<221> NAME/KEY: source
<222> LOCATION: (1)..(1472)
<223> OTHER INFORMATION: /note="Description of Unknown: Escherichia-
Shigella sequence"

<400> SEQUENCE: 65
cgccctgatt gacggctata cacatgcaag tcgaacggta acaggaaaca gcttgcttct 60
ttgctgacga gtggcggacg ggtgagtaat gtctgggaaa ctgcctgatg gagggggata 120
actactggaa acggtagcta ataccgcata acgtcgcaag accaaagagg gggaccttcg 180
ggcctcttgc catcggatgt gcccagatgg gattagctag taggtggggt aacggctcca 240
tccctaggcg agccgaatcc ttagcctggt ctgagaggaa tgaccagcca cactgggact 300
gagaacacgg tccagactcc tacgggaggc agcagtgggg aatattgcac aatgggcgca 360
agcctgatgc agccatgccg cgtgtatgaa gaaggccttc gggttgtaaa gtactttcag 420
cggggaggaa gggagtaaag ttaataccct ttgctcattg acgttacccg cagaagaagc 480
accggctaac tccgtgccag cagccgcggt aatacggagg gtgcaagcgt taatcggaat 540
tactgggcgt aaagcgcacg caggcggttt gttaagtcag atgtgaaatc cccgggctca 600
acctgggaac tgcatctgat actggcaagc ttgagtctcg tagagggggg tagaattcca 660
ggtgtagcgg tgaaatgcgt agagatctgg aggaataccg gtggcgaagg cggccccctg 720
gacgaagact gacgctcagg tgcgaaagcg tggggagcaa acaggattag ataccctggt 780
agtccacgcc gtaaacgatg tcgacttgga ggttgtgccc ttgaggcgtg gcttccggag 840
ctaacgcgtt aagtcgaccg cctggggagt acggccgcaa ggttaaaact caaatgaatt 900
gacgggggcc cgcacaagcg gtggagcatg tggtttaatt cgatgcaacg cgaagaacct 960
tacctggtct tgacatccac gggaagtttt cagagatgag aatgtgcctt cgggaaccgt 1020
gagacaggtg ctgcatggct gtcgtcagct cgtgttgtga aatgttgggt taagtcccgc 1080
aacgagcgca acccttatcc tttgttgcca gcggtccggc cgggaactca aaggagactg 1140
ccagtgataa actggaggaa ggtggggatg acgtccaggt catcatggcc cttacgaacc 1200
agggctacac acgtgcctac aatggacgca tccaaagaga gagcgaaccc tgcccgcgag 1260
agcaagcgga cctcataaag tgcgtcgtag tccggattgg agtctgcaac tcgactccat 1320
gaagtcggaa tcgctagtaa tcgtggatca gaatgccacg gtgaatacgt tcccgggcct 1380
tgtacacacc gcccgtcaca ccatgggagt gggttgcaaa agaagtaggt agcttaacct 1440
tcgggagggc gcttaccact ttggatgcga gg 1472

<210> SEQ ID NO 66
<211> LENGTH: 1374
<212> TYPE: DNA
<213> ORGANISM: Blautia sp.

<400> SEQUENCE: 66
agagtttgat catggctcag gatgaacgct agctacaggc ttaacacatg caagtcgagg 60
ggcagcatgg tcttagcttg ctaaggccga tggcgaccgg cgcacgggtg agtaacacgt 120
atccaacctg ccgtctactc ttggacagcc ttctgaaagg aagattaata caagatggca 180
tcatgagtcc gcatgttcac atgattaaag gtattccggt agacgatggg gatgcgttcc 240
attagatagt aggcggggta acggcccacc tagtcttcga tgggtagggg ttctgagagg 300
aaggtccccc acattggaac tgagacacgg cccaaactca tacgggaggc agcagtgggg 360
aatattgcac aatgggggaa accctgatgc agcgacgccg cgtgaaggat gaagtatttc 420
ggtatgtaaa cttctatcag cagggaagaa aatgacggta cctgactaag aagccccggc 480
taactacgtg ccagcagccg cggtaatacg taggggggcaa gcgttatccg gatttactgg 540
gtgtaaaggg agcgtagacg gcagtgcaag tctgaagtga aagcccgggg ctcaaccccg 600
ggactgcttt ggaaactgtg cagctagagt gtcggagagg caagcggaat tcctagtgta 660
gcggtgaaat gcgtagatat taggaggaac accagtggcg aaggcggctt gctggacgat 720
gactgacgtt gaggctcgaa agcgtgggga gcaaacagga ttagataccc tggtagtcca 780
cgccgtaaac gatgactact aggtgtcggg gagcaaagct cttcggtgcc gcagccaacg 840
caataagtag tccacctggg gagtacgttc gcaagaatga aactcaaagg aattgacggg 900
gacccgcaca agcggtggag catgtggttt aattcgaagc aacgcgaaga accttacctg 960
ctcttgacat ccctctgacc gctctttaat cggagctttc cttcgggaca gaggagacag 1020
gtggtgcatg gttgtcgtca gctcgtgtcg tgagatgttg ggttaagtcc cgcaacgagc 1080
gcaaccctta tggtcagtta ctacgcaaga ggactctggc cagactgccg ttgacaaaac 1140
ggaggaaggt ggggatgacg tcaaatcatc atgcccttta tgacttgggc tacacacgta 1200
ctacaatggc gttaaacaaa gagaagcgag accgcgaggt ggagcaaaac tcggaaacaa 1260
cgtcccagtt cggactgcag gctgcaactc gcctgcacga agtcggaatt gctagtaatc 1320
gcagatcagc atgctgcggt gaatacgttc ccgggccttg cactcaccgc ccgt 1374

<210> SEQ ID NO 67
<211> LENGTH: 1440
<212> TYPE: DNA
<213> ORGANISM: Tyzzerella sp.

<400> SEQUENCE: 67
taagatgaac gctggcggcg tgcttaacac atgcaagtcc tatgaagcgc ttaaacggat 60
ttcttcggat tgaagttttt gtgactgagt ggcggacggg tgagtaacgc gtgggtaact 120
tgcctcatac agggggataa cagttagaaa tgactgctaa taccgcataa gcgcacagtg 180
ctgcatggca cagtgtgaaa aactccggtg gtatgagatg gacccgcgtc tgattagcta 240
gttggtgggg taacggccta ccaaggcgac gatcagtagc cggcctgaga gggtgaacgg 300
ccacattggg actgagacac ggcccaaact cctacgggag gcagcagtgg ggaatattgc 360
acaatggggg aaaccctgat gcagcgacgc cgcgtgagcg aagaagtatt tcggtatgta 420
aagctctatc agcagggaag aaaatgacgg tacctgacta agaagcaccg gctaaatacg 480
tgccagcagc cgcggtaata cgtatggtgc aagcgttatc cggatttact gggtgtaaag 540
ggagcgtaga cggttgtgta agtctgatgt gaaagcccgg ggctcaaccc cgggactgca 600
ttggaaacta tgtaactaga gtgtcggaga ggtaagcgga attcctagtg tagcggtgaa 660
atgcgtagat attaggagga acaccagtgg cgaaggcggc ttactggacg atcactgacg 720

```
ttgaggctcg aaagcgtggg gagcaaacag gattagatac cctggtagtc cacgccgtaa    780

acgatgacta ctaggtgtcg gggcccataa gggcttcggt gccgcagcaa acgcaataag    840

tattccacct ggggagtacg ttcgcaagaa tgaaactcaa aggaattgac ggggacccgc    900

acaagcggtg gagcatgtgg tttaattcga agcaacgcga agaaccttac ctggtcttga    960

catcccactg accggacagt aatgtgtcct ttcctccggg acagtggaga caggtggtgc   1020

atggttgtcg tcagctcgtg tcgtgagatg ttgggttaag tcccgcaacg agcgcaaccc   1080

ctatccttag tagccagcag taagatgggc actctaggga gactgccagg gataacctgg   1140

aggaaggtgg ggatgacgtc aaatcatcat gccccttatg acttgggcta cacacgtgct   1200

acaatggcgt aaacaaagtg aagcgaagtc gtgaggccaa gcaaatcaca aaaataacgt   1260

ctcagttcgg attgtagtct gcaactcgac tacaagaagc tggaatcgct agtaatcgca   1320

gatcagaatg ctgcggtgaa tacgttcccg ggtcttgtac acaccgcccg tcacaccatg   1380

ggagtcgaaa atgcccgaag tcggtgacct aacgaaagaa ggagccgccg aaggcaggtt   1440
```

<210> SEQ ID NO 68
<211> LENGTH: 1370
<212> TYPE: DNA
<213> ORGANISM: Ruminococcus gauvreauii

<400> SEQUENCE: 68

```
atgaacgctg gcggcgtgcc taacacatgc aagtcgaacg aagcgcttga acggatatct     60

tcggactgaa gttcttgcga ctgagtggcg gacgggtgag taacgcgtgg gtaacctgcc    120

tcatacaggg ggataacagt tagaaatgac tgctaatacc gcataagcgc acagcttcgc    180

atggagcagt gtgaaaaact ccggtggtat gagatggacc cgcgtcagat tagctagttg    240

gcagggtaac ggcctaccaa ggcgacgatc tgtagccgac ctgagagggt gaccggccac    300

attgggactg agacacggcc caaactccta cgggaggcag cagtggggaa tattgcacaa    360

tgggggaaac cctgatgcag cgacgccgcg tgagcgaaga agtatttcgg tatgtaaagc    420

tctatcagca gggaagataa tgacggtacc tgactaagaa gctccggcta aatacgtgcc    480

agcagccgcg gtaatacgta tggagcaagc gttatccgga tttactgggt gtaaagggag    540

cgtagacggt ttgacaagtc tgatgtgaaa ttccagggct taaccctgga cctgcattgg    600

aaactgtcgg actagagtgt cggagaggtg agtggaattc ctagtgtagc ggtgaaatgc    660

gtagatatta ggaggaacac cagtggcgaa ggcggctcac tggacgataa ctgacgttga    720

ggctcgaaag cgtggggagc aaacaggatt agataccctg gtagtccacg ccgtaaacga    780

tgtgtactag gtgttgggga gcaaagctct tcggtgccgt cgcaaacgca gtaagtacac    840

cacctgggga gtacgttcgc aagaatgaaa ctcaaaggaa ttgacgggga cccgcacaag    900

cggtggagca tgtggtttaa ttcgaagcaa cgcgaagaac cttaccaaat cttgacatcg    960

gagtgaccgc tctttaatcg gagctttcct tcgggacact ccagacaggt ggtgcatggt   1020

tgtcgtcagc tcgtgtcgtg agatgttggg ttaagtcccg caacgagcgc aacccttatc   1080

cttagtagcc agcaagtgaa gttgggcact ctagggagac tgccagggat aacctggagg   1140

aaggtgggga tgacgtcaaa tcatcatgcc ccttatgatt tgggctacac acgtgctaca   1200

atggcgtaaa caaagggaag cgatcacgtg agtgtgagca aatctcaaaa ataacgtccc   1260

agttcggact gtagtctgca acccgactac acgaagctgg aatcgctagt aatcgcaggt   1320

cagcatactg cggtgaatac gttcccgggt cttgcacaca ccgcccgtca               1370
```

<210> SEQ ID NO 69
<211> LENGTH: 1366
<212> TYPE: DNA
<213> ORGANISM: Fusobacterium sp.

<400> SEQUENCE: 69
agagtttgat cctggctcag gatgaacgct gacagaatgc ttaacacatg caagtatact 60
tgatccttcg ggtgatggtg gcggacgggt gagtaacgcg taaagaactt gccctgcagt 120
ctgggacaac atttggaaac gaatgctaat cccgcataag cccacagctc ggcatcgagc 180
agagggaaaa ggagtgatct gctttgagat ggcctcgcgt ccgattagct ggttggtgag 240
gtgacggccc atcaaggcaa cgatcggtag ccggactgag aggttgaacg gccacattgg 300
gattgagaca cggcccttac tcctacggga ggcagcagtg gggaatattg gacaatggac 360
caaaagtctg atccagcaat tctgtgtgca cgatgaagtt tttcggaatg taaagtgctt 420
tcagttggga cgaagtaagt gacggtacca acagaagaag cgacggctaa atacgtgcca 480
gcagccgcgg taatacgtat gtcgcaagcg ttatccggat ttattgggcg taaagcgcgt 540
ctaggcggtt tggtaagtct gatgtgaaaa tgcggggctc aactccgtat tgcgttggaa 600
actgccaaac tagagtactg gagaggtggg cggaactaca agtgtagagg tgaaattcgt 660
agatatttgt aggaatgccg atggggaagc cagcccactg gacagatact gacgctaaag 720
cgcgaaagcg tgggtagcaa acaggattag ataccctggt agtccacgcc gtaaacgatg 780
attactaggt gttgggggtc gaacctcagc gcccaagcta acgcgataag taatccgcct 840
ggggagtacg tacgcaagta tgaaactcaa aggaattgac ggggacccgc acaagcggtg 900
gagcatgtgg tttaattcga cgcaacgcga ggaaccttac cagcgtttga catcctaaga 960
aattagcaga gatgcttttg tgccccttcg gggaactta gtgacaggtg gtgcatggct 1020
gtcgtcagct cgtgtcgtga gatgttgggt taagtcccgc aacgagcgca acccctttcg 1080
tatgttgcca tcattaagtt gggcactcat gcgatactgc ctgcgatgag caggaggaag 1140
gtggggatga cgtcaagtca tcatgcccct tatacgctgg gctacacacg tgctacaatg 1200
ggtagtacag agagtcgcaa acctgcgagg gggagctaat ctcagaaaac tattctcagt 1260
tcggattgta ctctgcaact cgagtacatg aagttggaat cgctagtaat cgcaaatcag 1320
ctatgttgcg gtgaatacgt tctcgggtct tgtacacacc gcccgt 1366

<210> SEQ ID NO 70
<211> LENGTH: 1361
<212> TYPE: DNA
<213> ORGANISM: Fusobacterium sp.

<400> SEQUENCE: 70
agagtttgat cctggctcag gacgaacgct ggcggcgtgc ctaacacatg caagtcgagc 60
gattctcttc ggagaagagc ggcggacggg tgagtaacgc gtgggtaacc tgccctgtac 120
acacggataa cataccgaaa ggtatgctaa tacgggataa tatataagag tcgcatgact 180
tttatatcaa agatttttcg gtacaggatg gacccgcgtc tgattagctt gttggcgggg 240
taacggccca ccaaggcgac gatcagtagc cgacctgaga gggtgatcgg ccacattgga 300
actgagacac ggtccaaact cctacgggag gcagcagtgg ggaatattgc acaatgggcg 360
caagcctgat gcagcaacgc cgcgtgagcg atgaaggcct tcgggtcgta aagctctgtc 420
ctcaaggaag ataatgacgg tacttgagga ggaagccccg gctaactaca tgccagcagc 480
cgcggtaata cgtatgtcgc aagcgttatc cggatttatt gggcgtaaag cgcgtctagg 540
tggtttggta agtctgatgt gaaaatgcgg ggctcaactc cgtattgcgt tggaaactgc 600
caaactagag tactggagag gtaggcggaa ctacaagtgt agaggtgaaa ttcgtagata 660
tttgtaggaa tgccgatggg gaagccagcc tactggacag atactgacgc taaagcgcga 720
aagcgtgggt agcaaacagg attagatacc ctggtagtcc acgccgtaaa cgatgattac 780
taggtgttgg gggtcgaacc tcagcgccca agctaacgcg ataagtaatc cgcctgggga 840
gtacgtacgc aagtatgaaa ctcaaaggag ttgacgggga cccgcacaag cggtggagca 900
tgtggtttaa ttcgacgcaa cgcgaggaac cttaccagcg tttgacatcc taggaatgag 960
aaagagattt cttagtgctc cttcgggaga acctagagac aggtggtgca tggctgtcgt 1020
cagctcgtgt cgtgagatgt tgggttaagt cccgcaacga gcgcaacccc tattgtatgt 1080
tgccatcatt aagttgggca ctcatgcgat actgcctgcg atgagcagga ggaaggtggg 1140
gatgacgtca agtcatcatg ccccttatac gctgggctac acacgtgcta caatgggcag 1200
tacagagaga agcaataccg cgaggtggag ccaaacttaa aaaccagtct cagttcggat 1260
tgtaggctga aactcgccta catgaagctg gagttactag taatcgcgaa tcagaatgtc 1320
gcggtgaata cgtacccggg tcttgtacac accgcccgtc a 1361

<210> SEQ ID NO 71
<211> LENGTH: 1360
<212> TYPE: DNA
<213> ORGANISM: Unknown
<220> FEATURE:
<223> OTHER INFORMATION: Bacteria
<220> FEATURE:
<221> NAME/KEY: source
<222> LOCATION: (1)..(1360)
<223> OTHER INFORMATION: /note="Description of Unknown: Lachnospiraceae sequence"

<400> SEQUENCE: 71
gatgaaccct tgcggcgtgc ttaacacatg caagtcgaac gggaaacatt ttattgaagc 60
ttcggcagat ctagcttgtt tctagtggcg gacgggtgag taacgcgtgg gcaacctgcc 120
tcacactggg ggataacagt cagaaatggc tgctaatacc gcataagcgc acagcatcgc 180
atgatgcagt gtgaaaaact ccggtggtgt gagatggacc cgcgttggat tagctagttg 240
gcagggcagc ggcctaccaa ggcgacgatc catagccggc ctgagagggt gaacggccac 300
attgggactg agacacggcc cagactccca cgggaggcag cagtggggaa tattgcacaa 360
tgggggaaac cctgatgcag cgacgccgcg tgaaggaaga agtatctcgg tatgtaaact 420
tctatcagca gggaagaaaa tgacggtacc tgactaagaa gccccggcta actacgtgcc 480
agcagccgcg gtaatacgta gggggcaagc gttatccgga tttactgggt gtaaagggag 540
cgtagacggt gttgcaagtc tgatgtgaaa ggcgggggct caacccctgg actgcattgg 600
aaactgtgat actcgagtgc cggagaggta agcggaattc ctagtgtagc ggtgaaatgc 660
gtagatatta gaaggaatac cagtggcgaa ggcggcttac tggacggtaa ctgacgttga 720
ggctcgaaag cgtggggagc aaacaagatt aagaaacctc tgggtagtcc acgcccgtaa 780
acgaaggaat aaaggggtcg ggagcagagc ttttcggtgc cgcagcaaac ccaataagta 840
ttccaccttg agaggacgtt cgcaagaatg aaactcaaag gaattgacgg gggacccgca 900
caagcggtgg agcatgtggt ttaattcgaa gcaacgcgaa gaaccttacc aagtcttgac 960
atccctctga ccgcacctta accggtgctt tccttcggga cagaggagac aggtggtgca 1020
tggttgtcgt cagctcgtgt cgtgagatgt tgggttaagt cccgcaacga gcgcaaccct 1080
tatccttagt agccagcggt ccggccgggc actctgggga gactgccagg gataacctgg 1140
aggaaggtgg ggatgacgtc aaatcatcat gccccttatg atttgggcta cacacgtgct 1200
acaatggcgt aaacaaaggg aagcgatcac gtgagtgcga gcaaatctca aaaataacgt 1260
cccagttcgg actgtagtct gcaacccgac tacacgaagc tggaatcgct agtaatcgca 1320
ggtcagcata ctgcggtgaa tacgttcccg ggtcttgtac 1360

<210> SEQ ID NO 72
<211> LENGTH: 1332
<212> TYPE: DNA
<213> ORGANISM: Blautia sp.

<400> SEQUENCE: 72
gctcaggatg aacgctggcg gcgtgcttaa cacatgcaag tcgagcgaag cacttgccat 60
tgactcttcg gaagatttgg catttgactg agcggcggac gggtgagtaa cgcgtgggta 120
acctgcctca tacgggggaa taacagttag aaatggctgc taatgccgca taaccgcaca 180
ggaccgcatg gactggtgtg aaaaactgag gtggtatgag atgggcccgc gtctgattag 240
gttagttggc ggggtaacgg cccaccaagc cgacgatcag tagccgacct gagagggacc 300
ggccacattg ggactgagac atggcccaga ctcctacggg aggcagcagt ggggaatatt 360
gcacaatgga ggaaactctg atgcagcgac gccgcatgaa ggaagaagta tctcggtatg 420
taaacttcta tcagcaggga agaaaatgac ggtacctgac taagaagccc cggctaacta 480
cgtgccagca gccgcggtaa tacgtagggg gcaagcgtta tccggattta ctgggtgtaa 540
agggagcgta gacggacggg caagtctgat gtgaaagccc ggggcttaac cccgggactg 600
cattggaaac tgtccatctt gagtgccgga gaggtaagcg gaattcctag tgtagcggtg 660
aaatgcgtag atattaggag gaacaccagt ggcgaaggcg gcttactgga cggtaactga 720
cgttgaggct cgaaagcgtg gggagcaaac aggattagat accctggtag tccacgccgt 780
aaacgatcaa taatgggtgt cgggttgcaa agcaatccgg tgccgcagca aacgcagtaa 840
gtattccccc tcgggagtac gttcgcaaga atgaaactca aaggaaggga cggggatccg 900
cacaagcggc ggagcatgtg gtttaattag aagcaacgcg aagaacctta ccaagtcttg 960
acatctgcct gaccgttcct taaccggaac tatctttcgg gacaggcaag acaggtggtg 1020
catggttgtc gtcagctcgt gtcgtgagat gttgggttaa gtcccgcaac gagcgcaacc 1080
cctgtcctta gtagccagca gtccggctgg gcactctagg gagactgccg gggtaaccc 1140 ggaggaaggc ggggaggagg tcaaatcatc atgcccccc tgatttgggc tacacacgtg 1200
gtacaatggc gtaaacaaag ggaagcggag tggtgacgct gagcaaatct caaaaataac 1260
gtcccacttc ggactgcagt ctgcaactcg actgcacgaa gctggaatcg ctagtaatcg 1320
cgaatcagaa tg 1332

<210> SEQ ID NO 73
<211> LENGTH: 1311
<212> TYPE: DNA
<213> ORGANISM: Unknown
<220> FEATURE:
<223> OTHER INFORMATION: Bacteria
<220> FEATURE:
<221> NAME/KEY: source
<222> LOCATION: (1)..(1311)
<223> OTHER INFORMATION: /note="Description of Unknown: Peptostreptococcaceae sequence"
<220> FEATURE:
<221> NAME/KEY: modified_base
<222> LOCATION: (725)..(725)
<223> OTHER INFORMATION: a, c, t, g, unknown or other
<220> FEATURE:
<221> NAME/KEY: misc_feature
<222> LOCATION: (725)..(725)
<223> OTHER INFORMATION: n is a, c, g, or t
<220> FEATURE:
<221> NAME/KEY: modified_base
<222> LOCATION: (727)..(727)
<223> OTHER INFORMATION: a, c, t, g, unknown or other
<220> FEATURE:
<221> NAME/KEY: misc_feature
<222> LOCATION: (727)..(727)
<223> OTHER INFORMATION: n is a, c, g, or t
<220> FEATURE:
<221> NAME/KEY: modified_base
<222> LOCATION: (740)..(740)
<223> OTHER INFORMATION: a, c, t, g, unknown or other
<220> FEATURE:
<221> NAME/KEY: misc_feature
<222> LOCATION: (740)..(740)
<223> OTHER INFORMATION: n is a, c, g, or t
<220> FEATURE:
<221> NAME/KEY: modified_base
<222> LOCATION: (747)..(748)
<223> OTHER INFORMATION: a, c, t, g, unknown or other
<220> FEATURE:
<221> NAME/KEY: misc_feature
<222> LOCATION: (747)..(748)
<223> OTHER INFORMATION: n is a, c, g, or t

<400> SEQUENCE: 73
gatgaacgct ggcggcgtgc ctaacacatg caagtcgagc gatttacttc ggtaaagagc 60
ggcggacggg tgagtaacgc gtgggtaacc tgccctgtac acacggataa cataccgaaa 120
ggtatgctaa tacgagataa tatgctttta tcgcatggta gaagtatcaa agcttttgcg 180
gtacaggatg gacccgcgtc tgattagcta gttggtaagg taacggctta ccaaggcaac 240
gatcagtagc cgacctgaga gggtgatcgg ccacattgga actgagacac ggtccaaact 300
cctacgggag gcagcagtgg ggaatattgc acaatgggcg aaagcctgat gcagcaacgc 360
cgcgtgagcg atgaaggcct tcgggtcgta aagctctgtc ctcaaggaag ataatgacgg 420
tacttgagga ggaagccccg gctaactacg tgccagcagc cgcggtaata cgtagggggc 480
tagcgttatc cggaattact gggcgtaaag ggtgcgtagg tggtttctta agtcagaggt 540
gaaaggctac ggctcaaccg tagtaagcct ttgaaactgg gaaacttgag tgcaggagag 600
gagagtggaa ttcctagtgt agcggtgaaa tgcgtagata ttaggaggaa caccagttgc 660
gaaggcggct ctctggactg taactgacac tgaggcacga aagcgtggga gcaaacaaga 720
ttagntnccc tggtagtccn cgccgtnncc gcccataaag agctgtcgga ggttaccccc 780
ttcggtggcg caggtaacgc aataaagaat tccgcctggg aaggaacgct tcgcaagagt 840
gaaattaaaa ggaatagacg gggacccgct caagtagtgg agcatgtggt ttaattcgaa 900
gcaacgcgaa gaactttctc taagcttgac atccttttga ccgatgccta atagcatcaa 960
tcccttctgg gacagaagtg acaggtggtg catggttgtt gtcagctcgt gtcgtgagat 1020
gttgggttaa gtcccgcaac gagcgcaacc cttgccttta gttgccagca ttaagttggg 1080
cactctatag ggactgccag ggataacctg gaggaaggtg gggatgacgt caaatcatca 1140
tgccccttat gcttagggct acacacgtgc tacaatgggt ggtacagagg gcagccaagt 1200
cgtgaggcgg agctaatccc ttaaagccat tctcagttcg gattgtaggc tgaaactcgc 1260
ctacatgaag ctggagttac tagtaatcgc agatcagaat gatgcggtga a 1311

<210> SEQ ID NO 74

<211> LENGTH: 1324
<212> TYPE: DNA
<213> ORGANISM: Intestinibacter sp.

<400> SEQUENCE: 74
cgtaagtaac ctgccctgta cacacggata acataccgaa aggtatgcta atacgggata 60
atatattttg atcgcatggt cgagatatca aagctccggc ggtacaccag ggaccccga 120 cagaggagct agttggtagt aatgtcacca aggcgacgat cagaagccga actgagaggg 180
ggatccgcac atgactgaga cacggtcaaa ctcctacggg aggcagcagt ggggaatatg 240
ccaatgggcg aaagctgatg cagcacgcgc gtgagcgatg aggctcgggt cgtaaagctc 300
gtctcaagga agataatgac ggtacttgag gaggaagccc cggctaacta cgtgccagca 360
gccgcggtaa tacgtagggg gctagcgtta tccggaatta ctgggcgtaa agggtgcgta 420
ggcggtcttt caagtcagga gtgaaaggct acggctcaac cgtagtaagc tcttgaaact 480
gtaagacttg agtgcaggag aggagagtgg aattcctagt gtagcggtga aatgcgtaga 540
tattaggagg aacaccagtt gcgaaggcgg ctctctggac tgtaactgac gctgaggcac 600
gaaagcgtgg ggagcaaaca ggattagata ccctggtagt ccacgccgta aacgatgagt 660
actagctgtc ggaggttacc cccttcggtg gcgcagctaa cgcattaagt actccgcctg 720
ggaagtacgc tcgcaagagt gaaactcaaa ggaattgacg gggacccgca caagtagcgg 780
agcatgtggt ttaattcgaa gcaacgcgaa gaaccttacc taagcttgac atcccactga 840
cccttcccta atcggaagct tcccttcggg acagtggtga caggtggtgc atggttgtcg 900
tcagctcgtg tcgtgagatg ttgggttaag tcccgcaacg agcgcaaccc ttgcctttag 960
ttgccagcat taagttgggc actctagagg gactgccagg gataacccgg aggagtgggg 1020
atgacgtcaa atcatcatgc cccttatgcta ggctacacac gtgctacaat gggtggtcag 1080
aggccagcca gtcgtgaggc cgagctatcc cataagccat tctcgtccgg attgtaggct 1140
gaactcgcct acatgagctg gaattacaag tatgcgatcg atgctgcgtg atgcgtccgg 1200
gtcttgtaca caccgcccgt cacaccatgg gagttggggg cgcccgaagc cggattgcta 1260
accttttgga agcgtccgtc gaaggtgaaa ccaataactg gggtgaagtc gtaacaaggt 1320
aacc 1324

<210> SEQ ID NO 75
<211> LENGTH: 1288
<212> TYPE: DNA
<213> ORGANISM: Peptoclostridium sp.

<400> SEQUENCE: 75
gaaagcggcg gacgggtgag taacgcgtag gcaacctgcc ccatacagag ggatagcatc 60
tggaaacgga tattaatacc tcataatact tagagatcac atggtaacta agtcaaagat 120
ttatcggtat gggatgggcc tgcgtctgat tagctagttg gtggggtaac ggctcaccaa 180
ggcgacgatc agtagccgac ctgagagggt gatcggccac attggaactg agacacggtc 240
caaactccta cgggaggcag cagtggggaa tattgcacaa tgggcgcaag cctgatgcag 300
caacgccgcg tgagcgatga aggccttcgg gtcgtaaagc tctgtcctca aggaagataa 360
tgacggtact tgaggaggaa gccccggcta actacgtgcc agcagccgcg gtaatacgta 420
gggggctagc gttatccgga tttactgggc gtaaagggtg cgtaggcggt ctttcaagtc 480
aggagttaaa ggctacggct caaccgtagt aagctcctga tactgtctga cttgagtgca 540
ggagaggaaa gcggaattcc cagtgtagcg gtgaaatgcg tagatattgg gaggaacacc 600

```
agtagcgaag gcggctttct ggactgtaac tgacgctgag gcacgaaagc gtggggagca    660

aacaggatta gataccctgg tagtccacgc tgtaaacgat gagtactagg tgtcggaggt    720

taccccccttc ggtgccgcag ctaacgcatt aagtactccg cctggggagt acgcacgcaa    780

gtgtgaaact caaaggaatt gacggggacc cgcacaagta gcggagcatg tggtttaatt    840

cgaagcaacg cgaagaacct tacctaggct tgacatcctt ctgaccgagg actaatctcc    900

tctttccctc cggggacaga agtgacaggt ggtgcatggt tgtcgtcagc tcgtgtcgtg    960

agatgttggg ttaagtcccg caacgagcgc aacccttgtc tttagttgcc atcattaagt   1020

tgggcactct agagagactg ccagggataa cctggaggaa ggtggggatg acgtcaaatc   1080

atcatgcccc ttatgcctag ggctacacac gtgctacaat gggtggtaca gagggcagcc   1140

aagccgtgag gtggagcaaa tcccttaaag ccattctcag ttcggattgt aggctgaaac   1200

tcgcctacat gaagctggag ttactagtaa tcgcagatca gaatgctgcg gtgaatgcgt   1260

tcccgggtct tgcacacacc gcccgtca                                       1288


<210> SEQ ID NO 76
<211> LENGTH: 1391
<212> TYPE: DNA
<213> ORGANISM: Sutterella sp.

<400> SEQUENCE: 76

ctggctcagg atgaacgcta gcgacaggct taacacatgc aagtcgaggg gcatcacggg     60

aggtagcaat accttctggt ggcgaccggc gcacgggtga gtaacacgta tgcaacctgc    120

cctgtacaga gggacaagcg gtggaaacgc cgtctaatcc cgcatgcact cttccggggg    180

catccccggg agagtaaagg agagatccgg tacaggatgg acatgcggcg cattagttag    240

ttggcggggt aacggcccac caagacgacg atgcgtaggg gttctgagag gaaggtcccc    300

cacattggaa ctgagacacg gtccaaactc ctacgggagg cagcagtgag gaatattggt    360

caatgggcgg aagcctgaac cagccaagtc gcgtgaggga agacggccct acgggttgta    420

aacctctttt gtcggggagc aatgccgcct ttgcgaaggc ggagggagag tacccgaaga    480

aaaagcaccg gctaactacg tgccagcagc cgcggtaata cgtagggtgc aagcgttaat    540

cggaattact gggcgtaaag cgtgcgcagg cggttctgta agacagatgt gaaatccccg    600

ggctcaacct gggaattgca tttgtgactg caggactaga gttcatcaga ggggggtgga    660

attccaagtg tagcagtgaa atgcgtagat atttggaaga acaccaatgg cgaaggcagc    720

cccctgggat gcgactgacg ctcatgcacg aaagcgtggg gagcaaacag gattagatac    780

cctggtagtc cacgccctaa acgatgtcta ctggttgttg ggattaata tccttggtaa     840

cgaagctaac gcgtgaagta gaccgcctgg ggagtacggt cgcaagatta aaactcaaag    900

gaattgacgg ggacccgcac aagcggtgga tgatgtggat taattcgatg atacgcgagg    960

aaccttaccc gggctcaaac ggcacagtga tacttttgaa aggaggtagc tctacggaga   1020

ctgtgccgag gtgctgcatg gttgtcgtca gctcgtgccg tgaggtgtcg gcttaagtgc   1080

cataacgagc gcaaccccta ttgtcagttg ccagcaggta aagctgggga ctctgacgag   1140

actgccggcg caagctgaga ggaaggcggg gatgacgtca aatcagcacg gcccttacgt   1200

ccggggcgac acacgtgtta caatggcagg cacagcggga agccacccgg cgacggggag   1260

cggaacccga aagcctgtct cagttcggat cggagtctgc aactcgactc cgtgaagctg   1320

gattcgctag taatcgcgca tcagccatgg cgcggtgaat acgttcccgg gccttgtaca   1380
```

caccgcccgt a 1391

<210> SEQ ID NO 77
<211> LENGTH: 1357
<212> TYPE: DNA
<213> ORGANISM: Collinsella sp.
<220> FEATURE:
<221> NAME/KEY: modified_base
<222> LOCATION: (766)..(766)
<223> OTHER INFORMATION: a, c, t, g, unknown or other
<220> FEATURE:
<221> NAME/KEY: misc_feature
<222> LOCATION: (766)..(766)
<223> OTHER INFORMATION: n is a, c, g, or t

<400> SEQUENCE: 77
acggcacccc tctccggagg gaagcgagtg gcgaacggct gagtaacacg tggagaacct 60
gccccctccc ccgggatagc cgcccgaaag gacgggtaat accggatacc cccgggcgcc 120
gcatggcgcc cgggctaaag ccccgacggg aggggatggc tccgcggccc atcaggtaga 180
cggcggggtg acggcccacc gtgccgacaa cgggtagccg ggttgagaga ccgaccggcc 240
agattgggac tgagacacgg cccagactcc tacgggaggc agcagtgggg aatcttgcgc 300
aatgggggga accctgacgc agcgacgccg cgtgcgggac ggaggccttc gggtcgtaaa 360
ccgctttcag cagggaagag tcaagactgt acctgcagaa gaagccccgg ctaactacgt 420
gccagcagcc gcggtaatac gtagggggcg agcgttatcc ggattcattg ggcgtaaagc 480
gcgcgtaggc ggcccggcag gccgggggtc gaagcggggg gctcaacccc ccgaagcccc 540
cggaacctcc gcggcttggg tccggtaggg gagggtggaa cacccggtgt agcggtggaa 600
tgcgcagata tcgggtggaa caccggtggc gaaggcggcc ctctgggccg agaccgacgc 660
tgaggcgcga aagctggggg agcgaacagg attagatacc ctggtagtcc cagccgtaaa 720
cgatggacgc tgggtgtggg gggacgatcc ccccgtgccg cagccnacgc attaagcgtc 780
ccgcctgggg agtacggccg caaggctaaa actcaaagga attgacgggg gcccgcacaa 840
gcagcggagc atgtggctta attcgaagca acgcgaagaa ccttacggcg catccccccg 900
aggcccacgg ggggtccgcc gcgtgggtca gaggagcgca tacgggaggt gcatggttgt 960
cgtcagctcg tgtcgtgaga tgttgggtta agtcccgcaa cgagcgcaac cccccgccgcg 1020 tgttgccatc gggtgatgcc gggaacccac gcgggaccgc cgccgtcaag gcggaggagg 1080
gcggggacga cgtcaagtca tcatgcccct tatgccctgg gctgcacacg tgctacaatg 1140
gccggtacag agggatgcca ccccgcgagg gggagcggat cccggaaagc cggccccagt 1200
tcggattggg ggctgcaacc cgcccccatg aagtcggagt tgctagtaat cgcggatcag 1260
catgccgcgg tgaatgcgtt cccgggcctt gtacacaccg cccgtcacac cacccgagtc 1320
gtctgcaccc gaagtcgccg gcccaaccgc aagggg 1357

<210> SEQ ID NO 78
<211> LENGTH: 1432
<212> TYPE: DNA
<213> ORGANISM: Phascolarctobacterium sp.

<400> SEQUENCE: 78
agagttgatc tggctcagat tgaacgctgg cggcaggctt aatacatgca agtcgaacgg 60
taacagcaaa aaagcttgct tttttggctg acgagtggcg gacgggtgag taatacctag 120
gaagctgcct aaacgagggg gataacacct ggaaacgggt gctaataccg catgataccg 180
caaggtcaaa ggttggttta ccaatcgcgt ttagatgcgc ctaggaggga ttagctagtt 240
ggtggggtaa cggctcacca aggcgatgat cagtagccgg tctgagagga tgaacggcca 300
cattgggact gagacacggc ccagactcct acgggaggca gcagtgggga atcttccgca 360
atgggcgaaa gcctgacgga gcaatgccgc gtgagtgatg aagggattcg tcccgtaaag 420
ctctgttgta tatgacgaat gtgcagattg tgaataatga tttgtaatga cggtagtata 480
cgaggaagcc acggctaact acgtgccagc agccgcggta atacgtaggt ggcgagcgtt 540
gtccggaatt attgggcgta aagagcatgt aggcggtttt ttaagtctgg agtgaaaatg 600
cggggctcaa ccccgtatgg ctctggatac tggaagactt gagtgcagga gaggaaaggg 660
gaattcccag tgtagcggtg aaatgcgtag atattgggag gaacaccagt ggcgaaggcg 720
cctttctgga ctgtgtctga cgctgagatg cgaaagccag ggtagcgaac gggattagat 780
accccggtag tcctggccgt aaacgatggg tactaggtgt gggaggtatc gaccccttcc 840
gtgccggagt taacgcaata agtaccccgc ctggggagta cgtccgcaag gatgaaactc 900
aaaggaattg acgggggccc gcacaagcgg tggagtatgt ggtttaattc gacgcaacgc 960
gaagaacctt accaaggctt gacattgatt gaaagaccta gagataggtc cctctcttcg 1020
gagacaagaa aacaggtggt gcatggctgt cgtcagctcg tgtcgtgaga tgttgggtta 1080
agtcccgcaa cgagcgcaac ccctatccta tgttaccagc gggtaatgcc ggggactcat 1140
aggagactgc caaggacaac ttggaggaag gcggggatga cgtcaagtca tcatgcccct 1200
tatgtcttgg gctacacacg tactacaatg gtcggcaaca gagggaagca aagccgcgag 1260
gcagagcaaa ccccagaaac ccgatctcag ttcggattgc aggctgcaac tcgcctgcat 1320
gaagtcggaa tcgctagtaa tcgcaggtca gcatactgcg gtgattacta tcccgggcgt 1380
tgtactcacc gcccgtcagg cggagttcgt acttcaaatg tgccacactg gg 1432

<210> SEQ ID NO 79
<211> LENGTH: 253
<212> TYPE: DNA
<213> ORGANISM: Clostridium sp.

<400> SEQUENCE: 79
tacgtaggtg gcaagcgttg tccggattta ctgggcgtaa agggagcgta ggcggatttt 60
taagtgggat gtgaaatacc cgggctcaac ctgggtgctg cattccaaac tggaaatcta 120
gagtgcagga ggggaaagtg gaattcctag tgtagcggtg aaatgcgtag agattaggaa 180
gaacaccagt ggcgaaggcg actttctgga ctgtaactga cgctgaggct cgaaagcgtg 240
gggagcaaac agg 253

<210> SEQ ID NO 80
<211> LENGTH: 253
<212> TYPE: DNA
<213> ORGANISM: Clostridium sp.

<400> SEQUENCE: 80
tacgtaggtg gcgagcgtta tccggattta ctgggcgtaa agggagcgta ggcggatgat 60
taagtgggat gtgaaatacc cgggctcaac ttgggtgctg cattccaaac tggttatcta 120
gagtgcagga gaggagagtg gaattcctag tgtagcggtg aaatgcgtag agattaggaa 180
gaacaccagt ggcgaaggcg actctctgga ctgtaactga cgctgaggct cgaaagcgtg 240
gggagcaaac agg 253

<210> SEQ ID NO 81

<211> LENGTH: 1402
<212> TYPE: DNA
<213> ORGANISM: Turicibacter sp.

<400> SEQUENCE: 81
agagtttgat cctggctcag gatgaacgct agcgataggc ctaacacatg caagtcgagg 60
ggcagcacat gagtagcaat acgatggtgg cgaccggcgc acgggtgagt aacacgtatg 120
caacctacct ttaacagggg aataacccgt tgaaaaacgg actaatactc cataacacag 180
gggtcccgca tgggaatatt tgttaaagat ttatcggttg aagatgggca tgcgttccat 240
tagctagttg gtagggtaaa ggcctaccaa ggcgacgatg cgtagccgac ctgagagggt 300
gaacggccac actgggactg agacacggcc cacactccta cgggaggcag cagtagggaa 360
tcttcggcaa tgggcgaaag cctgaccgag caacgccgcg tgaatgatga aggccttcgg 420
gttgtaaaat tctgttataa gggaagaacg actttagtag gaaatggcta gagtgtgacg 480
gtaccttatg agaaagccac ggctaactac gtgccagcag ccgcggtaat acgtaggtgg 540
cgagcgttat ccggaattat tgggcgtaaa gagcgcgcag gtggttgatt aagtctgatg 600
tgaaagccca cggcttaacc gtggagggtc attggaaact ggtcgacttg agtgcagaag 660
agggaagtgg aattccatgt gtagcggtga aatgcgtaga gatatggagg aacaccagtg 720
gcgaaggcgg cttcctggtc tgtaactgac actgaggcgc gaaagcgtgg ggagcaaaca 780
ggattagata ccctggtagt ccacgccgta aacgatgagt gctaagtgtt gggggtcgaa 840
cctcagtgct gaagttaacg cattaagcac tccgcctggg gagtacggtc gcaagactga 900
aactcaaagg aattgacggg gacccgcaca agcggtggag catgtggttt aattcgaagc 960
aacgcgaaga accttaccag gtcttgacat accattgacc gttctagaga taggattttc 1020
ccttcgggga caatggatac aggtggtgca tggttgtcgt cagctcgtgt cgtgagatgt 1080
tgggttaggt cccgcaacga gcgcaacccc tgtcgttagt tgccagcatt cagttgggga 1140
ctctaacgag actgccagtg acaaactgga ggaaggtggg gatgacgtca aatcatcatg 1200
ccccttatga cctgggctac acacgtgcta caatggttgg tacaaagaga agcgaagcgg 1260
tgacgtggag caaacctcat aaagccaatc tcagttcgga ttgtaggctg caactcgcct 1320
acatgaagtt ggaatcgcta gtaatcgcga atcagaatgt cgcggtgaat acgttcccgg 1380
gtcttgtaca caccgcccgt ca 1402

<210> SEQ ID NO 82
<211> LENGTH: 1409
<212> TYPE: DNA
<213> ORGANISM: Streptococcus sp.

<400> SEQUENCE: 82
tgcaagtaga acgctgaaga ctggtgcttg caccggttgg aagagttgcg aacgggtgag 60
taacgcgtag gtaacctgcc tgatagcggg ggataactat tggaaacgat agctaatacc 120
gcataacagg gaataacaca tgttattttt ttgaaagggg caattgctcc actatcagat 180
ggacctgcgt tgtattagct agtaggtgag gtaacggctc acctaggcga cgatacatag 240
ccgacctgag agggtgatcg gccacactgg gactgagaca cggcccagac tcctacggga 300
ggcagcagta gggaatcttc ggcaatgggg gcaaccctga ccgagcaacg ccgcgtgagt 360
gaagaaggtt ttcggatcgt aaagctctgt tgtaagagaa gaacgttgag tagagtggaa 420
agttactcaa gtgacggtat cttaccagaa agggacggct aactacgtgc cagcagccgc 480
ggtaatacgt aggtcccgag cgttgtccgg atttattggg cgtaaagcga gcgcaggcgg 540

```
tttaataagt ctgaagttaa aggcagtggc tcaaccattg ttcgctttgg aaactgttaa    600
acttgagtgc agaaggggag agtggaattc catgtgtagc ggtgaaatgc gtagatatat    660
ggaggaacac cggtggcgaa agcggctctc tggtctgtaa ctgacgctga ggctcgaaag    720
cgtgggtagc gaacaggatt agataccctg gtagtccacg ccgtaaacga tgagtgctag    780
gtgttgggtc ctttccggga ctcagtgccg acgctaacgc attaagcact ccgcctgggg    840
agtacgaccg caaggttgaa actcaaagga attgacgggg gcccgcacaa gcggtggagc    900
atgtggttta attcgaagca acgcgaagaa ccttaccagg tcttgacatc ccgatgctat    960
ccctagagat agggagttac ttcggtacat cggtgacagg tggtgcatgg ttgtcgtcag   1020
ctcgtgtcgt gagatgttgg gttaagtccc gcaacgagcg caacccctat tgttagttgc   1080
catcattcag ttgggcactc tagcgagact gccggtaata aaccggagga aggtggggat   1140
gacgtcaaat catcatgccc cttatgacct gggctacaca cgtgctacaa tggttggtac   1200
aacgagttgc gagtcggtga cggcaagcta atctcttaaa gccaatctca gttcggattg   1260
taggctgcaa ctcgcctaca tgaagtcgga atcgctagta atcgcggatc agcacgccgc   1320
ggtgaatacg ttcccgggcc ttgtacacac cgcccgtcac accacgagag tttgtaacac   1380
ccaaagtcgg tgaggtaacc ttcggagcc                                     1409
```

<210> SEQ ID NO 83
<211> LENGTH: 1517
<212> TYPE: DNA
<213> ORGANISM: Streptococcus sp.

<400> SEQUENCE: 83

```
agagtttgat catggctcag gacgaacgcc ggcggcgtgc ctaatacatg caagtagaac     60
gctgaagact ttagcttgct aaagttggaa gagttgcgaa cgggtgagta acgcgtaggt    120
aacctgccta ctagcggggg ataactattg gaaacgatag ctaataccgt ataacagcat    180
ttaacacatg ttagatgctt gaaaggagca attgcttcac tagtagatgg acctgcgttg    240
tattagctag ttggtgaggt aacggctcac caaggcgacg atacatagcc gacctgagag    300
ggtgatcggc cacactggga ctgagacacg gcccagactc ctacgggagg cagcagtagg    360
gaatcttcgg caatgggggc aaccctgacc gagcaacgcc gcgtgagtga agaaggtttt    420
cggatcgtaa agctctgttg taagagaaga acgtgtgtga gagtggaaag ttcacacagt    480
gacggtaact taccagaaag ggacggctaa ctacgtgcca gcagccgcgg taatacgtag    540
gtcccgagcg ttgtccggat ttattgggcg taaagcgagc gcaggcggtt taataagtct    600
gaagttaaag gcagtggctt aaccattgtt cgctttggaa actgttagac ttgagtgcag    660
aaggggagag tggaattcca tgtgtagcgg tgaaatgcgt agatatatgg arggaaacac    720
cggtggcgaa agcggctctc tggtctgtaa ctgacgctga ggctcgagaa gcgtggggag    780
caaacaggat tagataccct ggtagtccac gccgtaagcg atgagtgcta ggtgttaggc    840
cctttccggg gcttagtgcc gcagctaacg cattaagcac tccgcctggg gagtacgacc    900
gcaaggttga aactcaaagg aattgacggg ggcccgcaca agcggtggag catgtggttt    960
aattcgaagc aacgcgaaga accttaccag gtcttgacat cccgatgcta ttcctagaga   1020
taggaagttt cttcggaaca tcggtgacag gtggtgcatg gttgtcgtca gctcgtgtcg   1080
tgagatgttg ggttaagtcc cgcaacgagc gcaaccccta ttgttagttg ccatcattaa   1140
gttgggcact ctagcgagac tgccggtaat aaaccggagg aaggtgggga tgacgtcaaa   1200
```

```
tcatcatgcc ccttatgacc tggctacac acgtgctaca atggcggtca acagagggaa   1260

gcaatactgt gaagtggagc aaaccccctaa aagccgtccc agttcggatt gcaggctgca   1320

acccgcctgt atgaagttgg aatcgctagt aatcgcggat cagcatgccg cggtgaatac   1380

gttcccgggc cttgtacaca ccgcccgtca caccatgaga gtcgggaaca cccgaagtcc   1440

gtagcctaac tttcacgagg gggcgcggcc gaaggtgggt tcgataattg ggtgaagtc   1500

gtaacaaggt aaccgta                                                   1517


<210> SEQ ID NO 84
<211> LENGTH: 252
<212> TYPE: DNA
<213> ORGANISM: Streptococcus sp.

<400> SEQUENCE: 84

tacgtaggtc ccgagcgttg tccggattta ttgggcgtaa agcgagcgca ggcggtttaa     60

taagtctgaa gttaaaggca gtggcttaac catttttcgc tttggaaact gttagacttg    120

agtgcagaag ggagagtgg aattccatgt gtagcggtga aatgcgtaga tatatggagg    180

aacaccggtg gcgaaagcgg ctctctggtc tgtaactgac gctgaggctc gaaagcgtgg    240

ggagcaaaca gg                                                        252


<210> SEQ ID NO 85
<211> LENGTH: 1422
<212> TYPE: DNA
<213> ORGANISM: Streptococcus sp.

<400> SEQUENCE: 85

agagtttgat cctggctcag gacgaacgct ggcggcgtgc ctaatacatg caagtcgagc     60

gagcggaact aacagattta cttcggtaat gacgttagga aagcgagcgg cggatgggtg    120

agtaacacgt ggggaacctg ccccatagtc tgggatacca cttggaaaca ggtgctaata    180

ccggataaga aagcagatcg catgatcagc ttttaaaagg cggcgtaagc tgtcgctatg    240

ggatggcccc gcggtgcatt agctagttgg taaggtaaag gcttaccaag gcaatgatgc    300

atagccgagt tgagagactg atcggccaca ttgggactga gacacggccc aaactcctac    360

gggaggcagc agtagggaat cttccacaat ggacgcaagt ctgatggagc aacgccgcgt    420

gagtgaagaa ggttttcgga tcgtaaagct ctgttgttgg tgaagaagga tagaggtagt    480

aactggcctt tatttgacgg taatcaacca gaaagtcacg gctaactacg tgccagcagc    540

cgcggtaata cgtaggtggc aagcgttgtc cggatttatt gggcgtaaag cgagcgcagg    600

cggtttaata agtctgaagt taaaggcagt ggcttaacca ttgttcgctt tggaaactgt    660

tagacttgag tgcagaaggg gagagtggaa ttccatgtgt agcggtgaaa tgcgtagata    720

tatggaggaa caccggtggc gaaagcggct ctctggtctg taactgacgc tgaggctcga    780

aagcgtgggg agcaaacagg attagatacc ctggtagtcc acgccgtaaa cgatgagtgc    840

taggtgttag gccctttccg ggcttagtg ccgcagctaa cgcattaagc actccgcctg    900

gggagtacga ccgcaaggtt gaaactcaaa ggaattgacg ggggcccgca caagcggtgg    960

agcatgtggt ttaattcgaa gcaacgcgaa gaaccttacc aggtcttgac atcccgatgc   1020

tattcctaga gataggaagt ttcttcggaa catcggtgac aggtggtgca tggttgtcgt   1080

cagctcgtgt cgtgagatgt tgggttaagt cccgcaacga gcgcaacccc tattgttagt   1140

tgccatcatt aagttgggca ctctagcgag actgccggta ataaaccgga ggaaggtggg   1200

gatgacgtca agtcatcatg ccccttatga cctgggctac acacgtgcta caatgggcag   1260
```

tacaacgaga agcgagcctg cgaaggcaag cgaatctctg aaagctgttc tcagttcgga 1320
ctgcagtctg caactcgact gcacgaagct ggaatcgcta gtaatcgcgg atcagcacgc 1380
cgcggtgaat acgttcccgg gccttgcaca caccgcccgt ca 1422

<210> SEQ ID NO 86
<211> LENGTH: 1536
<212> TYPE: DNA
<213> ORGANISM: Streptococcus sp.

<400> SEQUENCE: 86
agagtttgat cctggctcag gacgaacgct ggcggcgtgc ctaatacatg caagtggaac 60
gcacagttag tatgtagttt actacaacat tacttgtgag tcgcgaacgg gtgagtaacg 120
cgtaggtaac ctgccttgta gcgggggata actattggaa acgatagcta ataccgcata 180
acagttgata actcatgtta ttagcttgaa agatgcaaca gcatcactac gagatggacc 240
tgcgttgtat tagctagttg gtgaggtaaa ggctcaccaa ggccacgata catagccgac 300
ctgagagggt gatcggccac attgggactg agacacggcc caaactccta cgggaggcag 360
cagtagggaa tcttcggcaa tggggggcaac cctgaccgag caacgccgcg tgagtgaaga 420
aggttttcgg atcgtaaagc tctgttgtaa gagaagaacg ttgatgagag tggaaaattc 480
atcaagtgac ggtatcttac cagaaaggga cggctaacta cgtgccagca gccgcggtaa 540
tacgtaggtc ccgagcgttg tccggattta ttgggcgtaa agcgagcgca ggcggtttcg 600
taagtctgaa gttaaaggca gtggctcaac cattgttcgc tttggaaact gcgagacttg 660
agtgcagaag ggagagtgg aattccatgt gtagcggtga aatgcgtaga tatatggagg 720
aacaccggtg gcgaaagcgg ctctctggtc tgtaactgac gctgaggctc gaaagcgtgg 780
ggagcaaaca ggattagata ccctggtagt ccacgccgta aacgatgagt gctaggtgtt 840
aggccctttc cggggcttag tgccgcagct aacgcattaa gcactccgcc tggggagtac 900
gaccgcaagg ttgaaactca aaggaattga cgggggcccg cacaagcggt ggagcatgtg 960
gtttaattcg aagcaacgcg aagaacctta ccaggtcttg acatcccgat gcccgctcta 1020
gagatagagt tttacttttg tacatcggtg acaggtggtg catggttgtc gtcagctcgt 1080
gtcgtgagat gttgggttaa gtcccgcaac gagcgcaacc cctattgtta gttgccatca 1140
ttgagttggg cactctagcg agactgccgg taataaaccg gaggaaggtg gggatgacgt 1200
caaatcatca tgccccttat gacctgggct acacacgtgc tacaatggct ggtacaacga 1260
gtcgcaagcc ggtgacggca agctaatctc ttaaagccag tctcagttcg gattgtaggc 1320
tgcaactcgc ctacatgaag tcggaatcgc tagtaatcgc ggatcagcac gccgcggtga 1380
atacgttccc gggccttgta cacaccgccc gtcacaccac gagagtttgt aacacccgaa 1440
gtcggtgagg taacctttta ggagccagcc gcctaaggtg ggatagatga ttggggtgaa 1500
gtcgtaacaa ggtagccgta tcggaaggtg cggctg 1536

<210> SEQ ID NO 87
<211> LENGTH: 1393
<212> TYPE: DNA
<213> ORGANISM: Streptococcus sp.
<220> FEATURE:
<221> NAME/KEY: modified_base
<222> LOCATION: (1381)..(1381)
<223> OTHER INFORMATION: a, c, t, g, unknown or other
<220> FEATURE:
<221> NAME/KEY: misc_feature
<222> LOCATION: (1381)..(1381)

<223> OTHER INFORMATION: n is a, c, g, or t

<400> SEQUENCE: 87

```
agactttagc ttgctaaagt tggaagagtt gcgaacgggt gagtaacgcg taggtaacct     60
gcctactagc gggggataac tattggaaac gatagctaat accgcataac agcatttaac    120
ccatgttaga tgcttgaaag gagcaattgc ttcactagta gatggacctg cgttgtatta    180
gctagttggt gaggtaacgg ctcaccaagg cgacgataca tagccgacct gagagggtga    240
tcggccacac tgggactgag acacggccca gactcctacg ggaggcagca gtagggaatc    300
ttcggcaatg gggcaaccc tgaccgagca acgccgcgtg agtgaagaag gttttcggat    360
cgtaaagctc tgttgtaaga gaagaacgtg tgtgagagtg gaaagttcac acagtgacgg    420
taacttacca gaaagggacg gctaactacg tgccagcagc cgcggtaata cgtaggtccc    480
gagcgttgtc cggatttatt gggcgtaaag cgagcgcagg cggtttaata agtctgaagt    540
taaaggcagt ggcttaacca ttgttcgctt tggaaactgt tagacttgag tgcagaaggg    600
gagagtggaa ttccatgtgt agcggtgaaa tgcgtagata tatggaggaa caccggtggc    660
gaaagcggct ctctggtctg taactgacgc tgaggctcga aagcgtgggg agcaaacagg    720
attagatacc ctggtagtcc acgccgtaaa cgatgagtgc taggtgttag gccctttccg    780
gggcttagtg ccgcagctaa cgcattaagc actccgcctg gggagtacga ccgcaaggtt    840
gaaactcaaa ggaattgacg gggcccgca caagcggtgg agcatgtggt ttaattcgaa    900
gcaacgcgaa gaaccttacc aggtcttgac atcccgatgc tattcctaga gataggaagt    960
ttcttcggaa ctgtgagact tgagggcaga agggtagagt gcacttgtat ggggagctgt   1020
ggaatgcgtt cccgcaacga gcgcaacccc tattgttagt tgccatcatt aagttgggca   1080
ctctagcgag actgccggta ataaaccgga ggaaggtggg gatgacgtca aatcatcatg   1140
ccccttatga cctgggctac acacgtgcta caatggttgg tacaacgagt cgcgagtcgg   1200
tgacggcaag caaatctctt aaagccaatc tcagttcgga ttgtaggctg caactcgcct   1260
acatgaagtc ggaatcgcta gtaatcgcgg atcagcacgc cgcggtgaat acgttcccgg   1320
gccttgtaca caccgcccgt cacaccacga gagtttgtaa cacccgaagt cggtgaggta   1380
nccttttagg agc                                                      1393
```

<210> SEQ ID NO 88
<211> LENGTH: 1510
<212> TYPE: DNA
<213> ORGANISM: Streptococcus sp.

<400> SEQUENCE: 88

```
agagtttgat cctggctcag gacgaacgct ggcggcgtgc ctaatacatg caagtagaac     60
gctgaagaaa ggagcttgct tcttttggat gagttgcgaa cgggtgagta acgcgtaggt    120
aacctgcctt gtagcggggg ataactattg gaaacgatag ctaataccgc ataacagctt    180
ttgacacatg ttagaagctt gaaagatgca attgcatcac tacgagatgg acctgcgttg    240
tattagctag taggtagggt aacggcctac ctaggcgacg atacatagcc gacctgagag    300
ggtgatcggc cacactggga ctgagacacg gcccagactc ctacgggagg cagcagtagg    360
gaatcttcgg caatgggggc aaccctgacc gagcaacgcc gcgtgagtga agaaggtttt    420
cggatcgtaa agctctgttg taagagaaga acgtgtgtga gagtggaaag ttcacacagt    480
gacggtaact taccagaaag ggacggctaa ctacgtgcca gcagccgcgg taatacgtag    540
gtcccgagcg ttgtccggat ttattgggcg taaagcgagc gcaggcggtt taataagtct    600
```

gaagttaaag gcagtggctt aaccattgtt cgctttggaa actgttaaac ttgagtgcag 660
aaggggagag tggaattcca tgtgtagcgg tgaaatgcgt agatatatgg aggaacaccg 720
gtggcgaaag cggctctctg gtctgtaact gacgctgagg ctcgaaagcg tggggagcaa 780
acaggattag ataccctggt agtccacgcc gtaaacgatg agtgctaggt gttaggccct 840
ttccggggct tagtgccgca gctaacgcat taagcactcc gcctggggag tacgaccgca 900
aggttgaaac tcaaaggaat tgacgggggc ccgcacaagc ggtggagcat gtggtttaat 960
tcgaagcaac gcgaagaacc ttaccaggtc ttgacatccc agtgaccgct ctagagatag 1020
agtttttctt cggaacactg gtgacaggtg gtgcatggtt gtcgtcagct cgtgtcgtga 1080
gatgttgggt taagtcccgc aacgagcgca acccttattg ttagttgcca tcattcagtt 1140
gggcactcta gcgagactgc cggtaataaa ccggaggaag gtggggatga cgtcaaatca 1200
tcatgcccct tatgacctgg gctacacacg tgctacaatg gttggtacaa cgagtcgcaa 1260
gtcggtgacg gcaagcaaat ctcttaaagc caatctcagt tcggattgta ggctgcaact 1320
cgcctacatg aagcaggaat tgctagtaat ggcaggtcag catactgccg tgaatacgtt 1380
cccgggcctt gtacacaccg cccgtcacac catgagagtc tgtaacaccc gaagtcggta 1440
gtctaactac ggaggacgcc gccgaaggtg ggacagataa ttggggtgaa gtcgtaacaa 1500
ggtagccgta 1510

<210> SEQ ID NO 89
<211> LENGTH: 1442
<212> TYPE: DNA
<213> ORGANISM: Streptococcus sp.

<400> SEQUENCE: 89
ctaatacatg cgaggagaac gctgaagact ttcttttgct atagttggga gagttgctaa 60
cgggtgagta acgcgtaggt gacctgccta ctagcggggg ataactattg caaacgatag 120
ctaataccgc ataacagcct ttaacccatg ttagatgctt gaaaggagca attgcttcac 180
tagtagatgg acctgcgttg tattagctag ttggtgaggt aacggctcac caaggcgacg 240
atacatagcc gacctgagag ggtgatcggc cacactggga ctgagacacg gcccatactc 300
ctacgggagg caccagtagg gaatcttcgg gaatgggggc aaccctgacc gagcaacgcc 360
gcgtgagtga agaaggtttt cggatcgtaa agctctgttg taagagaaga acgtgtgtga 420
gagtggaaag ttcacactgt gacggtaact taccagaaag ggacggctaa ctacgtgcca 480
gcagccgcgg taatacgtag gtcccgagcg ttgtccggat ttattgggcg taaagcgagc 540
gcaggcggtt taataagtct gaagttaaag gcagtggctt aaccattgtt cgctttggaa 600
actgttagac ttgagtgcat aaggggagag tggaattcca tgtgtagcgg tgaaatgcgt 660
agatatatgg aggaacaccg gtggcgaaag cggctctctg gtctgtaact gacgttgagg 720
ctcgaaagcg tggggagcaa acaggattag ataccctggt agtccacgct gtaaacgatg 780
agtggtaggt gttaggccct ttctggggtt tagtgccgca gattacgcat taagccattc 840
gcctggggag tacgaccgca aggttgaaac ttaaaggaat tgacgggggc ccgcacaagc 900
ggtggagcat gtggtttaat tagaagcaac gcgaagaacc ttaccaggtc ttgacatccc 960
gatgctattc ttagagatag gaagtttctt cggaacatcg gtgacaggtg gtgcatggtt 1020
gtcgtcagct cgtgtcgaga gatgttgggt taagtccctc aacgagcgca acccctattt 1080
ttatttgcca tcattaagtt gggcaatcta gcgagactgc cggtaataaa ccggaggaag 1140
gtggggatga cgtcaaatca tcatgctcct tatgtcatgg ggtacacacg tggtacaatg 1200
gttggtacaa cgagtcgcga gttggtgaag gcaagcaaat ctcttaaagc caatatcagt 1260
tcggattgta ggctgcaaat agcctacatg tagtcggaat tgttagtaat cggggatcag 1320
cactccgcgg tgaatacgtt tccgggcctt gtacaccccg cccgtctaca ccacgagagt 1380
ttgtaacacc cgaagtcggt gaggtaactc ttttaggagc cagccgccta aggtgggata 1440
ga 1442

<210> SEQ ID NO 90
<211> LENGTH: 1397
<212> TYPE: DNA
<213> ORGANISM: Anaerostipes sp.

<400> SEQUENCE: 90
ctacctgcag tcgacgaaca ccttatttga ttttcttcgg aactgaagat ttggtgattg 60
agtggcggac gggtgagtaa cgcgtgggta acctgccctg tacaggggga taacagtcag 120
aaatgactgc taataccgca taagaccaca gcaccgcatg gtgcaggggt aaaaactccg 180
gtggtacagg atggacccgc gtctgattag ctggttggtg aggtaacggc tcaccaaggc 240
gacgatcagt agccggcttg agaaagtgaa cggccacatt gggactgaga cacggcccaa 300
actcctacgg gaggcagcag tggggaatat tgcacaatgg gggaaaccct gatgcagcga 360
cgccgcgtga gtgaagaagt atctcggtat gtaaagctct atcagcaggg aagaaaatga 420
cggtacctga ctaagaagcc ccggctaact acgtgccagc agccgcggta atacgtaggg 480
ggcaagcgtt atccggaatt actgggtgta aagggtgcgt aggtggtatg gcaagtcaga 540
agtgaaaacc cagggcttaa ctctgggact gcttttgaaa ctgtcagact ggagtgcagg 600
agaggtaagc ggaattccta gtgtagcggt gaaatgcgta gatattagga ggaacatcag 660
tggcgaaggc ggcttactgg actgaaactg acactgaggc acgaaagcgt ggggagcaaa 720
caggattaga taccctggta gtccacgccg taaacgatga atactaggtg tcggggccgt 780
agaggcttcg gtgccgcagc caacgcagta agtattccac ctggggagta cgttcgcaag 840
aatgaaactc aaaggaattg acggggaccc gcacaagtag cggagcatgt ggtttaattc 900
gaagcaacgc gaagaacctt acctaagctt gacatccttt tgaccgatgc ctaatcgcat 960
ctttcccttc ggggacagaa gtgacaggtg gtgcatggtt gtcgtcagct cgtgtcgtga 1020
gatgttgggt taagtcccgc aacgagcgca acccttgcct ttagttgcca tcattaagtt 1080
gggcactcta gagggactgc cagggataac ctggaggaag gtggggatga cgtcaaatca 1140
tcatgcccct tatgcttagg gctacacacg tgctacaatg ggtggtacag agggcagcga 1200
agtcgtgagg ccaagctaat cccttaaagc cattctcagt tcggattgta ggctgaaacc 1260
cgcctacatg aagctggagt tactagtaat cgcagatcag aatgctgcgg tgaatgcgtt 1320
cccgggtctt gtacacaccg cccgtcacac catgggagtt gggggcgccc gaagccggct 1380
agctactttg gaagcgt 1397

<210> SEQ ID NO 91
<211> LENGTH: 1435
<212> TYPE: DNA
<213> ORGANISM: Lachnoclostridium sp.

<400> SEQUENCE: 91
ggggggctta acacatgcaa gtcgaacgaa gcgctttcgc tttaatcttc ggaggaaaga 60
ggaagtgact gagtggcgga cgggtgagta acgcgtgggt aacctgcctc atacaggggg 120

```
ataacagtta gaaatggctg ctaataccgc ataagcatac agcaccgcat ggtgcagtgt    180

gaaaaactcc ggtggtataa gatggacccg cgtctgatta ggtagttggt ggggtaacgg    240

cctaccaagc cgacgatcag tagccgacct gagagggtga ccggccacat tgggactgag    300

acacggccca aactcctacg ggaggcagca gtggggaata ttgcacaatg gggaaaccc    360

tgatgcagcg acgccgcgtg aaggaagaag tatttcggta tgtaaacttc tatcagcagg    420

gaagaaaatg acggtacctg actaagaagc cccggctaac tacgtgccag cagccgcggt    480

aatacgtagg gggcaagcgt tatccggatt tactgggtgt aaagggagcg tagacggaag    540

tgcaagtctg aagtgaaagc ccggggctca accccgtgac tgctttggaa actgtgcttc    600

tagagtgtcg gagaggtaag cggaattcct agtgtagcgg tgaaatgcgt agatattagg    660

aggaacatca gtggcgaagg cggcttactg gcgataaact gacgttgagg ctcgaaagcg    720

tggggagcaa acaggattag ataccctggt agtccacgcc gtaaacgatg aatactaggt    780

gtcgggaagc acagcttttc ggtgccgccg caaacgcatt aagtattcca cctggggagt    840

acgttcgcaa gaatgaaact caaaggaatt gacggggacc cgcacaagcg gtggagcatg    900

tggtttaatt cgaagcaacg cgaagaacct taccaagtct tgacatcccg gtgaccggac    960

agtaatgtgt ccttttcttc ggaacaccgg tgacaggtgg tgcatggttg tcgtcagctc   1020

gtgtcgtgag atgttgggtt aagtcccgca acgagcgcaa cccttatccc cagtagccag   1080

cggttcggcc gggcactctg aggagactgc cagggataac ctggaggaag gtggggatga   1140

cgtcaaatca tcatgcccct tatgacttgg gctacacacg tgctacaatg gcgtaaacaa   1200

agggaagcga gaccgtgagg tggagcaaat cccaaaaata acgtctcagt tcggactgta   1260

gtctgcaacc cgactacacg aagctggaat cgctagtaat cgcagatcag aatgctgcgg   1320

tgaatacgtt cccgggtctt gtacacaccg cccgtcacac catgggagtt ggaaatgccc   1380

gaagtcagtg acccaaccgc aaggagggag ctgccgaagg caggttcgat aactg        1435
```

<210> SEQ ID NO 92
<211> LENGTH: 1493
<212> TYPE: DNA
<213> ORGANISM: Roseburia sp.

<400> SEQUENCE: 92

```
agagtttgat cctggctcag gatgaacgct ggcggcgtgc ttaacacatg caagtcgaac     60

gaagcacttt aacttgattt tttcggaatg attgttcttg tgactgagtg gcggacgggt    120

gagtaacgcg tgggtaacct gcctcataca gggggataac agttagaaat gactgctaat    180

accgcataag cgcacggtat cgcatgatac agtgtgaaaa actccggtgg tatgagatgg    240

acccgcgtct gattagctag ttggcggggt aacggcccac caaggcgacg atcagtagcc    300

gacctgagag ggtgaccggc cacattggga ctgagacacg gcccaaactc ctacgggagg    360

cagcagtggg gaatattgca caatgggcga aagcctgatg cagcgacgcc gcgtgaacga    420

aaaagtattt cggtatgtaa agttctatca gcagggaaga taatgacggt acctgactaa    480

gaagcaccgg ctaaatacgt gccagcagcc gcggtaatac gtatggtgca agcgttatcc    540

ggatttactg ggtgtaaagg gagcgcaggc ggtacggcaa gtctgatgtg aaagcccggg    600

gctcaacccc ggtactgcat tggaaactgt cgaactagag tgtcggaggg gtaagcggaa    660

ttcctagtgt agcggtgaaa tgcgtagata ttaggaggaa caccagtggc gaaggcggct    720

tactggacga caactgacgc tgaggcgcga aagcgtgggg agcaaacagg attagatacc    780
```

ctggtagtcc acgctgtaaa cgatgaatac taggtgtggg aggactgacc ccttccgtgc 840
cgcagttaac acaataagta ttccacctgg ggagtacggc cgcaaggctg aaactcaaag 900
gaattgacgg gggcccgcac aagcagtgga ttatgtggtt taattcgacg caacgcgaag 960
aaccttacca ggacttgaca tccaactaac gaagtagaga tacattaggt gcccttcggg 1020
gaaagttgag acaggtggtg catggttgtc gtcagctcgt gtcgtgagat gttgggttaa 1080
gtcccgcaac gagcgcaacc cctattgtta gttgctacgc aagagcactc tagcgagact 1140
gccgttgaca aaacggagga aggcggggac gacgtcaaat catcatgccc cttatgtcct 1200
gggctacaca cgtaatacaa tggccgtcaa caaagggaag caaagccgcg aggtggagca 1260
aatccccaaa aacggtctca gttcggattg caggctgcaa ctcgcctgca tgaagctgga 1320
attgctagta atcgtggatc agcatgccac ggtgaatacg ttcccgggcc ttgtacacac 1380
cgcccgtcac accatgagag tcgggaacac ccgaagtccg tagtctaacc gcaaggaggg 1440
cgcggccgaa ggtgggtccg gtaattgggg tgaagtcgta acaaggtaac cgt 1493

<210> SEQ ID NO 93
<211> LENGTH: 1289
<212> TYPE: DNA
<213> ORGANISM: Fusobacterium sp.

<400> SEQUENCE: 93
agtggcgaac gggtgagtaa cgcgtgagga acctgccttt cagtgggggga caacagttgg 60 aaacgactgc taataccgca tgatactttt tggaggcatc tctgaaaagt caaagcttta 120
tgtgctgaaa gatggtctcg cgtctgatta gctagttggt gaggtaacgg ctcaccaagg 180
cgacgatcag tagccggtct gagaggatga acggccacat tgggactgag atacggccca 240
gactcctacg ggaggcagca gtggggaata ttgggcaatg ggggaaaccc tgacccagca 300
acgccgcgtg aaggaagaag gccttcgggt tgtaaacttc ttttaccagg gacgaagaac 360
gtgacggtac ctggagaaaa agcaacggct aactacgtgc cagcagccgc ggtaatacgt 420
aggttgcaag cgttatccgg atttattggg cgtaaagcgc gtctaggcgg tttggtaagt 480
ctgatgtgaa aatgcggggc tcaactccgt attgcgttgg aaactgctaa actagagtac 540
tggagaggta ggcggaacta caagtgtaga ggtgaaattc gtagatattt gtaggaatgc 600
cgatggggaa gccagcctac tggacagata ctgacgctaa agcgcgaaag cgtggggagc 660
aaacaggatt agataccctg gtagtccacg ctgtaaacga tgagtactag gtgtcggagg 720
ttaccccctt cggtgccgca gctaacgcat taagtactcc gcctggggag tacgcacgca 780
agtgtggaac tcaaaggaat tgacggggac ccgcacaagt agcggagcat gtggtttaat 840
tcgaagcaac gcgaagaacc ttacctaggc ttgacatcct tctgaccgag gactaatctc 900
ctctttccct ccggggacag aagtgacagg tggtgcatgg ttgtcgtcag ctcgtgtcgt 960
gagatgttgg gttaagtccc gcaacgagcg caacccttgt ctttagttgc catcatttag 1020
ttgggcactc tggagagact gccagggata acctggagga aggtggggat gacgtcaaat 1080
catcatgccc cttatgccta gggctacaca cgtgctacaa tgggtggtac agagggcagc 1140
taagccgtga ggtggagcaa atcccttaaa gccattctca gttcggattg taggctgaaa 1200
ctcgcctaca tgaagctgga gttactagta atcgcagatc agaatgctgc ggtgaatgcg 1260
ttcccgggtc ttgtacacac cgcccgtca 1289

<210> SEQ ID NO 94
<211> LENGTH: 1366

<212> TYPE: DNA
<213> ORGANISM: Fusobacterium sp.

<400> SEQUENCE: 94

```
agagtttgat cctggctcag gatgaacgct gacagaatgc ttaacacatg caagtatact     60
tgatccttcg ggtgatggtg gcggacgggt gagtaacgcg taaagaactt gccctgcagt    120
ctgggacaac atttggaaac gaatgctaat cccgcataag cccacagctc ggcatcgagc    180
agagggaaaa ggagtgatct gctttgagat ggcctcgcgt ccgattagct ggttggtgag    240
gtgacggccc atcaaggcaa cgatcggtag ccggactgag aggttgaacg gccacattgg    300
gattgagaca cggcccttac tcctacggga ggcagcagtg ggaatattg gacaatggac    360
caaaagtctg atccagcaat tctgtgtgca cgatgaagtt tttcggaatg taaagtgctt    420
tcagttggga cgaagtaagt gacggtacca acagaagaag cgacggctaa atacgtgcca    480
gcagccgcgg taatacgtat gtcgcaagcg ttatccggat ttattgggcg taaagcgcgt    540
ctaggcggtt tggtaagtct gatgtgaaaa tgcggggctc aactccgtat tgcgttggaa    600
actgccaaac tagagtactg gagaggtggg cggaactaca agtgtagagg tgaaattcgt    660
agatatttgt aggaatgccg atggggaagc cagcccactg gacagatact gacgctaaag    720
cgcgaaagcg tgggtagcaa acaggattag ataccctggt agtccacgcc gtaaacgatg    780
attactaggt gttgggggtc gaacctcagc gcccaagcta acgcgataag taatccgcct    840
ggggagtacg tacgcaagta tgaaactcaa aggaattgac ggggacccgc acaagcggtg    900
gagcatgtgg tttaattcga cgcaacgcga ggaaccttac cagcgtttga catcctaaga    960
aattagcaga gatgcttttg tgccccttcg gggaactta gtgacaggtg gtgcatggct   1020
gtcgtcagct cgtgtcgtga gatgttgggt taagtcccgc aacgagcgca accccttcg   1080
tatgttgcca tcattaagtt gggcactcat gcgatactgc ctgcgatgag caggaggaag   1140
gtggggatga cgtcaagtca tcatgcccct tatacgctgg gctacacacg tgctacaatg   1200
ggtagtacag agagtcgcaa acctgcgagg gggagctaat ctcagaaaac tattctcagt   1260
tcggattgta ctctgcaact cgagtacatg aagttggaat cgctagtaat cgcaaatcag   1320
ctatgttgcg gtgaatacgt tctcgggtct tgtacacacc gcccgt                 1366
```

<210> SEQ ID NO 95
<211> LENGTH: 1361
<212> TYPE: DNA
<213> ORGANISM: Fusobacterium sp.

<400> SEQUENCE: 95

```
agagtttgat cctggctcag gacgaacgct ggcggcgtgc ctaacacatg caagtcgagc     60
gattctcttc ggagaagagc ggcggacggg tgagtaacgc gtgggtaacc tgccctgtac    120
acacggataa cataccgaaa ggtatgctaa tacgggataa tatataagag tcgcatgact    180
tttatatcaa agatttttcg gtacaggatg gacccgcgtc tgattagctt gttggcgggg    240
taacggccca ccaaggcgac gatcagtagc cgacctgaga gggtgatcgg ccacattgga    300
actgagacac ggtccaaact cctacgggag gcagcagtgg ggaatattgc acaatgggcg    360
caagcctgat gcagcaacgc cgcgtgagcg atgaaggcct tcgggtcgta aagctctgtc    420
ctcaaggaag ataatgacgg tacttgagga ggaagccccg gctaactaca tgccagcagc    480
cgcggtaata cgtatgtcgc aagcgttatc cggatttatt gggcgtaaag cgcgtctagg    540
tggtttggta agtctgatgt gaaaatgcgg ggctcaactc cgtattgcgt tggaaactgc    600
```

caaactagag tactggagag gtaggcggaa ctacaagtgt agaggtgaaa ttcgtagata 660
tttgtaggaa tgccgatggg gaagccagcc tactggacag atactgacgc taaagcgcga 720
aagcgtgggt agcaaacagg attagatacc ctggtagtcc acgccgtaaa cgatgattac 780
taggtgttgg gggtcgaacc tcagcgccca agctaacgcg ataagtaatc cgcctgggga 840
gtacgtacgc aagtatgaaa ctcaaaggag ttgacgggga cccgcacaag cggtggagca 900
tgtggtttaa ttcgacgcaa cgcgaggaac cttaccagcg tttgacatcc taggaatgag 960
aaagagattt cttagtgctc cttcgggaga acctagagac aggtggtgca tggctgtcgt 1020
cagctcgtgt cgtgagatgt tgggttaagt cccgcaacga gcgcaacccc tattgtatgt 1080
tgccatcatt aagttgggca ctcatgcgat actgcctgcg atgagcagga ggaaggtggg 1140
gatgacgtca agtcatcatg ccccttatac gctgggctac acacgtgcta caatgggcag 1200
tacagagaga agcaataccg cgaggtggag ccaaacttaa aaaccagtct cagttcggat 1260
tgtaggctga aactcgccta catgaagctg gagttactag taatcgcgaa tcagaatgtc 1320
gcggtgaata cgtacccggg tcttgtacac accgcccgtc a 1361

<210> SEQ ID NO 96
<211> LENGTH: 1415
<212> TYPE: DNA
<213> ORGANISM: Fusobacterium sp.

<400> SEQUENCE: 96
aatgcttaac acatgcaagt ctacttgatc cttcgggtga tggtggcgga cgggtgagta 60
acgcgtaaag aacttgcctt gcagtctggg acaacgtctg gaaacggacg ctaataccgg 120
atattatgcg agagtcgcat ggctctttca tgaaagctat atgcgctgca ggagagcttt 180
gcgtcccatt agttagttgg tgaggtaacg gctcaccaag accgcgatgg gtagccggcc 240
tgagagggtg aacggccaca aggggactga gacacggccc ttactcctac gggaggcagc 300
agtggggaat attggacaat ggaccaaaag tctgatccag caattctgtg tgcacgatga 360
cggtcttagg attgtaaagt gctttcaatc gggaaaaaga aagtgatggt accgatagaa 420
gaagcgacgg ctaaatacgt gccagcagcc gcggtaatac gtatgtcgca agcgttatcc 480
ggatttattg ggcgtaaagc gcgtctaggc ggtctggtaa gtctgatgtg gaaatgcggg 540
gctcaactcc gtattgcgtt ggaaactgcc agactagagt actggagagg tgggcggaac 600
tacaagtgta gaggtgaaat tcgtagatat ttgtaggaat gccgatagag aagtcagctc 660
actggacaga tactgacgct gaagcgcgaa agcatgggga gcaaacagga ttagataccc 720
tggtagtcca tgccgtaaac gatgattact aagcgtcggg ggtcgaacct cggcactcaa 780
gctaacgcga taagtaatcc gcctggggag tacgtacgca agtatgaaac tcaaaggaat 840
tgacggggac ccgcacaagt ggtggagcat gtggtttaat tggacgcaac gcgaggaact 900
ttaccagcgt gtgacatcct aggaatgaga aagagatttt tcagtgctcc ttcgggagaa 960
cccagagaca ggtggtgcat ggctgtggtc agctcgtgtc gtgagatgtt gggttaagtc 1020
ccgcaacgag cgcaacccct attgtatgtt gccatcatta agttgggcaa tcatgcgatg 1080
ctgcctgcga cgagcaggag gaaggtgggg atgaggtcaa gtcatcatgc ccgttatatg 1140
ctgggctaca cacgtgctac aatgggcagt acagagagaa gcaaatatgc gaggaggagc 1200
aaatgtcaga aagctgttcg tagttcggat tgtactctgc aactggagta catgaagttg 1260
gaatcagtag taatcgcaaa tcagcaatgt tgcggtgaat acgttctcgg gtctggtaca 1320
caccgcccgt cacaccacga gagttgattg cacctgaagt agcaggccta accgtaagga 1380
agggtggtcc gagggtgtgg ttagcgattg gggtg 1415

<210> SEQ ID NO 97
<211> LENGTH: 1395
<212> TYPE: DNA
<213> ORGANISM: Unknown
<220> FEATURE:
<223> OTHER INFORMATION: Bacteria
<220> FEATURE:
<221> NAME/KEY: source
<222> LOCATION: (1)..(1395)
<223> OTHER INFORMATION: /note="Description of Unknown: Lachnospiraceae sequence"

<400> SEQUENCE: 97
agagtttgat cctggctcag gatgaacgct ggcggcgtgc ttaacacatg caagtcgagc 60
gaagcgcttt tacggatttc ttcggattga agtgattgtg actgagcggc ggacgggtga 120
gtaacgcgtg ggtaacctgc ctcatacagg gggataacag ttagaaatga ctgctaatac 180
cgcataagcg cacagtaccg catgggtacg gtgtgaaaaa ctccggtggt atgagatgga 240
cccgcgtctg attaggtagt tggtggggta acggcctacc aagccaacga tcagtagccg 300
acctgagagg gcgaccggcc acattgggac tgagacacgg cccaaactcc tacgggaggc 360
agcagtgggg aatattgcac aatgggggaa accctgatgc agcgacgccg cgtgaaggat 420
gaagtatttc ggtatgtaaa cttctatcag cagggaagaa aataacggta cctgagtaag 480
aagccccggc taactacgtg ccagcagccg cggtaatacg tagggggcaa gcgttatccg 540
gatttactgg gtgtaaaggg agcgtagacg gaagtgcaag tctgatgtga aaacccgagg 600
ctcaaccacg ggactgcatt ggaaactgtg cttctagagt gccggagagg taagcggaat 660
tcctagtgta gcggtgaaat gcgtagatat taggaggaac accagtggcg aaggcggctt 720
actggacggt aactgacgtt gaggctcgaa agcgtgggga gcaaacagga ttagataccc 780
tggtagtcca cgccgtaaac gatgacttac tagggtgtcg ggcagcaaag ctgttcggtt 840
gccgcagcca tcgcaataag tagtccacct gggggagtac gttcgcaaga atgaaactca 900
aaggaattga cggggacccg cacaagcggt ggagcatgtg gtttaattcg aagcaacgcg 960
aagaacctta cctgctcttg acatccctct gaccggcaag taatgttgcc tttccttcgg 1020
gacagaggag acaggtggtg catggttgtc gtcagctcgt gtcgtgagat gttgggttaa 1080
gtcccgcaac gagcgcaacc cctatcttca gtagccagca tttaaggtgg gcactcagga 1140
gagactgcca gggataacct ggaggaaggt ggggatgacg tcaaatcatc atgcccctta 1200
tgagcagggc tacacacgtg ctacaatggc gtaaacaaag ggaagcgaaa gggtgacctg 1260
gagcaaatct cagaaataac gtctcagttc ggattgtagt ctgcaactcg actacatgaa 1320
gctggaatcg ctagtaatcg cgaatcagca tgtcgcggtg aatacgttcc cgggtcttgt 1380
actcaccgcc cgtca 1395

<210> SEQ ID NO 98
<211> LENGTH: 1388
<212> TYPE: DNA
<213> ORGANISM: Unknown
<220> FEATURE:
<223> OTHER INFORMATION: Bacteria
<220> FEATURE:
<221> NAME/KEY: source
<222> LOCATION: (1)..(1388)
<223> OTHER INFORMATION: /note="Description of Unknown: Peptostreptococcaceae sequence"

<400> SEQUENCE: 98
agagtttgat cctggctcag gatgaacgct ggcggcgtgc ctaacacatg caagttgagc 60
gatttacttc ggtaaagagc ggcggacggg tgagtaacgc gtgggtaacc taccctgtac 120
acacggataa cataccgaaa ggtatgctaa tacgggataa tatatttgag aggcatctct 180
tgaatatcaa aggtgagcca gtacaggatg gacccgcgtc tgattagcta gttggtaagg 240
taacggctta ccaaggcgac gatcagtagc cgacctgaga gggtgatcgg ccacattgga 300
actgagacac ggtccaaact cctacgggag gcagcagtgg ggaatattgc acaatgggcg 360
aaagcctgat gcagcaacgc cgcgtgagtg atgaaggcct tcgggtcgta aaactctgtc 420
ctcaaggaag ataatgacgg tacttgagga ggaagccccg gctaactacg tgccagcagc 480
cgcggtaata cgtagggggc tagcgttatc cggatttact gggcgtaaag ggtgcgtagg 540
cggtctttca agtcaggagt gaaaggctac ggctcaaccg tagtaagctc ttgaaactgg 600
gagacttgag tgcaggagag gagagtggaa ttcctagtgt agcggtgaaa tgcgtagata 660
ttaggaggaa caccagttgc gaaggcggct ctctggactg taactgacgc tgaggcacga 720
aagcgtgggg agcaaacagg attagatacc ctggtagtcc acgctgtaaa cgatgagtac 780
taggtgtcgg gggttacccc cttcggtgcc gcagctaacg cattaagtac tccgcctggg 840
aagtacgctc gcaagagtga aactcaaagg aattgacggg gacccgcaca agtagcggag 900
catgtggttt aattcgaagc aacgcgaaga accttaccta agcttgacat cccaatgaca 960
tctccttaat cggagagttc ccttcgggga cattggtgac aggtggtgca tggttgtcgt 1020
cagctcgtgt cgtgagatgt tgggttaagt cccgcaacga gcgcaaccct tgtctttagt 1080
tgccatcatt aagttgggca ctctagagag actgccaggg ataacctgga ggaaggtggg 1140
gatgacgtca aatcatcatg ccccttatgc ttagggctac acacgtgctg attatgctaa 1200
ggaaatagga tttactggac aattcttaat agagcctaag ccaaaagagc ctactaaaca 1260
tcaatatgat tttgatactg ctactgtttt aggattttta agaaagtata atctggataa 1320
atacttcaaa gtgaatatag aagcaaacca tgcaacactt gcaggacata ctttccaaca 1380
tgaattaa 1388

<210> SEQ ID NO 99
<211> LENGTH: 1457
<212> TYPE: DNA
<213> ORGANISM: Unknown
<220> FEATURE:
<223> OTHER INFORMATION: Bacteria
<220> FEATURE:
<221> NAME/KEY: source
<222> LOCATION: (1)..(1457)
<223> OTHER INFORMATION: /note="Description of Unknown: Lachnospiraceae sequence"

<400> SEQUENCE: 99
cgctggcggc gtgcttaaca catgcaagtc gaacgaagcg atttggagga agttttcgga 60
tgaaatctga attgactgag tggcggacgg gtgagtaacg cgtgggtaac ctgcctcaca 120
cagggggaca acagttagaa atggctgcta ataccgcata agcgcacagc ttcgcatgaa 180
gcagtgtgaa aaactccggt ggtgtgagat ggacccgcgt ctgattaggt agttggtggg 240
gtaacggcct accaagccga cgatcagtag ccgacctgag agggtgaccg gccacattgg 300
gactgagaca cggcccaaac tcctacggga ggcagcagtg gggaatattg cacaatgggg 360
gaaaccctga tgcagcgacg ccgcgtgagt gaagaagtat ttcggtatgt aaagctctat 420

-continued

```
cagcagggaa gaaaatgacg gtacctgact aagaagcccc ggctaactac gtgccagcag    480
ccgcggtaat acgtaggggg caagcgttat ccggatttac tgggtgtaaa gggagcgtag    540
acggcttggc aagtctgaag tgaaagcccg gggctcaacc ccgggactgc tttggaaact    600
gtcaggctag agtgctggag aggtaagtgg aattcctagt gtagcggtga aatgcataga    660
tattaggagg aacaccagtg gcgaaggcgg cttactggac agtaactgac gttgaggctc    720
gaaagcgtgg ggagcaaaca ggattagata ccctggtagt ccacgccgta aacgatgaat    780
actaggtgtt ggggagcaaa gctcttcggt gccgtcgcaa acgcaataag tattccacct    840
gggaagtacg ttcgcaagaa tgaaactcaa aggaattgac ggggacccgc acaagcggtg    900
gagcatgtgg tttaattcga agcaacgcga agaaccttac caagtcttga catcccattg    960
aaaagcccgt aacggggttc cctcttcgga gcaatggaga caggtggtgc atggttgtcg   1020
tcagctcgtg tcgtgagatg ttgggttaag tcccgcaacg agcgcaaccc ttatcctaag   1080
tagccagcag gtagagctgg gcactcttgg gagactgcca gggacaacct ggaggaaggt   1140
ggggatgacg tcaaatcatc atgcccctta tgatttgggc tacacacgtg ctacaatggc   1200
gtaaacaaag ggaagcgaag ctgtgaagct aagcaaatct caaaaataac gtctcagttc   1260
ggattgtagt ctgcaactcg actacatgaa gctggaatcg ctagtaatcg cggatcagaa   1320
tgccgcggtg aacacgttcc cgggtcttgt acacaccgcc cgtcacacca tgggagtcag   1380
taacgcccga agccagtgac ctaaccgcaa ggaaggagct gtcgaaggcg ggaccgataa   1440
ctggggtgaa gtcgtaa                                                  1457
```